(12) United States Patent
Huh et al.

(10) Patent No.: US 11,594,685 B2
(45) Date of Patent: Feb. 28, 2023

(54) ORGANIC LIGHT EMITTING DEVICE

(71) Applicant: LG CHEM, LTD., Seoul (KR)

(72) Inventors: Jung Oh Huh, Daejeon (KR); Dong Hoon Lee, Daejeon (KR); Boon Jae Jang, Daejeon (KR); Min Young Kang, Daejeon (KR); Dong Uk Heo, Daejeon (KR); Mi Yeon Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 953 days.

(21) Appl. No.: 16/323,770

(22) PCT Filed: Mar. 26, 2018

(86) PCT No.: PCT/KR2018/003540
§ 371 (c)(1),
(2) Date: Feb. 6, 2019

(87) PCT Pub. No.: WO2018/182259
PCT Pub. Date: Oct. 4, 2018

(65) Prior Publication Data
US 2019/0214571 A1    Jul. 11, 2019

(30) Foreign Application Priority Data

Mar. 30, 2017 (KR) .......... 10-2017-0040551

(51) Int. Cl.
*H01L 51/00* (2006.01)
*C07D 405/10* (2006.01)
(Continued)

(52) U.S. Cl.
CPC ...... *H01L 51/0067* (2013.01); *C07D 405/10* (2013.01); *C07D 405/14* (2013.01);
(Continued)

(58) Field of Classification Search
CPC .................................................. H01L 51/5036
See application file for complete search history.

(56) References Cited

U.S. PATENT DOCUMENTS

| | | | |
|---|---|---|---|
| 2003/0168970 A1 | 9/2003 | Tominaga et al. | |
| 2004/0161632 A1* | 8/2004 | Seo .............. | H01L 51/006 313/506 |

(Continued)

FOREIGN PATENT DOCUMENTS

| | | |
|---|---|---|
| CN | 101440082 A | 5/2009 |
| CN | 102786508 A | 11/2012 |

(Continued)

OTHER PUBLICATIONS

Xiang-Hua Zhao, "A 3-dimensional spiro-functionalized platinum(II) complex to suppress intermolecular . . . ", Chem. Commun., 2012, 48, 3854-3856.

*Primary Examiner* — Sean M DeGuire
(74) *Attorney, Agent, or Firm* — Dentons US LLP

(57) ABSTRACT

The present invention relates to an organic light emitting device comprising a light emitting layer and an electron transport layer which satisfy the following mathematical expressions, $E_{HOMO-ET} > E_{HOMO-BH}$ and $E_{LUMO-ET} > E_{LUMO-GH}$, and having improved driving voltage, efficiency, and lifetime.

9 Claims, 1 Drawing Sheet

(51) Int. Cl.
*C07D 405/14* (2006.01)
*C07D 409/10* (2006.01)
*C07D 471/04* (2006.01)
*H01L 51/50* (2006.01)
*C09K 11/06* (2006.01)

(52) U.S. Cl.
CPC ......... *C07D 409/10* (2013.01); *C07D 471/04* (2013.01); *C09K 11/06* (2013.01); *H01L 51/00* (2013.01); *H01L 51/0072* (2013.01); *H01L 51/0073* (2013.01); *H01L 51/0074* (2013.01); *H01L 51/50* (2013.01); *H01L 51/5004* (2013.01); *H01L 51/5036* (2013.01); *H01L 51/5072* (2013.01); *H01L 2251/5384* (2013.01); *H01L 2251/552* (2013.01)

(56) References Cited

U.S. PATENT DOCUMENTS

| | | |
|---|---|---|
| 2004/0251816 A1 | 12/2004 | Leo et al. |
| 2008/0193796 A1 | 8/2008 | Arakane et al. |
| 2008/0210960 A1 | 9/2008 | Ha et al. |
| 2010/0187552 A1 | 7/2010 | Lee et al. |
| 2010/0187977 A1 | 7/2010 | Kai et al. |
| 2010/0314644 A1 | 12/2010 | Nishimura et al. |
| 2011/0042660 A1* | 2/2011 | Kawamura ............ H05B 33/14 257/40 |
| 2011/0260138 A1 | 10/2011 | Xia et al. |
| 2011/0278555 A1 | 11/2011 | Inoue et al. |
| 2012/0068170 A1 | 3/2012 | Pflumm et al. |
| 2013/0075716 A1 | 3/2013 | Nishimura et al. |
| 2014/0197386 A1* | 7/2014 | Kim .................... H01L 51/0067 257/40 |
| 2015/0008394 A1 | 1/2015 | Oh et al. |
| 2015/0014667 A1* | 1/2015 | Li ....................... H01L 51/5096 257/40 |
| 2015/0200371 A1 | 7/2015 | Kim et al. |
| 2015/0295181 A1 | 10/2015 | Mujica-Fernaud et al. |
| 2015/0325800 A1 | 11/2015 | Ito et al. |
| 2015/0340618 A1 | 11/2015 | Lee et al. |
| 2016/0118599 A1 | 4/2016 | Jeong et al. |
| 2016/0133674 A1 | 5/2016 | Lee et al. |
| 2016/0211454 A1 | 7/2016 | Kim et al. |
| 2016/0260906 A1 | 9/2016 | Shin et al. |
| 2016/0276596 A1 | 9/2016 | Jang et al. |
| 2017/0033294 A1 | 2/2017 | Jang et al. |
| 2017/0186965 A1 | 6/2017 | Parham et al. |
| 2017/0217992 A1 | 8/2017 | Jun et al. |
| 2017/0222157 A1 | 8/2017 | Jatsch et al. |
| 2018/0053900 A1 | 2/2018 | Eum et al. |
| 2018/0208836 A1 | 6/2018 | Kuma et al. |

FOREIGN PATENT DOCUMENTS

| | | | |
|---|---|---|---|
| CN | 104774210 A | 7/2015 | |
| CN | 105612239 A | 5/2016 | |
| CN | 105810838 A | 7/2016 | |
| EP | 1437395 A2 | 4/2004 | |
| JP | 02285357 A | 11/1990 | |
| JP | 11329737 A | 11/1999 | |
| JP | 2003096072 A | 4/2003 | |
| JP | 2005285618 A | 10/2005 | |
| JP | 2009191232 A | 8/2009 | |
| JP | 2013183047 A | 9/2013 | |
| KR | 1020000051826 A | 8/2000 | |
| KR | 1020080067877 A | 7/2008 | |
| KR | 1020080071750 A | 8/2008 | |
| KR | 1020090021070 A | 2/2009 | |
| KR | 1020100007552 A | 1/2010 | |
| KR | 1020120034646 A | 4/2012 | |
| KR | 1020150004264 A | 1/2015 | |
| KR | 101537499 B1 | 7/2015 | |
| KR | 10-1593368 * | 2/2016 | ............ H01L 51/50 |
| KR | 101593368 B1 | 2/2016 | |
| KR | 1020160018406 A | 2/2016 | |
| KR | 10-2016-0051134 A | 5/2016 | |
| KR | 1020160047670 A | 5/2016 | |
| KR | 1020160055347 A | 5/2016 | |
| KR | 1020170032414 A | 3/2017 | |
| KR | 1020170039020 A | 4/2017 | |
| KR | 1020170063251 A | 6/2017 | |
| TW | 201615635 A | 5/2016 | |
| WO | 2002043449 A1 | 5/2002 | |
| WO | 2003012890 A2 | 2/2003 | |
| WO | 2008056746 A1 | 5/2008 | |
| WO | 2008062773 A1 | 5/2008 | |
| WO | 2010136109 A1 | 12/2010 | |
| WO | 2011132683 A1 | 10/2011 | |
| WO | 2011155507 A1 | 12/2011 | |
| WO | 2013149958 A1 | 10/2013 | |
| WO | 2013175747 A1 | 11/2013 | |
| WO | 2014072017 A1 | 5/2014 | |
| WO | 2014141725 A1 | 9/2014 | |
| WO | 2014185595 A1 | 11/2014 | |
| WO | 2015152650 A1 | 10/2015 | |
| WO | 2015169412 A1 | 11/2015 | |
| WO | 2016105141 A2 | 6/2016 | |
| WO | 2017010489 A1 | 1/2017 | |
| WO | 2017142304 A1 | 8/2017 | |

\* cited by examiner

[FIG. 1]
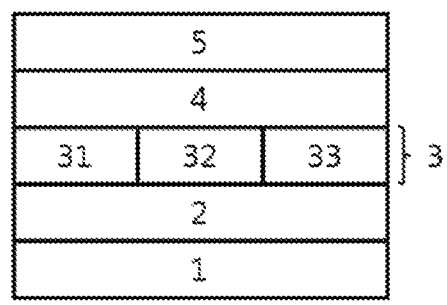
[FIG. 2]
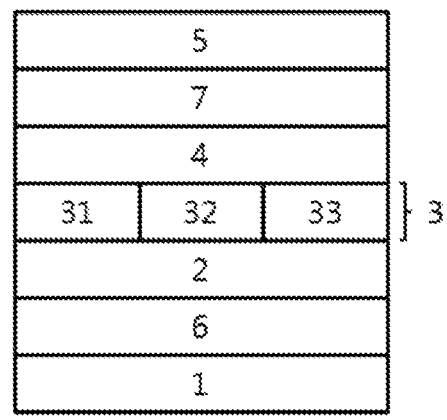

ORGANIC LIGHT EMITTING DEVICE

CROSS-REFERENCE TO RELATED APPLICATION(S)

This application is a National Stage Application of International Application No. PCT/KR2018/003540, filed Mar. 26, 2018 which claims the benefit of priority from Korean Patent Application No. 10-2017-0040551 filed on Mar. 30, 2017, the full disclosure of which is incorporated herein by reference.

TECHNICAL FIELD

The present invention relates to an organic light emitting device having improved driving voltage, efficiency and lifetime.

BACKGROUND ART

In general, an organic light emitting phenomenon refers to a phenomenon where electric energy is converted into light energy by using an organic material. The organic light emitting device using the organic light emitting phenomenon has excellent characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

In the organic light emitting device as described above, there is a continuing demand for developing an organic light emitting device having improved driving voltage, efficiency and lifetime.

PRIOR ART LITERATURE

Patent Literature (Patent Literature 0001) Korean Patent Laid-open Publication No. 10-2000-0051826

DETAILED DESCRIPTION OF THE INVENTION

Technical Problem

The present invention relates to an organic light emitting device having improved driving voltage, efficiency and lifetime.

Technical Solution

The present invention provides the following organic light emitting device:

The organic light emitting device comprises an anode, a hole transport layer, a light emitting layer, an electron transport layer, and a cathode, in this order, wherein the light emitting layer comprises a red light emitting layer, a green light emitting layer, and a blue light emitting layer, the electron transport layer is adjacent to the red light emitting layer, the green light emitting layer, and the blue light emitting layer, the electron transport layer comprises one or more layers, a layer adjacent to the red light emitting layer, the green light emitting layer and the blue light emitting layer in the electron transport layer satisfies the following mathematical expressions 1 and 2:

$$E_{HOMO-ET} > E_{HOMO-BH} \quad \text{[Mathematical Expression 1]}$$

in Mathematical Expression 1, $E_{HOMO-ET}$ is an absolute value of a HOMO energy level of a material comprising a layer adjacent to the red light emitting layer, the green light emitting layer and the blue light emitting layer in the electron transport layer, and $E_{HOMO-BH}$ is an absolute value of a HOMO energy level of a host material of the blue light emitting layer, $$E_{LUMO-ET} > E_{LUMO-GH} \quad \text{[Mathematical Expression 2]}$$

in Mathematical Expression 2, $E_{LUMO-ET}$ is an absolute value of a LUMO energy level of a material comprising a layer adjacent to the red light emitting layer, the green light emitting layer and the blue light emitting layer in the electron transport layer, and $E_{LUMO-GH}$ is an absolute value of a LUMO energy level of a host material of the green light emitting layer.

Advantageous Effects

The organic light emitting device described above is excellent in driving voltage, efficiency and lifetime.

BRIEF DESCRIPTION OF DRAWINGS

FIG. 1 shows an example of an organic light emitting device comprising an anode 1, a hole transport layer 2, a light emitting layer 3, an electron transport layer 4, and a cathode 5. In FIG. 1, the light emitting layer 3 has a structure in which a red light emitting layer 31, a green light emitting layer 32, and a blue light emitting layer 33 are arranged in parallel.

FIG. 2 shows an example of an organic light emitting device comprising an anode 1, a hole injection layer 6, a hole transport layer 2, a light emitting layer 3, an electron transport layer 4, an electron injection layer 7, and a cathode 5. In FIG. 2, the light emitting layer 3 has a structure in which a red light emitting layer 31, a green light emitting layer 32, and a blue light emitting layer 33 are arranged in parallel.

DETAILED DESCRIPTION OF THE EMBODIMENTS

Hereinafter, the present invention will be described in more detail to help understanding of the invention.

In the present specification,

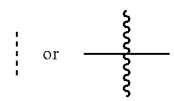

mean a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40, Specifically, the carbonyl group may be compounds having the following structures, but is not limited thereto.

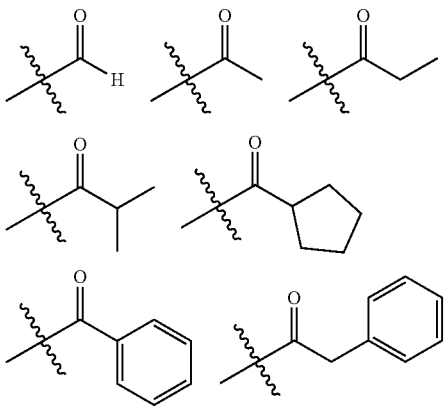

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

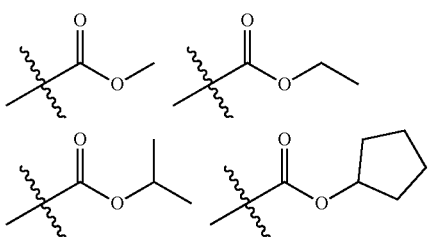

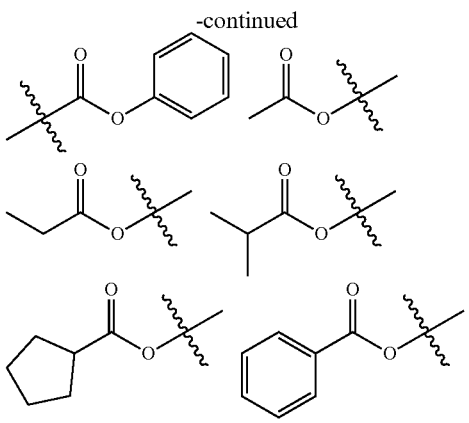

In the present specification, the number of carbon atoms in an imide group is not particularly limited, but is preferably 1 to 25. Specifically, the imide group may be compounds having the following structures, but is not limited thereto.

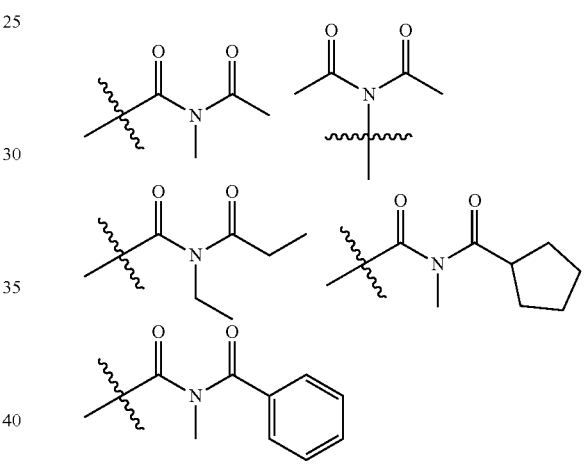

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, the alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(di-phenyl-1-yl)vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group or the like, but is not limited thereto.

In the present specification, a fluorenyl group may be substituted, and two substituent groups may be linked with each other to form a Spiro structure. In the case where the fluorenyl group is substituted,

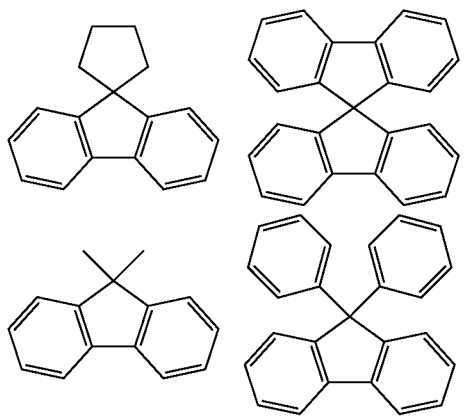

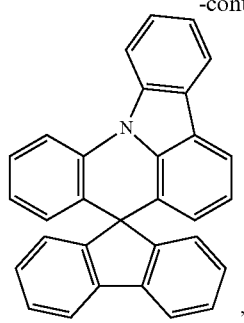

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heteroaryl group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

Hereinafter, the present invention will be described in detail for each configuration.

Anode and Cathode

The anode and cathode used in the present invention mean electrodes used in an organic light emitting device.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

Hole Injection Layer

The organic light emitting device according to the present invention may further include a hole injection layer between the anode and the hole transport layer described later.

The hole injection layer is a layer injecting holes from an electrode, and the hole injection material is preferably a compound which has an ability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer.

Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

Hole Transport Layer

The hole transport layer used in the present invention is a layer that receives holes from a hole injection layer formed on an anode or a cathode and transports the holes to the light emitting layer. The hole transport material is suitably a material having large mobility to the holes, which may receive holes from the anode or the hole injection layer and transfer the holes to the light emitting layer.

Specific examples thereof include an arylamine-based organic material, a conductive polymer, a block copolymer in which a conjugate portion and a non-conjugate portion are present together, and the like, but are not limited thereto.

Light Emitting Layer and Electron Transport Layer

The light emitting layer used in the present invention means a layer that can emit light in the visible light region by combining holes and electrons transported from an anode and a cathode, and is preferably a material having good quantum efficiency for fluorescence or phosphorescence.

Particularly, the organic light emitting device according to the present invention is an RGB organic light emitting device having color-variable characteristics, wherein the light emitting layer comprises a red light emitting layer, a green light emitting layer, and a blue light emitting layer. Specifically, the light emitting layer has a structure in which a red light emitting layer, a green light emitting layer and a blue light emitting layer are comprised in parallel, and makes contact with the electron transport layer described later. Its structure is schematically shown in FIG. 1.

As shown in FIG. 1, a red light emitting layer 31, a green light emitting layer 32 and a blue light emitting layer 33 are arranged in parallel on a hole transport layer 2, and at the same time are adjacent to the electron transport layer 4. On the other hand, the order can be changed except that the red light emitting layer 31, the green light emitting layer 32, and the blue light emitting layer 33 are arranged in parallel. In addition, the red light emitting layer 31, the green light emitting layer 32 and the blue light emitting layer 33 are not necessarily adjacent to each other, and it may be spaced apart between the respective light emitting layers.

On the other hand, conventionally, in order to manufacture a RGB organic light emitting device, each light emitting layer had a separate electron transport layer. This is due to the fact that, in consideration of the characteristics according to the materials contained in the respective light emitting layers, an electron transport a layer suitable therefor is necessary. However, in the present invention, it was found that, when a layer adjacent to the red light emitting layer, the green light emitting layer and the blue light emitting layer in the electron transport layer satisfies the following mathematical expressions 1 and 2, the characteristics of the RGB device can be exhibited even by a common electron transport layer. Thereby, there is an advantage that the manufacturing process can be simplified as compared with the case where a separate electron transport layer is formed in each light emitting layer.

Specifically, the Mathematical Expression 1 is as follows.

$$E_{HOMO\text{-}ET} > E_{HOMO\text{-}BH} \quad \text{[Mathematical Expression 1]}$$

in Mathematical Expression 1, $E_{HOMO\text{-}ET}$ is an absolute value of a HOMO energy level of a material comprising a layer adjacent to the red light emitting layer, the green light emitting layer and the blue light emitting layer in the electron transport layer (hereinafter, referred to as 'adjacent electron transport layer'), and $E_{HOMO\text{-}BH}$ is an absolute value of HOMO energy level of a host material of the blue light emitting layer.

The Mathematical Expression 1 means that the absolute value of a HOMO energy level of a material comprising an adjacent electron transport layer is larger than the absolute value of a HOMO energy level of a host material of the blue light emitting layer. Thereby, it is possible to prevent the holes transferred from the anode from being entered the electron transport layer and thus improve the lifetime of the organic light emitting device. On the other hand, when the host material of the blue light emitting layer is two or more kinds, $E_{HOMO\text{-}BH}$ means an absolute value of the average value of the HOMO energy levels of the respective host materials. For example, when n hosts are comprised, it means an absolute value of the value obtained by dividing the total sum of the HOMO energy levels of the respective hosts by n.

Specifically, the Mathematical Expression 2 is as follows.

$$E_{LUMO\text{-}ET} > E_{LUMO\text{-}GH} \quad \text{[Mathematical Expression 2]}$$

in Mathematical Expression 2, $E_{LUMO\text{-}ET}$ is an absolute value of a LUMO energy level of a material comprising an adjacent electron transport layer, and $E_{LUMO\text{-}GH}$ is an absolute value of a LUMO energy level of a host material of the green light emitting layer.

The Mathematical Expression 2 means that the absolute value of a LUMO energy level of a material comprising an adjacent electron transport layer is larger than the absolute value of the LUMO energy level of the host material of the green light emitting layer. Thereby, it is possible to control the amount of electrons transferred from the cathode to control the light emitting region biased to the hole transport layer side, thereby improving the lifetime of the organic light emitting device. On the other hand, when the host material of the green light emitting layer is two or more kinds, $E_{LUMO-GH}$ means an absolute value of the average value of the LUMO energy levels of the respective host materials. For example, when n hosts are comprised, it means an absolute value of the value obtained by dividing the total sum of the LUMO energy levels of the respective hosts by n.

Electron Transport Layer

The electron transport layer comprises one or more layers. In addition, any one of the electron transport layers comprises a compound represented by the following Chemical Formula 1. Preferably, a layer (adjacent electron transport layer) adjacent to the red light emitting layer, the green light emitting layer, and the blue light emitting layer in the electron transport layer comprises a compound represented by the following Chemical Formula 1. When the compound represented by the following Chemical Formula 1 is used, the above energy level relationship can be satisfied.

[Chemical Formula 1]

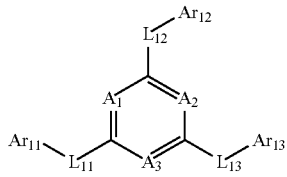

in Chemical Formula 1, $A_1$ to $A_3$ are each independently N or CR, with the proviso that at least two of $A_1$ to $A_3$ are N, R is hydrogen, or is bonded to $Ar_{11}$ or $Ar_{12}$ to form substituted or unsubstituted $C_{6-60}$ aryl; or substituted or unsubstituted $C_{2-60}$ heteroaryl containing at least one heteroatom selected from the group consisting of N, O and S, $L_{11}$ and $L_{12}$ are each independently a bond; a substituted or unsubstituted $C_{6-60}$ arylene; or substituted or unsubstituted $C_{2-60}$ heteroarylene containing at least one heteroatom selected from the group consisting of N, O and S, $Ar_{11}$ and $Ar_{12}$ are each independently substituted or unsubstituted $C_{6-60}$ aryl; tri($C_{6-60}$ aryl)silyl; or substituted or unsubstituted $C_{2-60}$ heteroaryl containing at least one heteroatom selected from the group consisting of N, O and S, or is boned bonded to the R to form substituted or unsubstituted $C_{6-60}$ aryl; or substituted or unsubstituted $C_{2-60}$ heteroaryl containing at least one heteroatom selected from the group consisting of N, O and S, $L_{13}$ is a bond; substituted or unsubstituted $C_{6-60}$ arylene; or substituted or unsubstituted $C_{2-60}$ heteroarylene containing at least one heteroatom selected from the group consisting of N, O and S, and $Ar_{13}$ is represented by the following Chemical Formula 2,

[Chemical Formula 2]

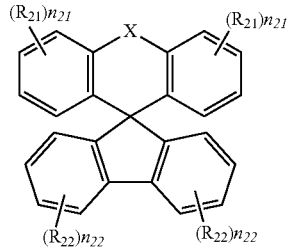

in Chemical Formula 2,

X is O, or S, $n_{21}$ and $n_{22}$ are each independently an integer of 1 to 4, at least one of $R_{21}$ and $R_{22}$ is connected to Arm and the rest are each independently hydrogen; deuterium; substituted or unsubstituted $C_{1-60}$ alkyl; substituted or unsubstituted $C_{6-60}$ aryl; or substituted or unsubstituted $C_{2-60}$ heteroaryl containing any one or more heteroatoms selected from the group consisting of N, O and S, or two adjacent $R_{21}$ or two adjacent $R_{22}$ can be connected to each other to form a benzene ring.

Preferably, the Chemical Formula 1 is any one selected from the group consisting of the following Chemical Formulas 1-1 to 1-5:

1-1

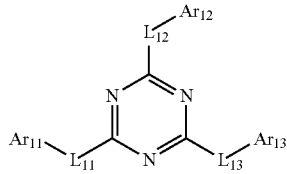

1-2

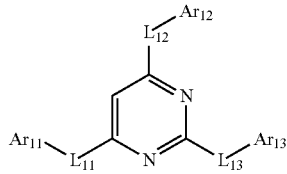

1-3

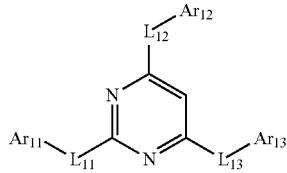

1-4

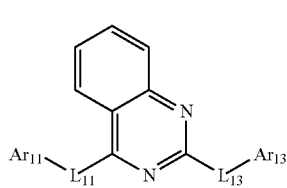

-continued

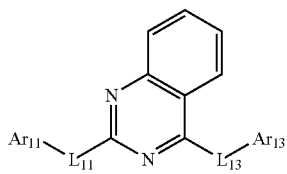

1-5 in Chemical Formulas 1-1 to 1-5,

Ar$_{11}$ and Ar$_{12}$ are each independently substituted or unsubstituted C$_{6-60}$ aryl; or substituted or unsubstituted C$_{2-60}$ heteroaryl containing at least one heteroatom selected from the group consisting of N, O and S, and Ar$_{13}$ is as defined above.

Preferably, L$_{11}$ and L$_{12}$ are each independently a bond; phenylene; or biphenylylene.

Preferably, Ar$_{11}$ and Ar$_{12}$ are each independently any one selected from the group consisting of:

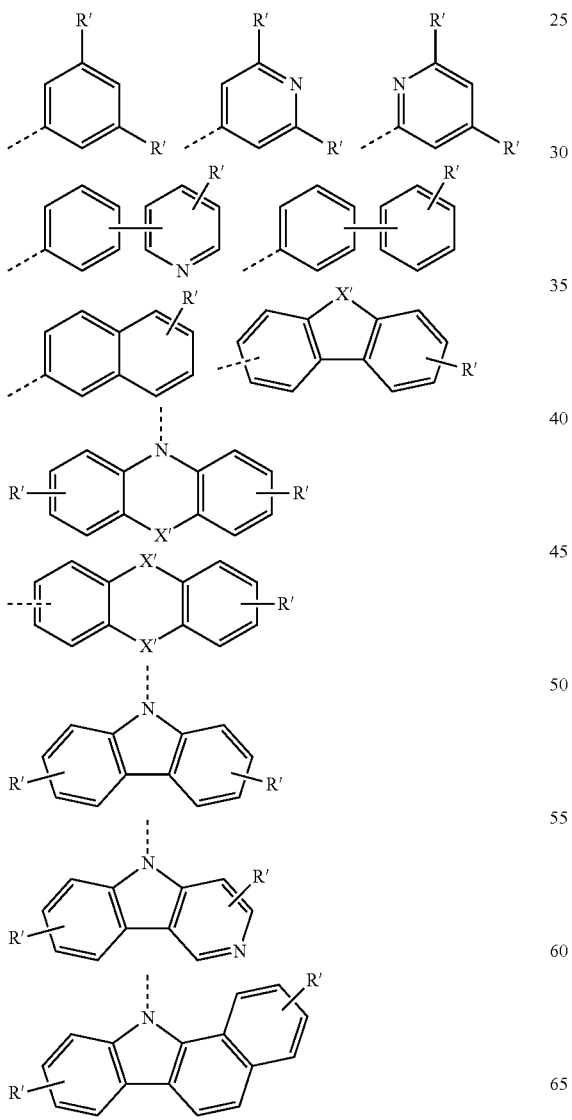

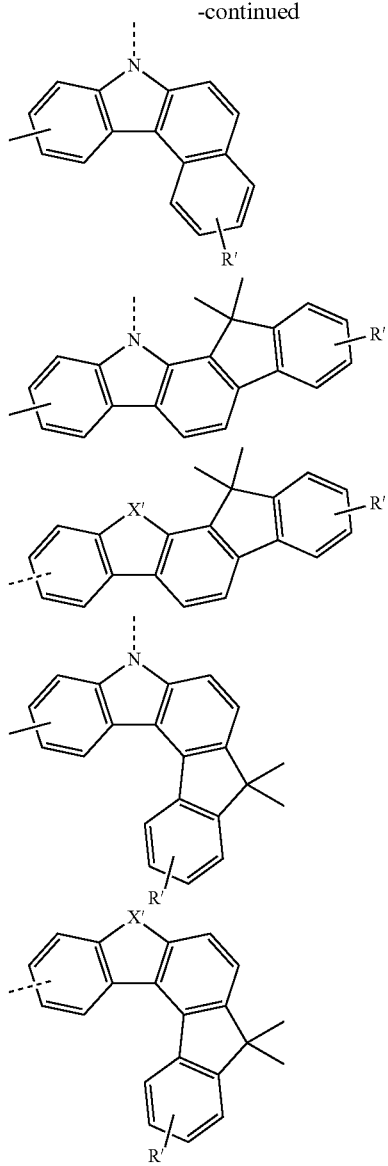

in the above formulas, each X' is independently O, S, NR'$_1$, CR'$_1$R'$_2$, or SiR'$_1$R'$_2$, wherein R'$_1$ and R'$_2$ are each independently hydrogen, substituted or unsubstituted C$_{1-60}$ alkyl, or substituted or unsubstituted C$_{6-60}$ aryl, each R' is independently hydrogen, cyano, methyl, trifluoromethyl, trimethylsilyl, triphenylsilyl, phenyl, biphenylyl, dibenzofuranyl, dibenzothiophenyl, or carbazolyl.

Preferably, L$_{13}$ is any one selected from the group consisting of:

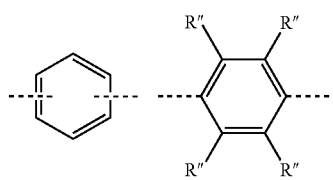

-continued

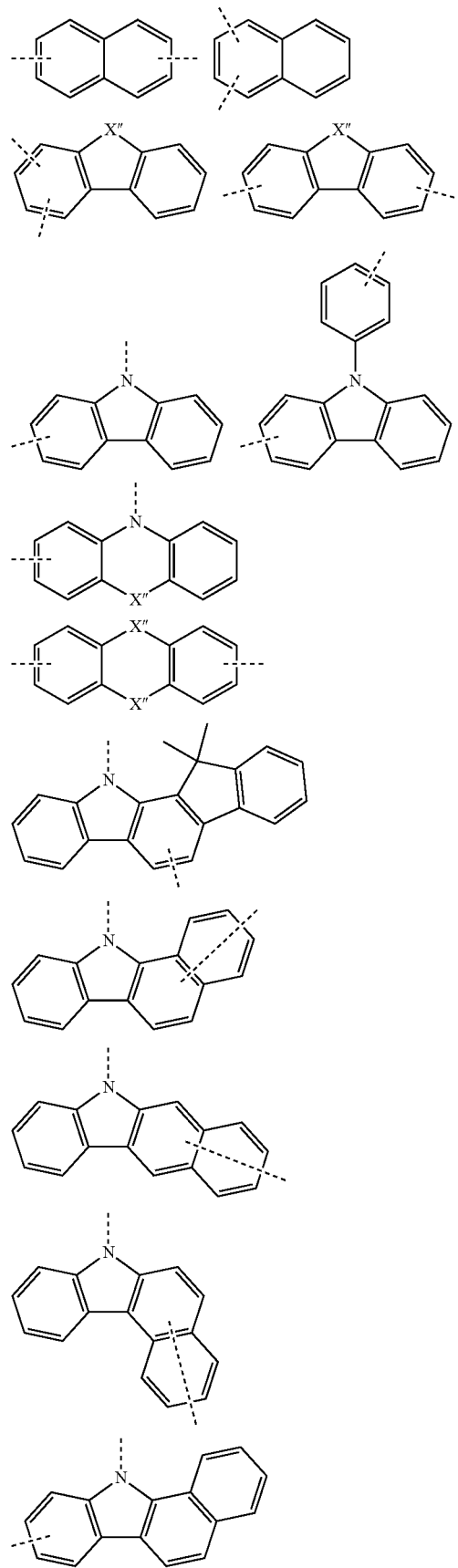

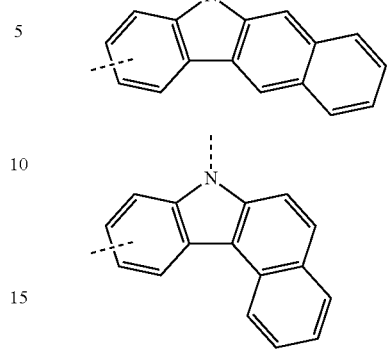

in the above formulas, each X" is independently O, S, NR"$_1$, CR"$_1$R"$_2$, or SiR"$_1$R"$_2$, wherein R"$_1$ and R"$_2$ are each independently hydrogen, substituted or unsubstituted C$_{1-60}$ alkyl, or substituted or unsubstituted C$_{6-60}$ aryl, and each R" is independently hydrogen, methyl, or phenyl.

The compound represented by the Chemical Formula 1 is any one selected from the group consisting of:

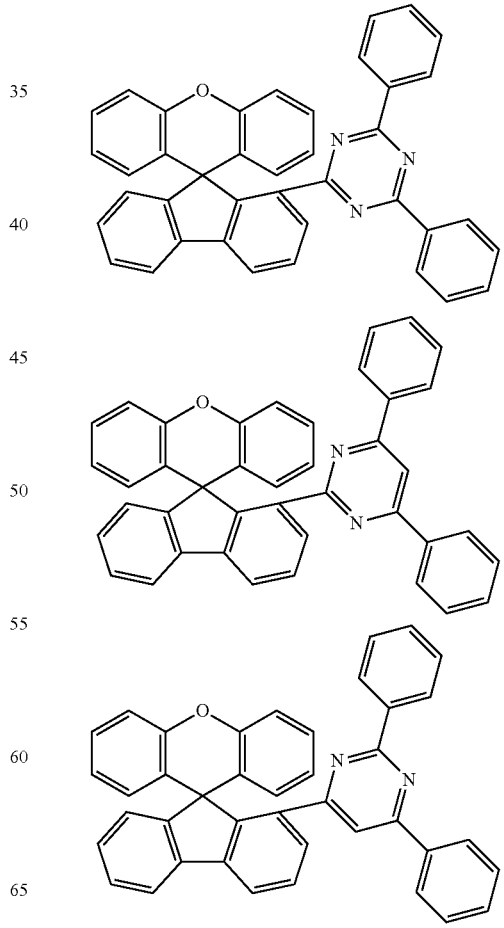

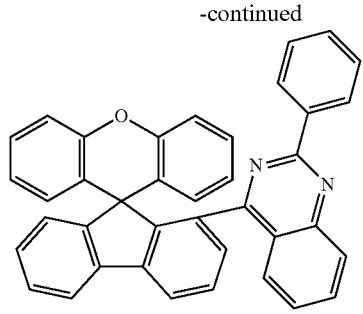
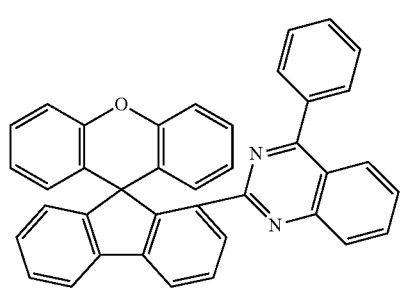
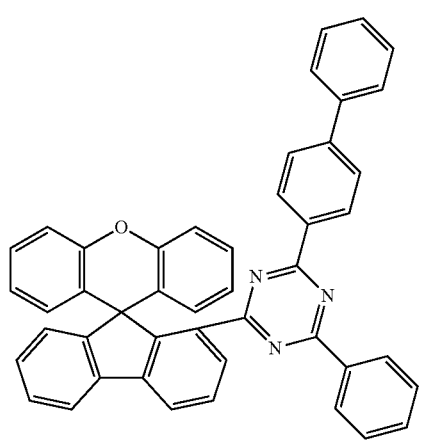
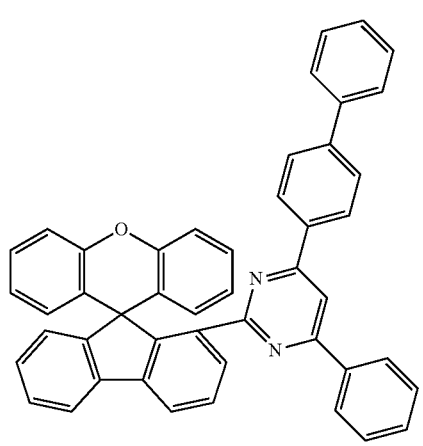
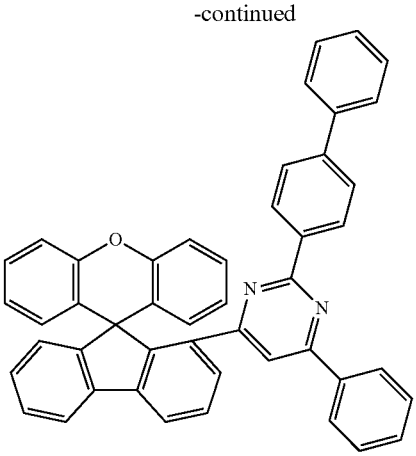
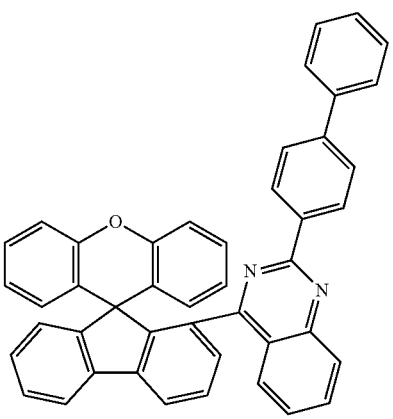
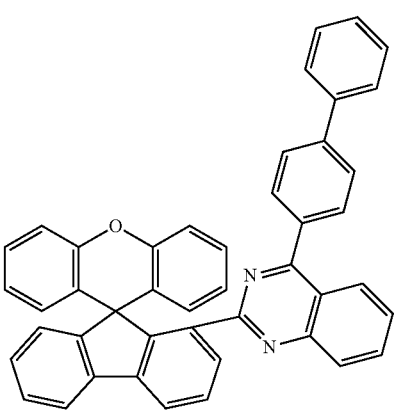
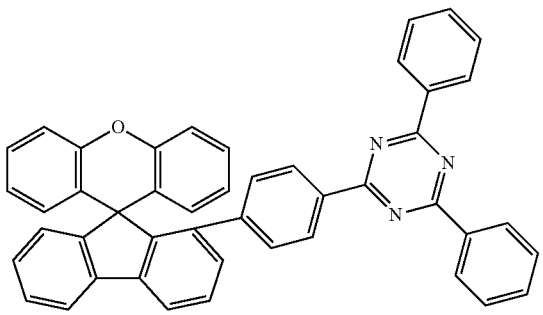

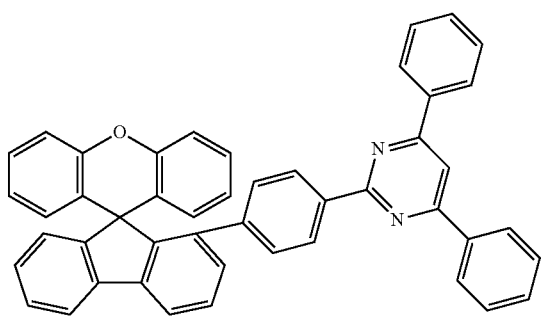
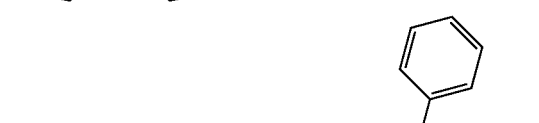
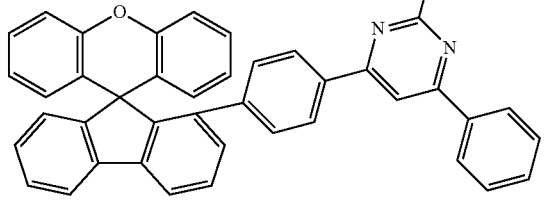
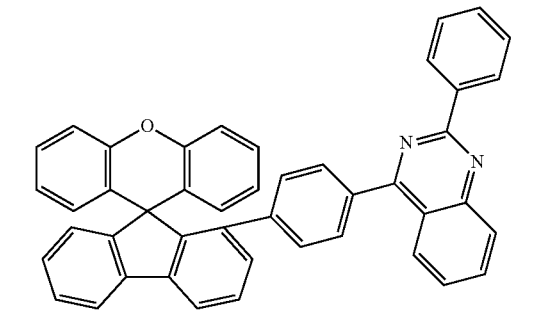
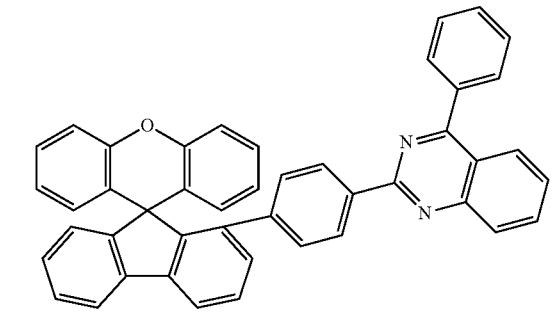
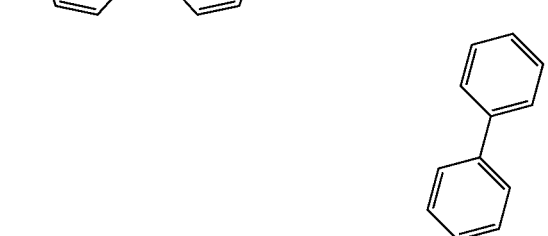
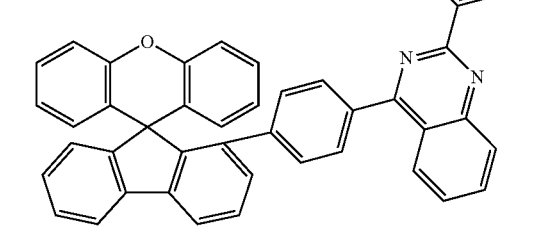
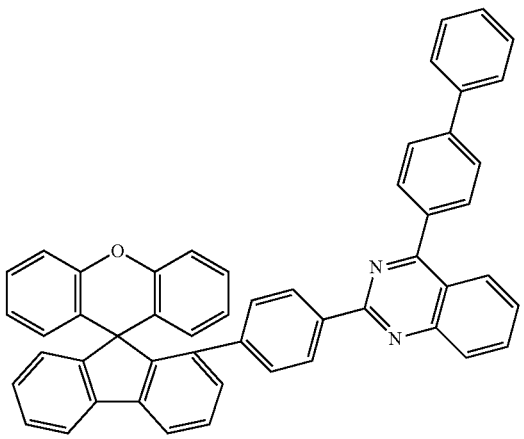
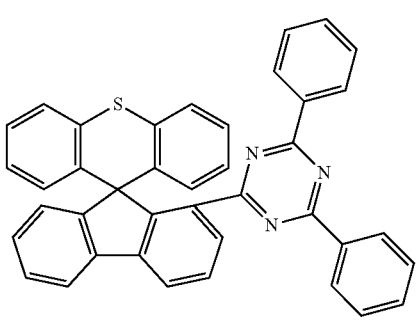
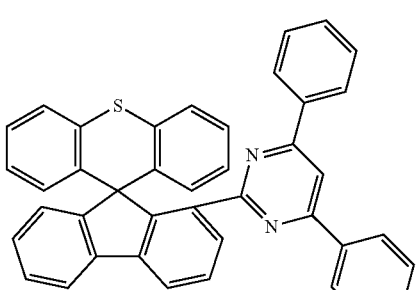
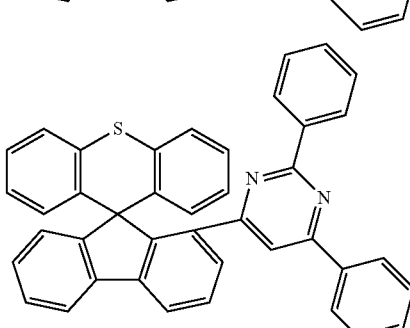
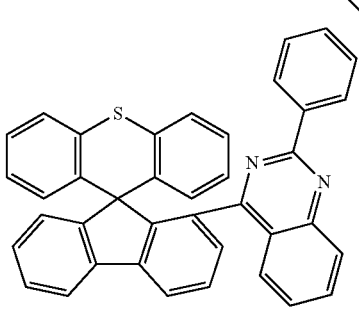

-continued
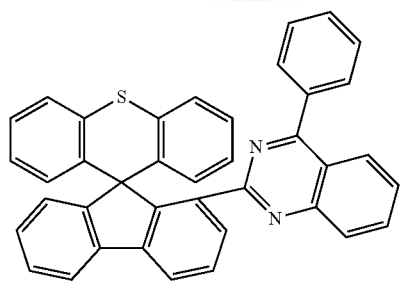
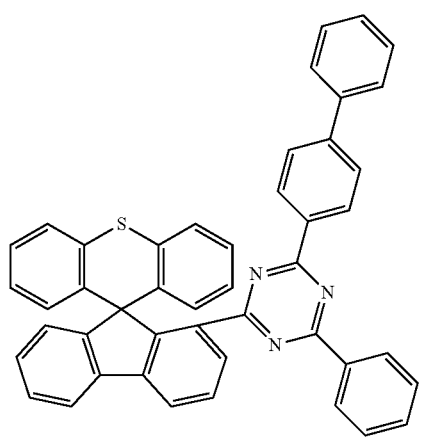
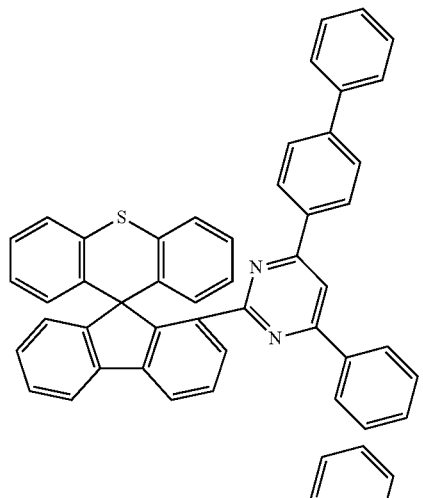
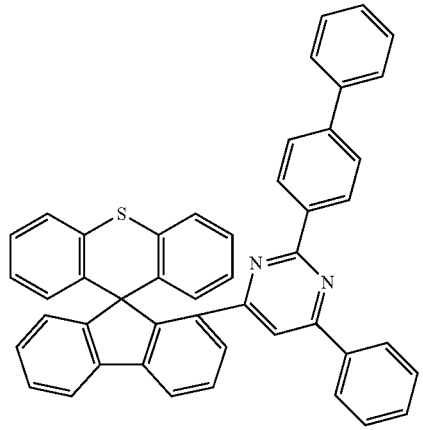
-continued
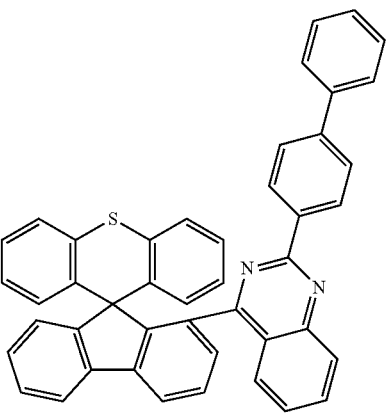
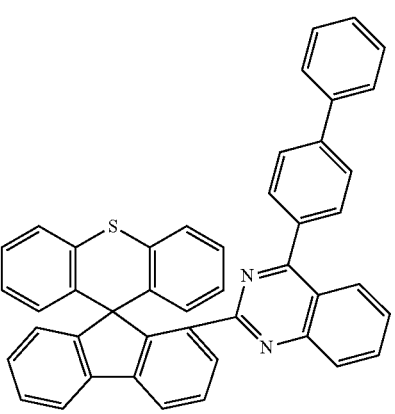
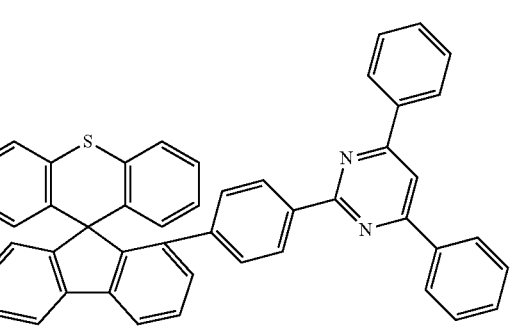
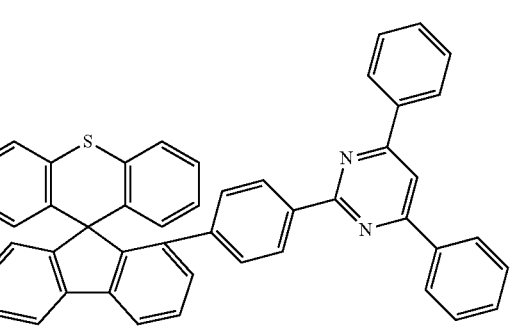

-continued
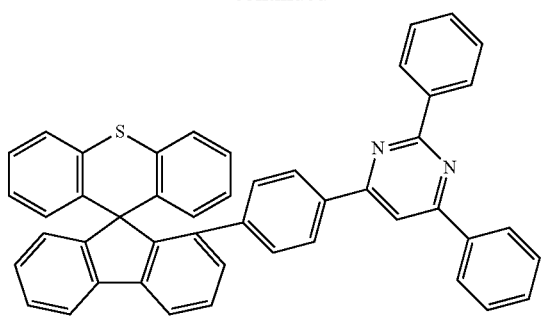
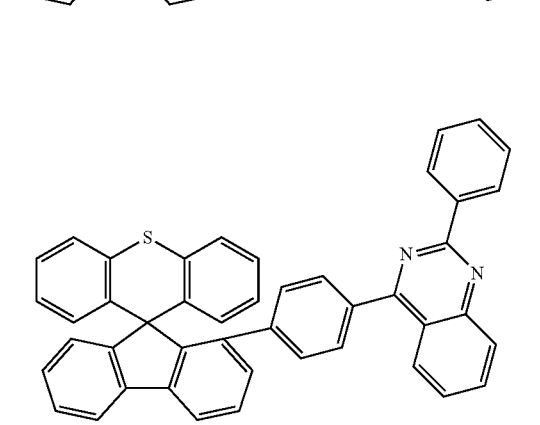
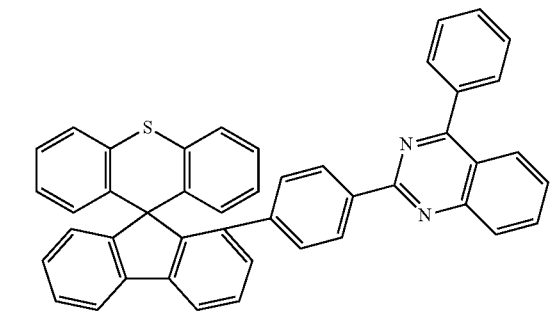
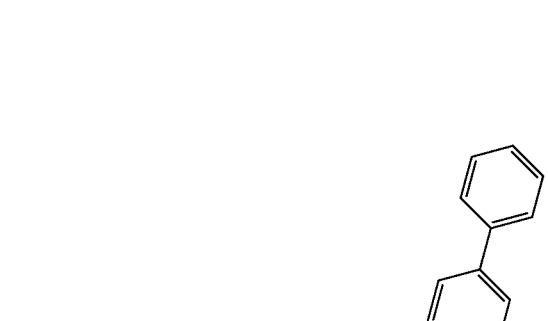
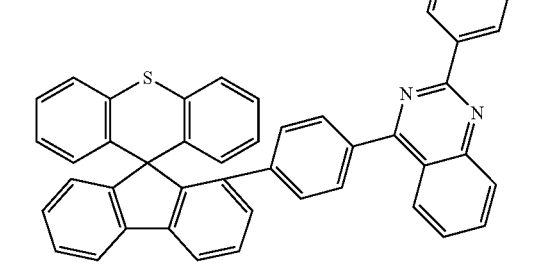
-continued
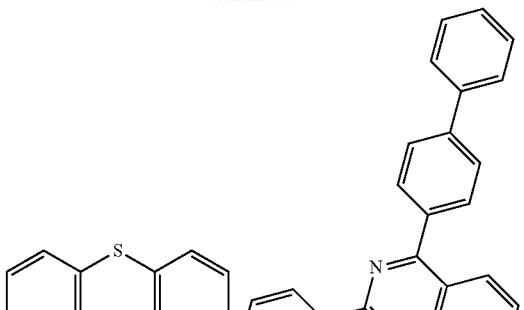
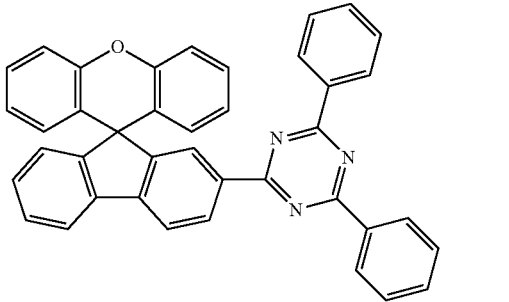
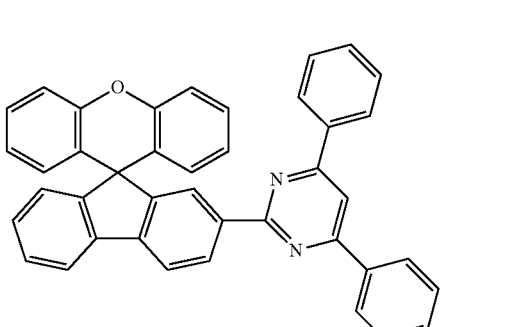
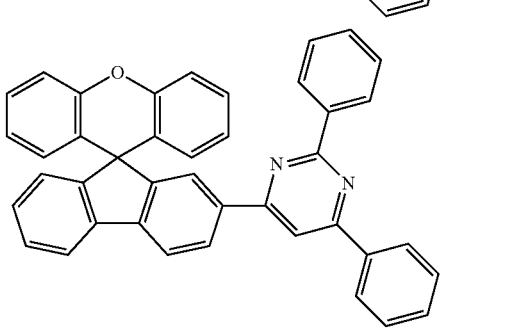
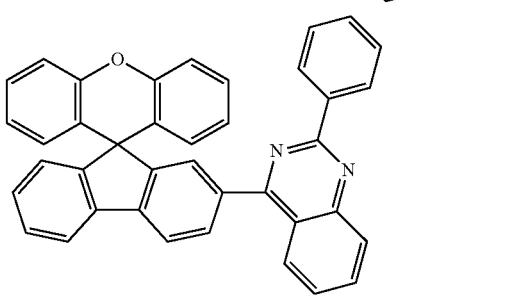

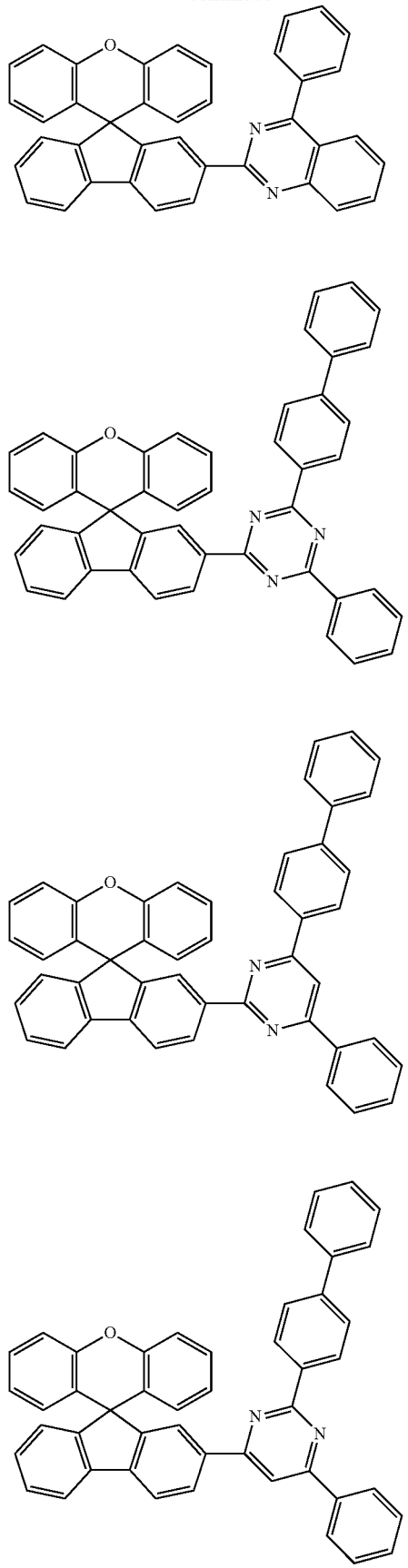
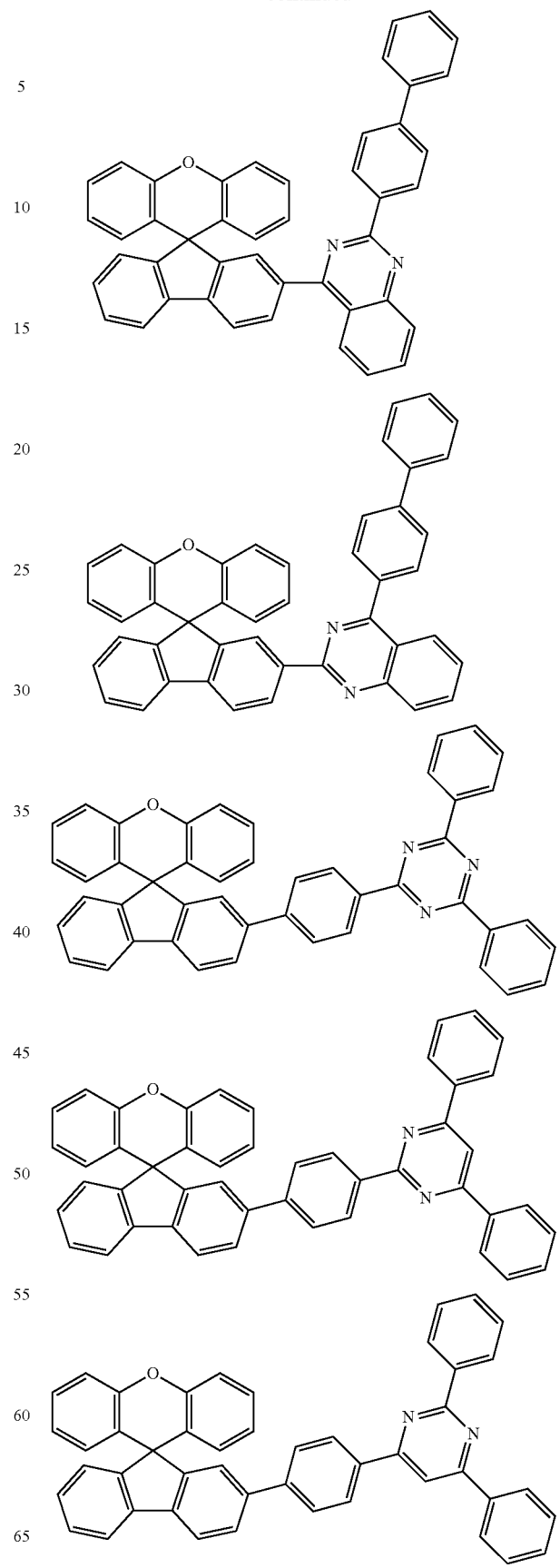

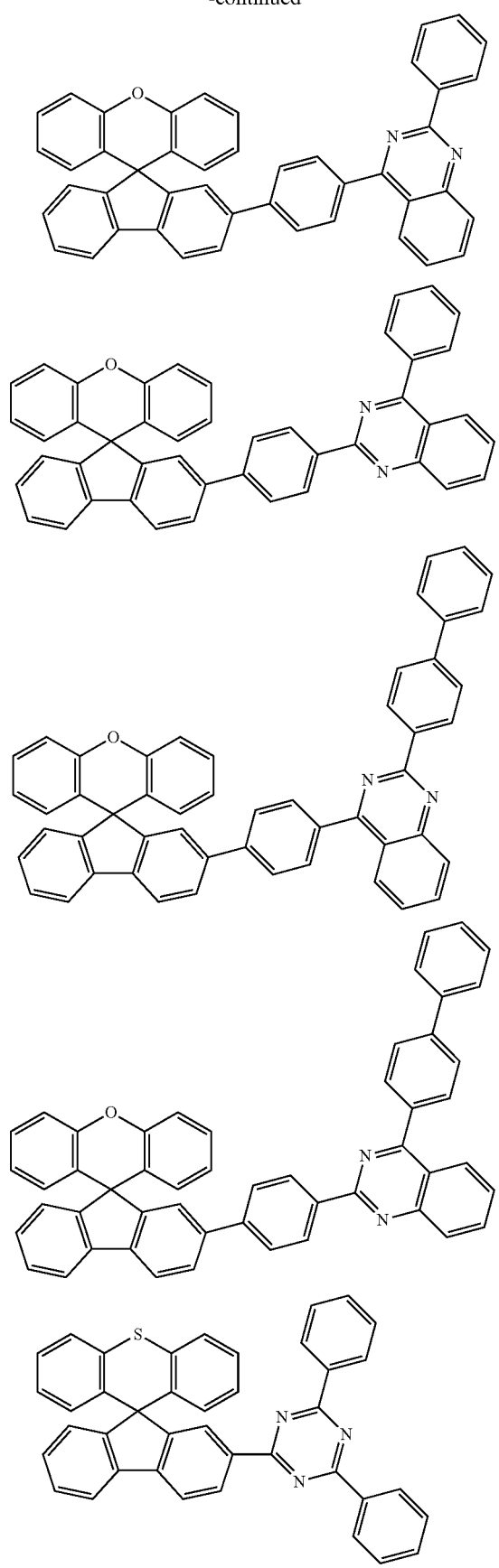

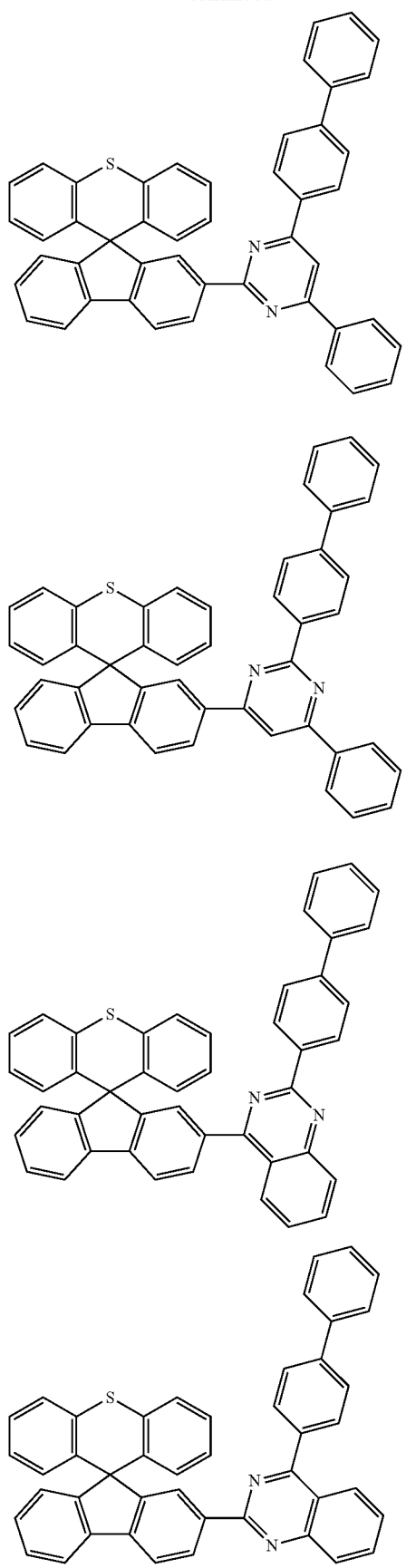
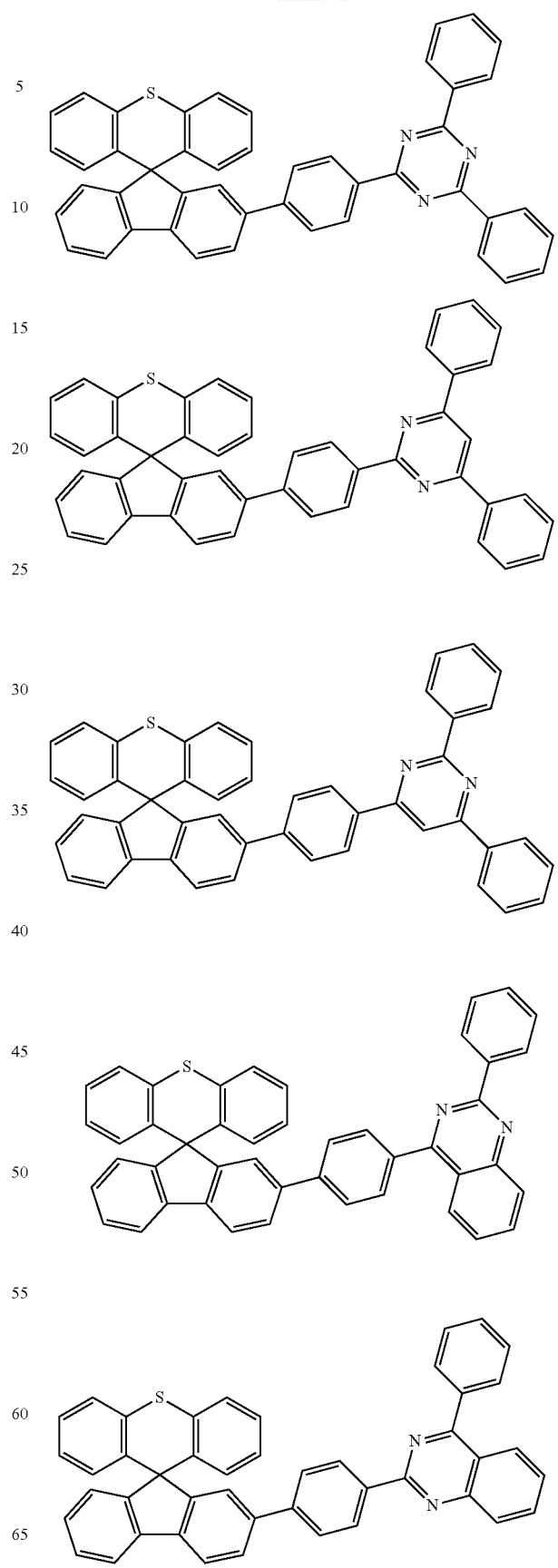

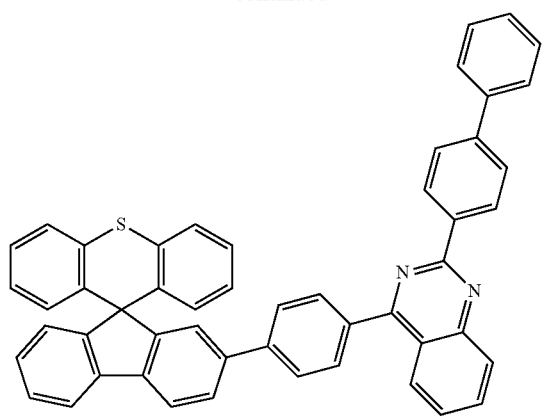
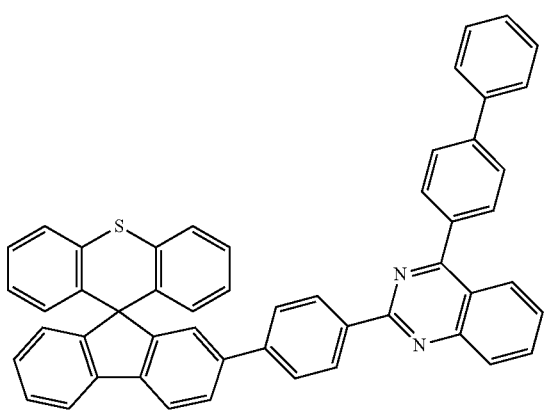
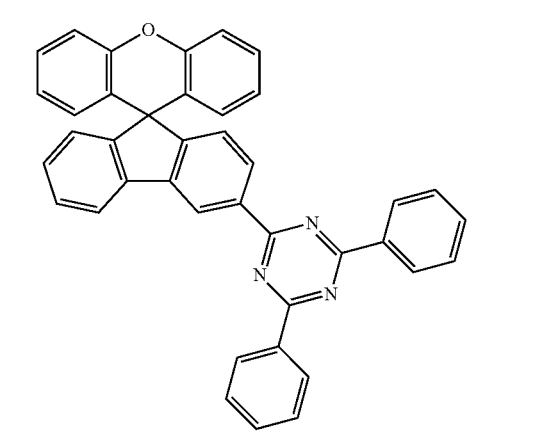
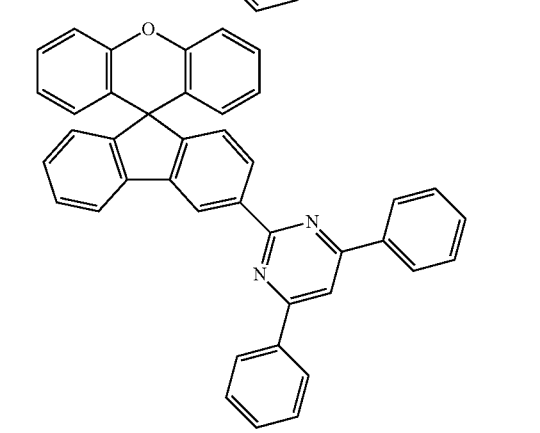
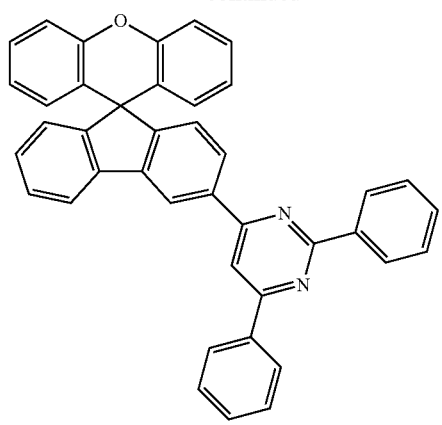
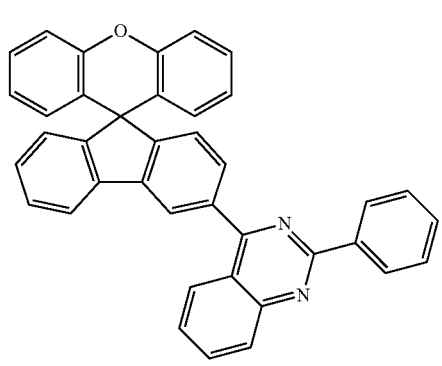
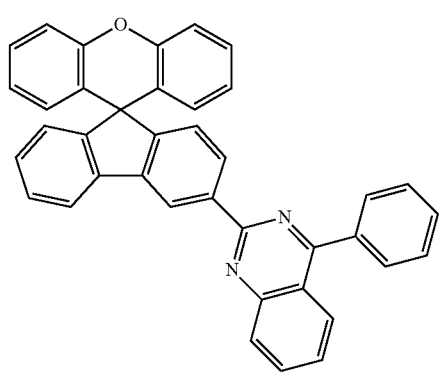
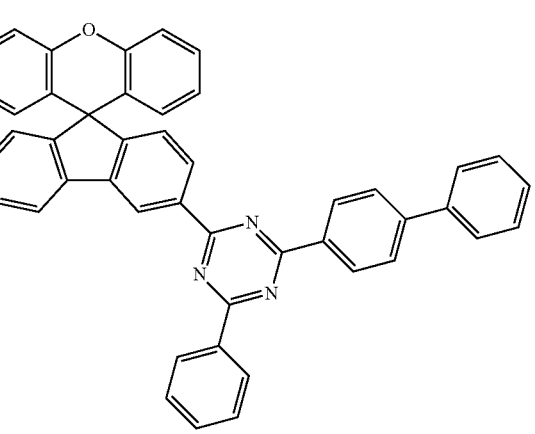

-continued
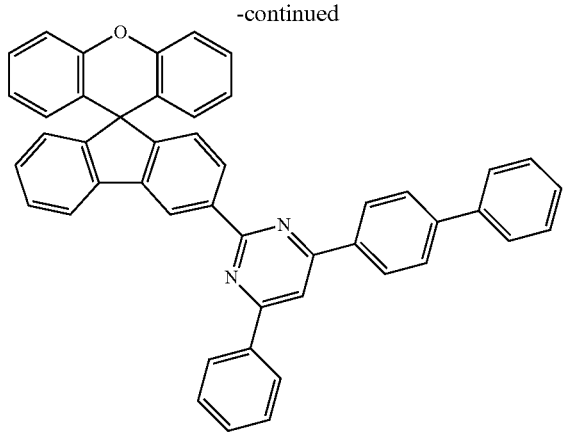
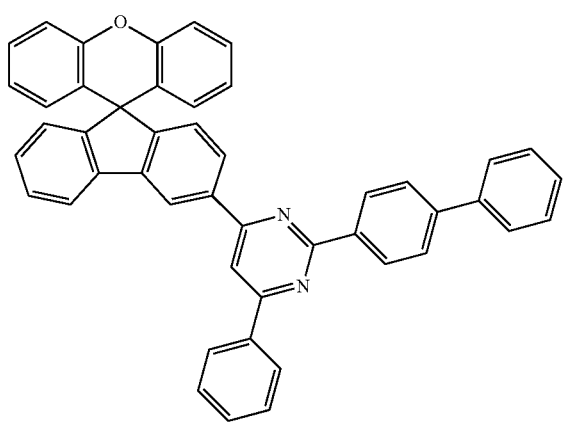
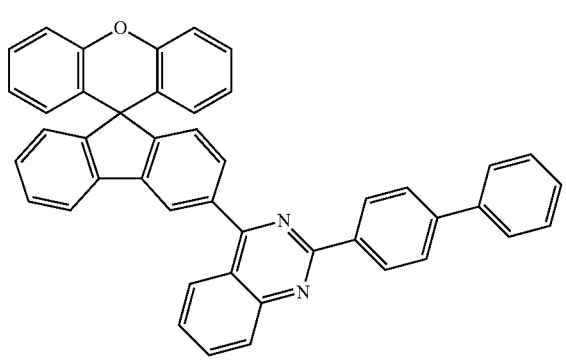
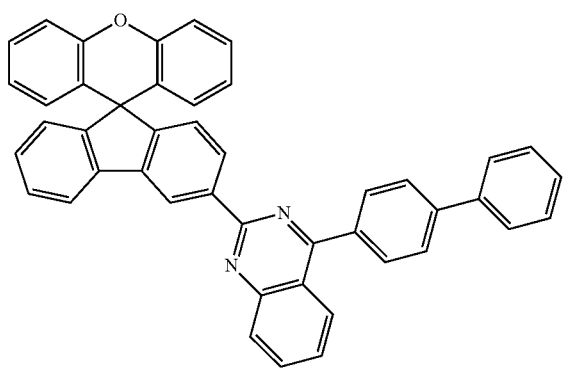
-continued
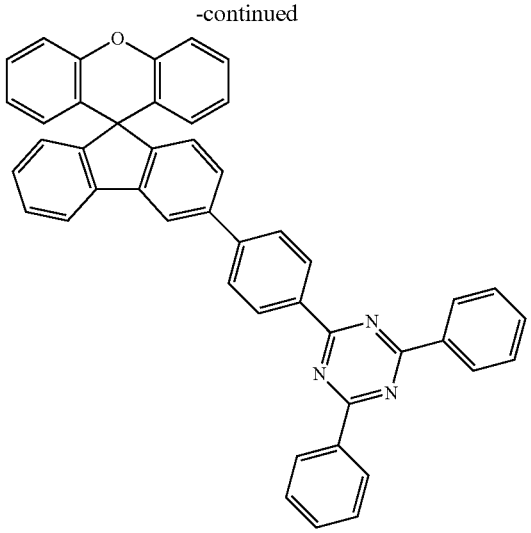
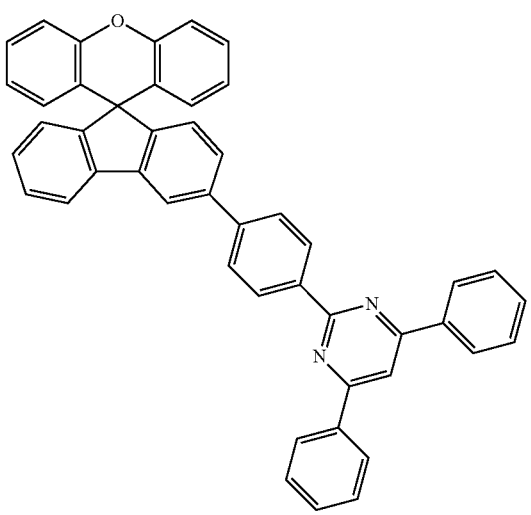

-continued
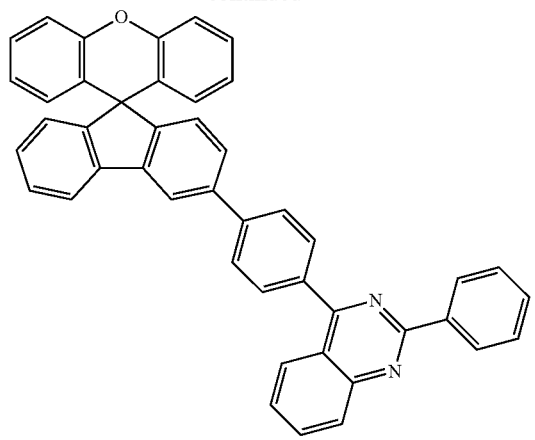
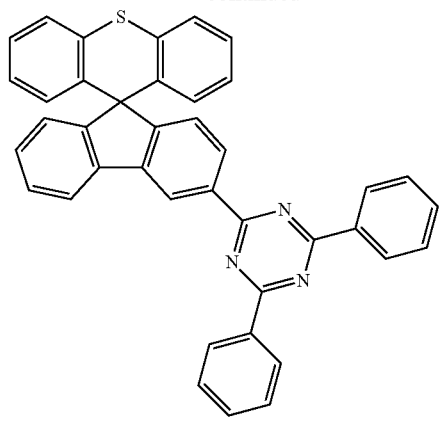
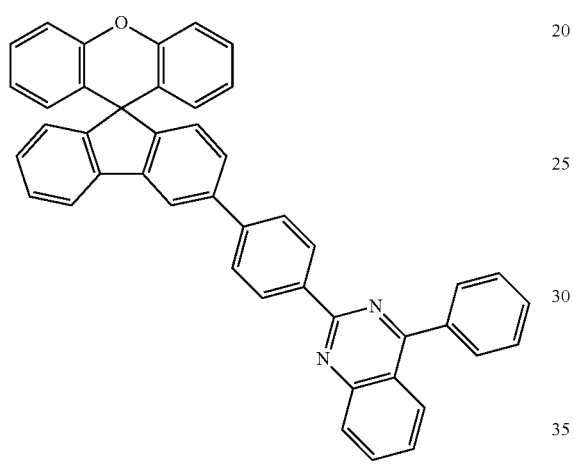
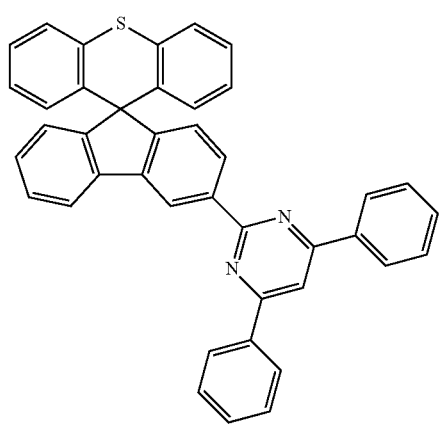
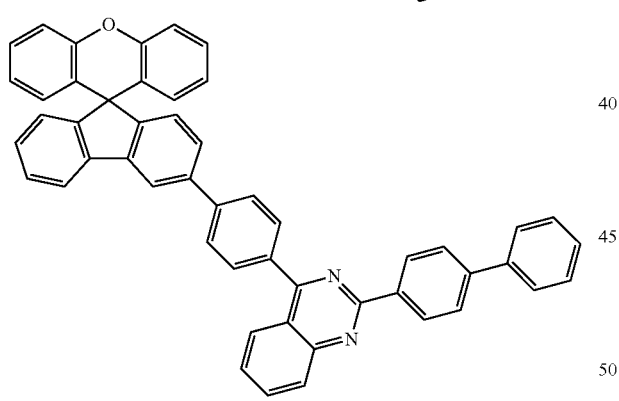
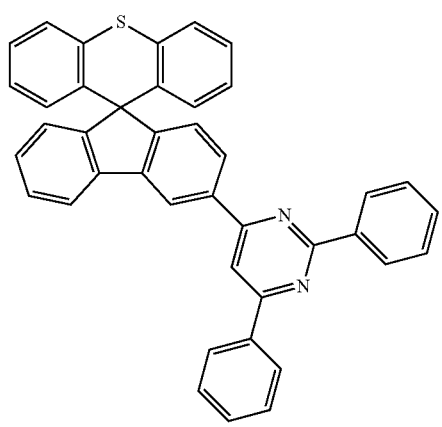
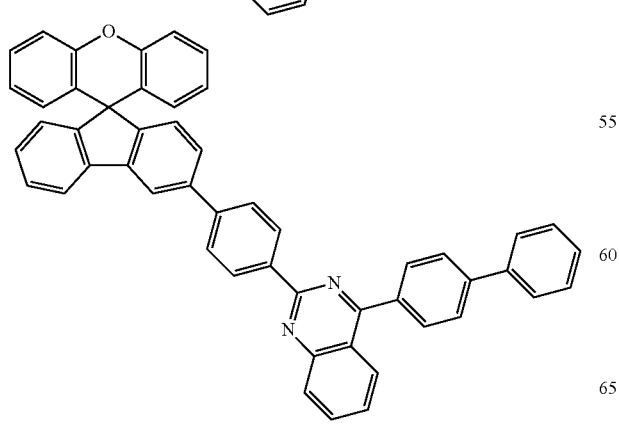
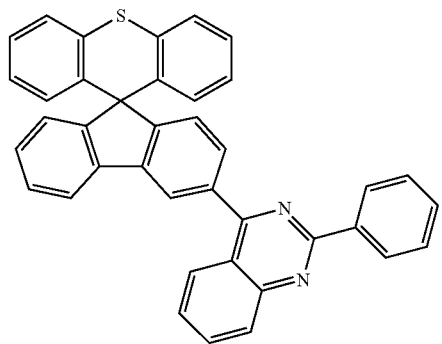

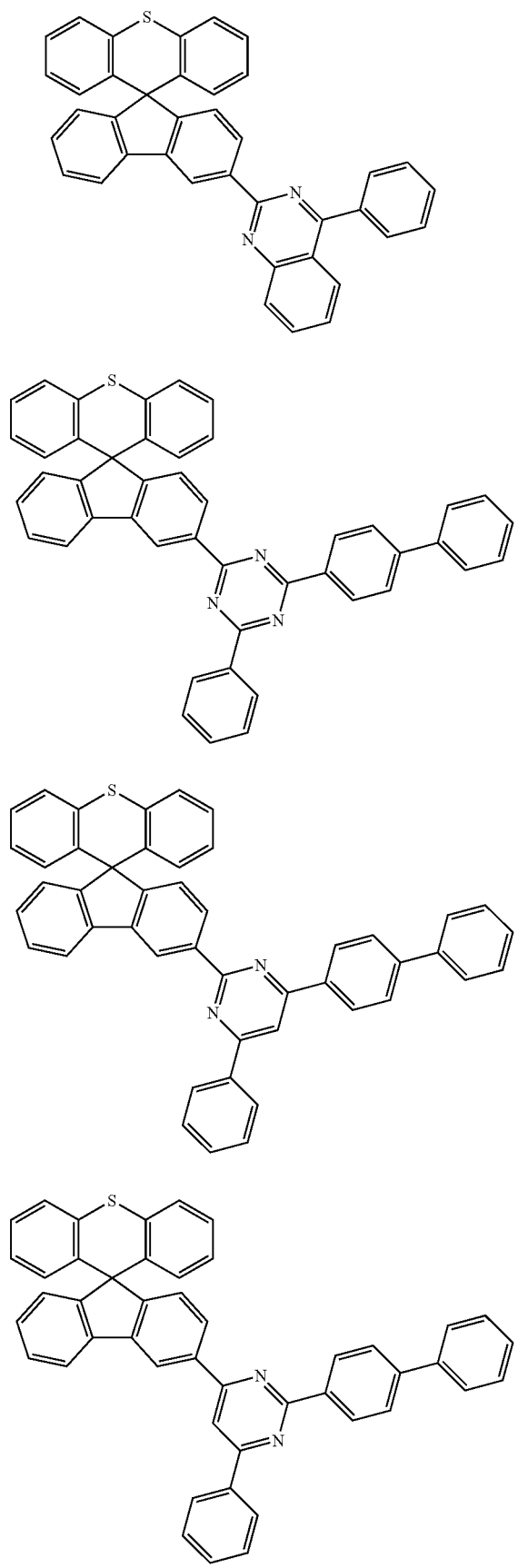 [SMILES: c1ccc(-c2nc(-c3ccc4c(c3)-c3ccccc3C43c4ccccc4Oc4ccccc43)nc3ccccc23)cc1 ; c1ccc(-c2ccc(-c3nc(-c4ccccc4)nc(-c4ccc5c(c4)-c4ccccc4C54c5ccccc5Oc5ccccc54)n3)cc2)cc1 ; c1ccc(-c2ccc(-c3cc(-c4ccccc4)nc(-c4ccc5c(c4)-c4ccccc4C54c5ccccc5Oc5ccccc54)n3)cc2)cc1 ; c1ccc(-c2ccc(-c3nc(-c4ccccc4)cc(-c4ccc5c(c4)-c4ccccc4C54c5ccccc5Oc5ccccc54)n3)cc2)cc1]
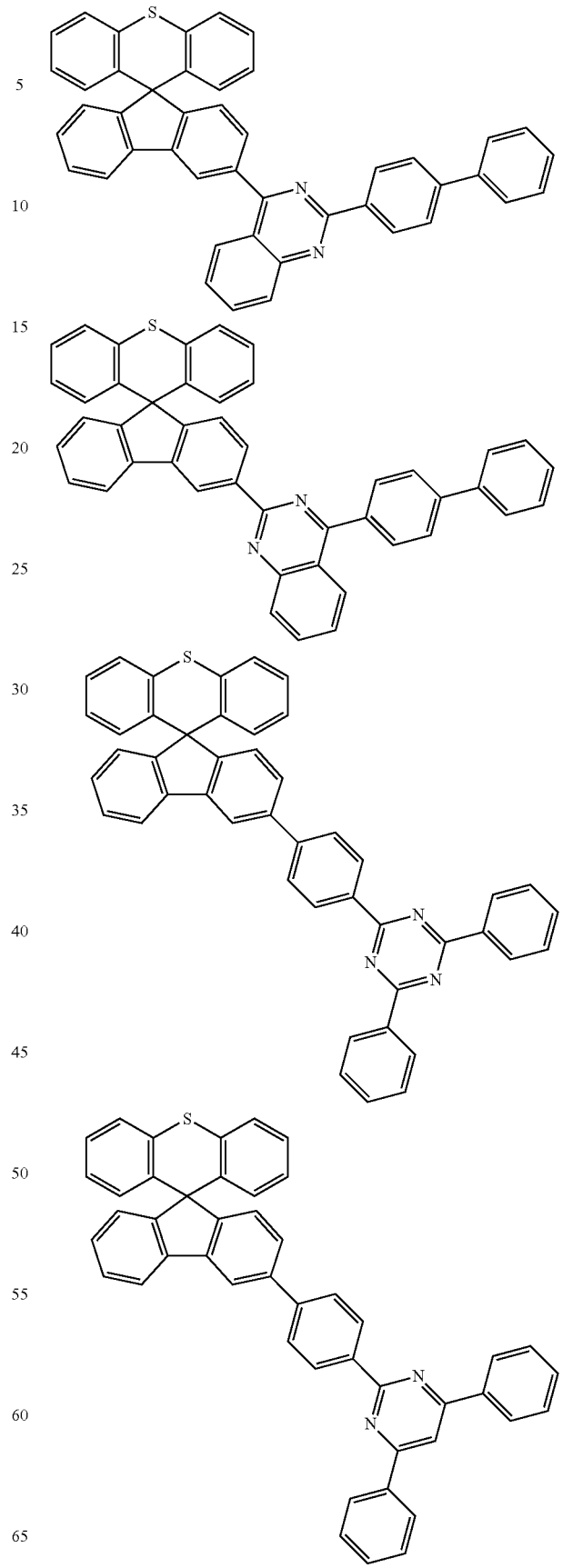

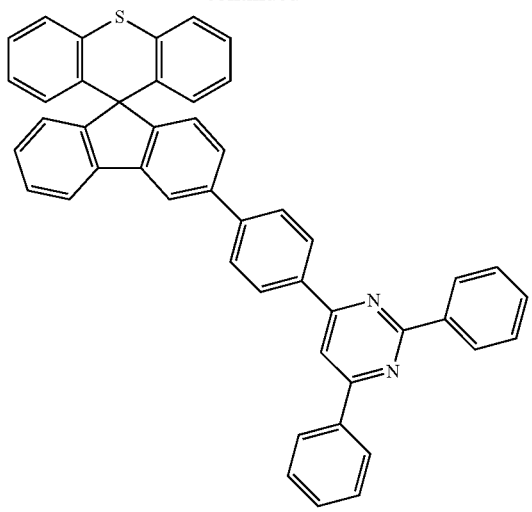
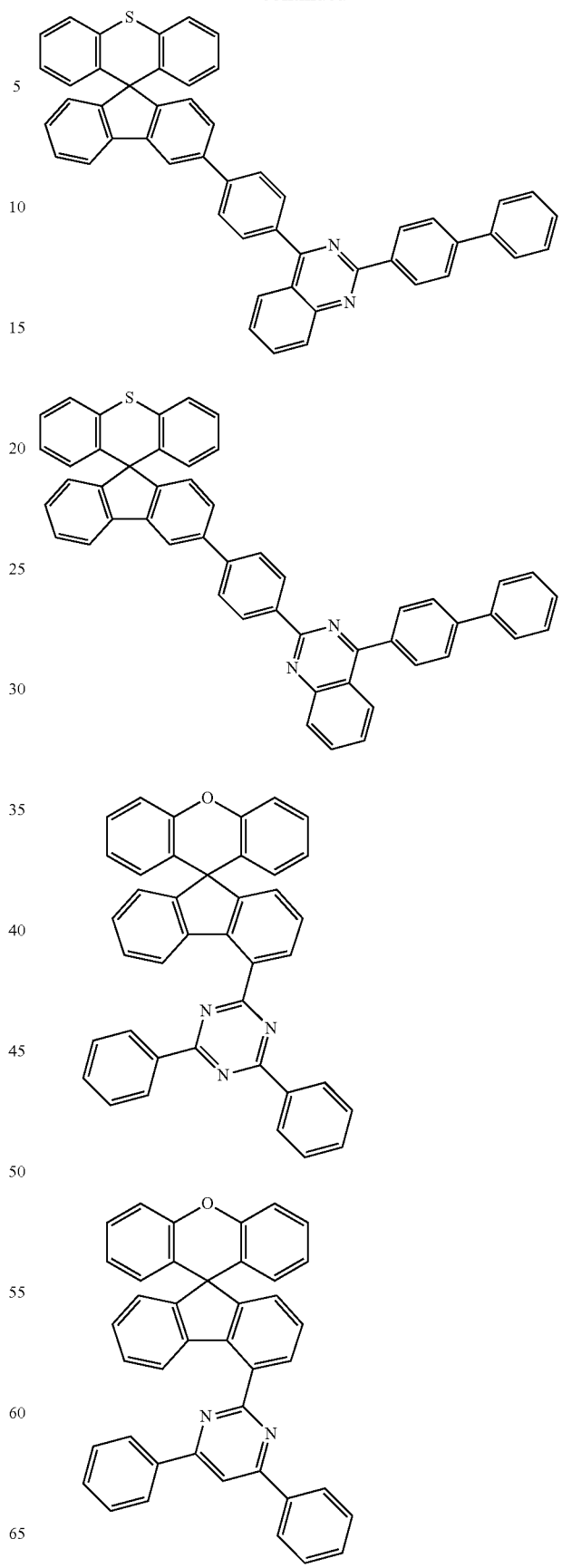

-continued
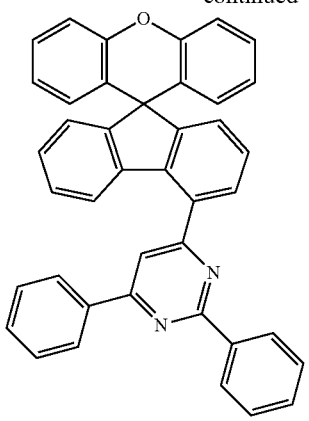
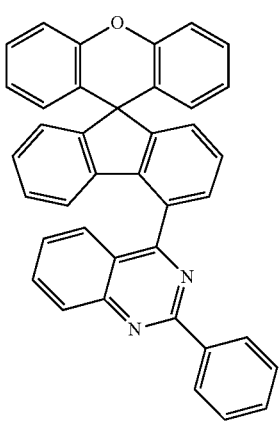
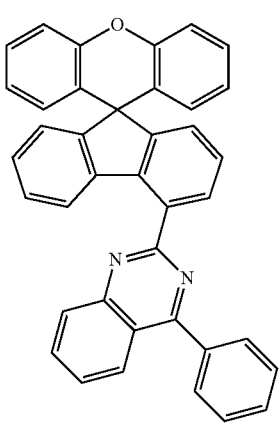
-continued
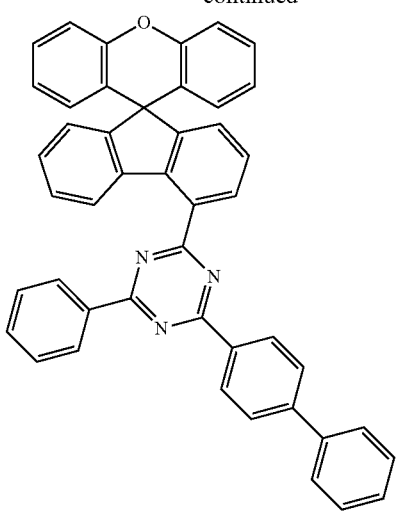
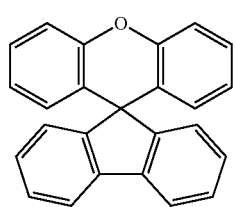
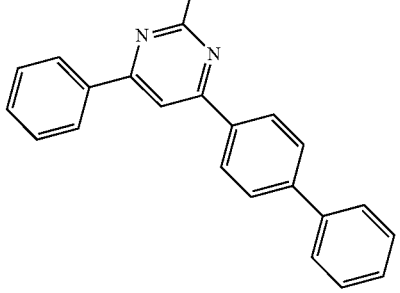
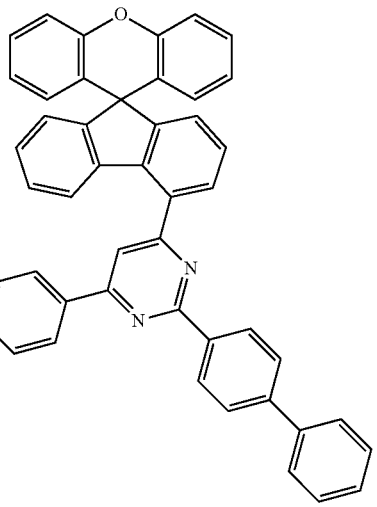

41
-continued
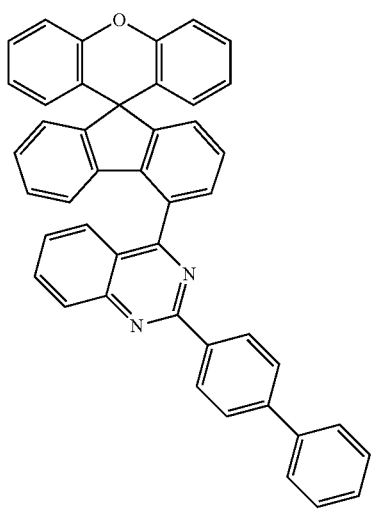
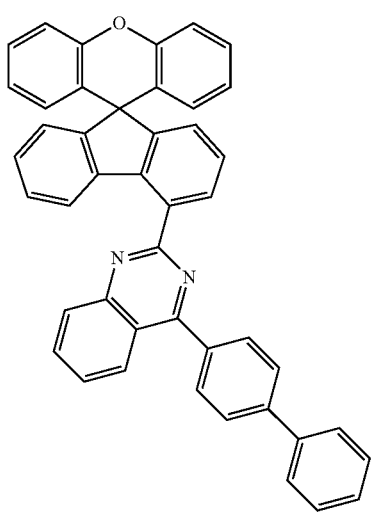
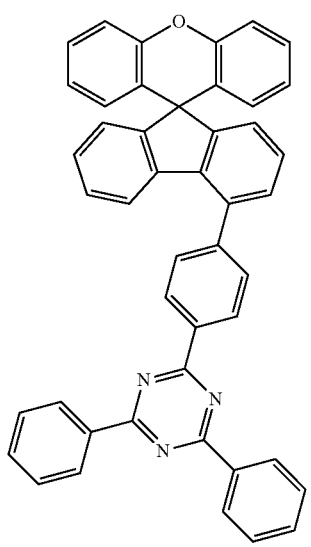
42
-continued
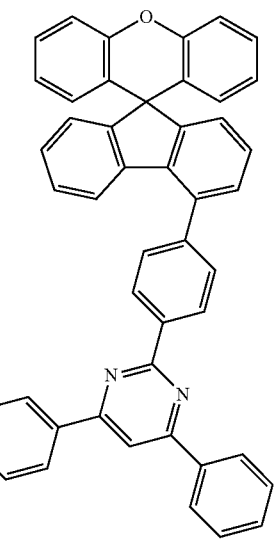
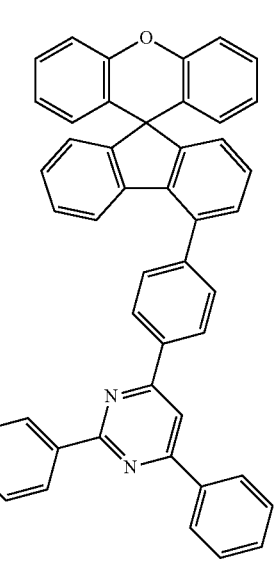
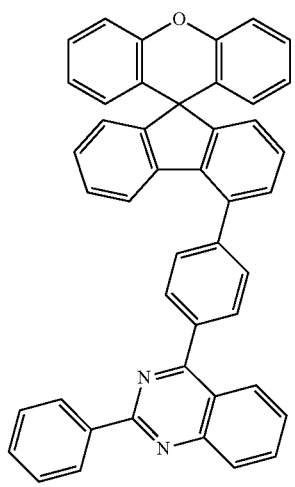

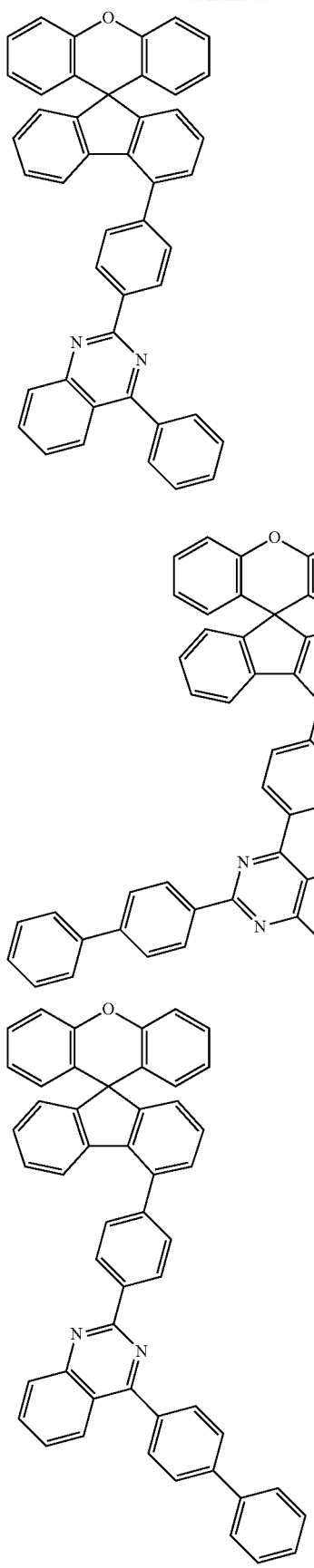
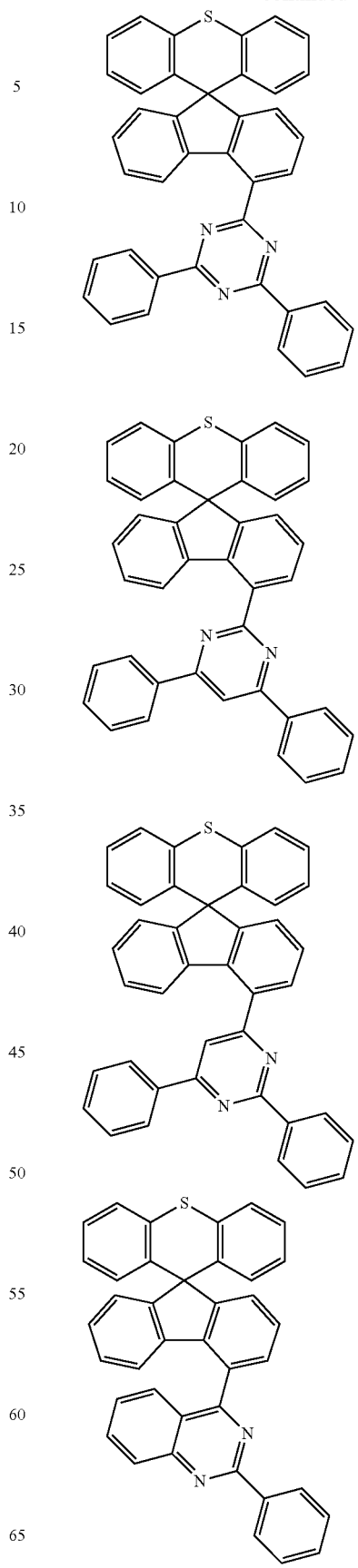

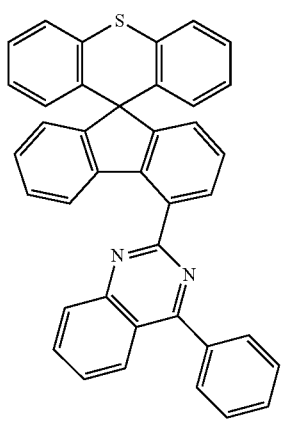
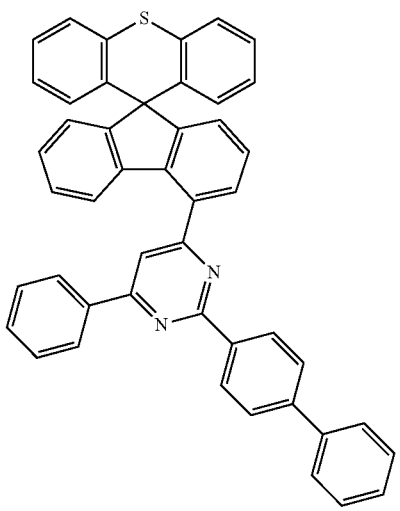
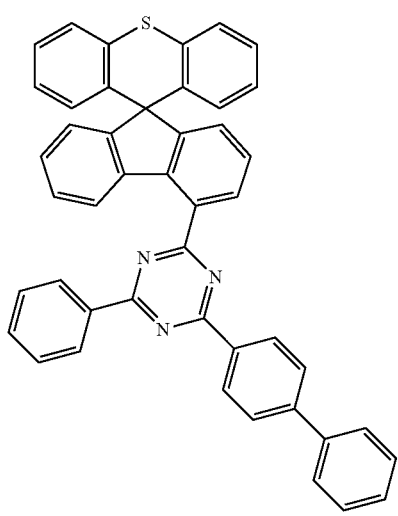
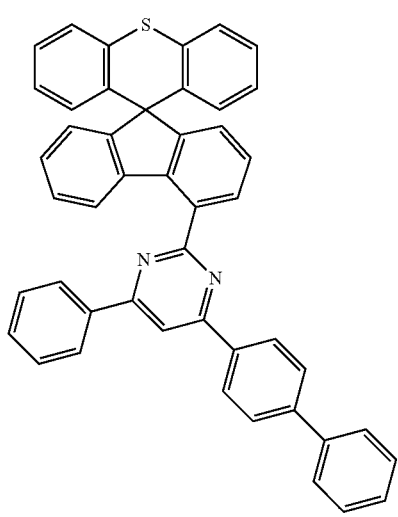
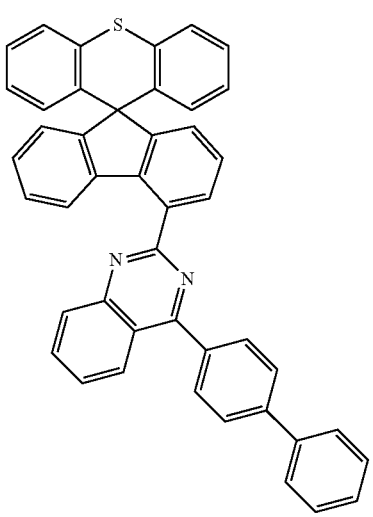

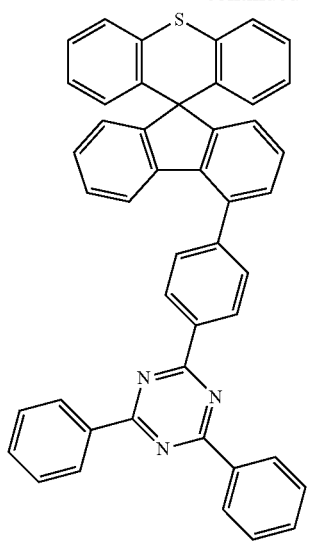
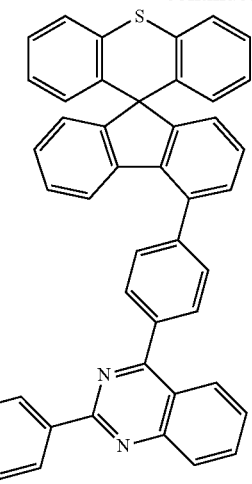
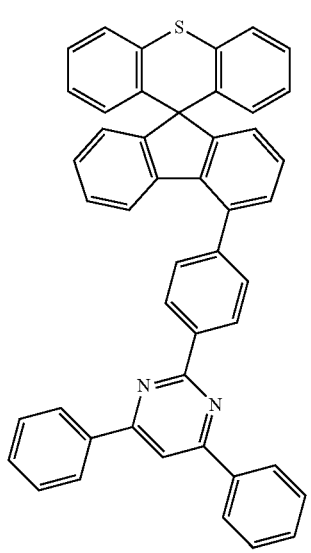
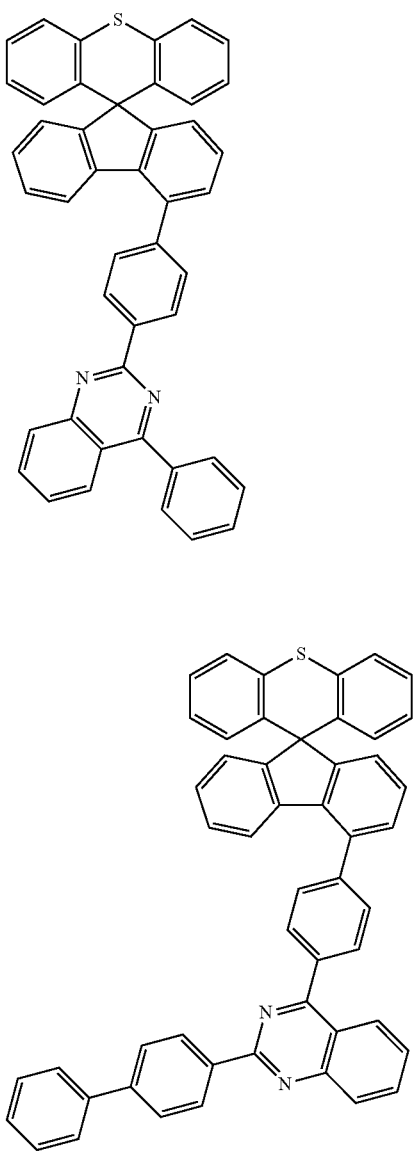
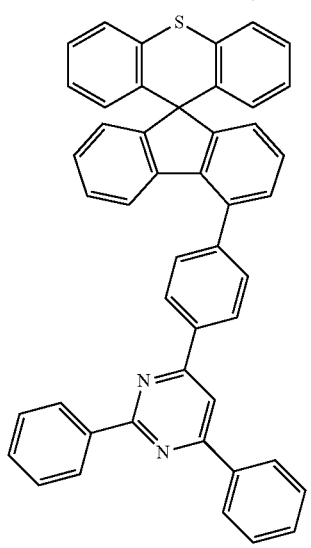

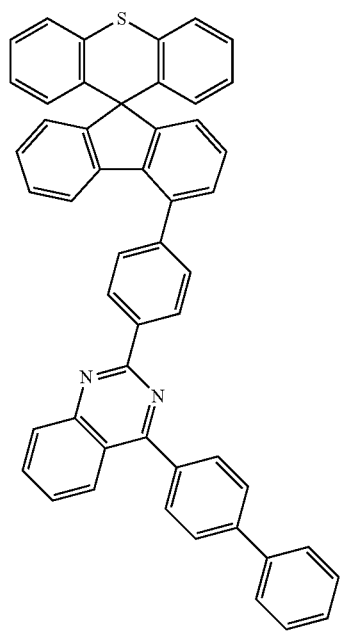 [SMILES: c1ccc(-c2ccc(-c3nc(-c4ccc(-c5cccc6c5-c5ccccc5C65c6ccccc6Oc6ccccc65)cc4)nc4ccccc34)cc2)cc1]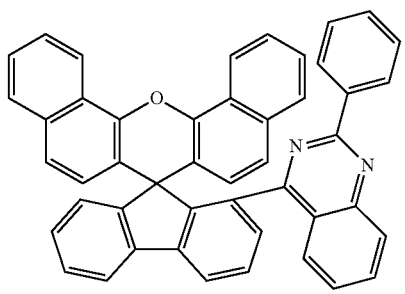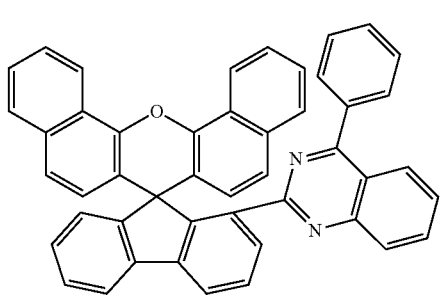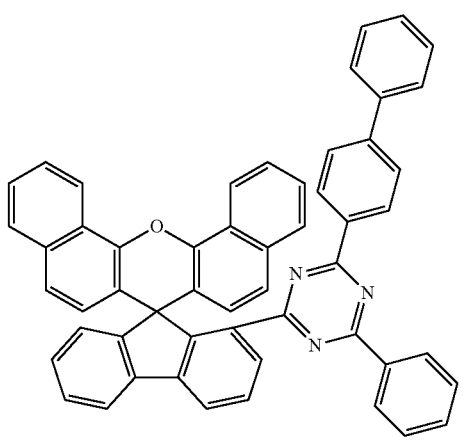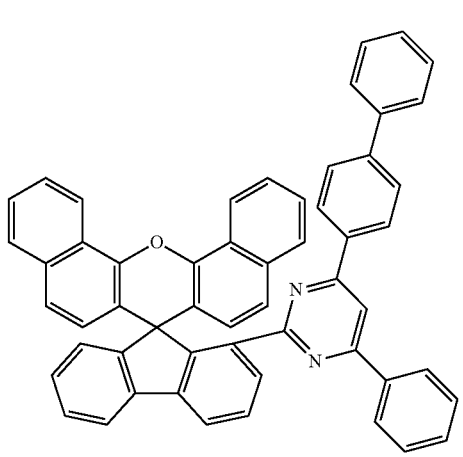

51
-continued
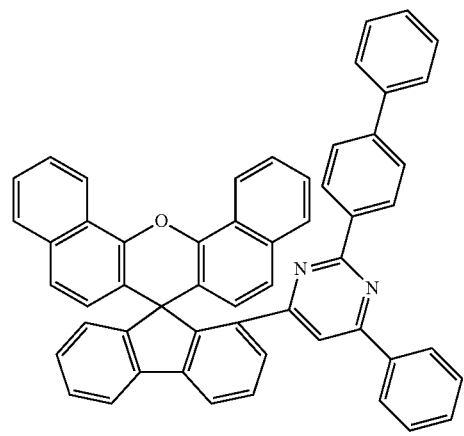
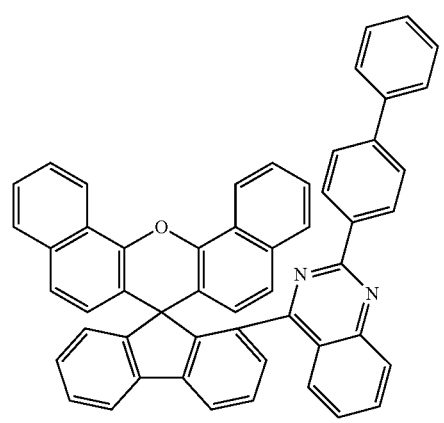
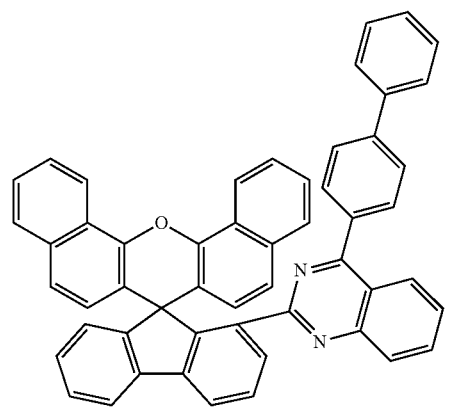
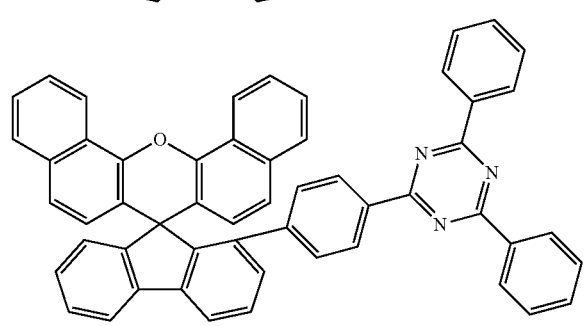
52
-continued
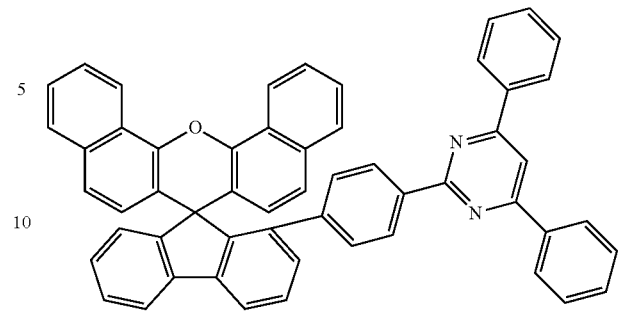
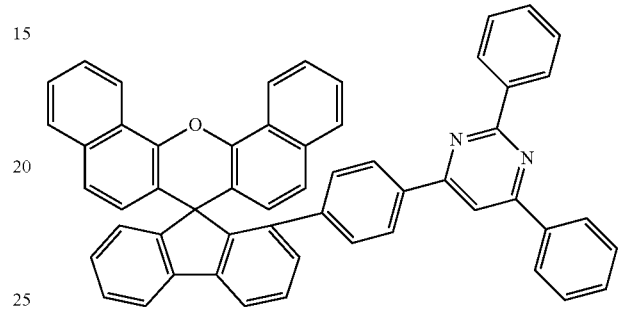
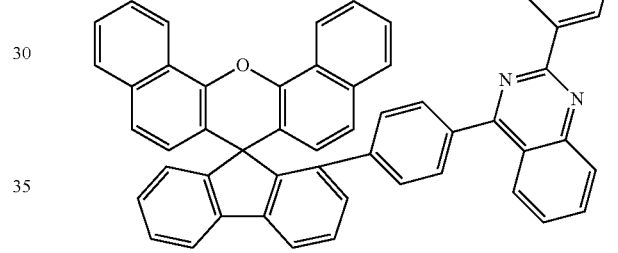
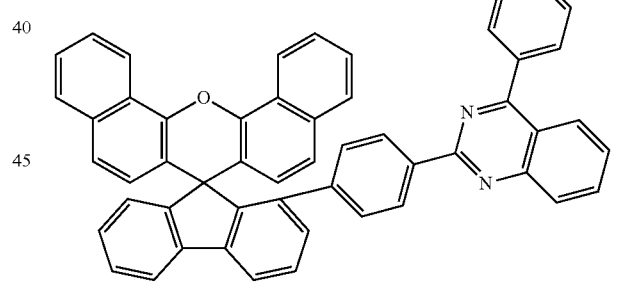
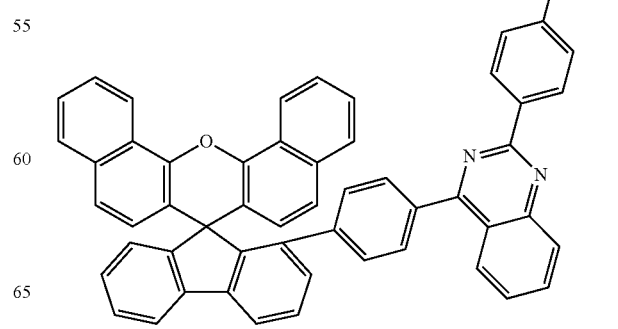

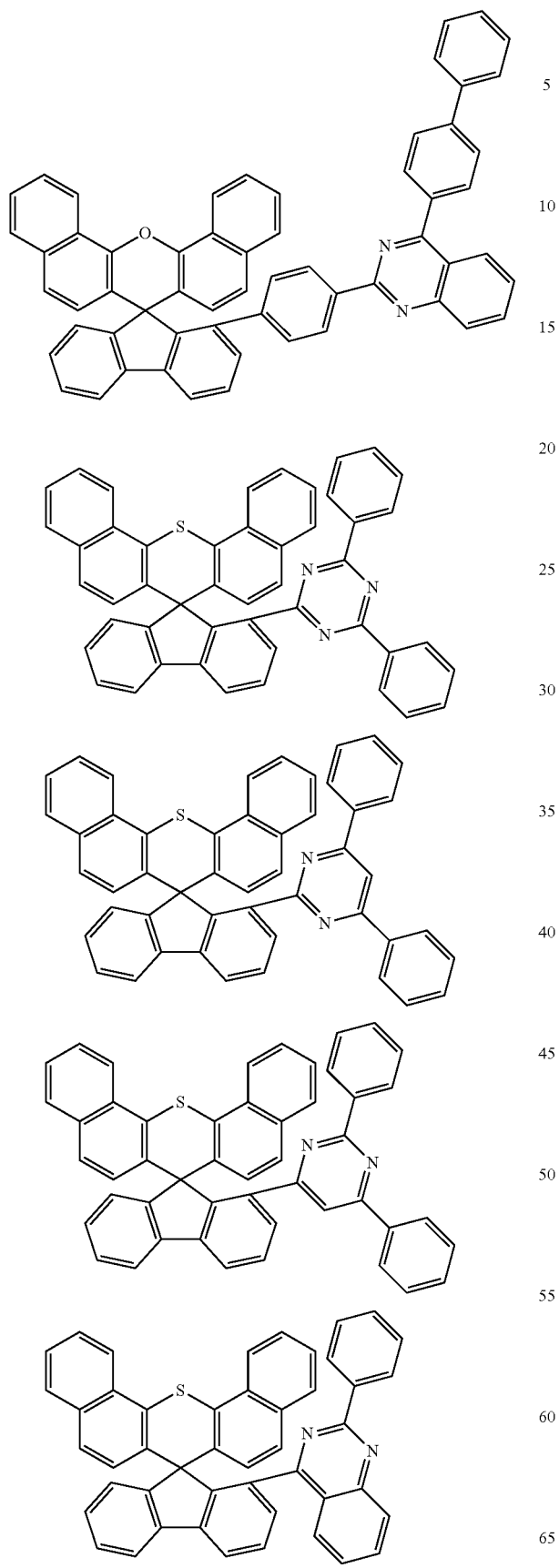
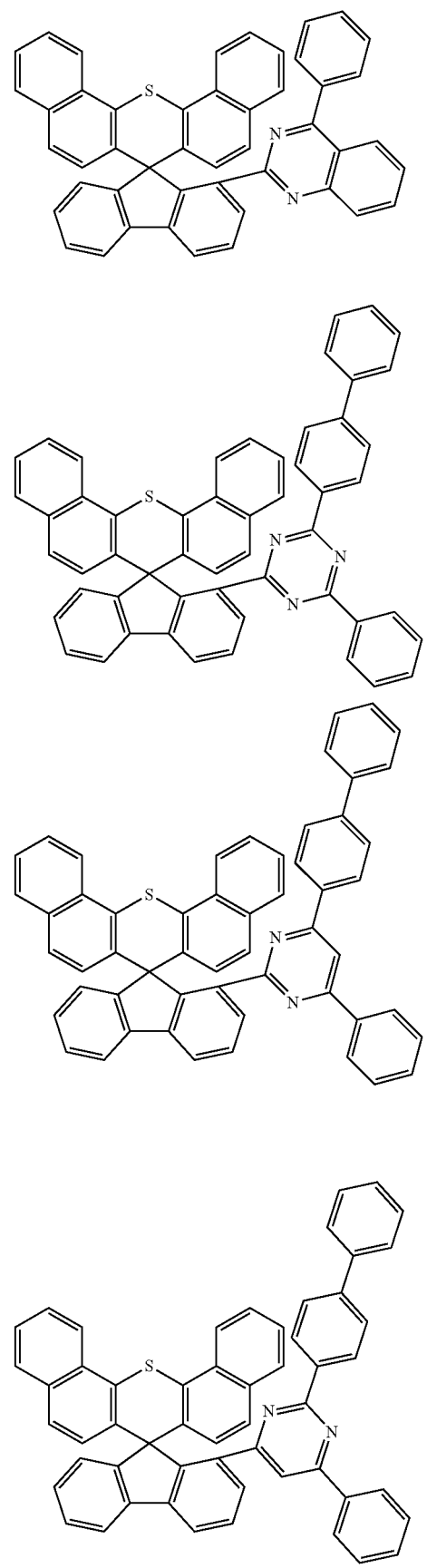

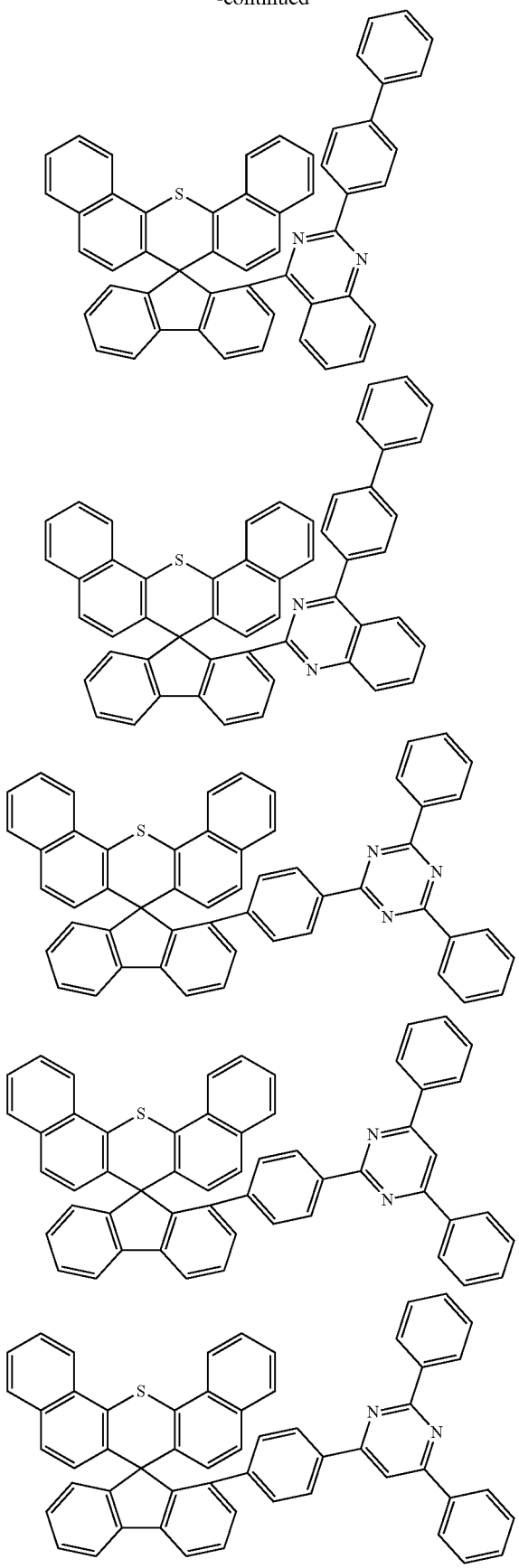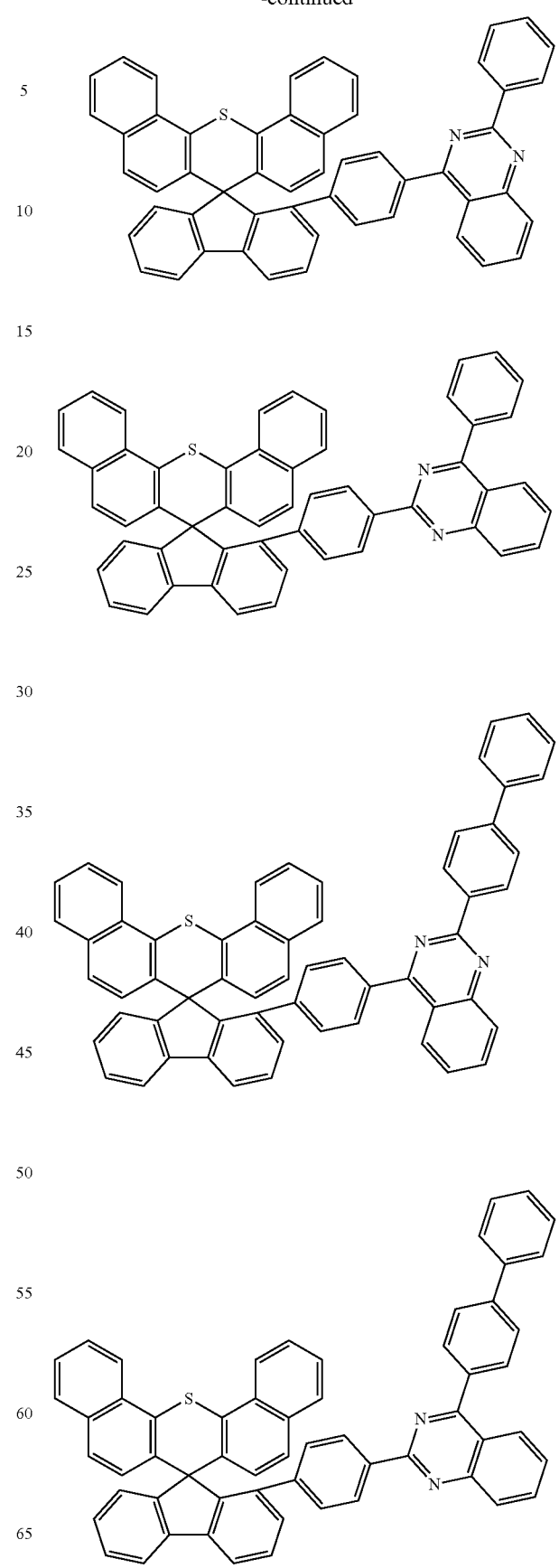

57
-continued
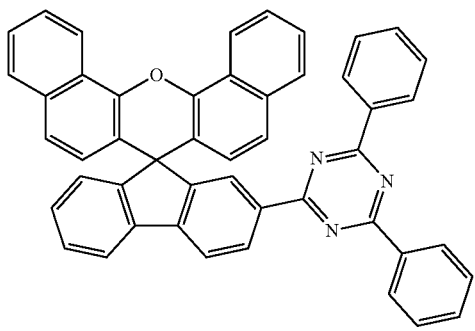
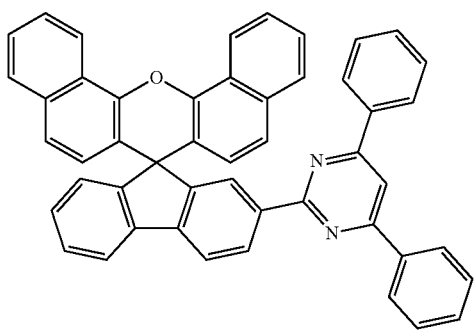
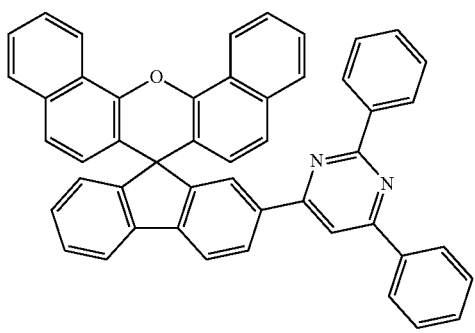
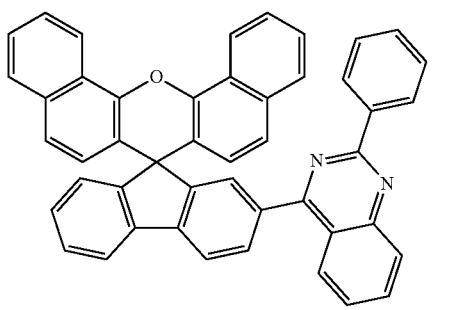
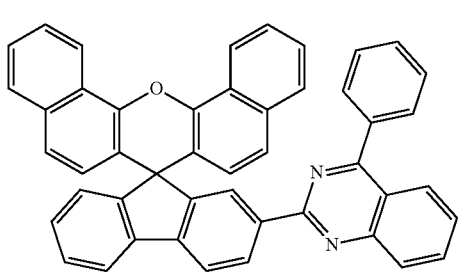
58
-continued
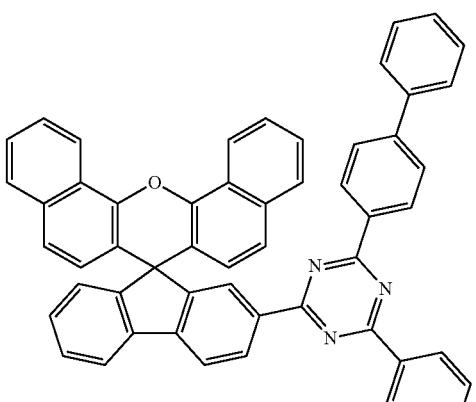
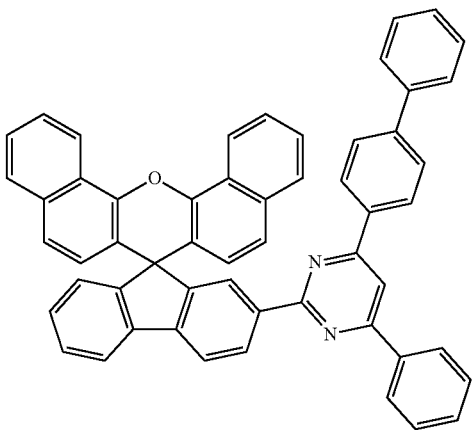
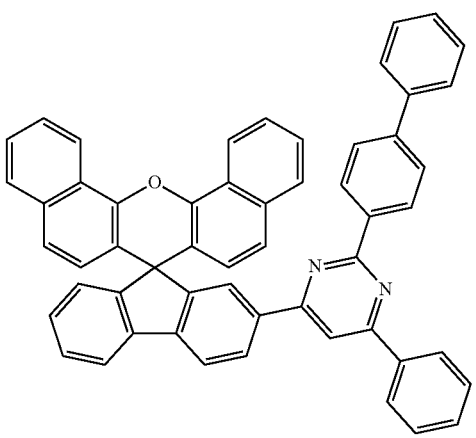
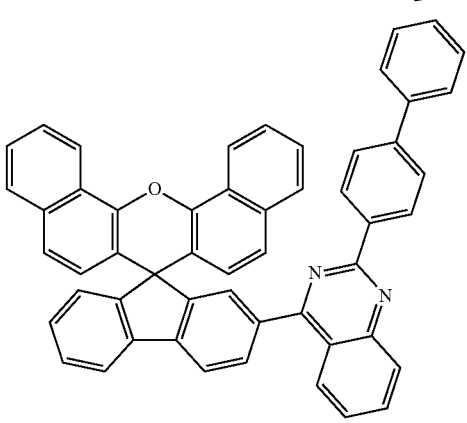

-continued
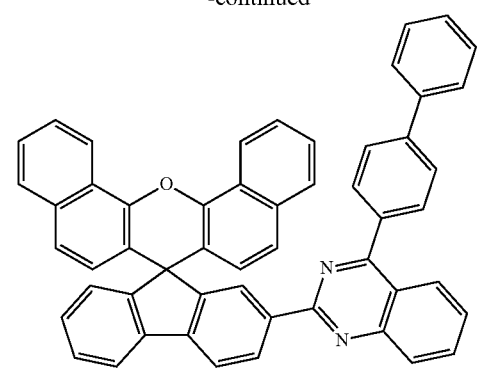
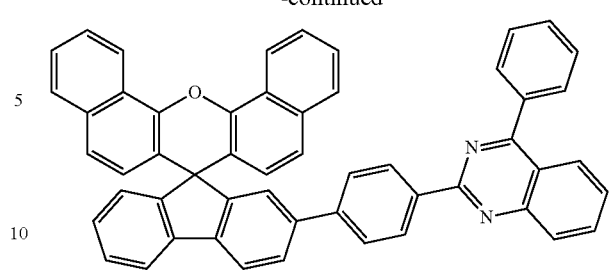
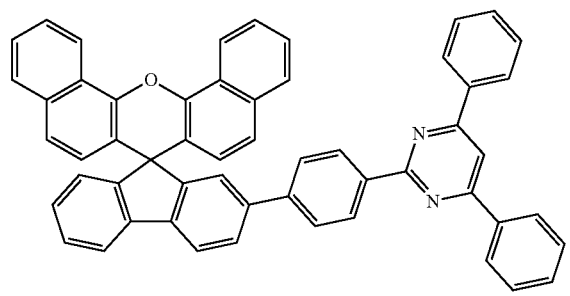
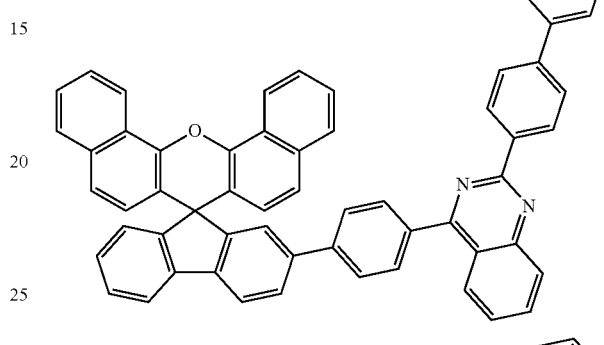
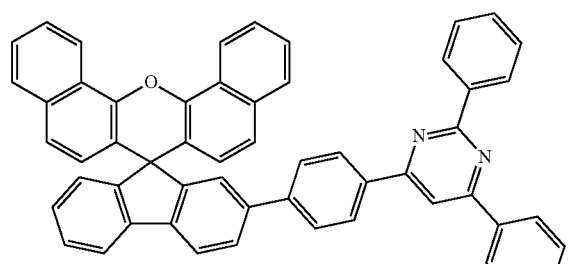

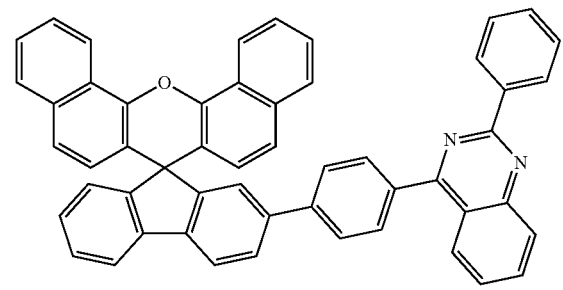
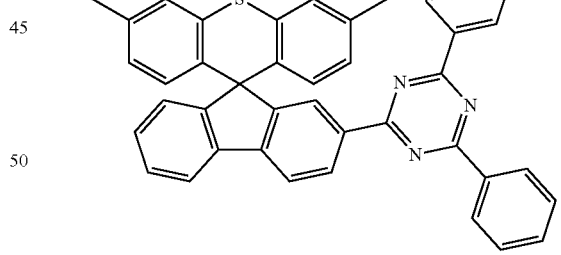
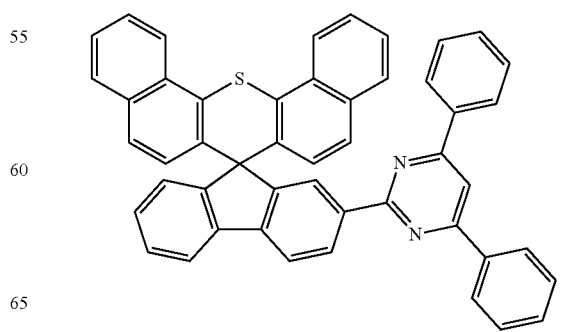

61
-continued
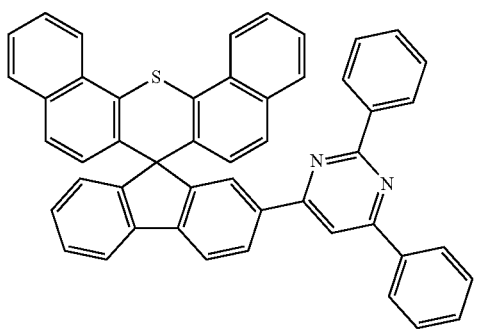
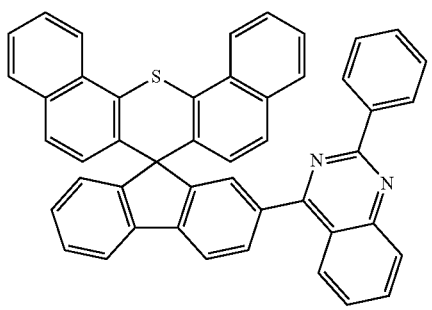
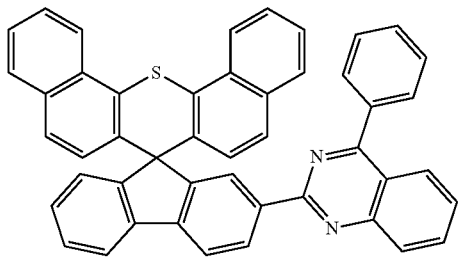
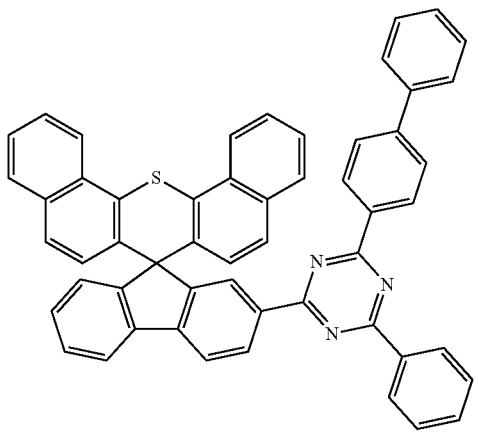
62
-continued
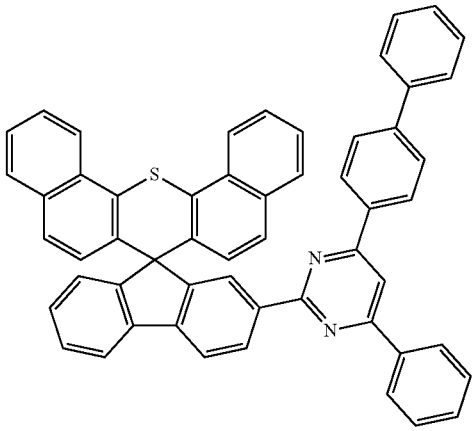
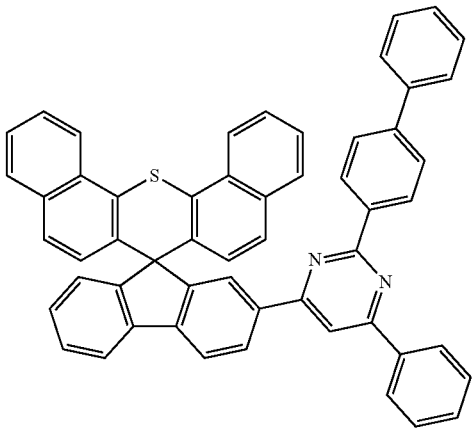
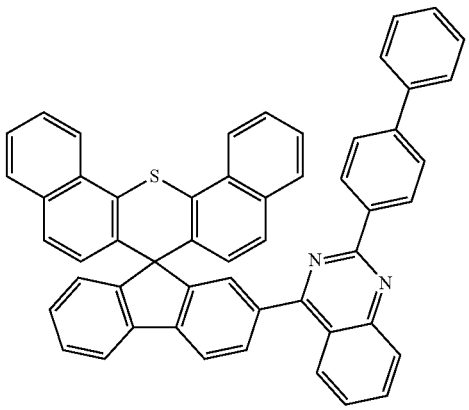
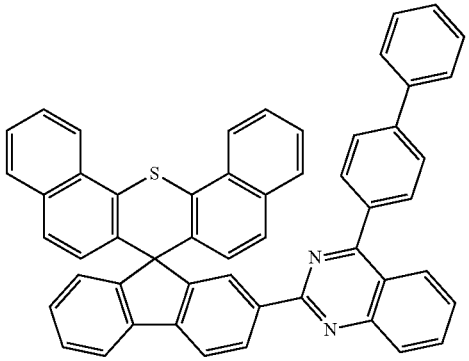

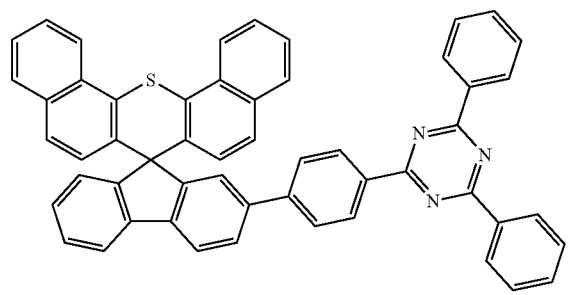
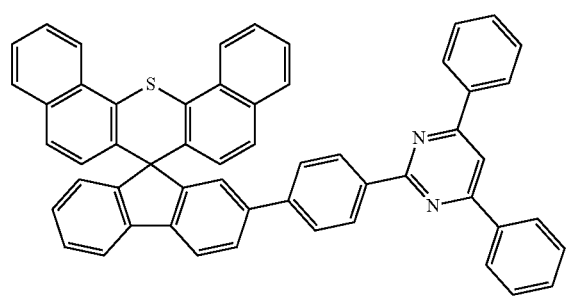
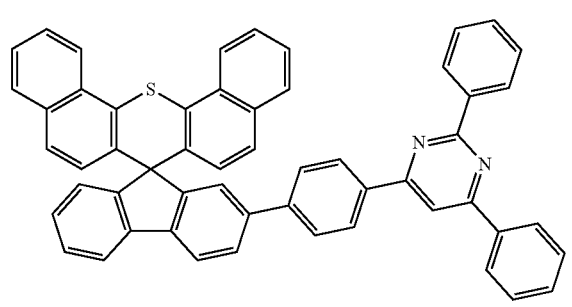
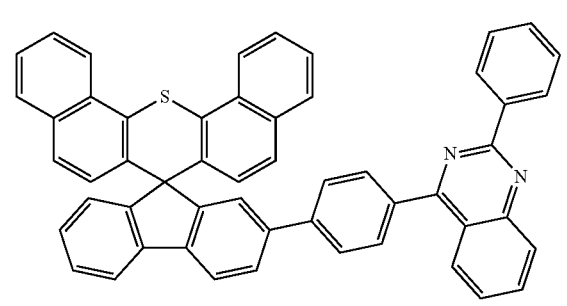
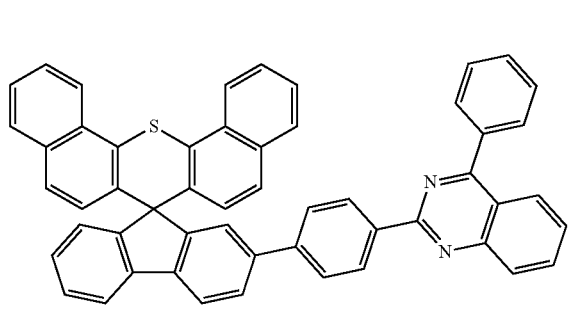
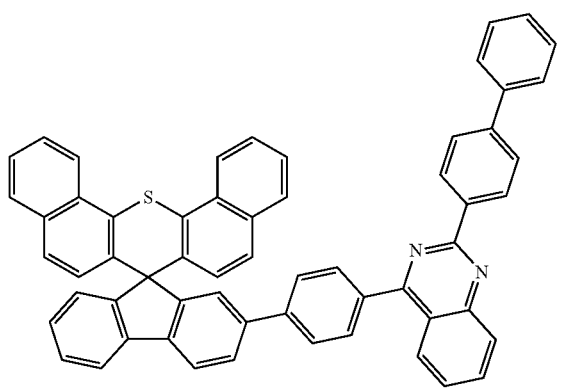
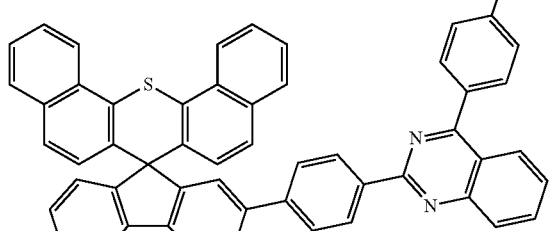
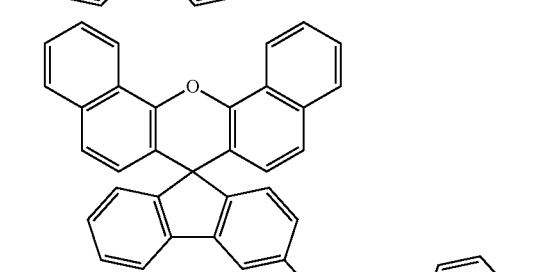

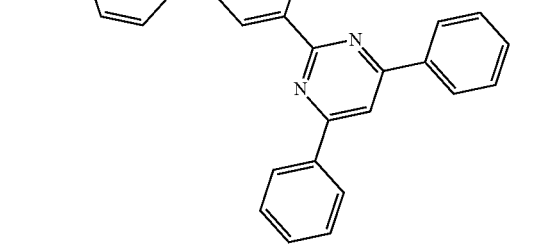

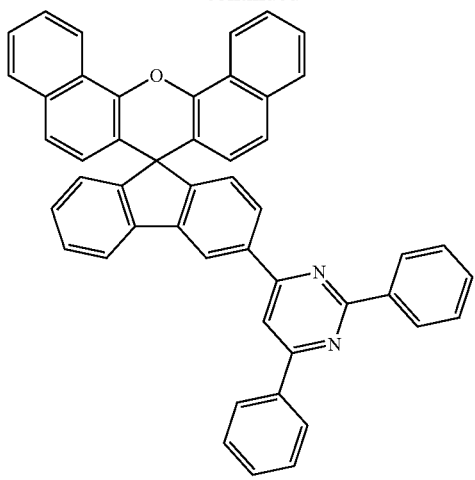
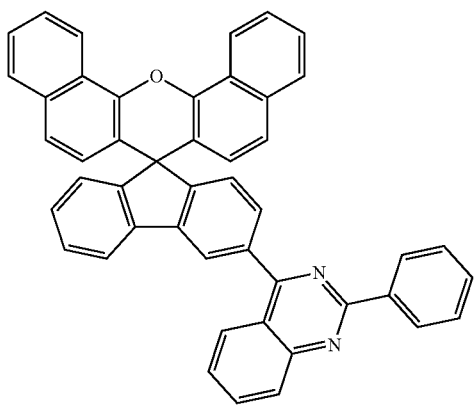
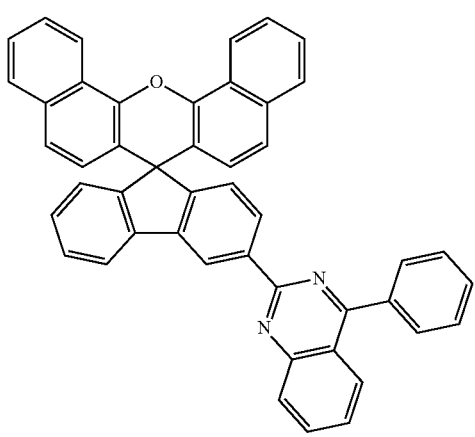
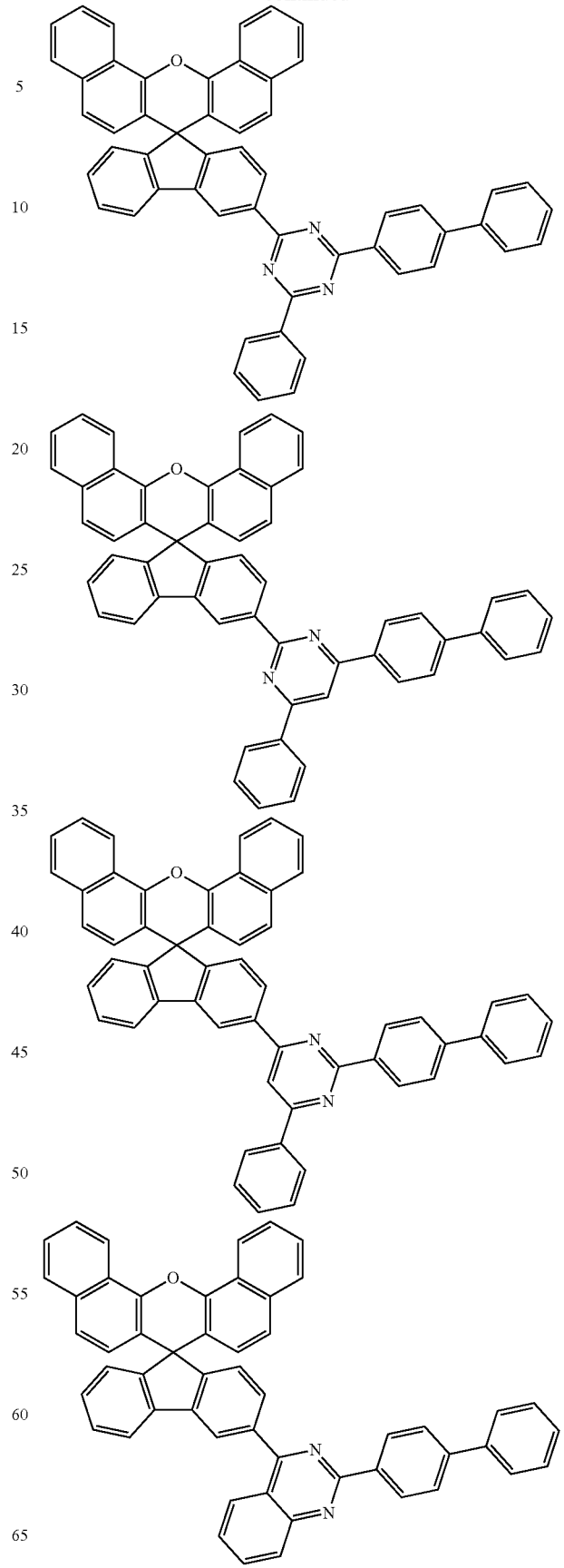

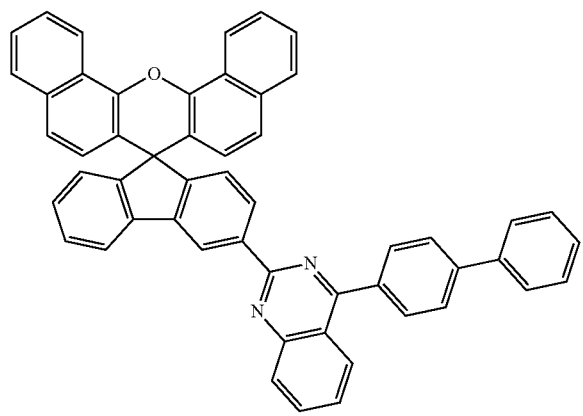
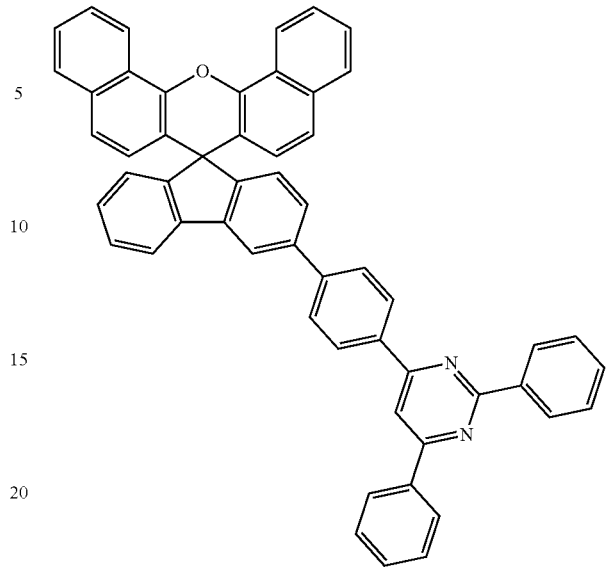
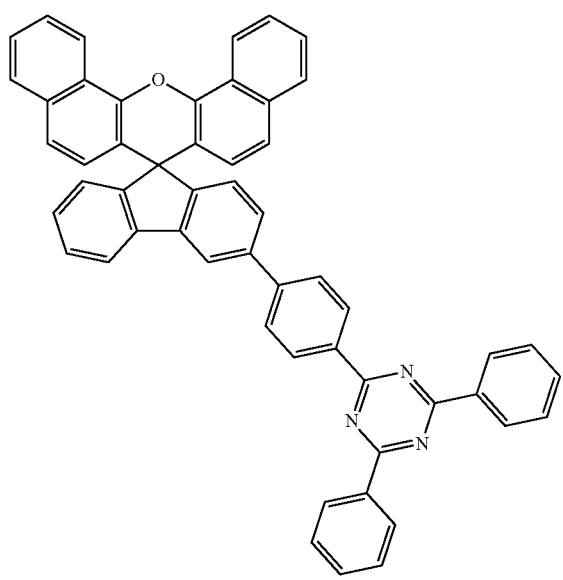
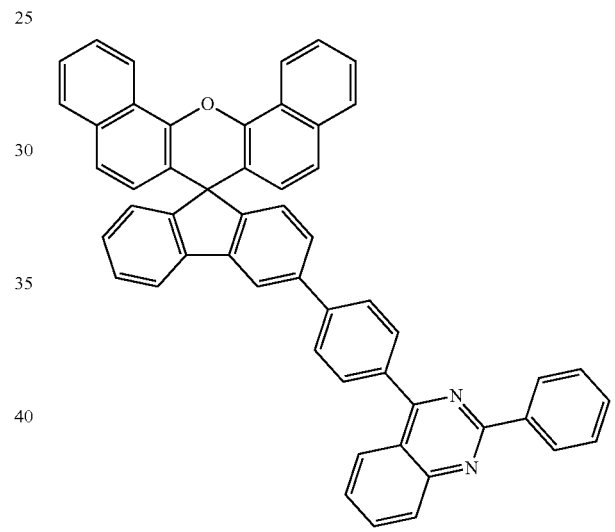
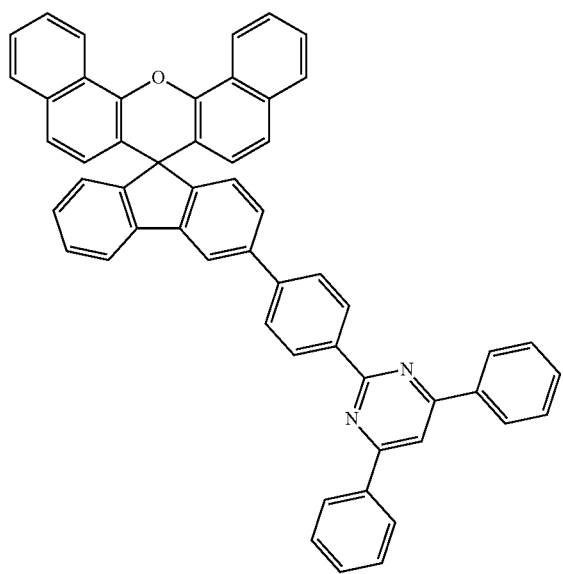
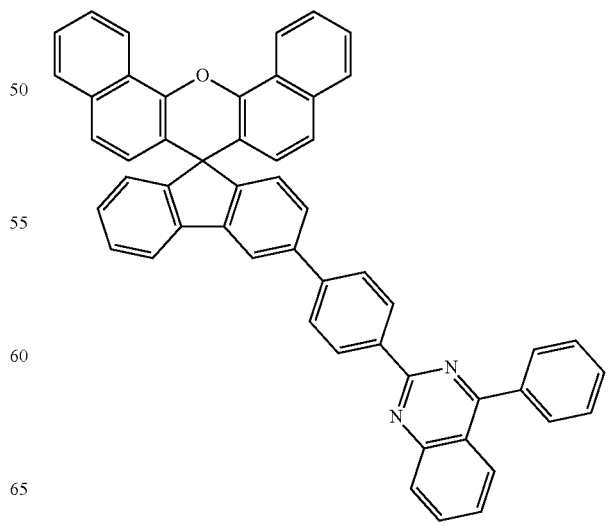

69
-continued
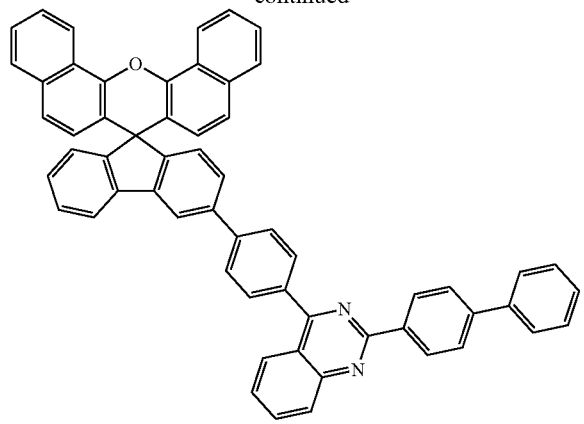
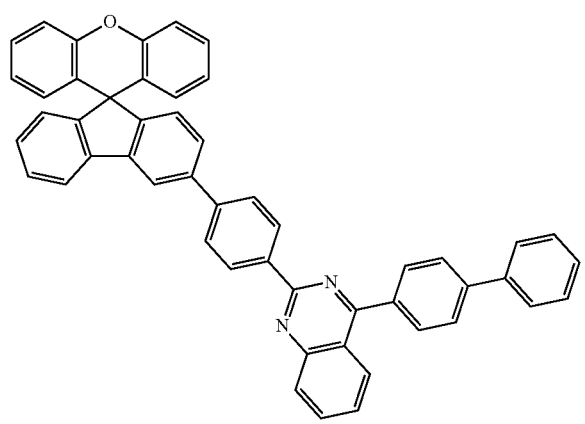
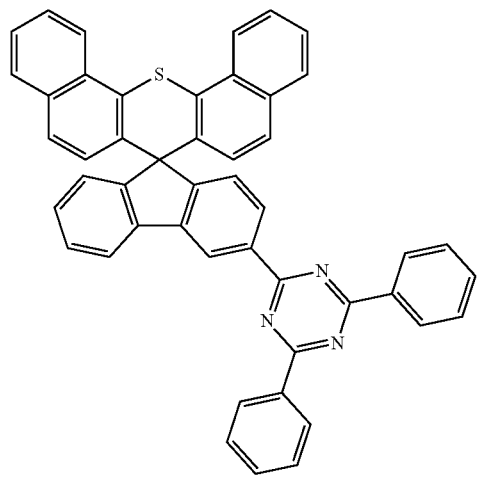
70
-continued
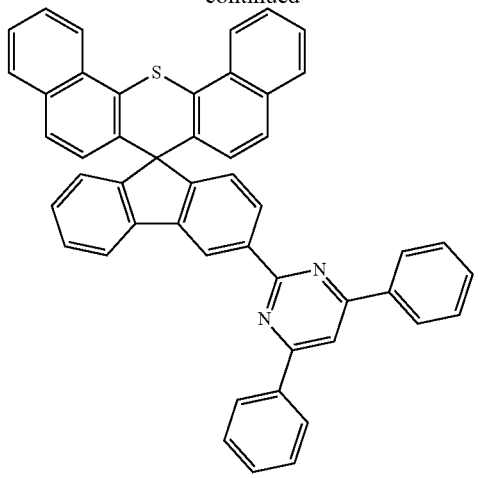
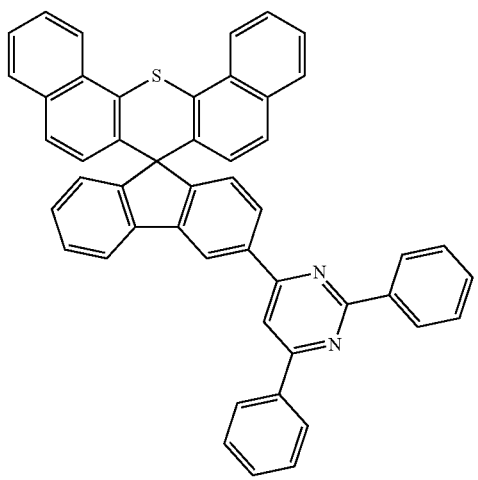
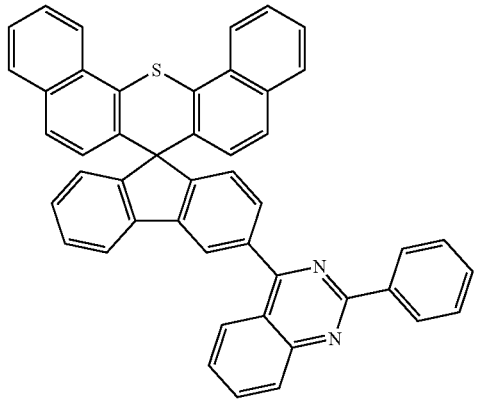

71
-continued
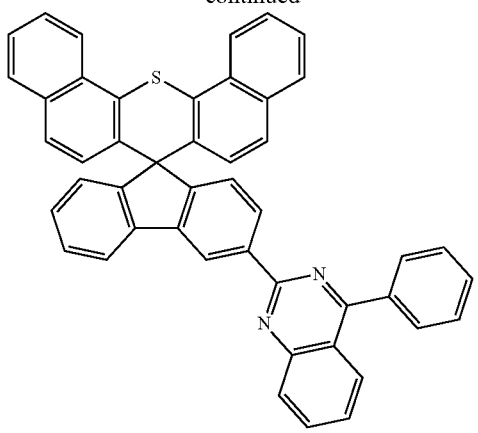
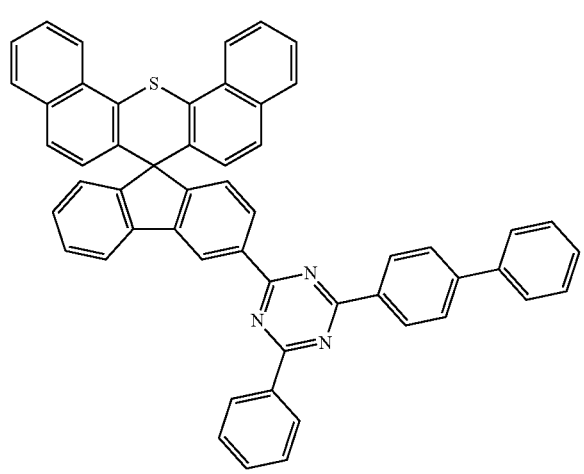
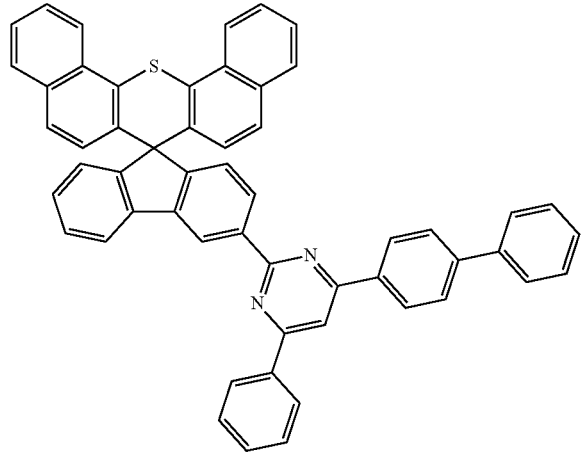
72
-continued
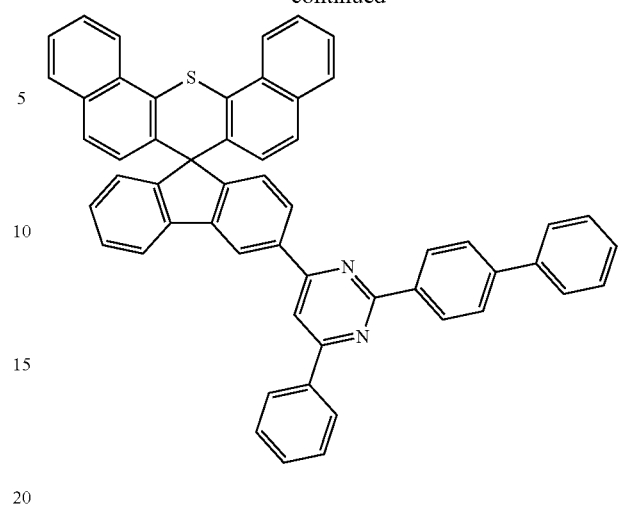
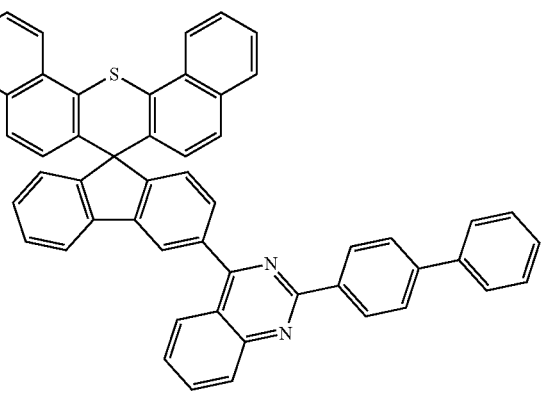
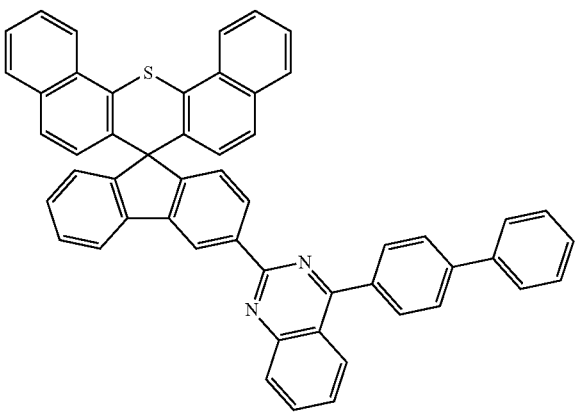

-continued
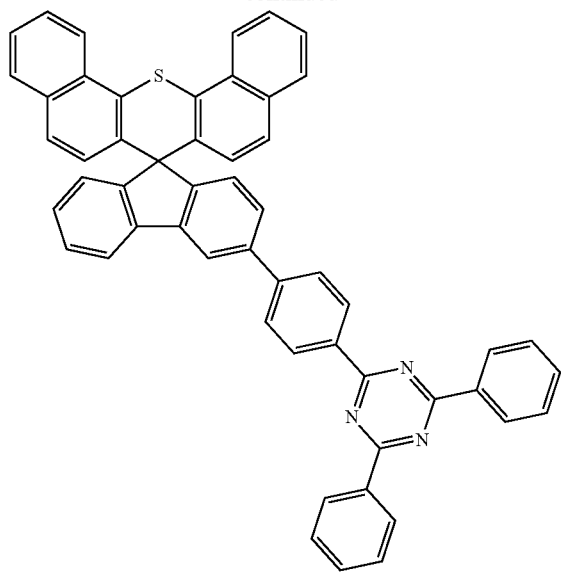
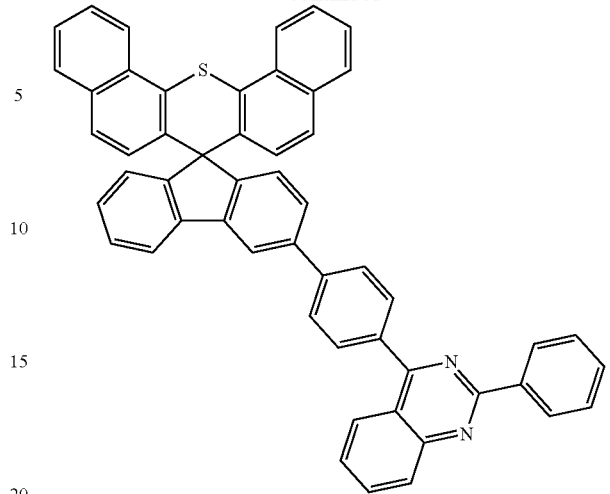
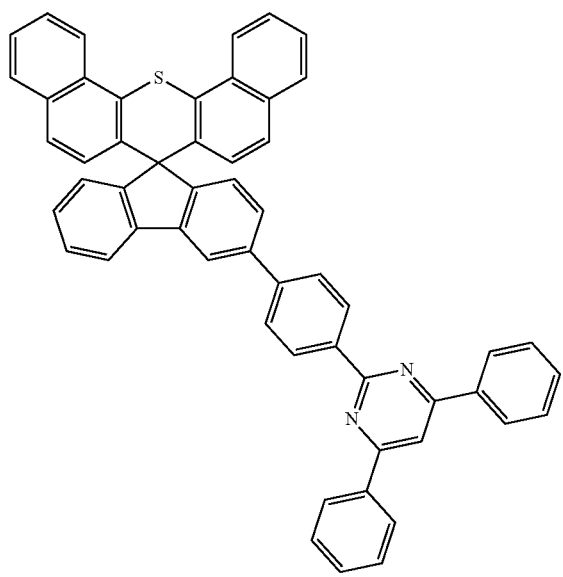
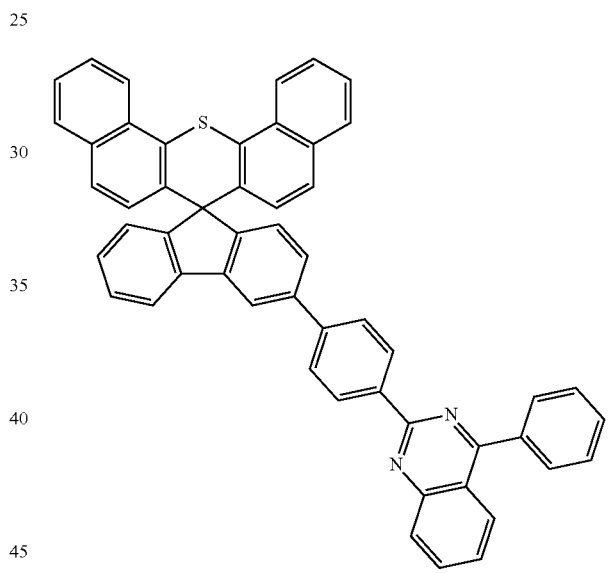
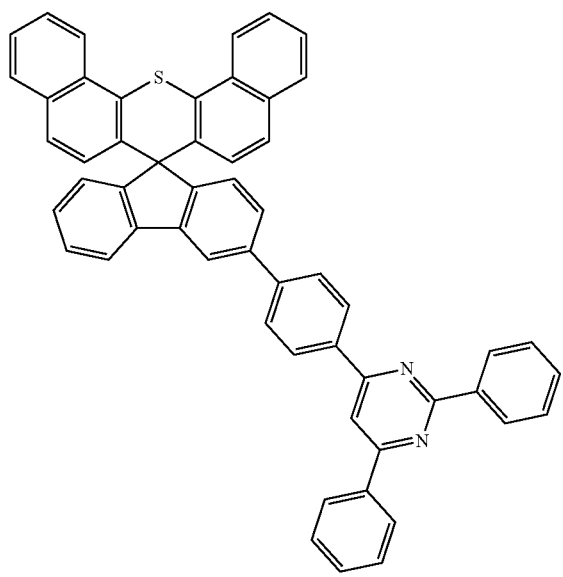
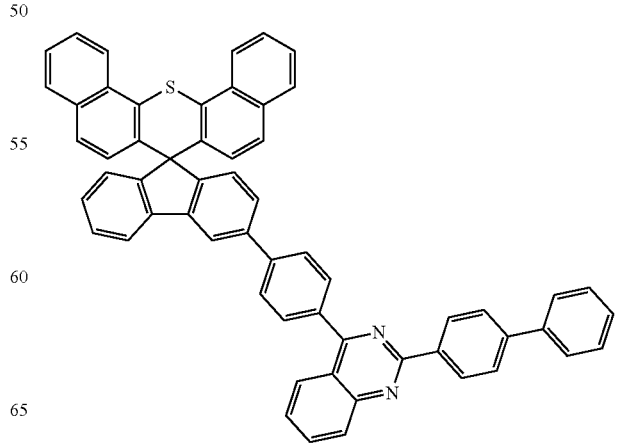

75
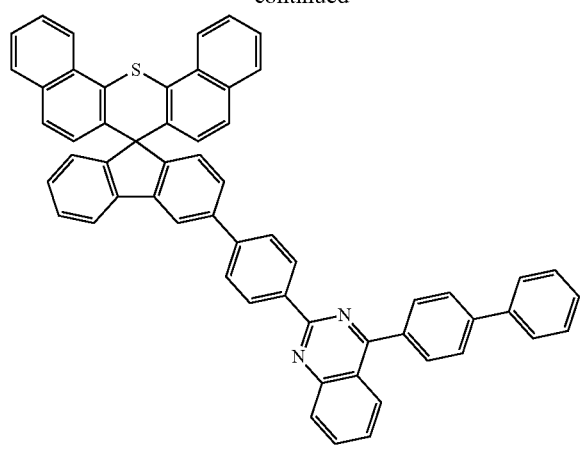
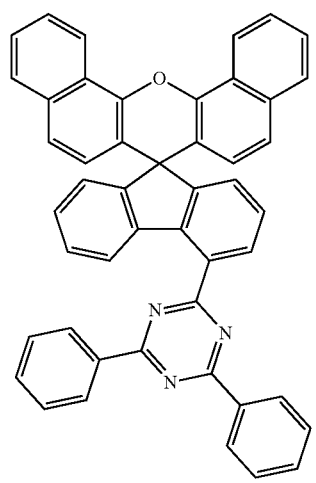
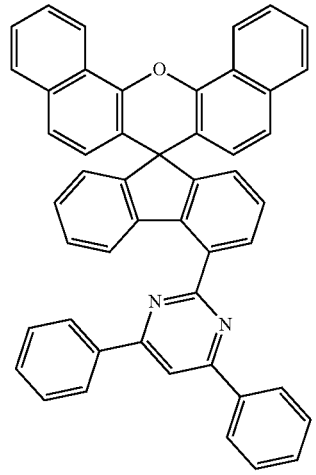
76
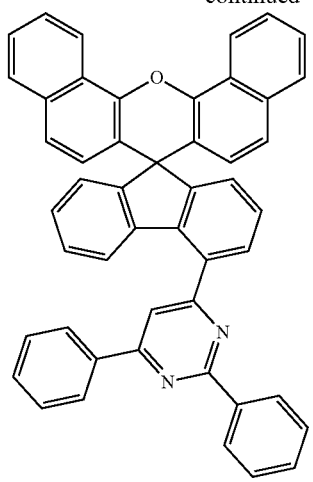
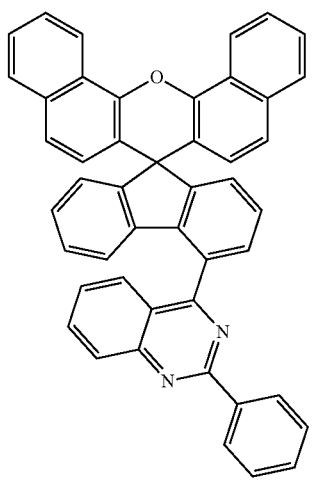

77
-continued
78
-continued
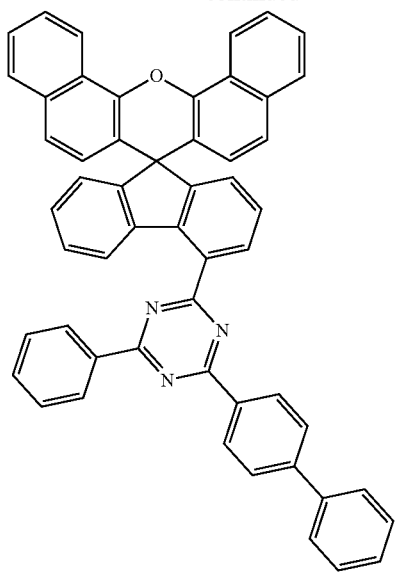
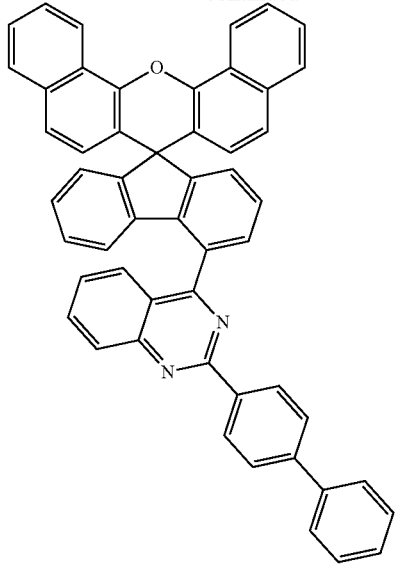
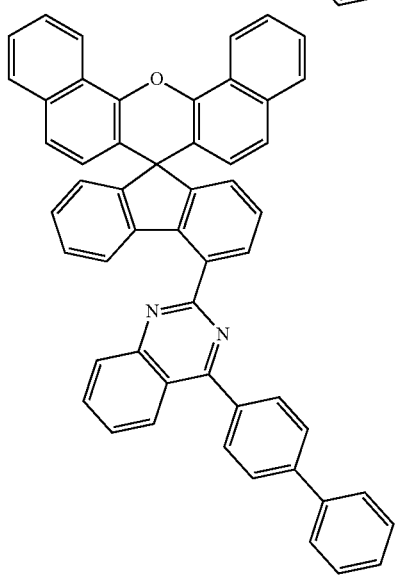
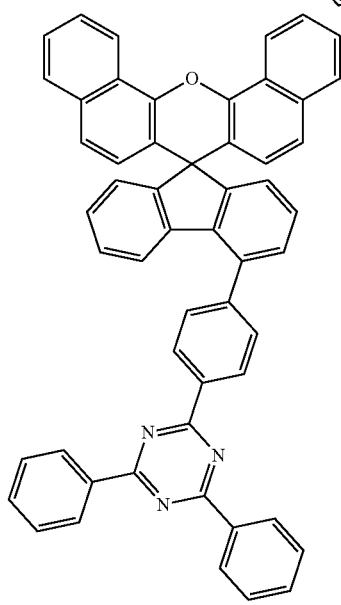

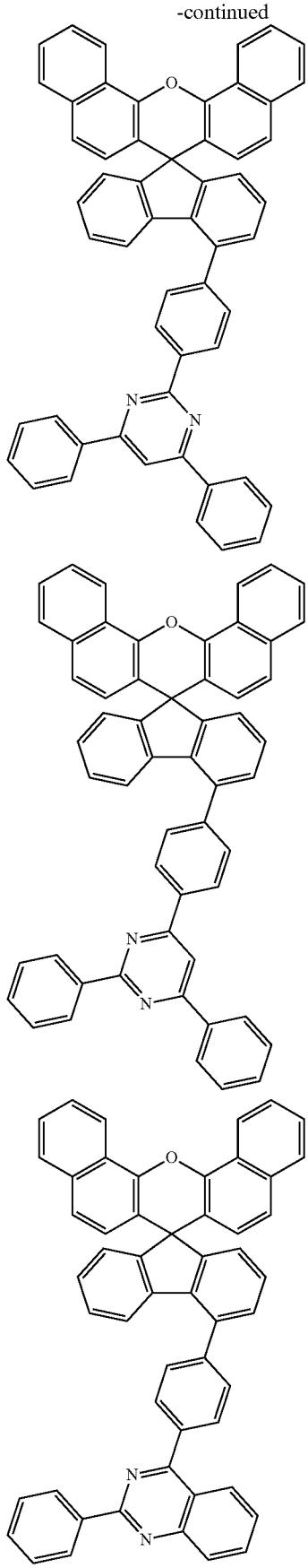
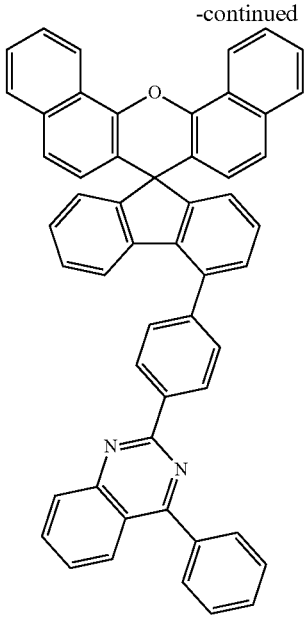
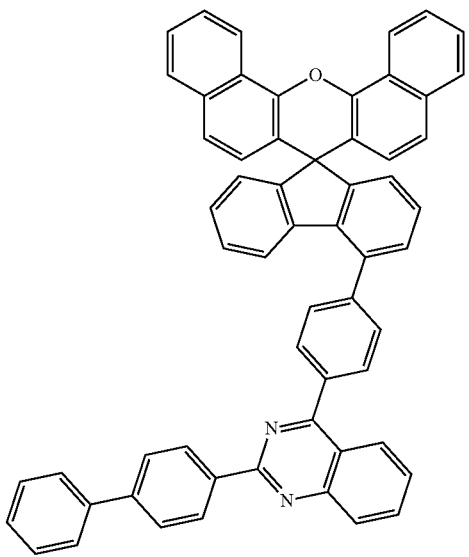

81
-continued
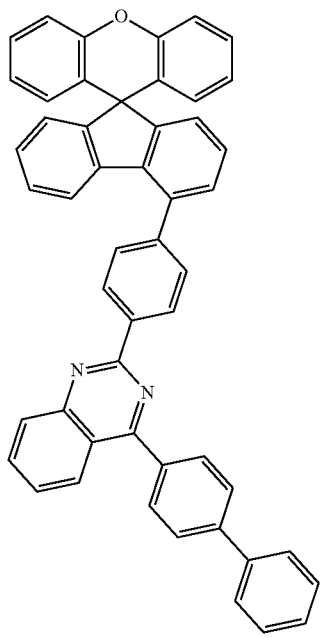
82
-continued
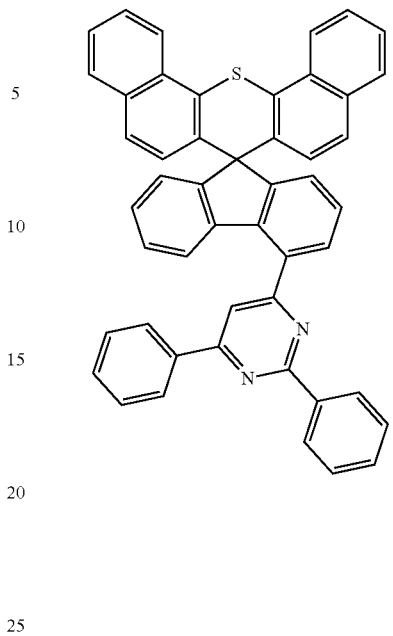
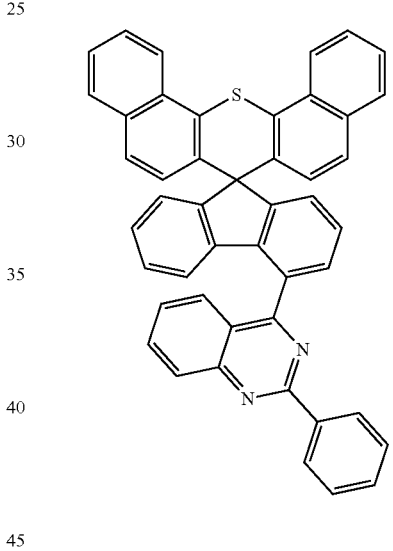
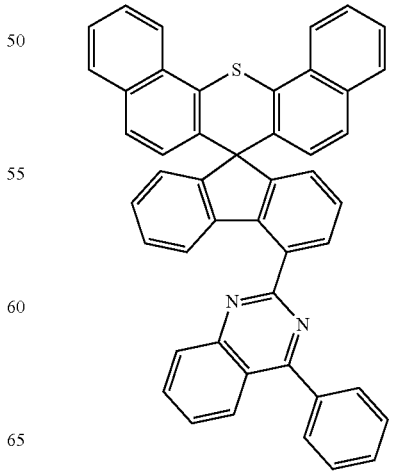

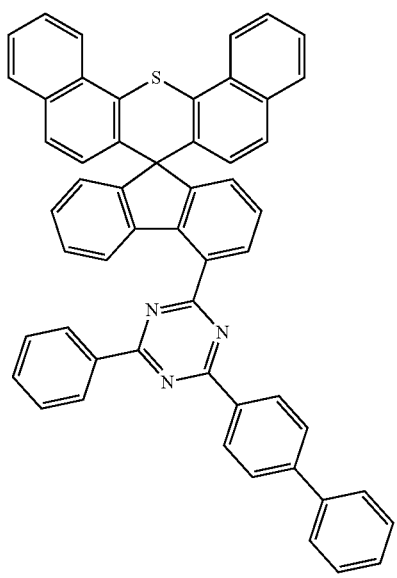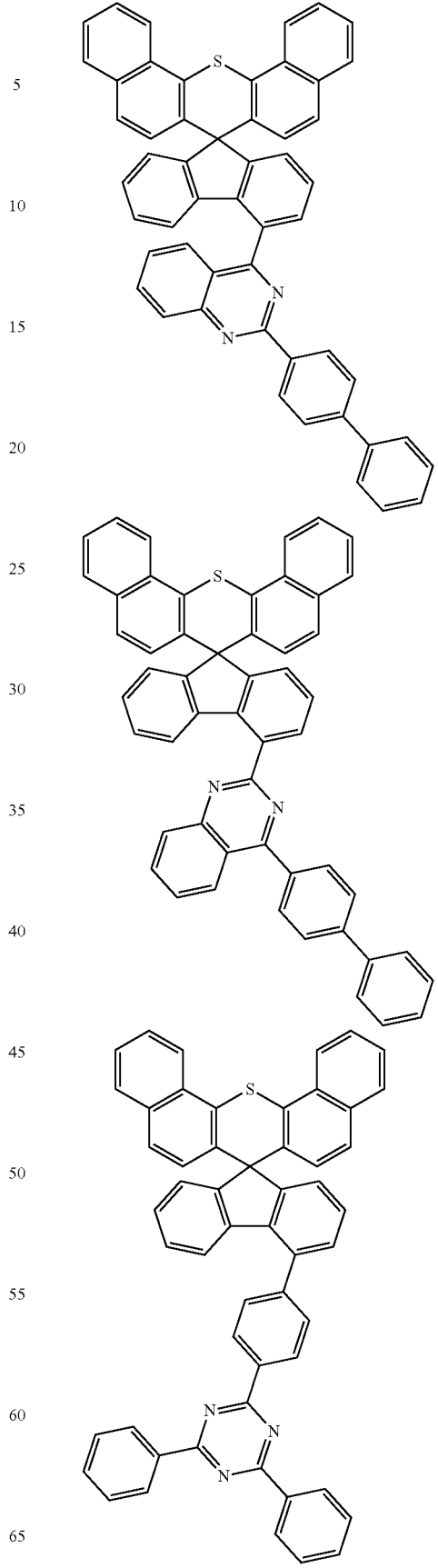

85
-continued
86
-continued
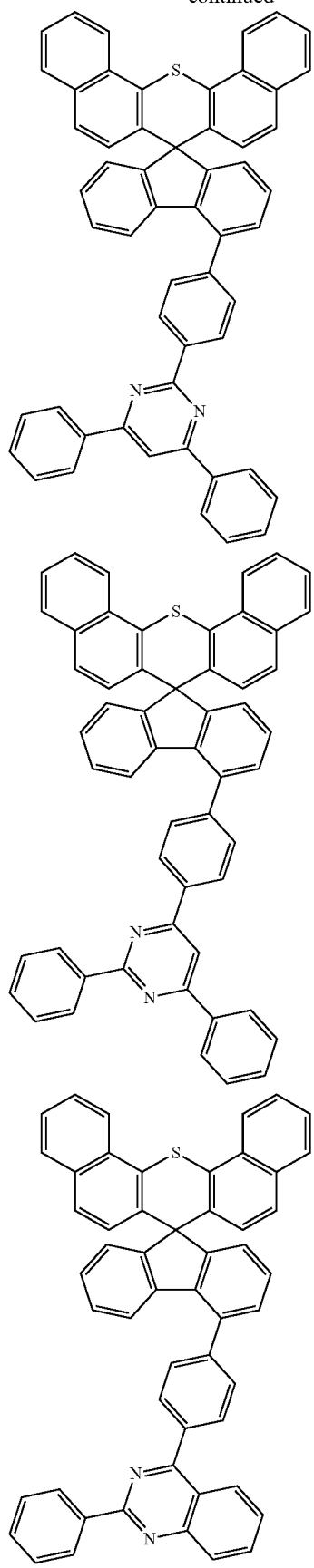
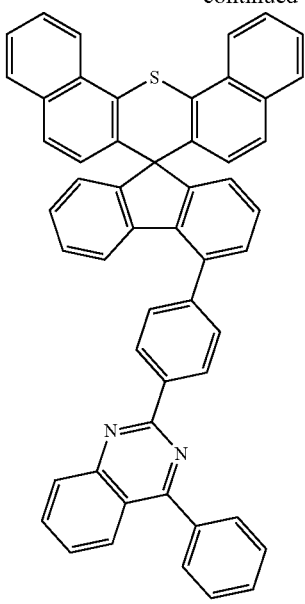
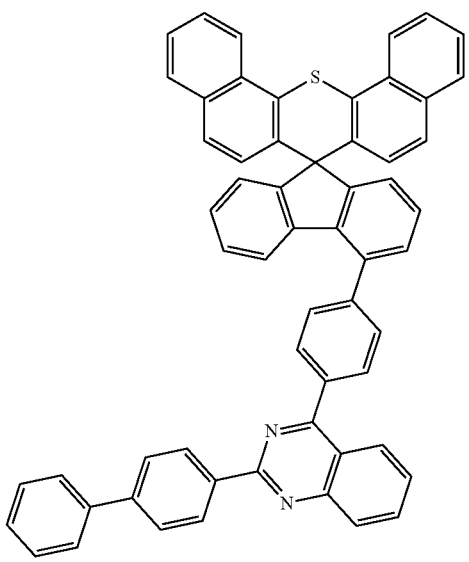

87
-continued
88
-continued
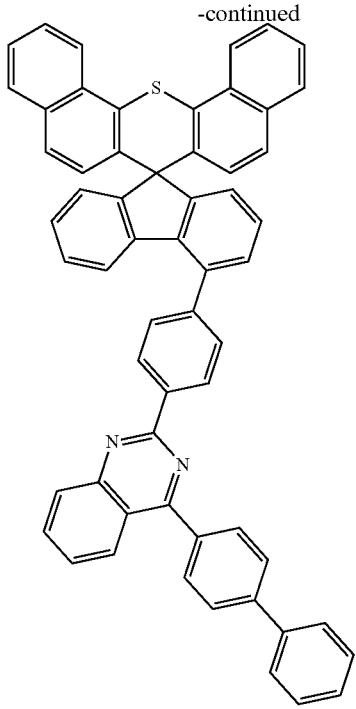
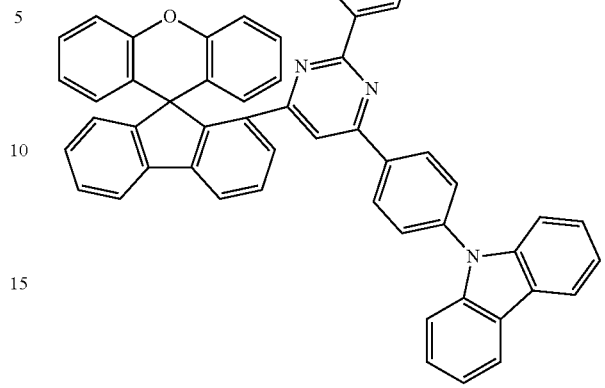
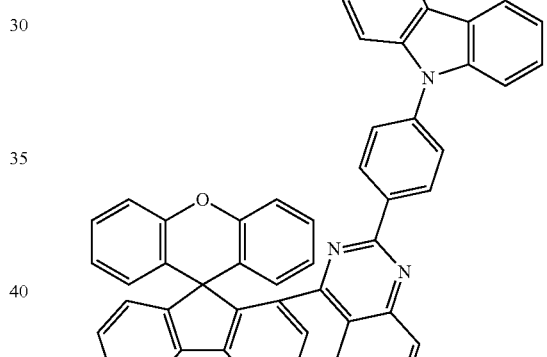
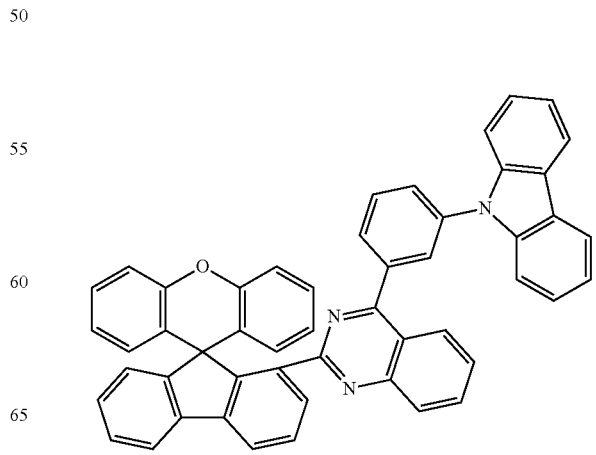

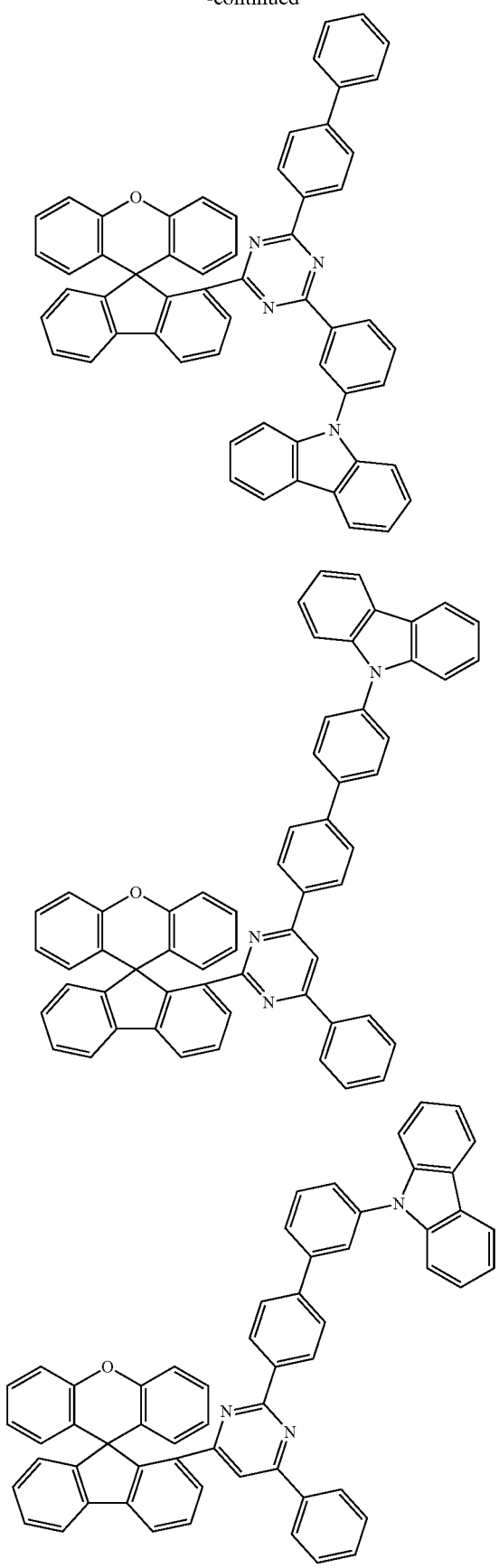
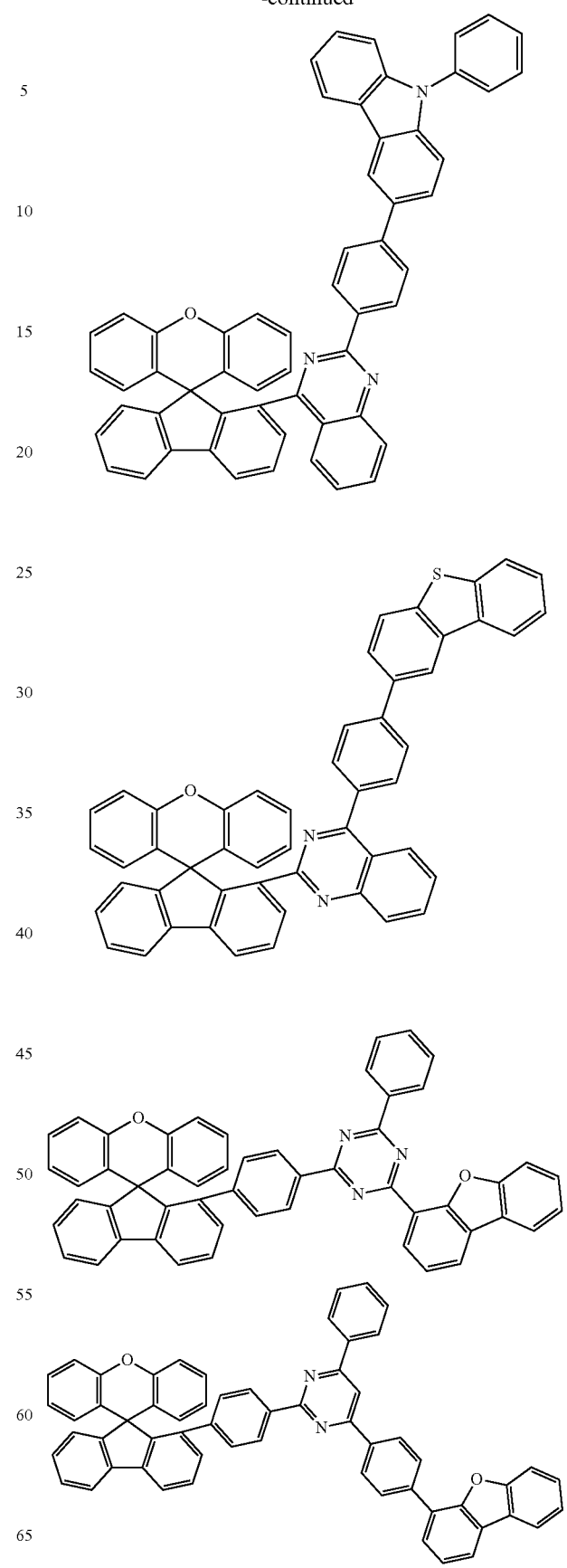

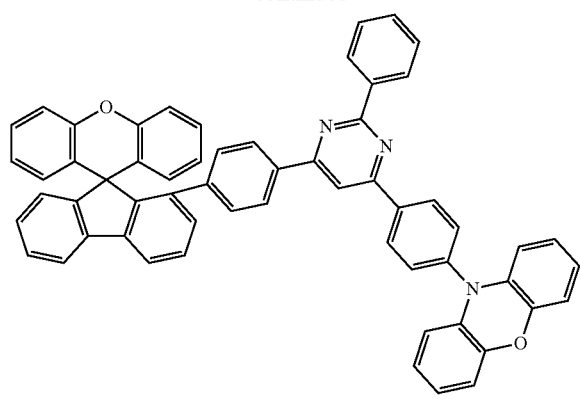
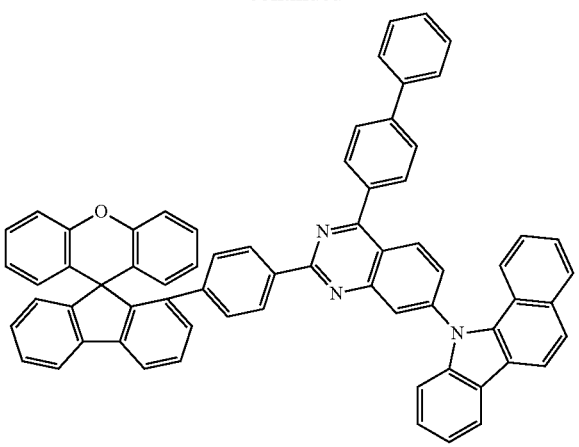
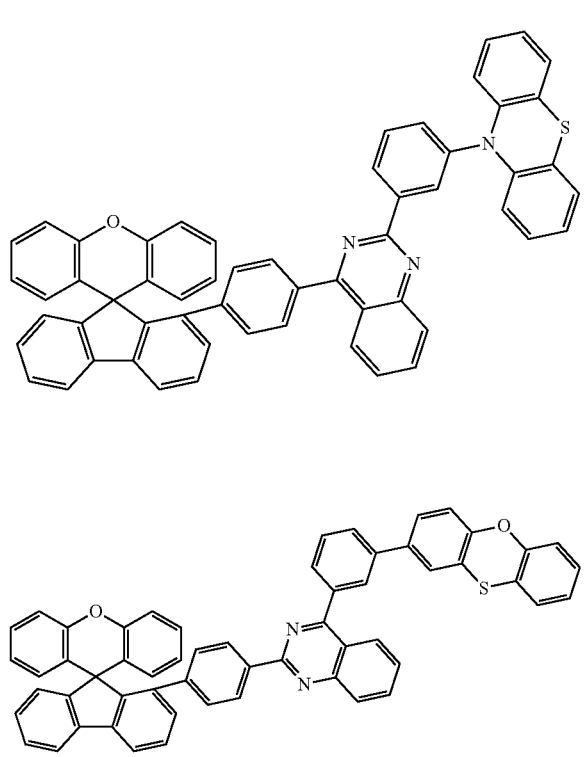
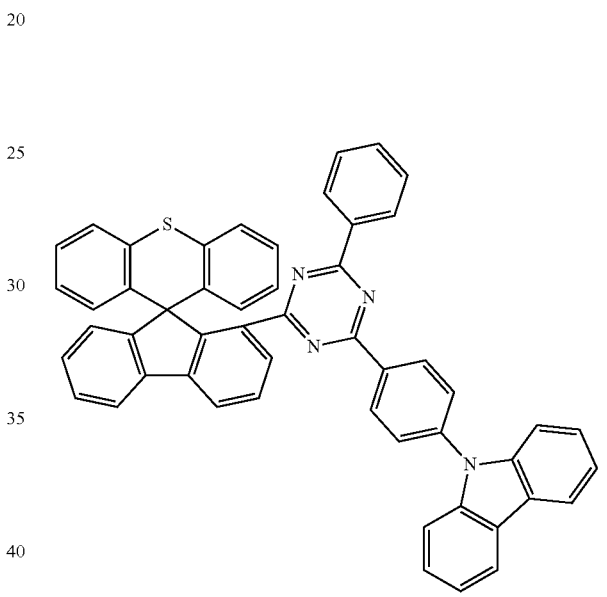
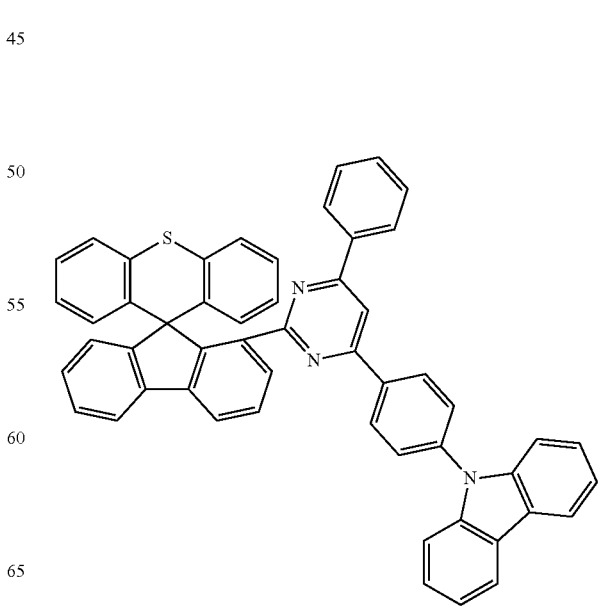

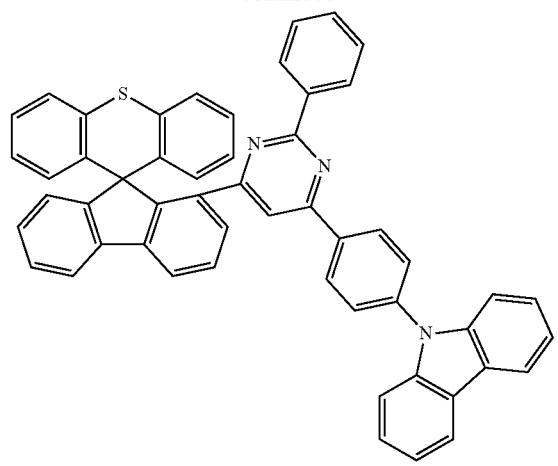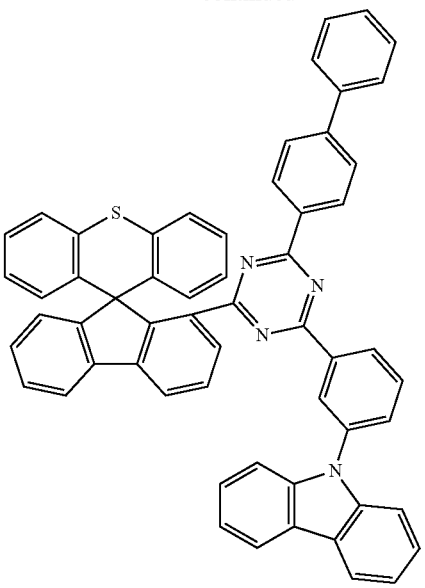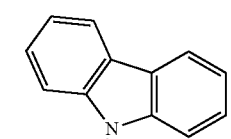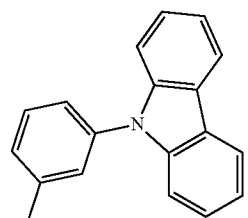

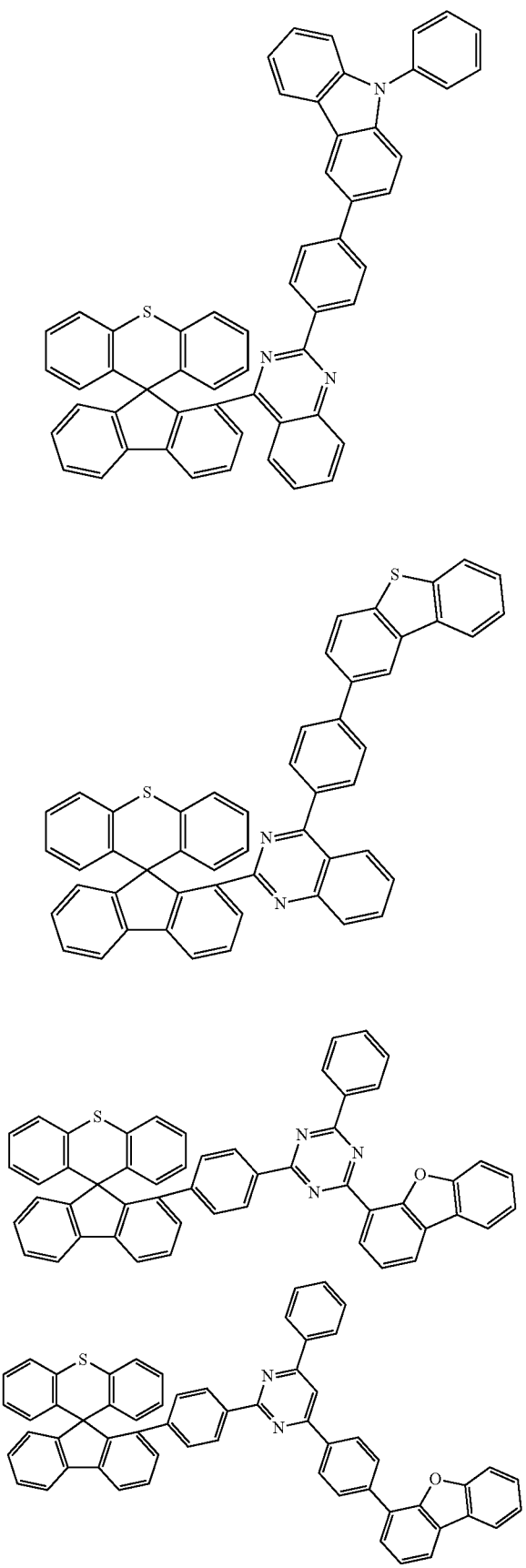
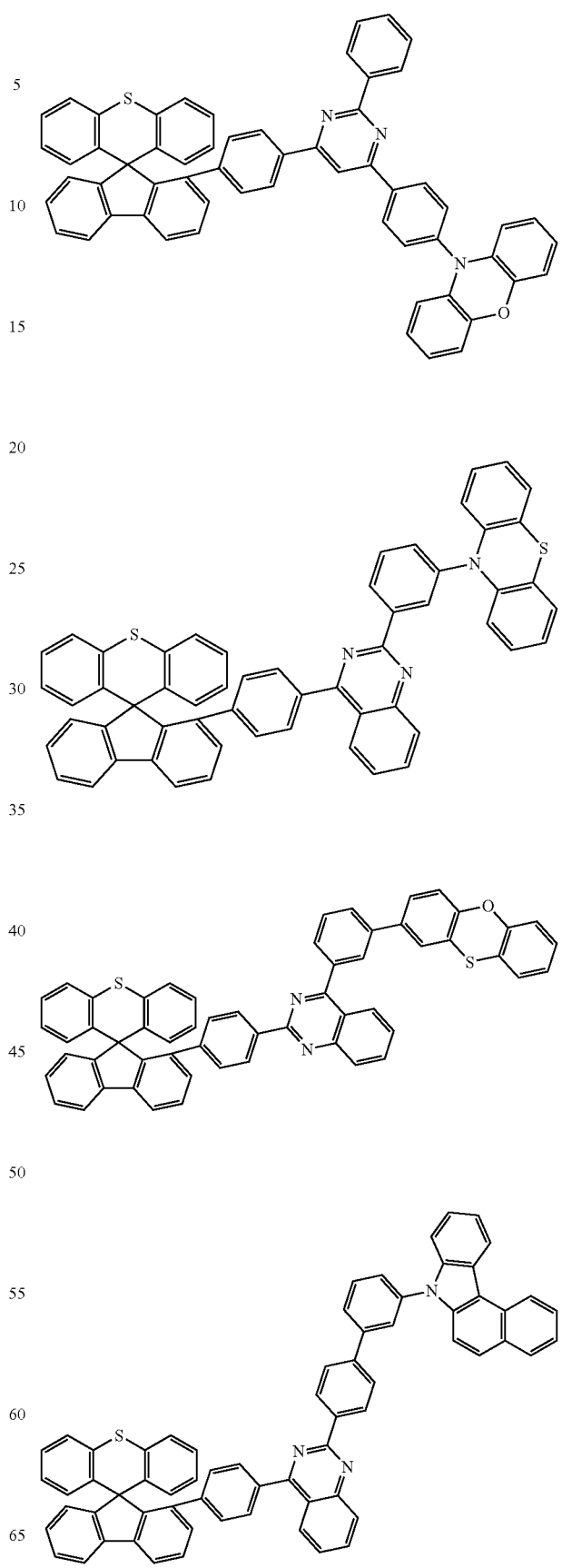

97
-continued
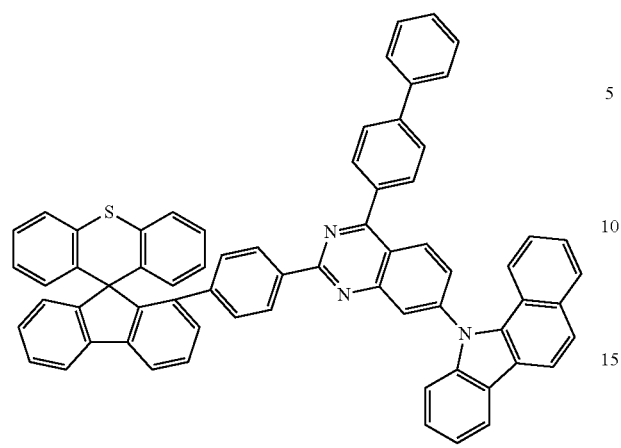
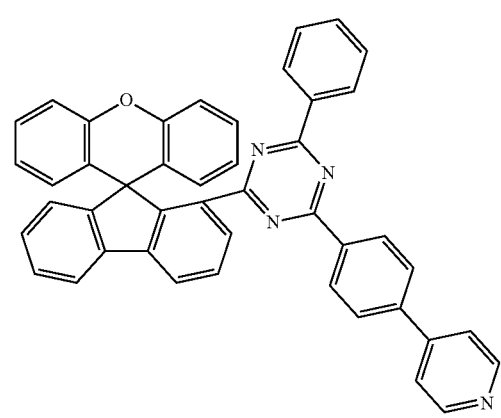
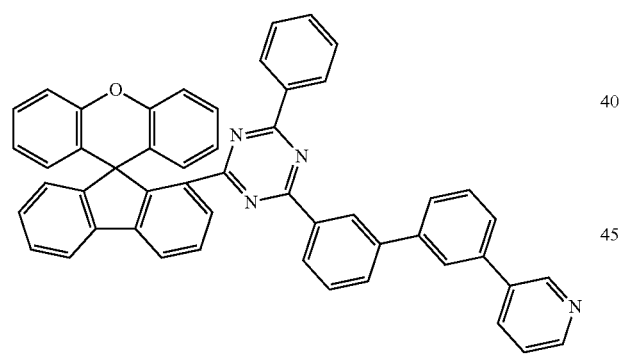
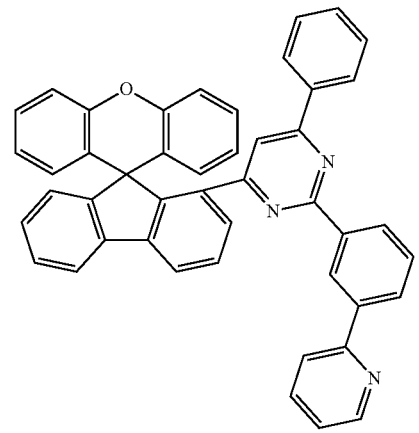
98
-continued
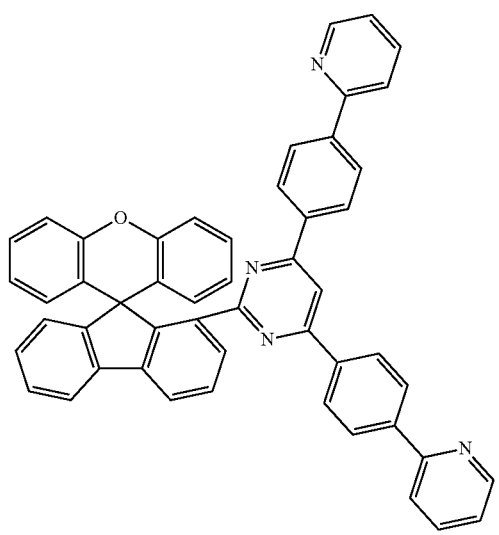
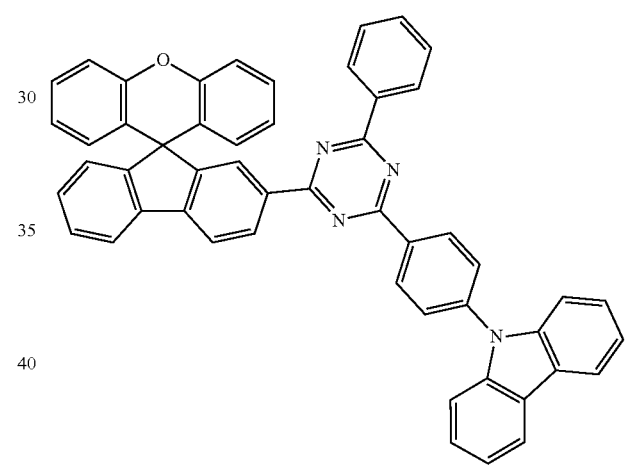
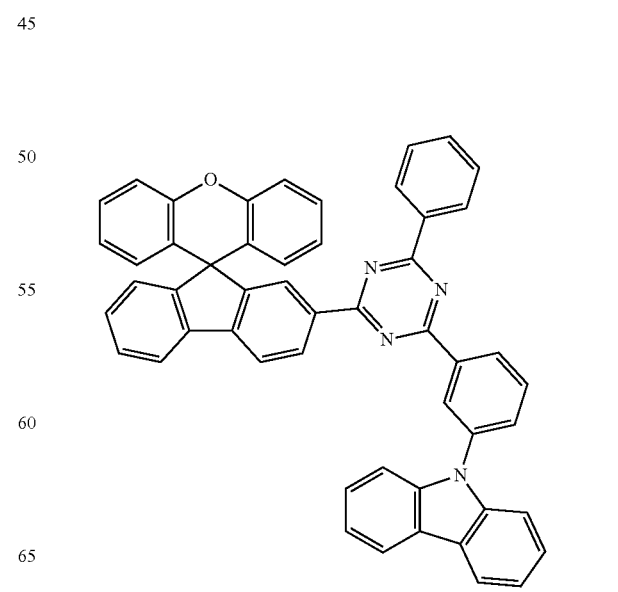

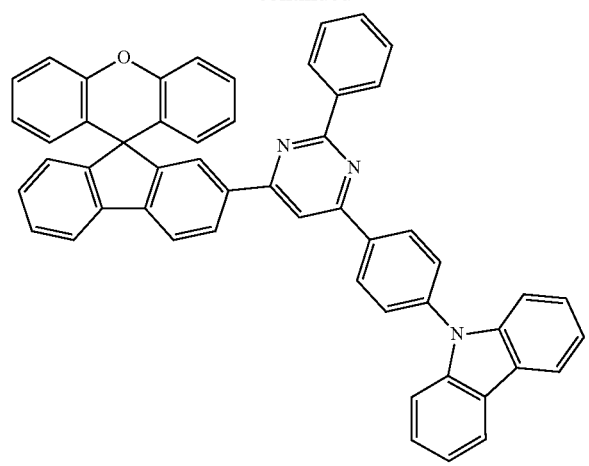
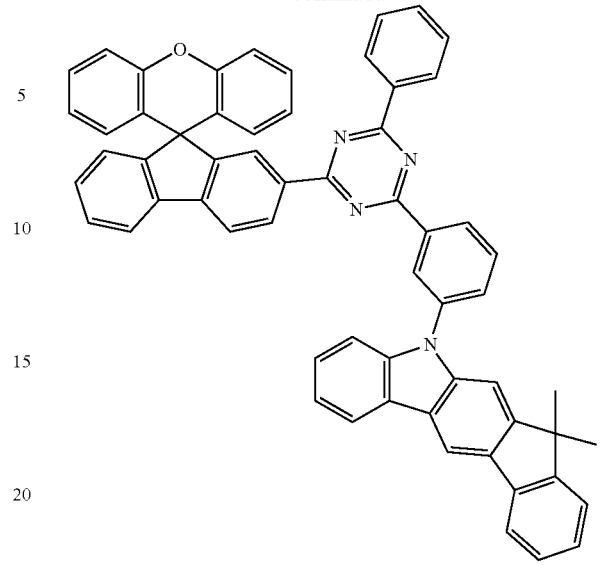
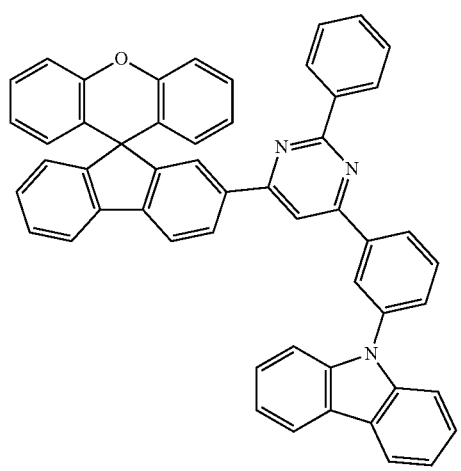
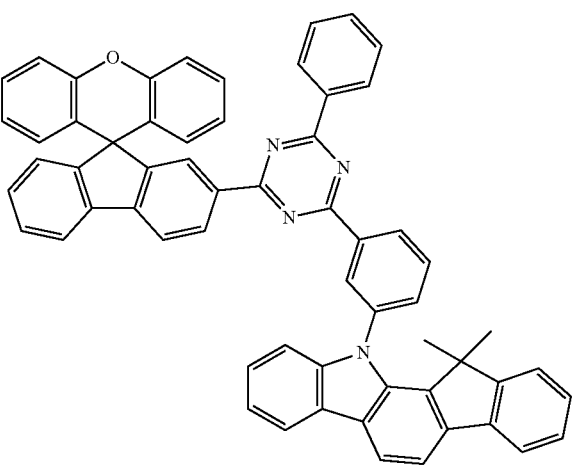
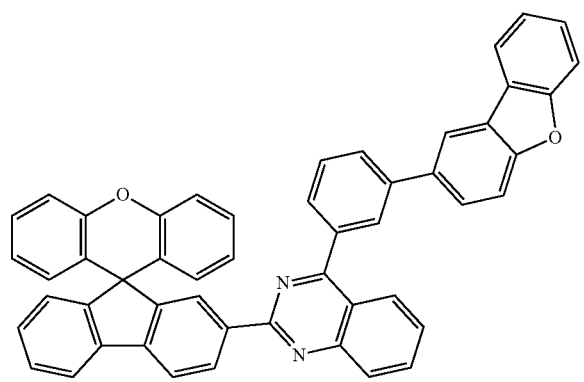
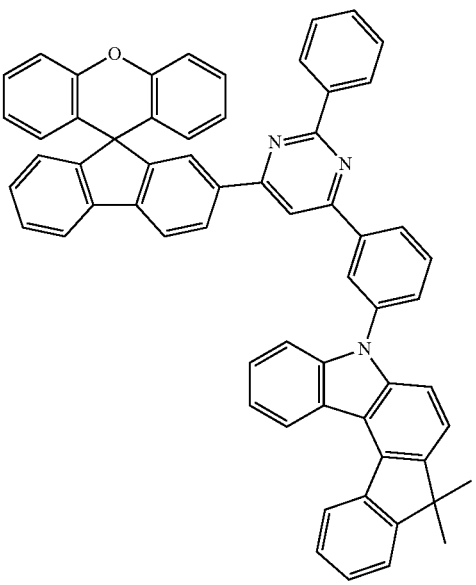

101
-continued
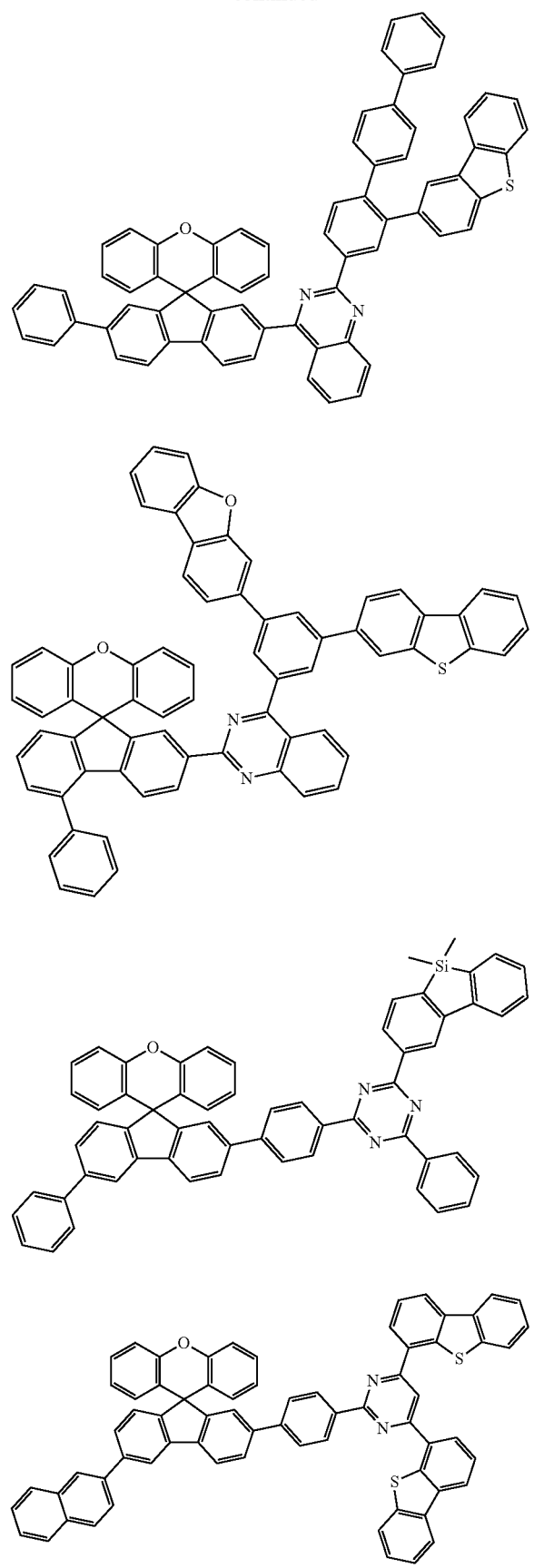
102
-continued
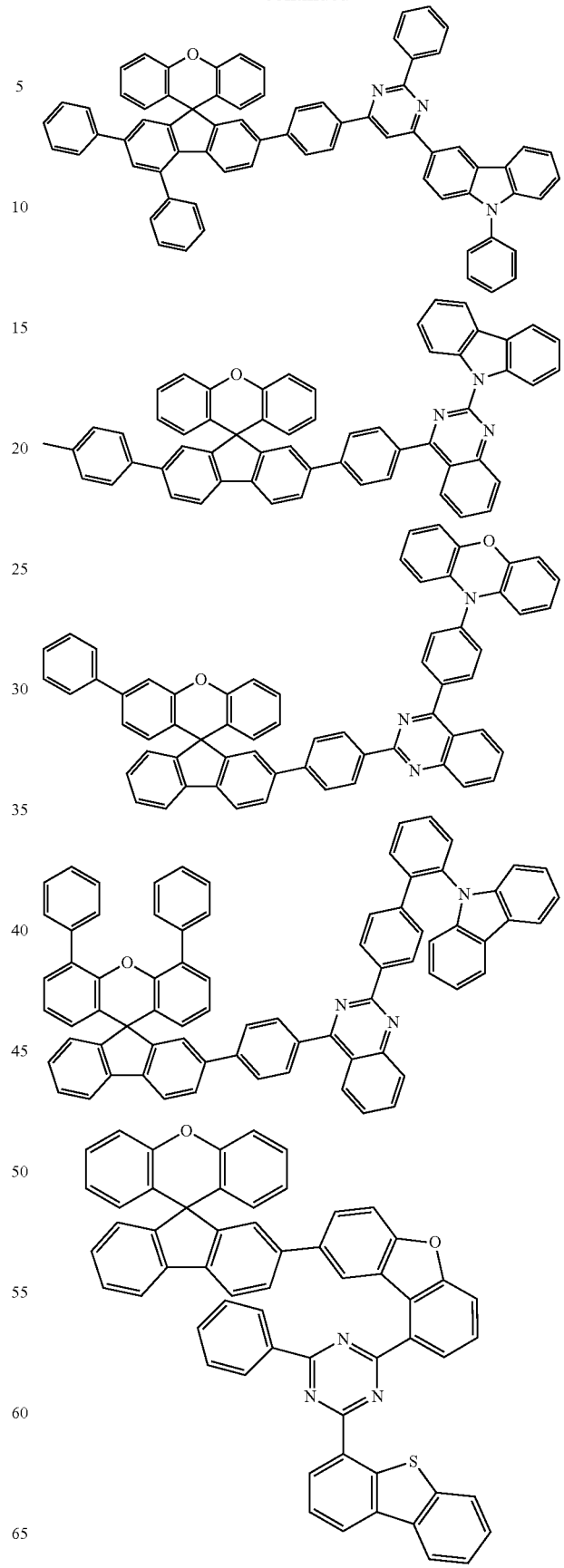

103
-continued
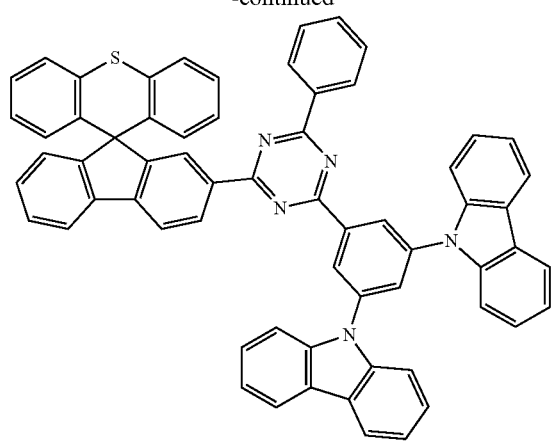
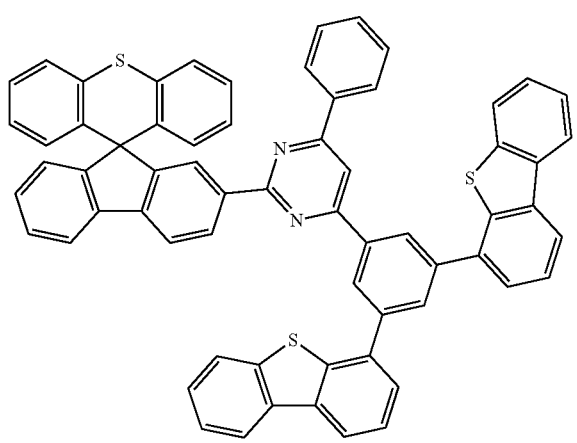
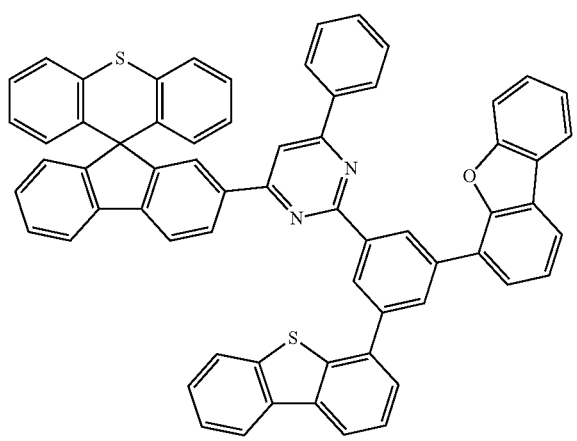
104
-continued
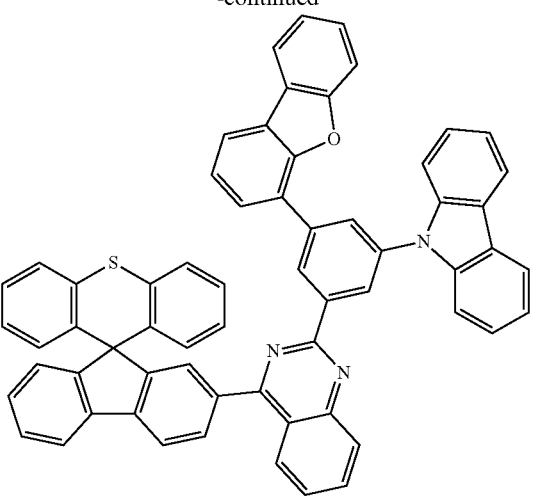
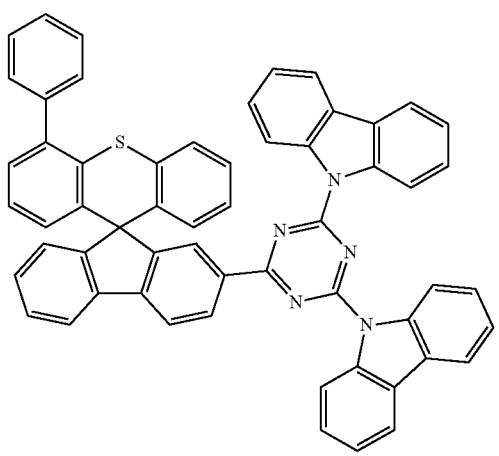
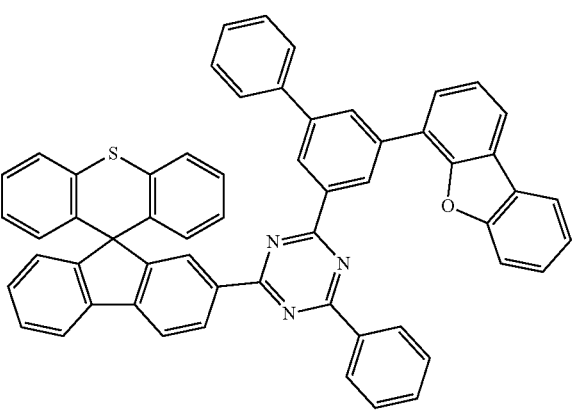

105
-continued
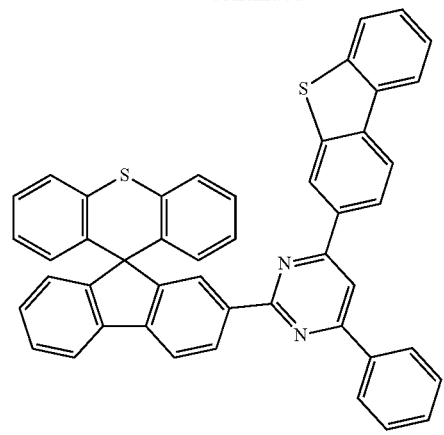
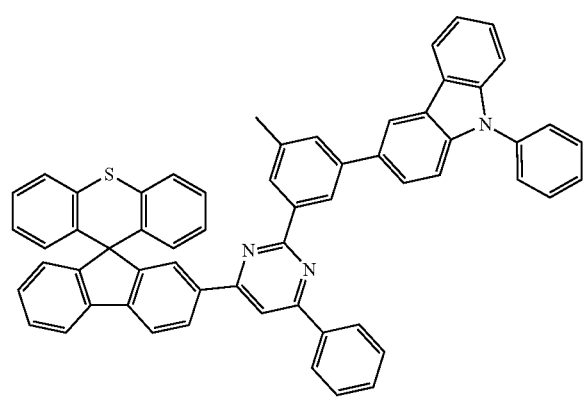
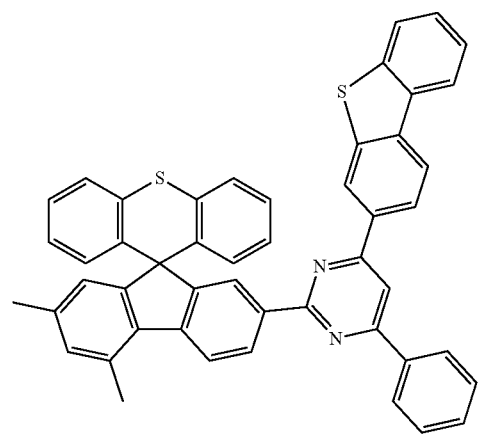
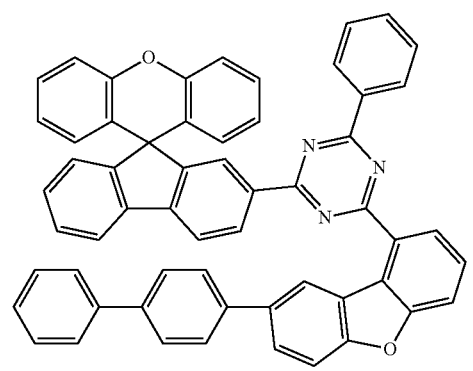
106
-continued
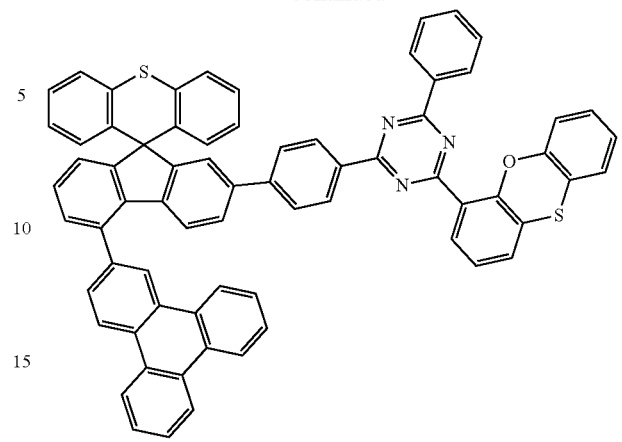
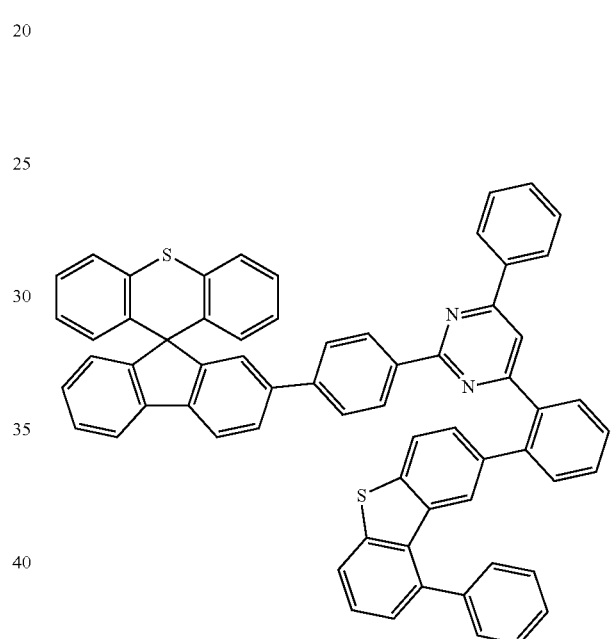
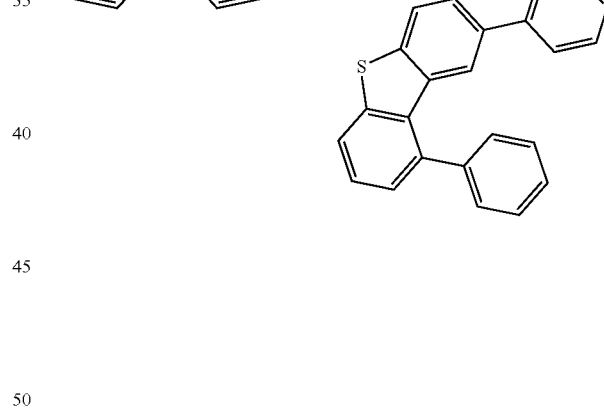
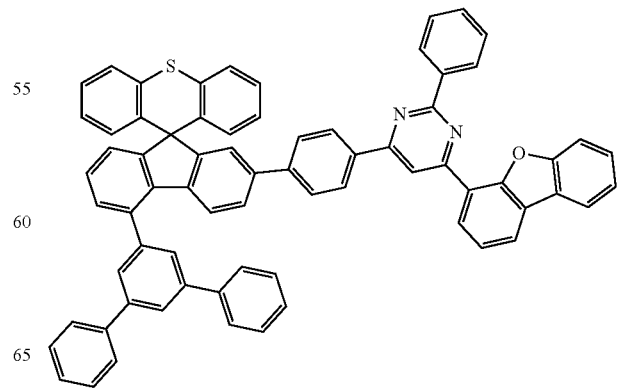

107
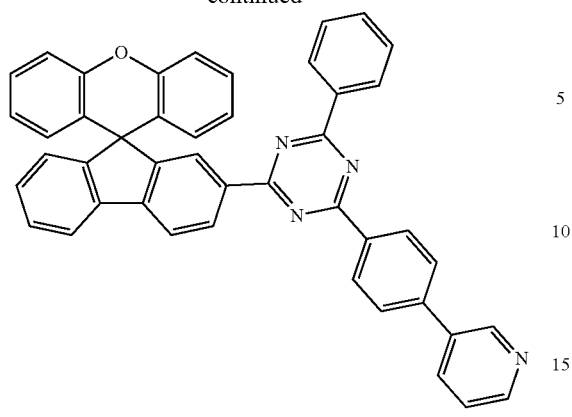
108
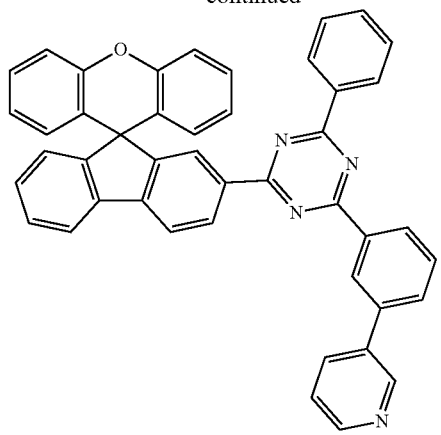
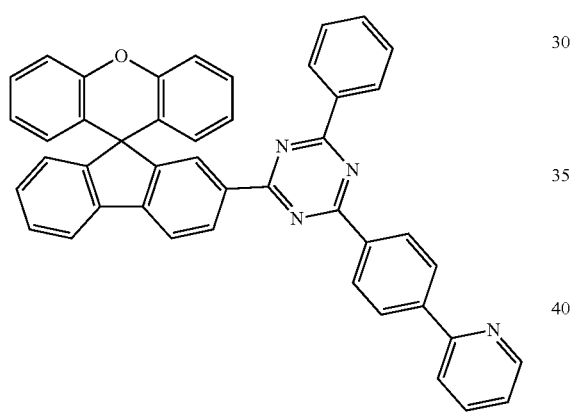
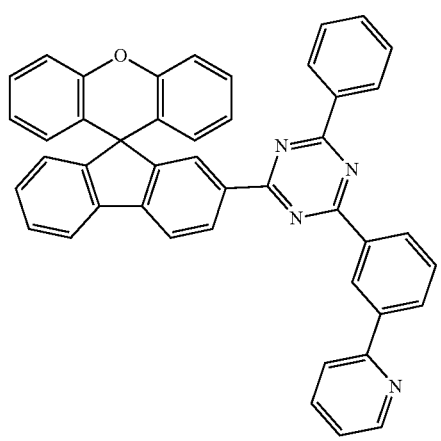
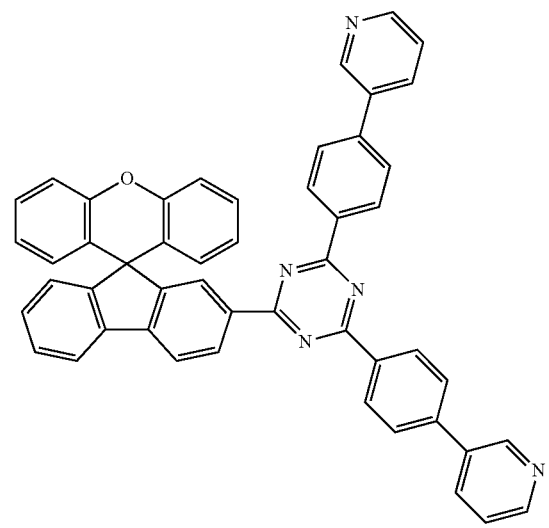

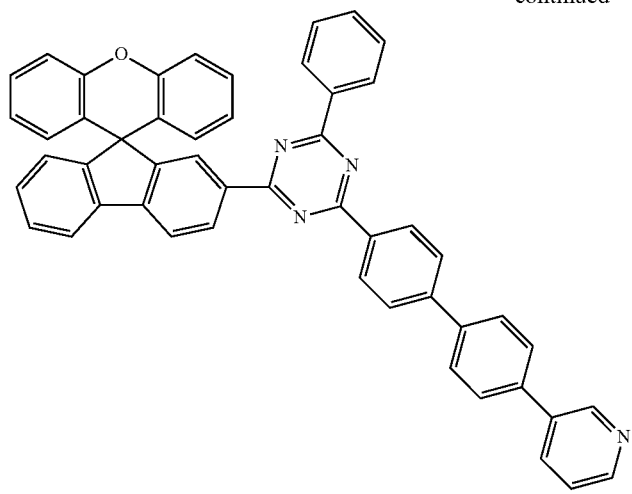
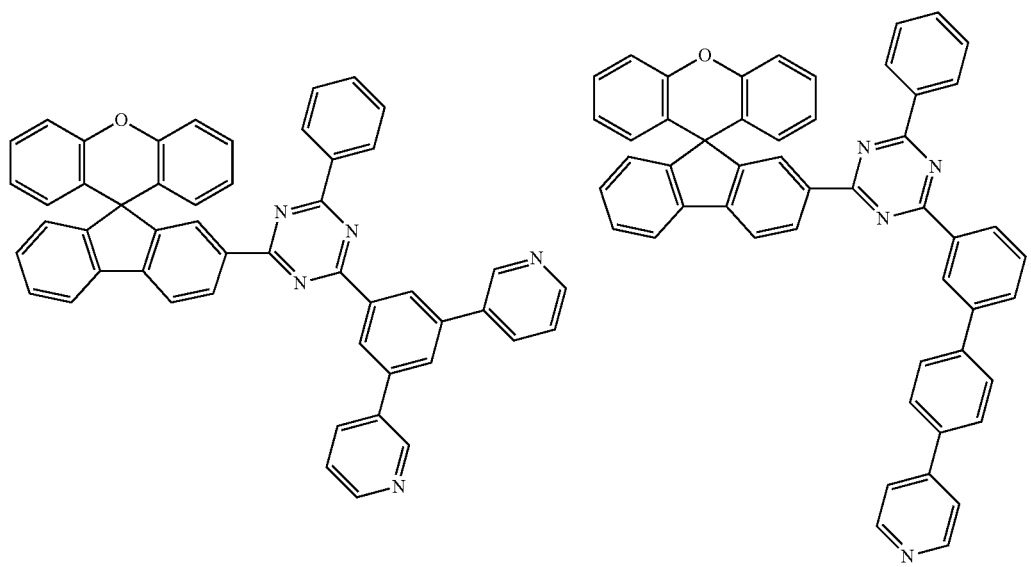
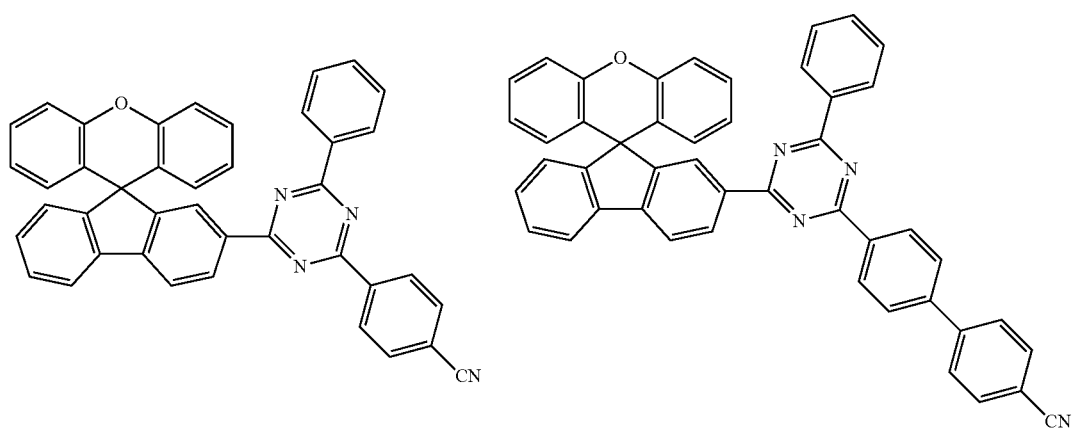

-continued
111 112
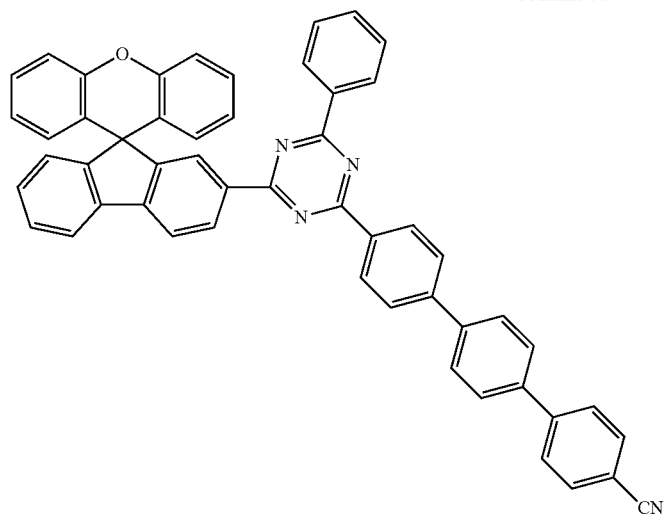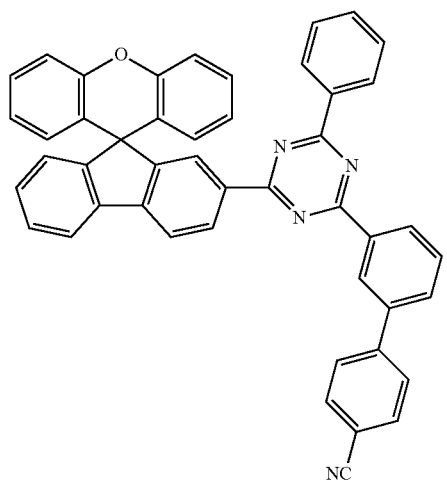
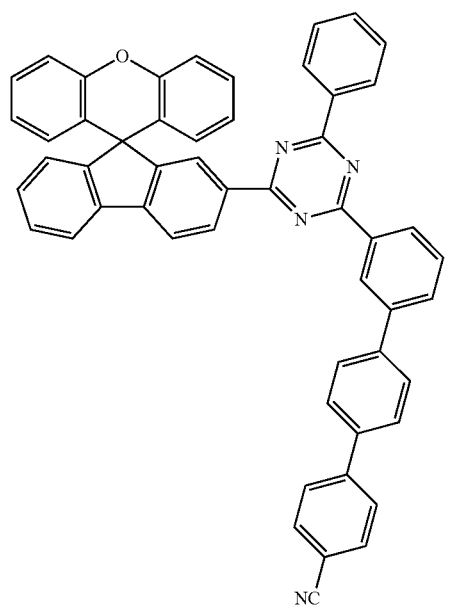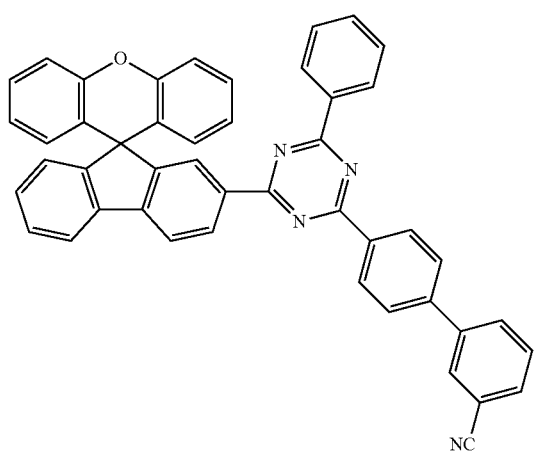
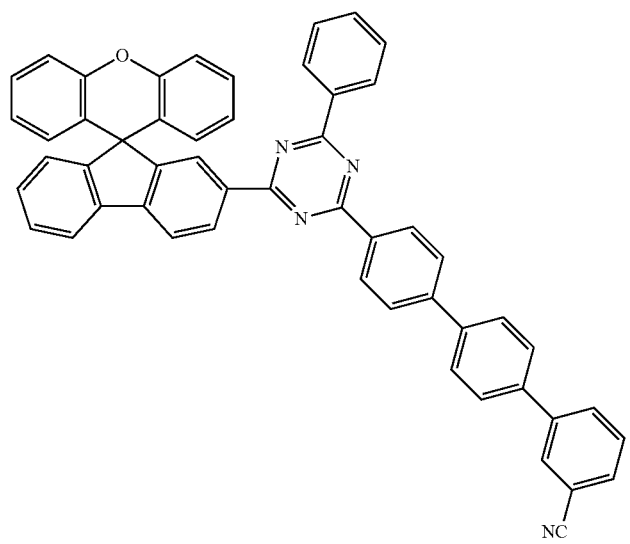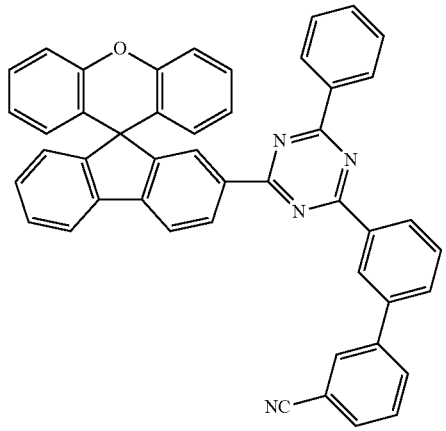

113 114
-continued
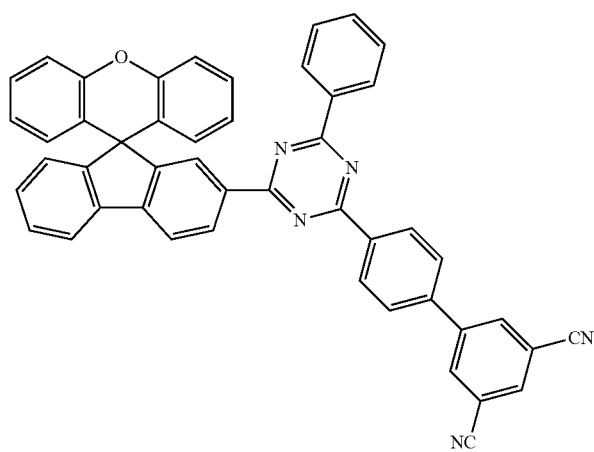
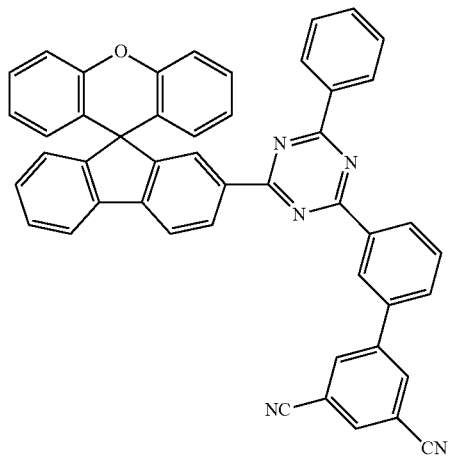
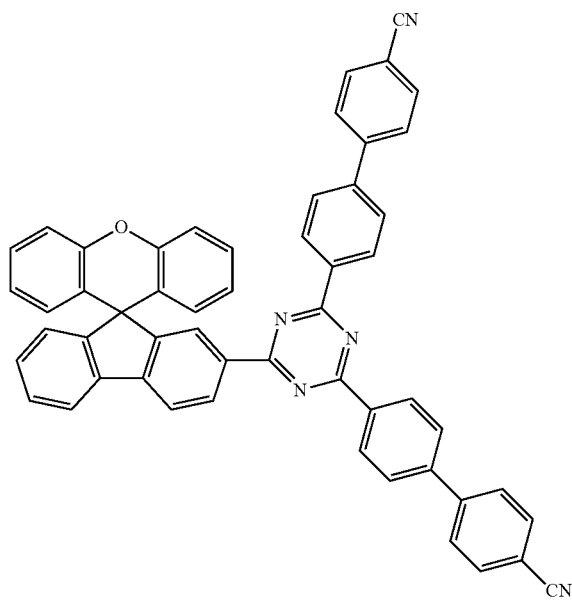
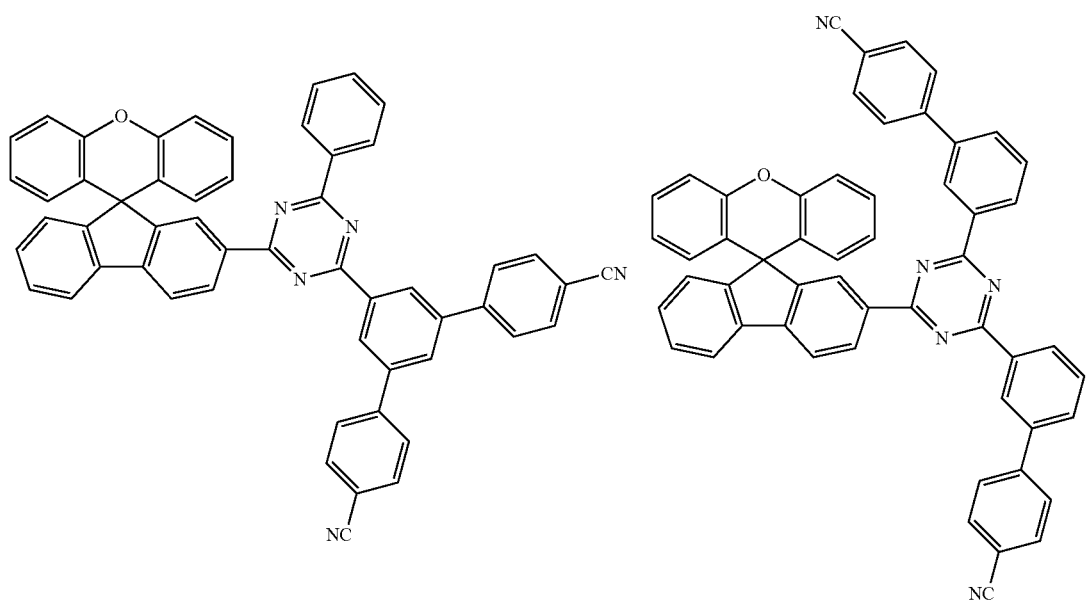

-continued
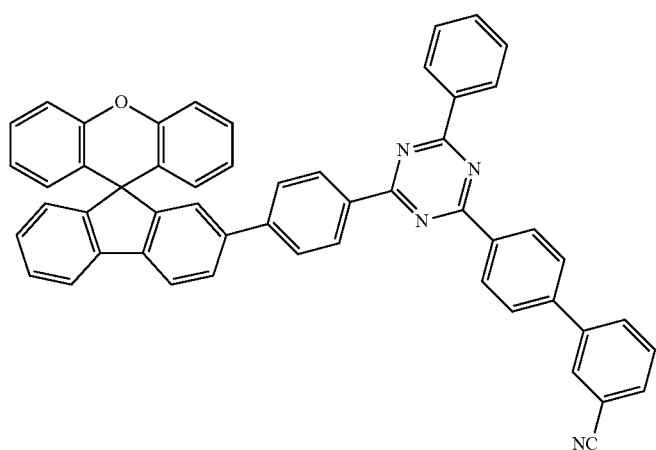
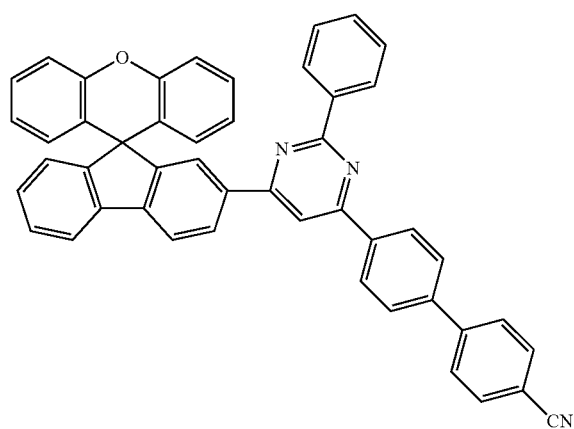
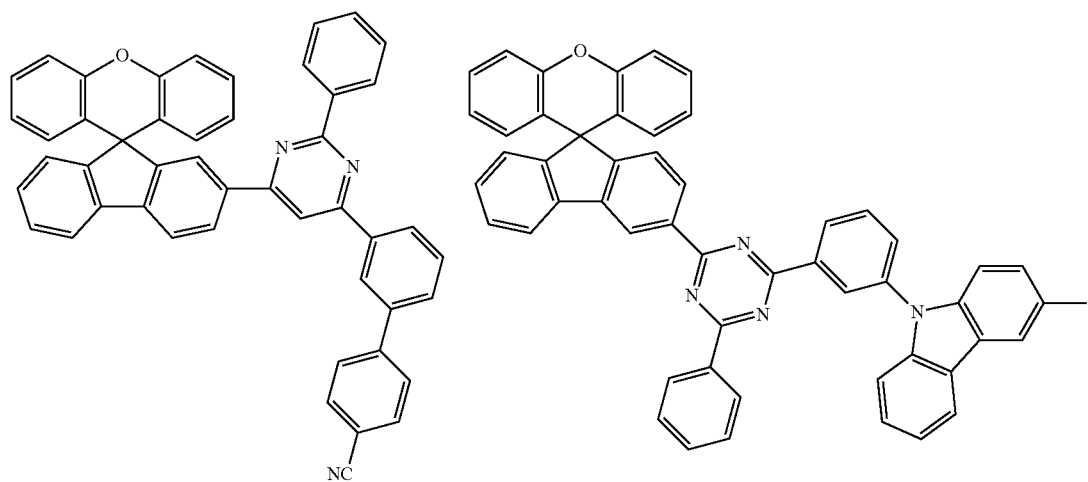

117
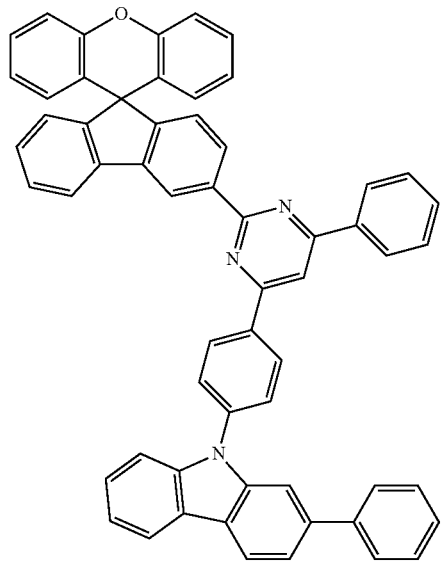
-continued
118
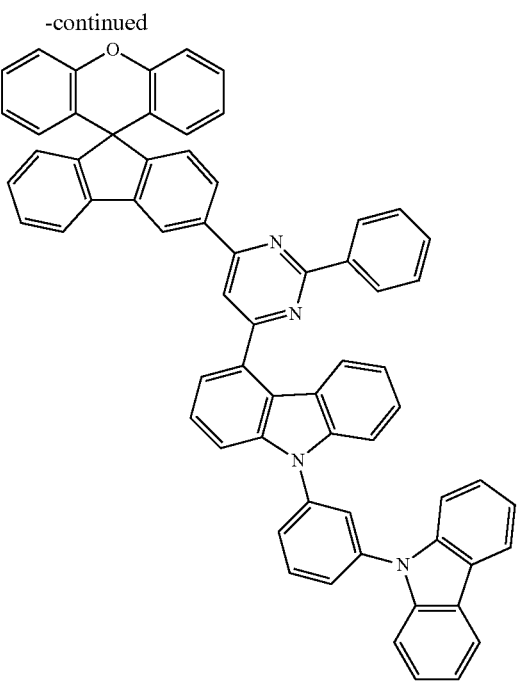
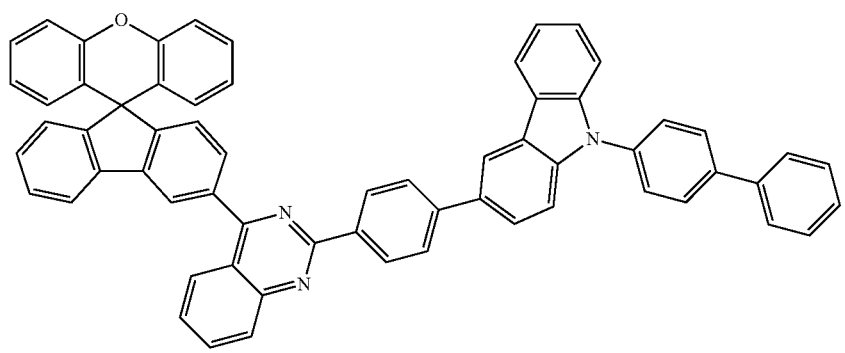
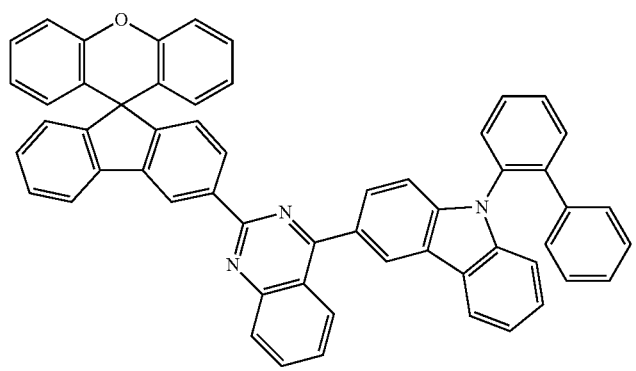

-continued
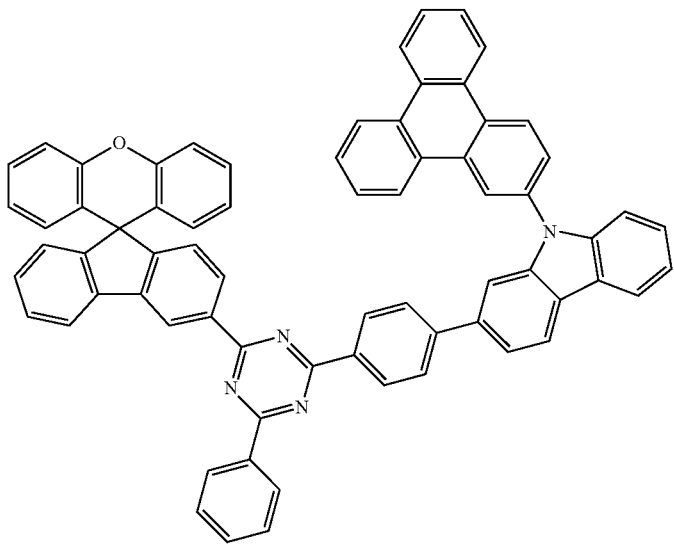
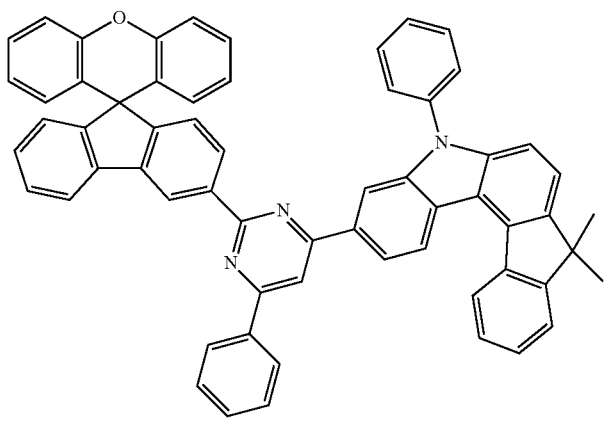
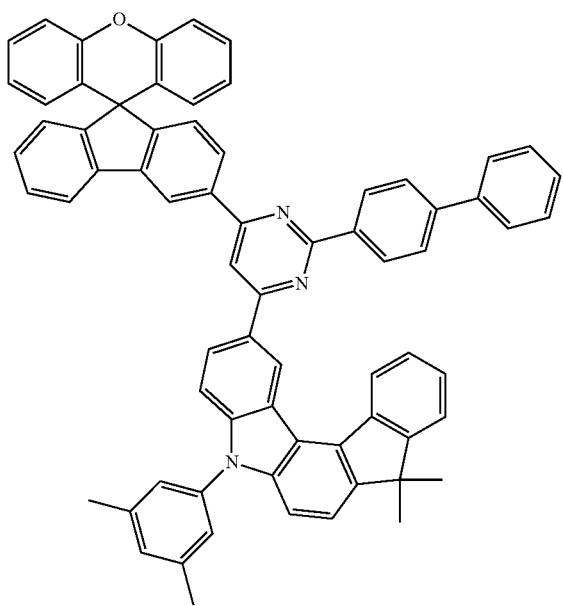

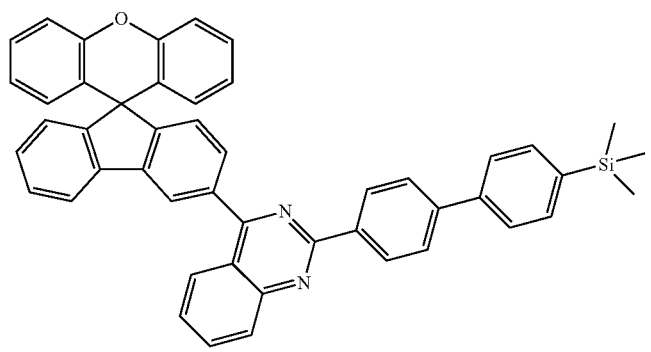
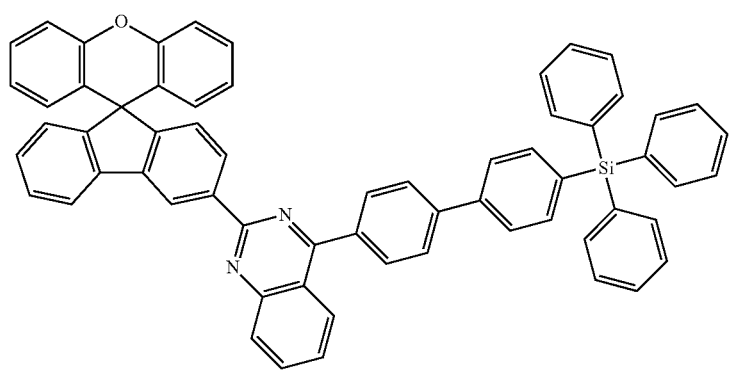
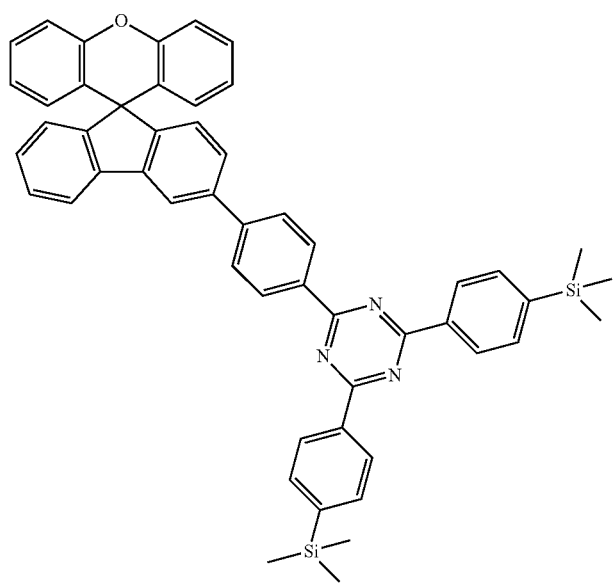

123
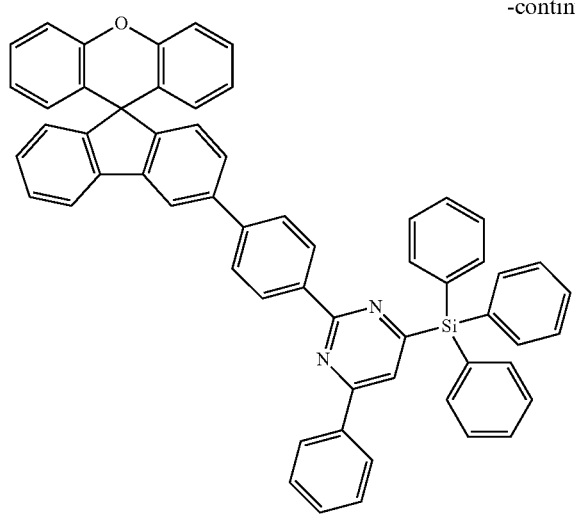
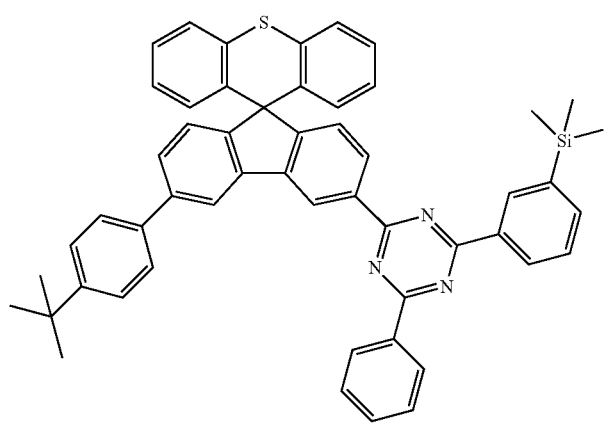
124
-continued
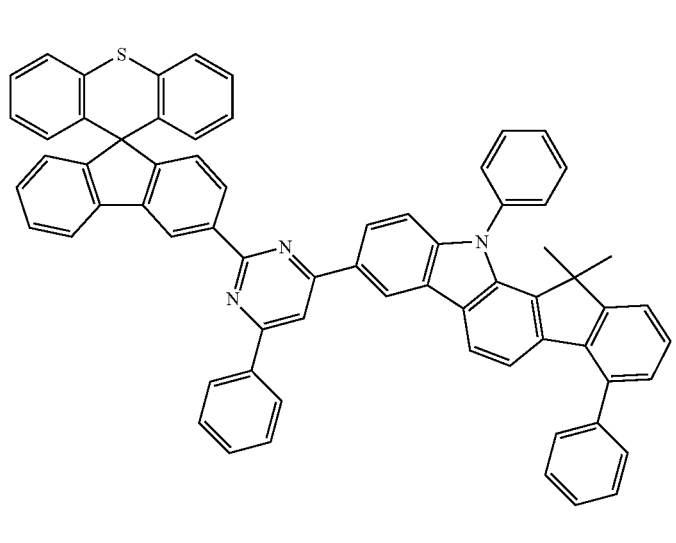
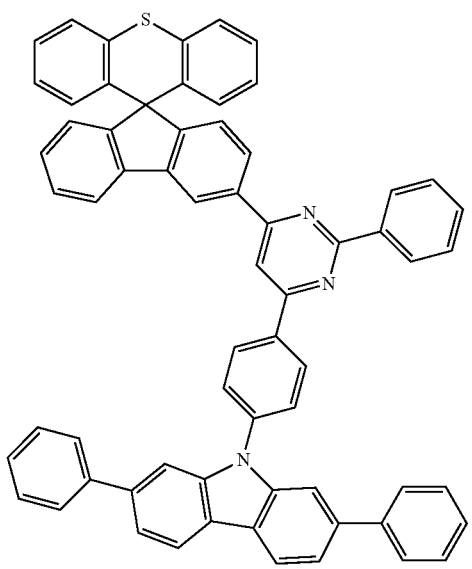

-continued
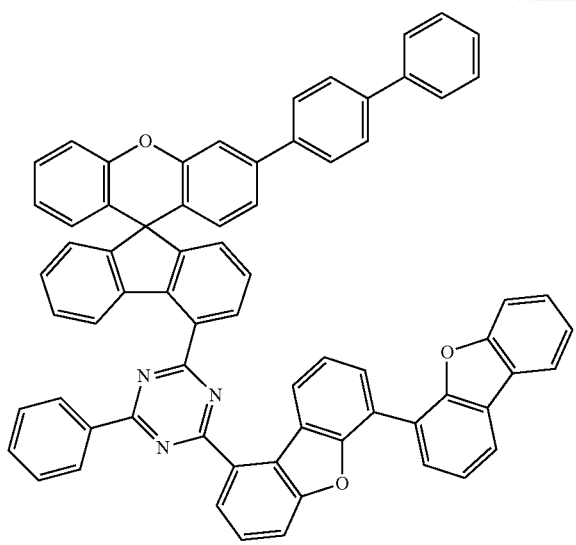
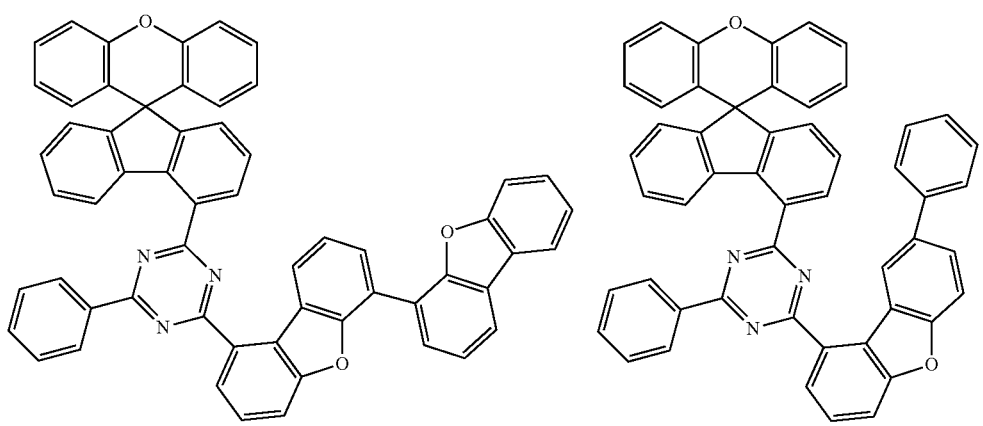
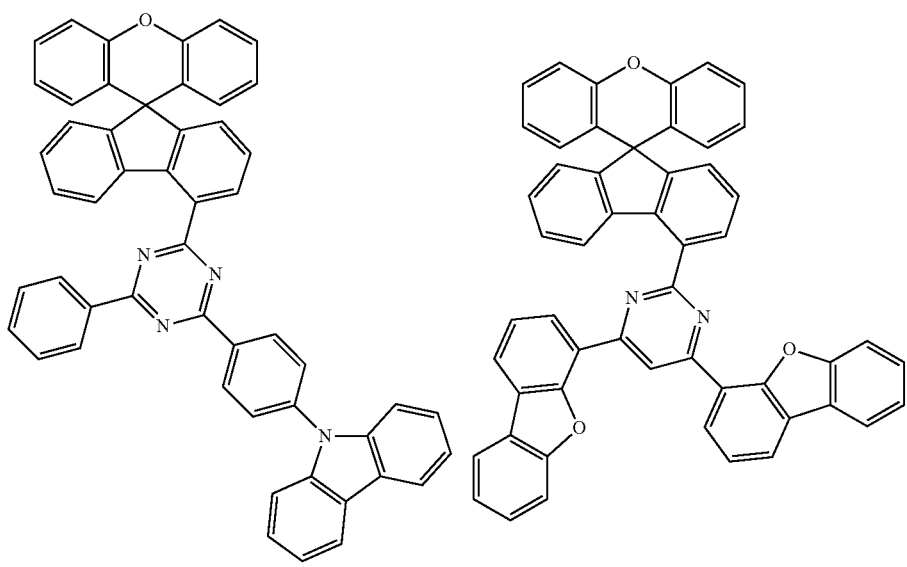

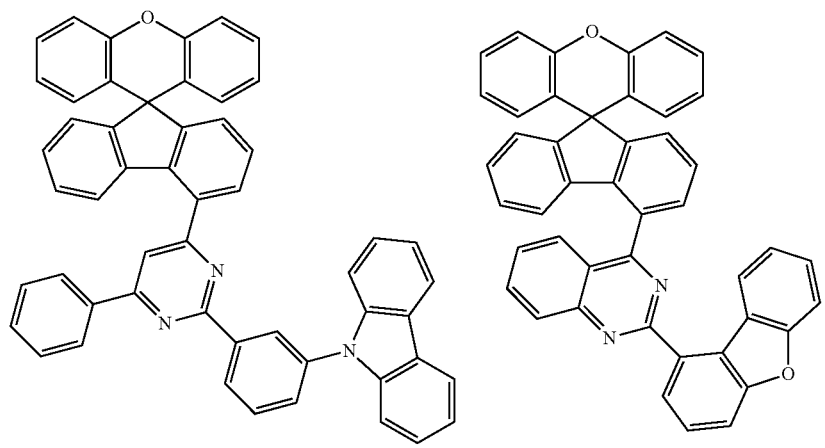
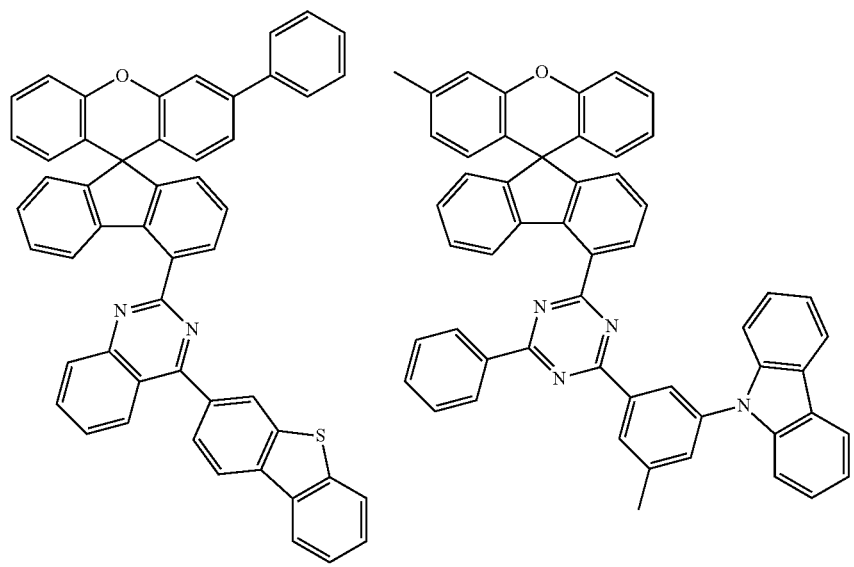
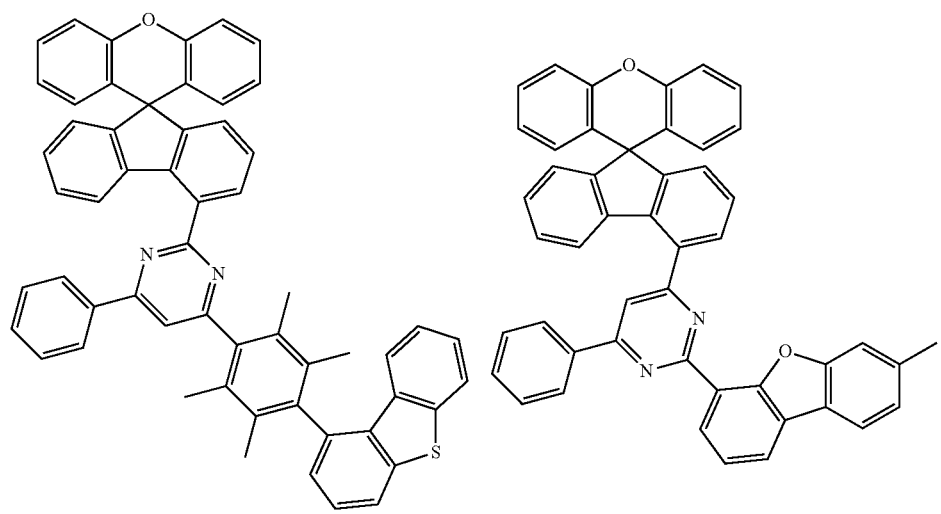

129
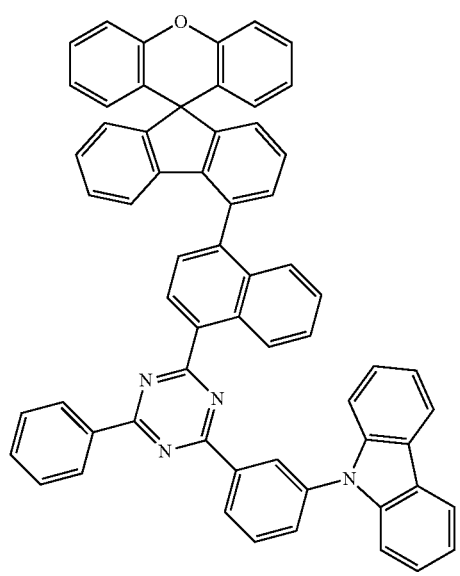
130
-continued
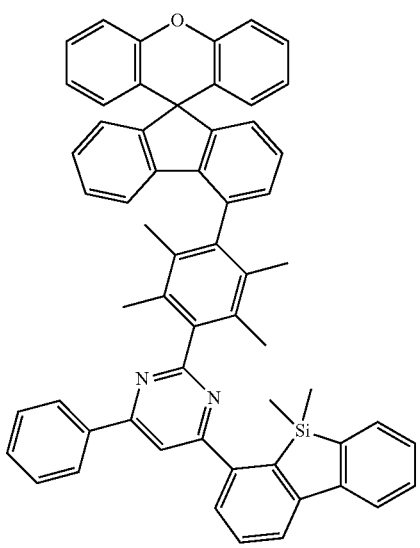
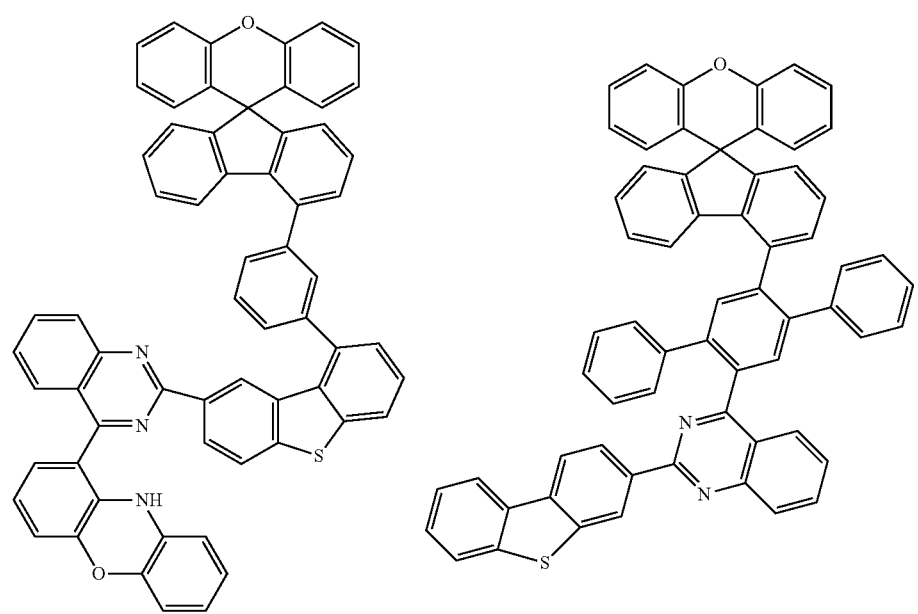

131
-continued
132
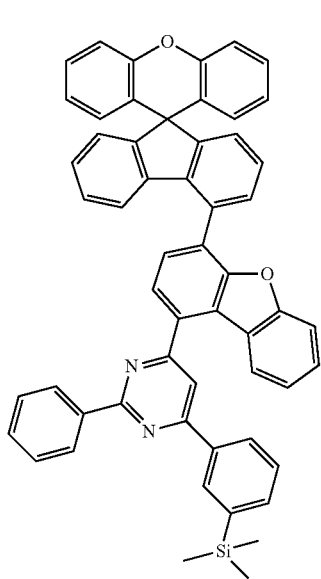
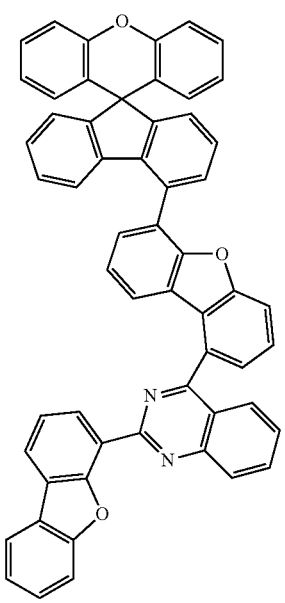
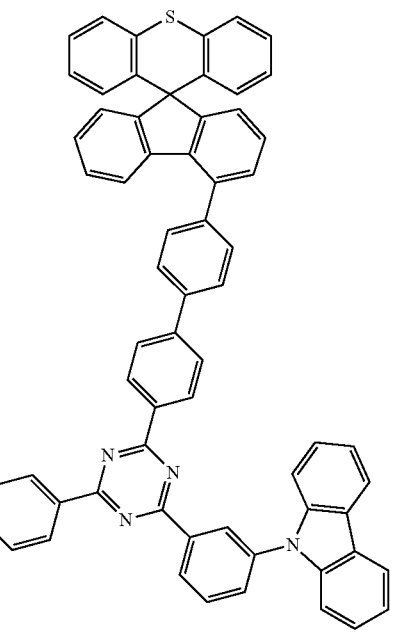
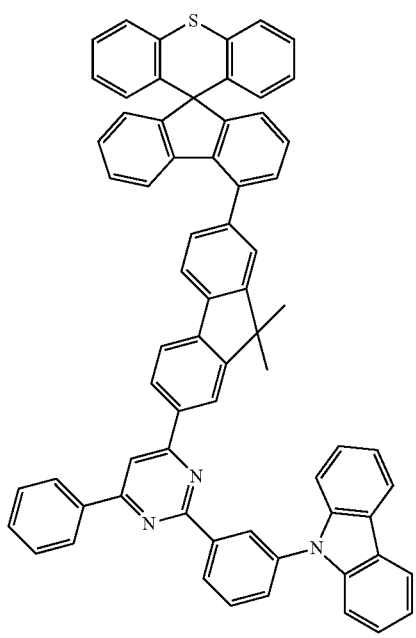
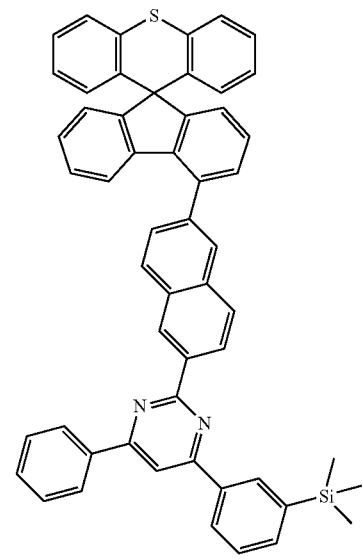
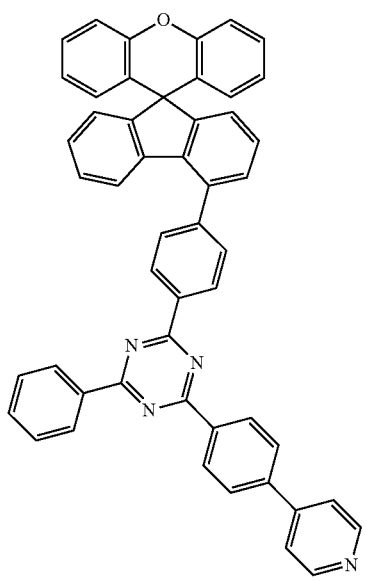

-continued
133
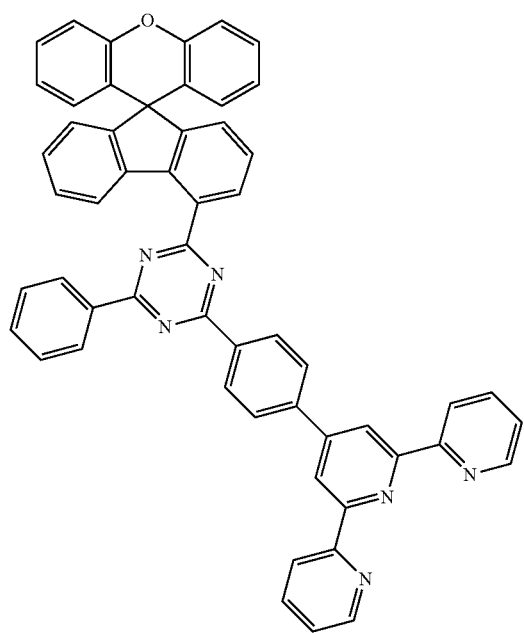
134
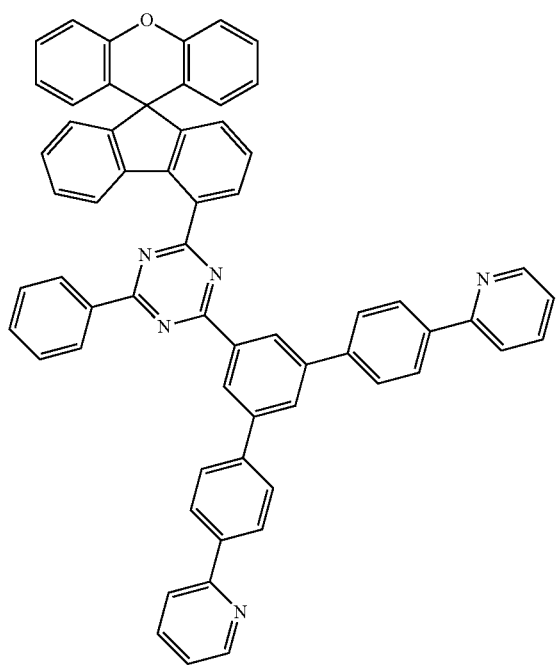
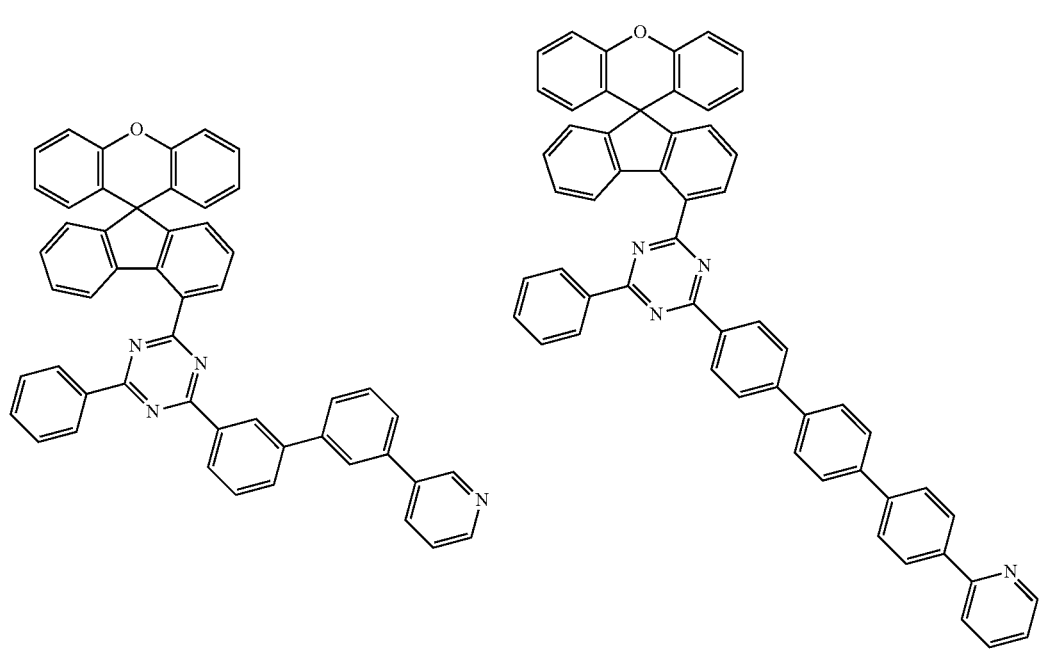

-continued
135
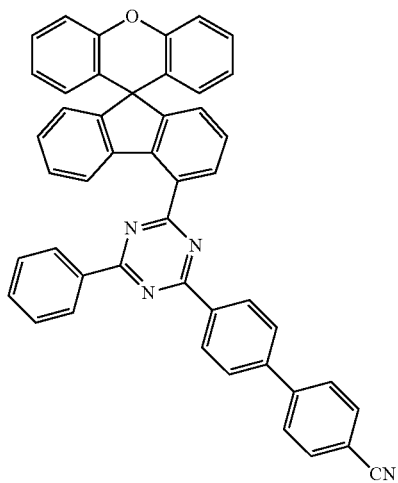
136
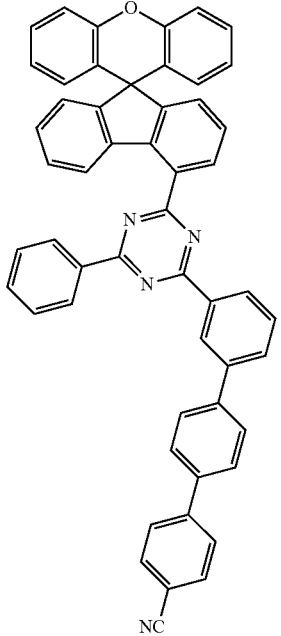
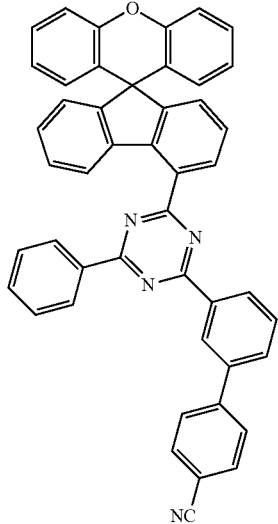
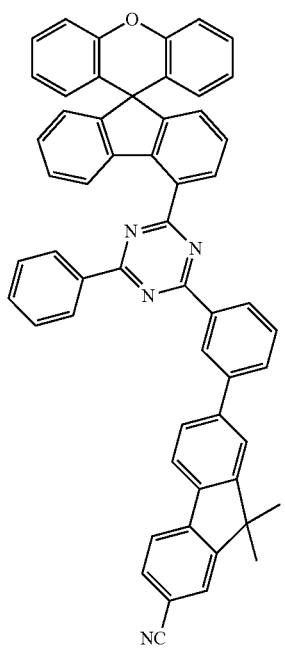
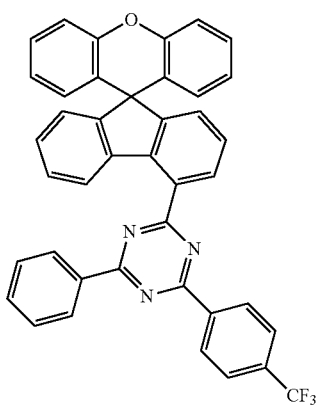
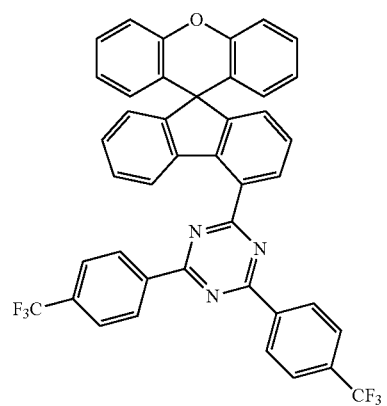

-continued
137
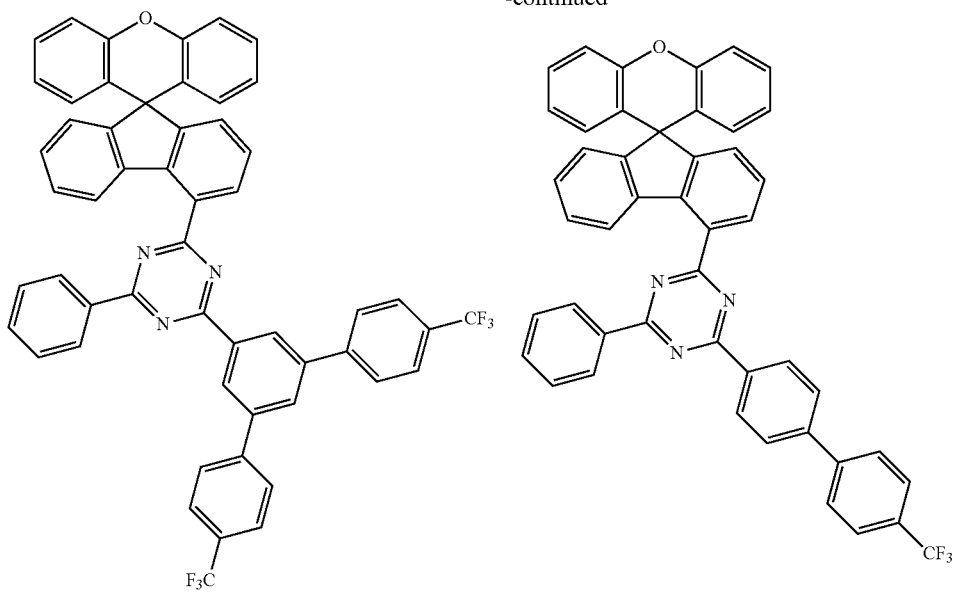
138
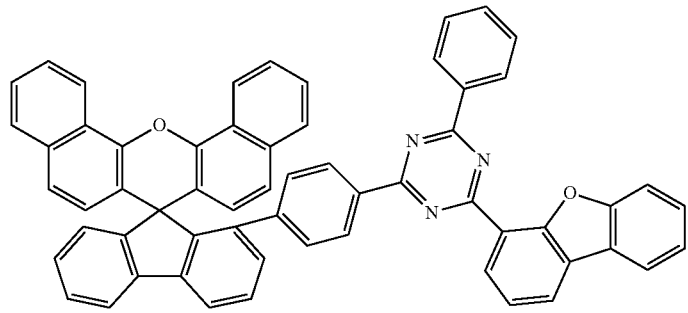
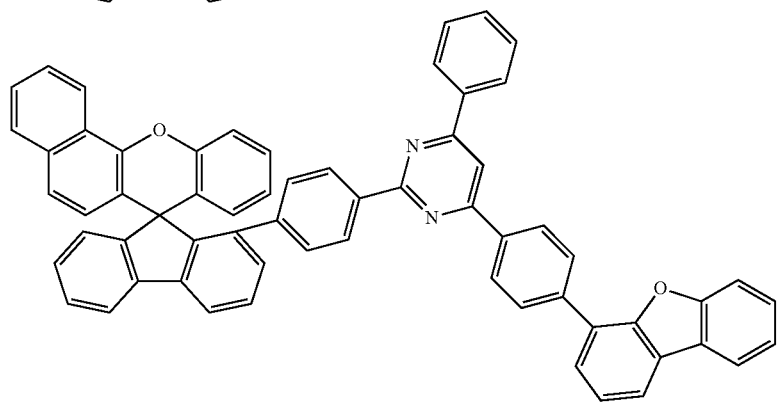
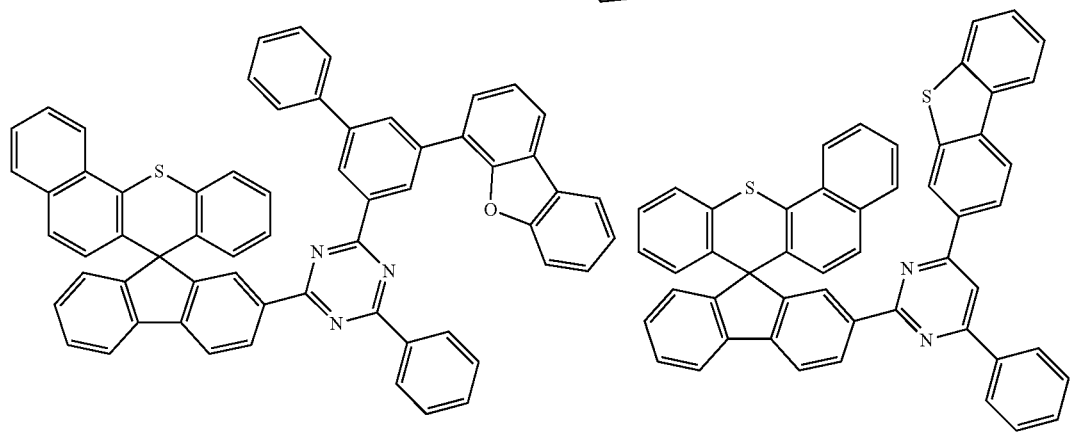

-continued
139
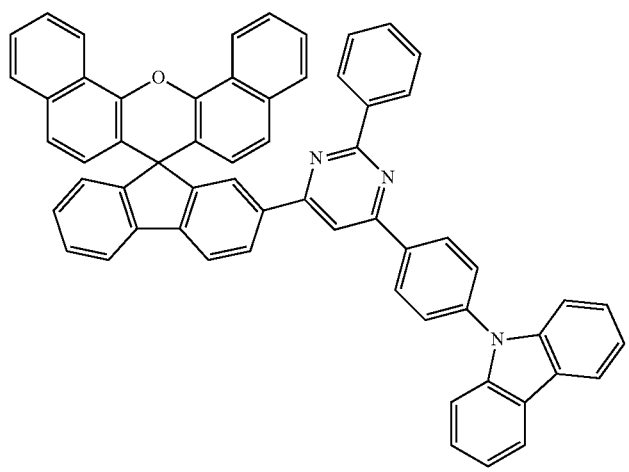
140
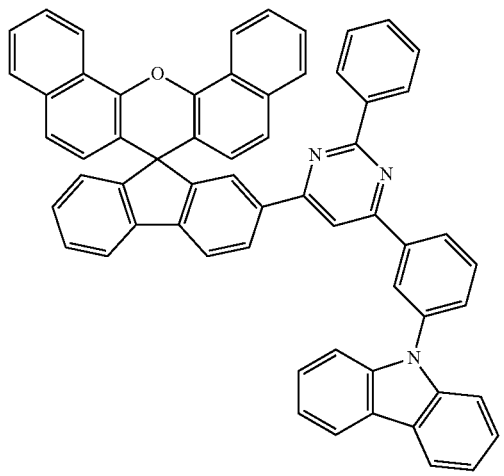
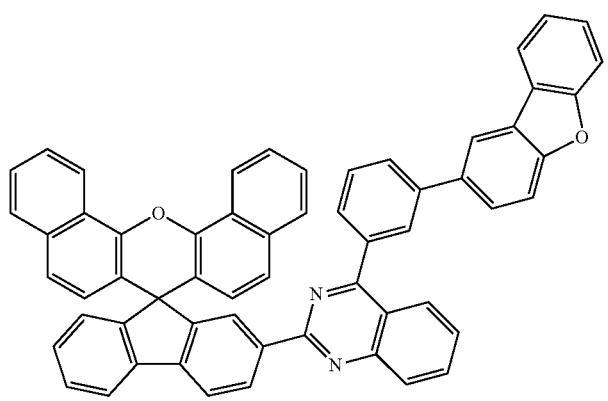
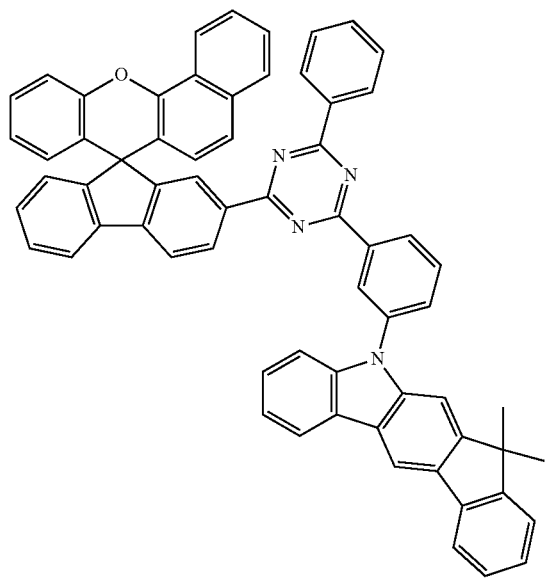

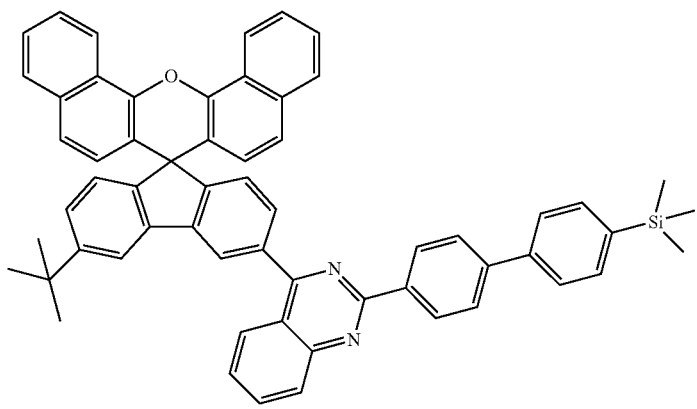

-continued
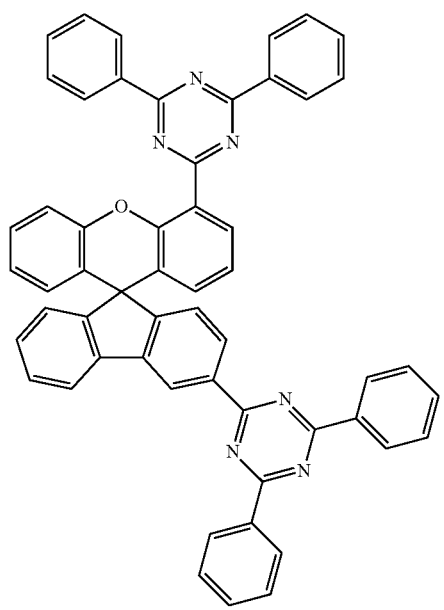
143
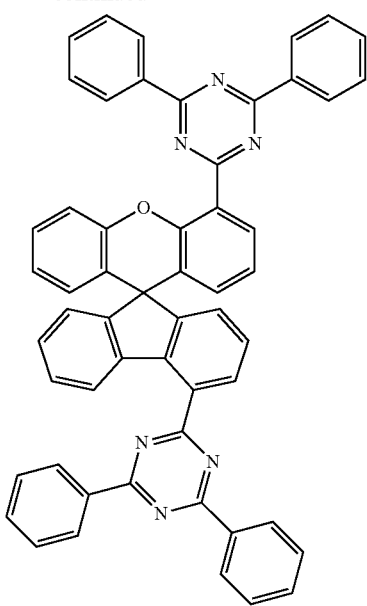
144
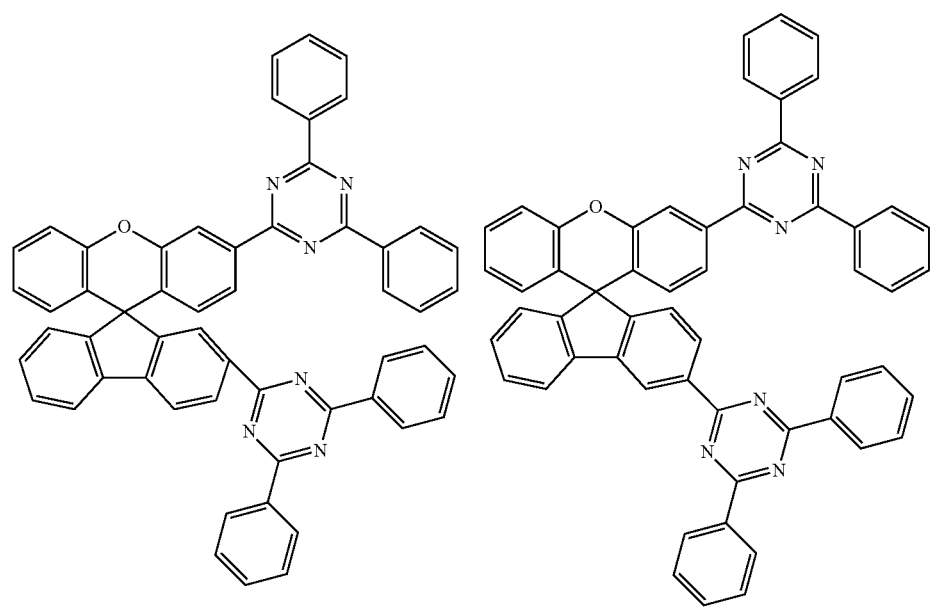

145 146
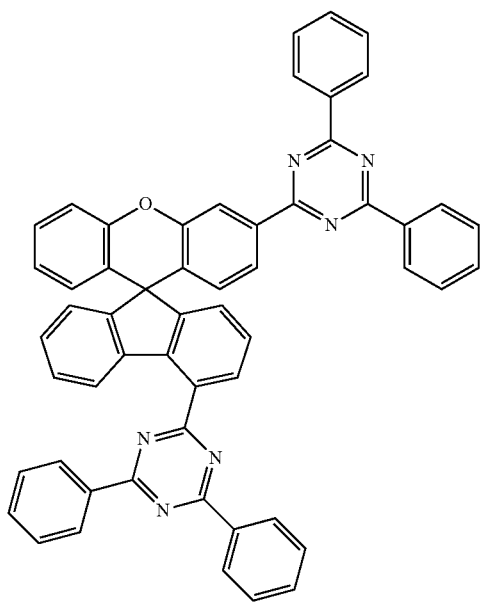
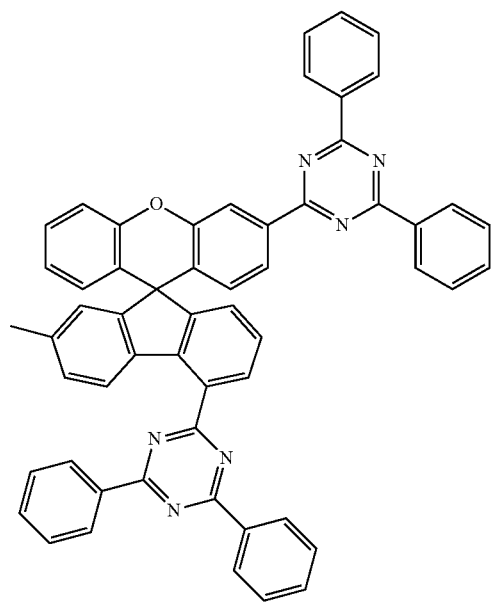
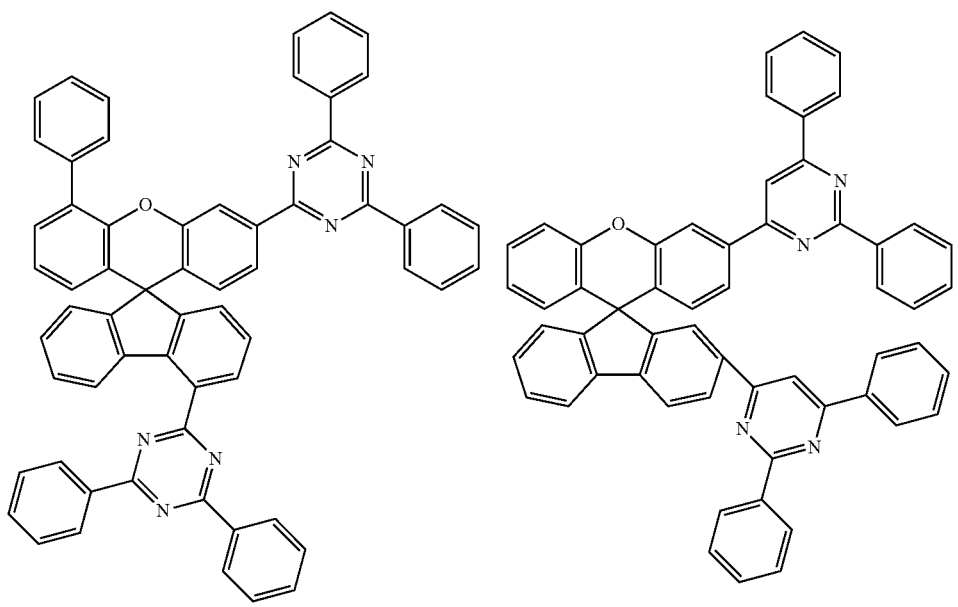

147 148
-continued
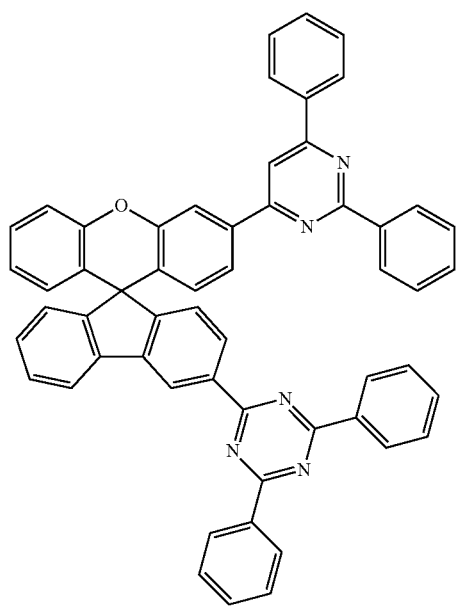
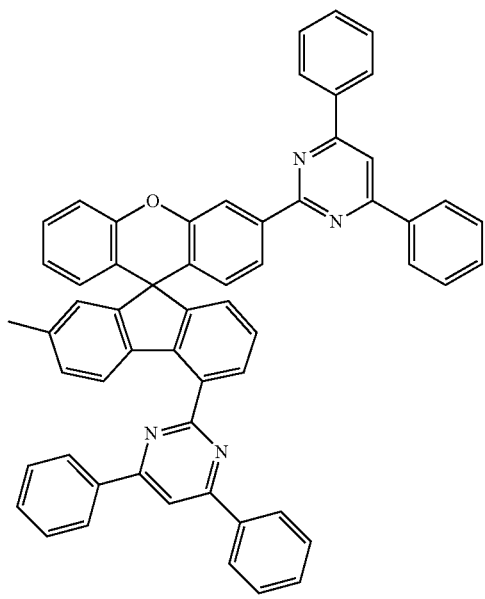
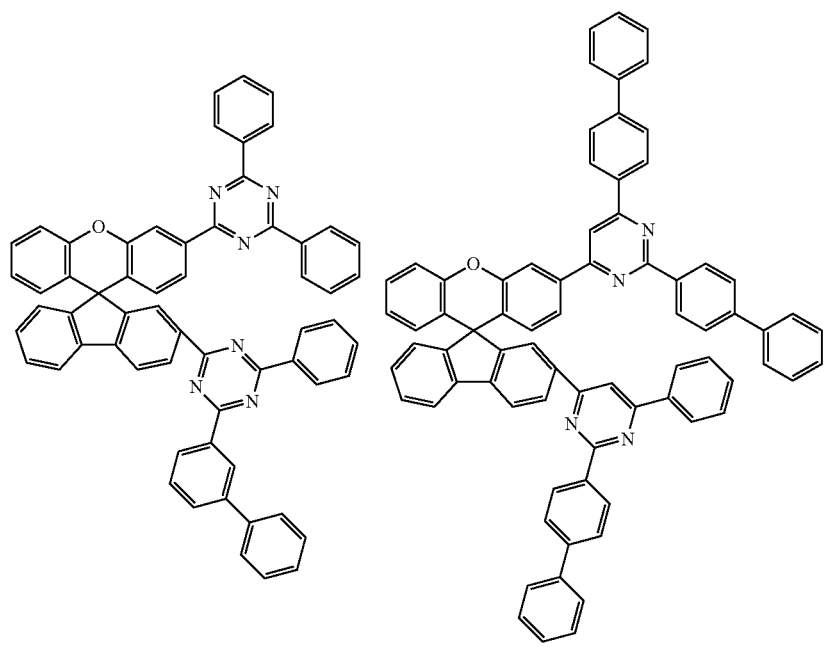

149
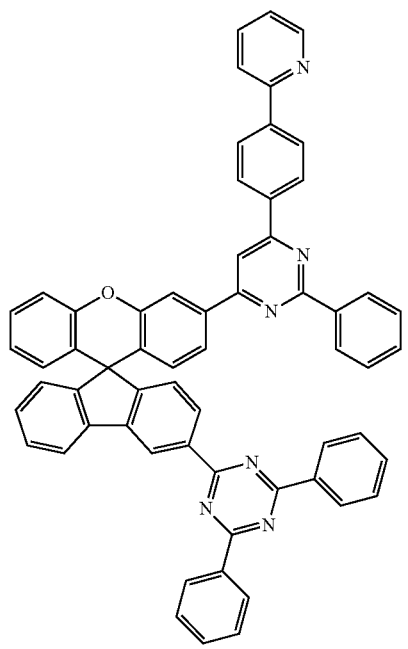
150
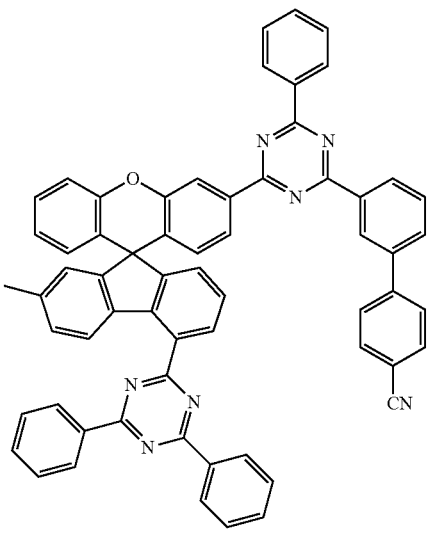
-continued
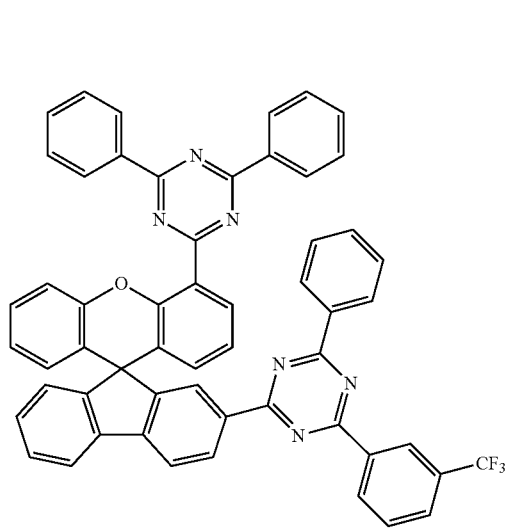
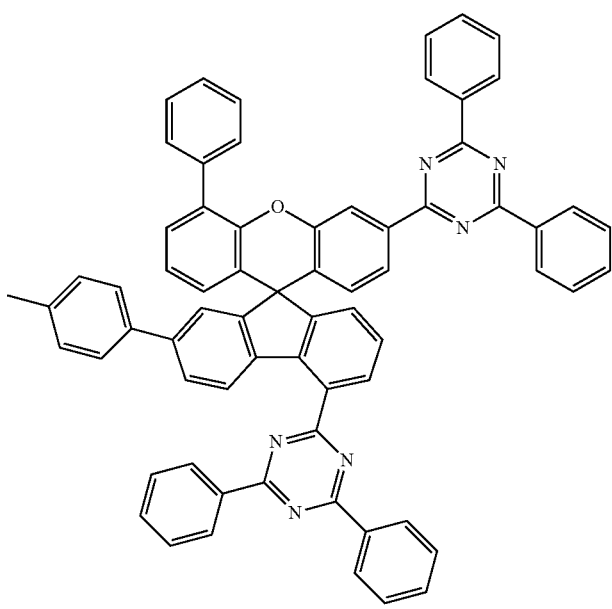

-continued
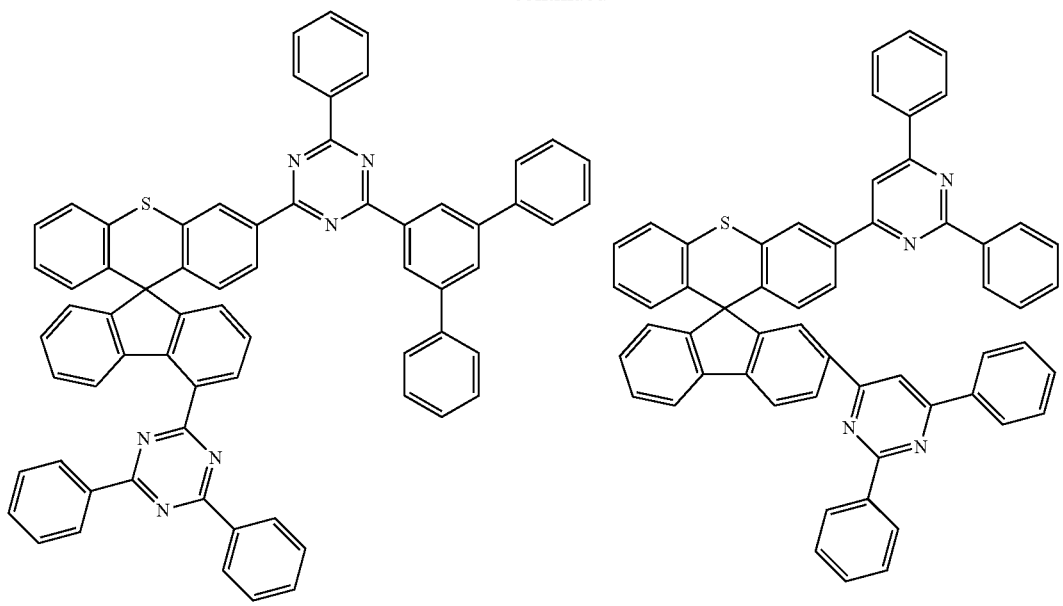
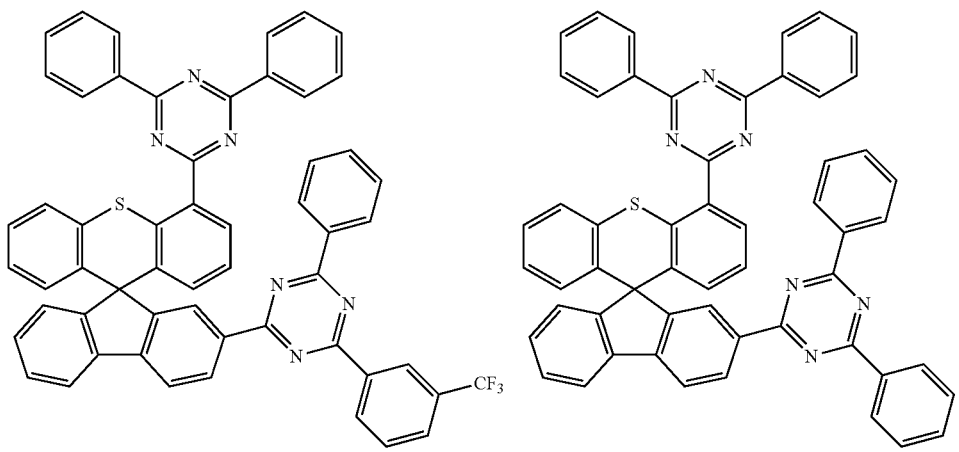
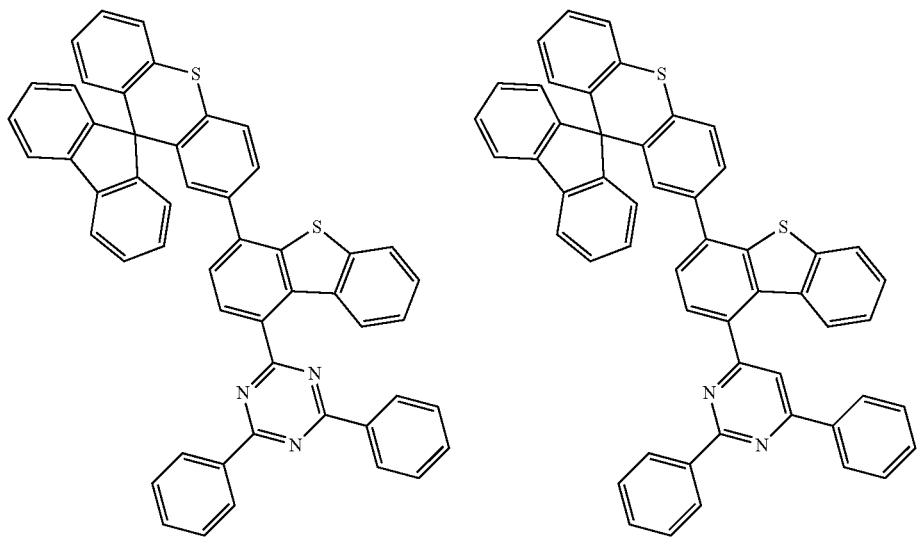

153
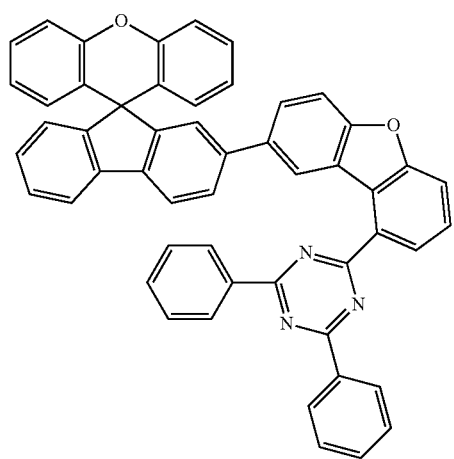
154
-continued
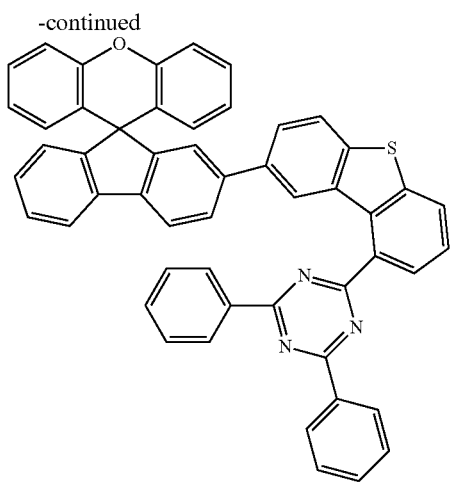
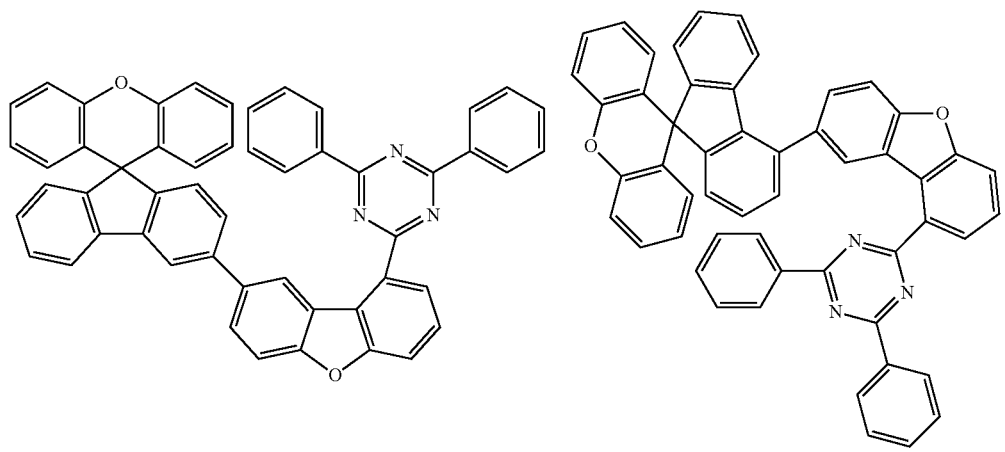
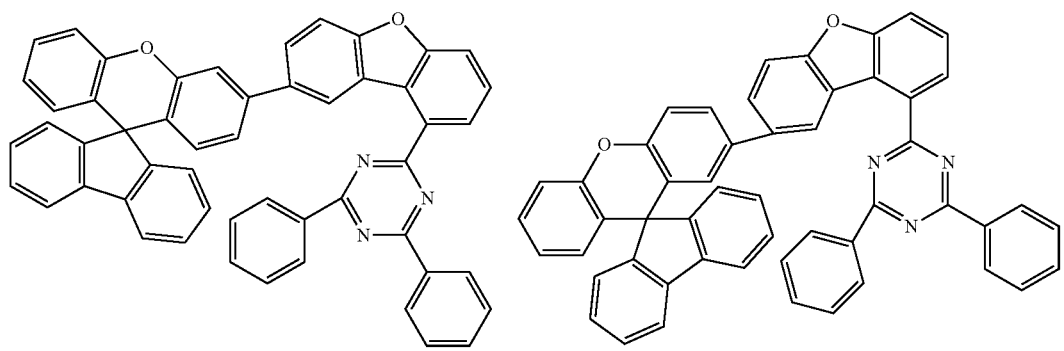

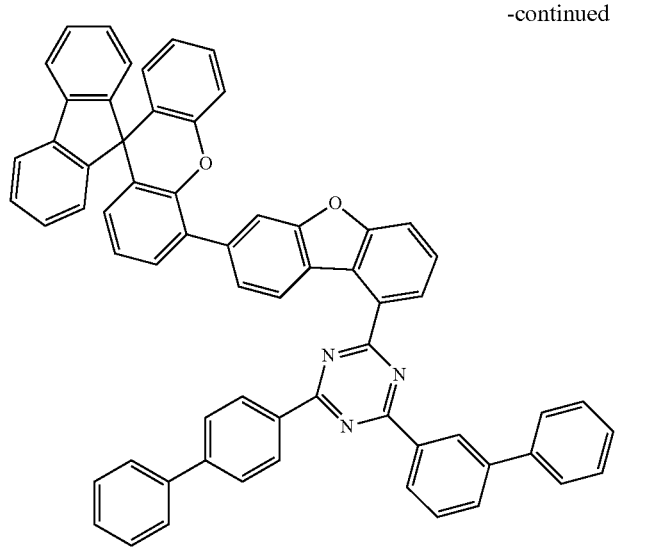
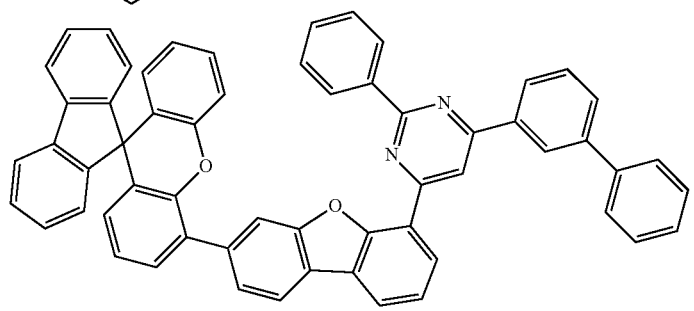
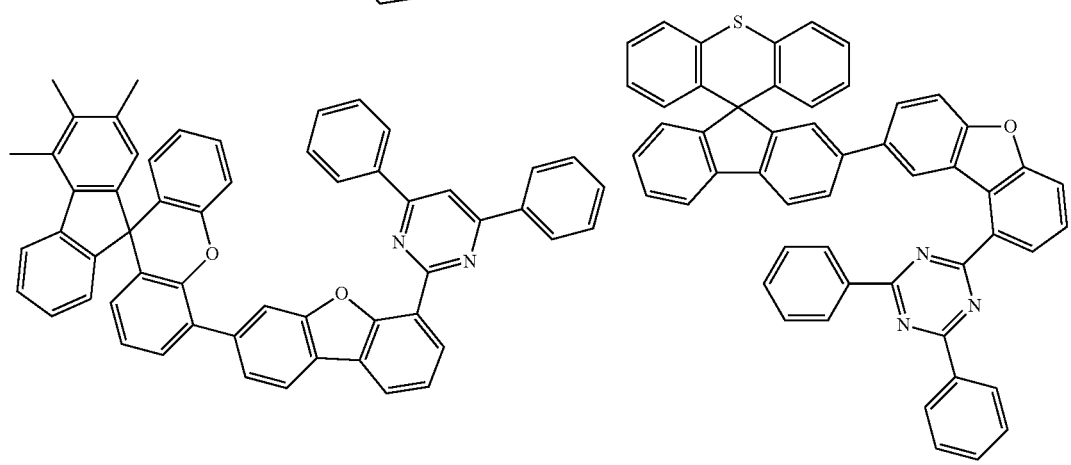
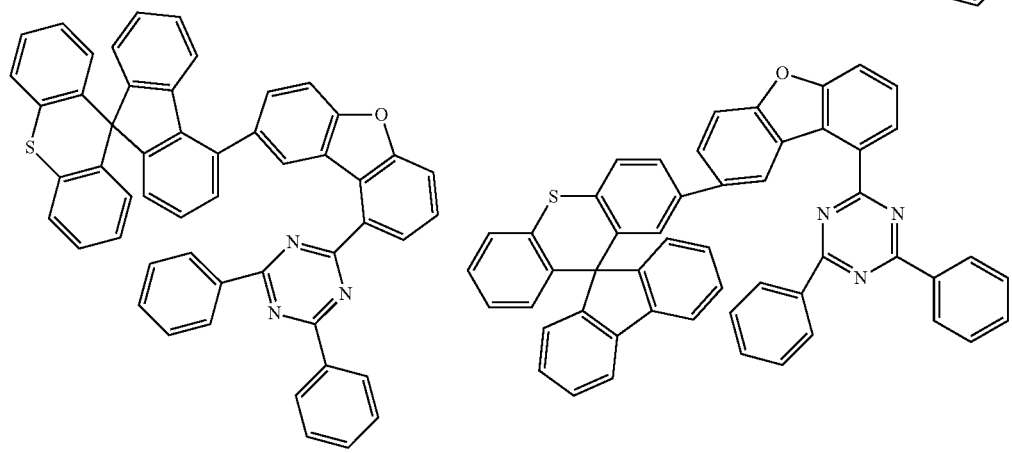

-continued
157
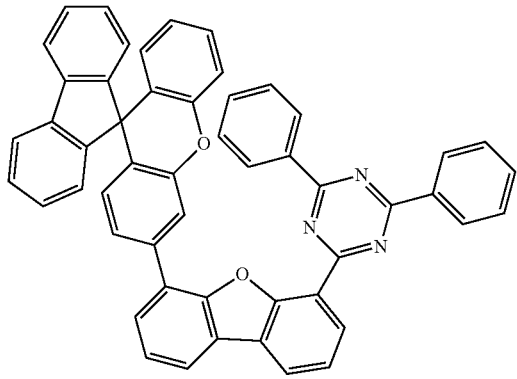
158
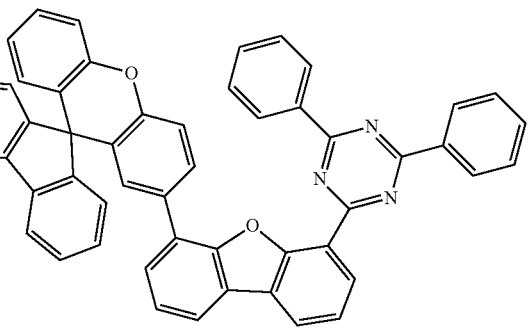
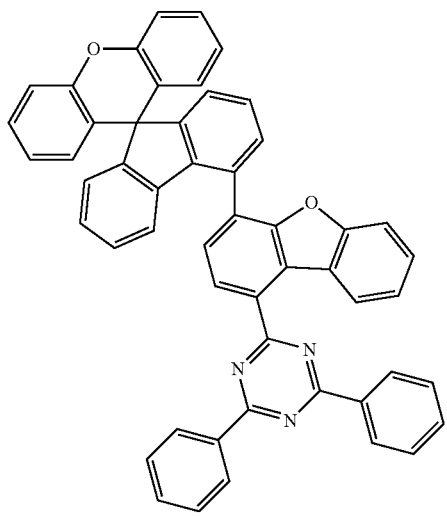
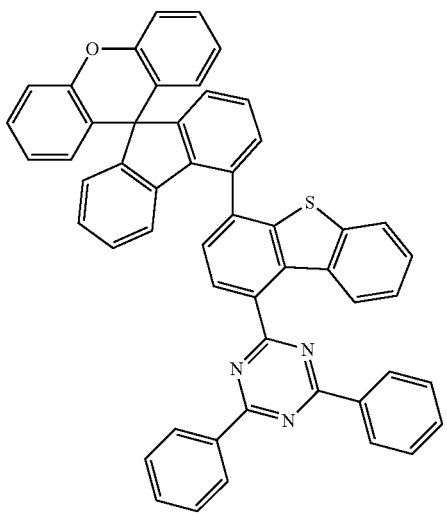
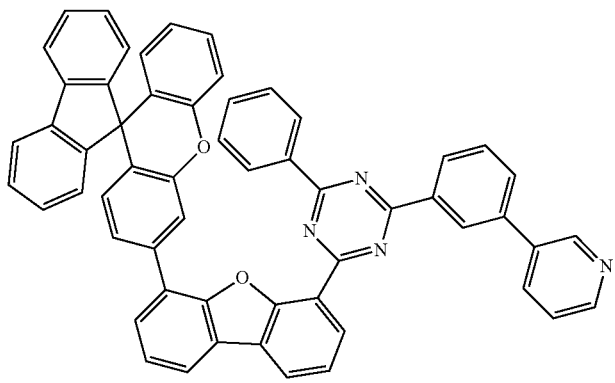
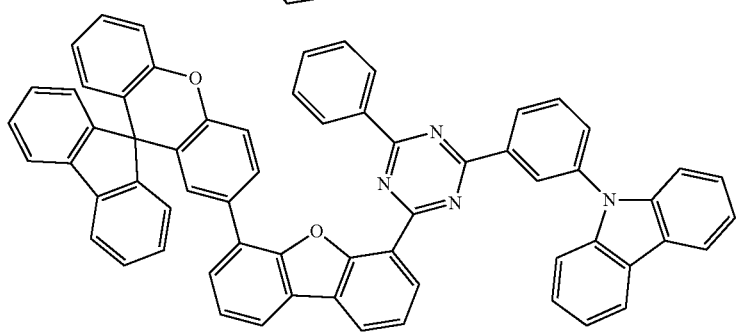

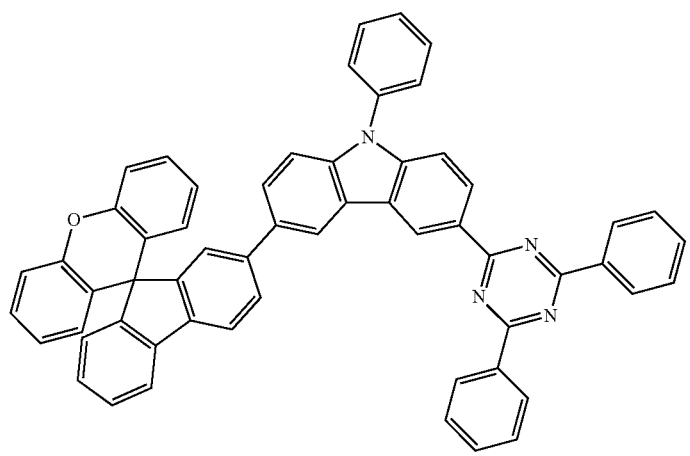
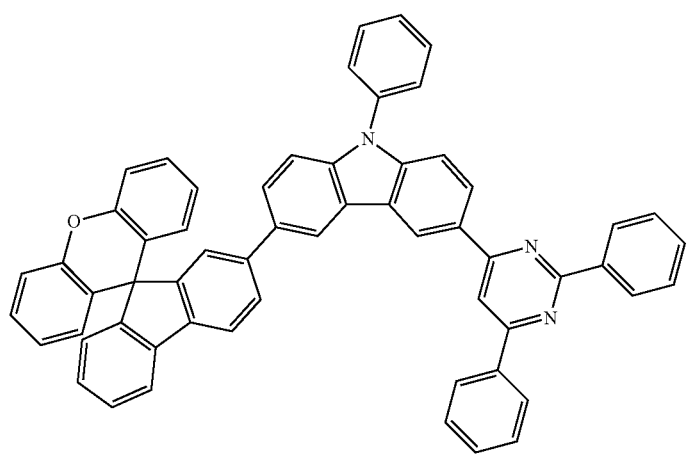
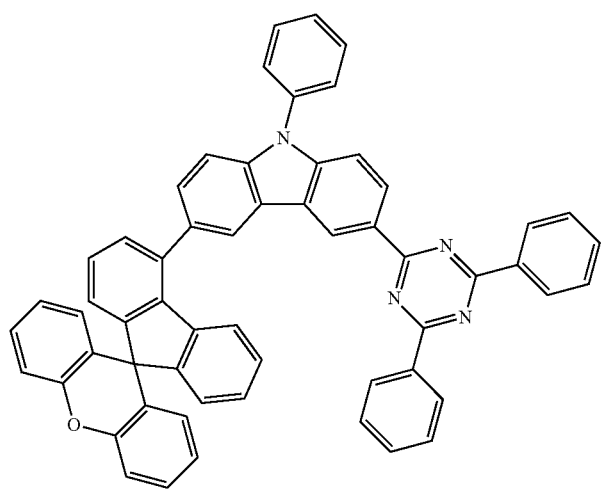

-continued
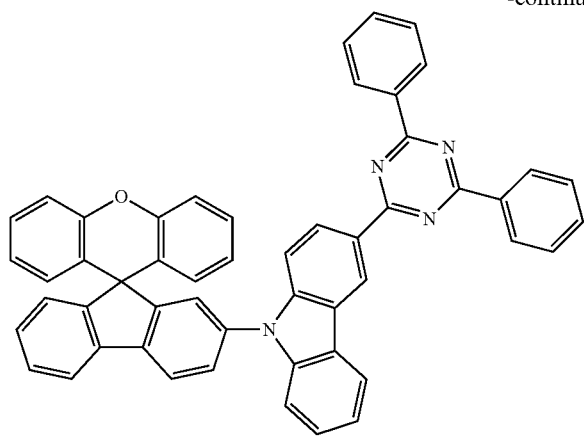
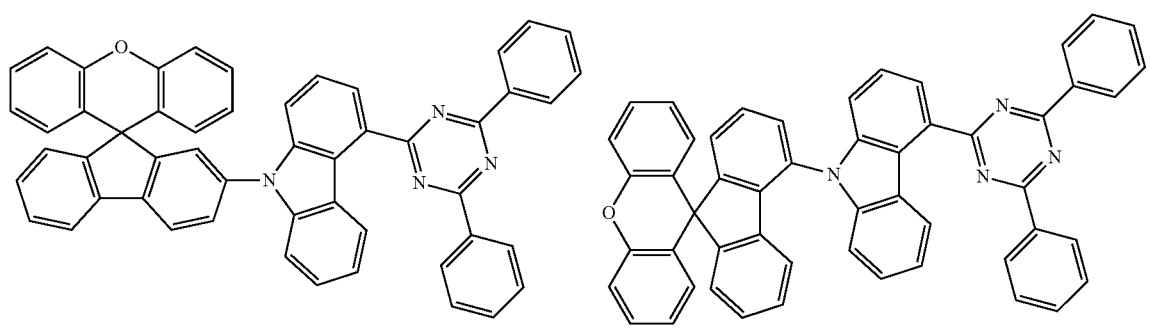
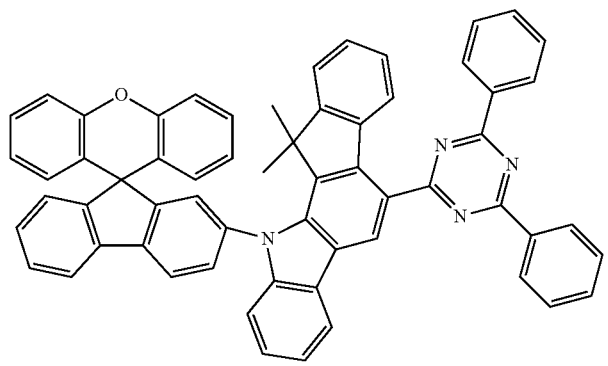
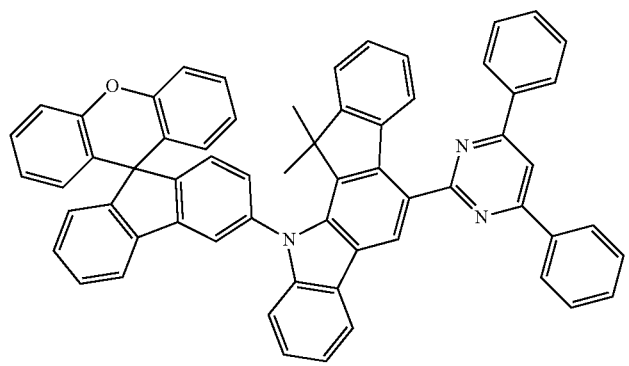

-continued
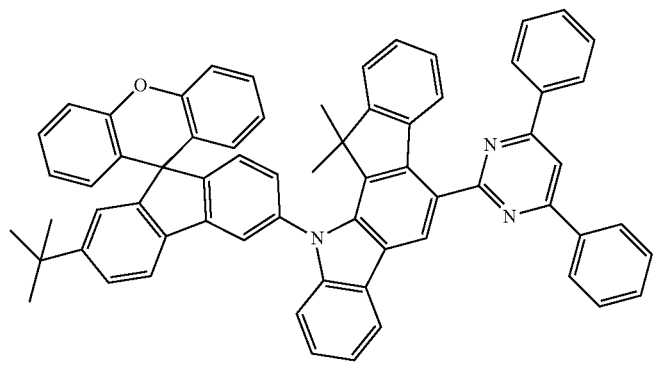
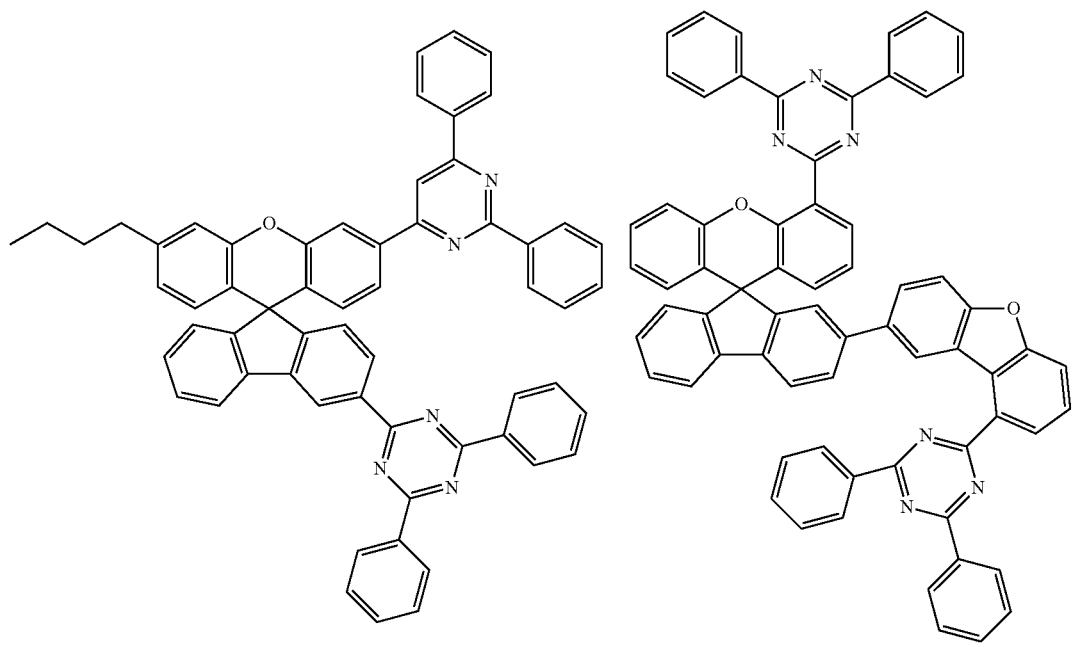
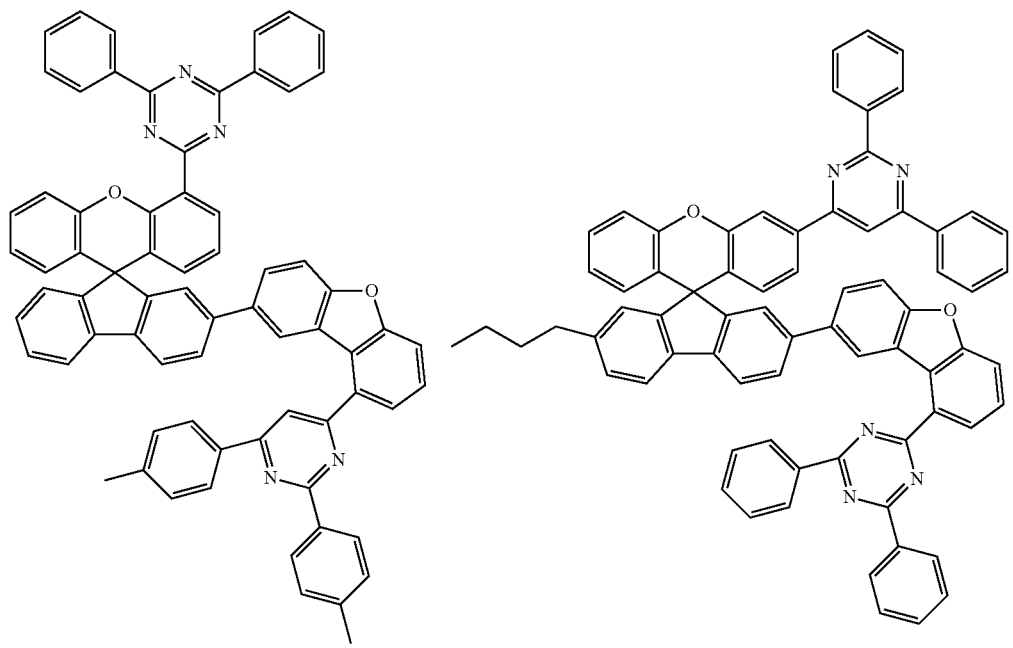

-continued
165
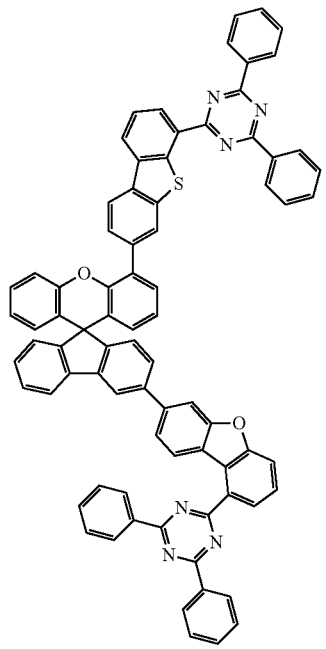  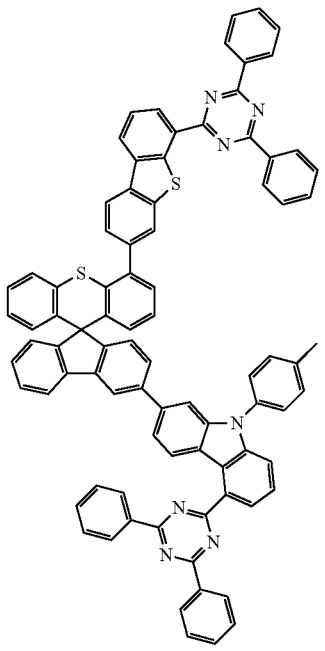
166
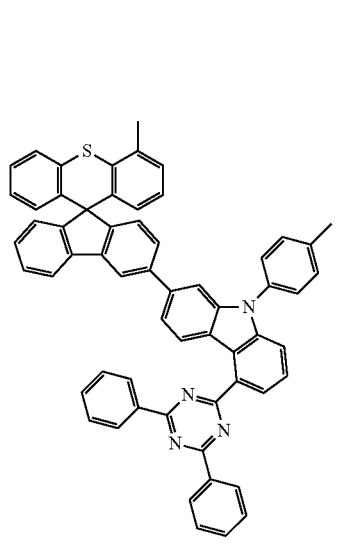 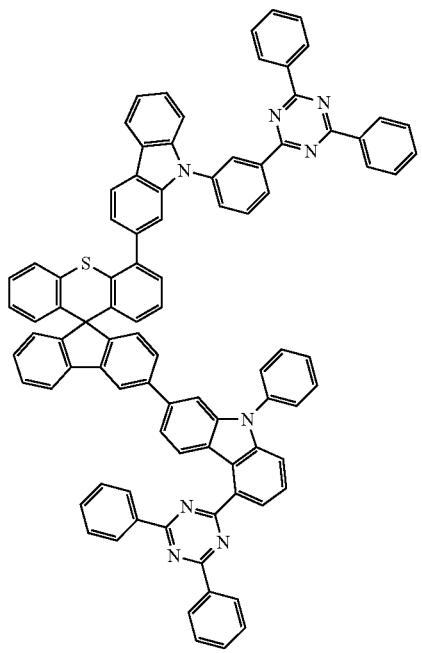 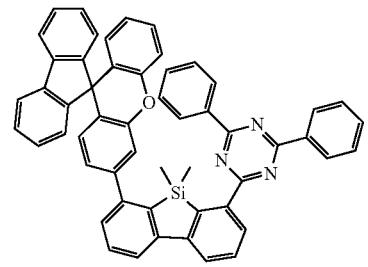
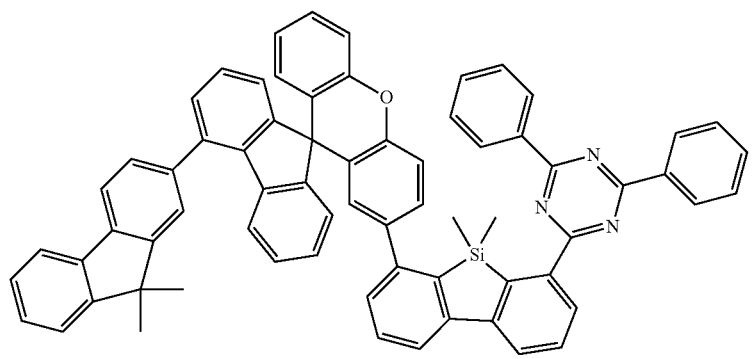

167
168
-continued
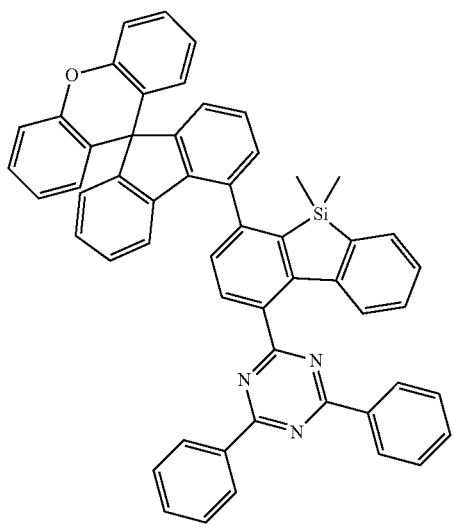
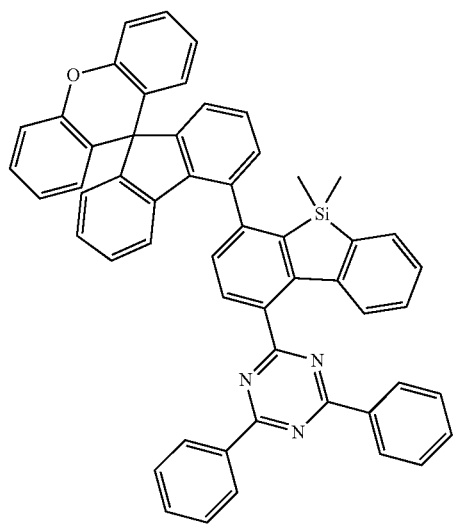
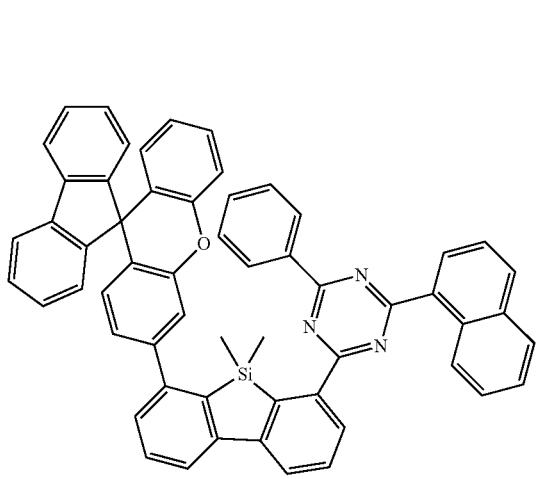
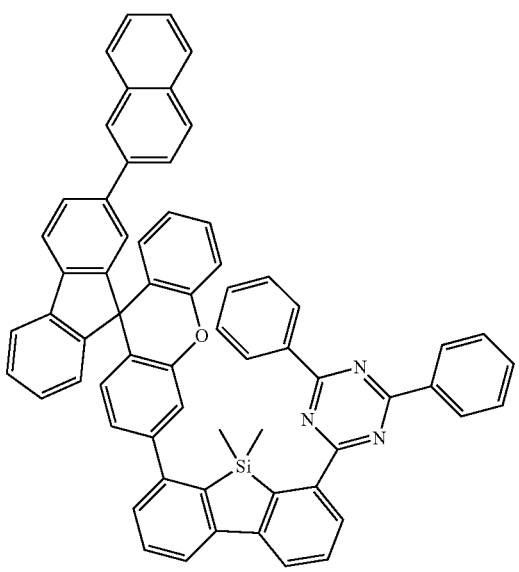
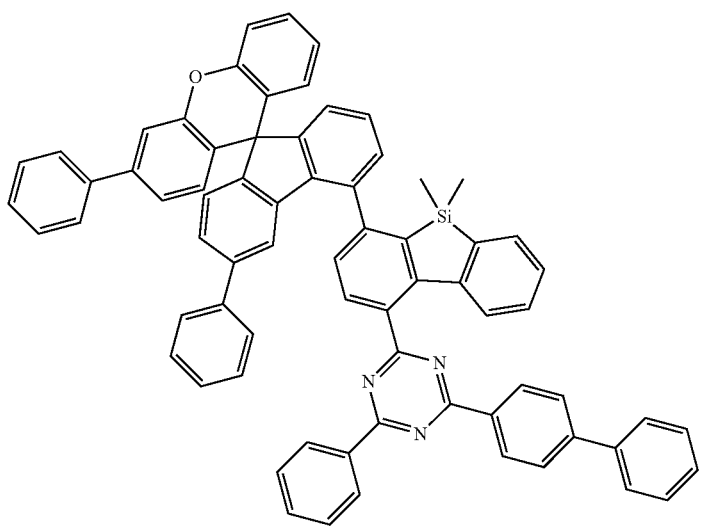

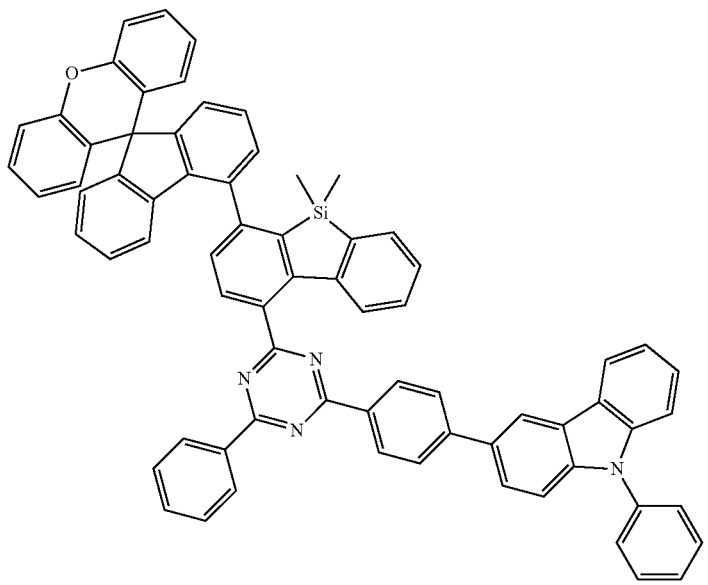
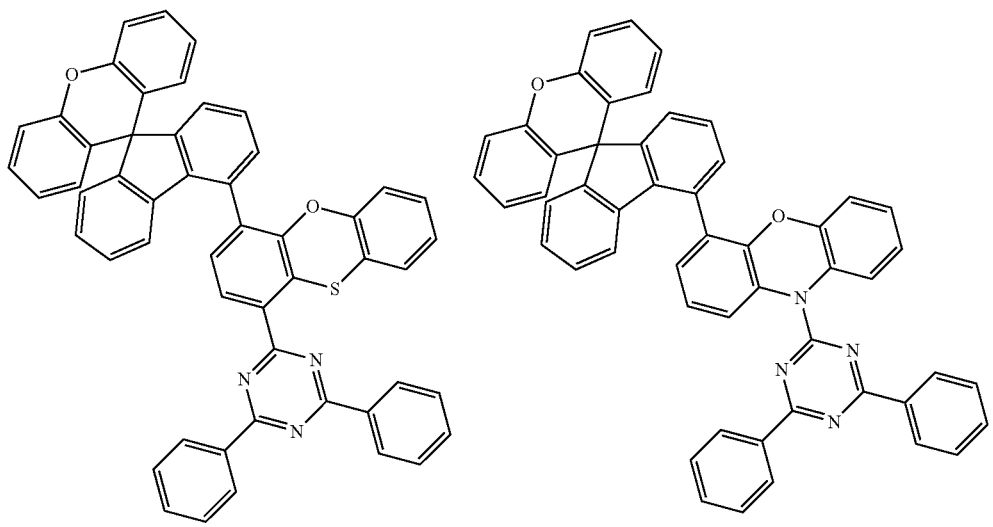
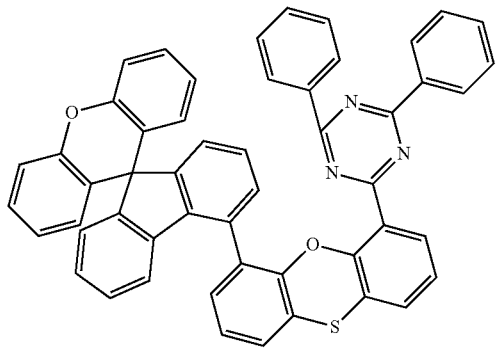

-continued
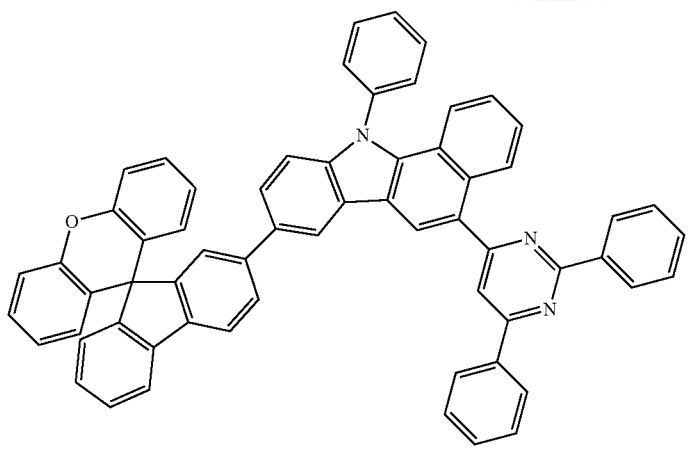
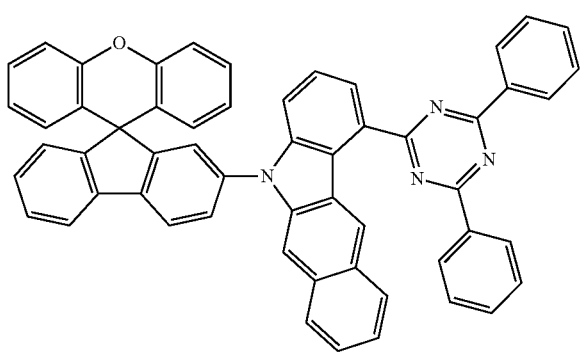
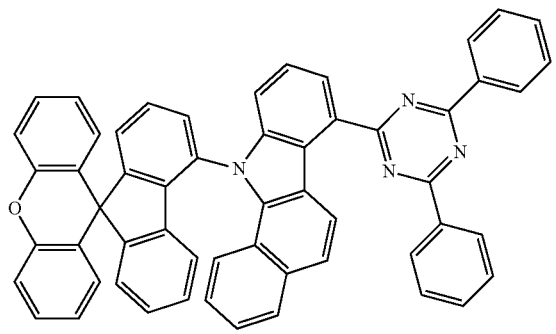
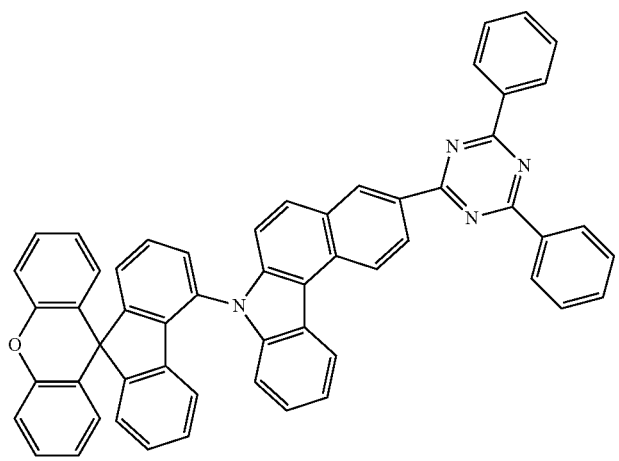

-continued
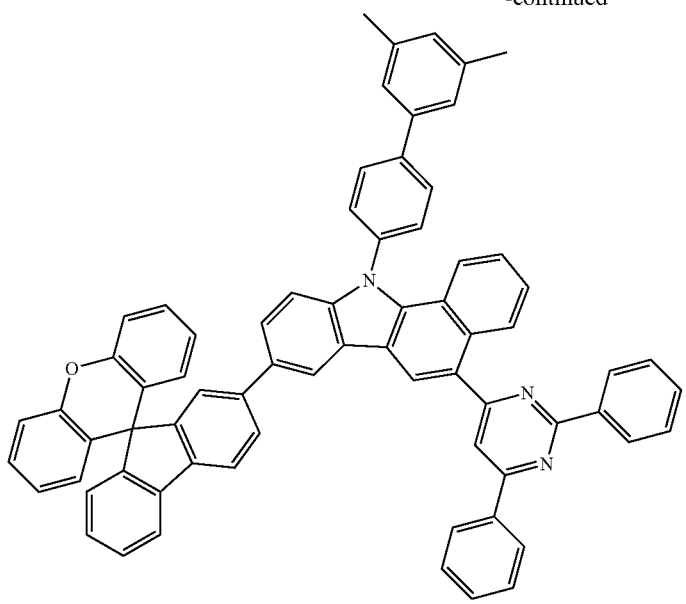
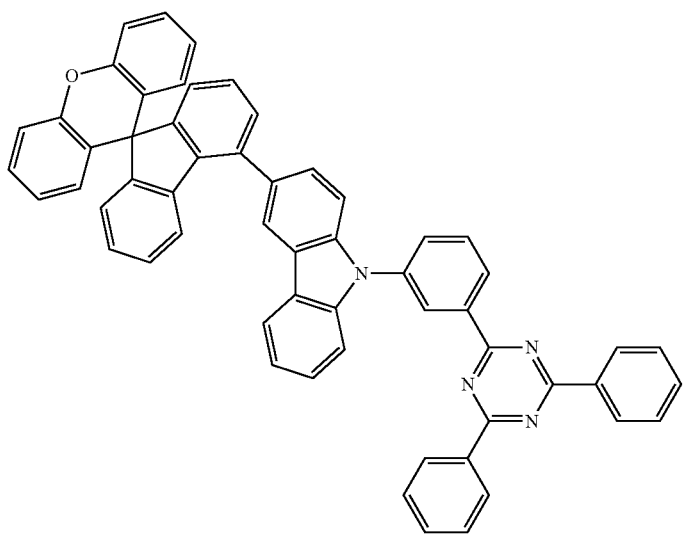
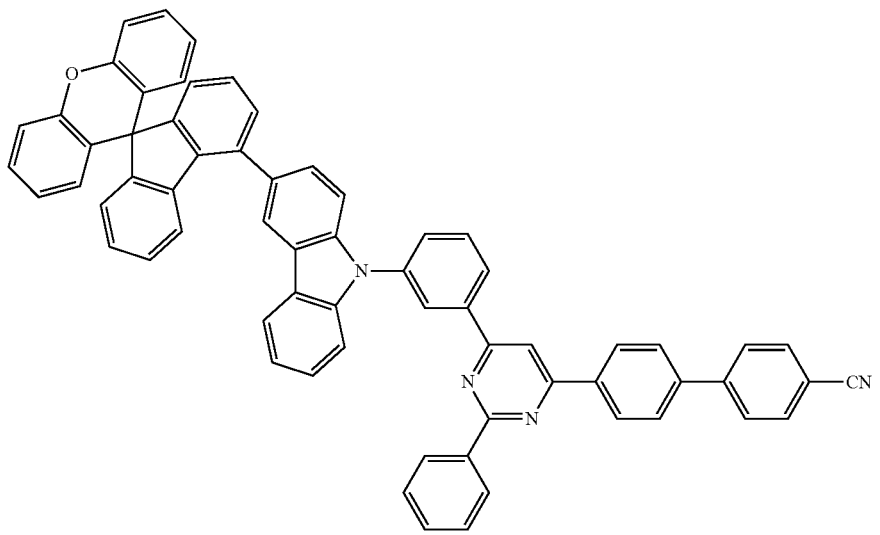

-continued
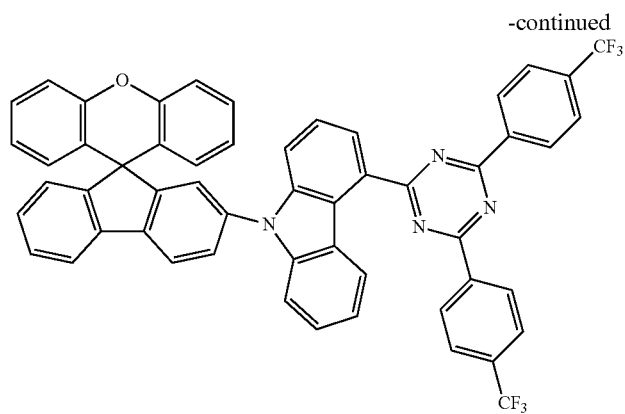
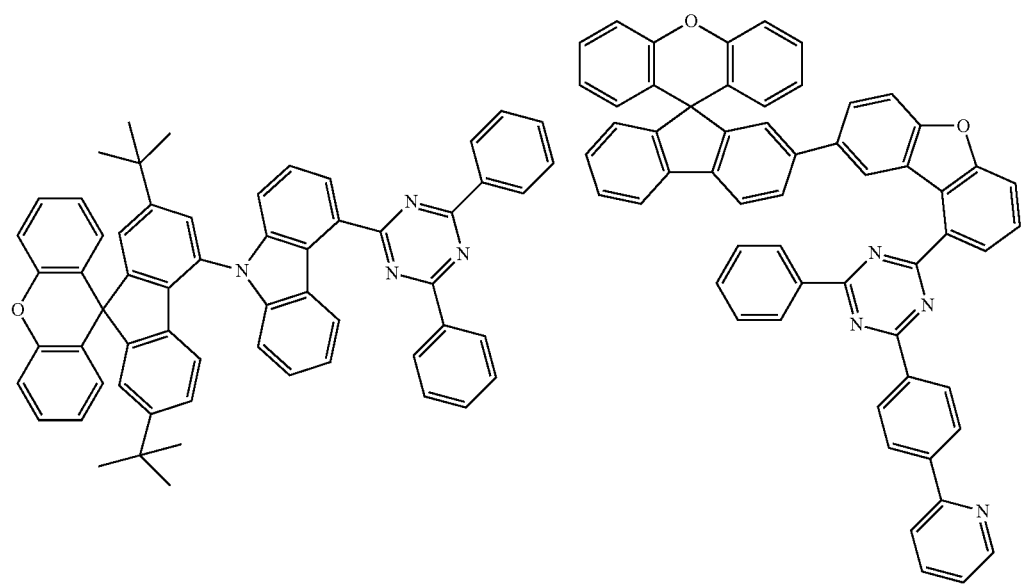
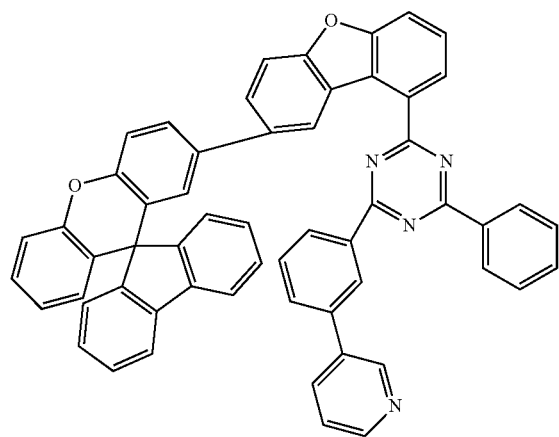

-continued
177
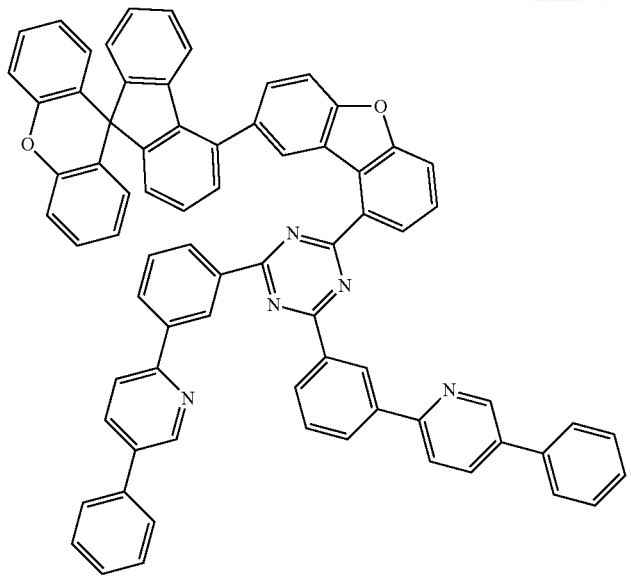
178
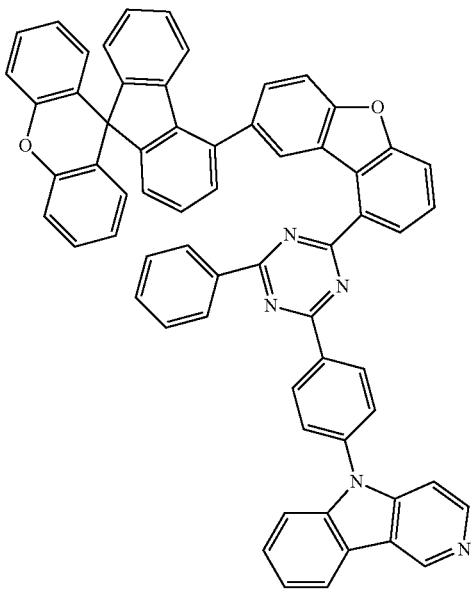
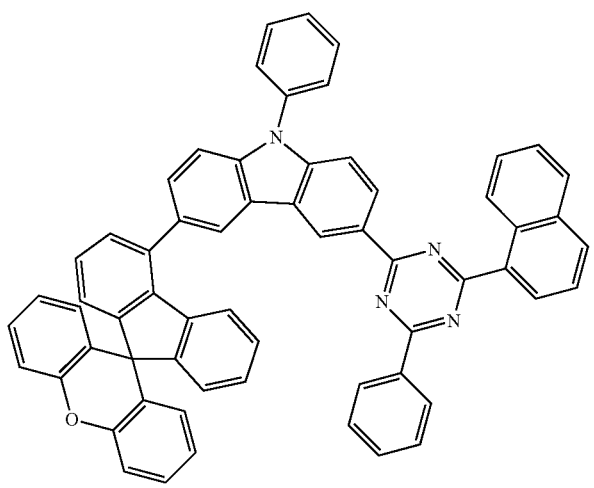
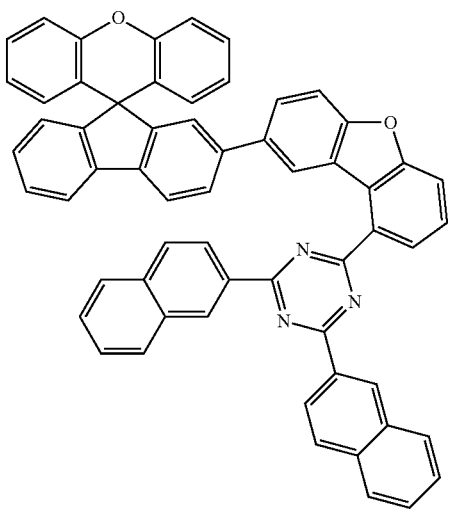
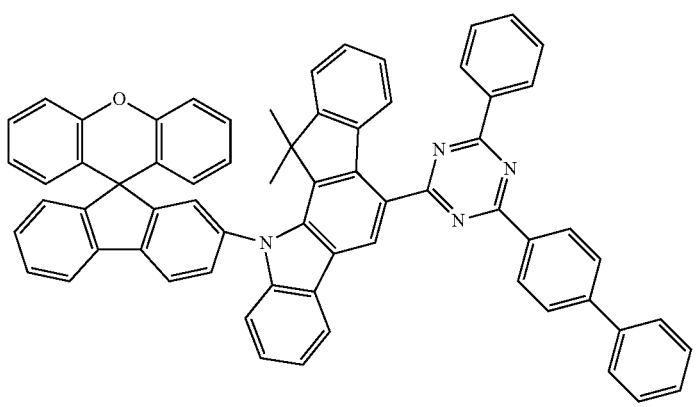

(Blue Light Emitting Layer)

On the other hand, the blue light emitting layer comprises a host and a dopant, and the host may comprise one or more kinds.

Preferably, the host of the blue light emitting layer is a compound represented by the following Chemical Formula 3-1 or 3-2. When the compound represented by the following Chemical Formula 3-1 or 3-2 is used, the relationship between the electron transport layer materials and the energy levels described above can be satisfied.

[Chemical Formula 3-1]

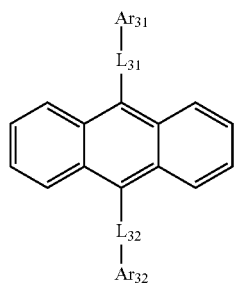

in Chemical Formula 3-1, $L_{31}$ and $L_{32}$ are each independently a bond; substituted or unsubstituted $C_{6-60}$ arylene; or substituted or unsubstituted $C_{2-60}$ heteroarylene containing at least one heteroatom selected from the group consisting of N, O and S, and $Ar_{31}$ and $Ar_{32}$ are each independently substituted or unsubstituted $C_{6-60}$ aryl; or substituted or unsubstituted $C_{2-60}$ heteroarylene containing at least one heteroatom selected from the group consisting of N, O and S,

[Chemical Formula 3-2]

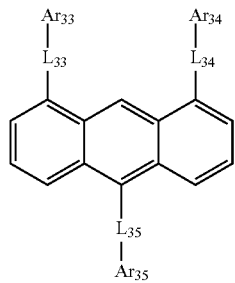

in Chemical Formula 3-2, $L_{33}$, $L_{34}$ and $L_{35}$ are each independently a bond; substituted or unsubstituted $C_{6-60}$ arylene; or substituted or unsubstituted $C_{2-60}$ heteroarylene containing at least one heteroatom selected from the group consisting of N, O and S, and $Ar_{33}$, $Ar_{34}$ and $Ar_{35}$ are each independently substituted or unsubstituted $C_{6-60}$ aryl; or substituted or unsubstituted $C_{2-60}$ heteroaryl comprising at least one heteroatom selected from the group consisting of N, O and S.

Preferably, $L_{31}$ and $L_{32}$ are each independently a bond, phenylene, naphthylene, or anthracenylene.

Preferably, $Ar_{31}$ and $Ar_{32}$ are each independently phenyl, phenyl substituted with one to five deuterium atoms, naphthyl, dibenzofuranyl, dibenzothiophenyl, thiophenyl substituted with phenyl, benzo[b]naphtho[1,2-d]furanyl, benzo[b]naphtho[2,3-d]furanyl, or benzo[d]naphtho[1,2-b]furanyl.

Preferably, $L_{33}$, $L_{34}$ and $L_{35}$ are each independently a bond, or phenylene.

Preferably, $Ar_{33}$, $Ar_{34}$ and $Ar_{35}$ are each independently phenyl, or dibenzofuranyl.

Representative examples of the compound represented by the Chemical Formula 3-1 or 3-2 are as follows:

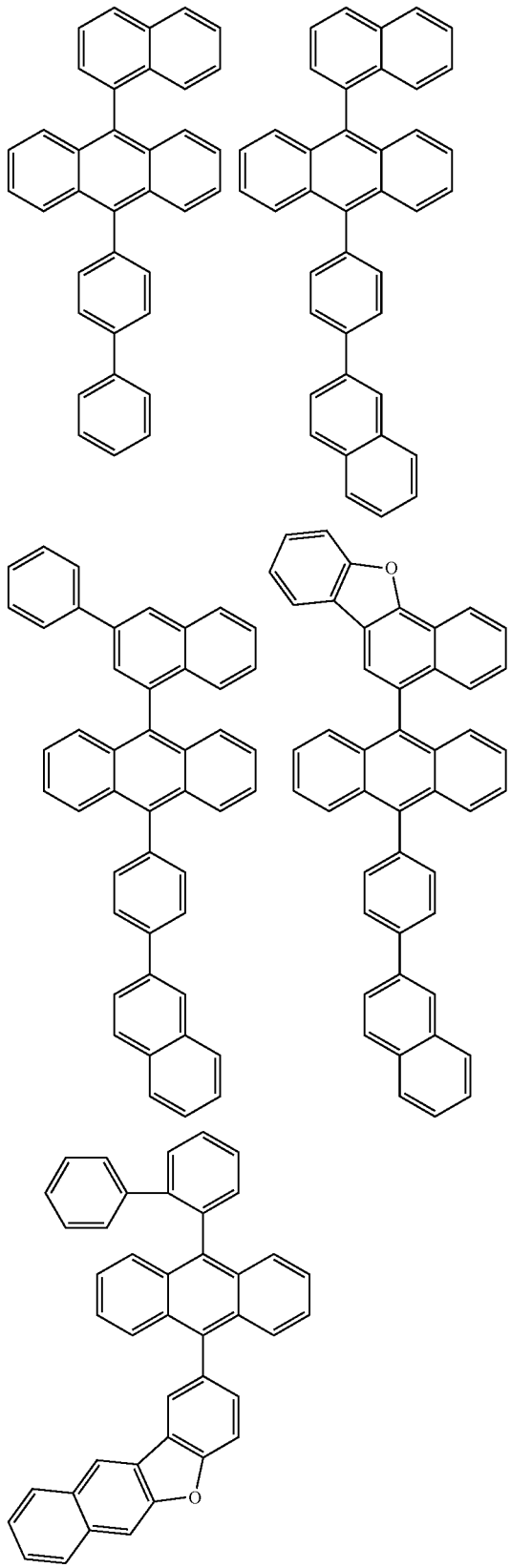

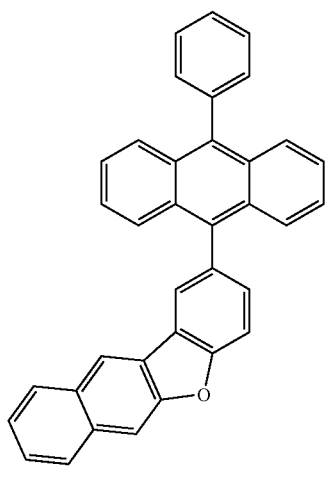
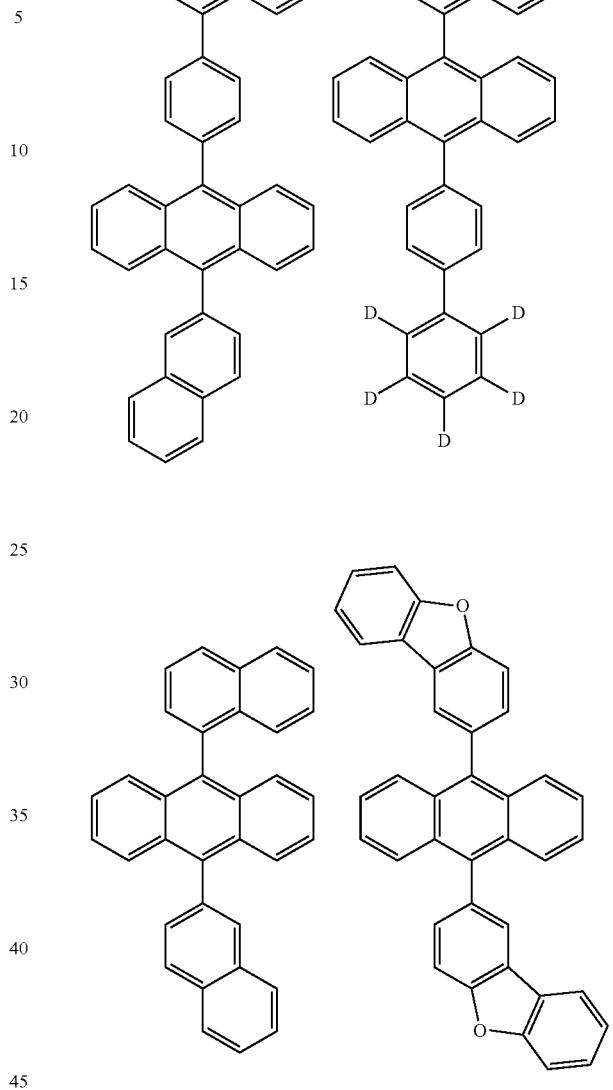
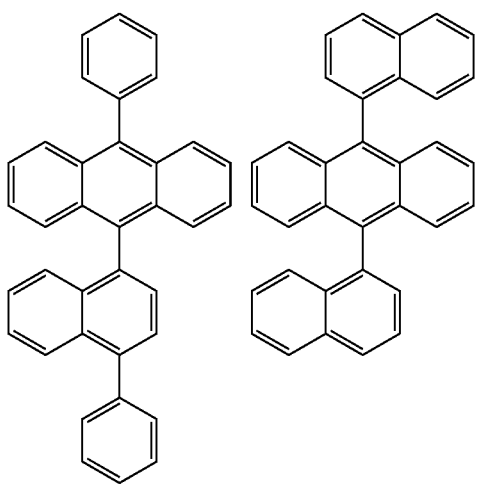

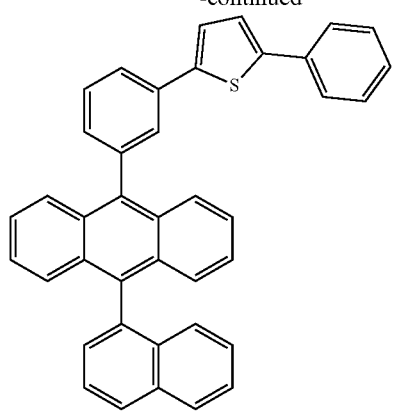
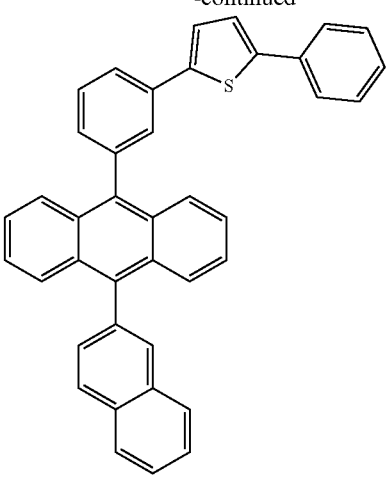

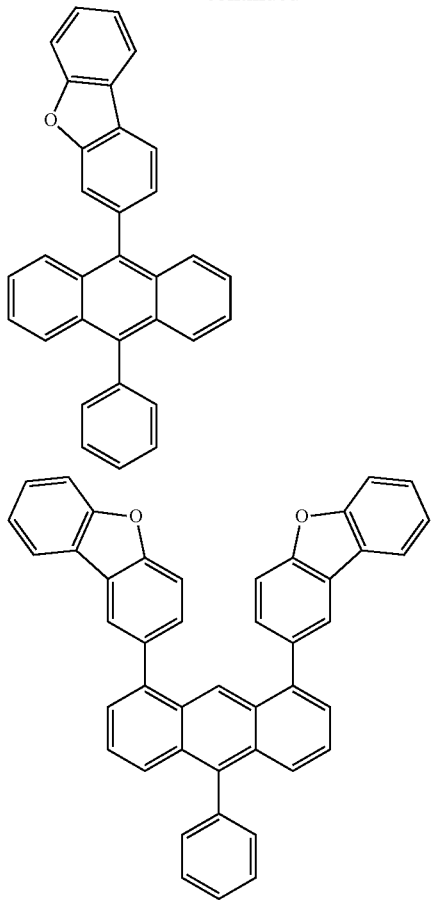
Further, the dopant of the blue light emitting layer is not particularly limited as long as it is used for an organic light emitting device. For example, the dopant of the blue light emitting layer may be any one selected from the group consisting of:
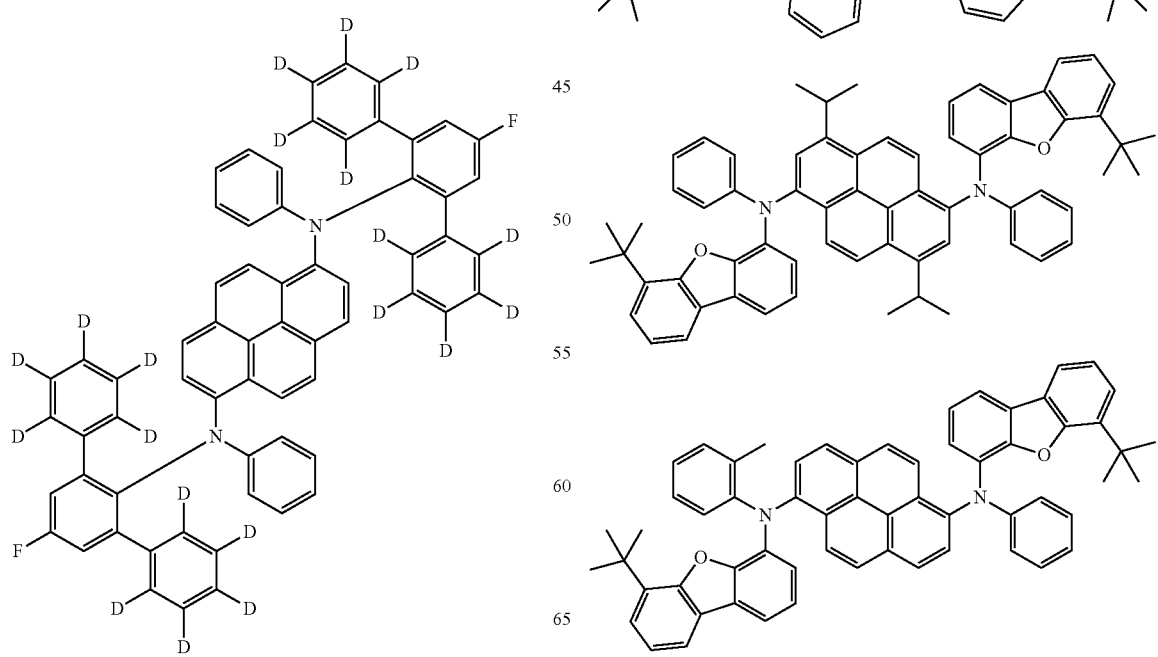
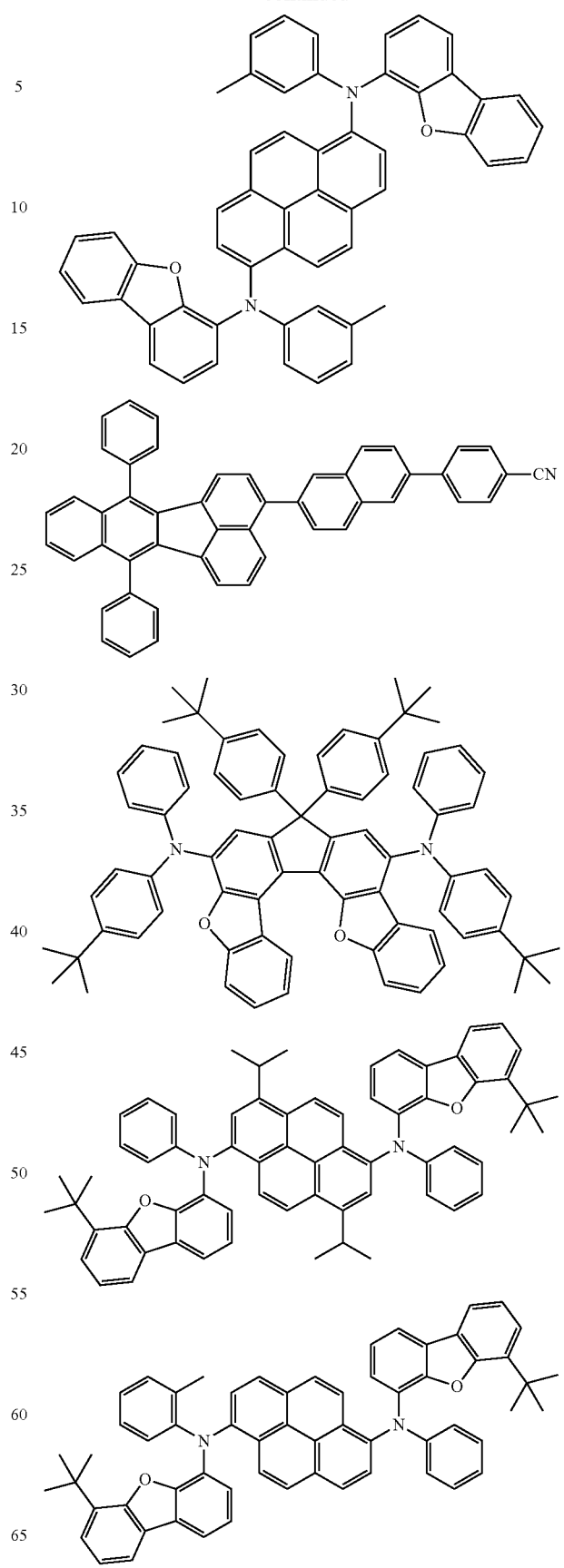

-continued

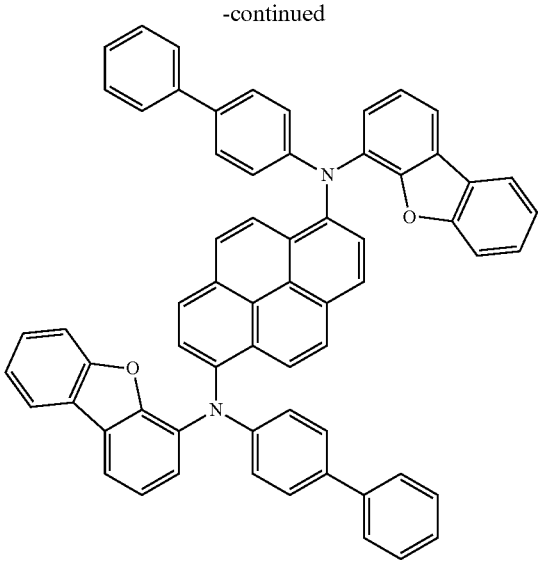

(Green Light Emitting Layer)

On the other hand, the green emitting layer comprises a host and a dopant, and the host may comprise one or more kinds. Preferably, the green light emitting layer comprises two hosts.

Preferably, the host of the green light emitting layer comprises (i) any one of the compounds represented by the following Chemical Formulas 4-1 to 4-4, and (ii) a compound represented by the following Chemical Formula 5:

[Chemical Formula 4-1]

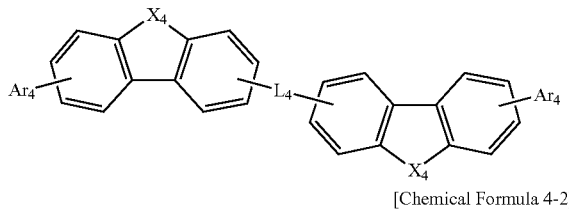

[Chemical Formula 4-2]

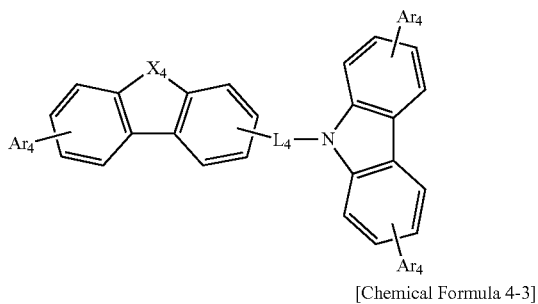

[Chemical Formula 4-3]

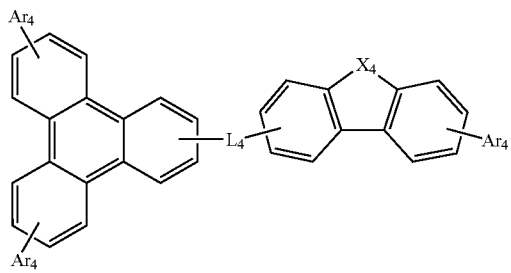

-continued

[Chemical Formula 4-4]

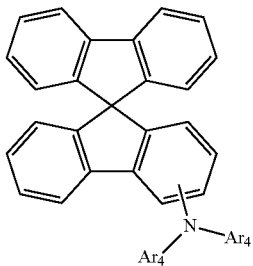

in Chemical Formulas 4-1 to 4-4, each $X_4$ is independently O, S, $NR_4$, $CR_4R_5$, or $SiR_4R_5$, wherein $R_4$ and $R_5$ are each independently hydrogen, substituted or unsubstituted $C_{1-60}$ alkyl, or substituted or unsubstituted $C_{6-60}$ aryl, each $L_4$ is independently a bond; substituted or unsubstituted $C_{6-60}$ arylene; or substituted or unsubstituted $C_{2-60}$ heteroarylene containing at least one heteroatom selected from the group consisting of N, O and S, and $Ar_4$ is independently hydrogen; substituted or unsubstituted $C_{6-60}$ aryl; or substituted or unsubstituted $C_{2-60}$ heteroaryl containing at least one heteroatom selected from the group consisting of N, O and S,

[Chemical Formula 5]

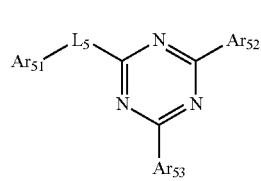

in Chemical Formula 5, $L_5$ is a bond; substituted or unsubstituted $C_{6-60}$ arylene: or substituted or unsubstituted $C_{2-60}$ heteroarylene containing at least one heteroatom selected from the group consisting of N, O and S, and $Ar_{51}$, $Ar_{52}$ and $Ar_{53}$ are each independently substituted or unsubstituted $C_{6-60}$ aryl; or substituted or unsubstituted $C_{2-60}$ heteroaryl containing at least one heteroatom selected from the group consisting of N, O and S.

Preferably, each $X_5$ is independently O, S, or $NR_4$ wherein $R_4$ is phenyl, phenyl substituted with methyl, biphenyline, terphenyline, quaterphenyline, naphthylphenyl, naphthyl, or phenanthrenyl.

Preferably, each $L_4$ is independently a bond, phenylene, dibenzofuranediyl, or phenylcarbazolyldiyl.

Preferably, each $Ar_4$ is independently hydrogen, phenyl, biphenylyl, dimethylfluorenyl, or carbazolyl.

Preferably, $L_5$ is a bond, phenylene, biphenylene, dibenzofuranediyl, or carbazolyl.

Preferably, $Ar_{51}$ is phenyl, biphenylyl, terphenyline, and any one selected from the group consisting of:

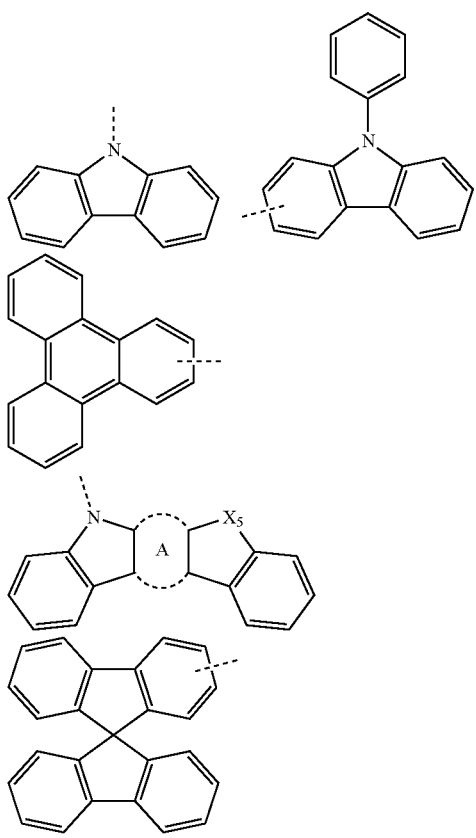
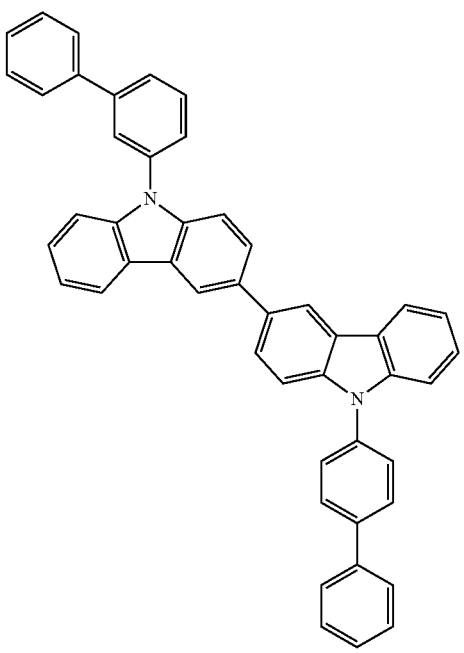
in the above formulas,
X$_5$ is N-(phenyl), or C(CH$_3$)$_2$,
A is a benzene ring fused with two adjacent pentagonal rings.
Preferably, Ar$_{52}$ and Ar$_{53}$ are each independently phenyl, biphenylyl, or carbazolyl.
Representative examples of the compounds represented by the above Chemical Formulas 4-1 to 4-4 are as follows:
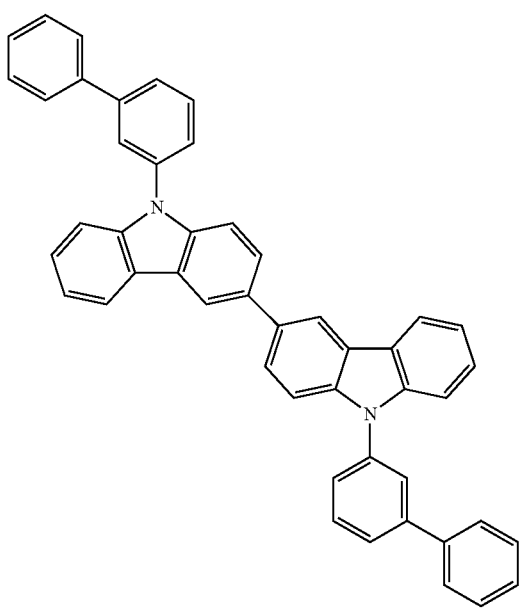
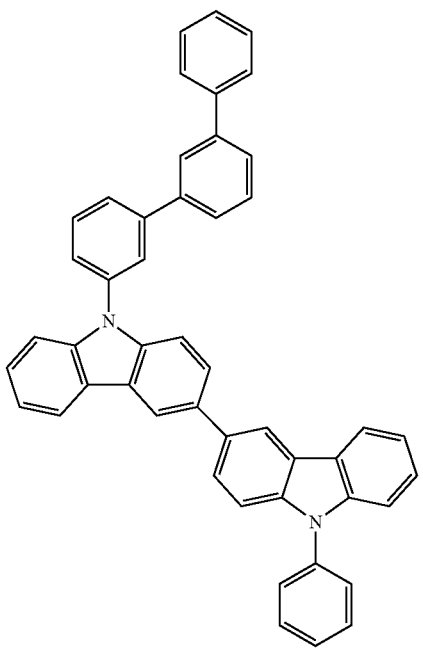

191
-continued
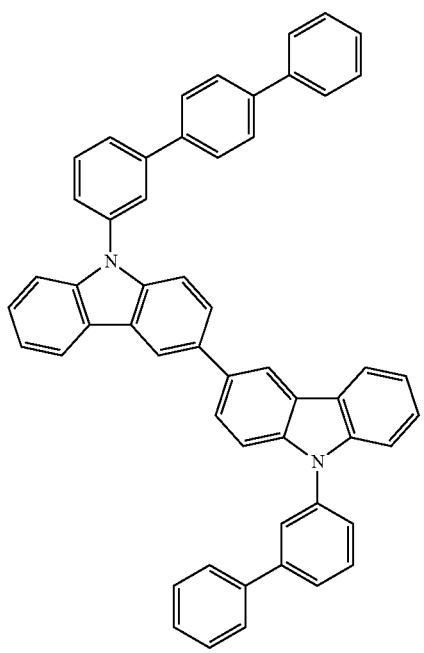
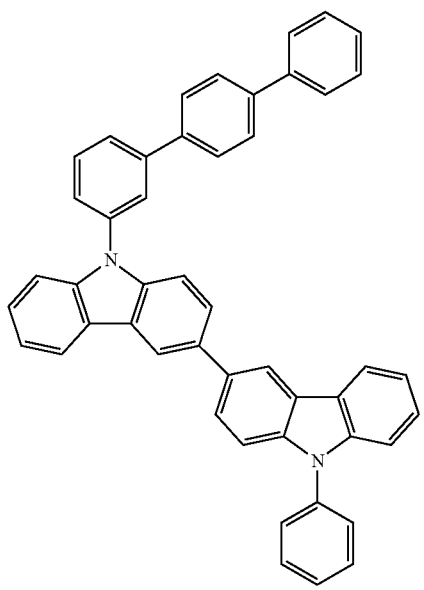 [SMILES: c1ccc(-c2ccc(-c3cccc(-n4c5ccccc5c5cc(-c6ccc7c(c6)c6ccccc6n7-c6ccccc6)ccc54)c3)cc2)cc1]
192
-continued
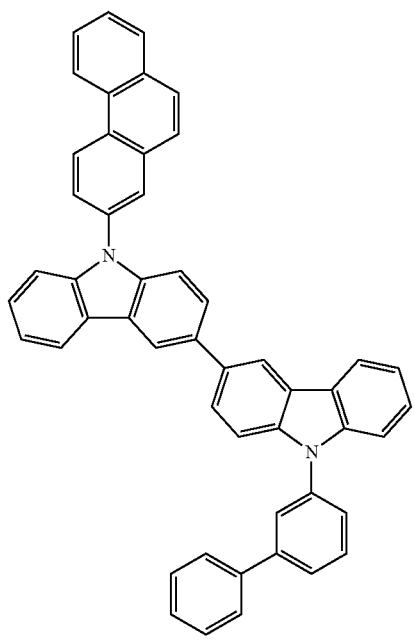
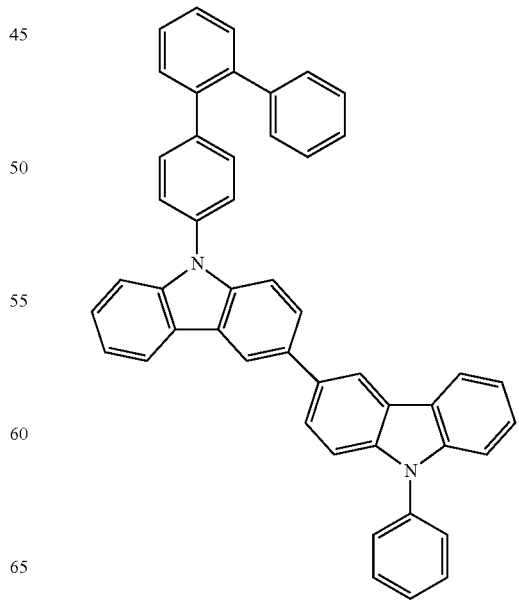

193
-continued
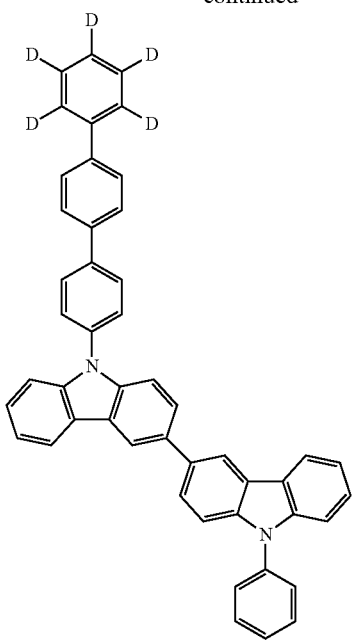
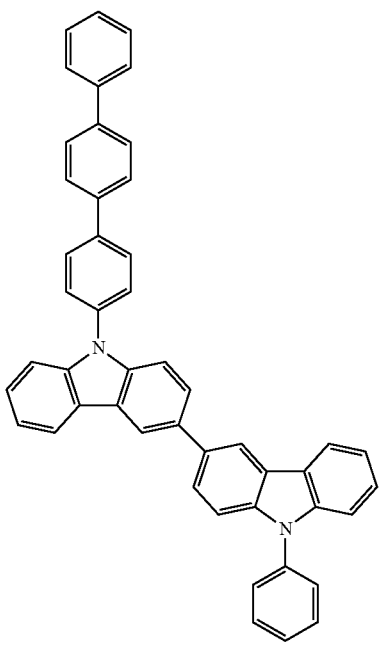
194
-continued
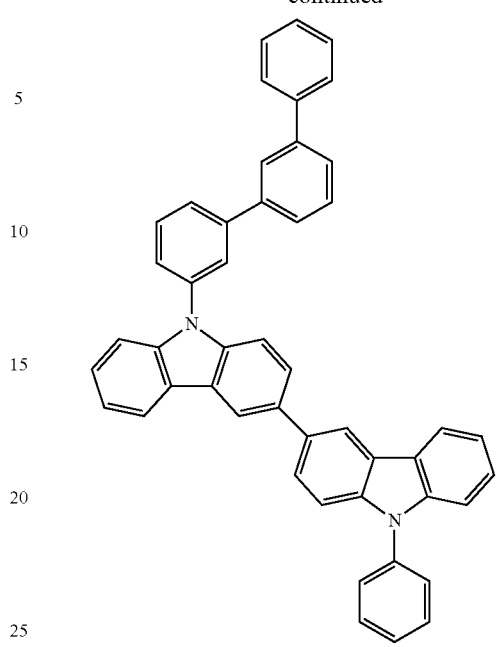
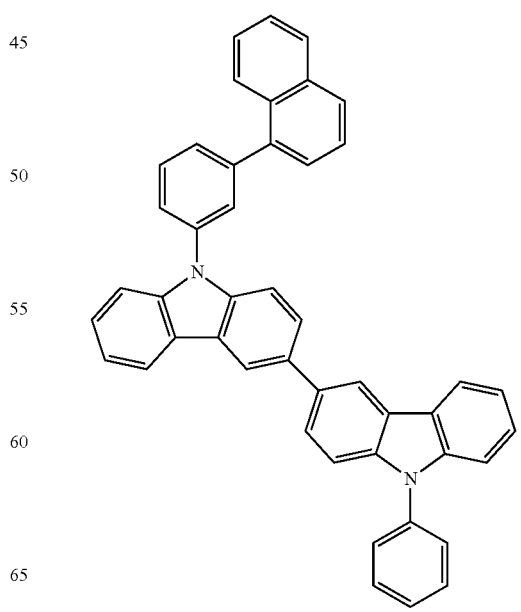

195
-continued
196
-continued
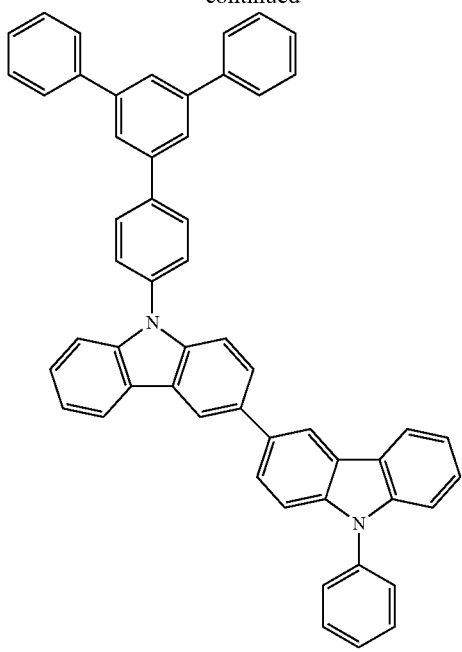
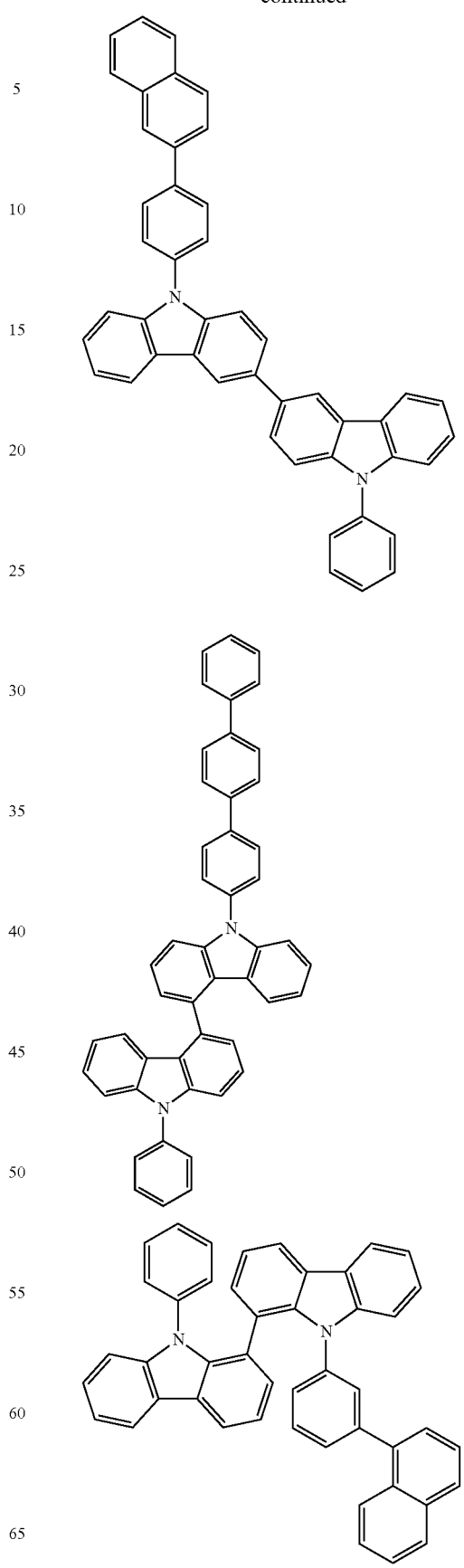
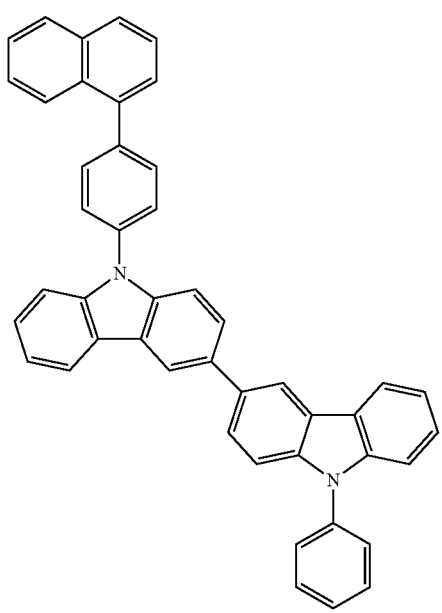

197
-continued
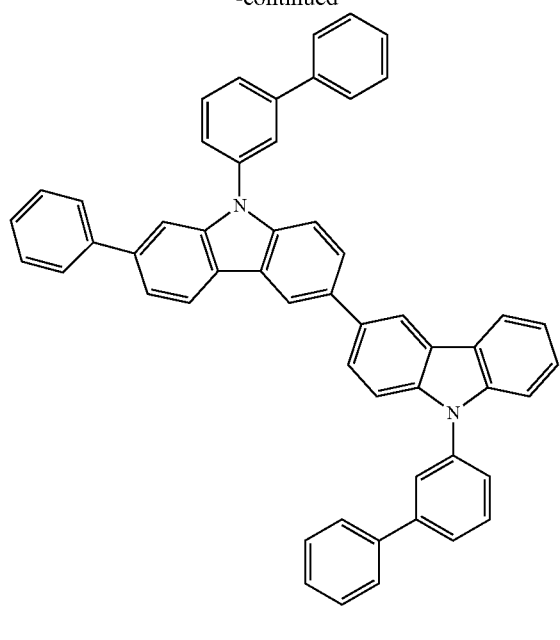
198
-continued
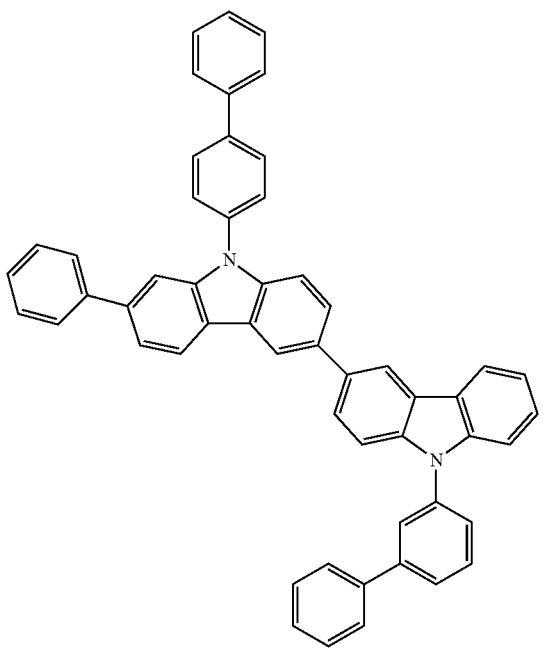
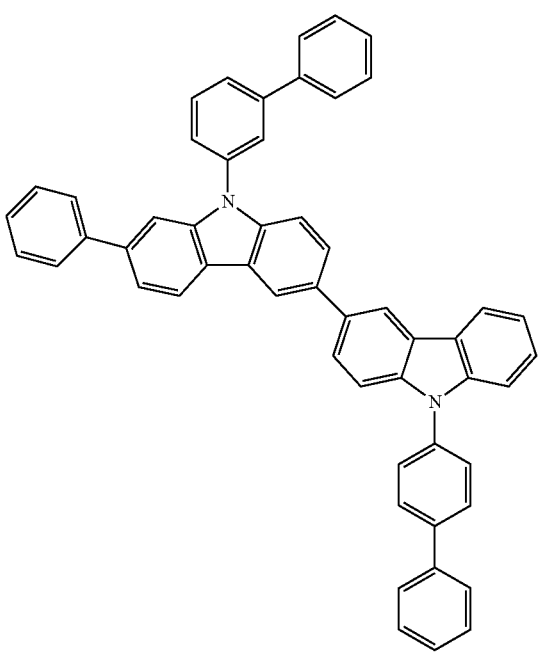
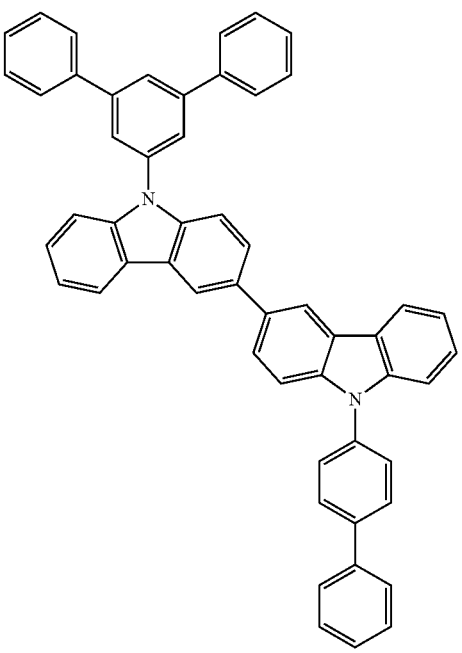

| 199 | 200 |
|---|---|
| 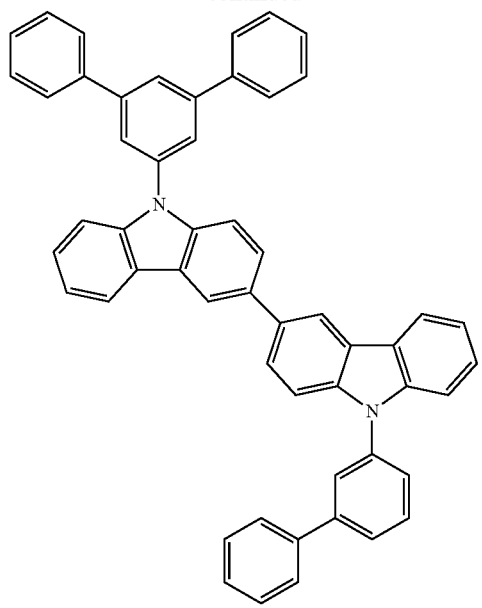 | 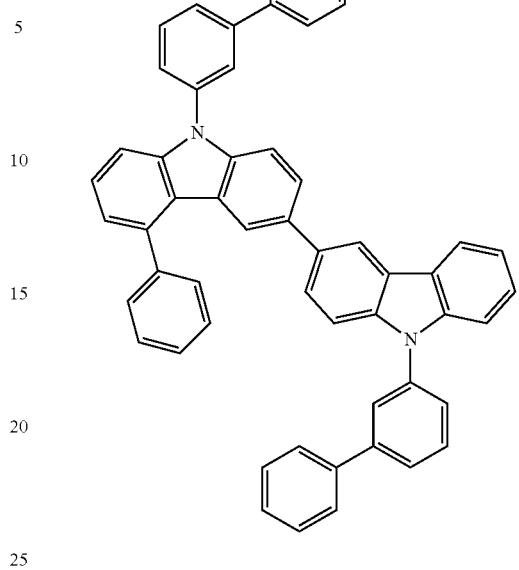 |
| 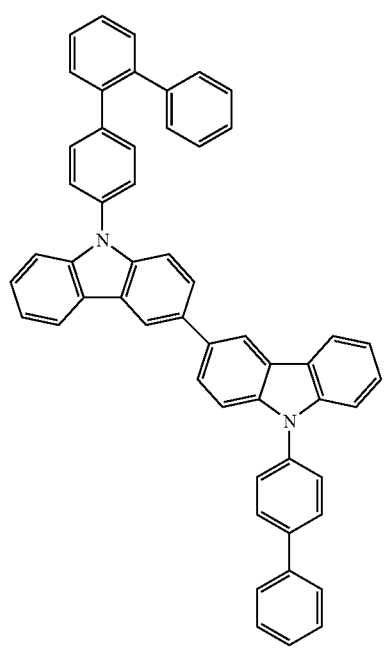 | 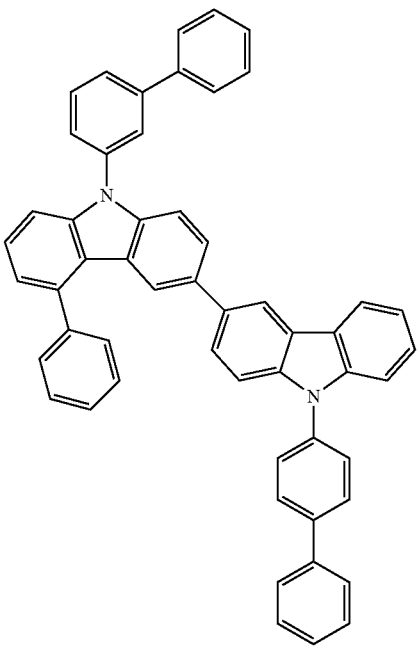 |

201
-continued
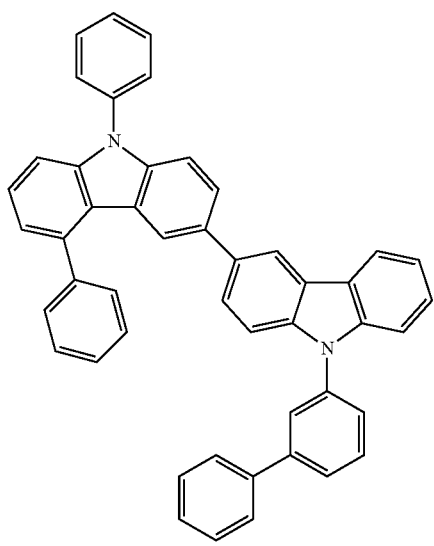
202
-continued
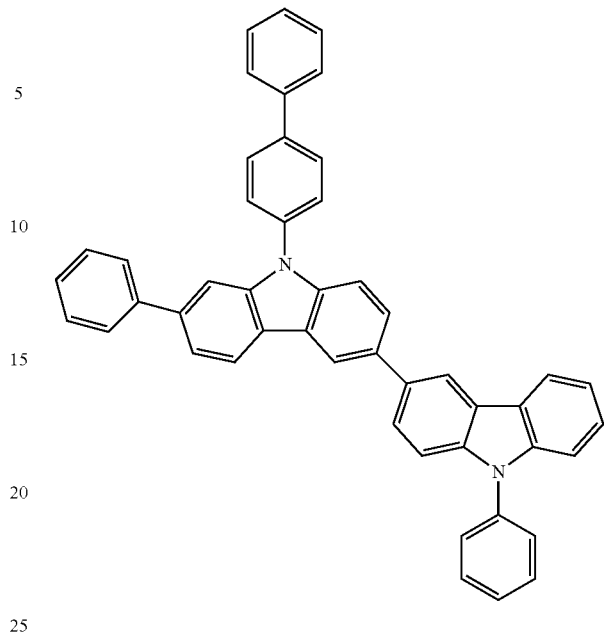
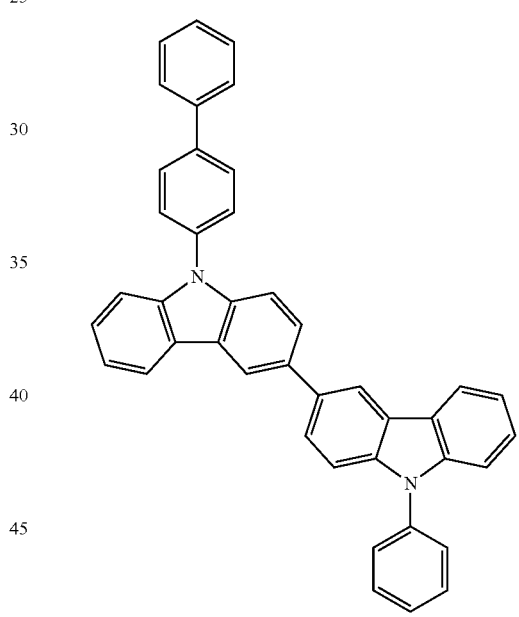
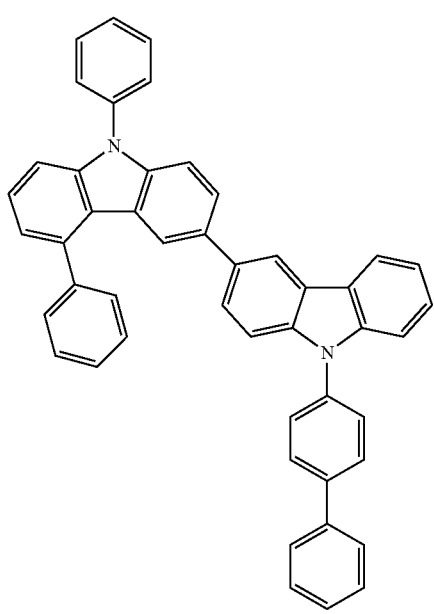

203
-continued
204
-continued
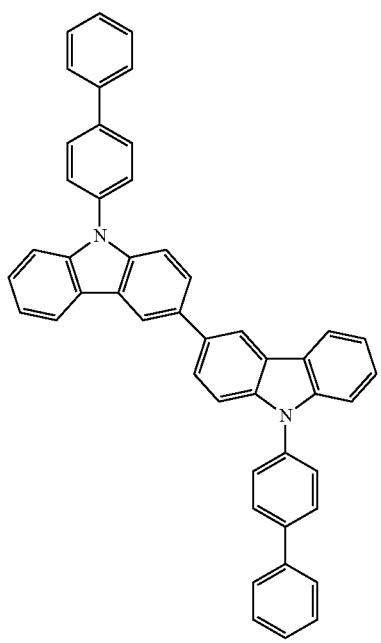
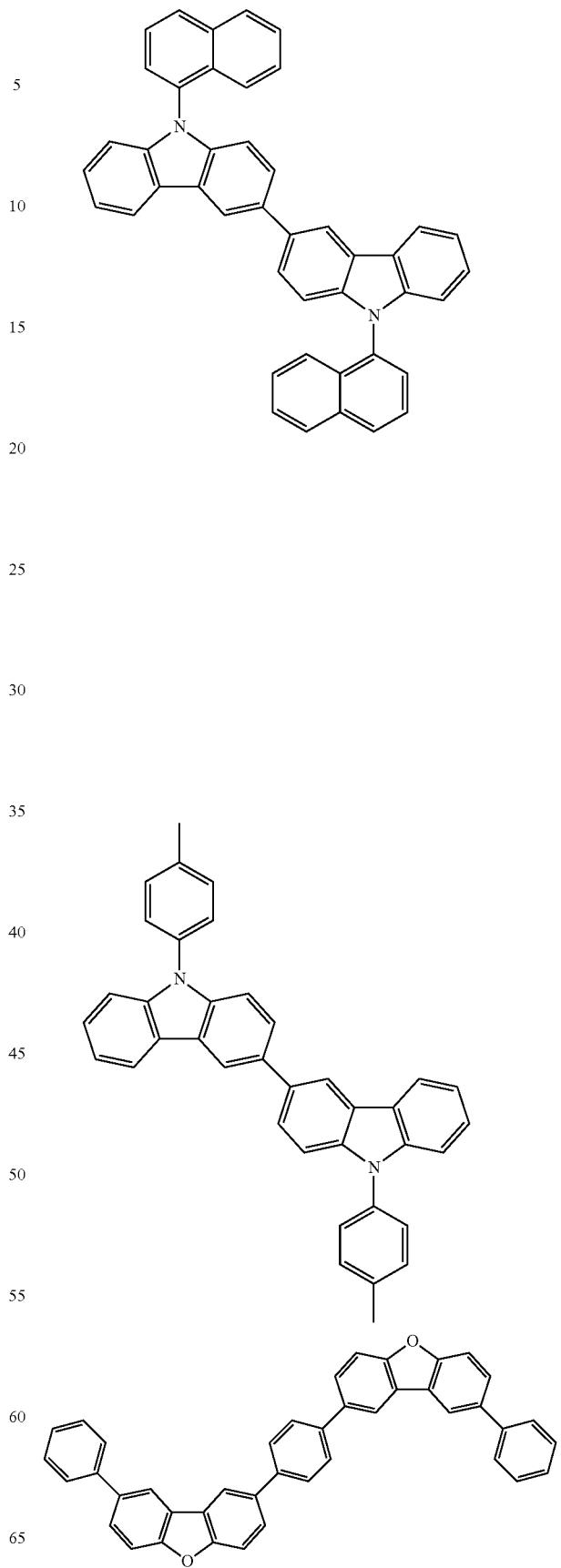

205
-continued
206
-continued
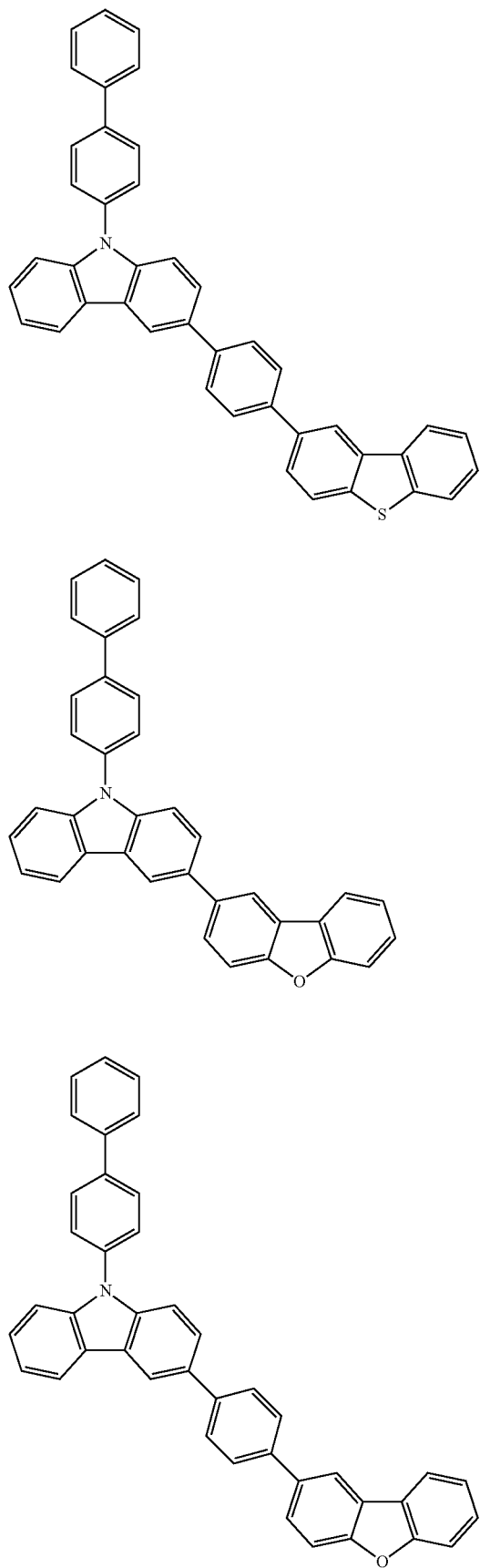 [SMILES: c1ccc(-c2ccc(-n3c4ccccc4c4cc(-c5ccc(-c6ccc7sc8ccccc8c7c6)cc5)ccc43)cc2)cc1 ; c1ccc(-c2ccc(-n3c4ccccc4c4cc(-c5ccc6oc7ccccc7c6c5)ccc43)cc2)cc1 ; c1ccc(-c2ccc(-n3c4ccccc4c4cc(-c5ccc(-c6ccc7oc8ccccc8c7c6)cc5)ccc43)cc2)cc1]
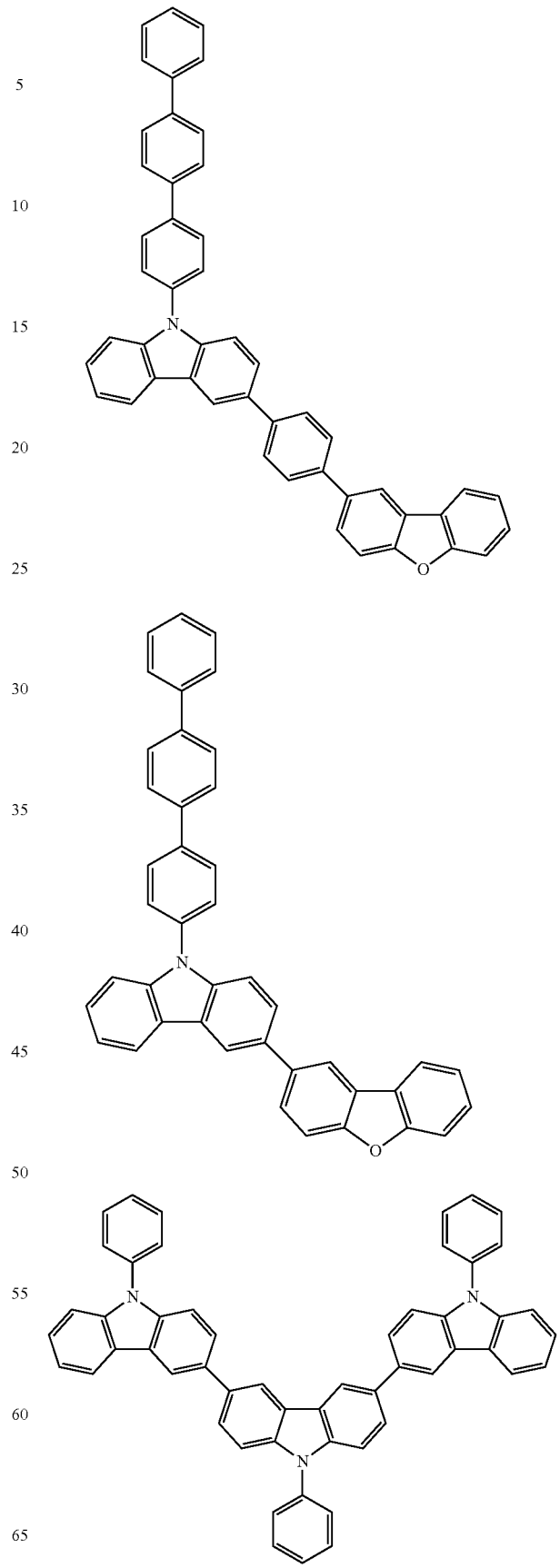

207
-continued
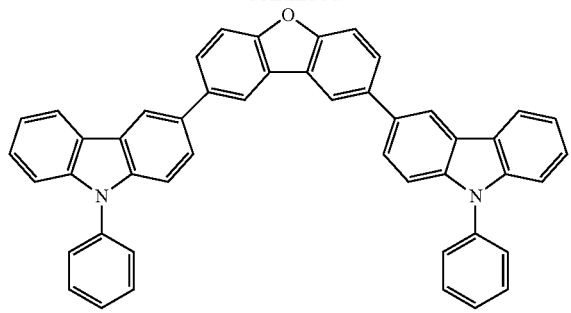
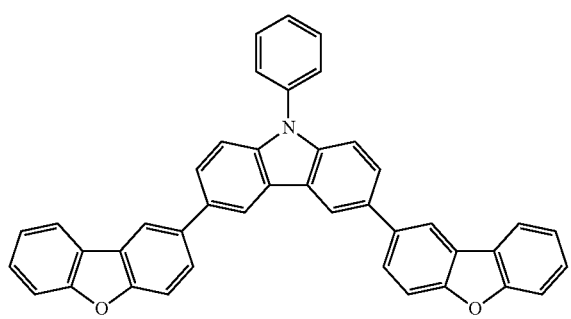
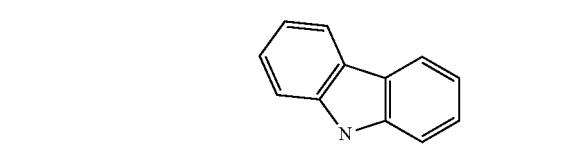
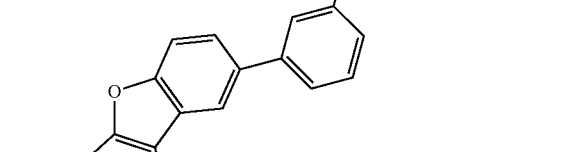
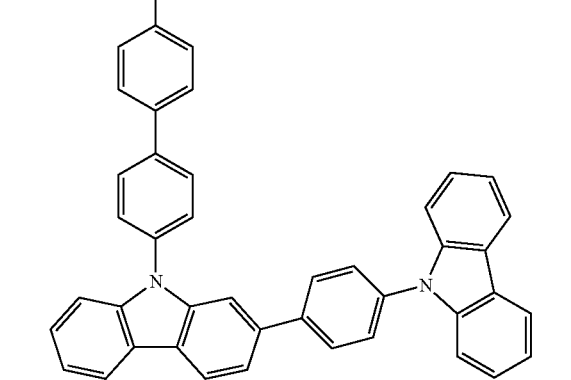
208
-continued
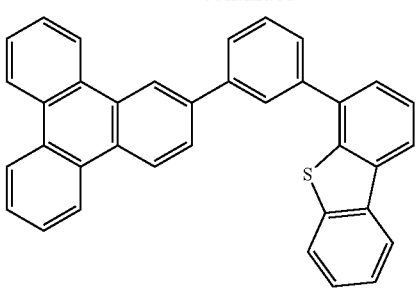
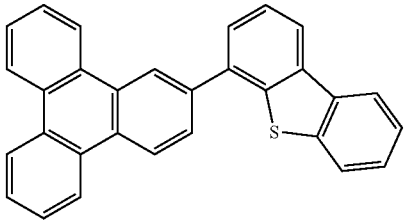
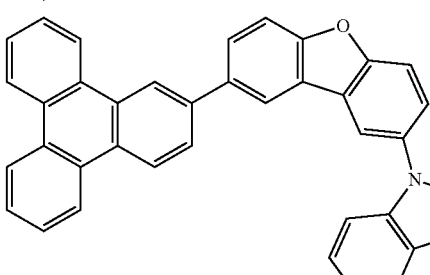
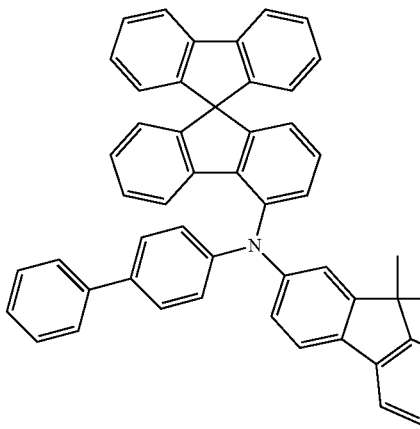
Representative examples of the compound represented by the Chemical Formula 5 are as follows:
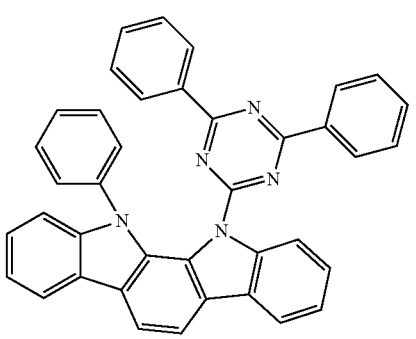

209
-continued
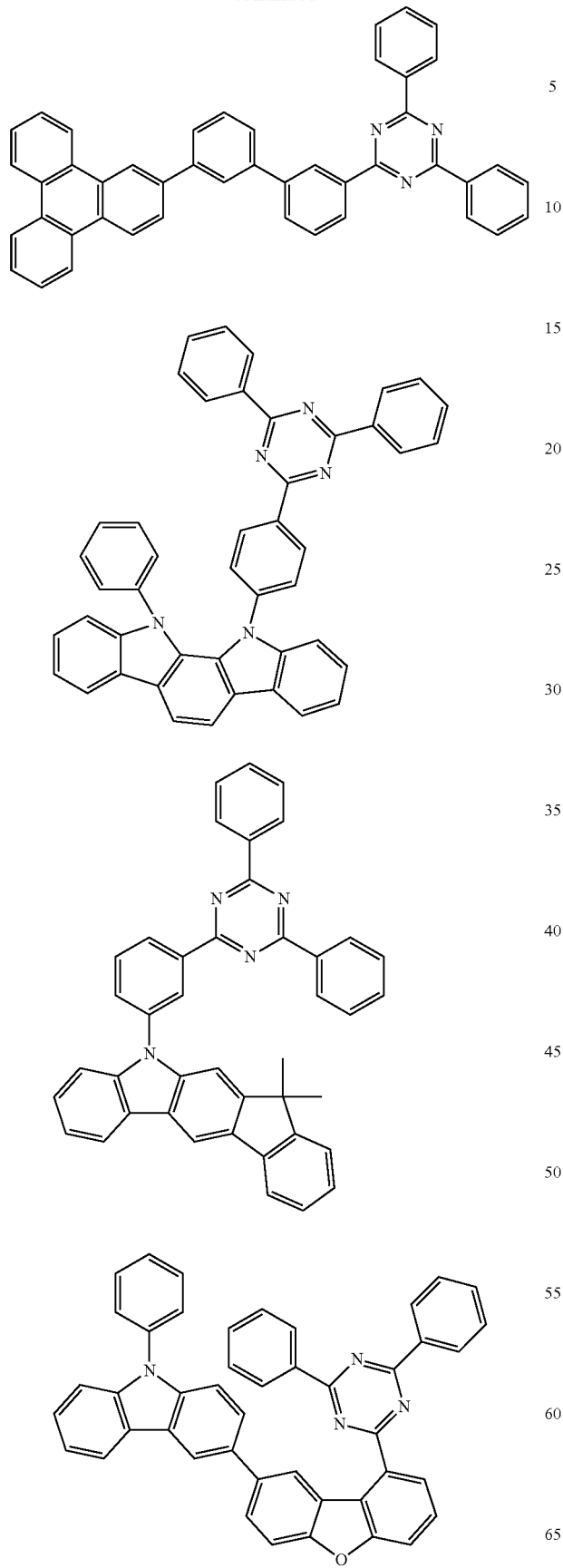
210
-continued
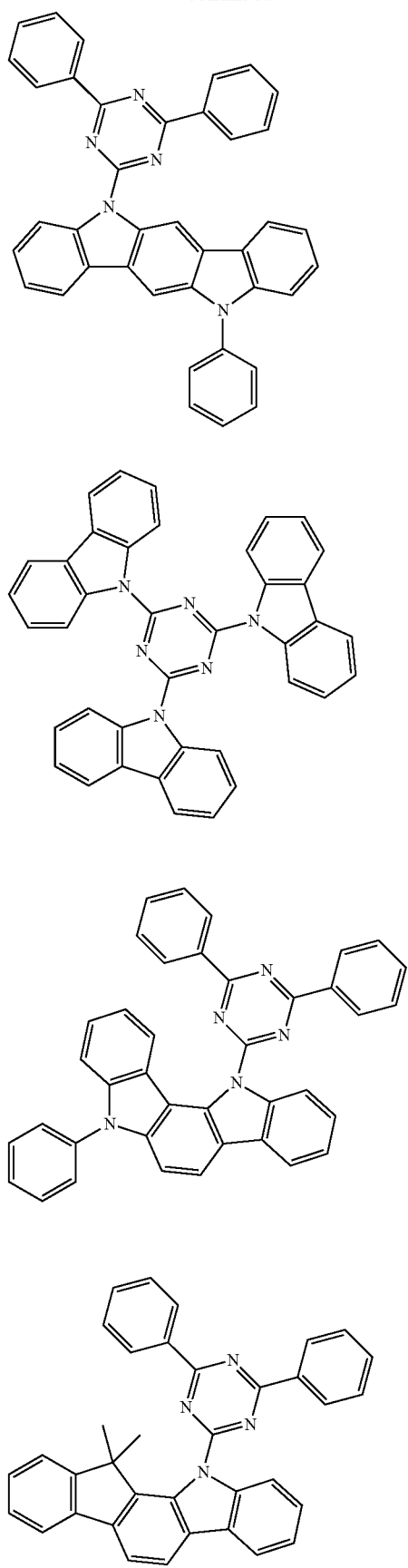

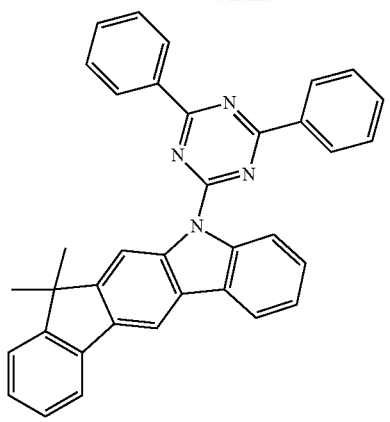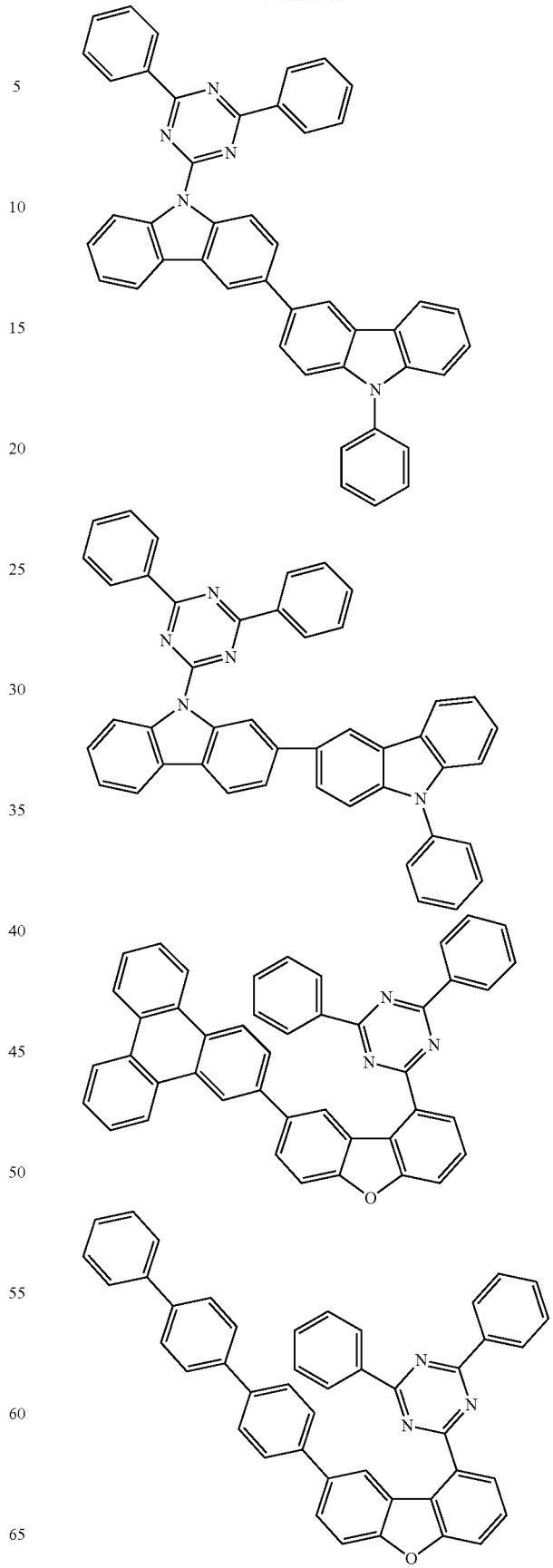

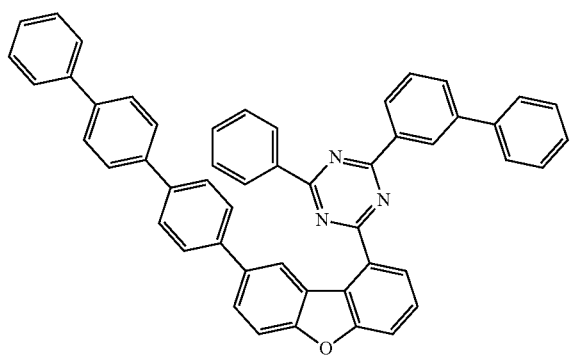

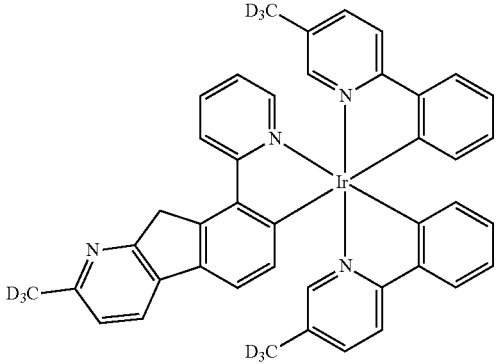

The dopant of the green light emitting layer is not particularly limited as long as it is used for an organic light emitting device. For example, the dopant of the green light emitting layer may be any one selected from the group consisting of:

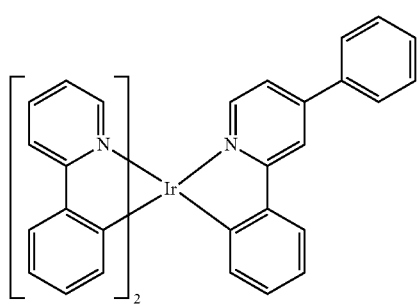

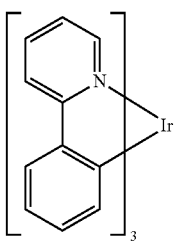

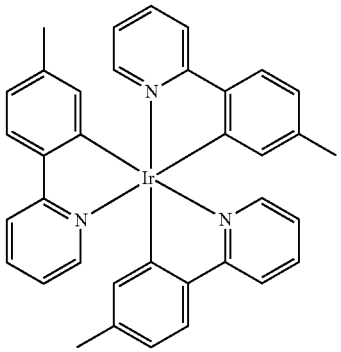

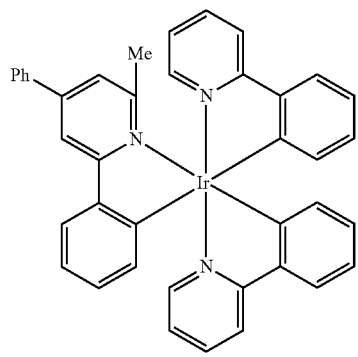

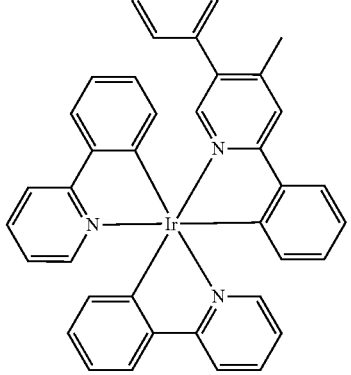

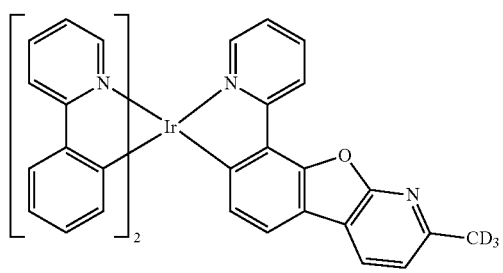

(Red Light Emitting Layer)

On the other hand, the red light emitting layer comprises a host and a dopant, and the host may comprise one or more kinds.

The host of the red light emitting layer is not particularly limited as long as it is used for an organic light emitting element. As an example, representative examples of the host of the red light emitting layer are as follows:

215
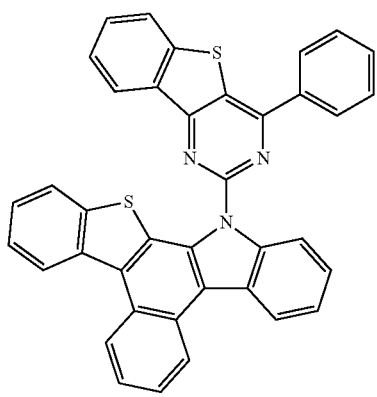
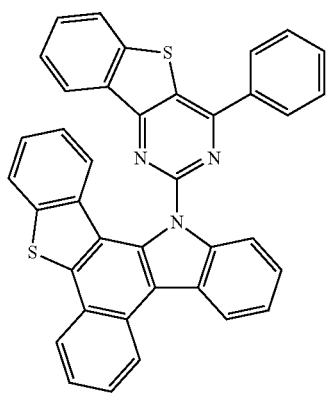
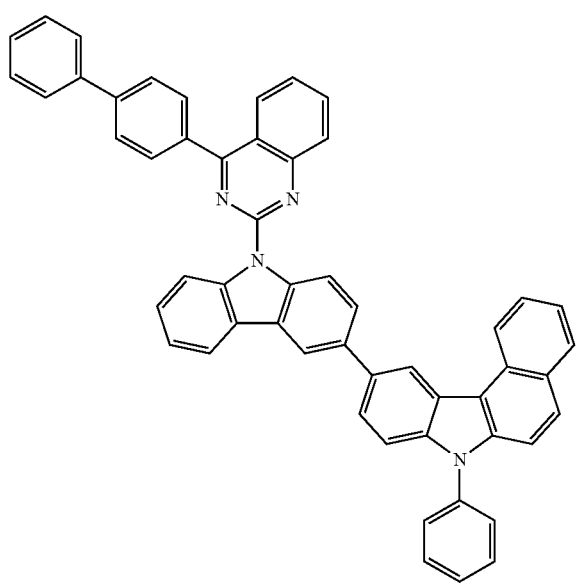
216
-continued
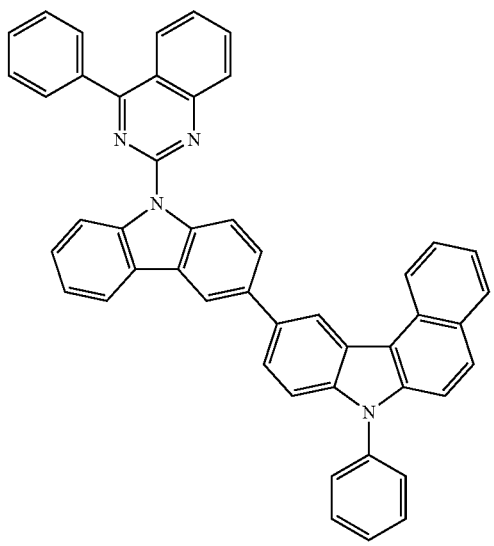
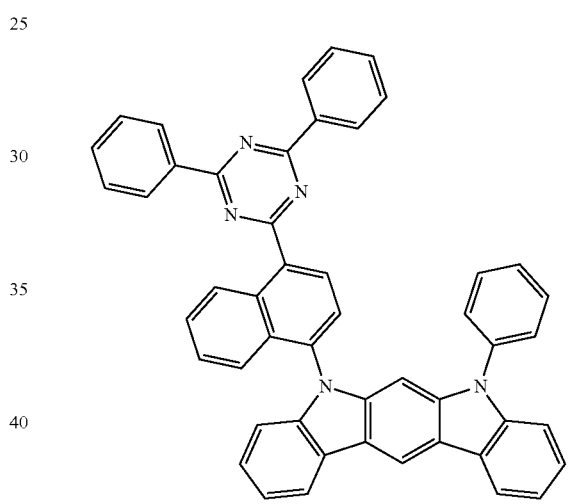
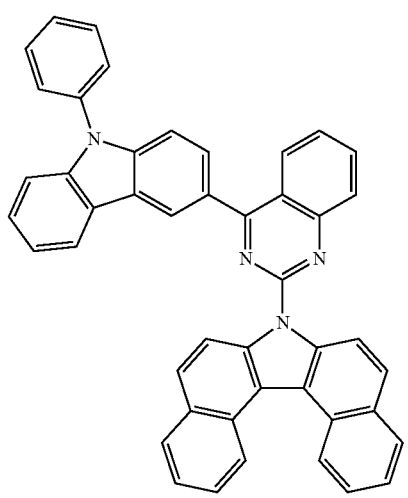

217
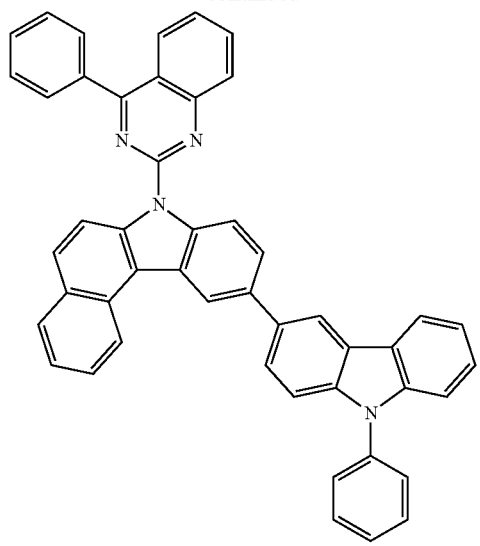
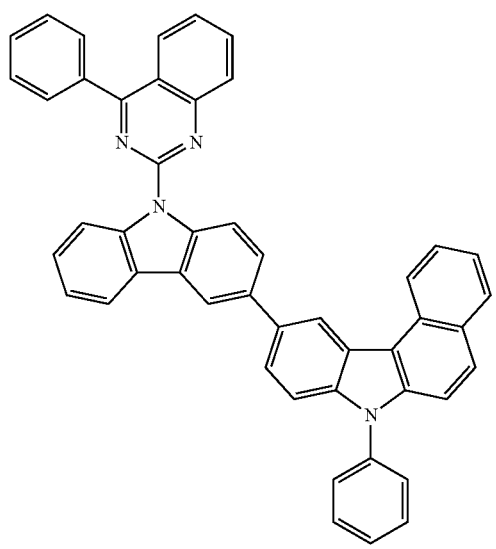
Further, the dopant of the red light emitting layer is not particularly limited as long as it is used for an organic light emitting device. For example, the dopant of the red light emitting layer may be any one selected from the group consisting of:
218
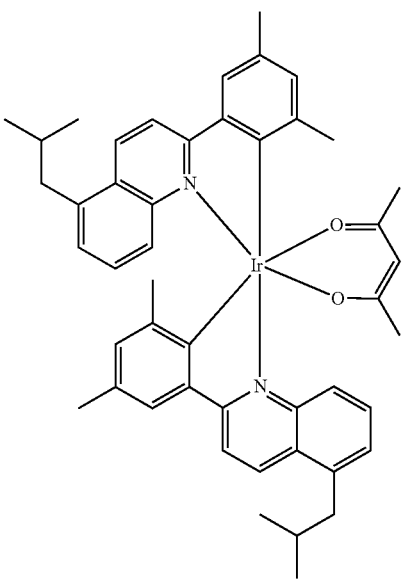
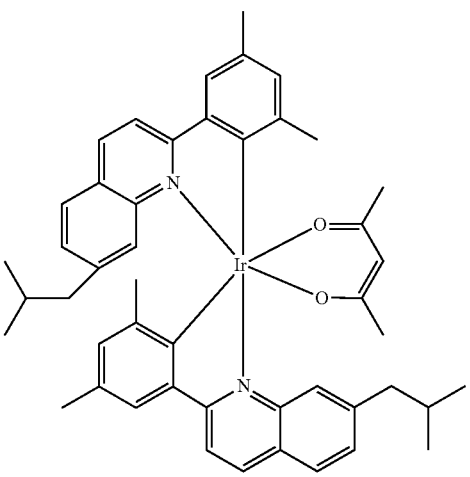
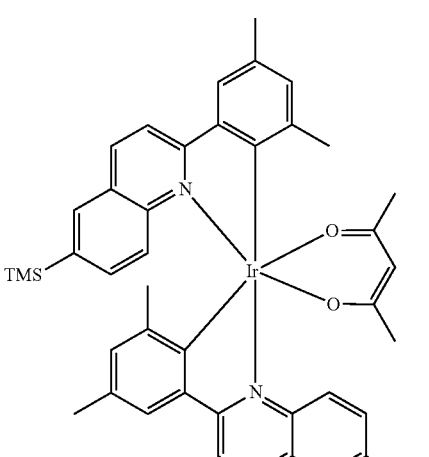

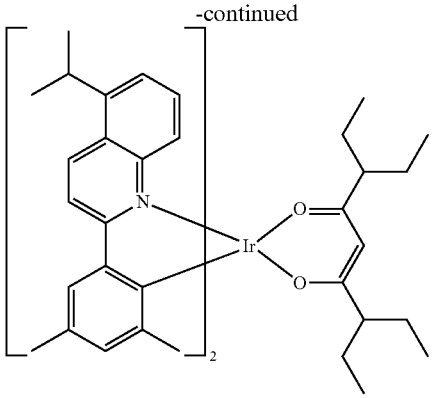

Electron Injection Layer

The organic light emitting device according to the present invention may further include an electron injection layer between the electron transport layer and the cathode. The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable.

Specific examples of materials that can be used for the electron injection layer include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

Organic Light Emitting Device

The structure of the organic light emitting device according to the present invention is illustrated in FIG. 1. FIG. 1 shows an example of an organic light emitting device comprising an anode 1, a hole transport layer 2, a light emitting layer 3, an electron transport layer 4, and a cathode 5, wherein the light emitting layer 3 has a structure in which a red light emitting layer 31, a green light emitting layer 32, and a blue light emitting layer 33 are arranged in parallel. In addition, when a hole injection layer 6 and an electron transport layer 7 are included, the structure of the organic light emitting device is illustrated in FIG. 2.

The organic light emitting device according to the present invention can be manufactured by sequentially stacking the above-described structures. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming the respective layers described above thereon, and then depositing a material that can be used as the cathode thereon. In addition to such a method, the organic light emitting device may be manufactured by sequentially depositing a cathode material, an organic material layer and an anode material on a substrate. Further, the light emitting layer may be formed by subjecting hosts and dopants to a vacuum deposition method and a solution coating method. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

Meanwhile, the organic light emitting device according to the present invention may be a front side emission type, a back side emission type, or a double side emission type according to the used material.

Hereinafter, preferred examples of the present invention will be described to help understanding of the invention. However, these examples are presented for illustrative purposes only, and the scope of the present invention is not limited thereto.

In the following, the HOMO and LUMO levels of the respective compounds were measured using AC-3 equipment (Model AC-3 available from Rinken Keiki). Specifically, a film obtained by vacuum-depositing a compound to be measured on an ITO substrate in a thickness of 1000 Å was used, and the quantum yield for photons generated by irradiating film with UV intensity of 10 nW was measured. Thereby, HOMO level and LUMO level were measured.

PREPARATION EXAMPLE 1

Blue Host

As the blue host (BH), the compounds shown in Table 1 below were used.

TABLE 1
| Name | Reference | Chemical Structure | HOMO (eV) |
| --- | --- | --- | --- |
| BH-1 | WO 2008/062773 | 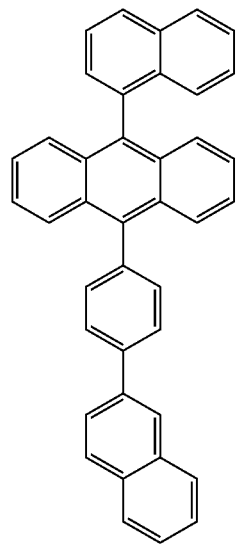 [SMILES: c1ccc2cc(-c3ccc(-c4c5ccccc5c(-c5cccc6ccccc56)c5ccccc45)cc3)ccc2c1] | 5.84 |
| BH-2 | US 2004/0161632 | 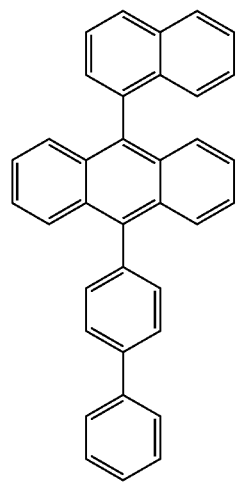 [SMILES: c1ccc(-c2ccc(-c3c4ccccc4c(-c4cccc5ccccc45)c4ccccc34)cc2)cc1] | 5.80 |
| BH-3 | WO 2014/141725 | 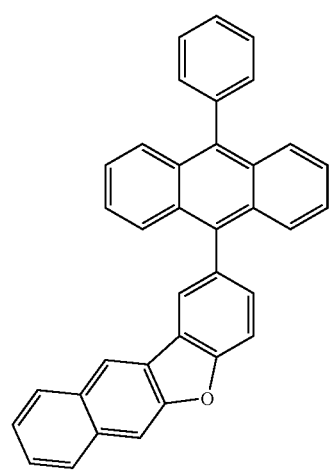 [SMILES: c1ccc(-c2c3ccccc3c(-c3ccc4oc5cc6ccccc6cc5c4c3)c3ccccc23)cc1] | 5.72 |

TABLE 1-continued
| Name | Reference | Chemical Structure | HOMO (eV) |
|---|---|---|---|
| BH-4 | WO 2017/010489 | 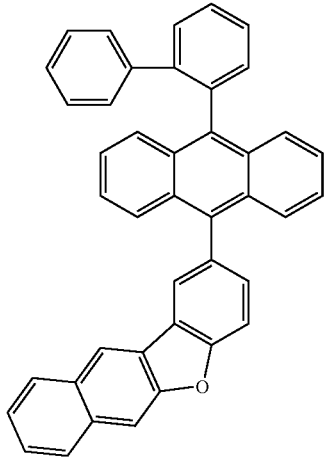 [SMILES: c1ccc(-c2ccccc2-c2c3ccccc3c(-c3ccc4oc5cc6ccccc6cc5c4c3)c3ccccc23)cc1] | 5.75 |
| BH-5 | KR 2010-007552 A | 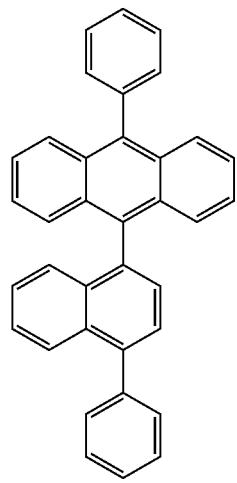 [SMILES: c1ccc(-c2ccc(-c3c4ccccc4c(-c4ccccc4)c4ccccc34)c3ccccc23)cc1] | 5.93 |
| BH-6 | KR 2017-039020 A | 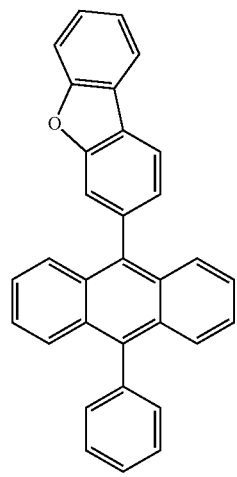 [SMILES: c1ccc(-c2c3ccccc3c(-c3ccc4c(c3)oc3ccccc34)c3ccccc23)cc1] | 5.91 |

TABLE 1-continued

| Name | Reference | Chemical Structure | HOMO (eV) |
|---|---|---|---|
| BH-7 | EP 1437395 A | 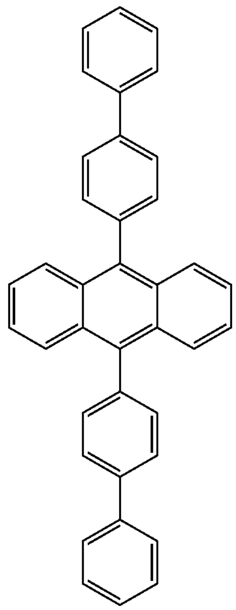 [SMILES: c1ccc(-c2ccc(-c3c4ccccc4c(-c4ccc(-c5ccccc5)cc4)c4ccccc34)cc2)cc1] | 6.07 |

PREPARATION EXAMPLE 2

Green Host

As one of the green hosts (GH), the compounds shown in Table 2 below were used.

TABLE 2

| Name | Reference | Chemical Structure | LUMO (eV) |
|---|---|---|---|
| GH1-1 | JP 2013-183047 A | 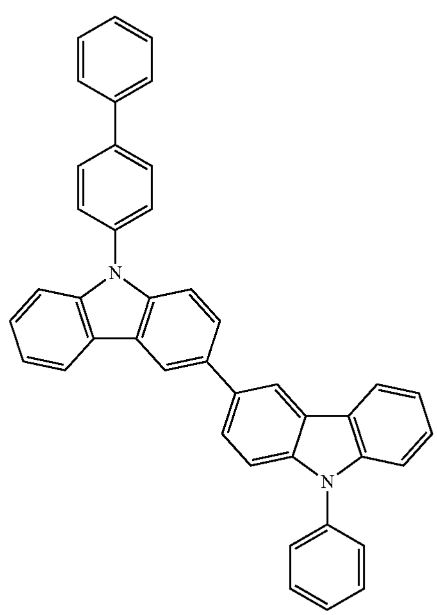 [SMILES: c1ccc(-c2ccc(-n3c4ccccc4c4cc(-c5ccc6c(c5)c5ccccc5n6-c5ccccc5)ccc43)cc2)cc1] | 2.29 |

TABLE 2-continued
| Name | Reference | Chemical Structure | LUMO (eV) |
|---|---|---|---|
| GH1-2 | JP 11329737 B | 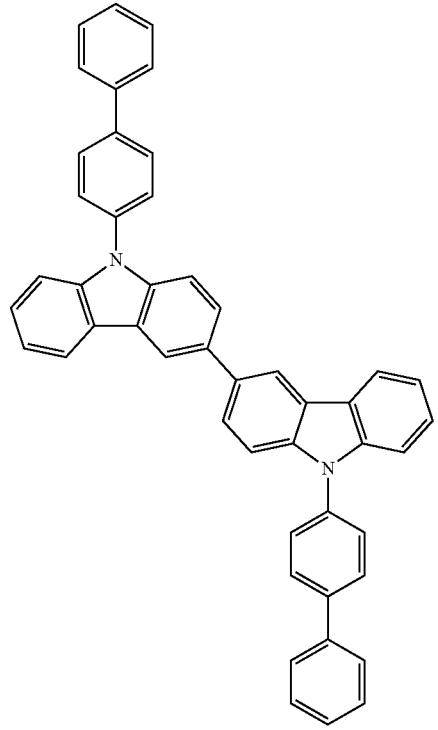 [SMILES: c1ccc(-c2ccc(-n3c4ccccc4c4cc(-c5ccc6c(c5)c5ccccc5n6-c5ccc(-c6ccccc6)cc5)ccc43)cc2)cc1] | 2.34 |
| GH1-3 | US 2014-0197386 | 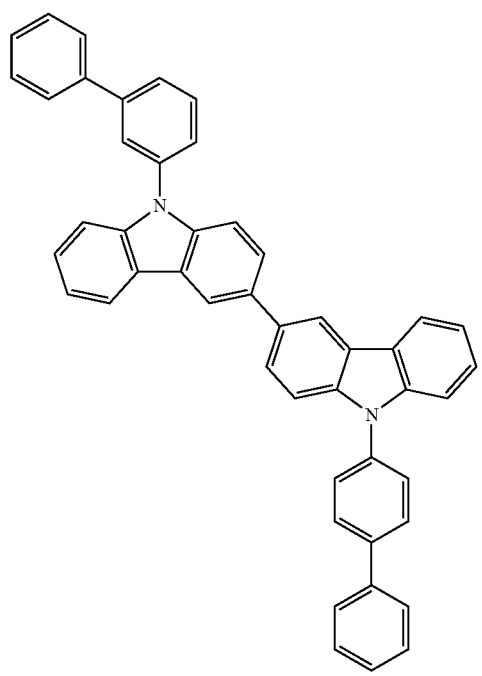 [SMILES: c1ccc(-c2ccc(-n3c4ccccc4c4cc(-c5ccc6c(c5)c5ccccc5n6-c5cccc(-c6ccccc6)c5)ccc43)cc2)cc1] | 2.33 |

TABLE 2-continued
| Name | Reference | Chemical Structure | LUMO (eV) |
|---|---|---|---|
| GH1-4 | US 2011-0260138 | 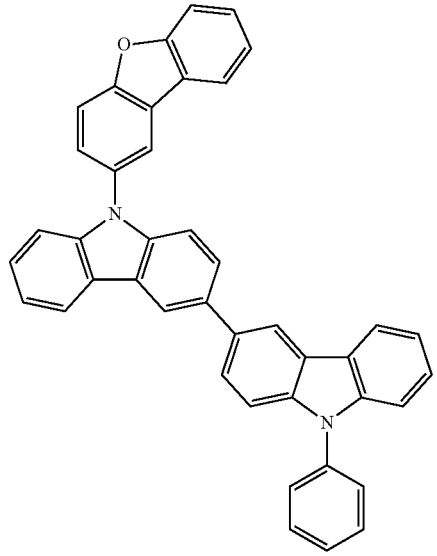 [SMILES: c1ccc(-n2c3ccccc3c3cc(-c4ccc5c(c4)c4ccccc4n5-c4ccc5oc6ccccc6c5c4)ccc32)cc1] | 2.23 |
| GH1-5 | JP 2013-183047 | 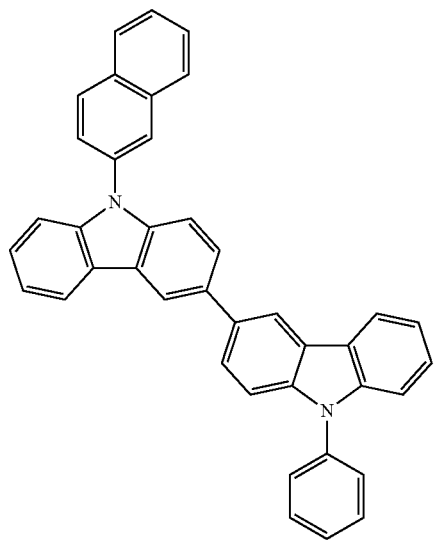 [SMILES: c1ccc(-n2c3ccccc3c3cc(-c4ccc5c(c4)c4ccccc4n5-c4ccc5ccccc5c4)ccc32)cc1] | 2.24 |

TABLE 2-continued
| Name | Reference | Chemical Structure | LUMO (eV) |
|---|---|---|---|
| GH1-6 | WO2011/155507 | 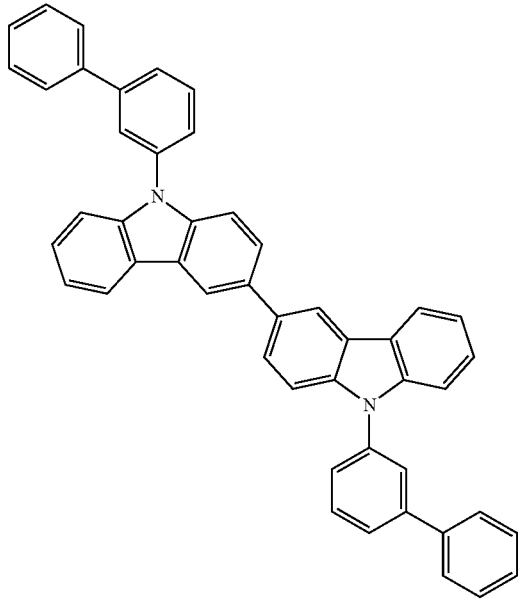 [SMILES: c1ccc(-c2cccc(-n3c4ccccc4c4cc(-c5ccc6c(c5)c5ccccc5n6-c5cccc(-c6ccccc6)c5)ccc43)c2)cc1] | 2.14 |
| GH1-7 | WO2017/142304 | 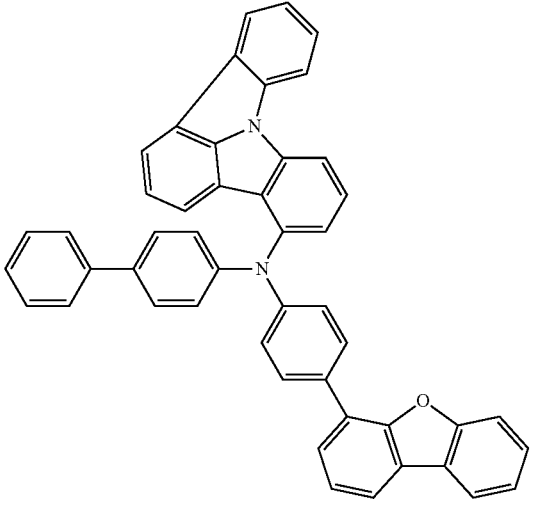 [SMILES: c1ccc(-c2ccc(N(c3ccc(-c4cccc5c4oc4ccccc45)cc3)c3cccc4c3c3cccc5c6ccccc6n4c53)cc2)cc1] | 2.66 |
As one of the green hosts (GH), the compounds shown in Table 3 below were used.

TABLE 3
| Name | Reference | Chemical structure | LUMO (eV) |
|---|---|---|---|
| GH2-1 | WO 2014/185595 | 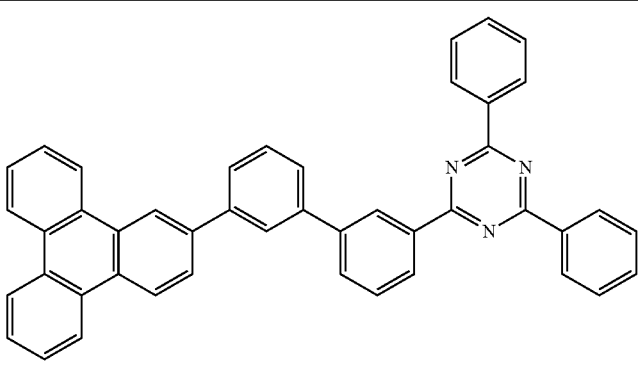 | 2.59 |
| GH2-2 | WO 2008/056746 | 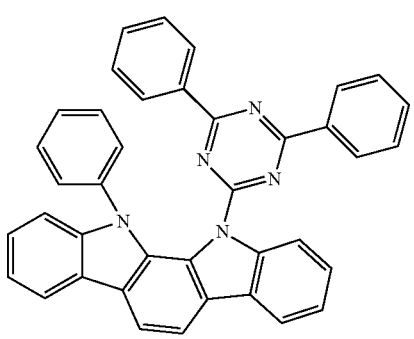 [SMILES: c1ccc(-c2nc(-c3ccccc3)nc(-n3c4ccccc4c4ccc5c6ccccc6n(-c6ccccc6)c5c43)n2)cc1] | 2.55 |
| GH2-3 | WO 2010/136109 | 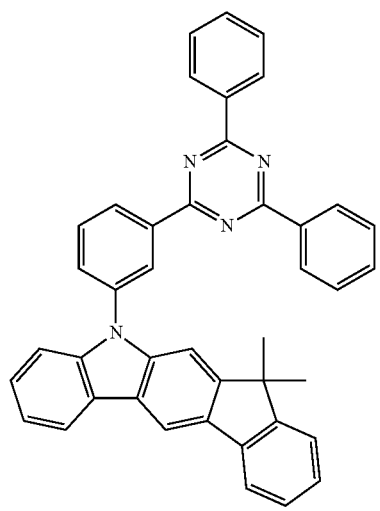 [SMILES: CC1(C)c2ccccc2-c2cc3c4ccccc4n(-c4cccc(-c5nc(-c6ccccc6)nc(-c6ccccc6)n5)c4)c3cc21] | 2.42 |
| GH2-4 | WO 2015/169412 | 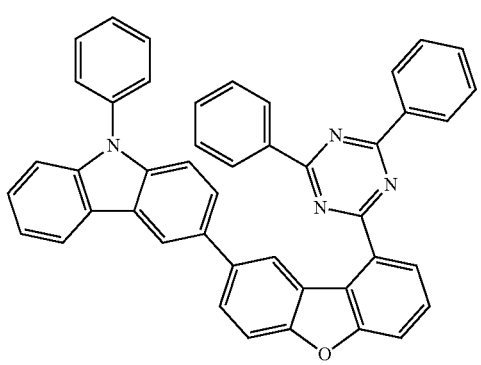 [SMILES: c1ccc(-c2nc(-c3ccccc3)nc(-c3cccc4oc5ccc(-c6ccc7c(c6)c6ccccc6n7-c6ccccc6)cc5c34)n2)cc1] | 2.60 |

TABLE 3-continued
| Name | Reference | Chemical structure | LUMO (eV) |
|---|---|---|---|
| GH2-5 | JP 02285357 B | 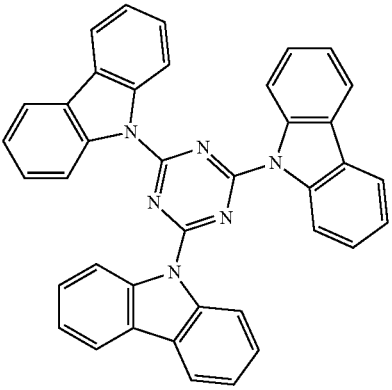 [SMILES: c1ccc2c(c1)c1ccccc1n2-c1nc(-n2c3ccccc3c3ccccc32)nc(-n2c3ccccc3c3ccccc32)n1] | 2.33 |
PREPARATION EXAMPLE 3
Hole Transport Material
As materials for hole transport, the compounds shown in Table 4 below were used.
TABLE 4
| Name | Reference | Chemical structure | HOMO (eV) | LUMO (eV) |
|---|---|---|---|---|
| ETL1-1 | WO 2016/105141 | 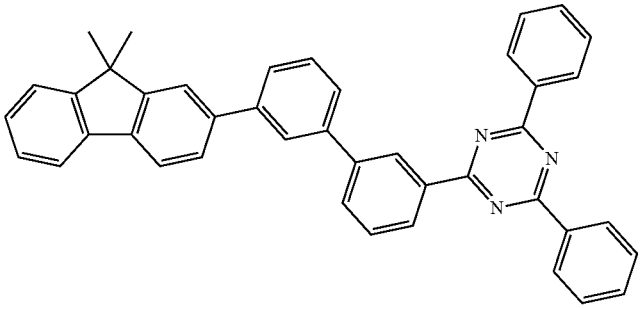 [SMILES: CC1(C)c2ccccc2-c2ccc(-c3cccc(-c4cccc(-c5nc(-c6ccccc6)nc(-c6ccccc6)n5)c4)c3)cc21] | 6.25 | 2.51 |
| ETL1-2 | WO 2011/132683 | 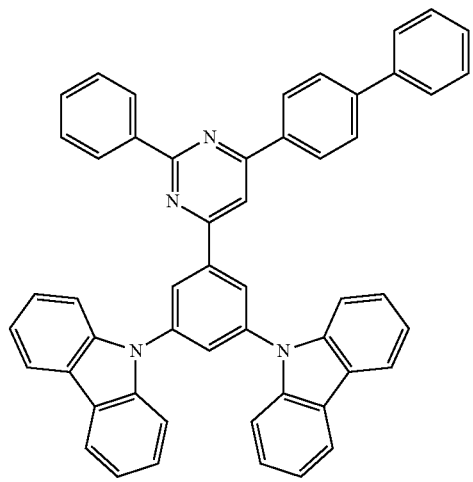 [SMILES: c1ccc(-c2ccc(-c3cc(-c4cc(-n5c6ccccc6c6ccccc65)cc(-n5c6ccccc6c6ccccc65)c4)nc(-c4ccccc4)n3)cc2)cc1] | 6.01 | 2.71 |

TABLE 4-continued
| Name | Reference | Chemical structure | HOMO (eV) | LUMO (eV) |
|------|-----------|--------------------|-----------|-----------|
| ETL1-3 | WO 2015/152650 | 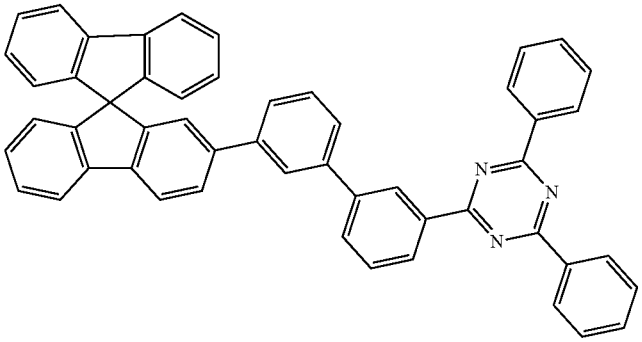 [SMILES: c1ccc(-c2nc(-c3ccccc3)nc(-c3cccc(-c4cccc(-c5ccc6c(c5)C5(c7ccccc7-c7ccccc75)c5ccccc5-6)c4)c3)n2)cc1] | 6.15 | 2.66 |
| ETL1-4 | (below, Preparation Example 3-1) | 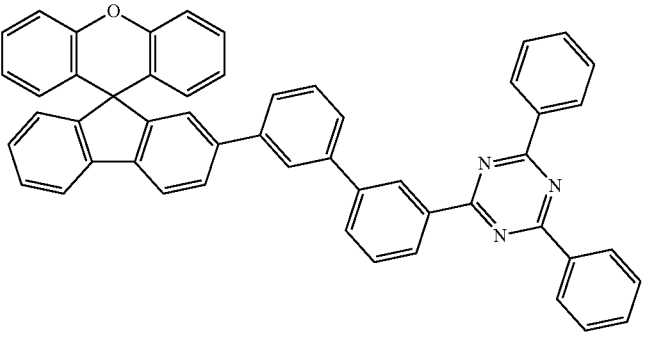 [SMILES: c1ccc(-c2nc(-c3ccccc3)nc(-c3cccc(-c4cccc(-c5ccc6c(c5)C5(c7ccccc7Oc7ccccc75)c5ccccc5-6)c4)c3)n2)cc1] | 6.05 | 2.75 |
| ETL1-5 | (below, Preparation Example 3-3) | 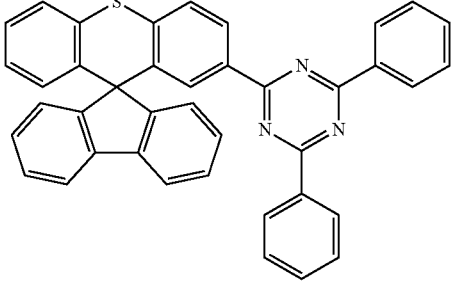 | 6.15 | 2.69 |
| ETL1-6 | (below, Preparation Example 3-2) | 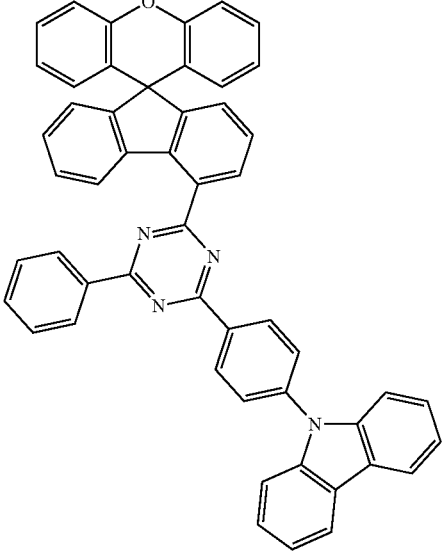 [SMILES: c1ccc(-c2nc(-c3ccc(-n4c5ccccc5c5ccccc54)cc3)nc(-c3cccc4c3-c3ccccc3C43c4ccccc4Oc4ccccc43)n2)cc1] | 6.04 | 3.05 |

TABLE 4-continued
| Name | Reference | Chemical structure | HOMO (eV) | LUMO (eV) |
|---|---|---|---|---|
| ETL1-7 | WO 2013/175747 | 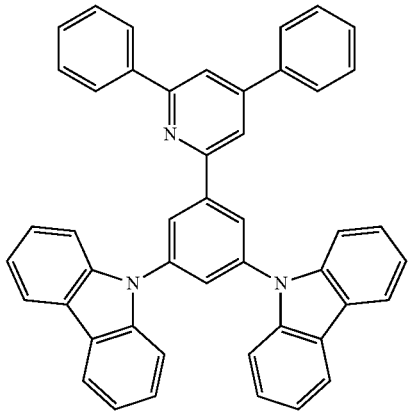 [SMILES: c1ccc(-c2cc(-c3ccccc3)nc(-c3cc(-n4c5ccccc5c5ccccc54)cc(-n4c5ccccc5c5ccccc54)c3)c2)cc1] | 5.85 | 2.38 |
| ETL1-8 | (below, Preparation Example 3-4) | 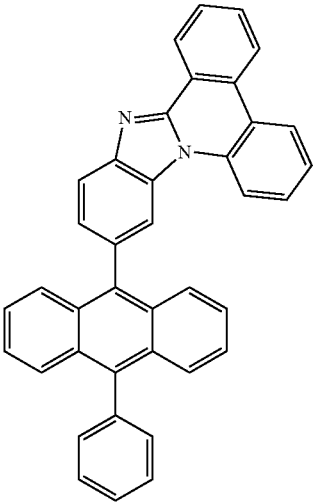 [SMILES: c1ccc(-c2c3ccccc3c(-c3ccc4nc5c6ccccc6c6ccccc6n5c4c3)c3ccccc23)cc1] | 5.75 | 2.86 |
| ETL1-9 | (below, Preparation Example 3-5) | 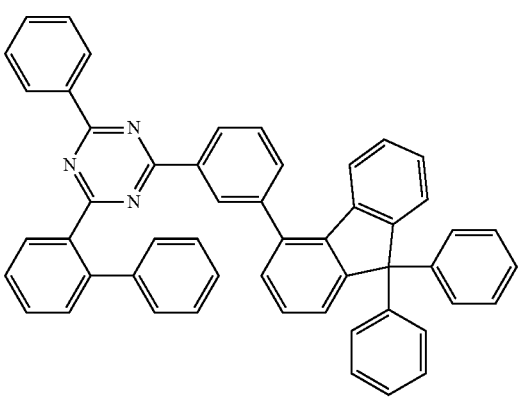 [SMILES: c1ccc(-c2nc(-c3cccc(-c4cccc5c4-c4ccccc4C5(c4ccccc4)c4ccccc4)c3)nc(-c3ccccc3-c3ccccc3)n2)cc1] | 6.28 | 2.33 |

PREPARATION EXAMPLE 3-1

Preparation of Compound ETL1-4

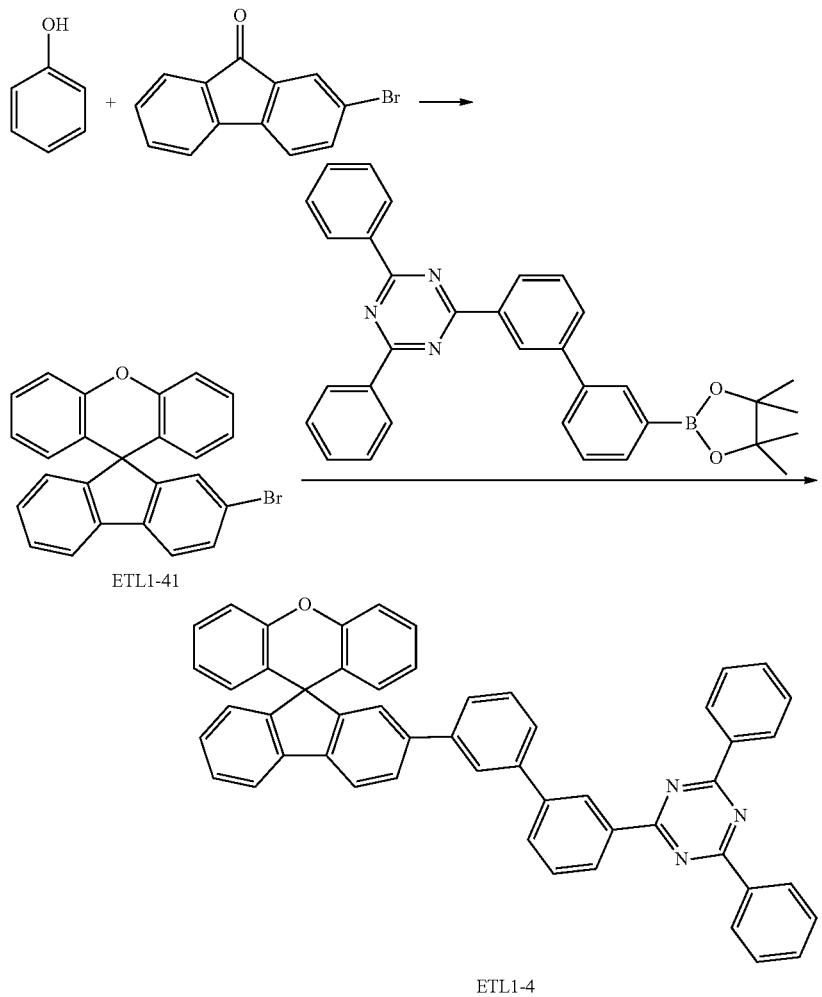

ETL1-4

1) Preparation of Compound ETL1-4i

A mixture of 2-bromo-9H-fluoren-9-one (10 g, 38.6 mmol), phenol (7.25 g, 77.2 mmol) and excess phosphoryl chloride (POCl$_3$) was refluxed at 120° C. After cooling to room temperature, excess ethanol was added thereto and filtered. The filtered solid was dissolved in pyridine, heated, cooled to room temperature and then filtered. Recrystallization was carried out with chloroform and ethyl acetate to obtain a compound ETL-4i (14 g, yield 87%).

MS: [M+H]$^+$=411

2) Preparation of Compound ETL1-4

The compound ETL-4i (10 g, 24.9 mmol), triazine boronic acid (12.26 g, 24 mmol) and potassium carbonate (10 g, 72.9 mmol) were dissolved in tetrahydrofuran (300 ml) and water (100 ml), and heated to 90° C. Pd(PPh$_3$)$_4$ (0.56 g, 0.48 mmol) was added thereto and then refluxed for 4 hours. After cooling to room temperature, the aqueous layer was removed. Magnesium sulfate was added to the organic layer, and the mixture was filtered, concentrated and purified by column chromatography to obtain a compound ETL1-4 (13 g, yield 75%).

MS: [M+H]$^+$=715

PREPARATION EXAMPLE 3-2

Preparation of Compound ETL1-6

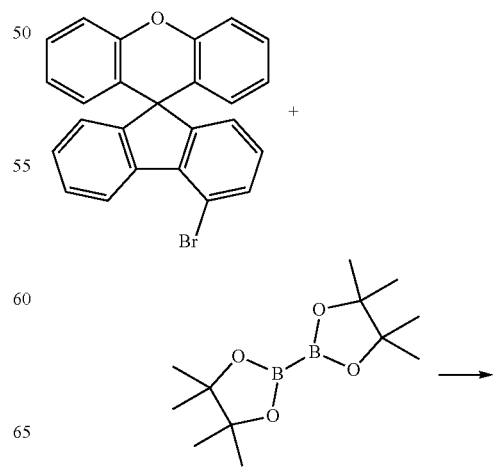

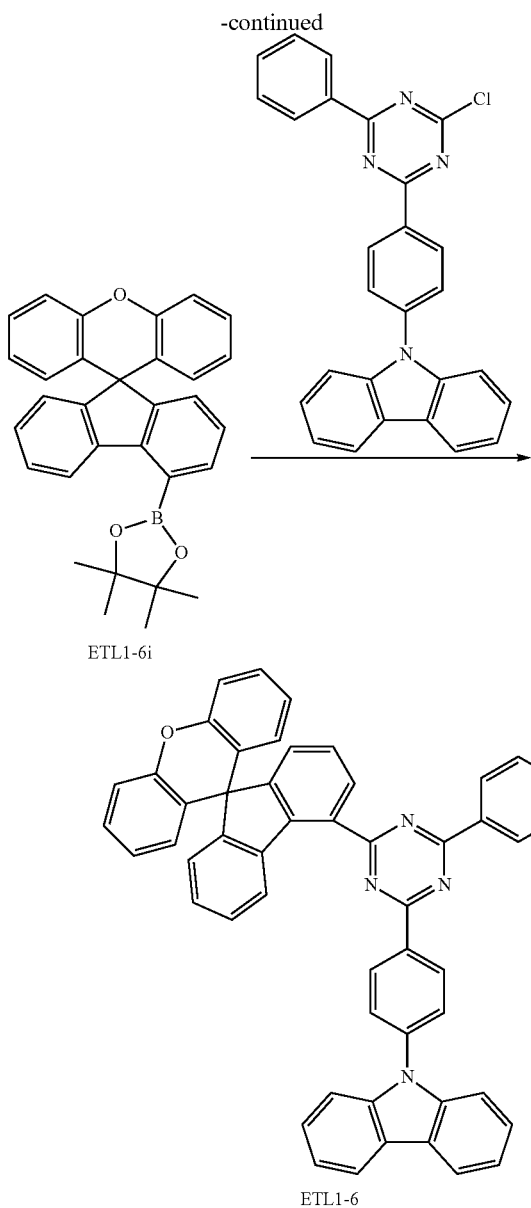

ETL1-6i

ETL1-6

1) Preparation of Compound ETL1-6i

4-Bromospiro[fluorene-9,9'-xanthene] (45 g, 109 mmol) and bispinacholato diboron (30 g, 119.9 mmol) were added to dioxane (1500 ml) and heated at 130° C. P(Cy)$_3$ and Pd(dba)$_2$ were mixed at a molar ratio of 2:1 (1.88 g in total), added thereto and refluxed for 4 hours. The mixture was cooled to room temperature, concentrated and purified by column chromatography to obtain a compound ETL1-6i (42 g, yield 84%).

MS: [M+H]$^+$458

2) Preparation of Compound ETL1-6

The compound ETL1-6i (10 g, 21.8 mmol) and 9-(4-(4-chloro-6-phenyl-1,3,5-triazin-2-yl)phenyl)-9H-carbazole (9.43 g, 21.8 mmol) and potassium carbonate (9 g, 65.4 mmol) were dissolved in tetrahydrofuran (300 ml) and water (100 ml) and heated to 90° C. Pd(PPh$_3$)$_4$ (0.50 g, 0.44 mmol) was added thereto and then refluxed for 4 hours. After cooling to room temperature, the aqueous layer was removed. Magnesium sulfate was added to the organic layer, and the mixture was filtered, concentrated and purified by column chromatography to obtain a compound ETL1-6 (11 g, yield 69%).

MS: [M+H]$^+$728

PREPARATION EXAMPLE 3-4

Preparation of Compound ETL1-5

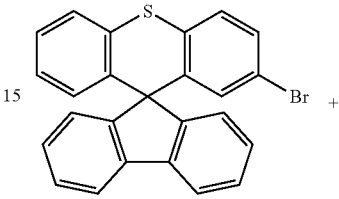

ETL1-5i

ETL1-5

1) Preparation of Compound ETL1-5i

2'-Bromospiro[fluorene-9,9'-thioxanthene] (45 g, 105 mmol) and bispinacholato diboron (29 g, 115.5 mmol) were added to dioxane (1500 ml) and dissolved by heating at 130° C. P(Cy)$_3$, and Pd(dba)$_2$ were mixed at a molar ratio of 2:1 (1.80 g in total), added thereto and refluxed for 4 hours. The mixture was cooled to room temperature, concentrated and purified by column chromatography to obtain a compound ETL1-5i (40 g, yield 80%).

MS: [M+H]$^+$474

2) Preparation of Compound ETL1-5

A compound ETL1-5(9 g, yield 74%) was obtained in the same manner as in the preparation of the compound ETL-6, except that a compound ETL1-5i (10 g, 21.1 mmol) was used instead of the compound ETL1-6i, and 2-chloro-4,6-diphenyl-1,3,5-triazine (5.6 g, 21.1 mmol) was used instead of 9-(4-(4-chloro-6-phenyl-1,3,5-triazin-2-yl)phenyl)-9H-carbazole.

MS: [M+H]$^+$579

PREPARATION EXAMPLE 3-4

Preparation of Compound ETL1-8

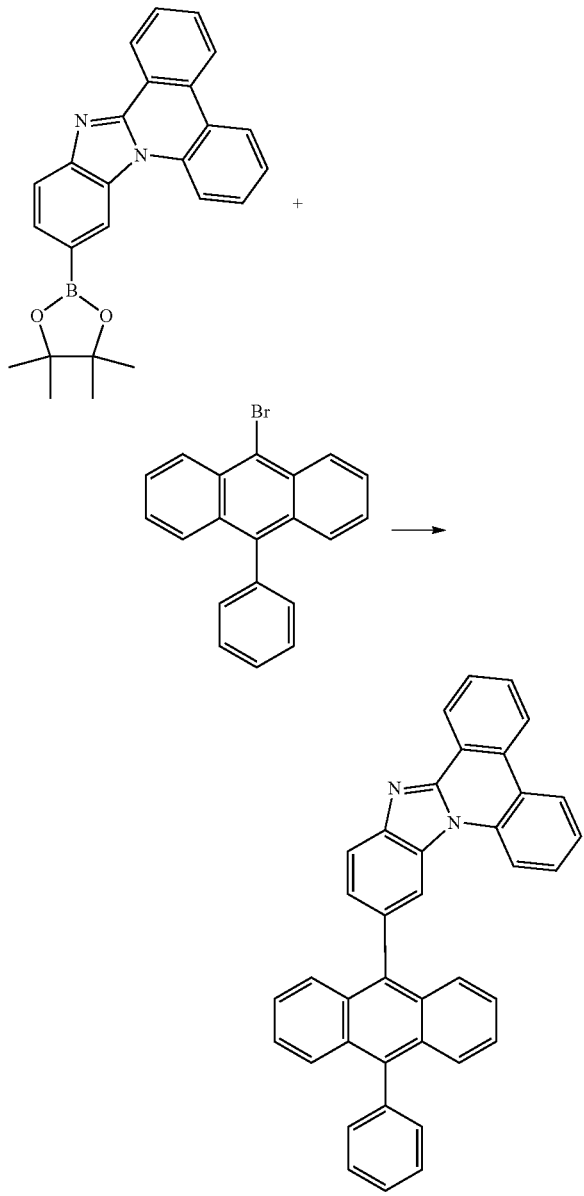

A compound ETL1-8 (11 g, yield 83%) was obtained in the same manner as in the preparation of the compound ETL-6, except that a compound ETL1-8i(10 g, 25.4 mmol) was used instead of the compound ETL1-6i, and 9-bromo-10-phenylanthracene (13.5 g, 25.4 mmol) was used instead of 9-(4-(4-chloro-6-phenyl-1,3,5-triazin-2-yl)phenyl)-9H-carbazole.

MS: [M+H]$^+$520

PREPARATION EXAMPLE 3-5

Preparation of Compound ETL1-9

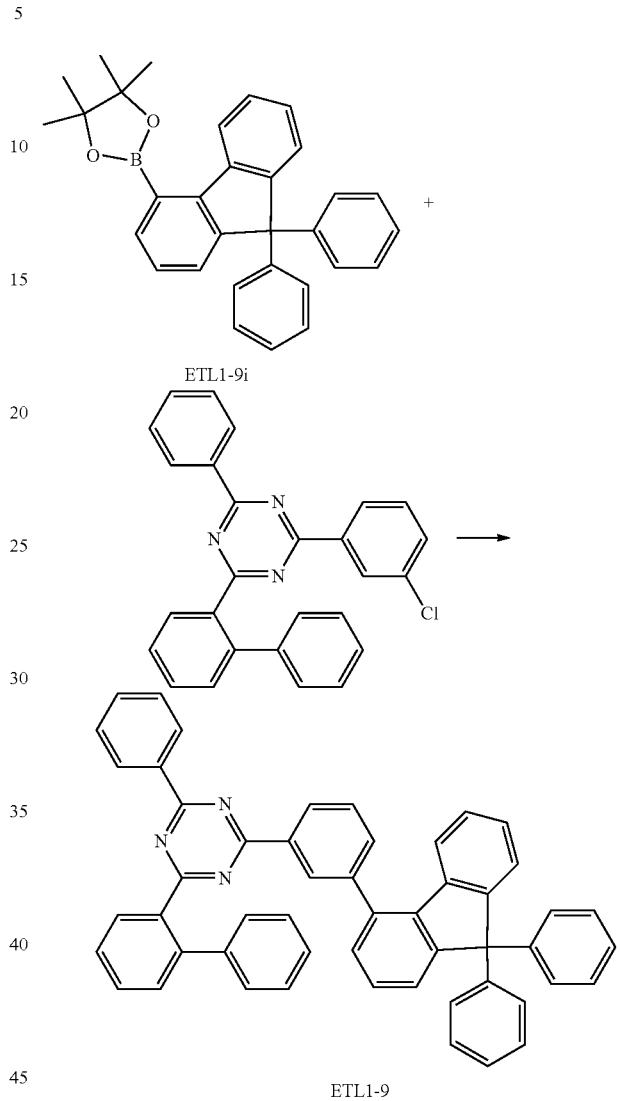

A compound ETL1-9 (11 g, yield 83%) was obtained in the same manner as in the preparation of the compound ETL1-6, except that a compound ETL1-9i(10 g, 22.5 mmol) was used instead of the compound ETL1-6i, and 2-(biphenyl-2-yl)-4-(3-chlorophenyl)-6-phenyl-1,3,5-triazine (9.4 g, 22.5 mmol) was used instead of 9-(4-(4-chloro-6-phenyl-1,3,5-triazin-2-yl)phenyl)-9H-carbazole.

MS: [M+H]$^+$701

EXAMPLES

Example 1

A glass substrate (corning 7059 glass) on which a thin film of ITO (indium tin oxide) was coated in a thickness of 1,000 Å was put into distilled water containing the dispersant dissolved therein and washed by the ultrasonic wave. In this case, the used detergent was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, ultrasonic washing was performed in the order of isopropyl alcohol, acetone, and methanol solvent, and dried.

On the ITO transparent electrode thus prepared, a compound HAT was subjected to thermal vacuum-deposition in a thickness of 500 Å to form a hole injection layer. A compound HT1 was vacuum-deposited thereon in a thickness of 400 Å to form a hole transport layer.

A blue light emitting layer, a green light emitting layer and a red light emitting layer were formed in parallel thereon. Specifically, a compound BH-1 and a compound BD-1 were vacuum-deposited at a weight ratio of 97.5:2.5 in a thickness of 350 Å to form a blue light emitting layer, a compound GH1-1, a compound GH2-1 and a compound GD-1 were vacuum-deposited at a weight ratio of 47:47:6 in a thickness of 350 Å to form a green light emitting layer, and a compound RH-1 and a compound RD-1 were vacuum-deposited at a weight ratio of 98:2 in a thickness of 350 Å to form a red light emitting layer.

A compound ETL1-1 compound was deposited on the light emitting layer in a thickness of 50 Å. Then, a compound ETL2-1 and a compound LiQ were vacuum-deposited at a weight ratio of 1:1 in a thickness of 250 Å to form an electron injection and transport layer. On the electron injection and transport layer, sequentially, lithium fluoride (LiF) was deposited in a thickness of 12 Å and aluminum was deposited in a thickness of 2,000 Å, to form a cathode. Thereby, an organic light emitting device was prepared,

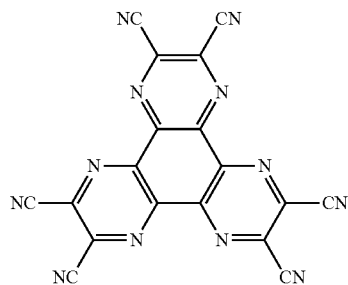

HAT

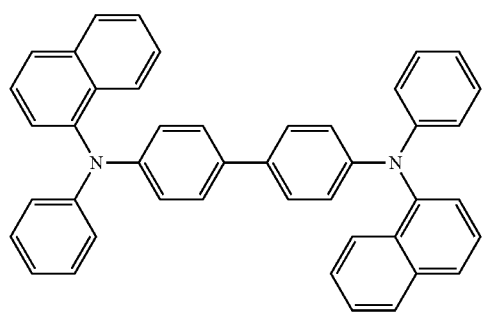

HT1

-continued

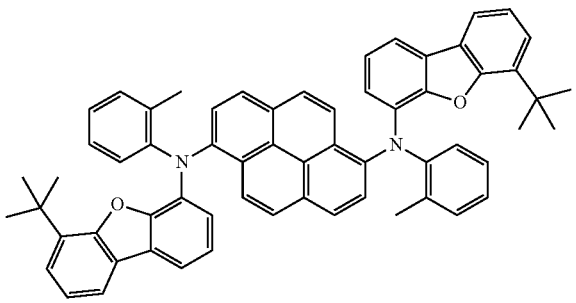

BD-1

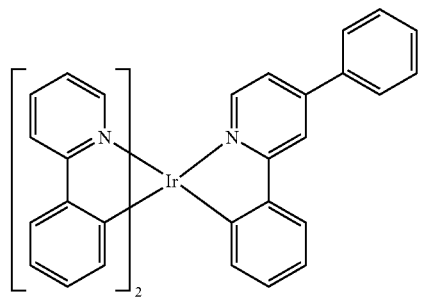

GD-1

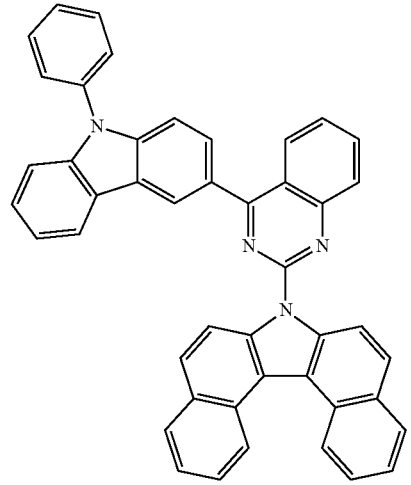

RH-1

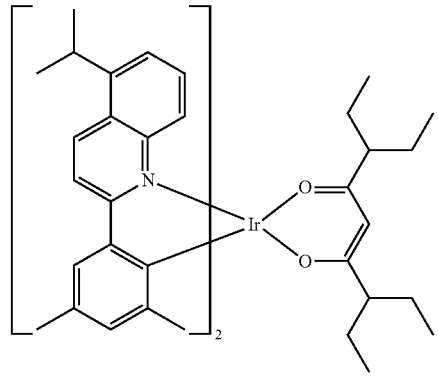

RD-1

ETL2-1

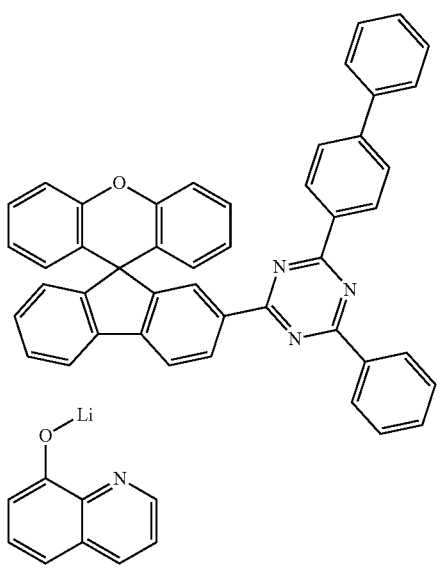

Liq

In the above process, the vapor deposition rate of the organic material was maintained at 0.4 to 0.7 Å/sec, the vapor deposition rate of lithium fluoride of the cathode was maintained at 0.3 Å/sec, the vapor deposition rate of aluminum was maintained at 2 Å/sec, and the degree of vacuum during vapor deposition was maintained at $2 \times 10^{-7} \sim 5 \times 10^{-6}$ torr to manufacture an organic light emitting device.

Examples 2 to 48 and Comparative Examples 1 to 13

The organic light emitting devices were manufactured in the same manner as in Example 1, except that the compounds shown in Tables 5 to 10 below were respectively used as the compounds used in the light emitting layer and the electron transport layer in Example 1. On the other hand, the compounds ETL2-2 to ETL2-15 in Tables 5 to 10 below are as follows.

ETL2-2

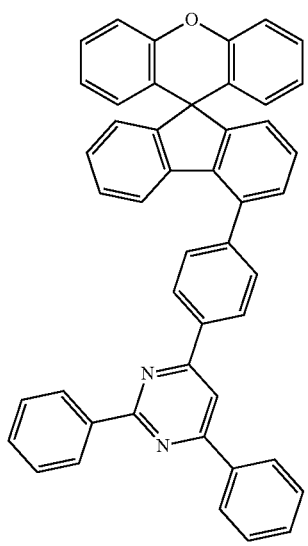

ETL2-3

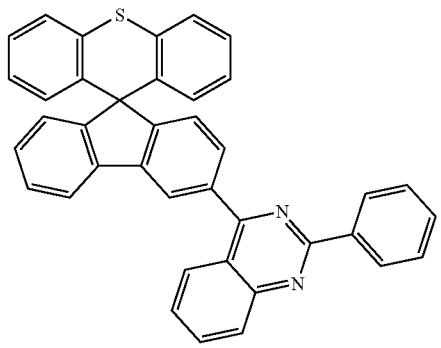

ETL2-4

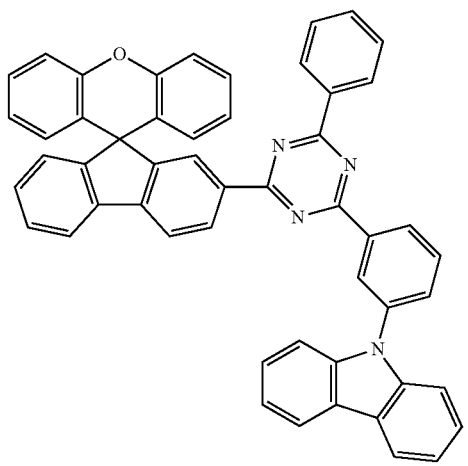

ETL2-5

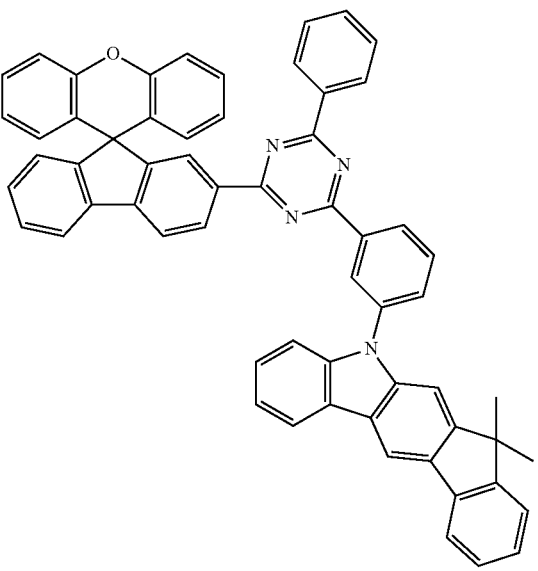

ETL2-6
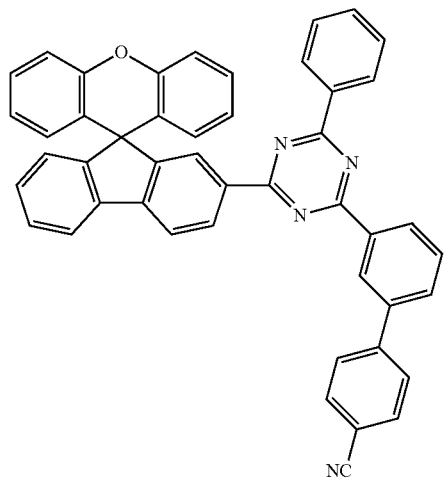
ETL2-7
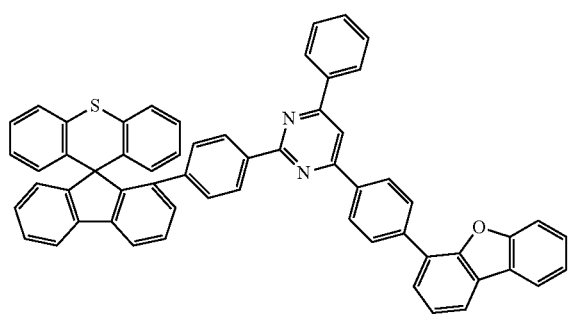
ETL2-8
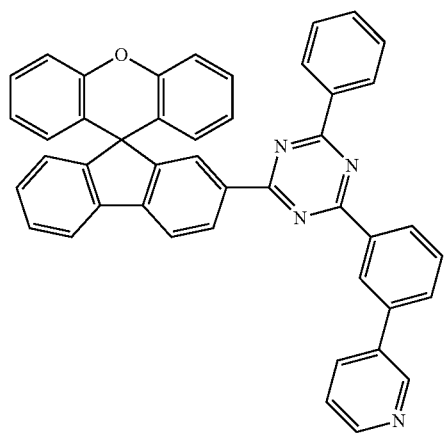
ETL2-9
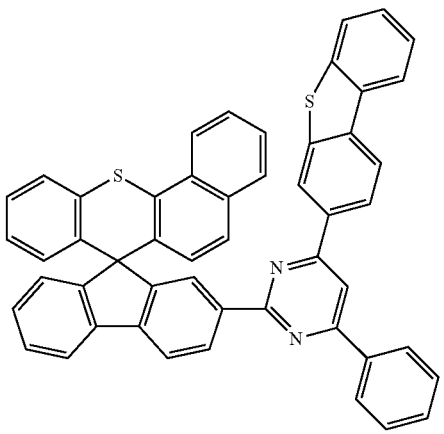
ETL2-10
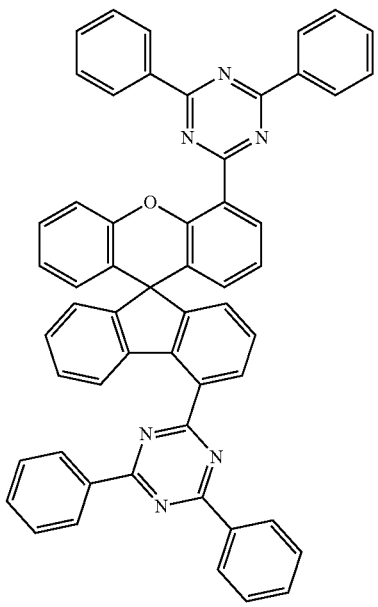
ETL2-11
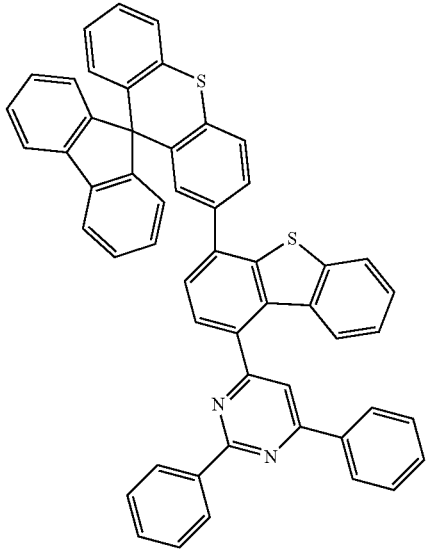

-continued

ETL2-12

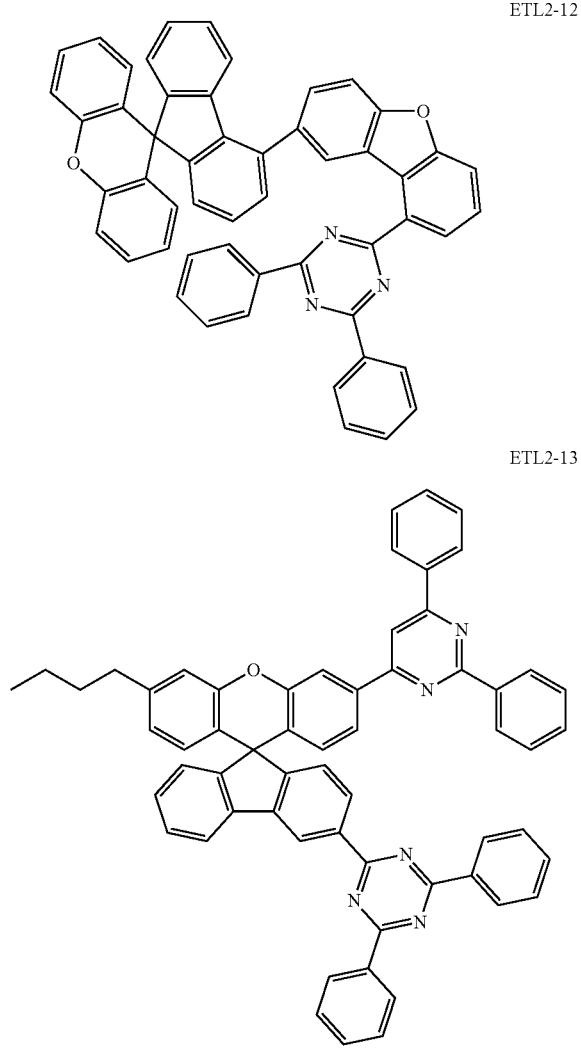

ETL2-13

ETL2-14

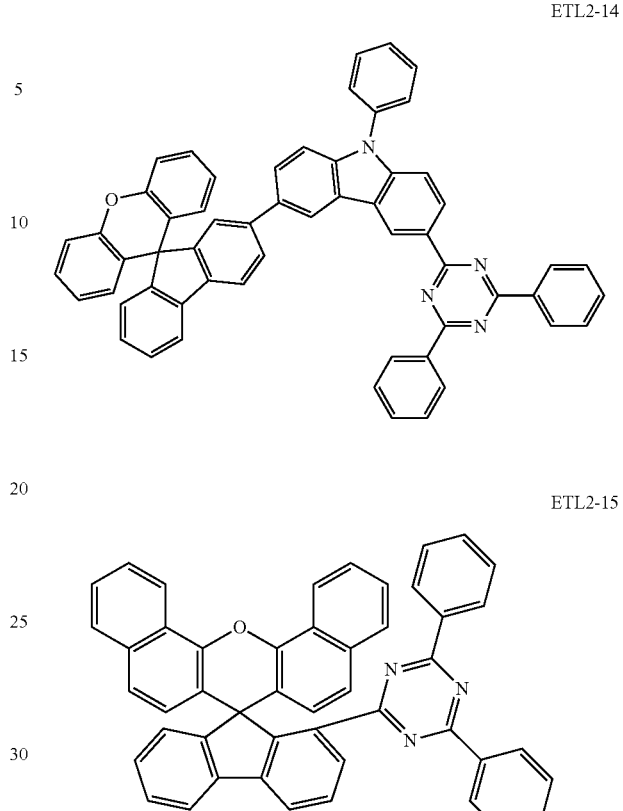

ETL2-15

The driving voltage and light emitting efficiency were measured at the current density of 10 mA/cm$^2$ for the organic light emitting devices manufactured in the Examples and Comparative Examples, and the time (LT98) at which the luminance became 98% relative to the initial luminance at the current density of 20 mA/cm$^2$ was measured. The results are shown in Tables 5 to 10 below.

TABLE 5

| Example No. | Light emitting layer | Electron transport layer | $E_{HOMO\text{-}ET}$ | $E_{HOMO\text{-}BH}$ | $E_{LUMO\text{-}ET}$ | $E_{LUMO\text{-}GH}$ | Voltage (V) | Efficiency (cd/A) | LT98 (hr) |
|---|---|---|---|---|---|---|---|---|---|
| 1 | BH-1 | ETL1-1 | 6.25 | 5.84 | 2.51 | 2.44 | 3.82 | 5.28 | 56 |
|   | GH1-1 & GH2-1 | ETL2-1 |  |  |  |  | 3.12 | 74.81 | 180 |
|   | RH-1 |  |  |  |  |  | 4.11 | 25.34 | 220 |
| 2 | BH-1 | ETL1-1 | 6.25 | 5.84 | 2.51 | 2.44 | 3.75 | 5.11 | 51 |
|   | GH1-1 & GH2-1 | ETL2-2 |  |  |  |  | 3.05 | 72.88 | 175 |
|   | RH-1 |  |  |  |  |  | 4.02 | 22.12 | 215 |
| 3 | BH-1 | ETL1-1 | 6.25 | 5.84 | 2.51 | 2.44 | 3.95 | 5.01 | 61 |
|   | GH1-1 & GH2-1 | ETL2-3 |  |  |  |  | 3.34 | 70.16 | 182 |
|   | RH-1 |  |  |  |  |  | 4.18 | 20.18 | 234 |
| 4 | BH-1 | ETL1-1 | 6.25 | 5.84 | 2.51 | 2.44 | 3.88 | 5.15 | 65 |
|   | GH1-1 & GH2-1 | ETL2-4 |  |  |  |  | 3.19 | 74.11 | 192 |
|   | RH-1 |  |  |  |  |  | 4.21 | 23.21 | 250 |
| 5 | BH-1 | ETL1-1 | 6.25 | 5.84 | 2.51 | 2.44 | 3.64 | 5.29 | 49 |
|   | GH1-1 & GH2-1 | ETL2-5 |  |  |  |  | 3.05 | 75.02 | 169 |
|   | RH-1 |  |  |  |  |  | 4.01 | 26.31 | 201 |
| 6 | BH-1 | ETL1-1 | 6.25 | 5.84 | 2.51 | 2.44 | 4.02 | 5.01 | 70 |
|   | GH1-1 & GH2-1 | ETL2-6 |  |  |  |  | 3.33 | 71.81 | 210 |
|   | RH-1 |  |  |  |  |  | 4.25 | 20.33 | 260 |
| 7 | BH-1 | ETL1-1 | 6.25 | 5.84 | 2.51 | 2.44 | 3.78 | 5.09 | 56 |
|   | GH1-1 & GH2-1 | ETL2-7 |  |  |  |  | 3.15 | 72.65 | 188 |
|   | RH-1 |  |  |  |  |  | 4.12 | 22.01 | 222 |
| 8 | BH-1 | ETL1-1 | 6.25 | 5.84 | 2.51 | 2.44 | 3.89 | 5.20 | 59 |
|   | GH1-1 & GH2-1 | ETL2-8 |  |  |  |  | 3.29 | 72.81 | 194 |
|   | RH-1 |  |  |  |  |  | 4.16 | 23.36 | 236 |

TABLE 5-continued

| Example No. | Light emitting layer | Electron transport layer | $E_{HOMO-ET}$ | $E_{HOMO-BH}$ | $E_{LUMO-ET}$ | $E_{LUMO-GH}$ | Voltage (V) | Efficiency (cd/A) | LT98 (hr) |
|---|---|---|---|---|---|---|---|---|---|
| 9 | BH-1<br>GH1-1 & GH2-1<br>RH-1 | ETL1-1<br>ETL2-9 | 6.25 | 5.84 | 2.51 | 2.44 | 3.86<br>3.24<br>4.32 | 5.00<br>70.65<br>19.58 | 62<br>181<br>229 |
| 10 | BH-1<br>GH1-1 & GH2-1<br>RH-1 | ETL1-1<br>ETL2-10 | 6.25 | 5.84 | 2.51 | 2.44 | 3.75<br>3.01<br>4.05 | 6.02<br>76.33<br>27.34 | 51<br>170<br>210 |

TABLE 6

| Example No. | Light emitting layer | Electron transport layer | $E_{HOMO-ET}$ | $E_{HOMO-BH}$ | $E_{LUMO-ET}$ | $E_{LUMO-GH}$ | Voltage (V) | Efficiency (cd/A) | LT98 (hr) |
|---|---|---|---|---|---|---|---|---|---|
| 11 | BH-1<br>GH1-1 & GH2-1<br>RH-1 | ETL1-1<br>ETL2-11 | 6.25 | 5.84 | 2.51 | 2.44 | 3.86<br>3.18<br>4.19 | 5.16<br>71.23<br>21.53 | 58<br>185<br>226 |
| 12 | BH-1<br>GH1-1 & GH2-1<br>RH-1 | ETL1-1<br>ETL2-12 | 6.25 | 5.84 | 2.51 | 2.44 | 3.81<br>3.09<br>4.06 | 5.28<br>74.71<br>25.25 | 52<br>160<br>196 |
| 13 | BH-1<br>GH1-1 & GH2-1<br>RH-1 | ETL1-1<br>ETL2-13 | 6.25 | 5.84 | 2.51 | 2.44 | 3.52<br>3.10<br>3.09 | 6.11<br>78.01<br>28.34 | 45<br>163<br>195 |
| 14 | BH-1<br>GH1-1 & GH2-1<br>RH-1 | ETL1-1<br>ETL2-14 | 6.25 | 5.84 | 2.51 | 2.44 | 3.88<br>3.19<br>4.21 | 5.14<br>74.01<br>23.22 | 62<br>196<br>248 |
| 15 | BH-1<br>GH1-1 & GH2-1<br>RH-1 | ETL1-1<br>ETL2-15 | 6.25 | 5.84 | 2.51 | 2.44 | 3.86<br>3.18<br>4.21 | 5.07<br>73.61<br>22.34 | 58<br>187<br>225 |
| 16 | BH-1<br>GH1-1 & GH2-1<br>RH-1 | ETL1-2<br>ETL2-1 | 6.01 | 5.84 | 2.71 | 2.44 | 4.01<br>3.32<br>4.24 | 5.01<br>69.98<br>22.33 | 65<br>200<br>240 |
| 17 | BH-1<br>GH1-1 & GH2-1<br>RH-1 | ETL1-3<br>ETL2-1 | 6.15 | 5.84 | 2.66 | 2.44 | 3.80<br>3.10<br>4.09 | 5.33<br>74.95<br>25.85 | 51<br>172<br>202 |
| 18 | BH-1<br>GH1-1 & GH2-1<br>RH-1 | ETL1-4<br>ETL2-1 | 6.05 | 5.84 | 2.75 | 2.44 | 3.81<br>3.09<br>4.08 | 5.38<br>74.68<br>25.75 | 50<br>171<br>210 |
| 19 | BH-1<br>GH1-1 & GH2-1<br>RH-1 | ETL1-5<br>ETL2-1 | 6.15 | 5.84 | 2.69 | 2.44 | 3.99<br>3.52<br>4.31 | 5.02<br>70.65<br>20.34 | 68<br>200<br>239 |
| 20 | BH-1<br>GH1-1 & GH2-1<br>RH-1 | ETL1-6<br>ETL2-1 | 6.04 | 5.84 | 3.05 | 2.44 | 3.91<br>3.45<br>4.29 | 5.06<br>72.88<br>20.85 | 65<br>195<br>231 |

TABLE 7

| Example No. | Light emitting layer | Electron transport layer | $E_{HOMO-ET}$ | $E_{HOMO-BH}$ | $E_{LUMO-ET}$ | $E_{LUMO-GH}$ | Voltage (V) | Efficiency (cd/A) | LT98 (hr) |
|---|---|---|---|---|---|---|---|---|---|
| 21 | BH-2<br>GH1-1 & GH2-2<br>RH-1 | ETL1-1<br>ETL2-4 | 6.25 | 5.80 | 2.51 | 2.42 | 3.91<br>3.23<br>4.28 | 5.21<br>74.56<br>24.23 | 69<br>202<br>259 |
| 22 | BH-2<br>GH1-2 & GH2-2<br>RH-1 | ETL1-2<br>ETL2-4 | 6.01 | 5.80 | 2.71 | 2.45 | 4.01<br>3.55<br>4.41 | 5.01<br>69.11<br>21.33 | 71<br>222<br>261 |
| 23 | BH-2<br>GH1-3 & GH2-2<br>RH-1 | ETL1-3<br>ETL2-4 | 6.15 | 5.80 | 2.66 | 2.44 | 3.89<br>3.21<br>4.22 | 5.31<br>75.61<br>25.41 | 61<br>192<br>241 |
| 24 | BH-2<br>GH1-4 & GH2-2<br>RH-1 | ETL1-4<br>ETL2-4 | 6.05 | 5.80 | 2.75 | 2.39 | 3.89<br>3.20<br>4.19 | 5.29<br>75.78<br>25.63 | 58<br>195<br>239 |
| 25 | BH-2<br>GH1-5 & GH2-2<br>RH-1 | ETL1-5<br>ETL2-4 | 6.15 | 5.80 | 2.69 | 2.40 | 4.23<br>3.41<br>4.49 | 5.01<br>69.36<br>22.33 | 72<br>232<br>269 |
| 26 | BH-2<br>GH1-6 & GH2-2<br>RH-1 | ETL1-6<br>ETL2-4 | 6.04 | 5.80 | 3.05 | 2.35 | 4.22<br>3.39<br>4.39 | 5.18<br>69.25<br>23.65 | 65<br>230<br>261 |

TABLE 7-continued

| Example No. | Light emitting layer | Electron transport layer | $E_{HOMO\text{-}ET}$ | $E_{HOMO\text{-}BH}$ | $E_{LUMO\text{-}ET}$ | $E_{LUMO\text{-}GH}$ | Voltage (V) | Efficiency (cd/A) | LT98 (hr) |
|---|---|---|---|---|---|---|---|---|---|
| 27 | BH-3 | ETL1-1 | 6.25 | 5.72 | 2.51 | 2.36 | 4.09 | 5.00 | 64 |
|  | GH1-1 & GH2-3 | ETL2-6 |  |  |  |  | 3.36 | 71.01 | 210 |
|  | RH-1 |  |  |  |  |  | 4.27 | 20.65 | 252 |
| 28 | BH-3 | ETL1-2 | 6.01 | 5.72 | 2.71 | 2.38 | 4.23 | 4.75 | 68 |
|  | GH1-2 & GH2-3 | ETL2-6 |  |  |  |  | 3.39 | 70.06 | 230 |
|  | RH-1 |  |  |  |  |  | 4.25 | 20.12 | 259 |
| 29 | BH-3 | ETL1-3 | 6.15 | 5.72 | 2.66 | 2.38 | 3.96 | 5.00 | 59 |
|  | GH1-3 & GH2-3 | ETL2-6 |  |  |  |  | 3.34 | 72.31 | 196 |
|  | RH-1 |  |  |  |  |  | 4.14 | 23.54 | 219 |
| 30 | BH-3 | ETL1-4 | 6.05 | 5.72 | 2.75 | 2.33 | 3.94 | 5.00 | 58 |
|  | GH1-4 & GH2-3 | ETL2-6 |  |  |  |  | 3.32 | 72.69 | 198 |
|  | RH-1 |  |  |  |  |  | 4.11 | 23.44 | 212 |

TABLE 8

| Example No. | Light emitting layer | Electron transport layer | $E_{HOMO\text{-}ET}$ | $E_{HOMO\text{-}BH}$ | $E_{LUMO\text{-}ET}$ | $E_{LUMO\text{-}GH}$ | Voltage (V) | Efficiency (cd/A) | LT98 (hr) |
|---|---|---|---|---|---|---|---|---|---|
| 31 | BH-3 | ETL1-5 | 6.15 | 5.72 | 2.69 | 2.33 | 4.21 | 4.86 | 70 |
|  | GH1-5 & GH2-3 | ETL2-6 |  |  |  |  | 3.56 | 68.32 | 230 |
|  | RH-1 |  |  |  |  |  | 4.31 | 18.58 | 268 |
| 32 | BH-3 | ETL1-6 | 6.04 | 5.72 | 3.05 | 2.28 | 4.19 | 4.99 | 65 |
|  | GH1-6 & GH2-3 | ETL2-6 |  |  |  |  | 3.51 | 69.23 | 216 |
|  | RH-1 |  |  |  |  |  | 4.25 | 20.99 | 252 |
| 33 | BH-4 | ETL1-1 | 6.25 | 5.75 | 2.51 | 2.47 | 3.90 | 5.19 | 61 |
|  | GH1-2 & GH2-1 | ETL2-8 |  |  |  |  | 3.31 | 72.11 | 198 |
|  | RH-1 |  |  |  |  |  | 4.18 | 23.25 | 236 |
| 34 | BH-4 | ETL1-2 | 6.01 | 5.75 | 2.71 | 2.45 | 3.99 | 5.02 | 68 |
|  | GH1-2 & GH2-2 | ETL2-8 |  |  |  |  | 3.38 | 70.36 | 206 |
|  | RH-1 |  |  |  |  |  | 4.25 | 21.35 | 248 |
| 35 | BH-4 | ETL1-3 | 6.15 | 5.75 | 2.66 | 2.38 | 3.87 | 5.21 | 58 |
|  | GH1-2 & GH2-3 | ETL2-8 |  |  |  |  | 3.25 | 73.21 | 187 |
|  | RH-1 |  |  |  |  |  | 4.07 | 25.10 | 215 |
| 36 | BH-4 | ETL1-4 | 6.05 | 5.75 | 2.75 | 2.47 | 3.87 | 5.32 | 57 |
|  | GH1-2 & GH2-4 | ETL2-8 |  |  |  |  | 3.21 | 73.69 | 190 |
|  | RH-1 |  |  |  |  |  | 4.06 | 25.62 | 212 |
| 37 | BH-4 | ETL1-5 | 6.15 | 5.75 | 2.69 | 2.34 | 3.99 | 5.00 | 66 |
|  | GH1-2 & GH2-5 | ETL2-8 |  |  |  |  | 3.55 | 69.21 | 215 |
|  | RH-1 |  |  |  |  |  | 4.35 | 21.10 | 255 |
| 38 | BH-5 | ETL1-1 | 6.25 | 5.93 | 2.51 | 2.46 | 3.45 | 5.75 | 48 |
|  | GH1-3 & GH2-1 | ETL2-10 |  |  |  |  | 2.91 | 71.52 | 160 |
|  | RH-1 |  |  |  |  |  | 3.99 | 24.41 | 192 |
| 39 | BH-5 | ETL1-2 | 6.01 | 5.93 | 2.71 | 2.44 | 3.65 | 5.84 | 49 |
|  | GH1-3 & GH2-2 | ETL2-10 |  |  |  |  | 3.02 | 73.01 | 171 |
|  | RH-1 |  |  |  |  |  | 4.06 | 25.11 | 195 |
| 40 | BH-5 | ETL1-3 | 6.15 | 5.93 | 2.66 | 2.38 | 3.44 | 5.78 | 50 |
|  | GH1-3 & GH2-3 | ETL2-10 |  |  |  |  | 2.90 | 71.63 | 171 |
|  | RH-1 |  |  |  |  |  | 4.00 | 24.65 | 200 |

TABLE 9

| Example No. | Light emitting layer | Electron transport layer | $E_{HOMO\text{-}ET}$ | $E_{HOMO\text{-}BH}$ | $E_{LUMO\text{-}ET}$ | $E_{LUMO\text{-}GH}$ | Voltage (V) | Efficiency (cd/A) | LT98 (hr) |
|---|---|---|---|---|---|---|---|---|---|
| 41 | BH-5 | ETL1-4 | 6.05 | 5.93 | 2.75 | 2.47 | 3.43 | 5.80 | 51 |
|  | GH1-3 & GH2-4 | ETL2-10 |  |  |  |  | 2.95 | 72.00 | 170 |
|  | RH-1 |  |  |  |  |  | 4.01 | 24.95 | 205 |
| 42 | BH-5 | ETL1-5 | 6.15 | 5.93 | 2.69 | 2.33 | 3.59 | 5.88 | 52 |
|  | GH1-3 & GH2-5 | ETL2-10 |  |  |  |  | 3.02 | 73.01 | 172 |
|  | RH-1 |  |  |  |  |  | 4.05 | 25.01 | 209 |
| 43 | BH-6 | ETL1-1 | 6.25 | 5.91 | 2.51 | 2.37 | 3.85 | 5.55 | 65 |
|  | GH1-6 & GH2-1 | ETL2-1 |  |  |  |  | 3.16 | 74.89 | 189 |
|  | RH-1 |  |  |  |  |  | 4.15 | 26.01 | 231 |
| 44 | BH-6 | ETL1-2 | 6.01 | 5.91 | 2.71 | 2.35 | 3.95 | 5.28 | 56 |
|  | GH1-6 & GH2-2 | ETL2-3 |  |  |  |  | 3.21 | 74.81 | 180 |
|  | RH-1 |  |  |  |  |  | 4.23 | 25.34 | 220 |

TABLE 9-continued

| Example No. | Light emitting layer | Electron transport layer | $E_{HOMO-ET}$ | $E_{HOMO-BH}$ | $E_{LUMO-ET}$ | $E_{LUMO-GH}$ | Voltage (V) | Efficiency (cd/A) | LT98 (hr) |
|---|---|---|---|---|---|---|---|---|---|
| 45 | BH-6 | ETL1-3 | 6.15 | 5.91 | 2.66 | 2.28 | 3.99 | 5.32 | 68 |
|  | GH1-6 & GH2-3 | ETL2-4 |  |  |  |  | 3.25 | 76.80 | 194 |
|  | RH-1 |  |  |  |  |  | 4.19 | 26.34 | 249 |
| 46 | BH-6 | ETL1-4 | 6.05 | 5.91 | 2.75 | 2.37 | 3.94 | 5.21 | 62 |
|  | GH1-6 & GH2-4 | ETL2-6 |  |  |  |  | 3.35 | 74.44 | 202 |
|  | RH-1 |  |  |  |  |  | 4.10 | 25.01 | 229 |
| 47 | BH-6 | ETL1-5 | 6.15 | 5.91 | 2.69 | 2.24 | 3.98 | 5.01 | 66 |
|  | GH1-6 & GH2-5 | ETL2-15 |  |  |  |  | 3.26 | 71.69 | 215 |
|  | RH-1 |  |  |  |  |  | 4.25 | 21.44 | 245 |
| 48 | BH-6 | ETL1-1 | 6.25 | 5.91 | 2.51 | 2.37 | 3.82 | 5.22 | 58 |
|  | GH1-6 & GH2-4 | ETL2-1 |  |  |  |  | 3.13 | 74.74 | 189 |
|  | RH-1 |  |  |  |  |  | 4.16 | 25.28 | 230 |

TABLE 10

| Comparative Example No. | Light emitting layer | Electron transport layer | $E_{HOMO-ET}$ | $E_{HOMO-BH}$ | $E_{LUMO-ET}$ | $E_{LUMO-GH}$ | Voltage (V) | Efficiency (cd/A) | LT98 (hr) |
|---|---|---|---|---|---|---|---|---|---|
| 1 | BH-5 | ETL1-7 | 5.85 | 5.93 | 2.38 | 2.46 | 3.74 | 4.02 | 25 |
|  | GH1-3 & GH2-1 | ETL2-10 |  |  |  |  | 3.01 | 61.02 | 99 |
|  | RH-1 |  |  |  |  |  | 4.02 | 21.26 | 171 |
| 2 | BH-5 | ETL1-7 | 5.85 | 5.93 | 2.38 | 2.44 | 3.89 | 4.58 | 24 |
|  | GH1-3 & GH2-2 | ETL2-10 |  |  |  |  | 3.22 | 59.8 | 101 |
|  | RH-1 |  |  |  |  |  | 4.18 | 20.97 | 166 |
| 3 | BH-5 | ETL1-7 | 5.85 | 5.93 | 2.38 | 2.38 | 3.61 | 4.09 | 19 |
|  | GH1-3 & GH2-3 | ETL2-10 |  |  |  |  | 3.10 | 55.98 | 89 |
|  | RH-1 |  |  |  |  |  | 4.05 | 21.85 | 175 |
| 4 | BH-5 | ETL1-7 | 5.85 | 5.93 | 2.38 | 2.47 | 4.05 | 4.45 | 18 |
|  | GH1-3 & GH2-4 | ETL2-10 |  |  |  |  | 3.26 | 58.11 | 121 |
|  | RH-1 |  |  |  |  |  | 4.01 | 21.02 | 175 |
| 5 | BH-5 | ETL1-7 | 5.85 | 5.93 | 2.38 | 2.33 | 4.01 | 5.00 | 15 |
|  | GH1-3 & GH2-5 | ETL2-10 |  |  |  |  | 3.55 | 67.31 | 100 |
|  | RH-1 |  |  |  |  |  | 4.07 | 19.02 | 160 |
| 6 | BH-1 | ETL1-8 | 5.75 | 5.84 | 2.86 | 2.44 | 4.30 | 4.98 | 24 |
|  | GH1-1 & GH2-1 | ETL2-1 |  |  |  |  | 3.12 | 71.05 | 171 |
|  | RH-1 |  |  |  |  |  | 4.01 | 13.87 | 205 |
| 7 | BH-2 | ETL1-8 | 5.75 | 5.80 | 2.86 | 2.42 | 4.25 | 4.05 | 28 |
|  | GH1-1 & GH2-2 | ETL2-4 |  |  |  |  | 3.35 | 72.35 | 180 |
|  | RH-1 |  |  |  |  |  | 4.29 | 24.34 | 211 |
| 8 | BH-5 | ETL1-8 | 5.75 | 5.93 | 2.86 | 2.46 | 4.00 | 5.01 | 16 |
|  | GH1-3 & GH2-1 | ETL2-10 |  |  |  |  | 3.01 | 70.36 | 149 |
|  | RH-1 |  |  |  |  |  | 4.05 | 22.78 | 178 |
| 9 | BH-1 | ETL1-9 | 6.28 | 5.84 | 2.33 | 2.44 | 3.99 | 5.01 | 41 |
|  | GH1-1 & GH2-1 | ETL2-1 |  |  |  |  | 4.38 | 55.12 | 75 |
|  | RH-1 |  |  |  |  |  | 4.24 | 20.25 | 199 |
| 10 | BH-2 | ETL1-9 | 6.28 | 5.80 | 2.33 | 2.42 | 4.11 | 5.03 | 44 |
|  | GH1-1 & GH2-2 | ETL2-4 |  |  |  |  | 4.18 | 59.63 | 101 |
|  | RH-1 |  |  |  |  |  | 4.28 | 22.58 | 221 |
| 11 | BH-7 | ETL1-2 | 6.01 | 6.07 | 2.71 | 2.44 | 4.98 | 4.02 | 21 |
|  | GH1-1 & GH2-1 | ETL2-1 |  |  |  |  | 3.35 | 69.87 | 197 |
|  | RH-1 |  |  |  |  |  | 4.21 | 22.34 | 235 |
| 12 | BH-7 | ETL1-6 | 6.04 | 6.07 | 3.05 | 2.35 | 5.01 | 4.55 | 31 |
|  | GH1-6 & GH2-2 | ETL2-4 |  |  |  |  | 3.38 | 69.22 | 234 |
|  | RH-1 |  |  |  |  |  | 4.40 | 23.61 | 259 |
| 13 | BH-6 | ETL1-1 | 6.25 | 5.91 | 2.51 | 2.63 | 3.83 | 5.24 | 55 |
|  | GH1-7 & GH2-4 | ETL2-1 |  |  |  |  | 3.89 | 61.35 | 88 |
|  | RH-1 |  |  |  |  |  | 4.12 | 25.20 | 230 |

DESCRIPTION OF SYMBOLS

1: anode
2: hole transport layer
3: light emitting layer
31: red light emitting layer
32: green light emitting layer
33: blue light emitting layer
4: electron transport layer
5: cathode
6: hole injection layer
7: electron injection layer

The invention claimed is:

1. An organic light emitting device comprising: an anode, a hole transport layer, a light emitting layer, an electron transport layer, and a cathode, in this order, wherein
the light emitting layer comprises a red light emitting layer, a green light emitting layer, and a blue light emitting layer in parallel,
the electron transport layer is adjacent to the red light emitting layer, the green light emitting layer, and the blue light emitting layer simultaneously,
the electron transport layer comprises one or more layers, a layer adjacent to the red light emitting layer, the green light emitting layer and the blue light emitting layer in the electron transport layer satisfies the following mathematical expressions 1 and 2:

$$E_{HOMO\text{-}ET} > E_{HOMO\text{-}BH}$$ [Mathematical Expression 1]

in Mathematical Expression 1,
$E_{HOMO\text{-}ET}$ is an absolute value of a HOMO energy level of a material comprised in the layer adjacent to the red light emitting layer, the green light emitting layer and the blue light emitting layer in the electron transport layer, and
$E_{HOMO\text{-}BH}$ is an absolute value of a HOMO energy level of a host material of the blue light emitting layer, $$E_{LUMO\text{-}ET} > E_{LUMO\text{-}GH}$$ [Mathematical Expression 2]

in Mathematical Expression 2,
$E_{LUMO\text{-}ET}$ is an absolute value of a LUMO energy level of the material comprised in the layer adjacent to the red light emitting layer, the green light emitting layer and the blue light emitting layer in the electron transport layer, and
$E_{LUMO\text{-}GH}$ is an absolute value of a LUMO energy level of a host material of the green light emitting layer,
wherein the material comprised in the layer adjacent to the red light emitting layer, the green light emitting layer and the blue light emitting layer in the electron transport layer comprises a compound represented by the following Chemical Formula 1:

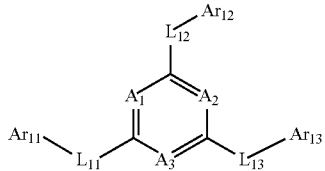

[Chemical Formula 1]

in Chemical Formula 1,
$A_1$ to $A_3$ are each independently N, or CR, with the proviso that at least two of $A_1$ to $A_3$ are N,
R is hydrogen, or is bonded to $Ar_{11}$ or $Ar_{12}$ to form a substituted or unsubstituted $C_{6\text{-}60}$ aryl; or a substituted or unsubstituted $C_{2\text{-}60}$ heteroaryl containing at least one heteroatom selected from the group consisting of N, O and S,
$L_{11}$ and $L_{12}$ are each independently a bond; a substituted or unsubstituted $C_{6\text{-}60}$ arylene; or a substituted or unsubstituted $C_{2\text{-}60}$ heteroarylene containing at least one heteroatom selected from the group consisting of N, O and S,
$Ar_{11}$ and $Ar_{12}$ are each independently a substituted or unsubstituted $C_{6\text{-}60}$ aryl; tri($C_{6\text{-}60}$ aryl)silyl; or a substituted or unsubstituted $C_{2\text{-}60}$ heteroaryl containing at least one heteroatom selected from the group consisting of N, O and S, or is bonded to the R to form a substituted or unsubstituted $C_{6\text{-}60}$ aryl; or a substituted or unsubstituted $C_{2\text{-}20}$ heteroaryl containing at least one heteroatom selected from the group consisting of N, O and S,
$L_{13}$ is a bond; a substituted or unsubstituted $C_{6\text{-}60}$ arylene; or a substituted or unsubstituted $C_{2\text{-}60}$ heteroarylene containing at least one heteroatom selected from the group consisting of N, O and S, and $Ar_{13}$ is represented by the following Chemical Formula 2,

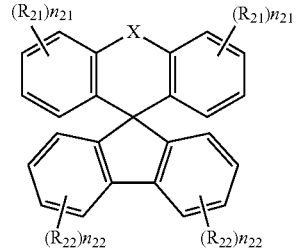

[Chemical Formula 2]

in Chemical Formula 2,
X is O, or S,
$n_{21}$ and $n_{22}$ are each independently an integer of 1 to 4,
at least one of $R_{21}$ and $R_{22}$ is connected to $Ar_{13}$, and the rest are each independently hydrogen; deuterium; a substituted or unsubstituted $C_{1\text{-}60}$ alkyl; a substituted or unsubstituted $C_{6\text{-}60}$ aryl; or a substituted or unsubstituted $C_{2\text{-}60}$ heteroaryl containing any one or more heteroatoms selected from the group consisting of N, O and S, or two adjacent $R_{21}$ or two adjacent $R_{22}$ optionally bond to each other to form a benzene ring,
wherein the host material of the blue light emitting layer is a compound represented by the following Chemical Formula 3-1 or 3-2,

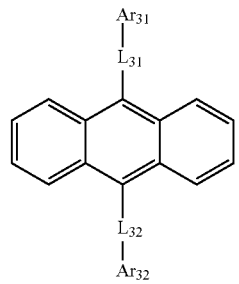

[Chemical Formula 3-1]

in Chemical Formula 3-1,
$L_{31}$ and $L_{32}$ are each independently a bond; a substituted or unsubstituted $C_{6\text{-}60}$ arylene; or a substituted or unsubstituted $C_{2\text{-}60}$ heteroarylene containing at least one heteroatom selected from the group consisting of N, O and S, and
$Ar_{31}$ and $Ar_{32}$ are each independently a substituted or unsubstituted $C_{6\text{-}60}$ aryl; or a substituted or unsubstituted $C_{2\text{-}60}$ heteroarylene containing at least one heteroatom selected from the group consisting of N, O and S,

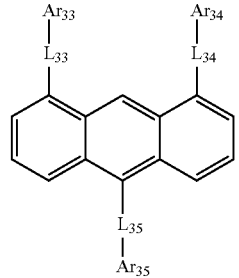

[Chemical Formula 3-2]

in Chemical Formula 3-2,
$L_{33}$, $L_{34}$ and $L_{35}$ are each independently a bond; a substituted or unsubstituted $C_{6\text{-}60}$ arylene; or a substituted or unsubstituted $C_{2-60}$ heteroarylene containing at least one heteroatom selected from the group consisting of N, O and S, and $Ar_{33}$, $Ar_{34}$ and $Ar_{35}$ are each independently a substituted or unsubstituted $C_{6-60}$ aryl; or a substituted or unsubstituted $C_{2-60}$ heteroaryl comprising at least one heteroatom selected from the group consisting of N, O and S, wherein the host material of the Green light emitting layer comprises (i) an one of the compounds represented by the following Chemical Formulas 4-1 to 4-4, and (ii) a compound represented by the following Chemical Formula 5:

[Chemical Formula 4-1]

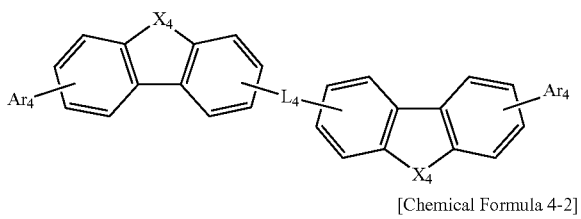

[Chemical Formula 4-2]

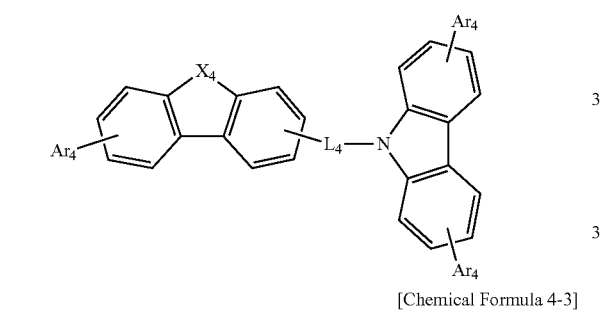

[Chemical Formula 4-3]

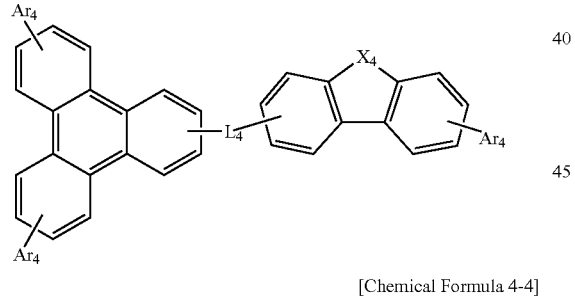

[Chemical Formula 4-4]

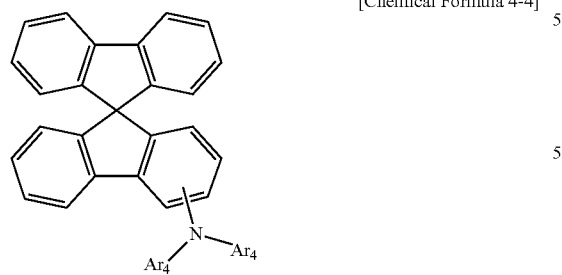

in Chemical Formulas 4-1 to 4-4, each $X_4$ is independently O, S, $NR_4$, $CR_4R_5$, or $SiR_4R_5$, wherein $R_4$ and $R_5$ are each independently hydrogen, a substituted or unsubstituted $C_{1-60}$ alkyl, or a substituted or unsubstituted $C_{6-60}$ aryl, each $L_4$ is independently a bond; a substituted or unsubstituted $C_{6-60}$ arylene; or a substituted or unsubstituted $C_{2-60}$ heteroarylene containing at least one heteroatom selected from the group consisting of N, O and S, and $Ar_4$ is independently hydrogen; a substituted or unsubstituted $C_{6-60}$ aryl; or a substituted or unsubstituted $C_{2-60}$ heteroaryl containing at least one heteroatom selected from the group consisting of N, O and S,

[Chemical Formula 5]

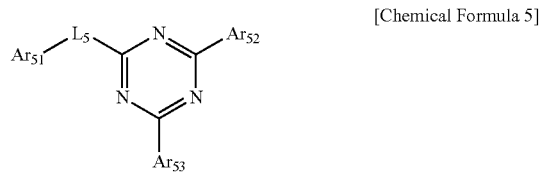

in Chemical Formula 5, $L_5$ is a bond; a substituted or unsubstituted $C_{6-60}$ arylene; or a substituted or unsubstituted $C_{2-60}$ heteroarylene containing at least one heteroatom selected from the group consisting of N, O and S, and $Ar_{51}$, $Ar_{52}$ and $Ar_{53}$ are each independently a substituted or unsubstituted $C_{6-60}$ aryl; or a substituted or unsubstituted $C_{2-60}$ heteroaryl containing at least one heteroatom selected from the group consisting of N, O and S.

2. The organic light emitting device of claim 1, wherein the Chemical Formula 1 is any one selected from the group consisting of the following Chemical Formulas 1-1 to 1-5:

1-1

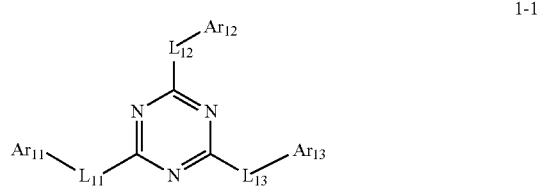

1-2

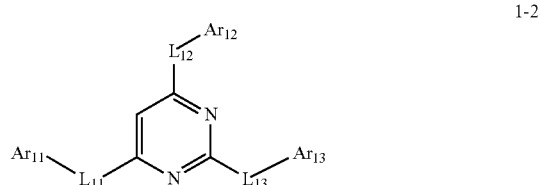

1-3

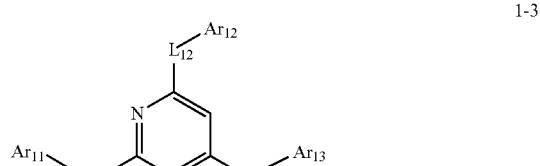

1-4

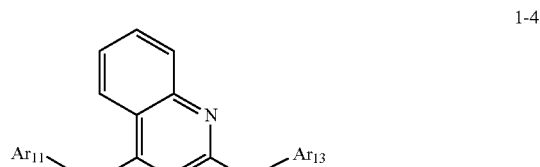

-continued

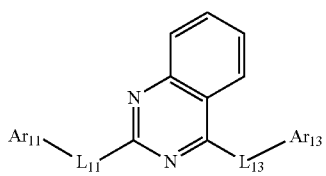
1-5 in Chemical Formulas 1-1 to 1-5, $Ar_{11}$ and $Ar_{12}$ are each independently a substituted or unsubstituted $C_{6-60}$ aryl; or a substituted or unsubstituted $C_{2-60}$ heteroaryl containing at least one heteroatom selected from the group consisting of N, O and S, and $Ar_{13}$ is as defined in claim 1.

3. The organic light emitting device of claim 1, wherein $L_{11}$ and $L_{12}$ are each independently a bond; phenylene; or biphenylylene.

4. The organic light emitting device of claim 1, wherein $Ar_{11}$ and $Ar_{12}$ are each independently any one selected from the group consisting of:

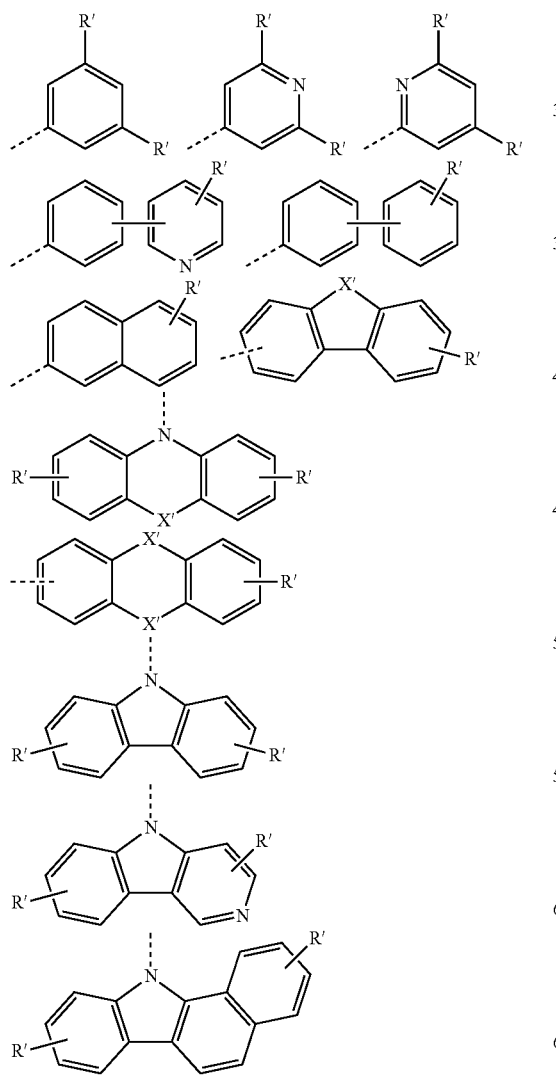

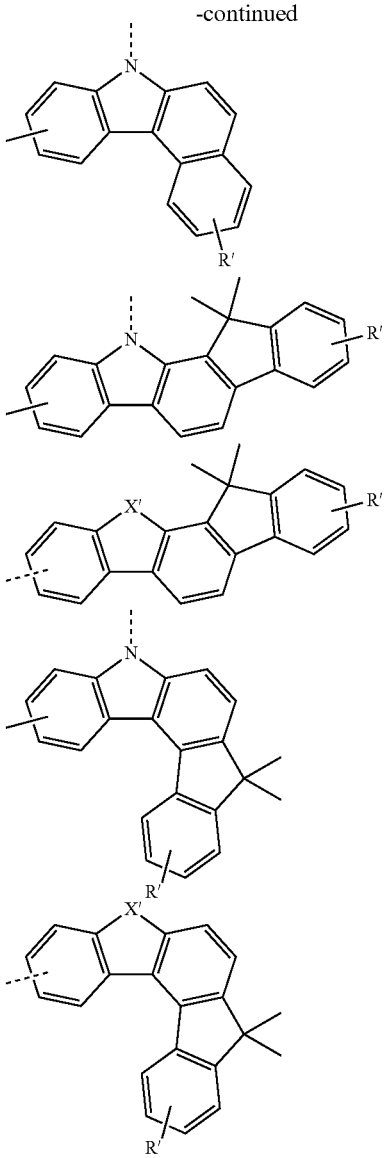

in the above formulas, each X' is independently O, S, $NR'_1$, $CR'_1R'_2$, or $SiR'_1R'_2$, wherein $R'_1$ and $R'_2$ are each independently hydrogen, a substituted or unsubstituted $C_{1-60}$ alkyl, or a substituted or unsubstituted $C_{6-60}$ aryl, each R' is independently hydrogen, cyano, methyl, trifluoromethyl, trimethylsilyl, triphenylsilyl, phenyl, biphenylyl, dibenzofuranyl, dibenzothiophenyl, or carbazolyl.

5. The organic light emitting device of claim 1, wherein $L_{13}$ is any one selected front the group consisting of:

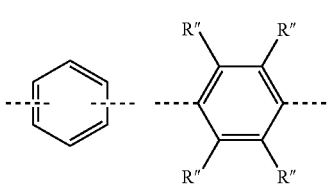

267
-continued

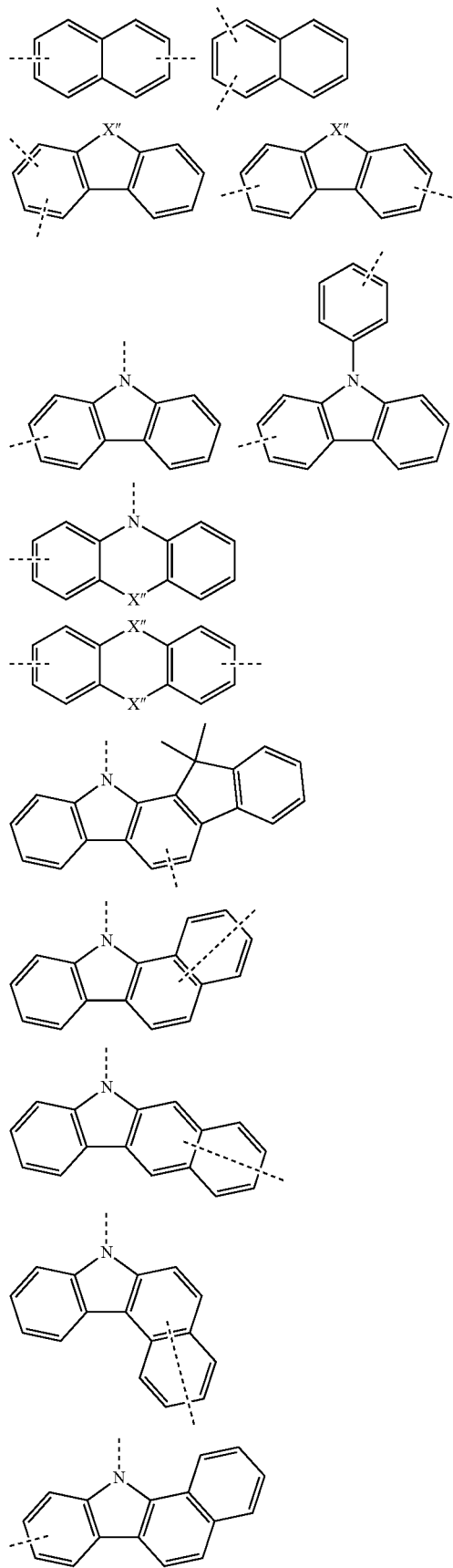

268
-continued

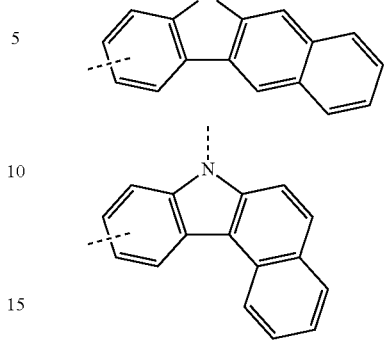

in the above formulas,
each X" is independently O, S, NR"$_1$, CR"$_1$R"$_2$, or SiR"$_1$R"$_2$,
wherein R"$_1$ and R"$_2$ are each independently hydrogen, a substituted or unsubstituted $C_{1-60}$ alkyl, or a substituted or unsubstituted $C_{6-60}$ aryl, and
each R" is independently hydrogen, methyl, or phenyl.

6. The organic light emitting device of claim 1, wherein the compound represented by the Chemical Formula 1 is any one selected from the group consisting of:

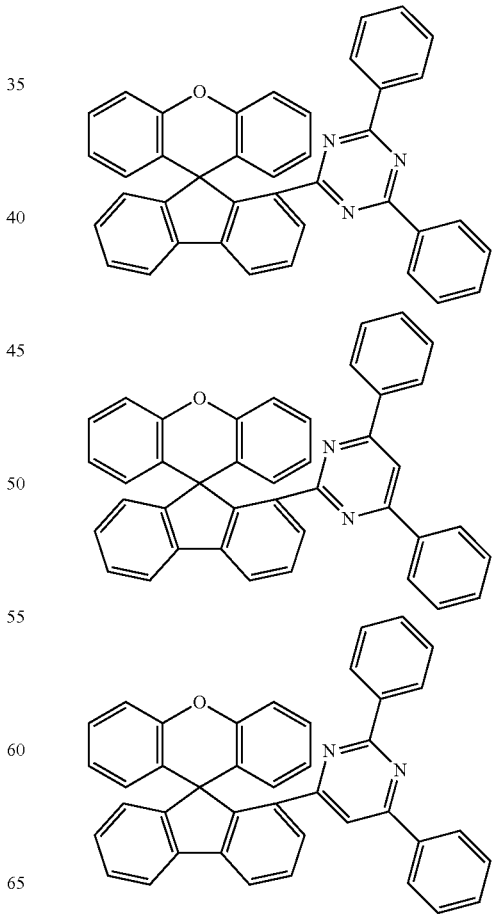

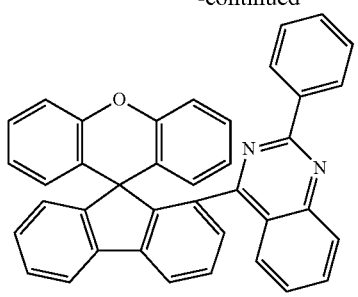
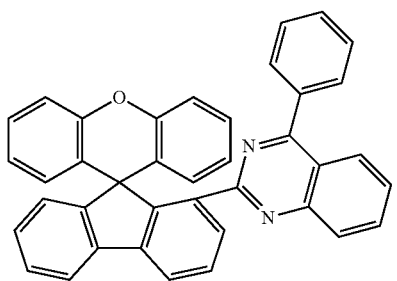
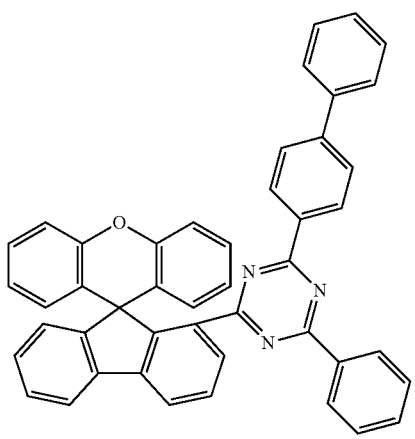
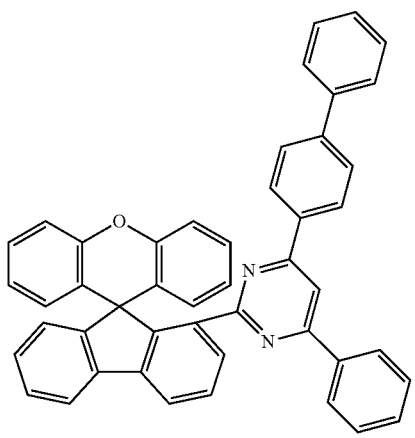
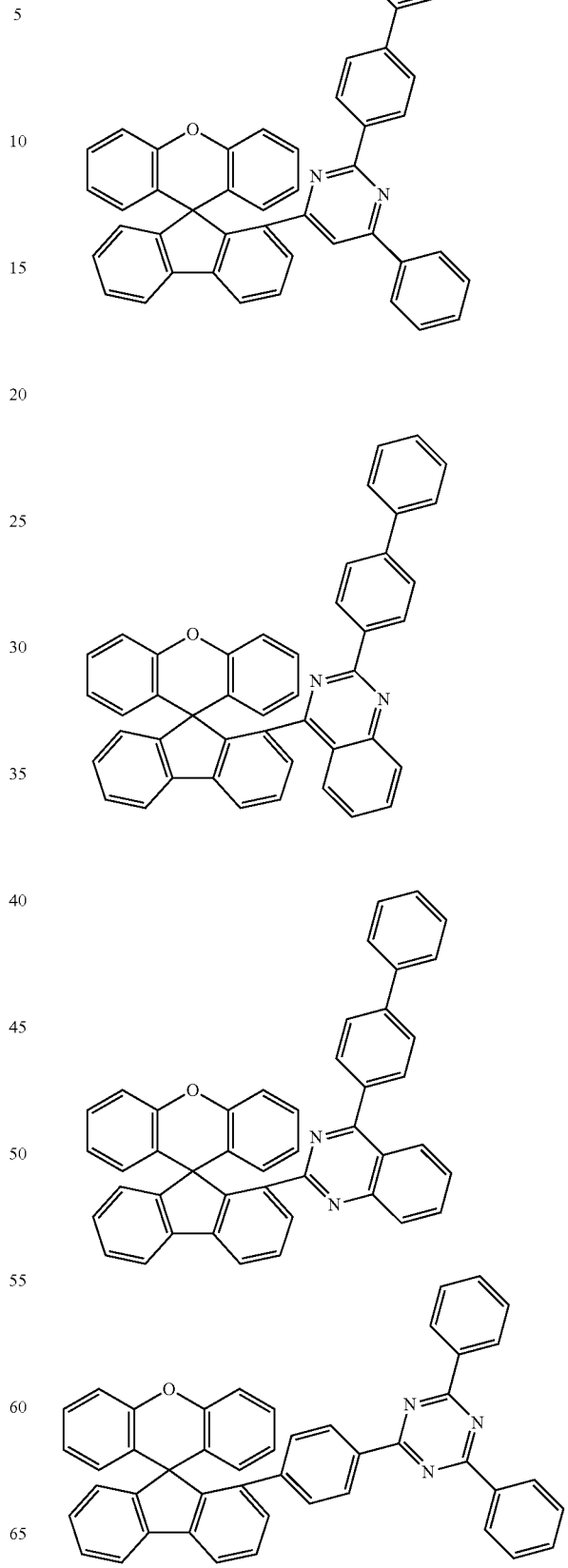

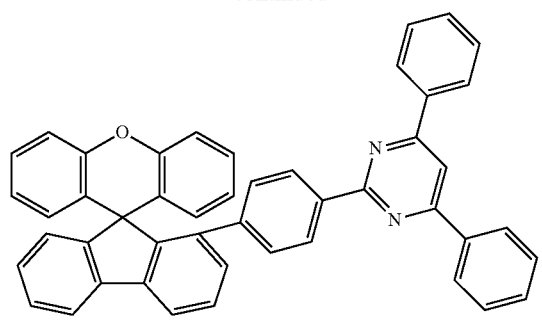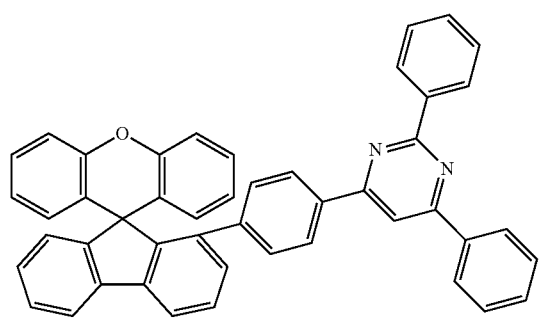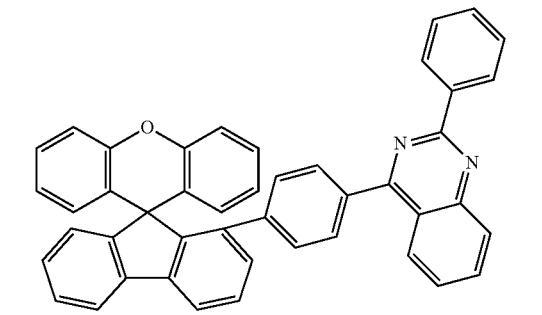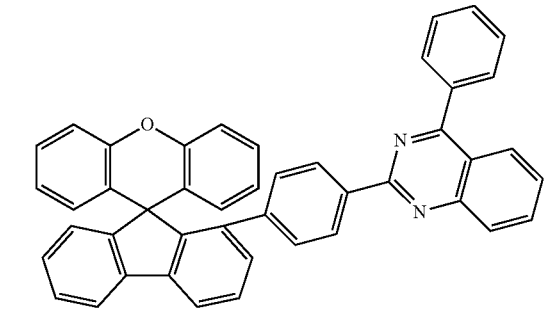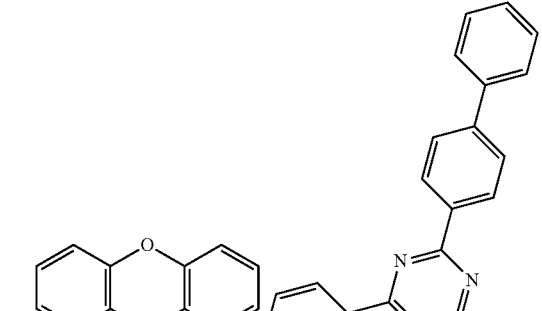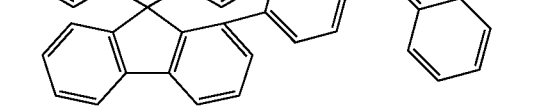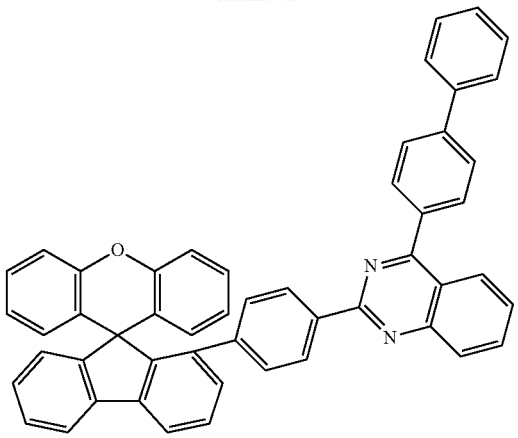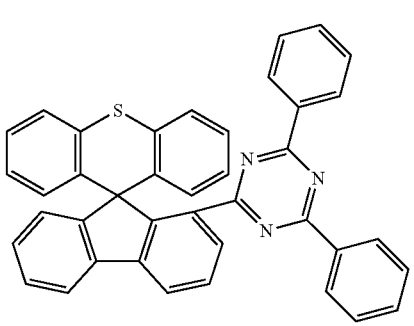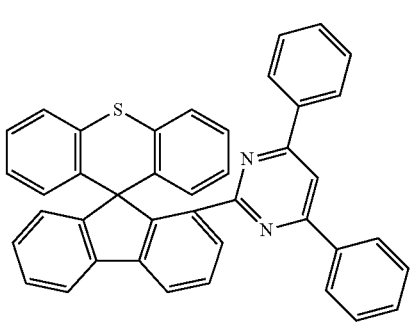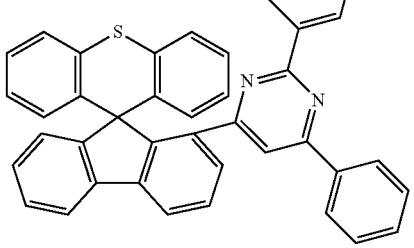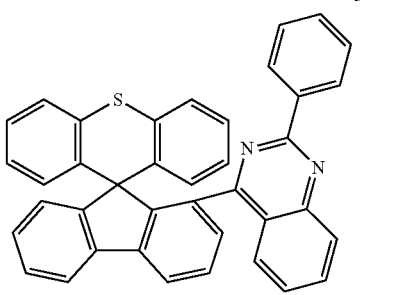

273
-continued
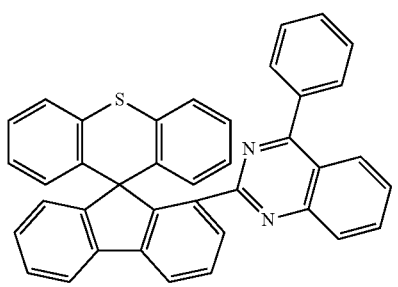
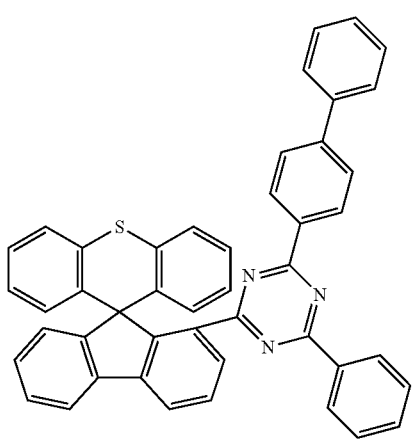
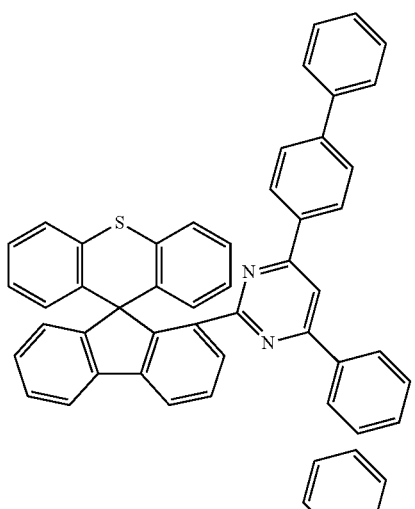
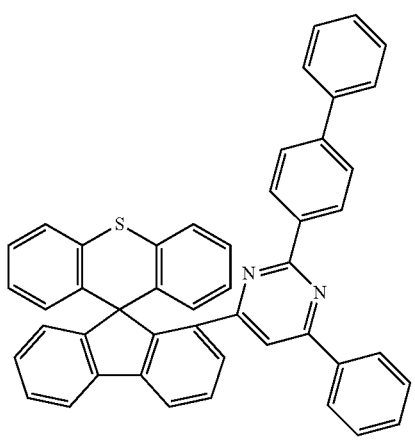
274
-continued
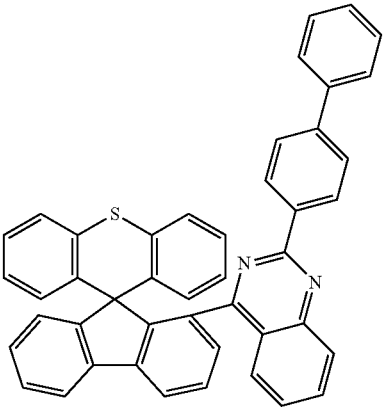
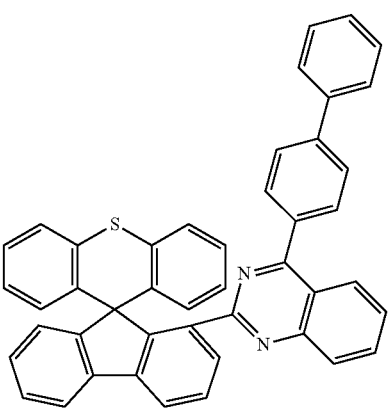
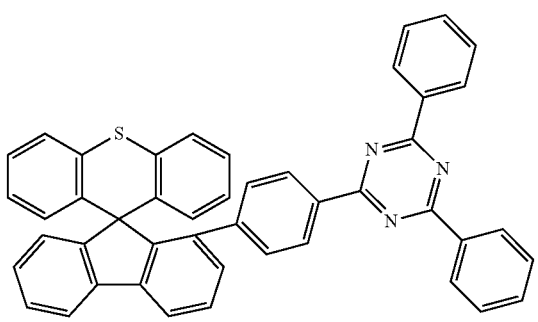
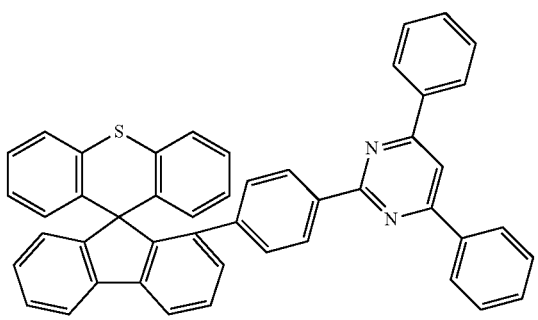

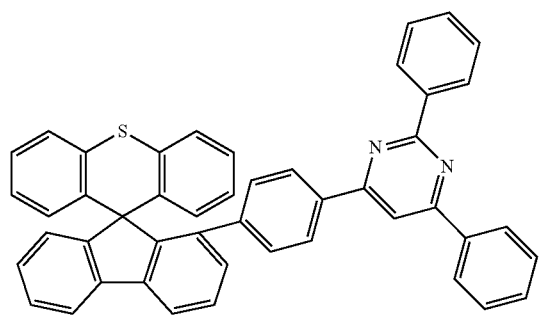
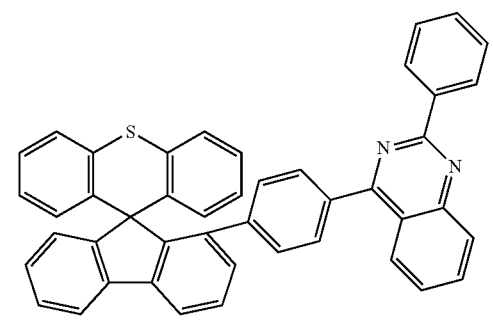
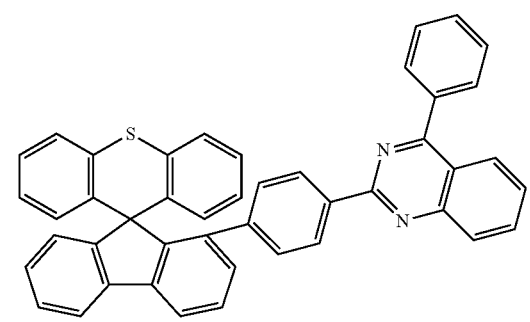
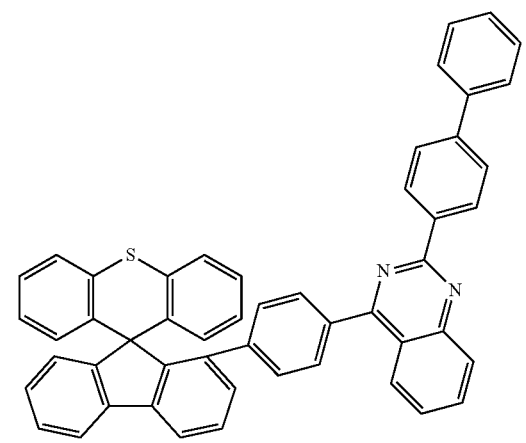
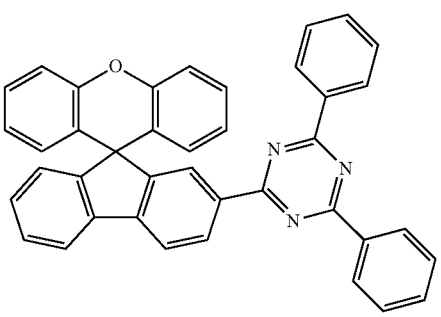
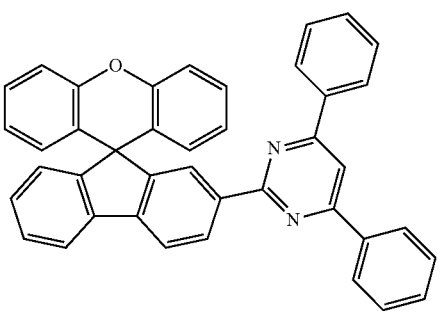
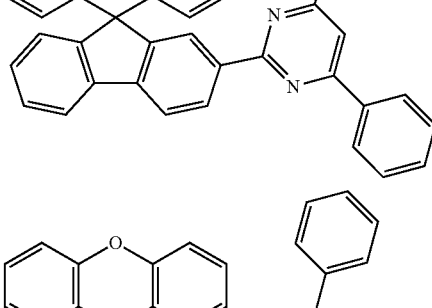
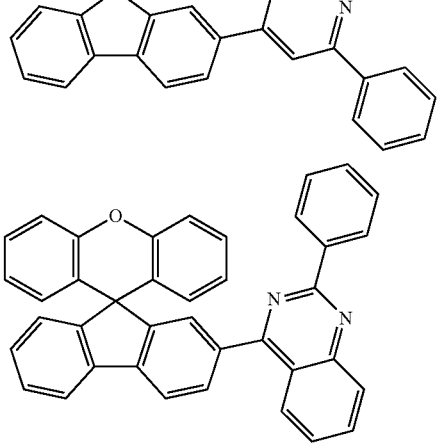

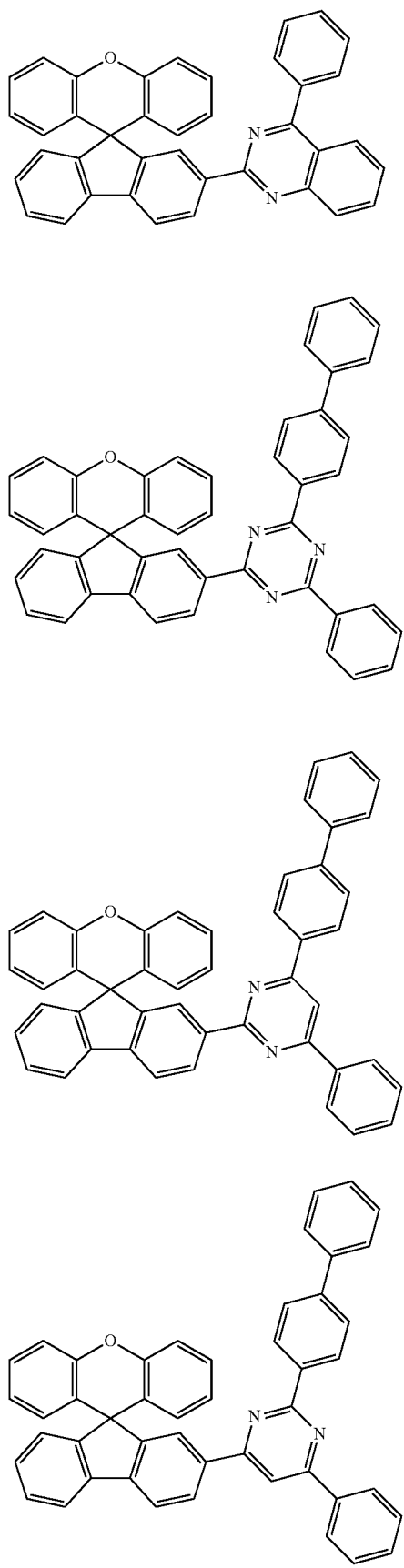
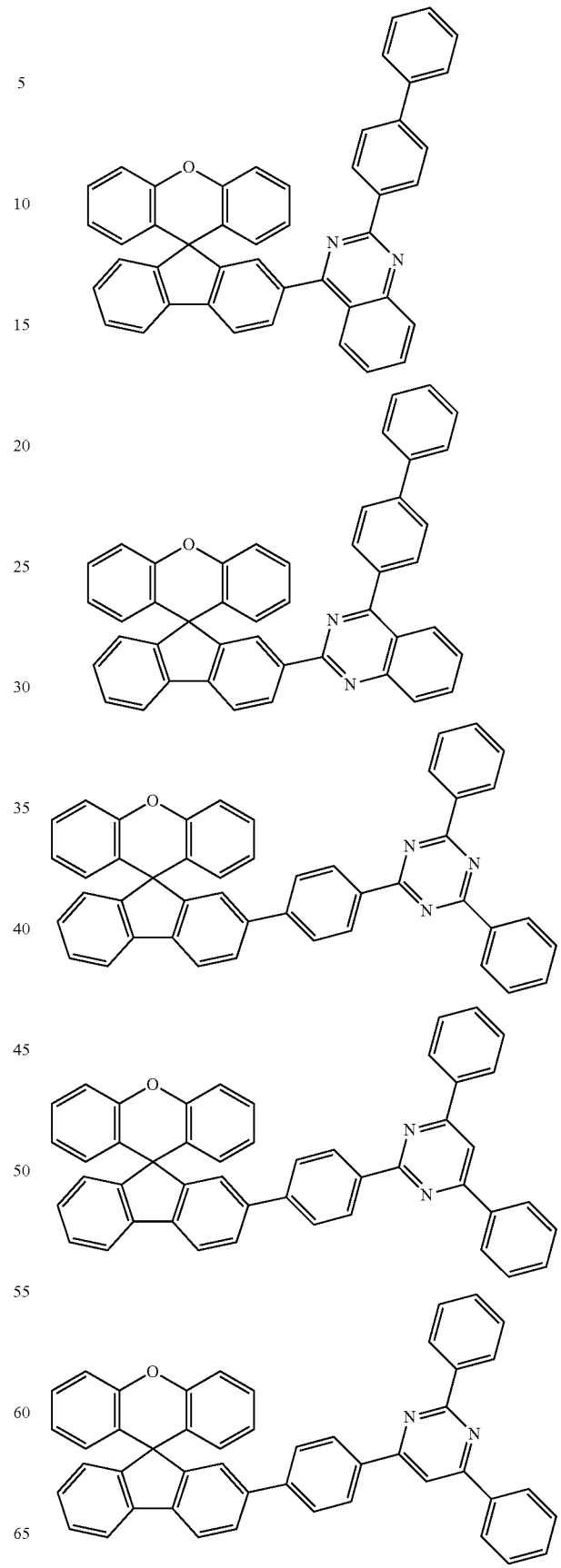

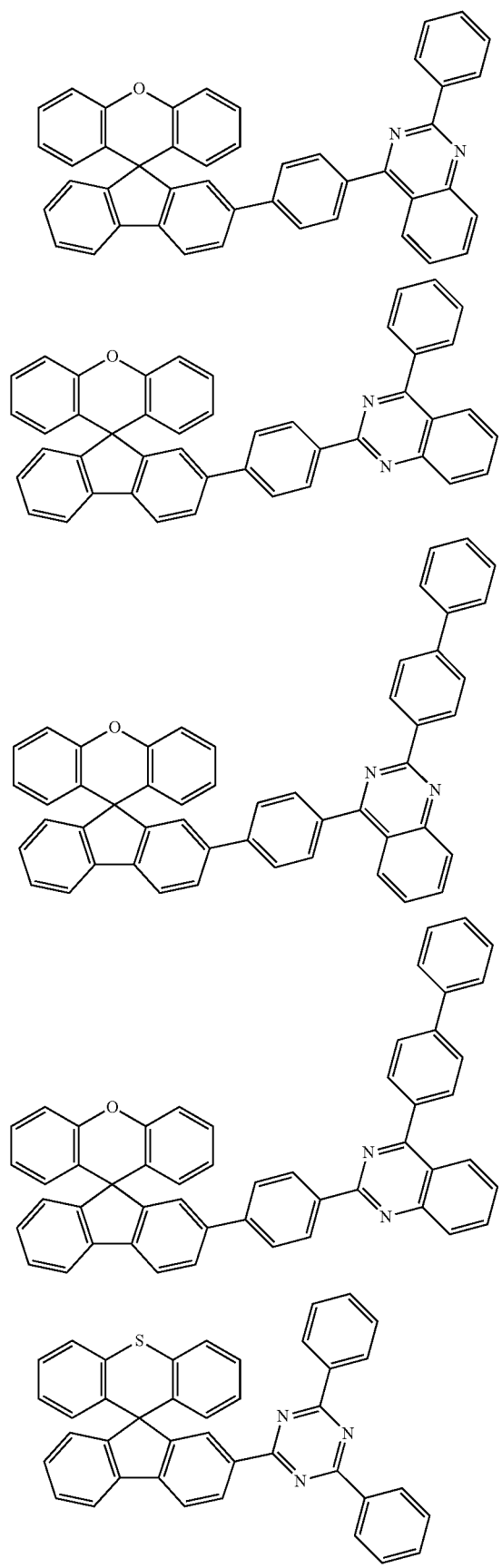

281
-continued
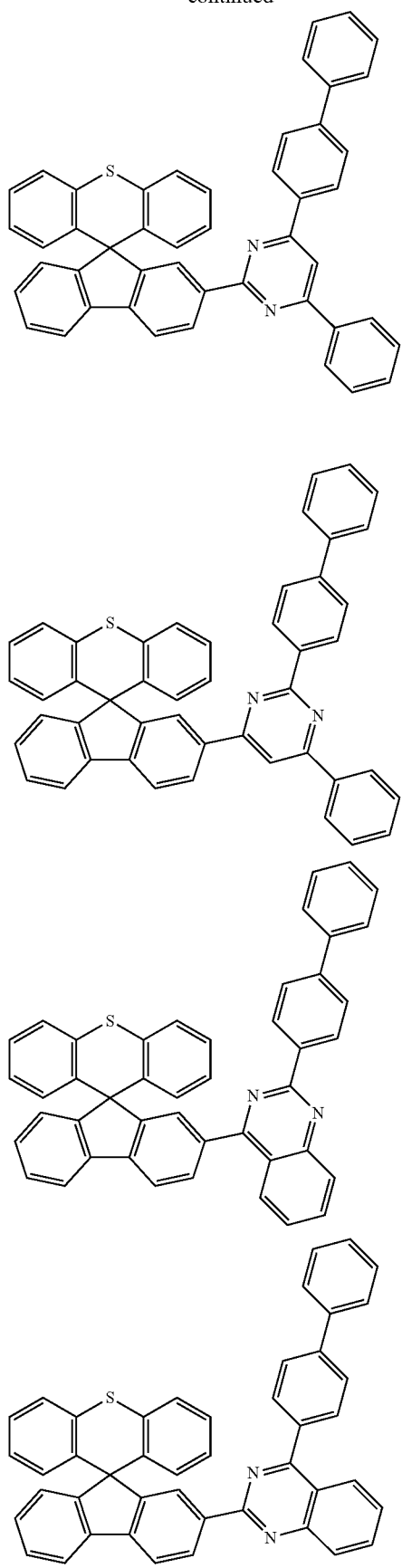
282
-continued
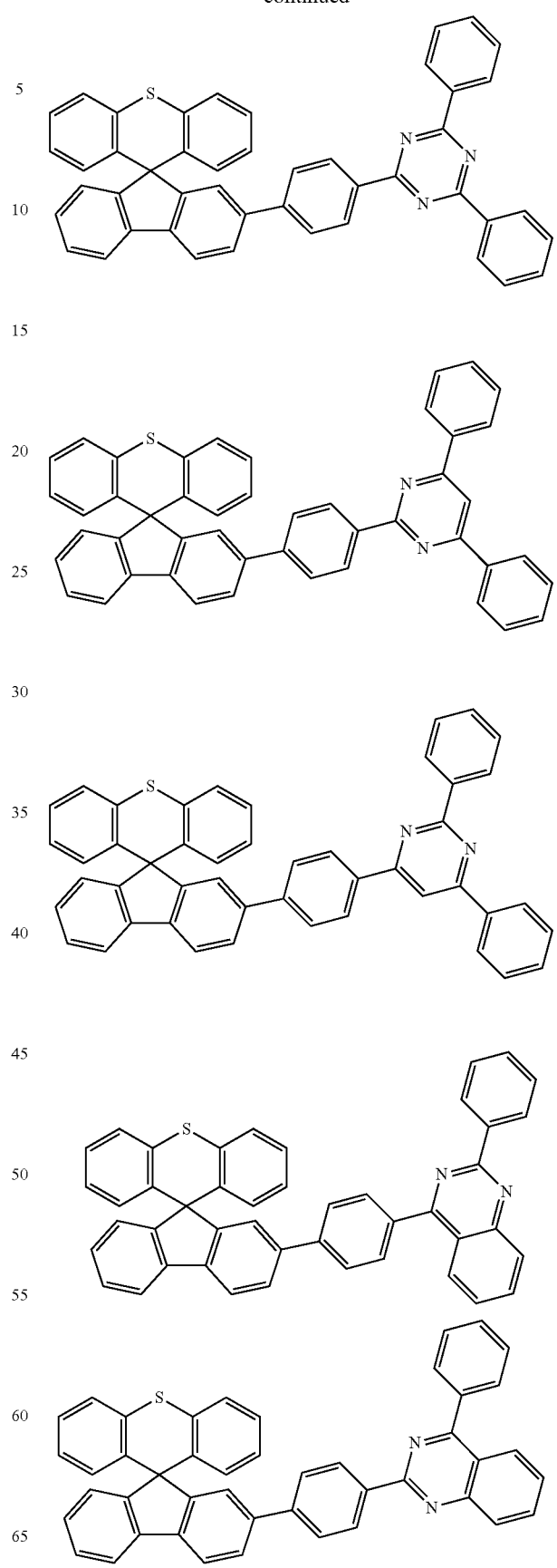

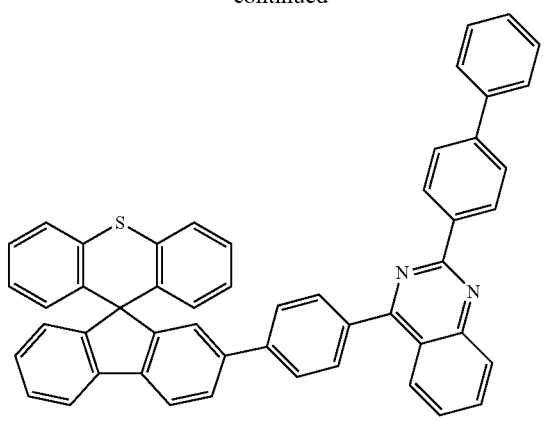
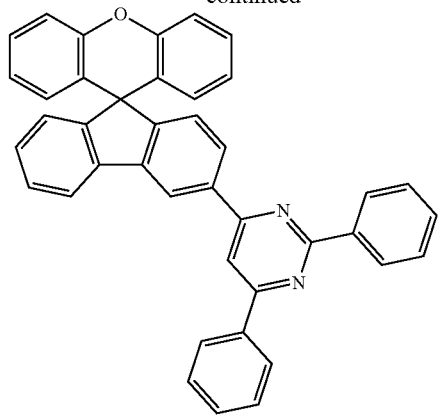
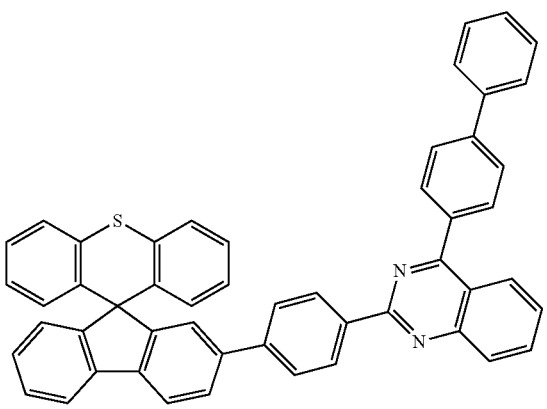
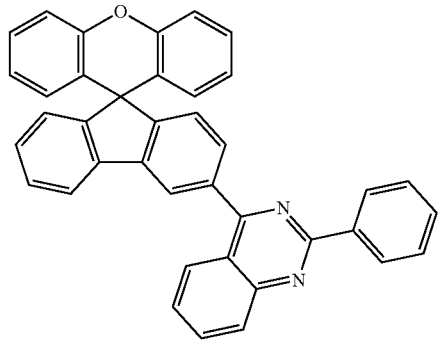
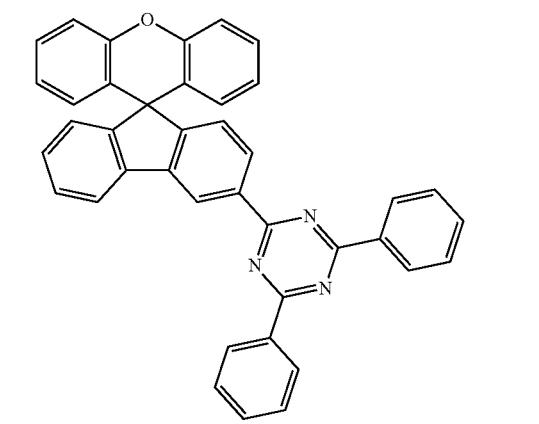
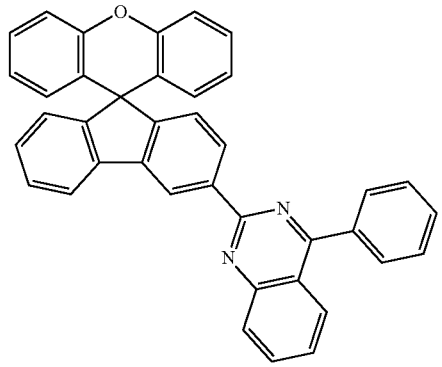
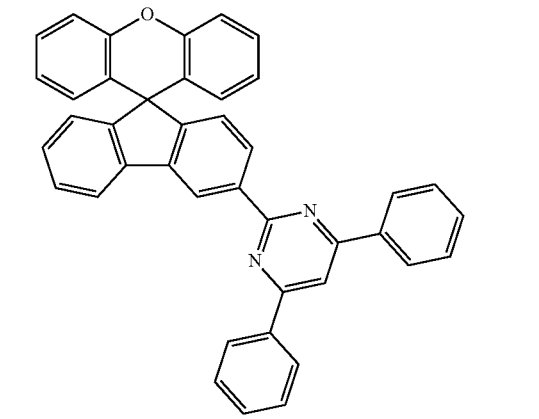
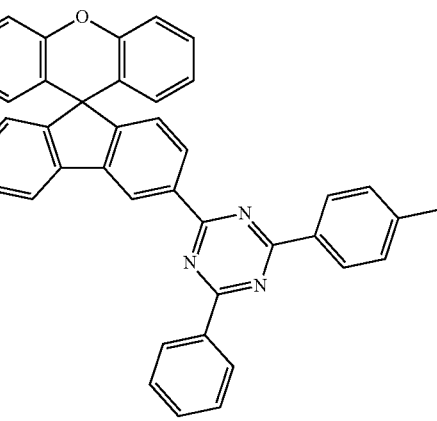

-continued
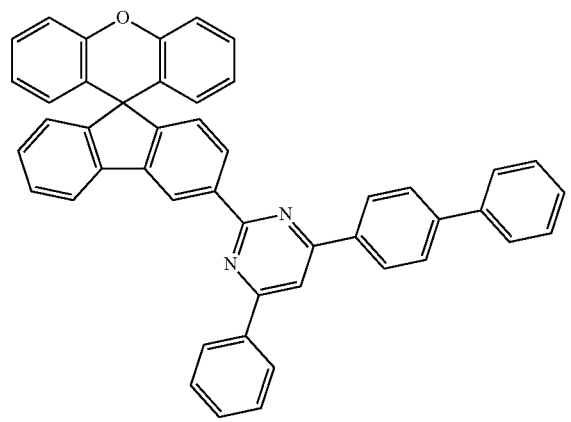
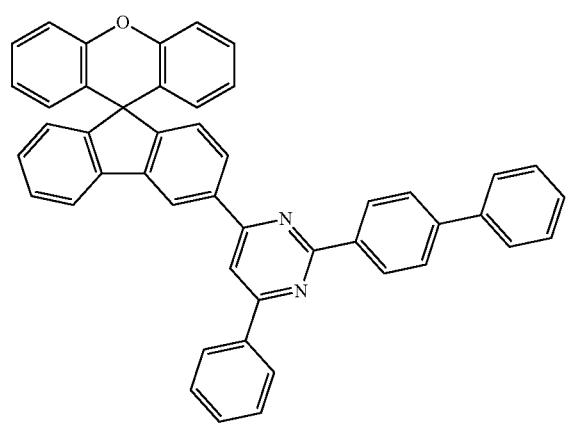
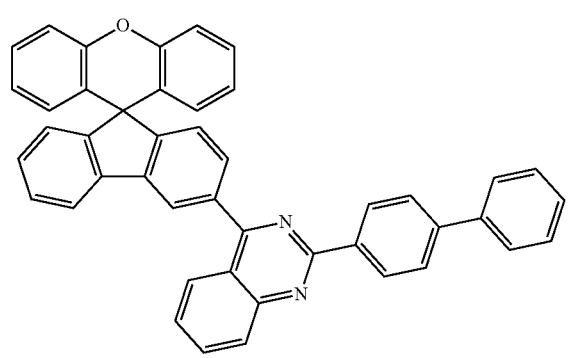
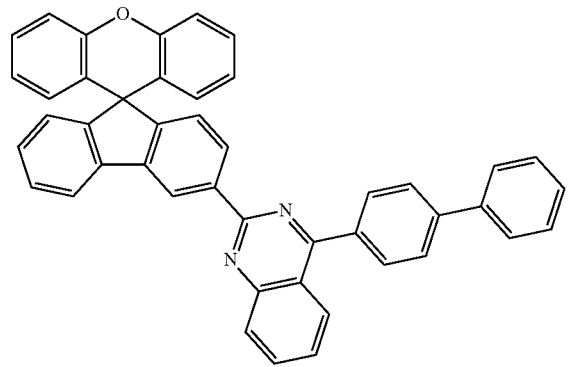
-continued
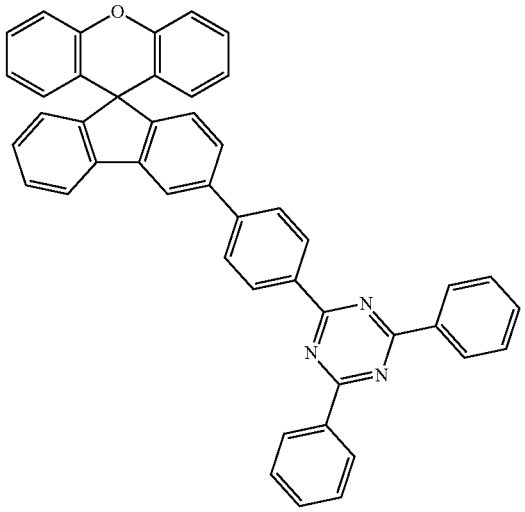
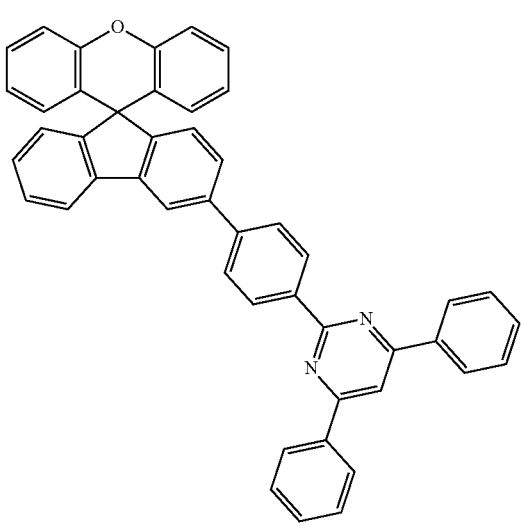
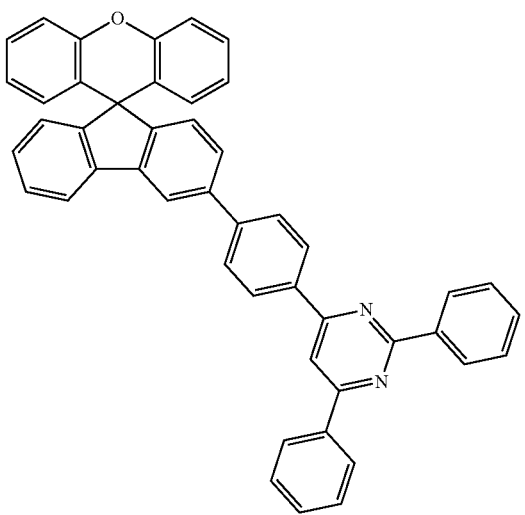

287
-continued
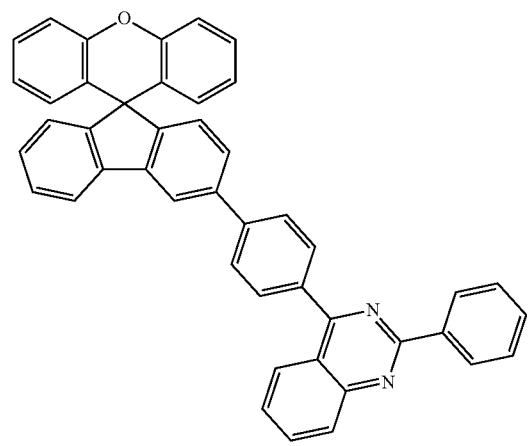
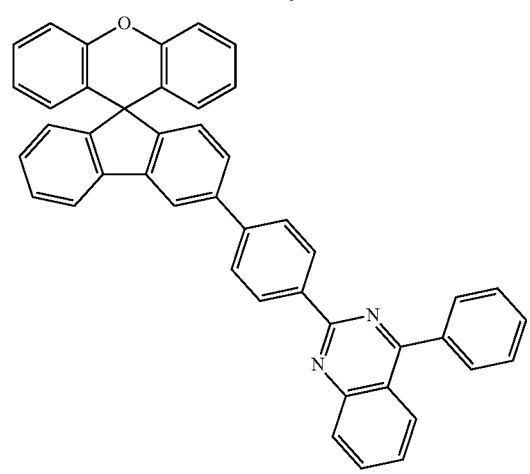
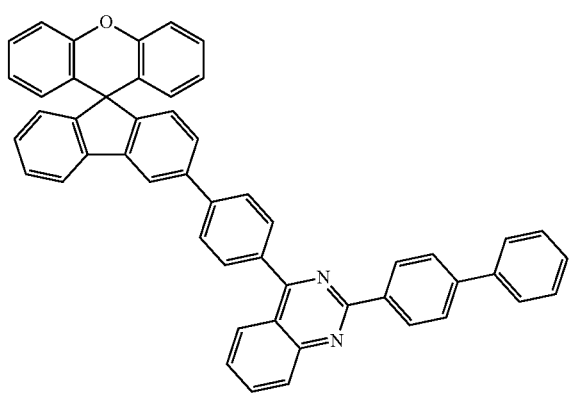
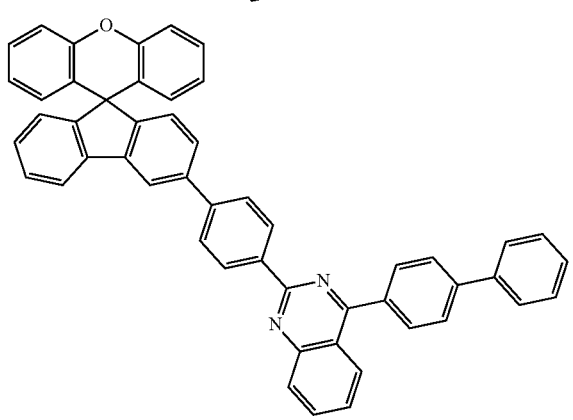
288
-continued
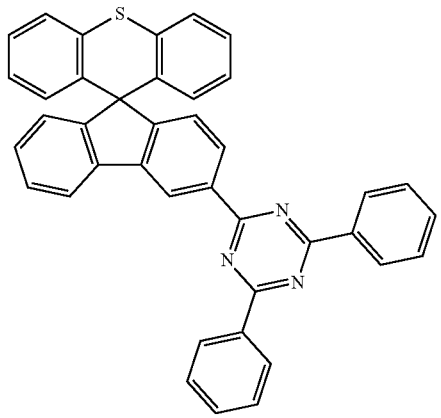
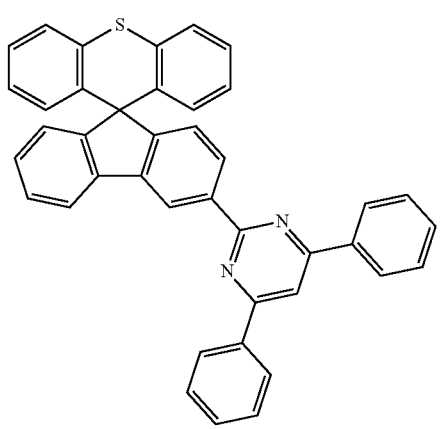
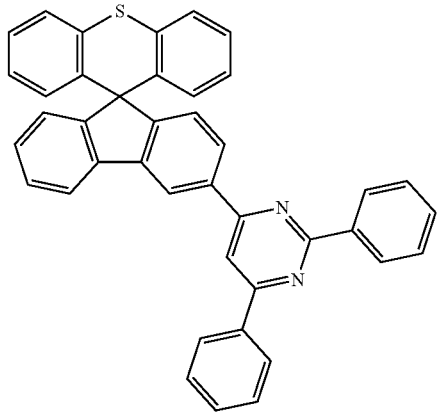
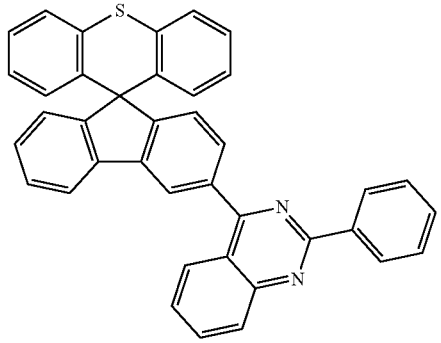

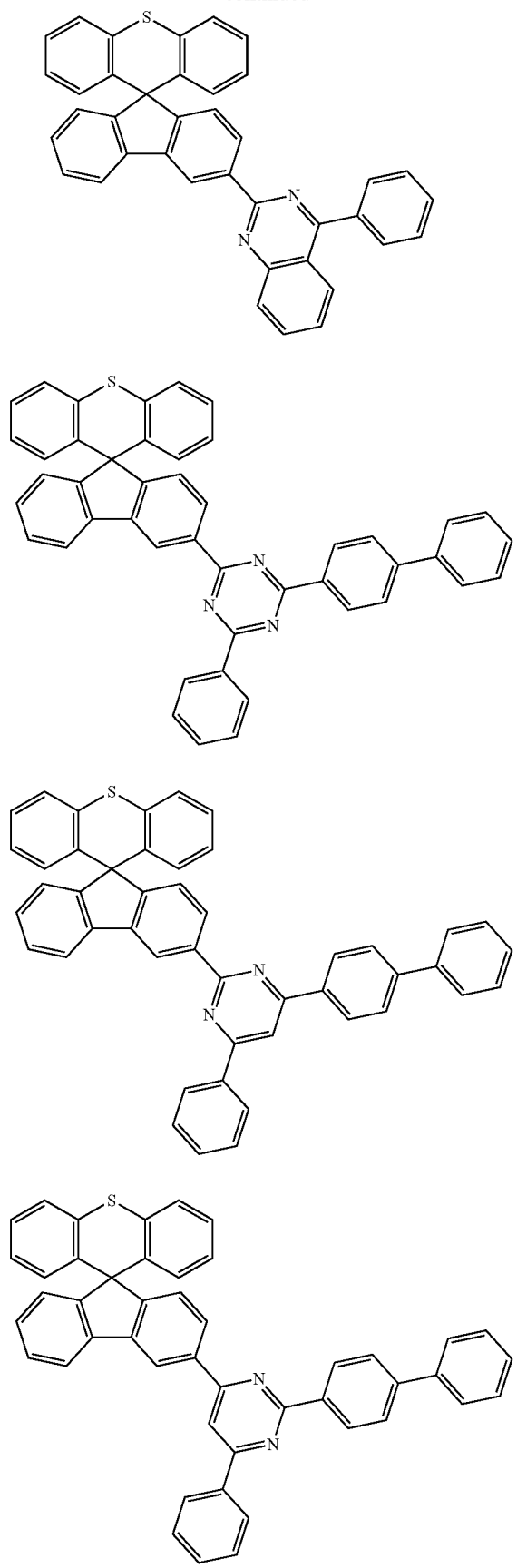
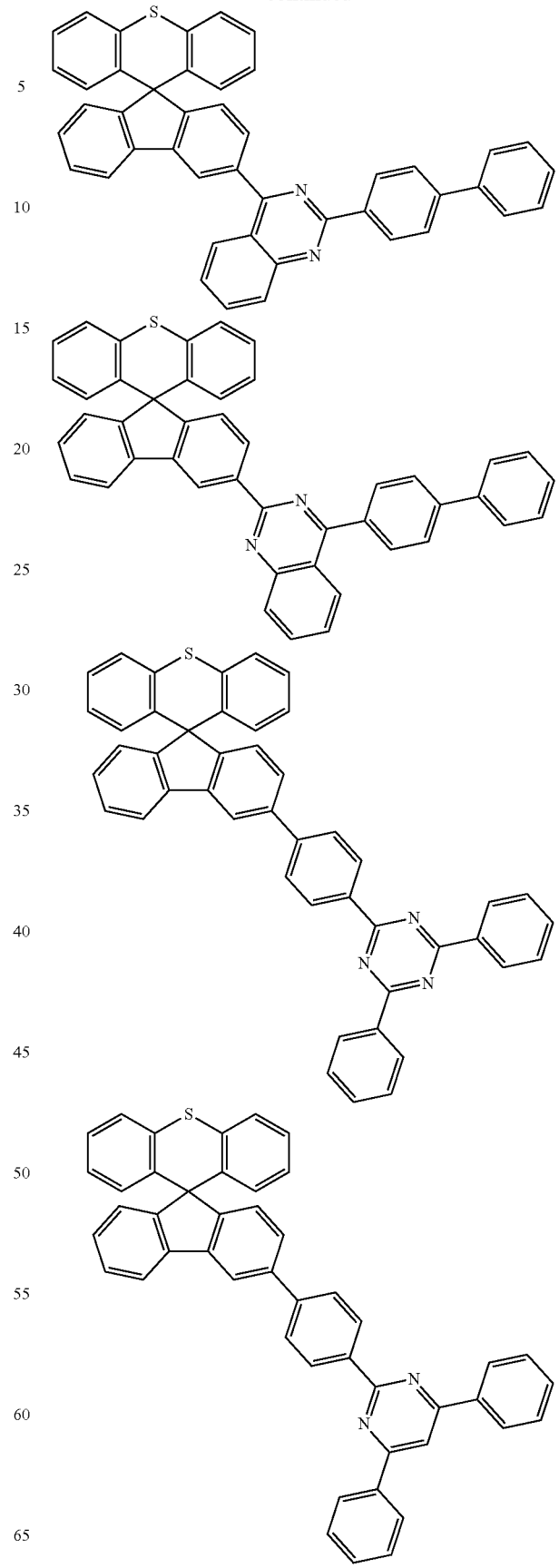

291
-continued
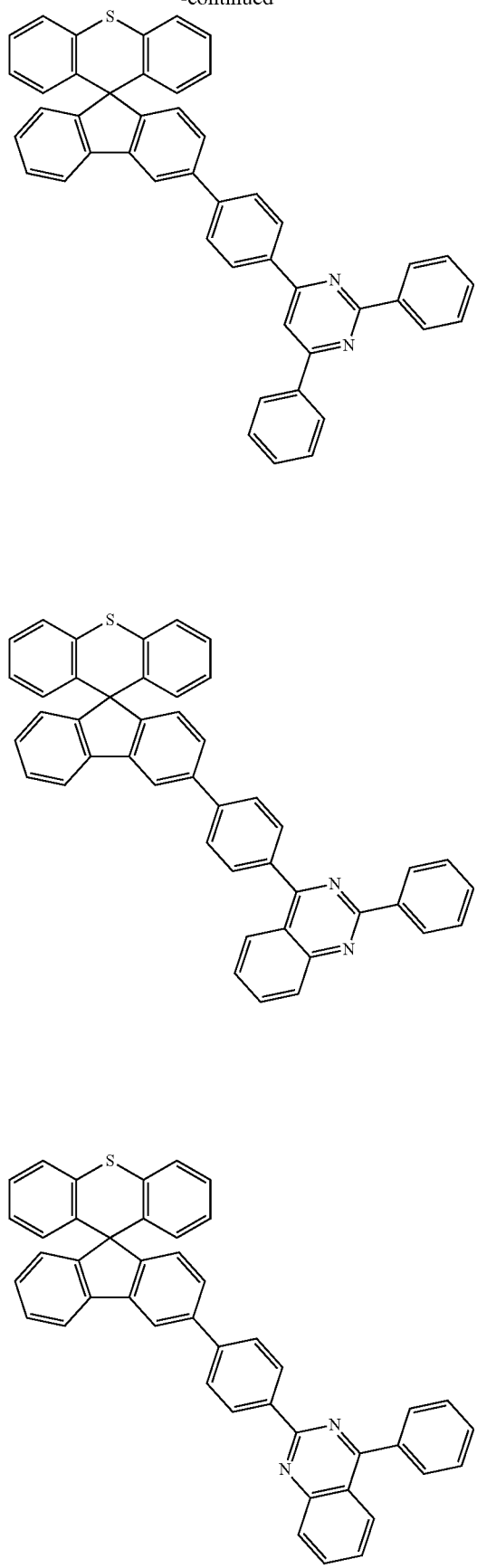
292
-continued
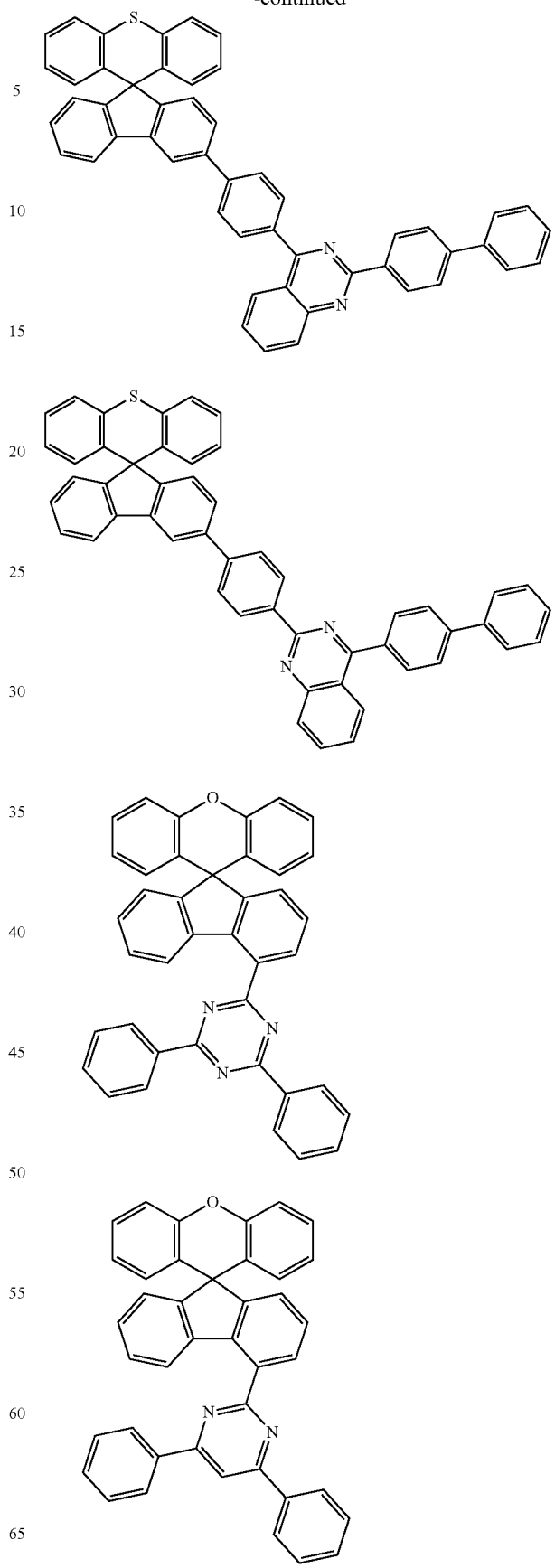

293
-continued
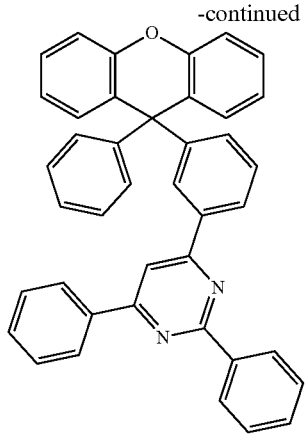
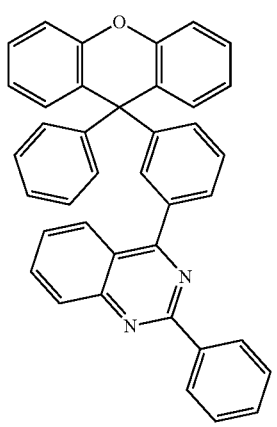
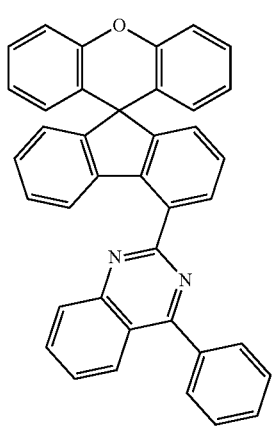
294
-continued
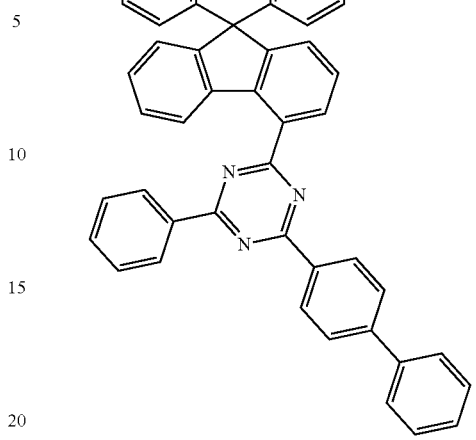
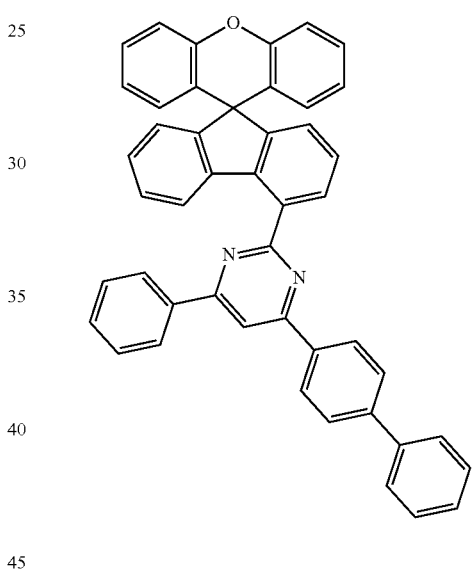
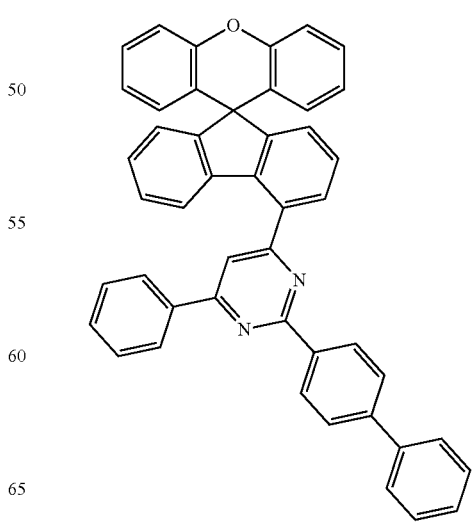

295
-continued
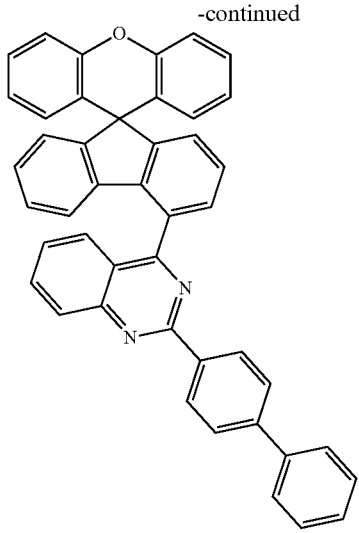
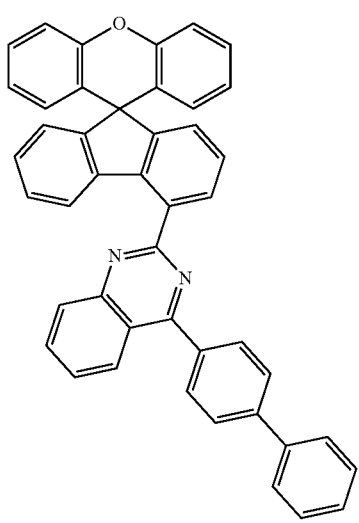
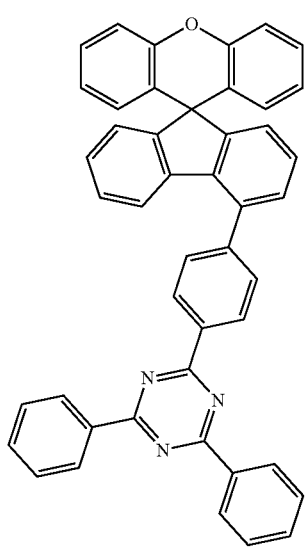
296
-continued
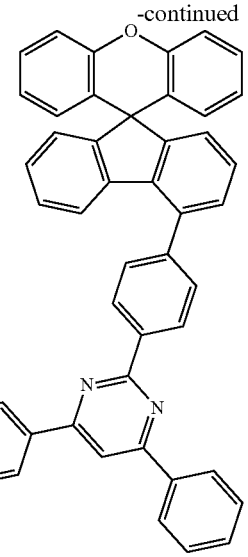
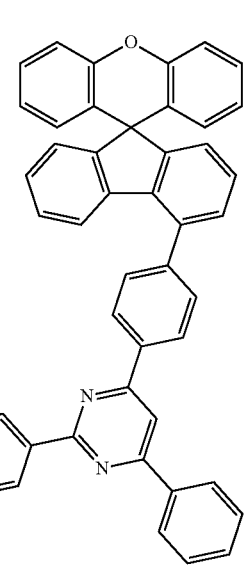
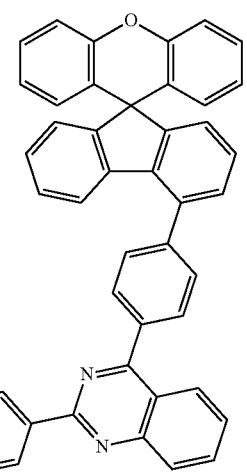

297
-continued
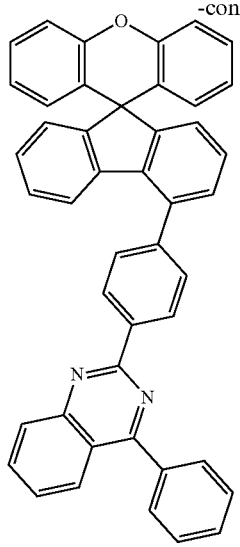
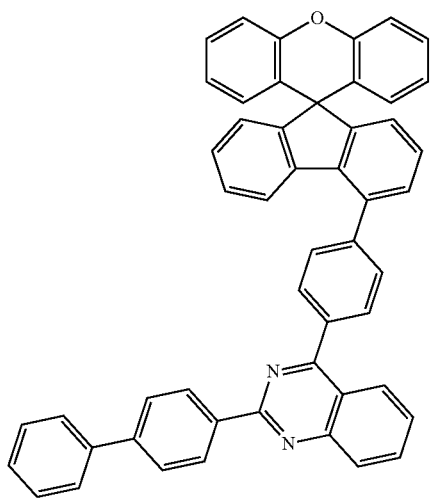
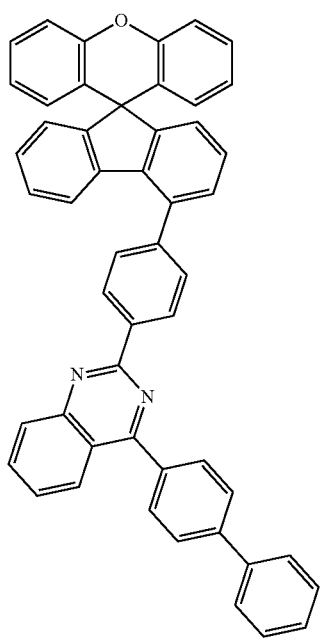
298
-continued
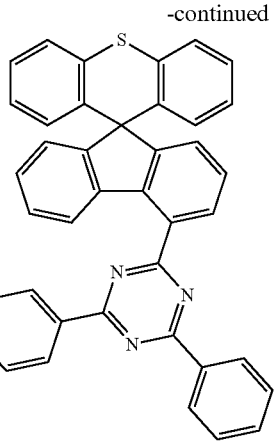
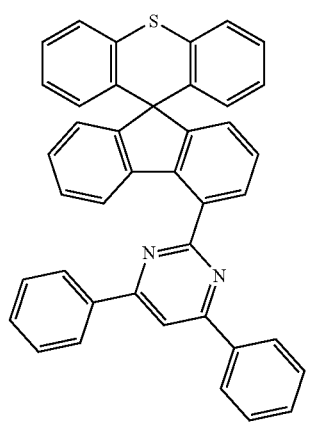
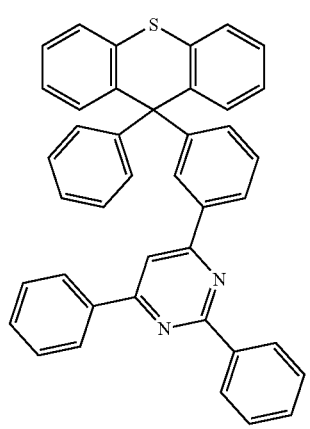
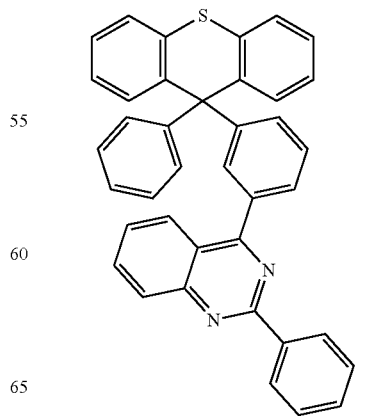

299
-continued
300
-continued
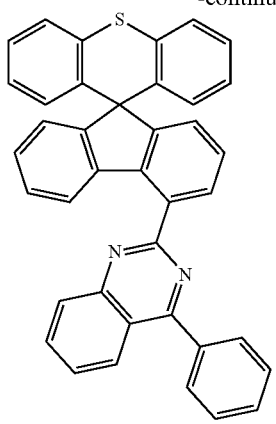
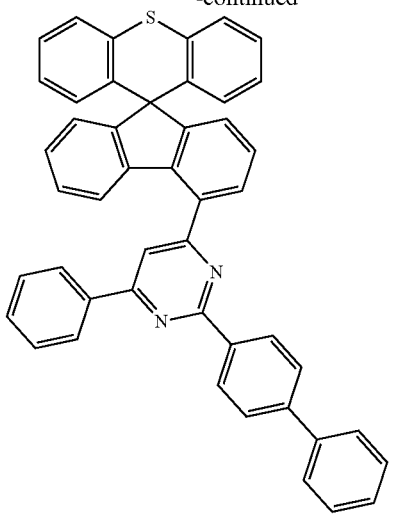
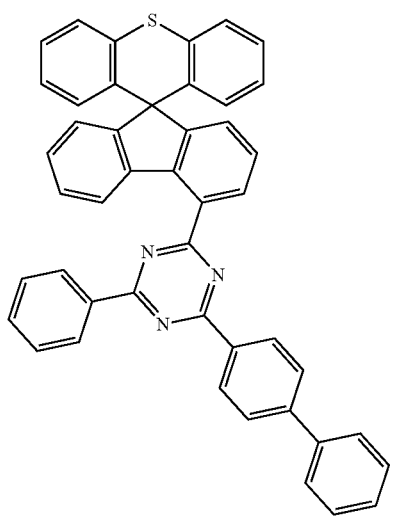
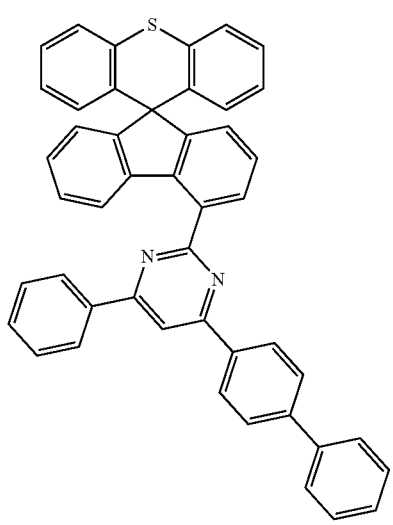

301
-continued
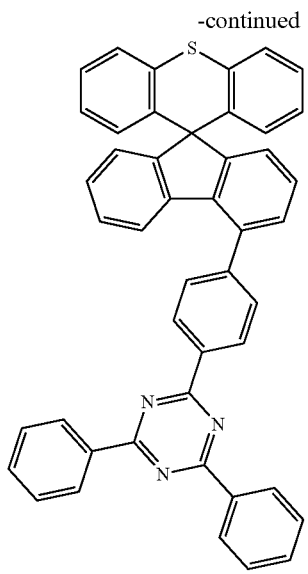
302
-continued
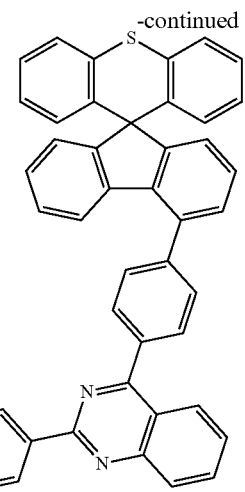
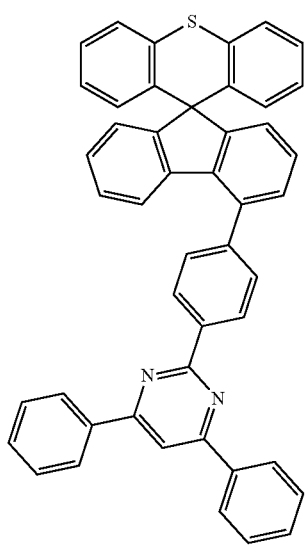
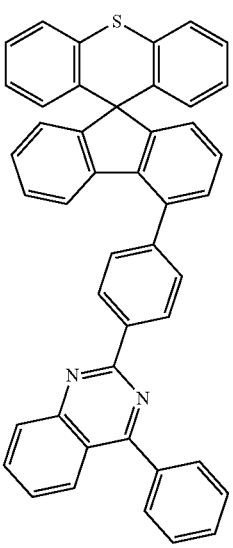
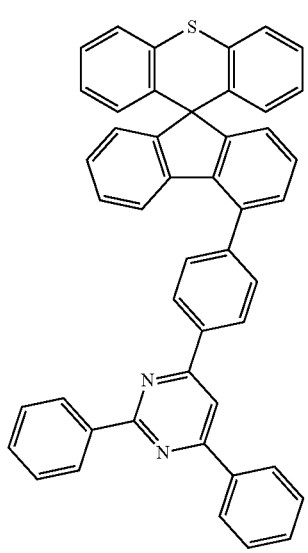
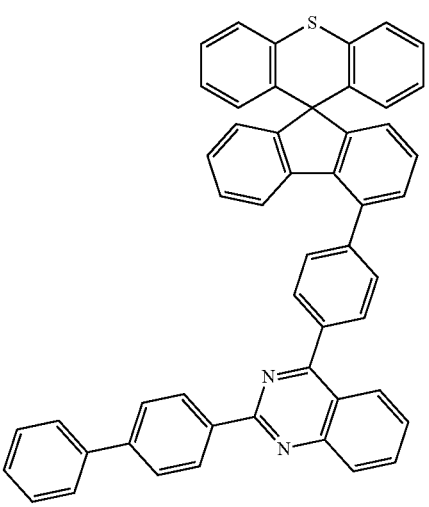

303
-continued
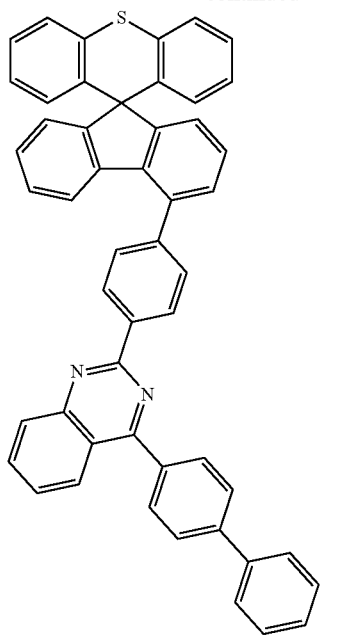
304
-continued
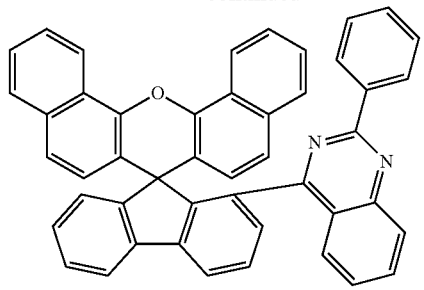
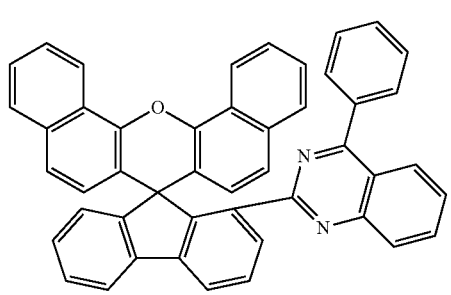
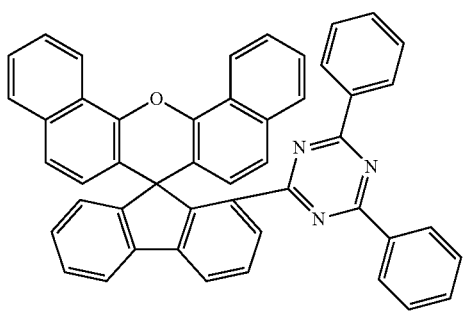
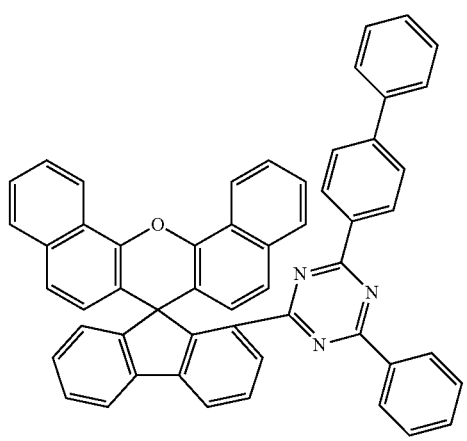
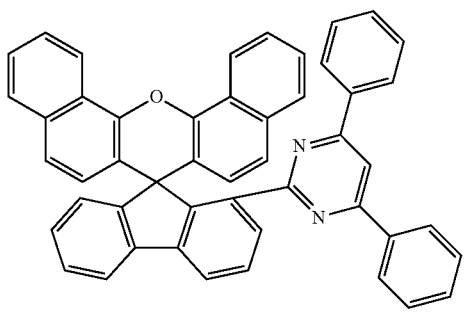
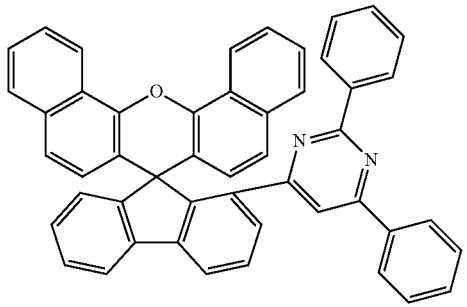
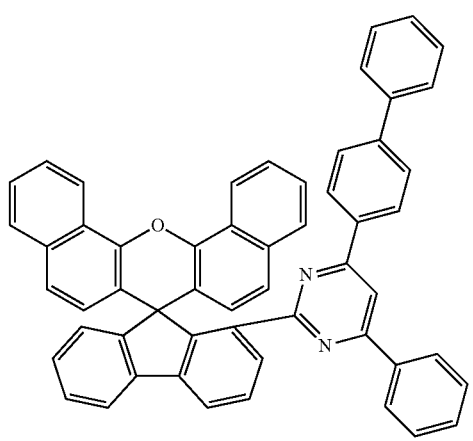

305
-continued
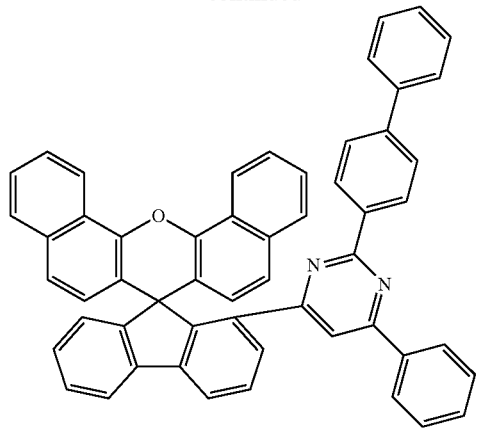
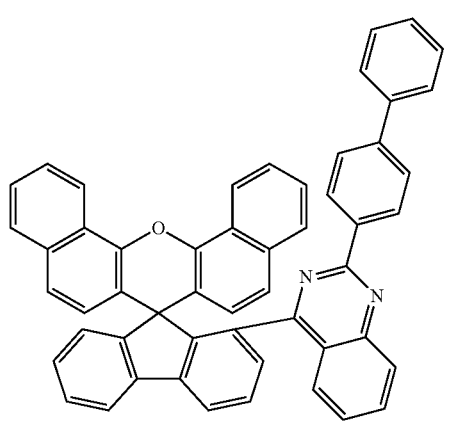
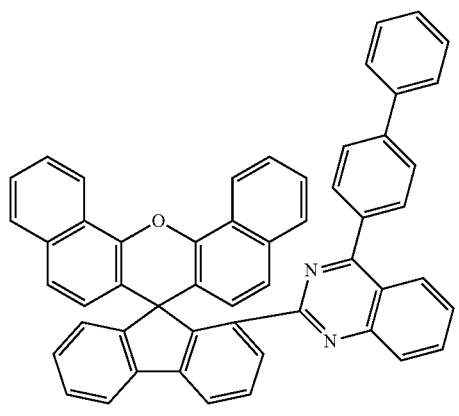
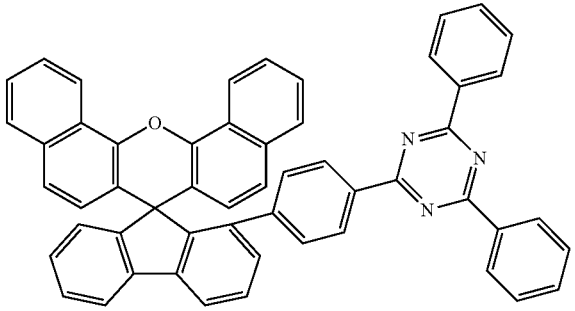
306
-continued
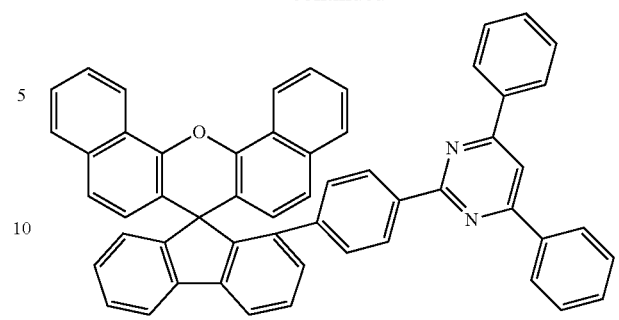
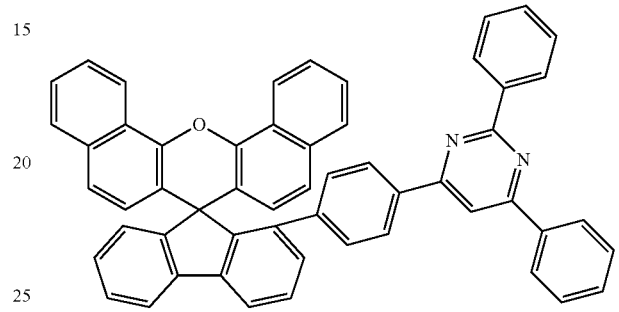
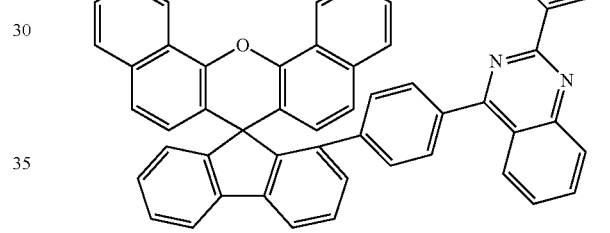
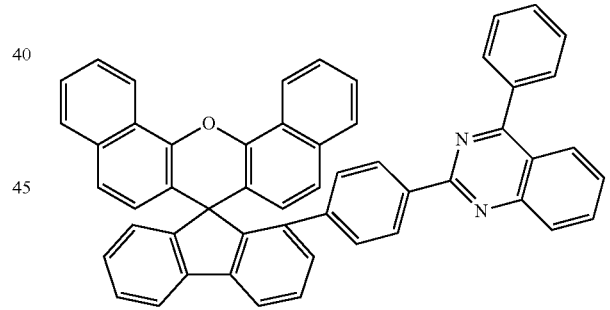
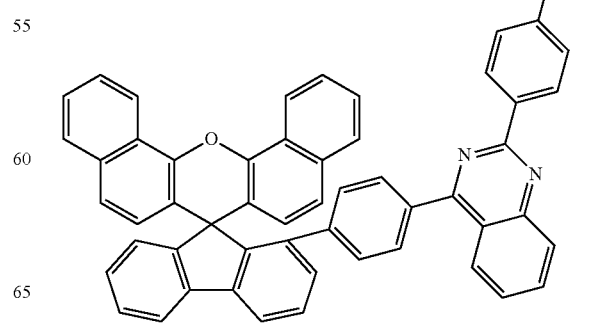

307
-continued
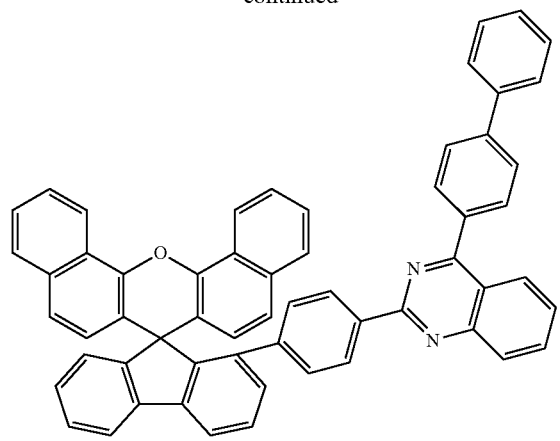
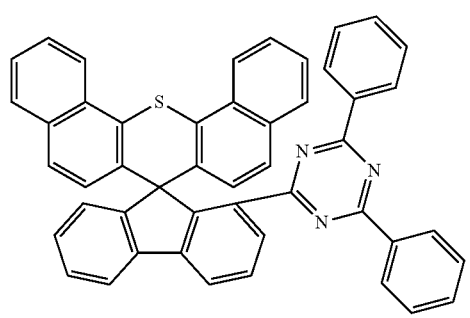
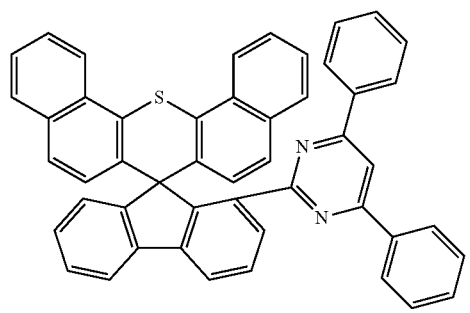
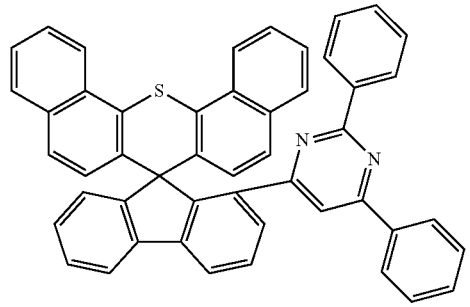
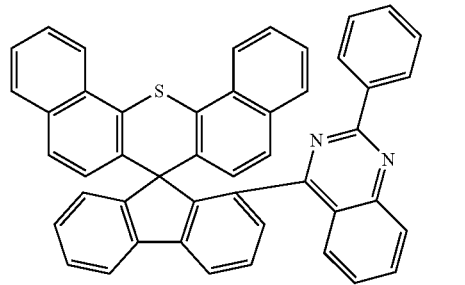
308
-continued
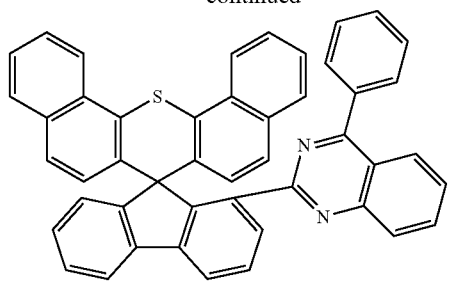
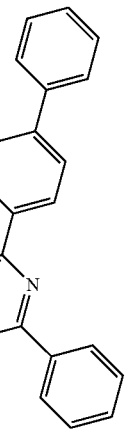
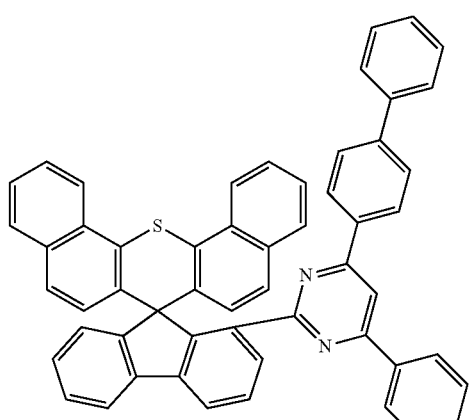
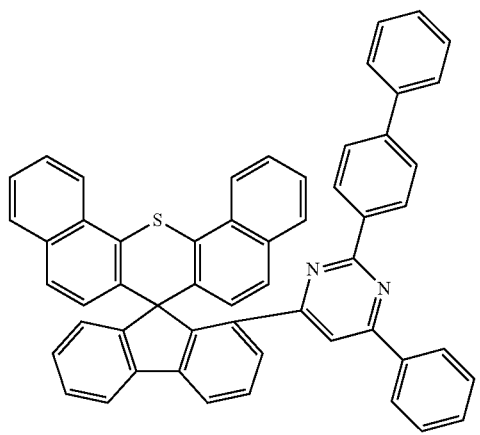

309
-continued
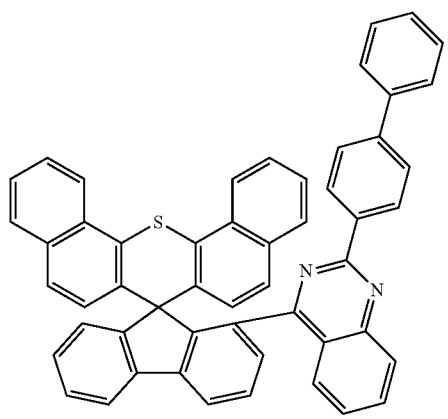
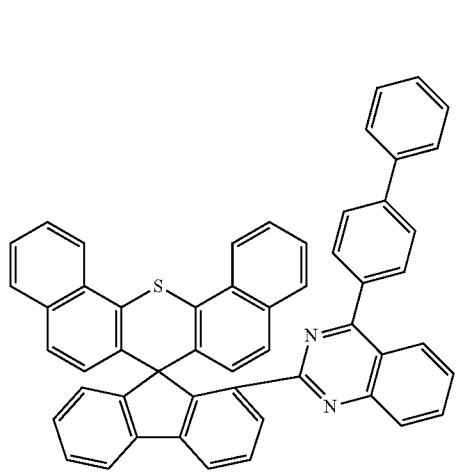
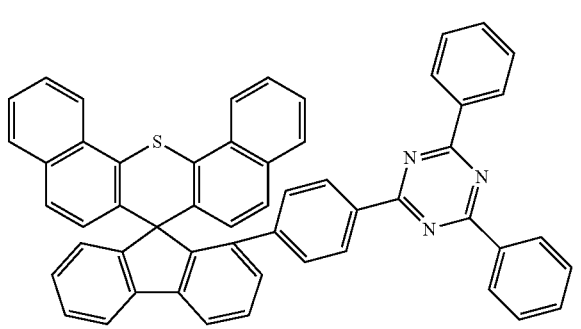
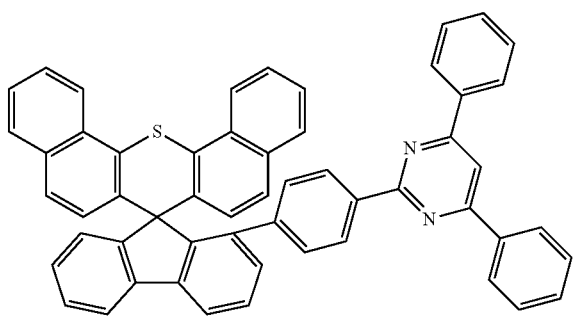
310
-continued
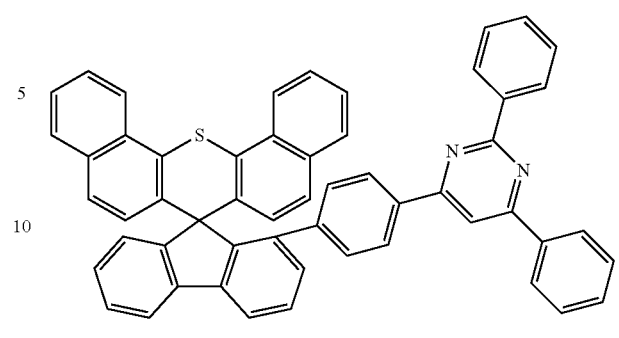
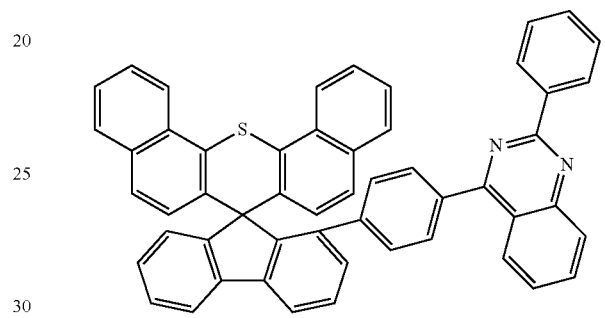
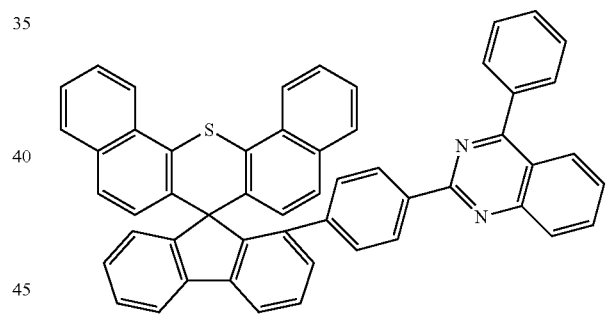
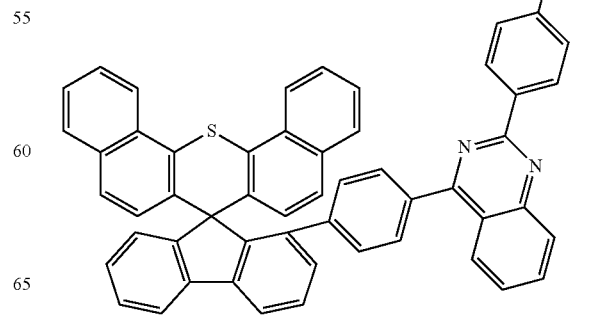

311
-continued
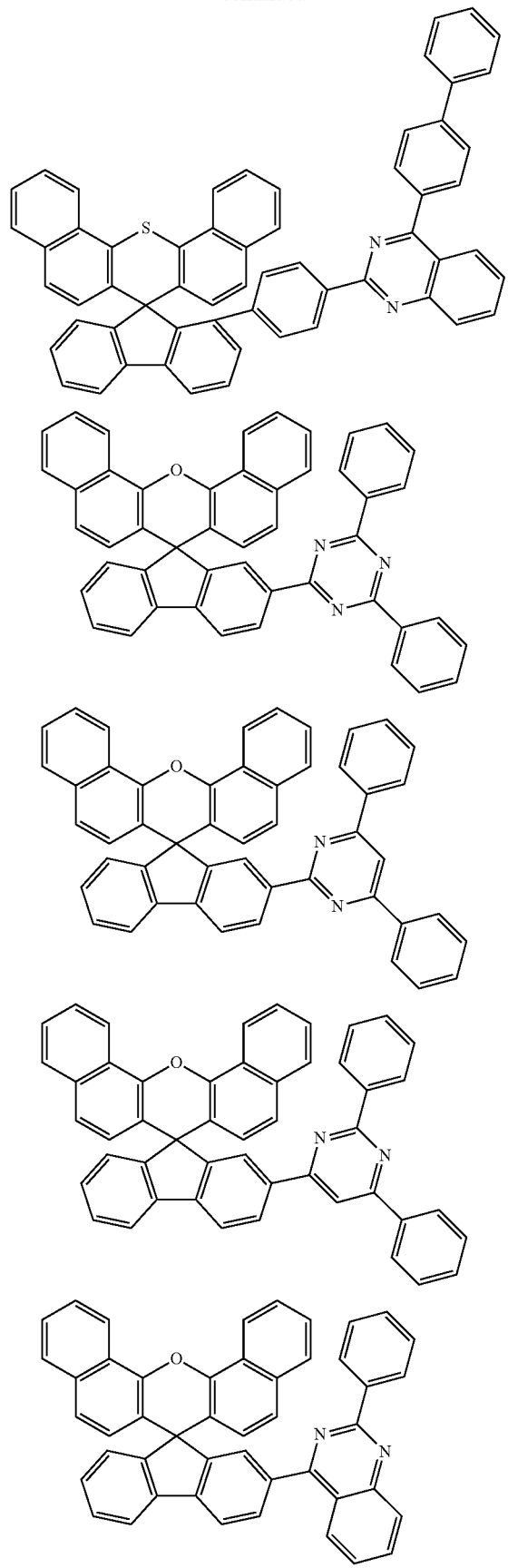
312
-continued
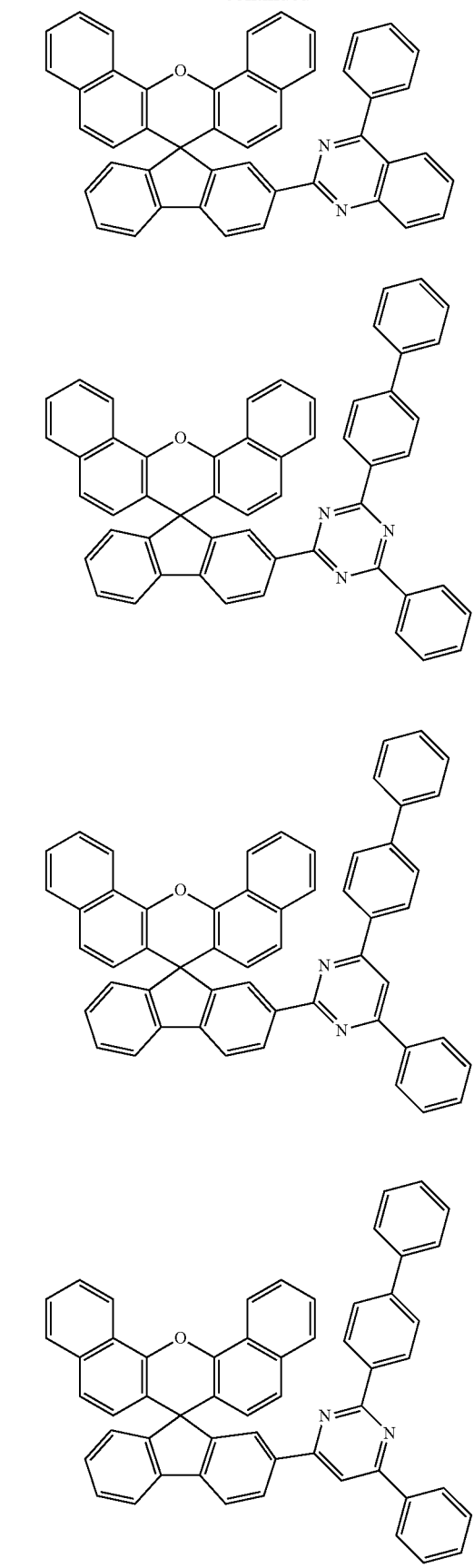

313
-continued
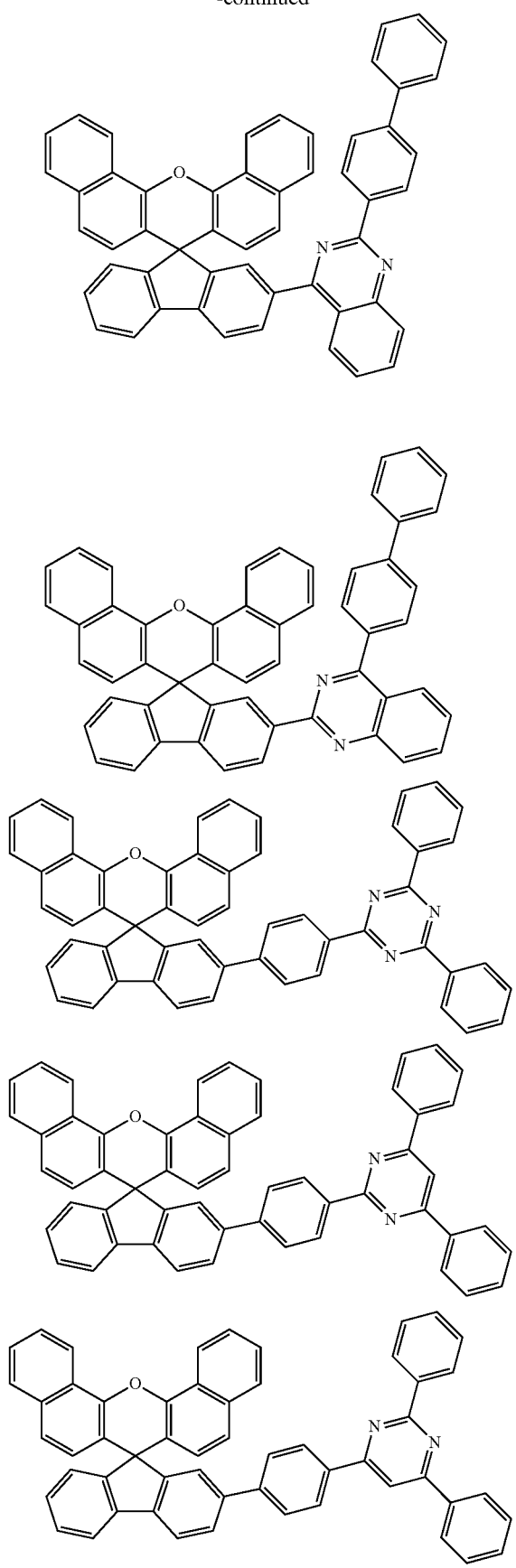
314
-continued
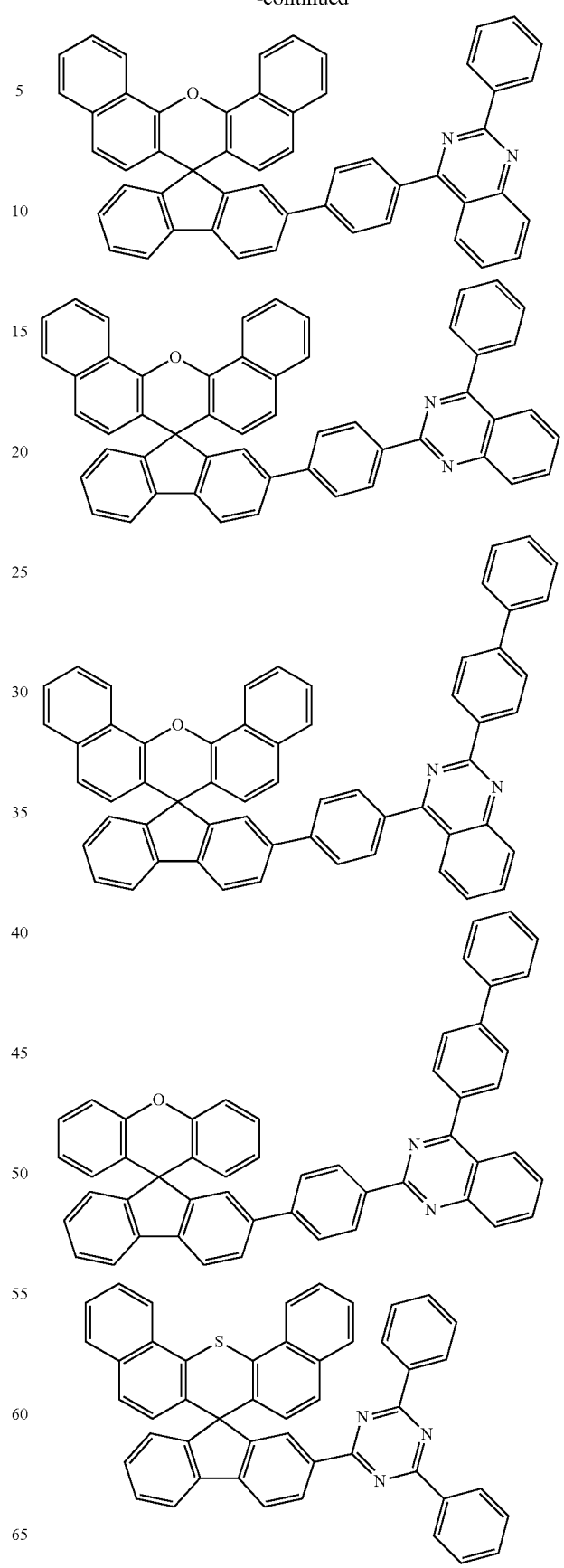

315
-continued
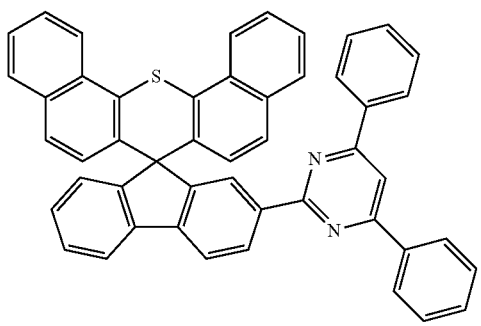
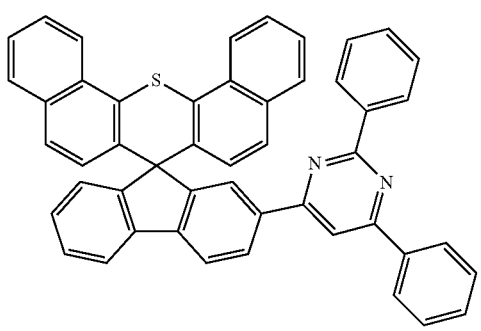
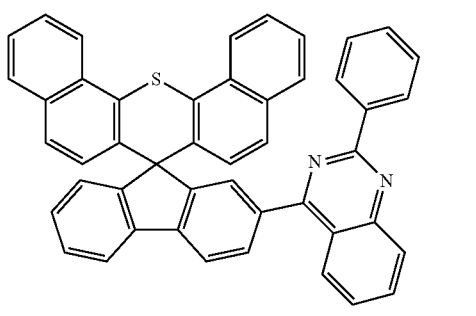
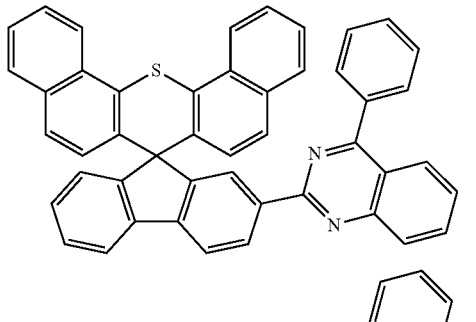
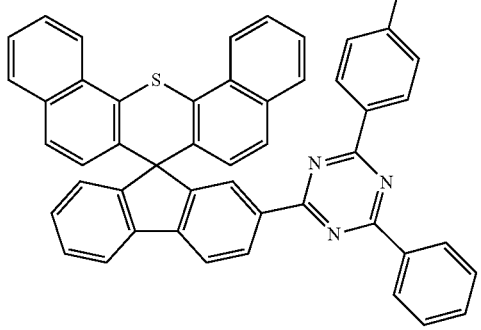
316
-continued
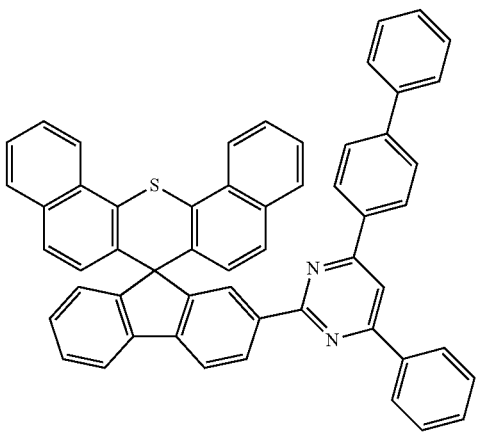
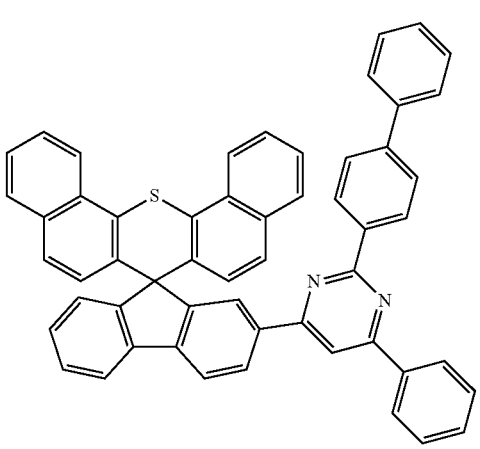
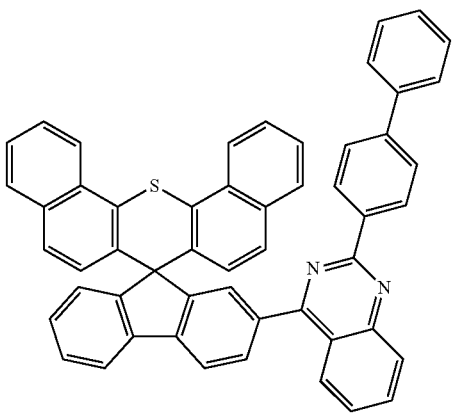
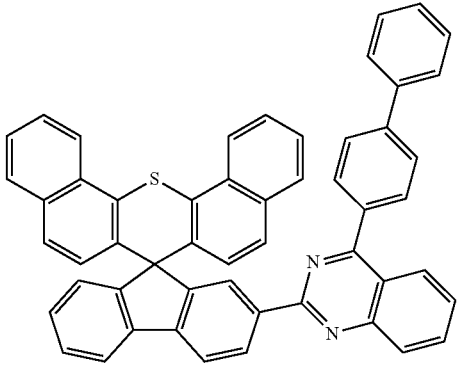

317
-continued
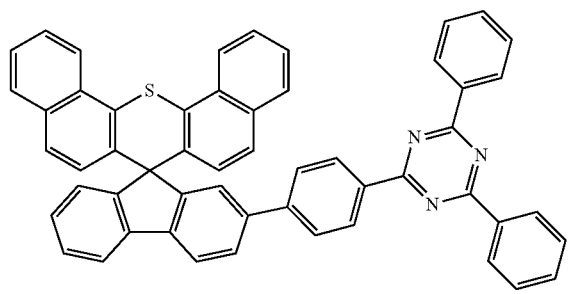
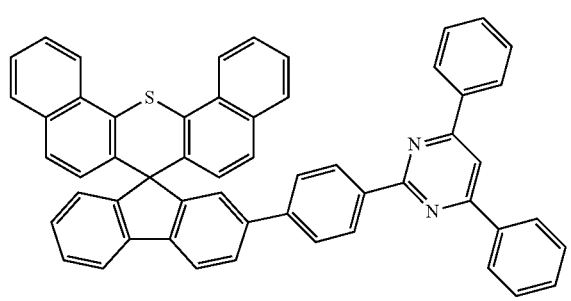
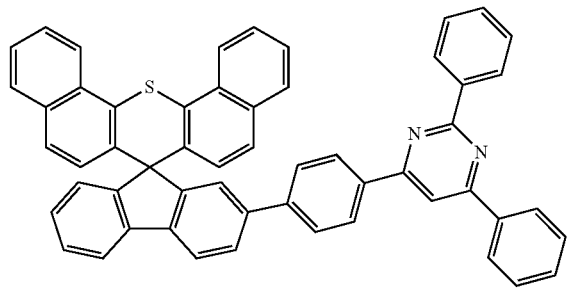
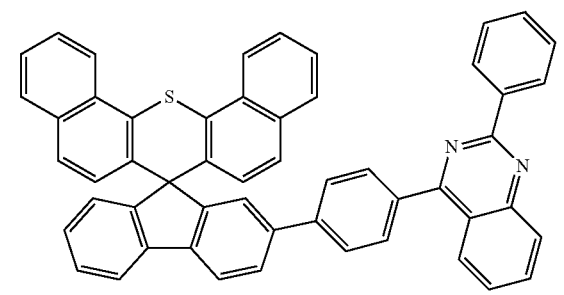
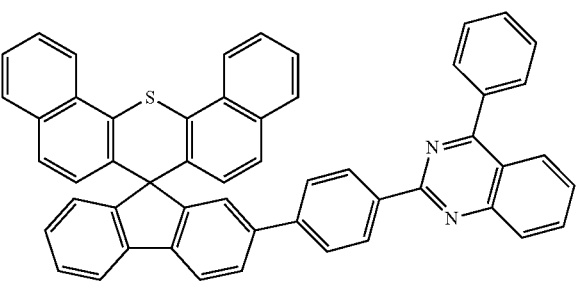
318
-continued
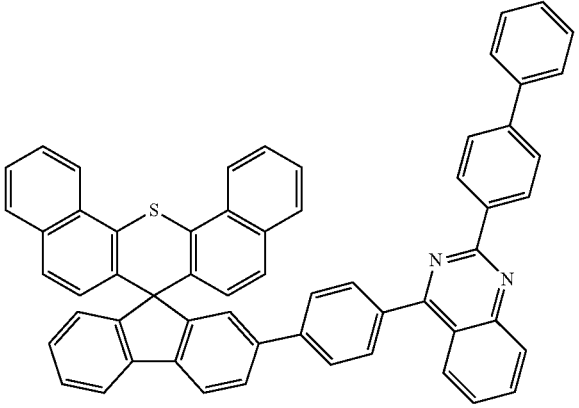
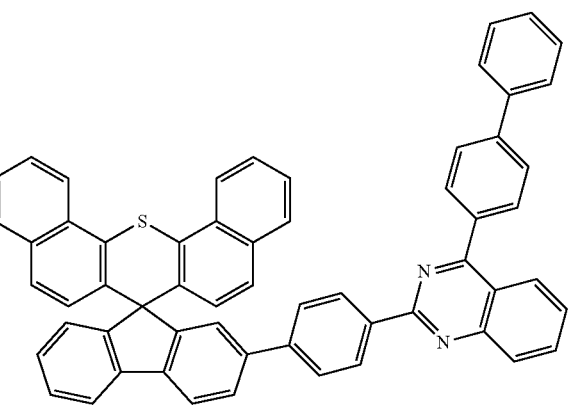
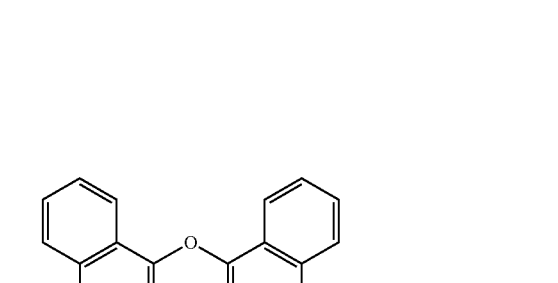
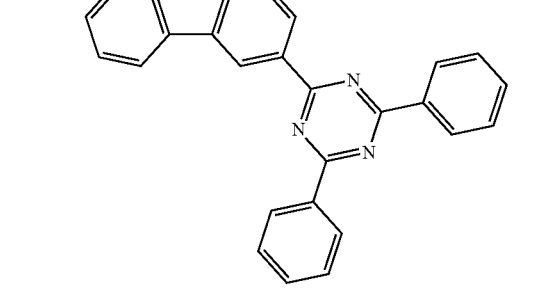

319
-continued
320
-continued
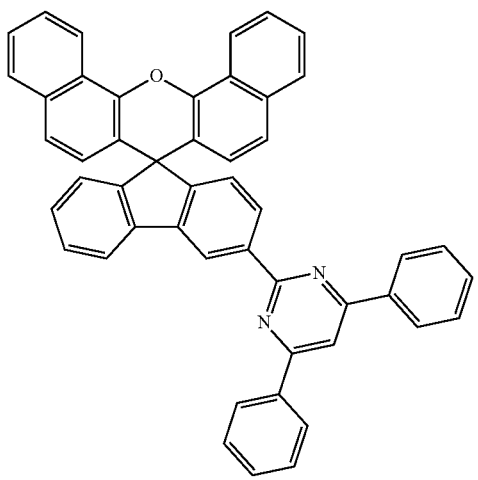
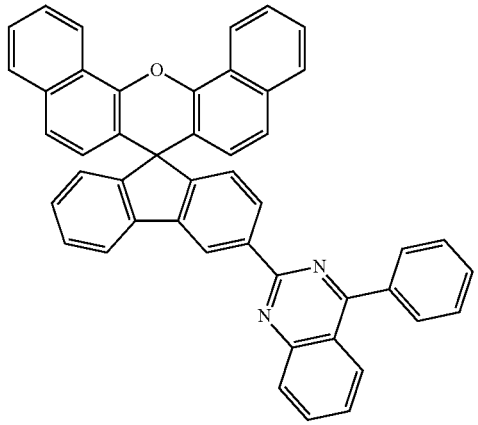
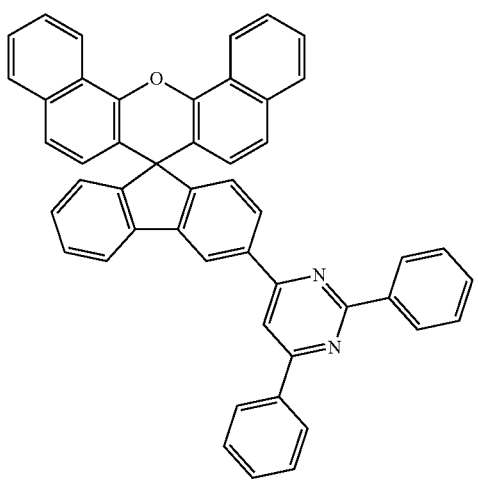
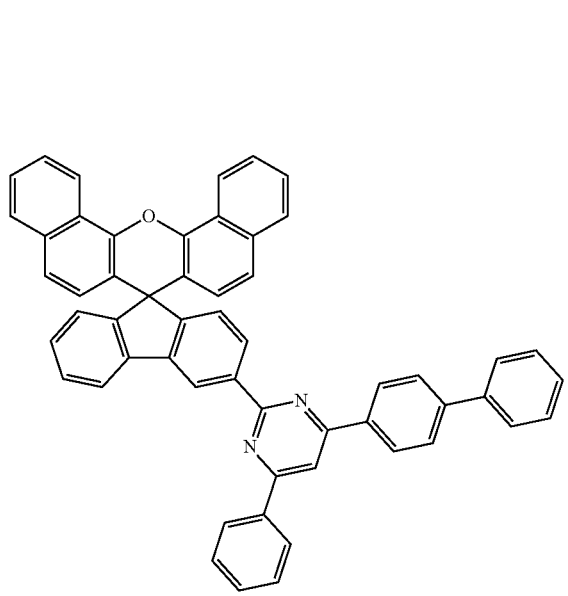
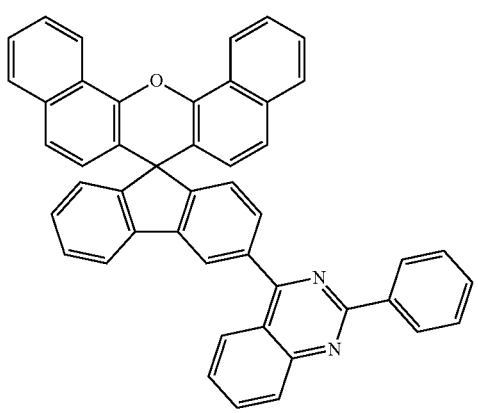

321
-continued
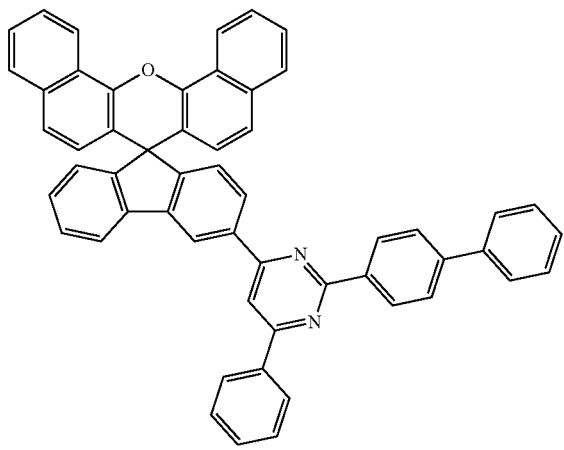
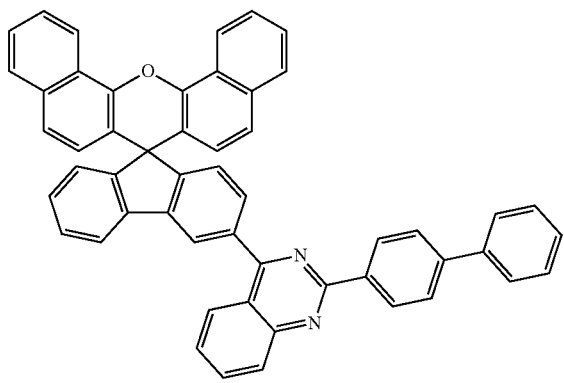
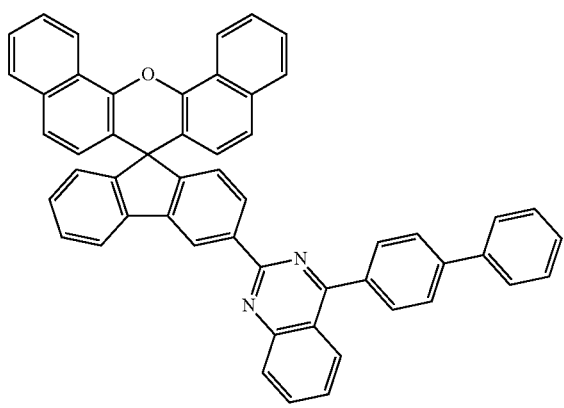
322
-continued
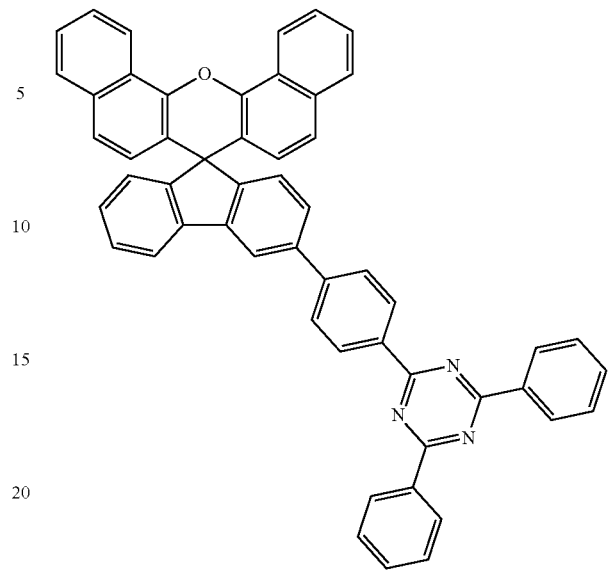
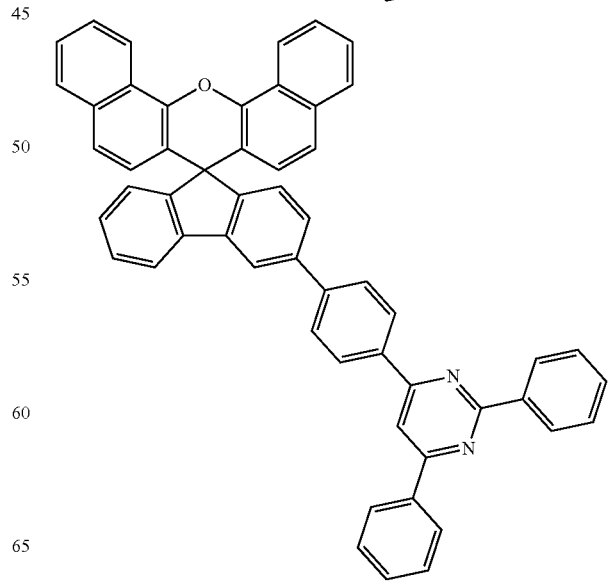

323
-continued
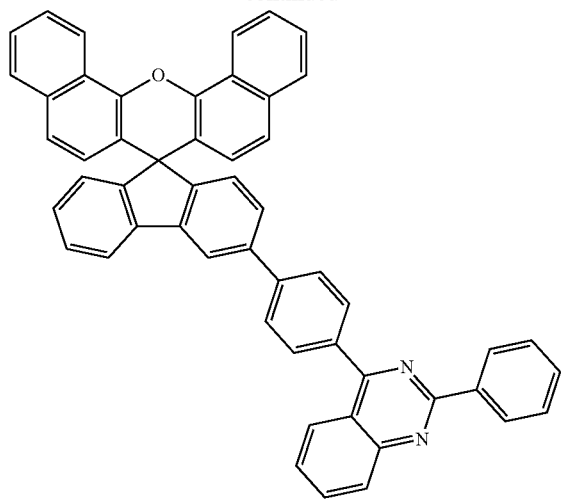
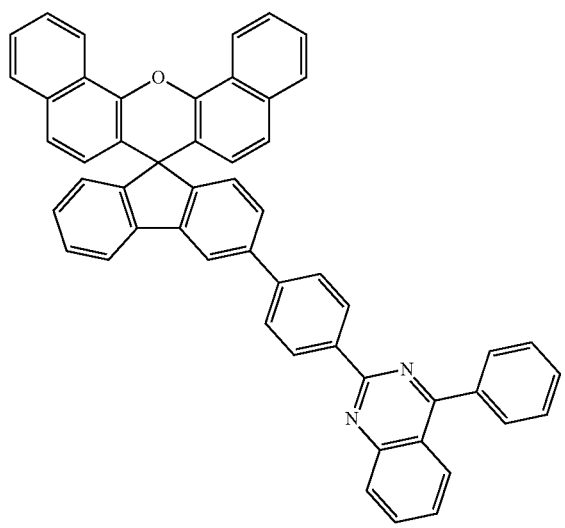
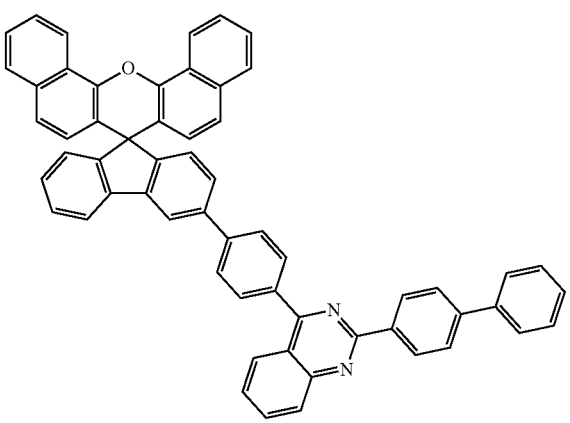
324
-continued
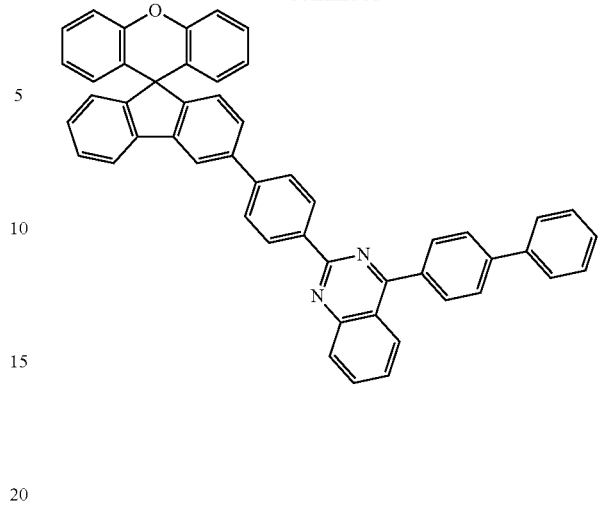
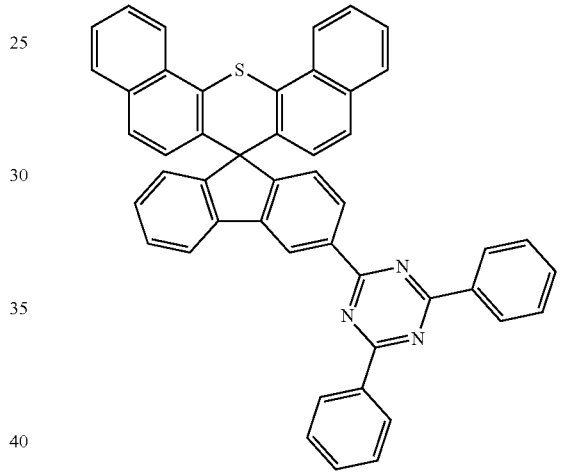
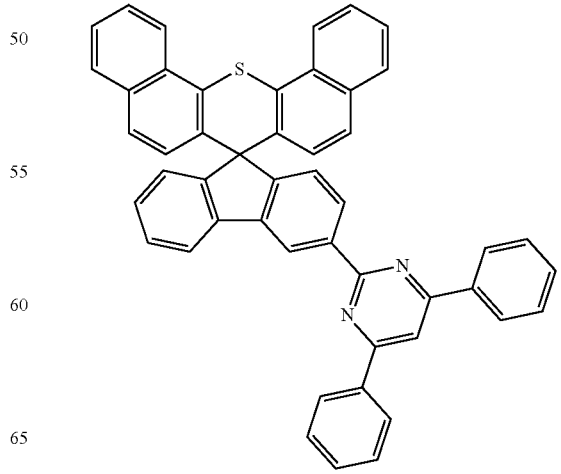

325
-continued
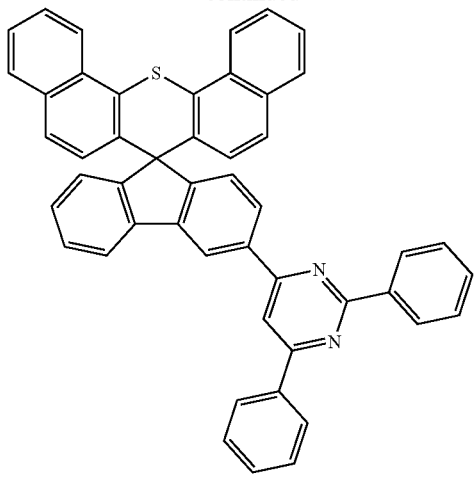
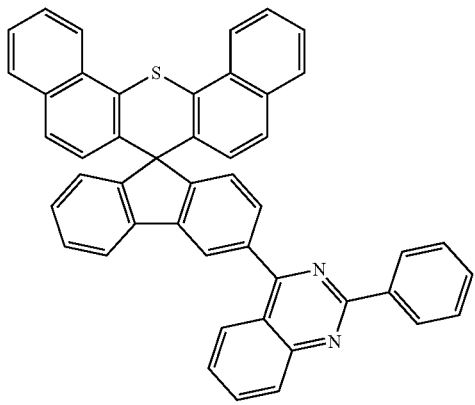
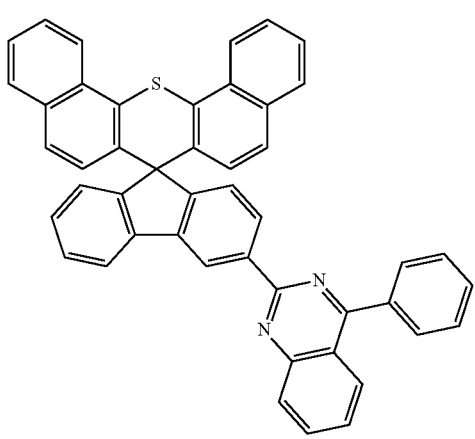
326
-continued
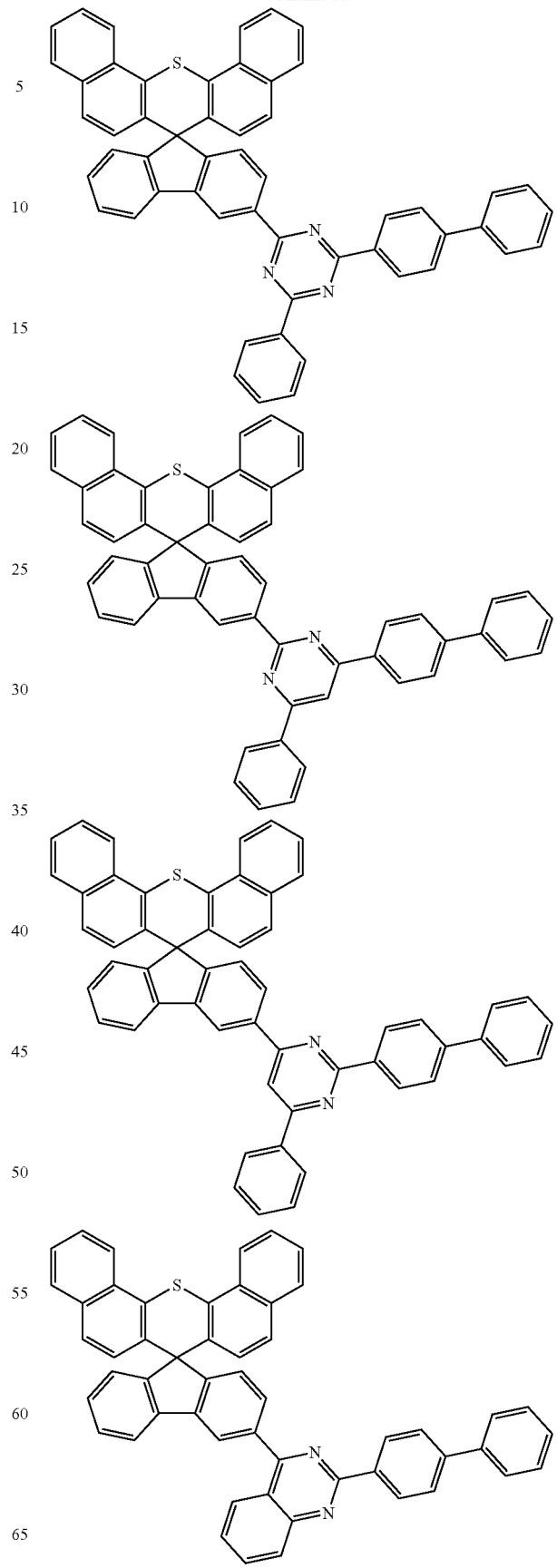

327
-continued
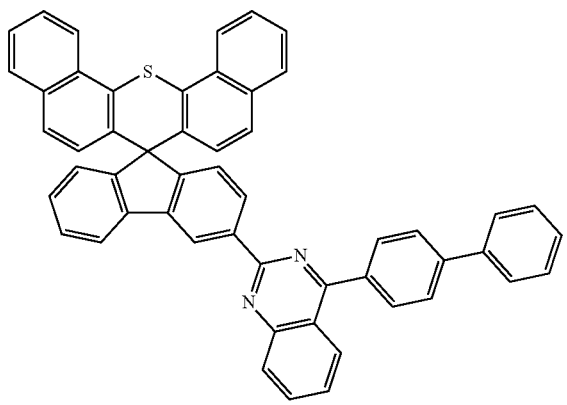
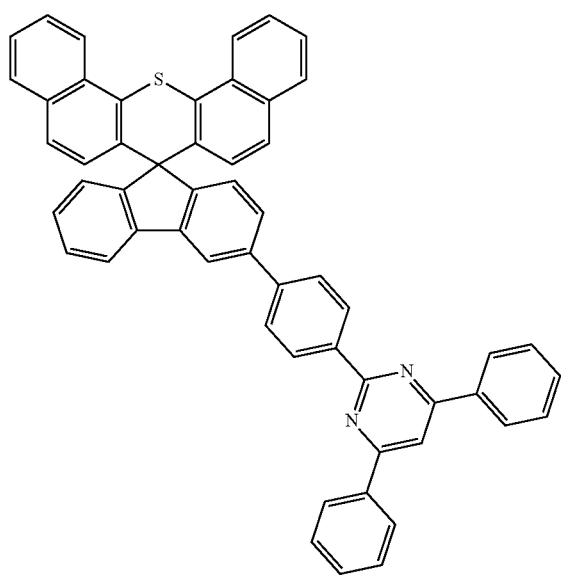
328
-continued
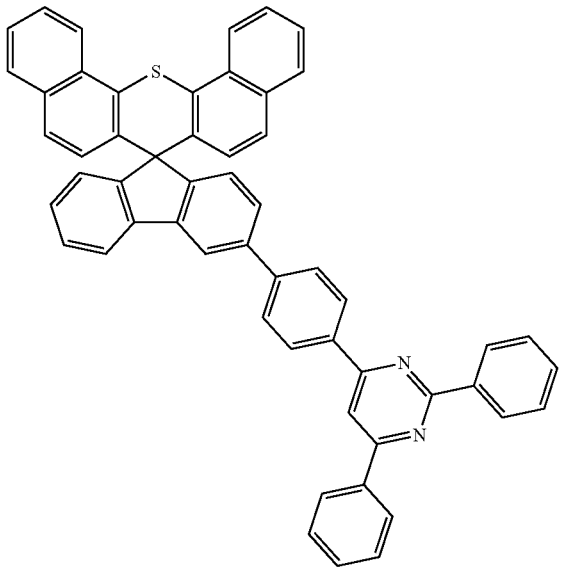
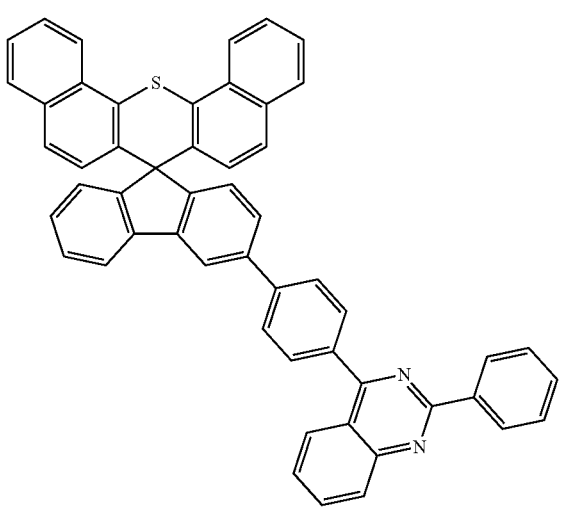

329
-continued
330
-continued
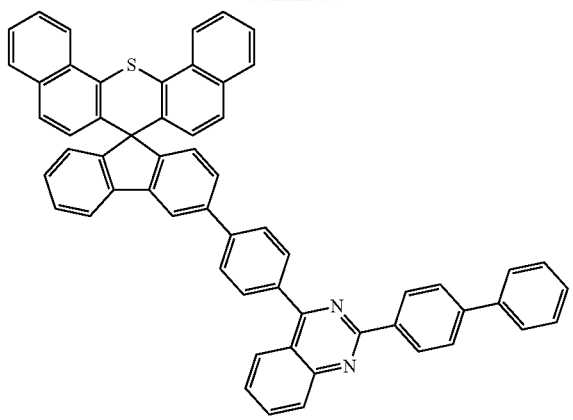
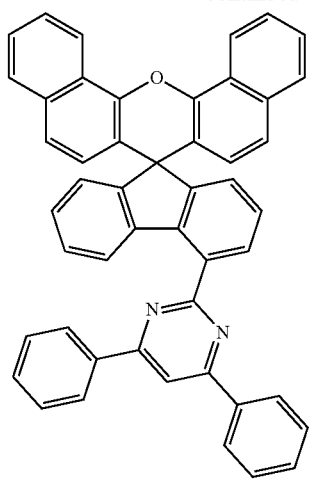
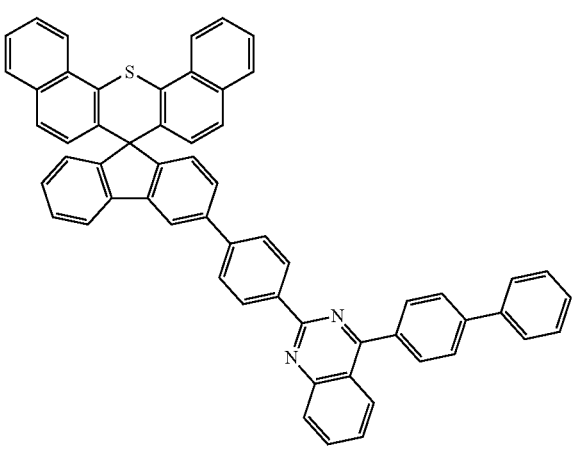
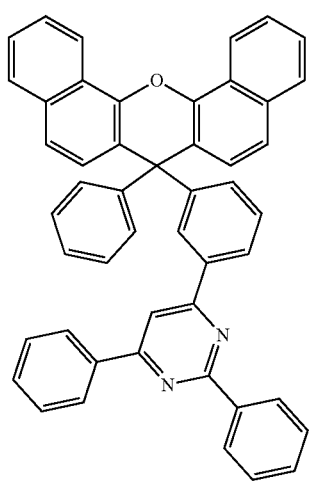
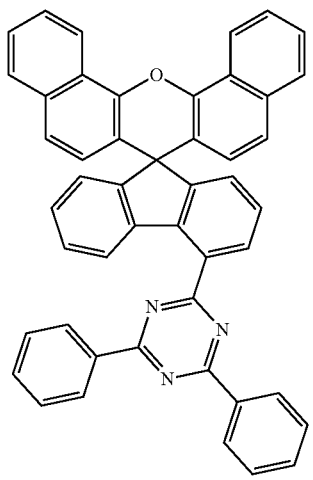
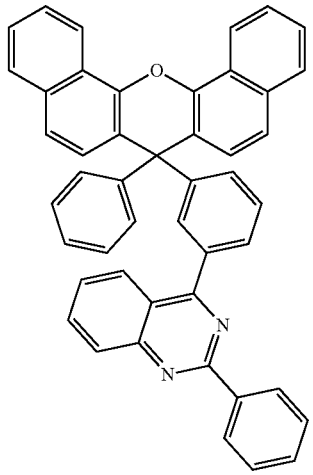

331
-continued
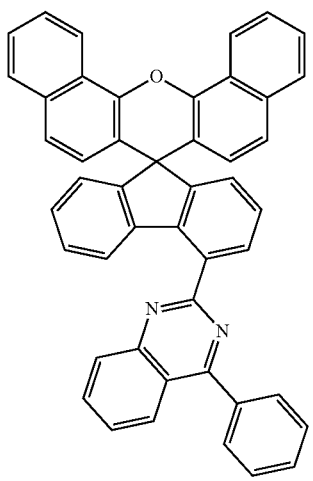
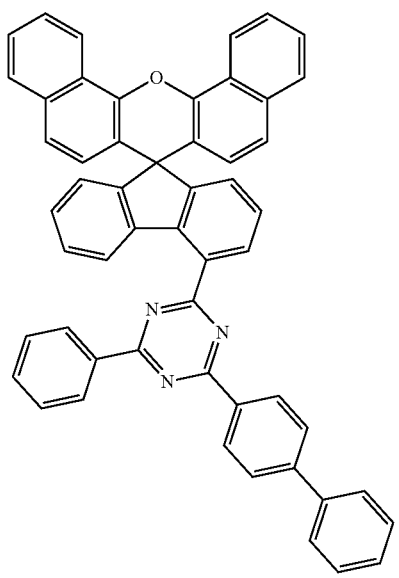
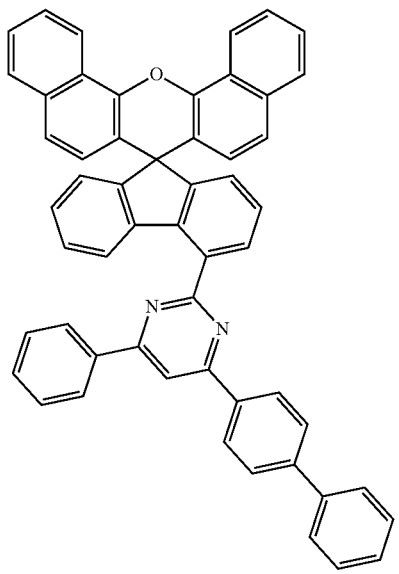
332
-continued
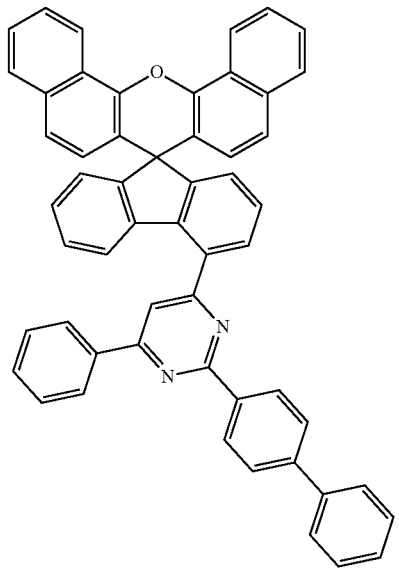
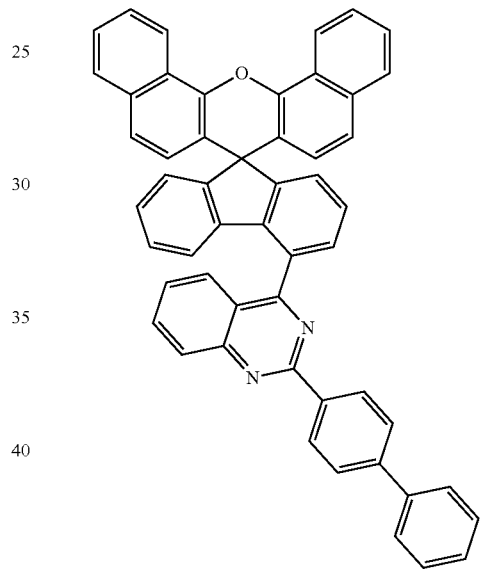
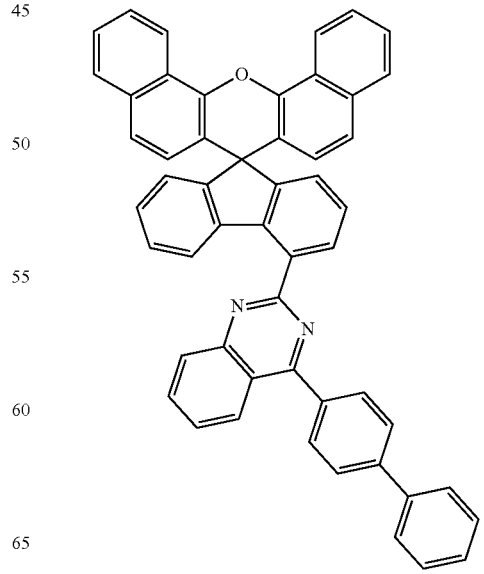

333
-continued
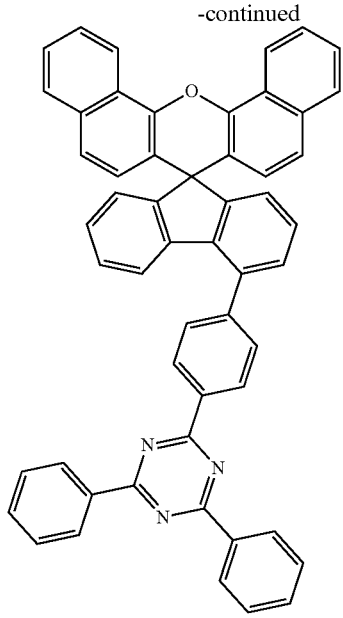
334
-continued
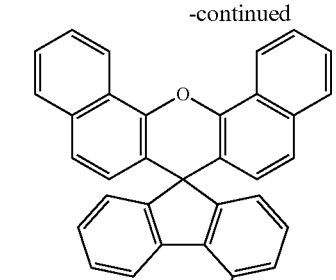
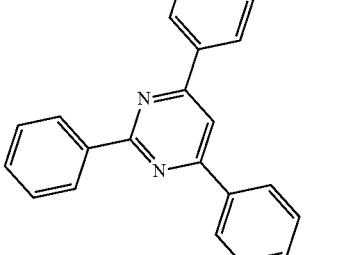
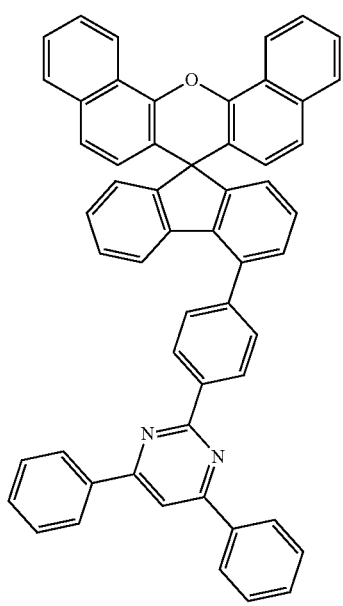
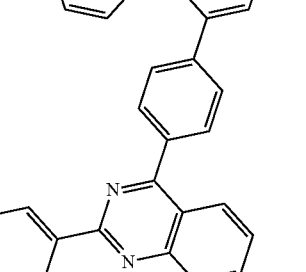
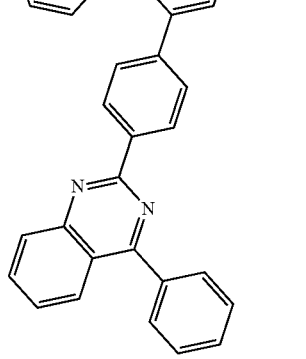

-continued
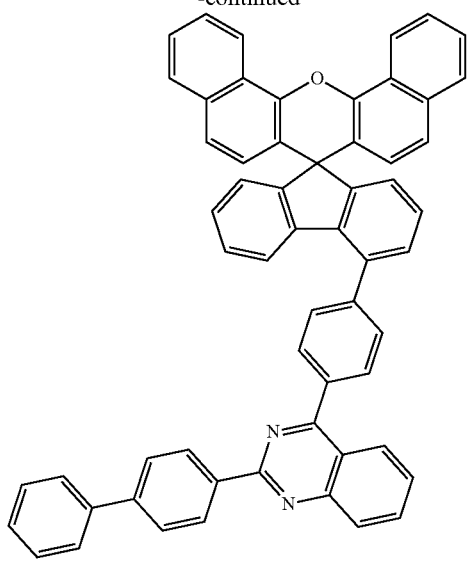
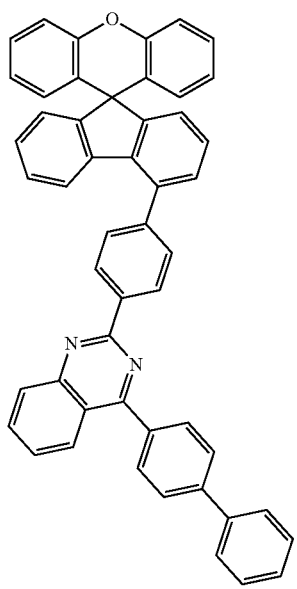
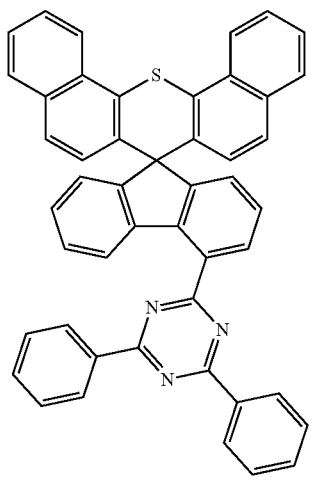
-continued
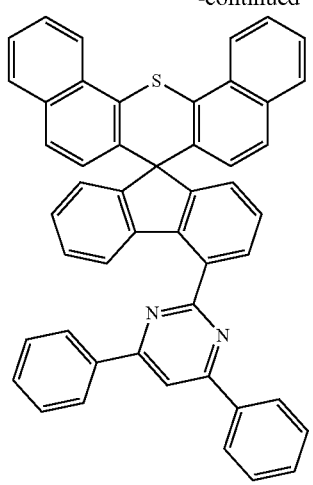
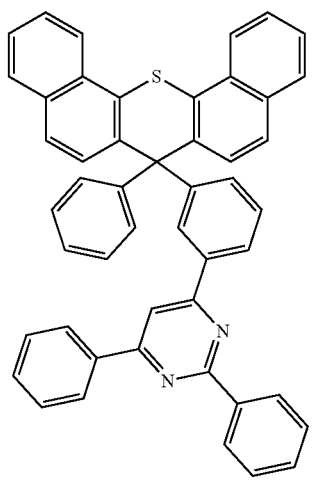
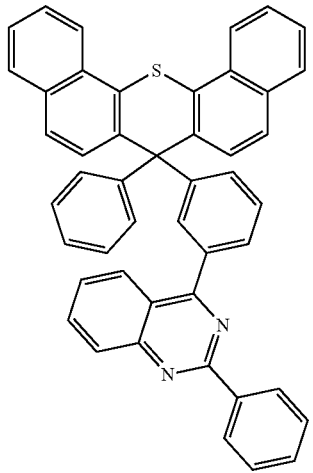

337
-continued
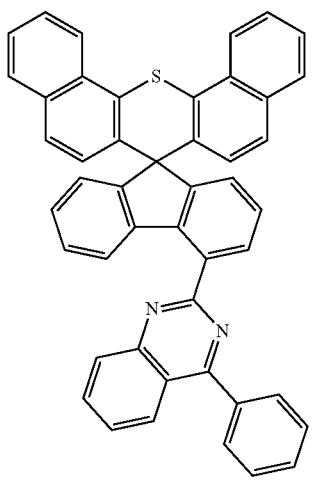
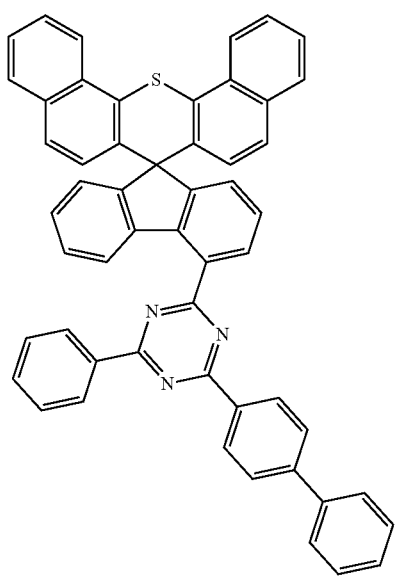
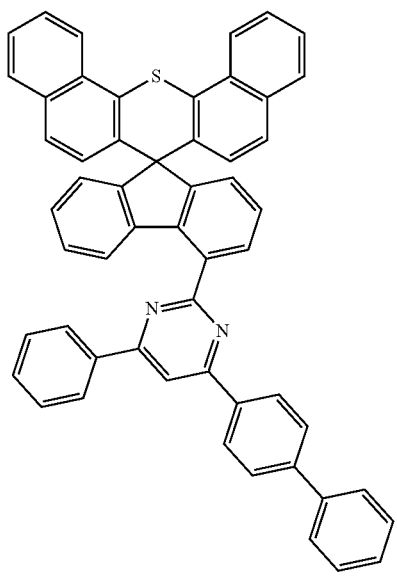
338
-continued
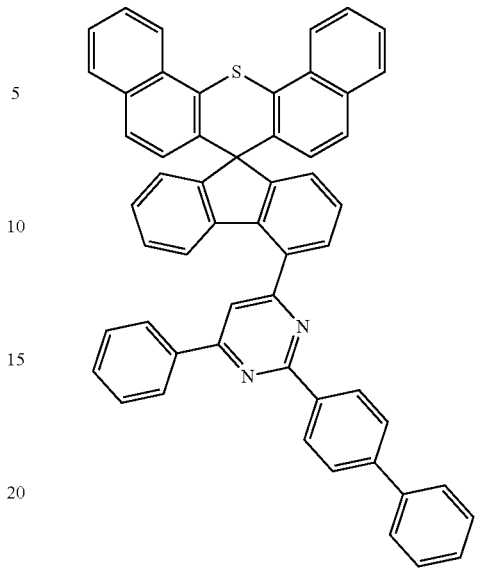
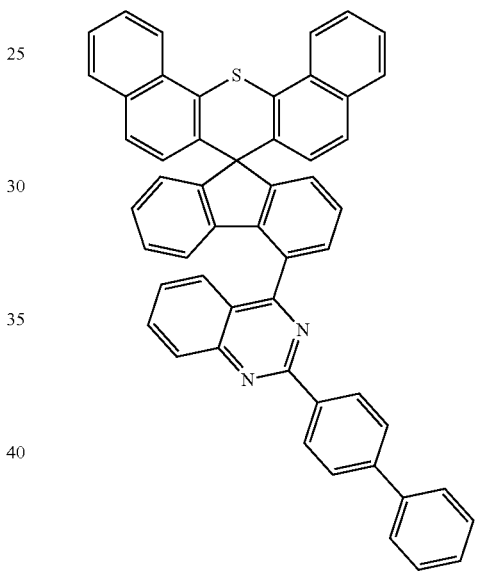
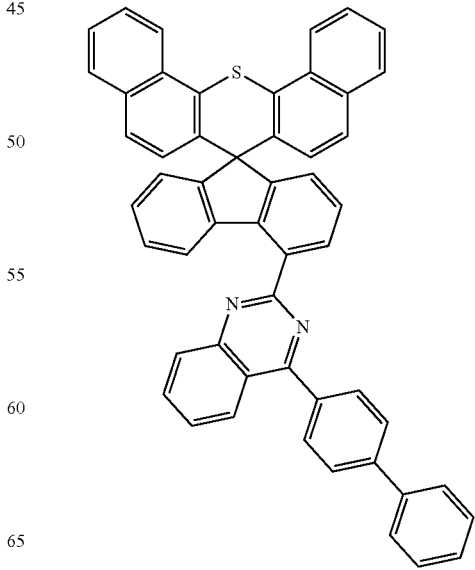

339
-continued
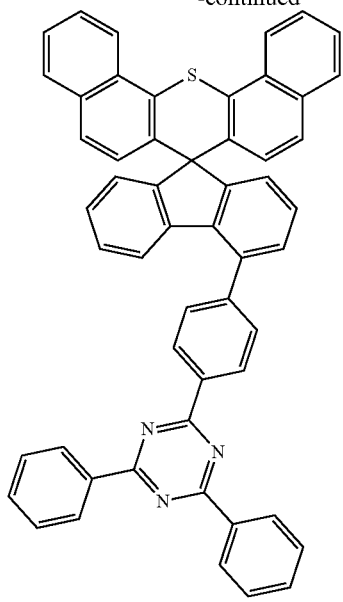
340
-continued
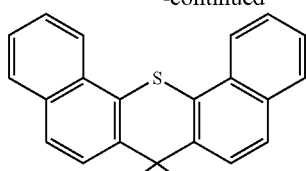
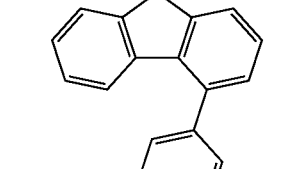
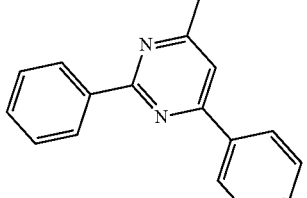
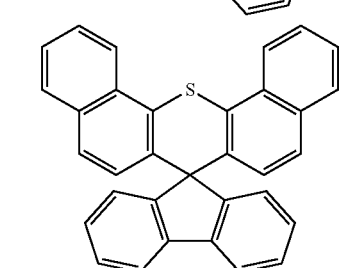
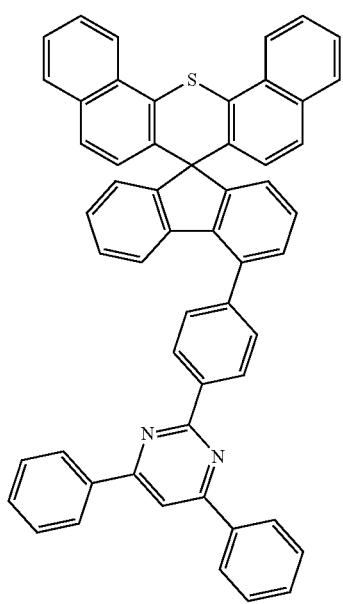
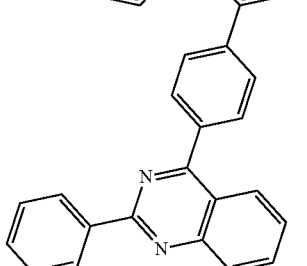
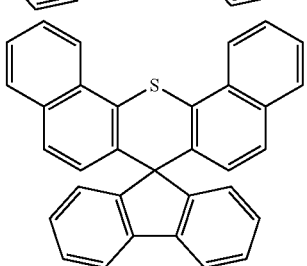
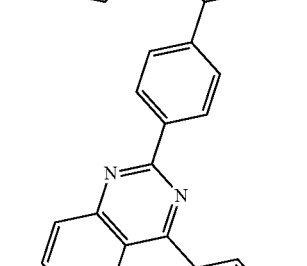

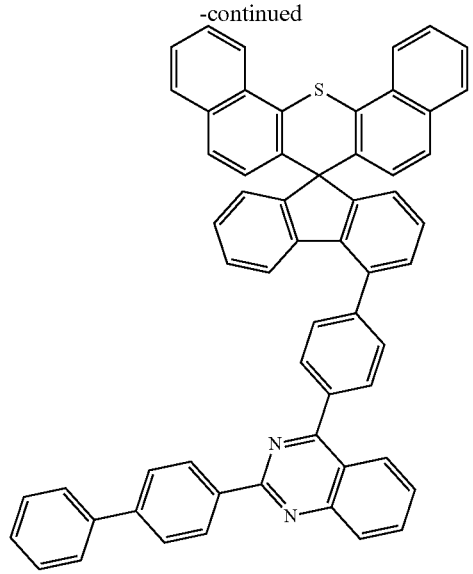
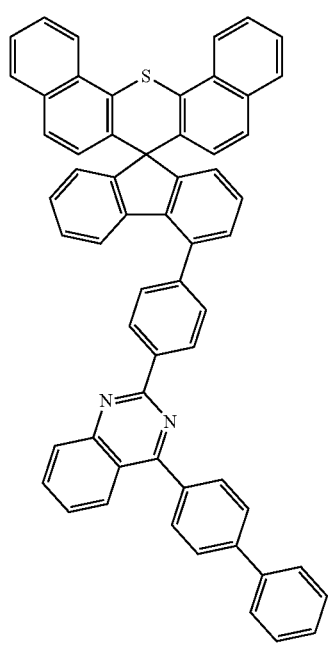 [SMILES: c1ccc(-c2ccc(-c3nc(-c4ccc(-c5cccc6c5-c5ccccc5C65c6ccc7ccccc7c6Sc6c5ccc5ccccc65)cc4)nc4ccccc34)cc2)cc1]

343
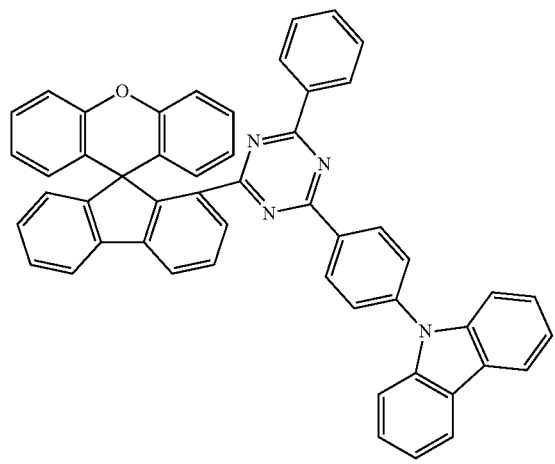
344
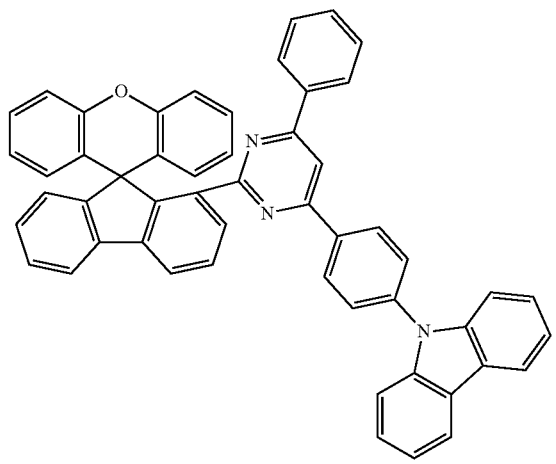
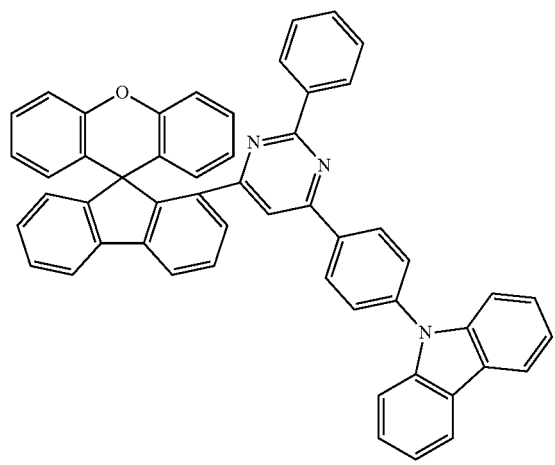
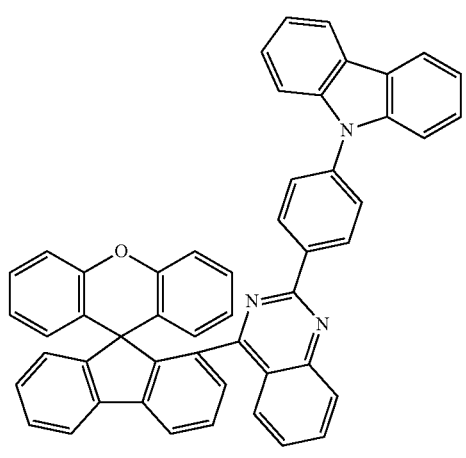
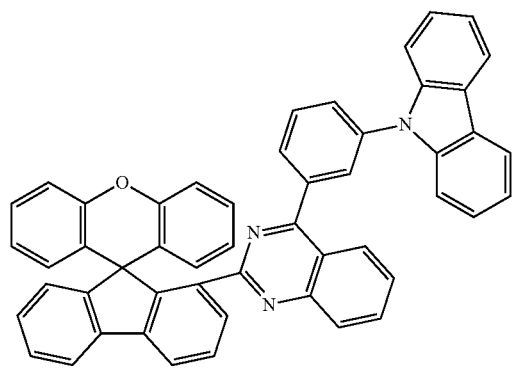
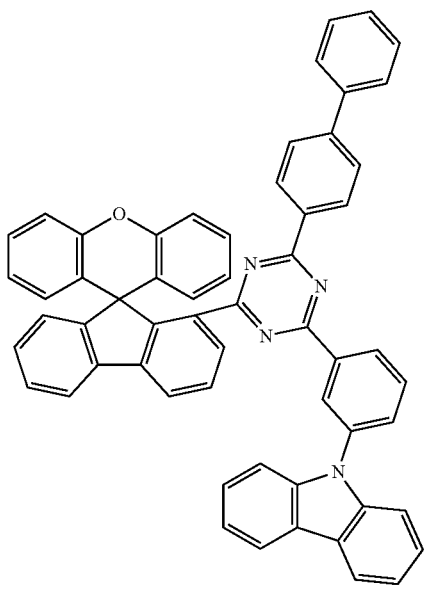

-continued
345
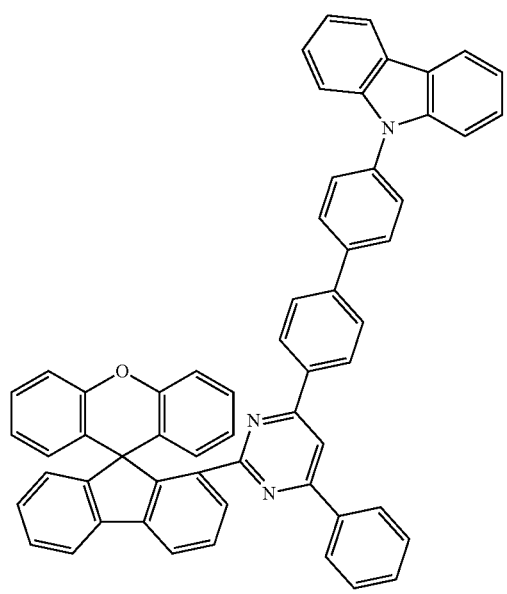
346
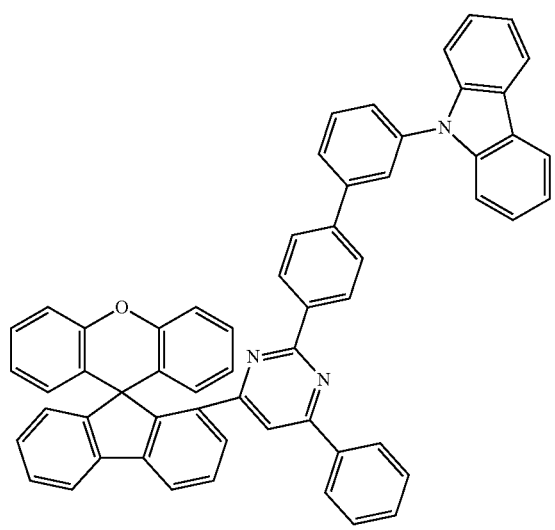
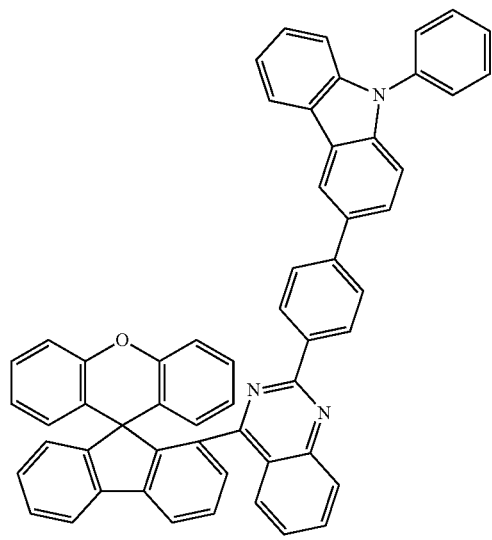
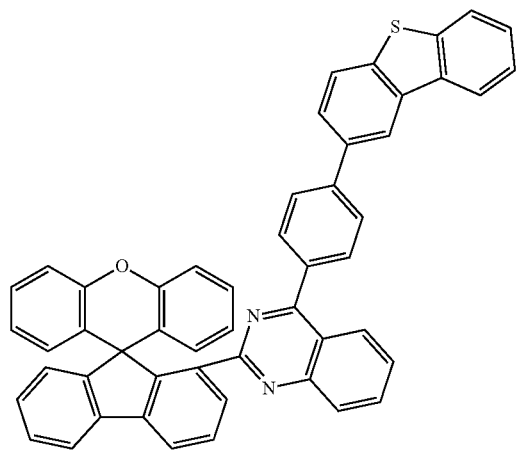
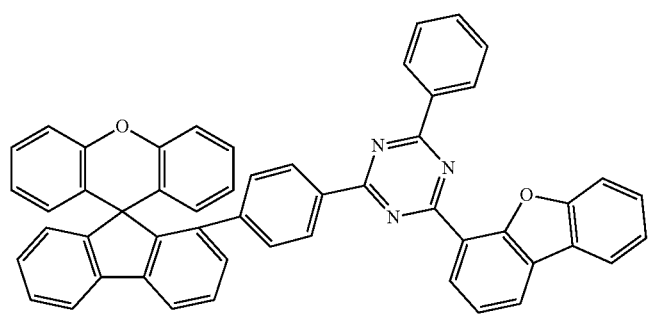

-continued
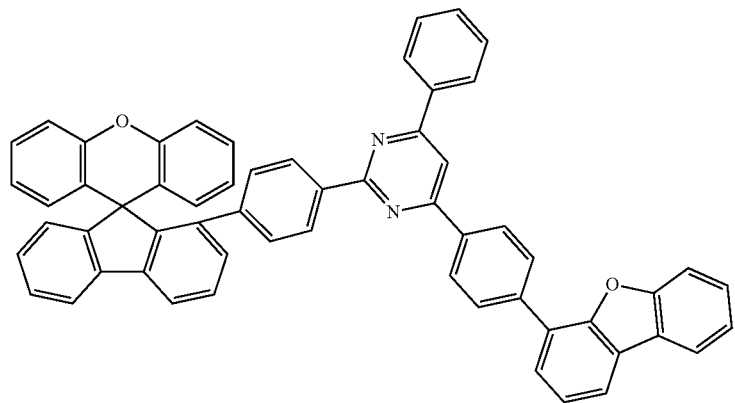
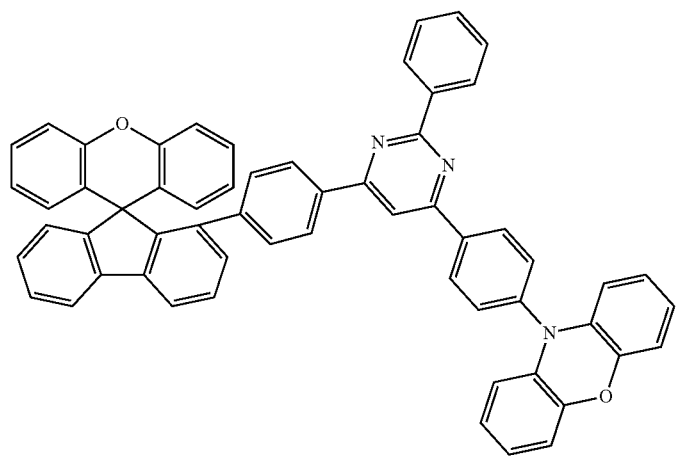
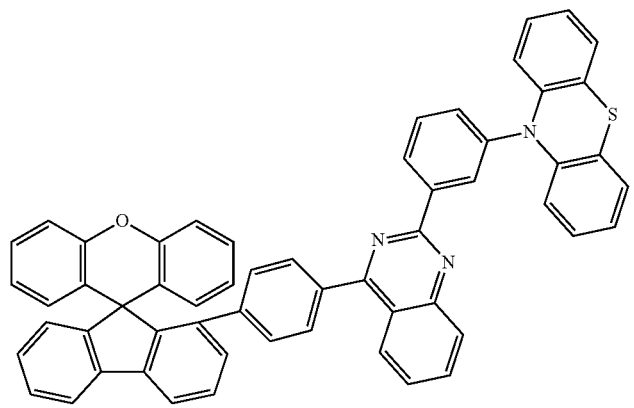
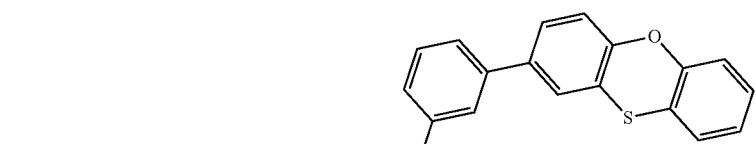
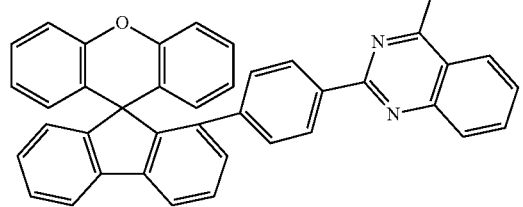

-continued
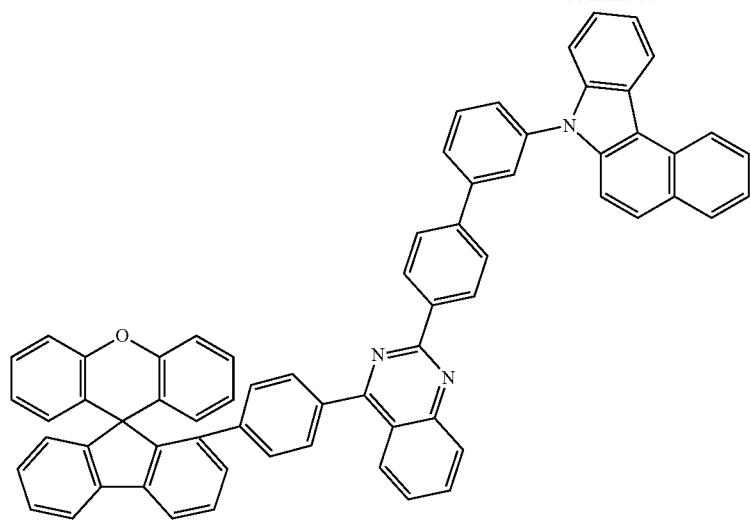
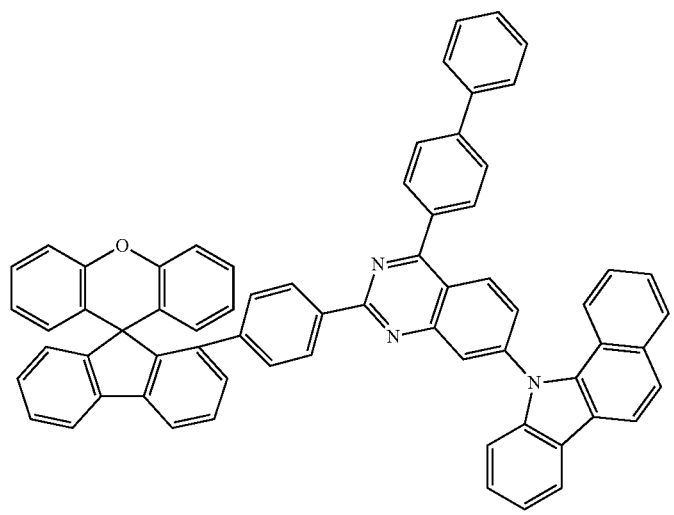
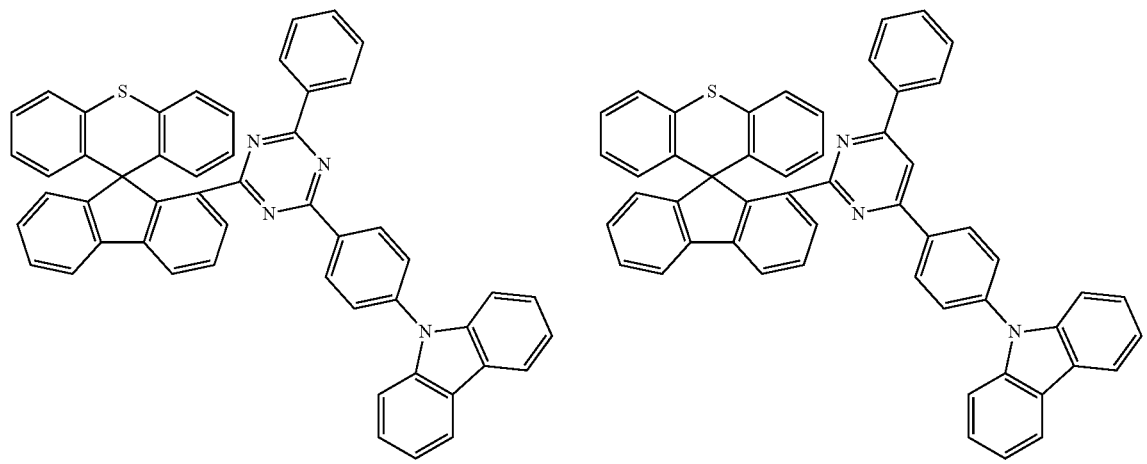

351
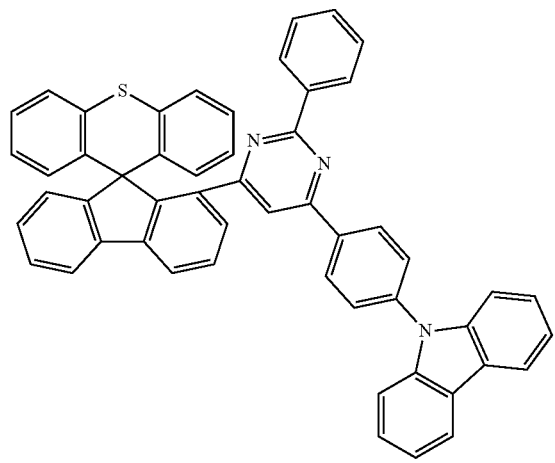
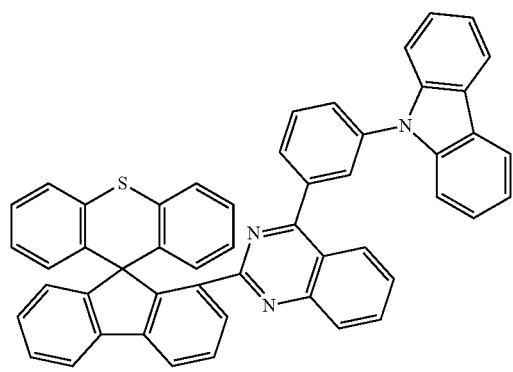
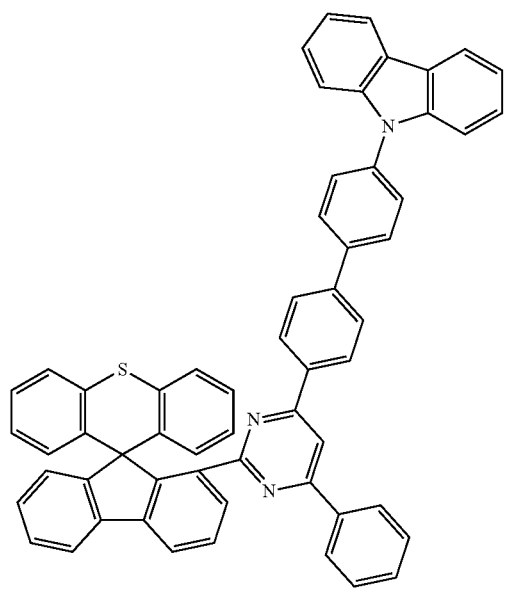
352
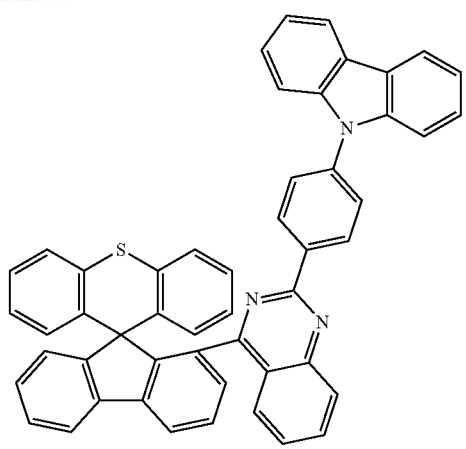
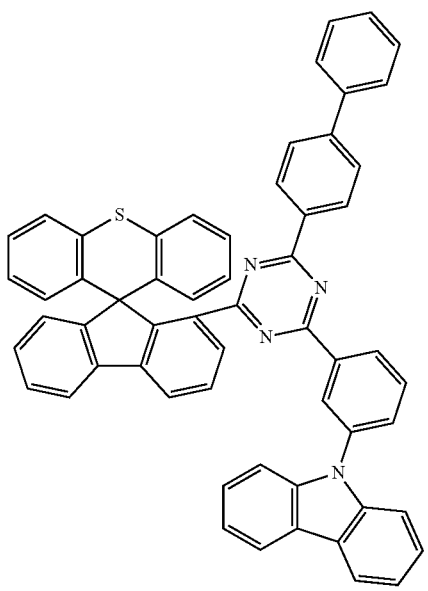
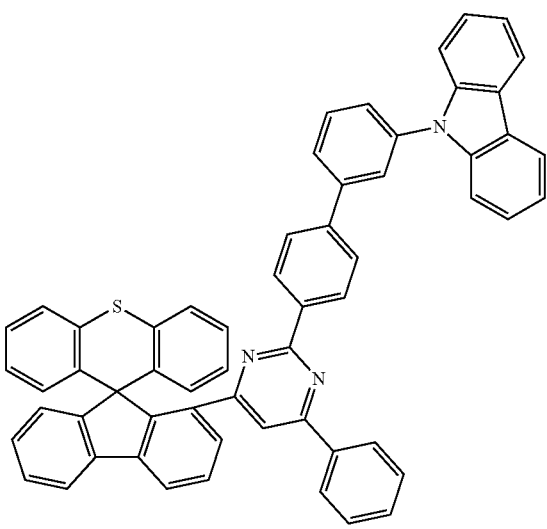

353 354
-continued
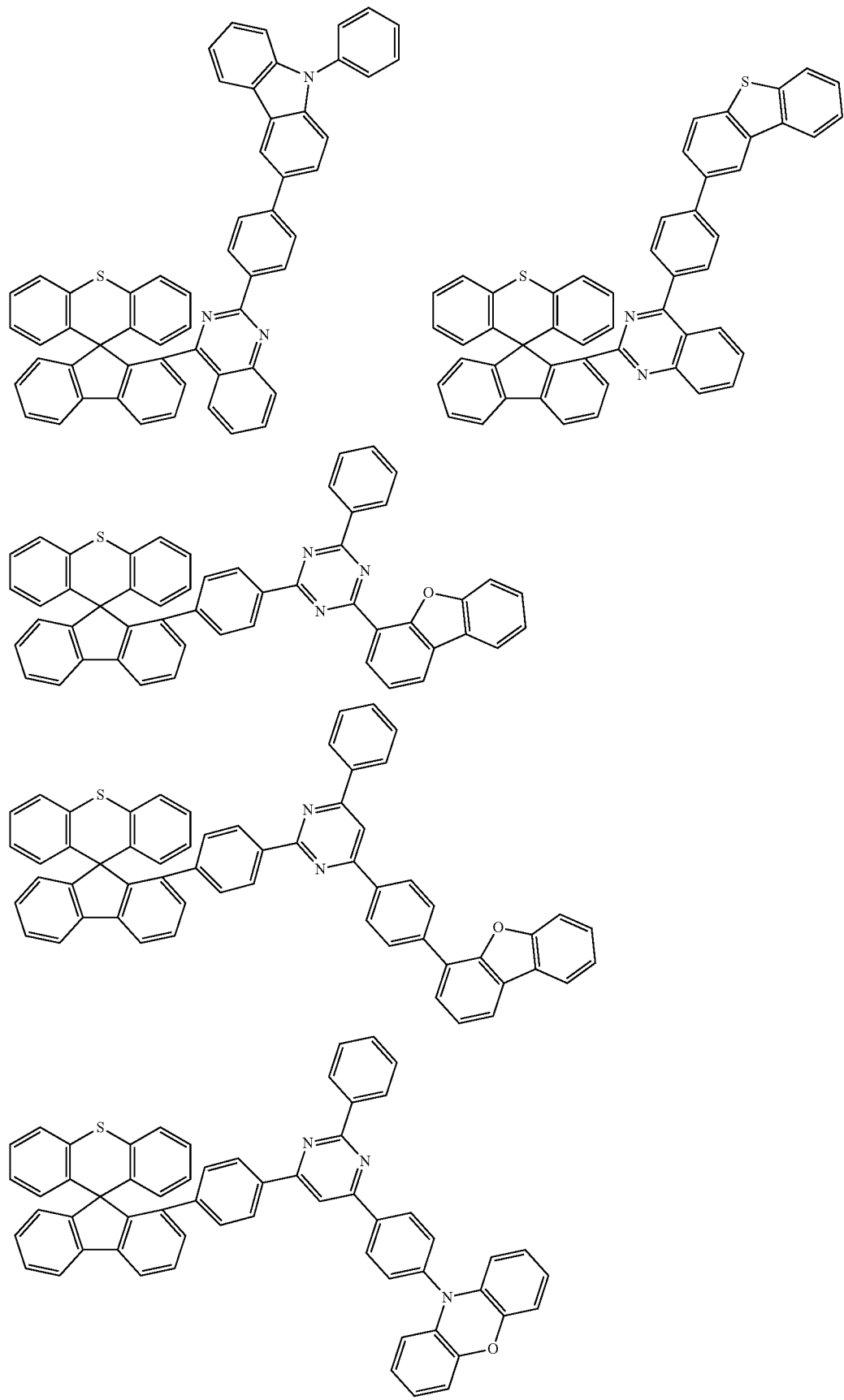

-continued
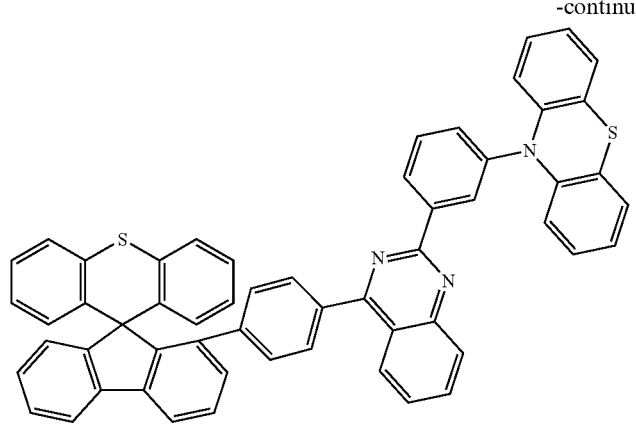
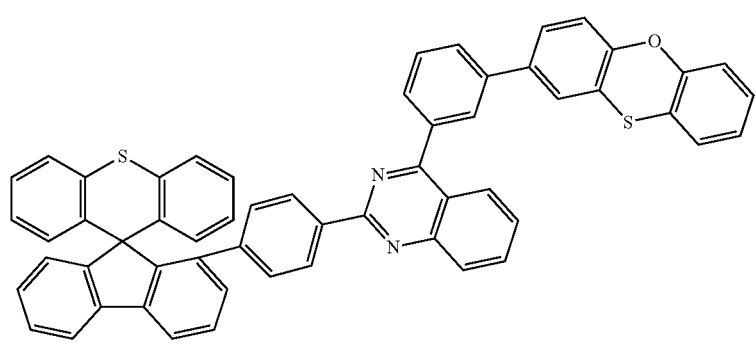
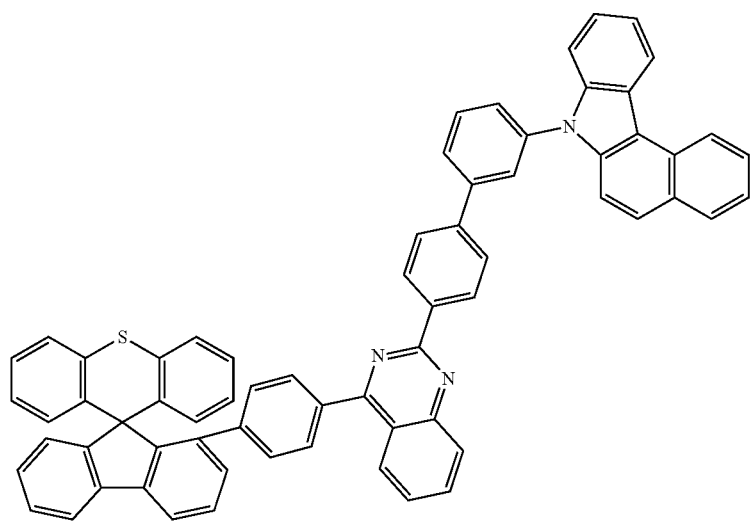

357
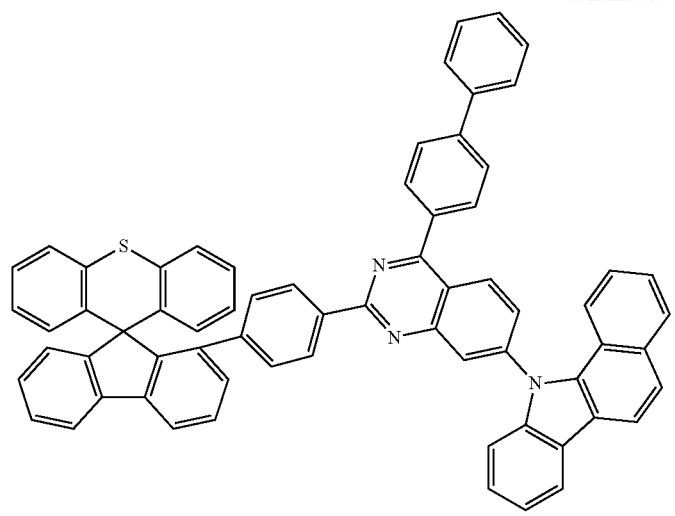
358
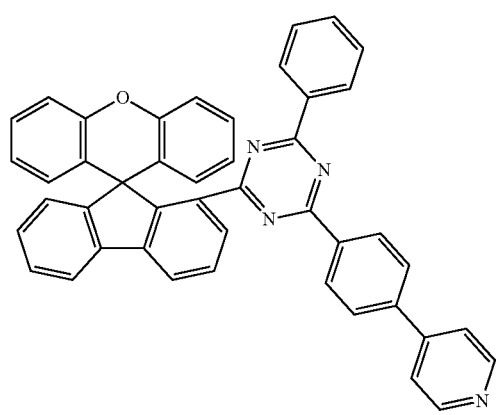
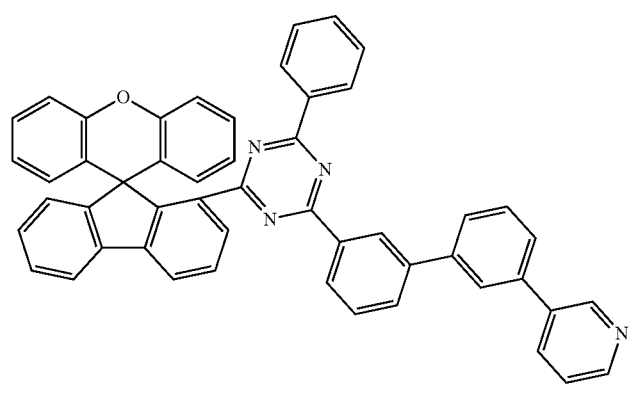
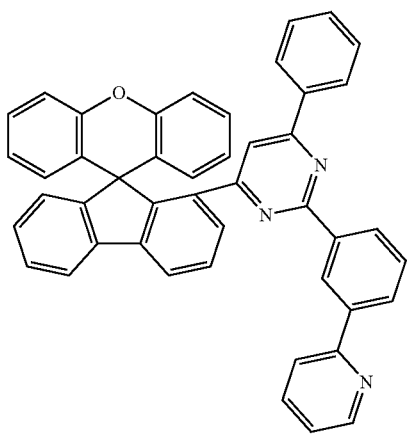
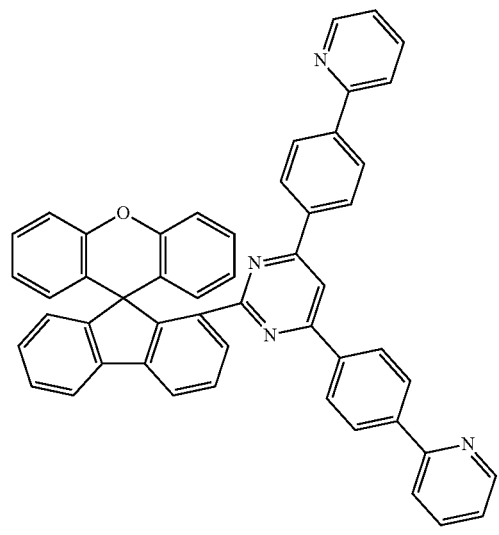
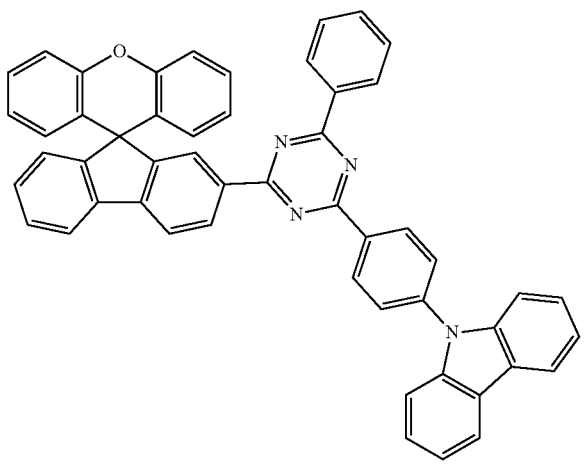

-continued
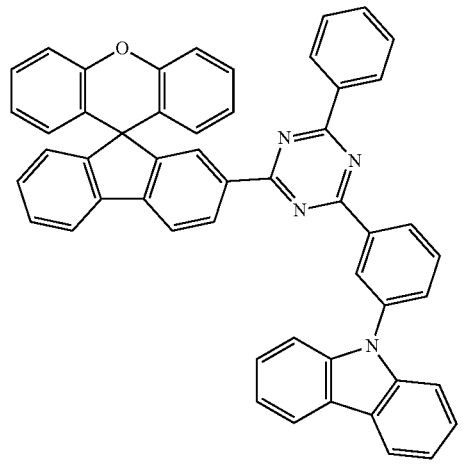
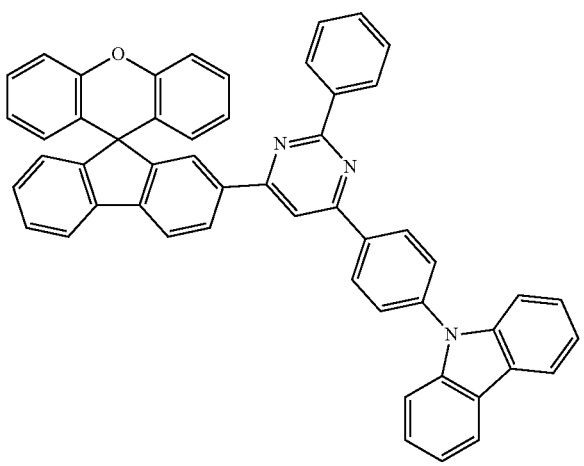
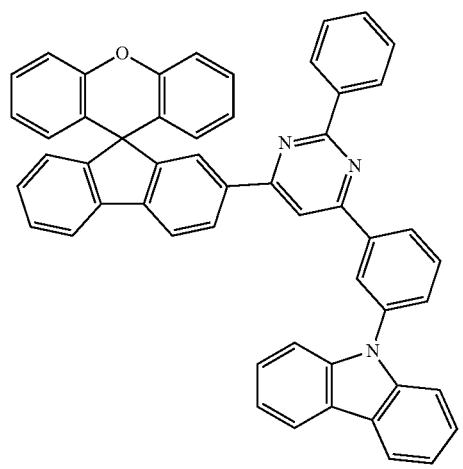
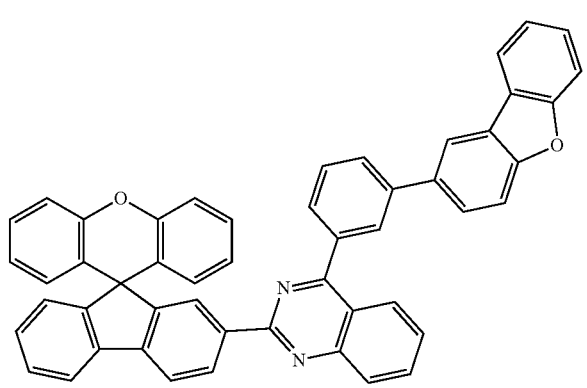
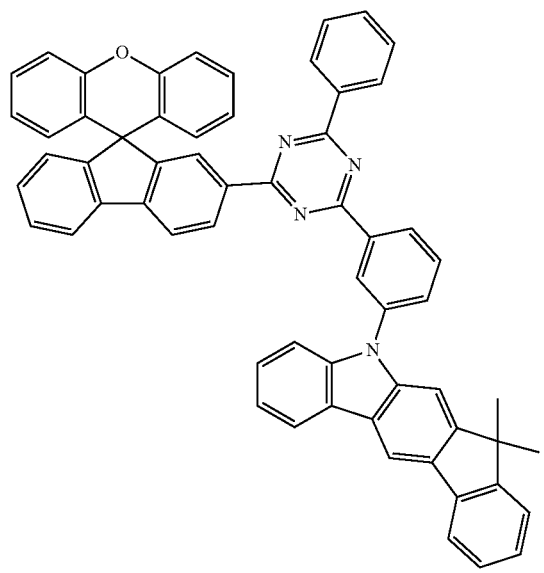
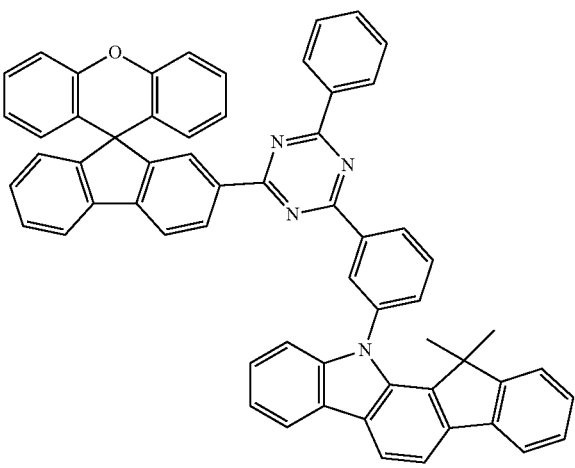

361
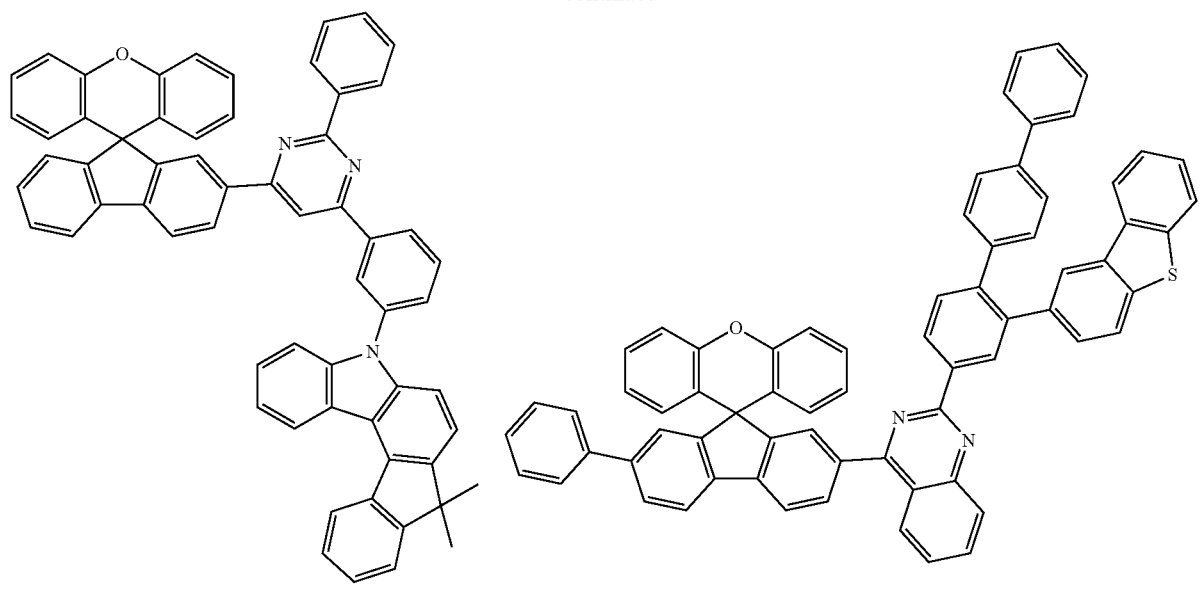
362
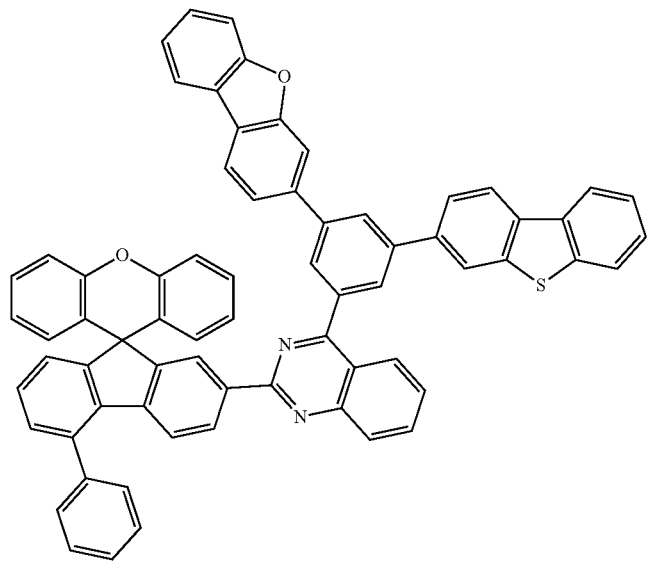
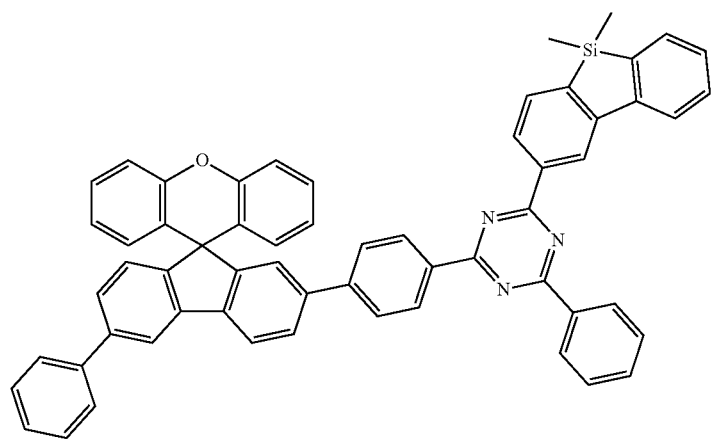

-continued
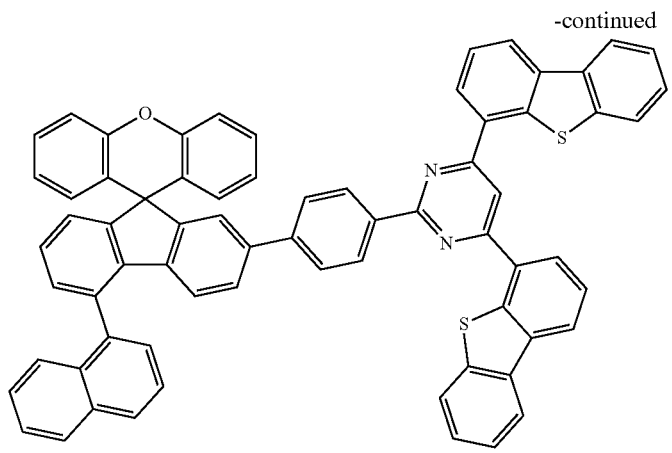
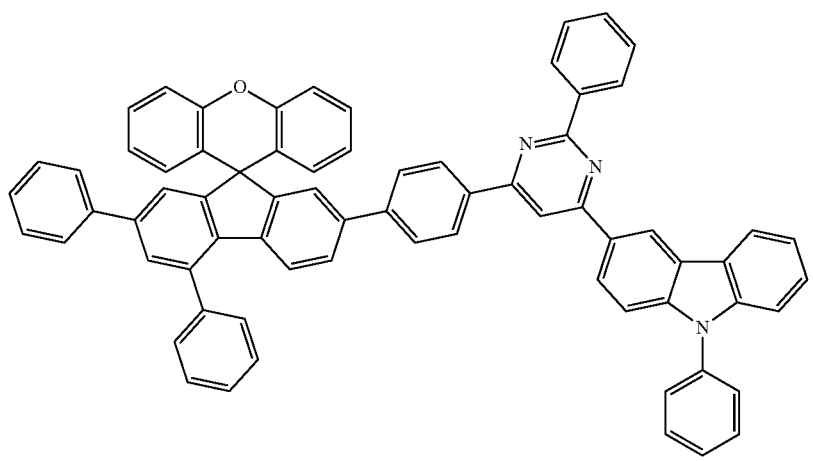
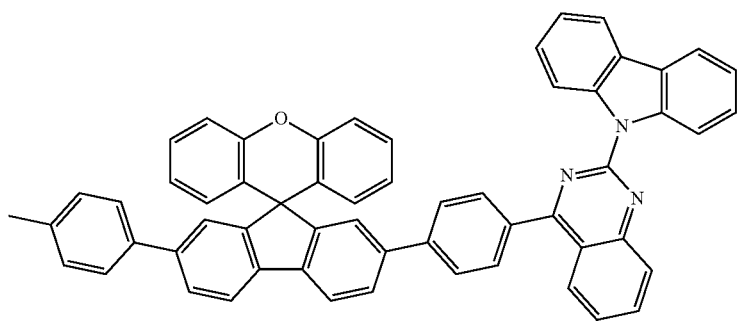
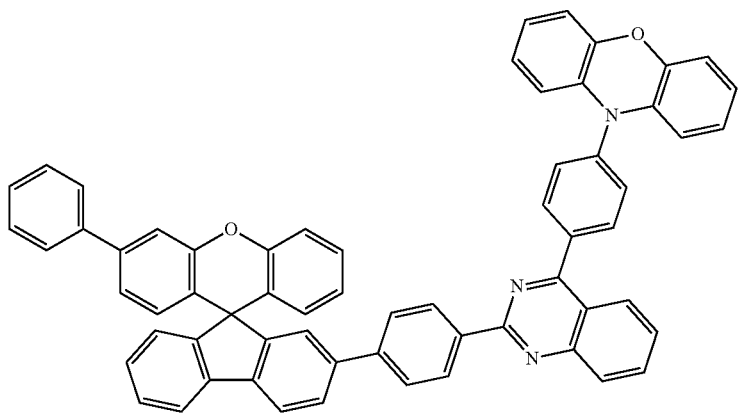

365 366
-continued
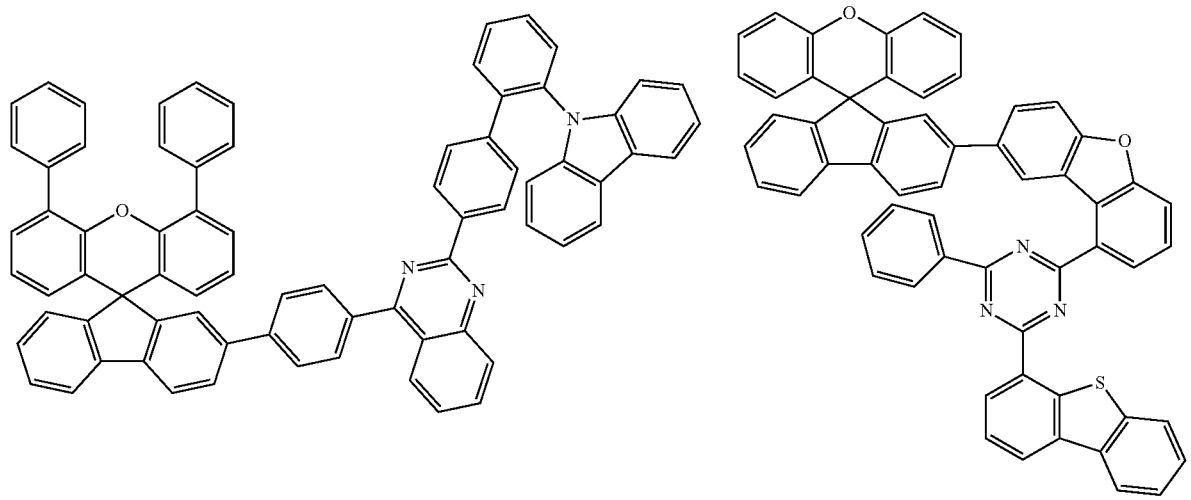
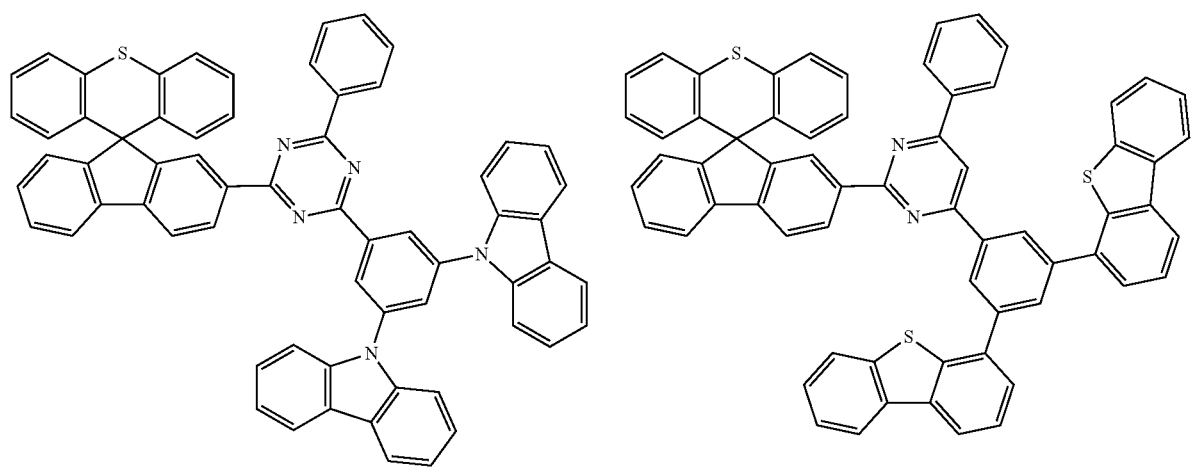
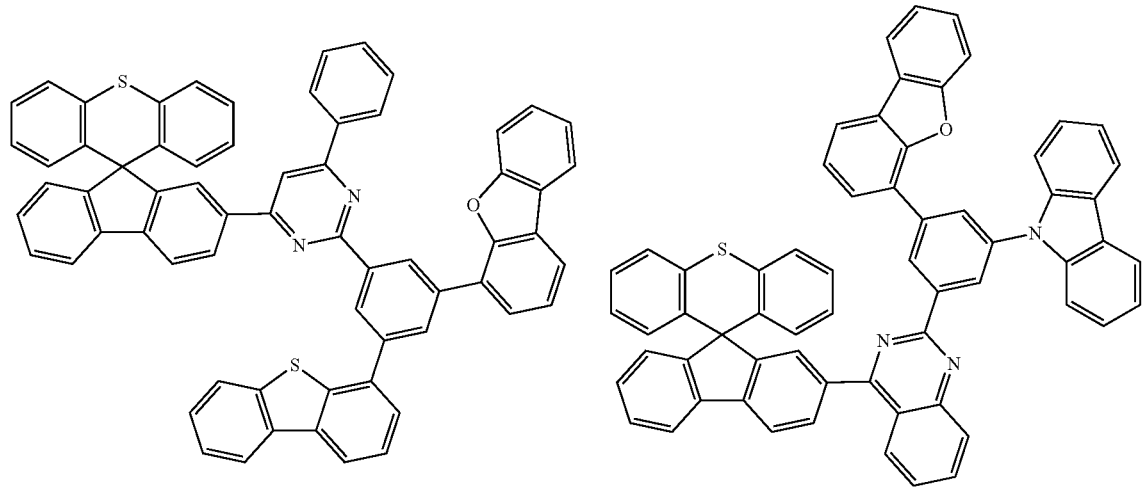

-continued
367 368
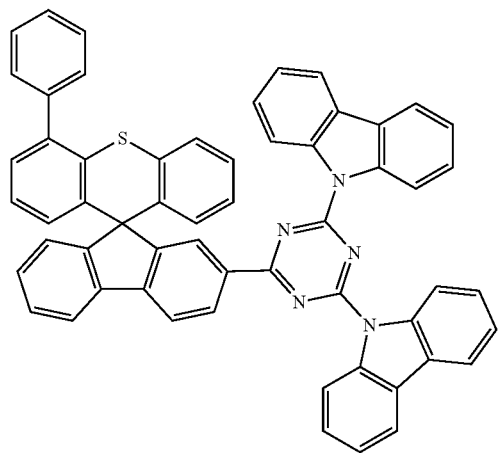 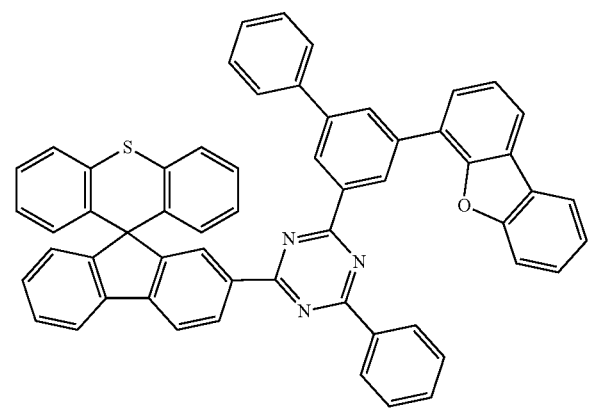
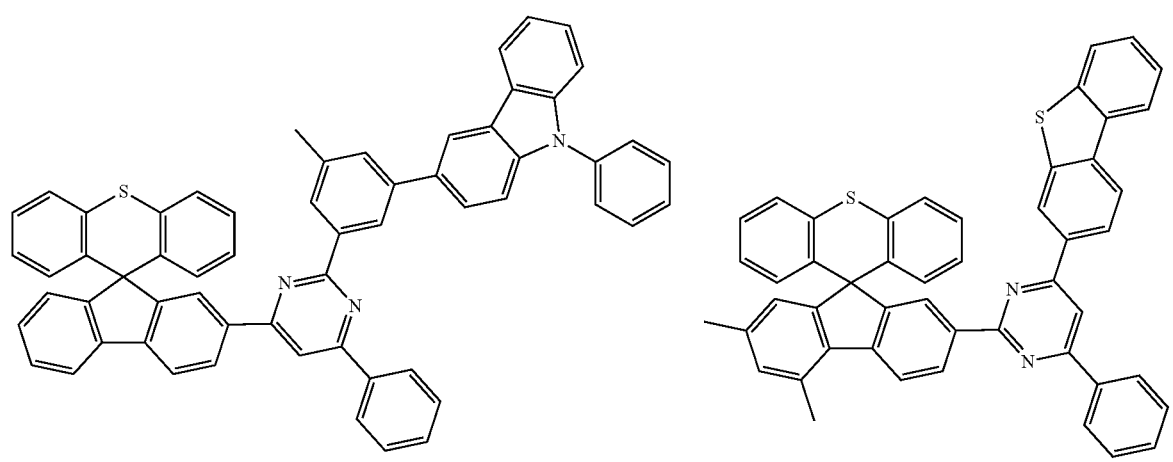
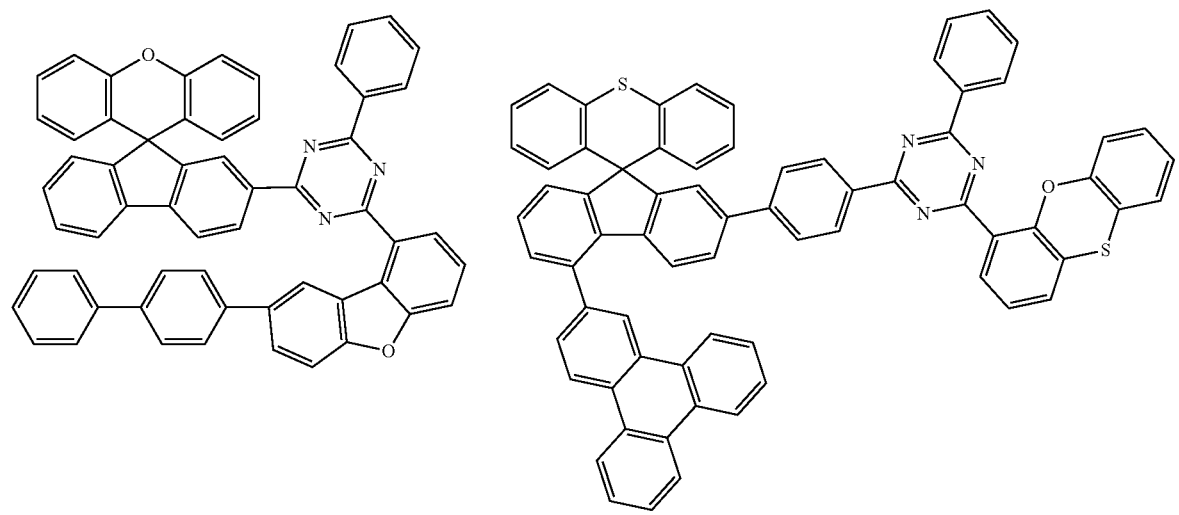

-continued
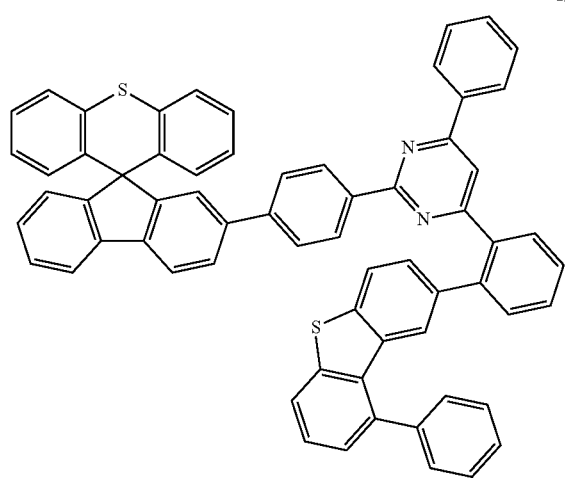
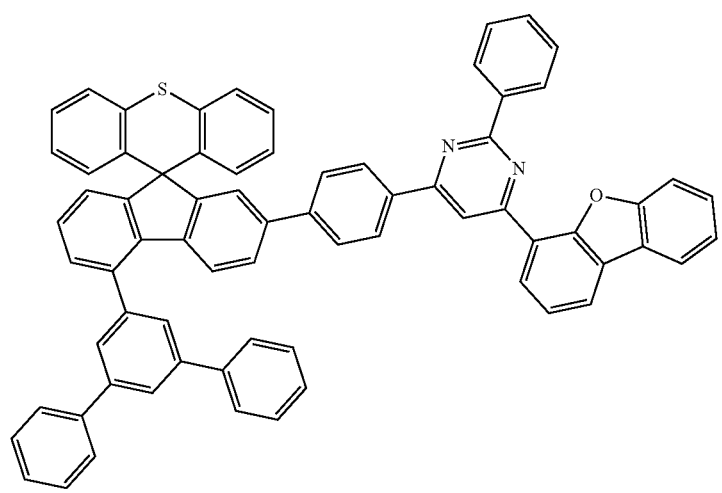
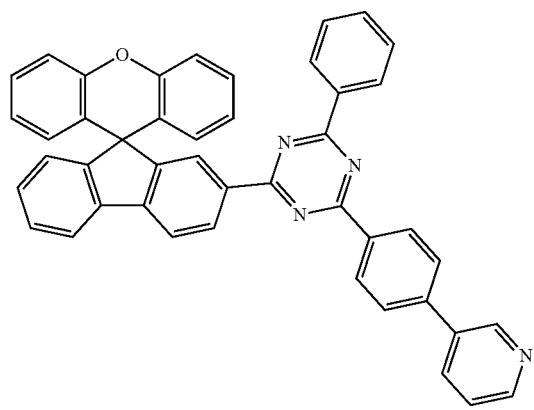
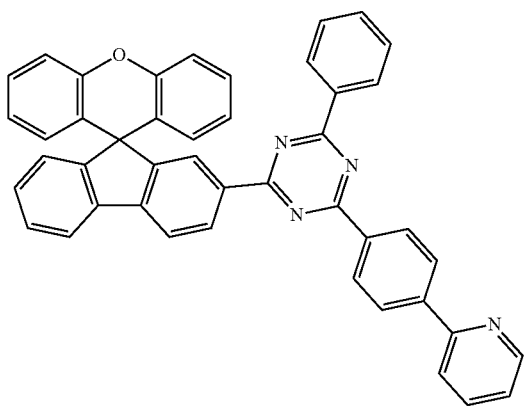

371
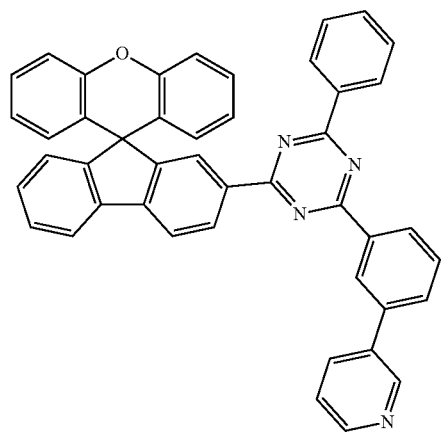
372
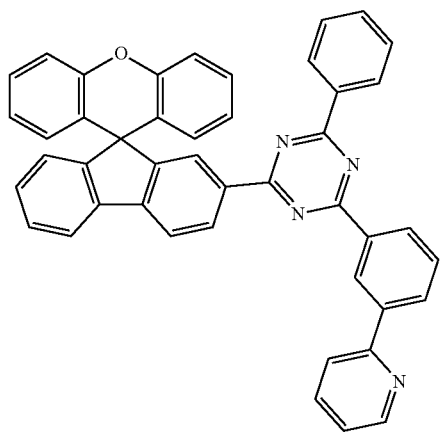
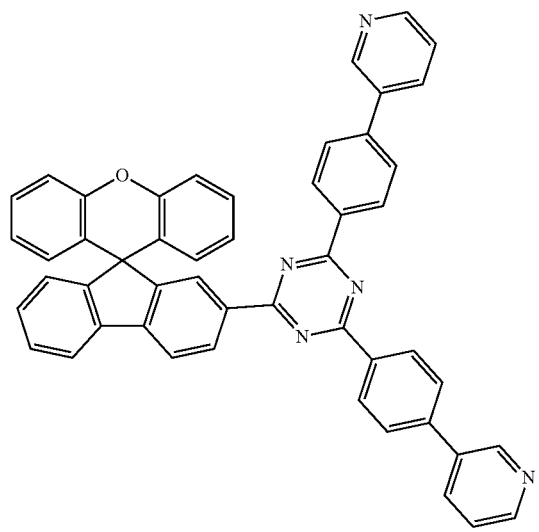
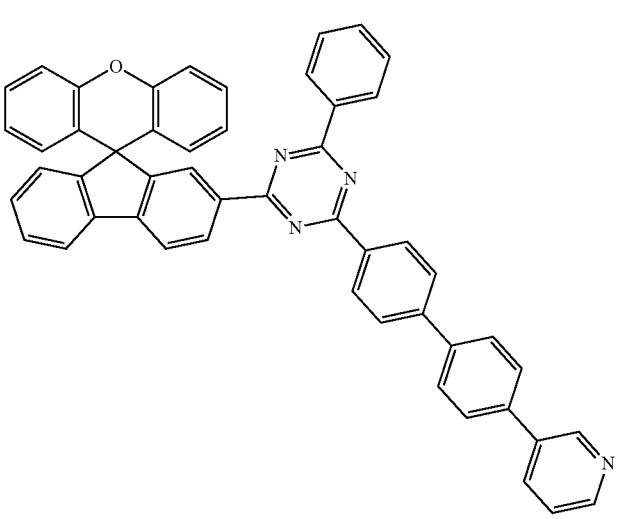
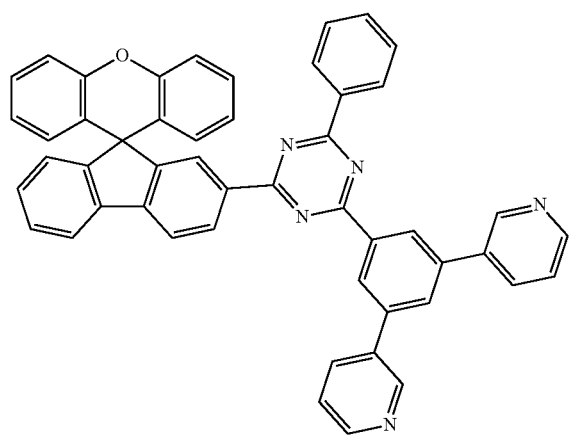
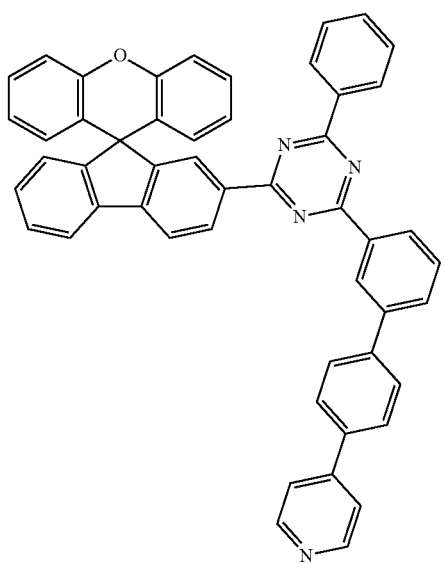

-continued
373
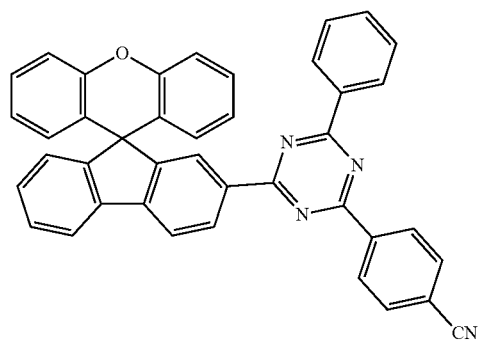
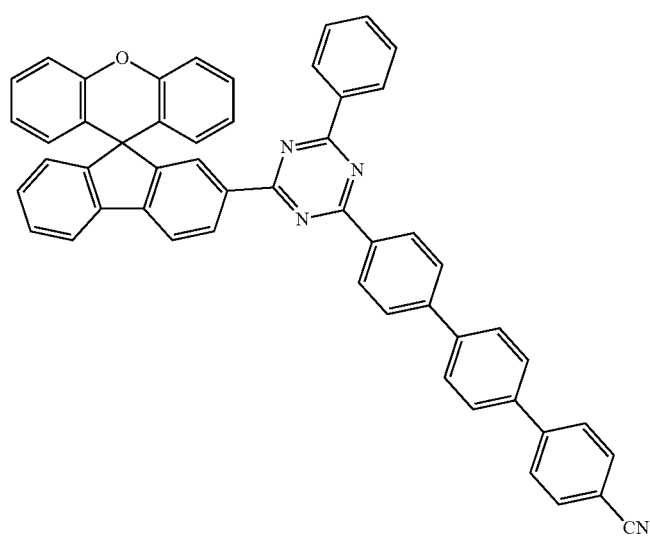
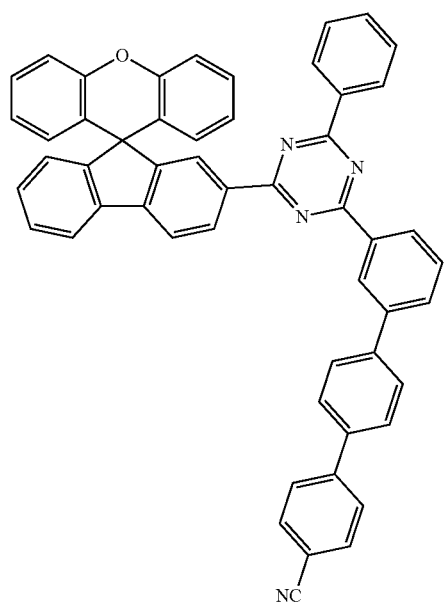
374
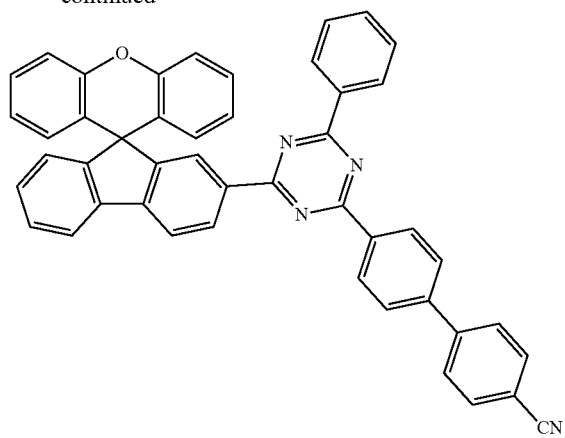
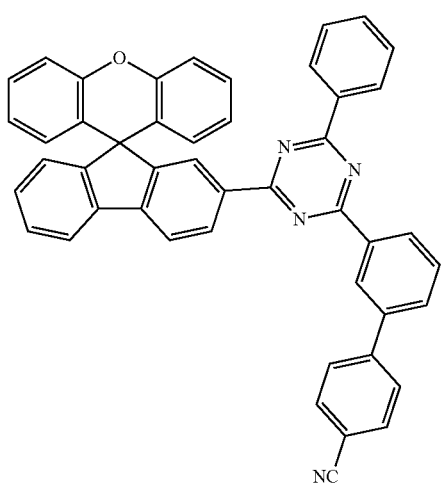
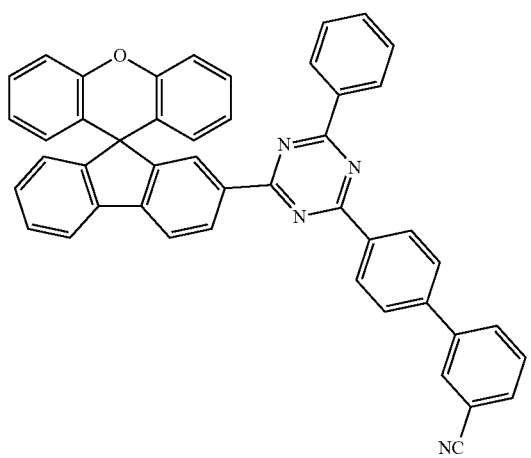

-continued
375
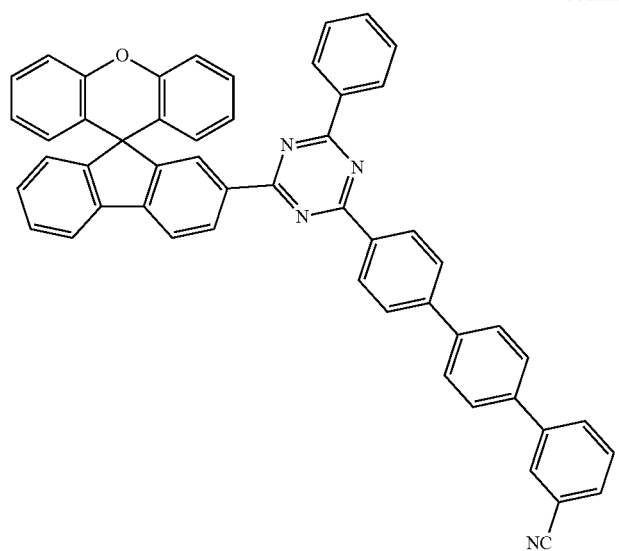
376
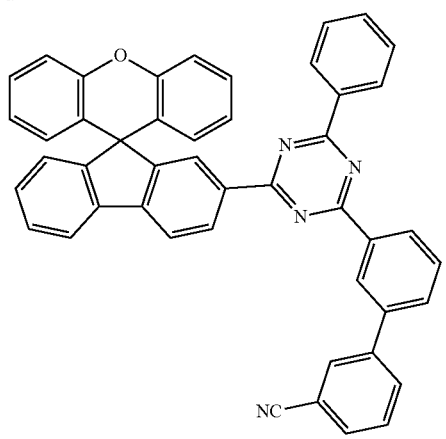
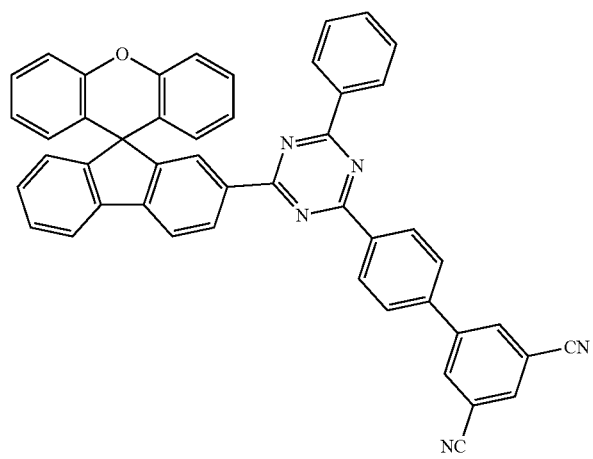
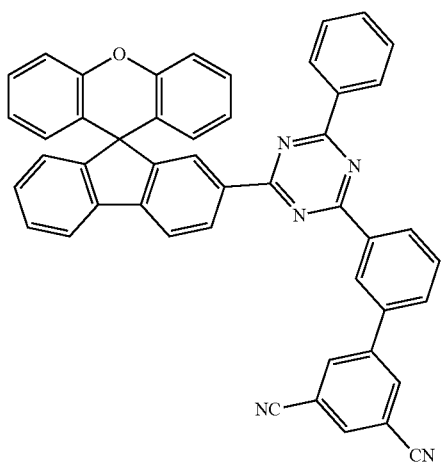
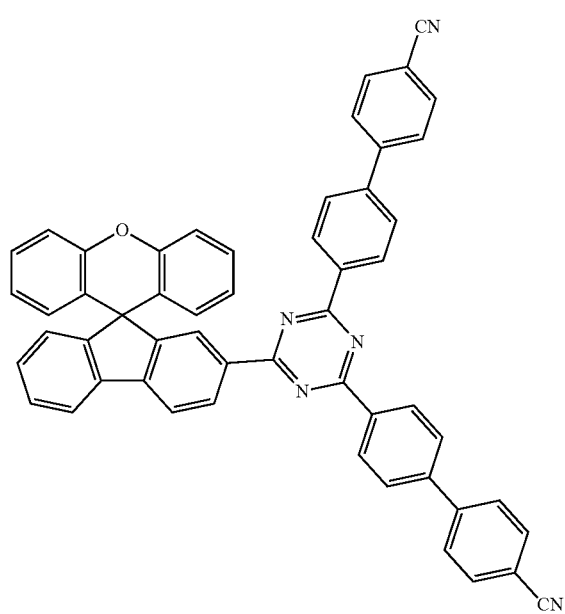
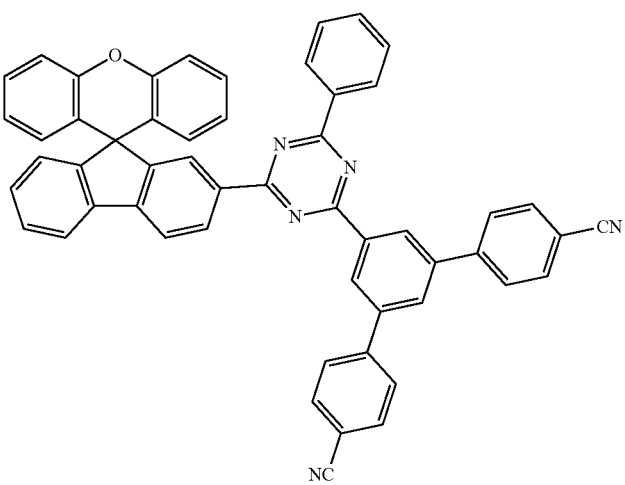

377
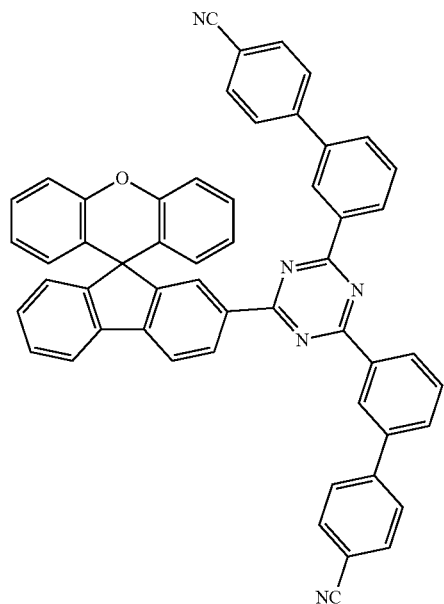
378
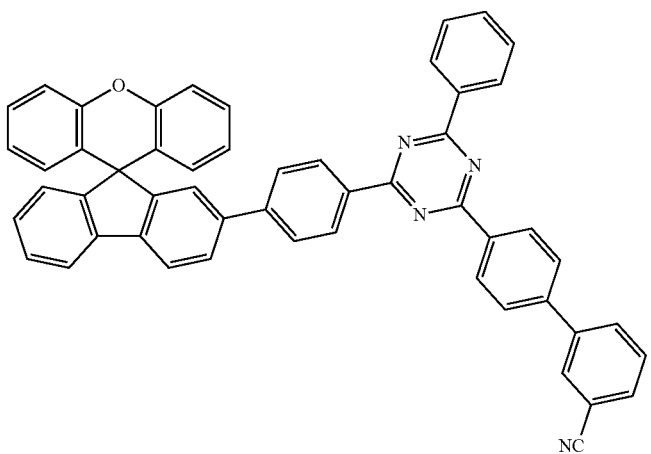
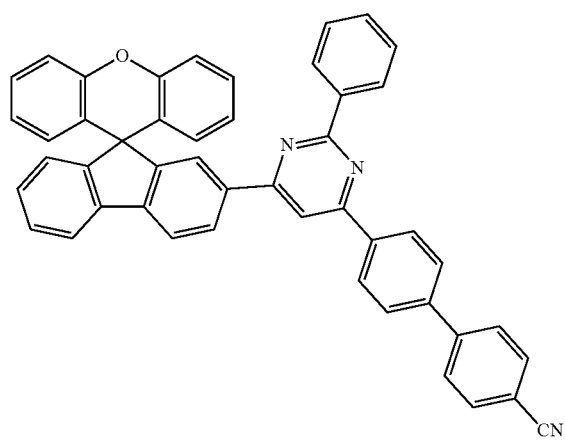
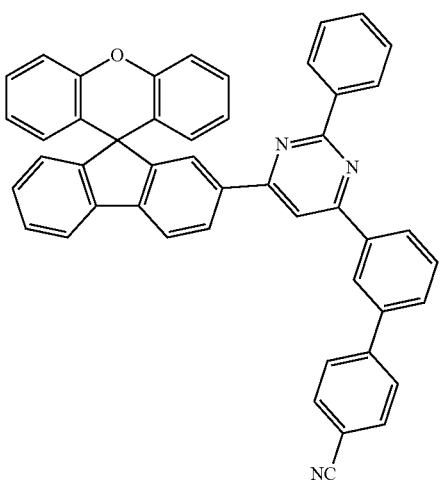
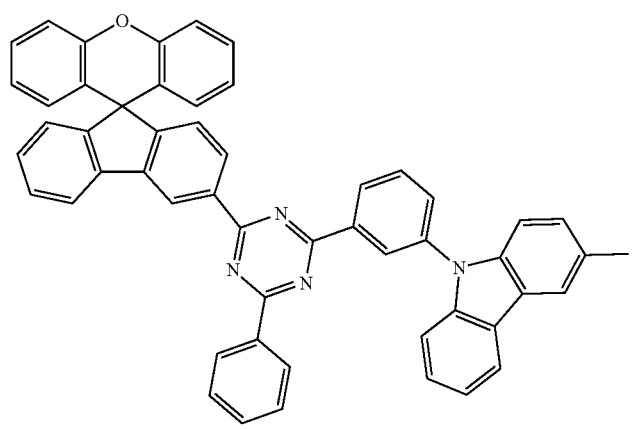
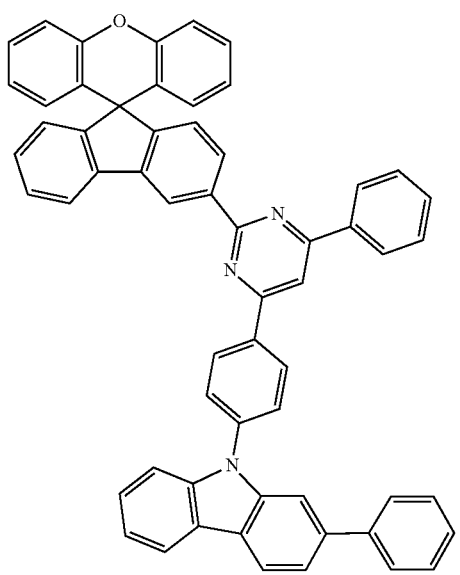

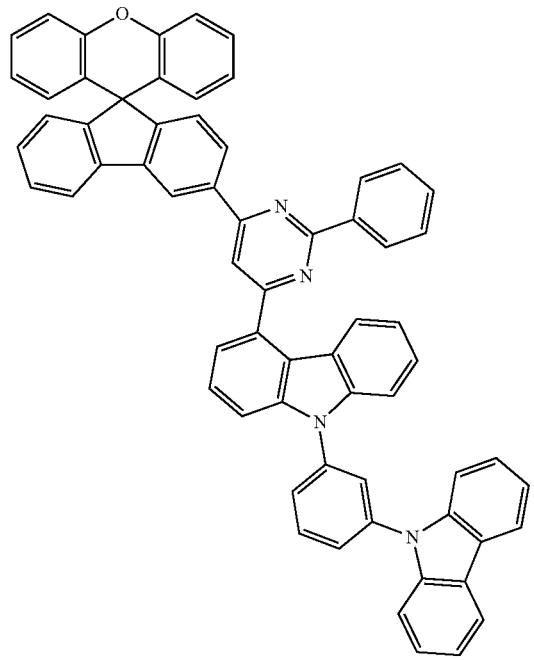
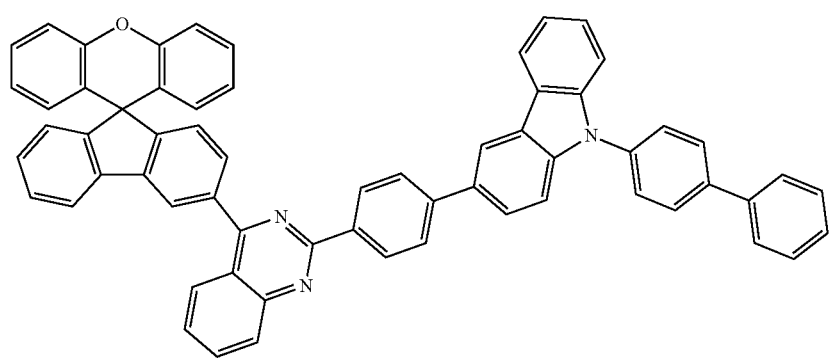
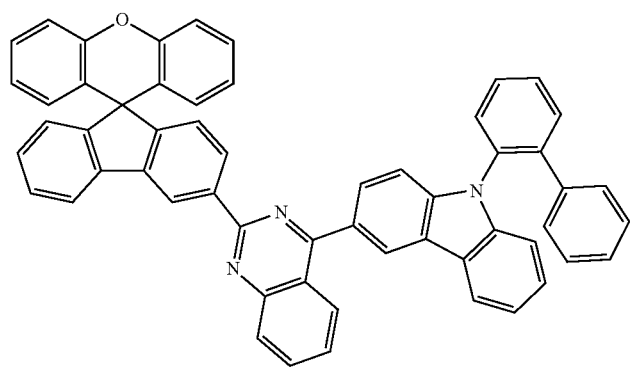

-continued
381
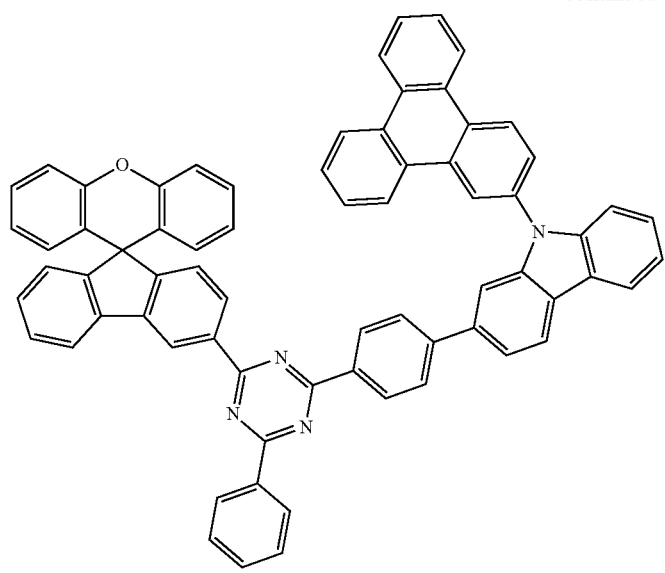
382
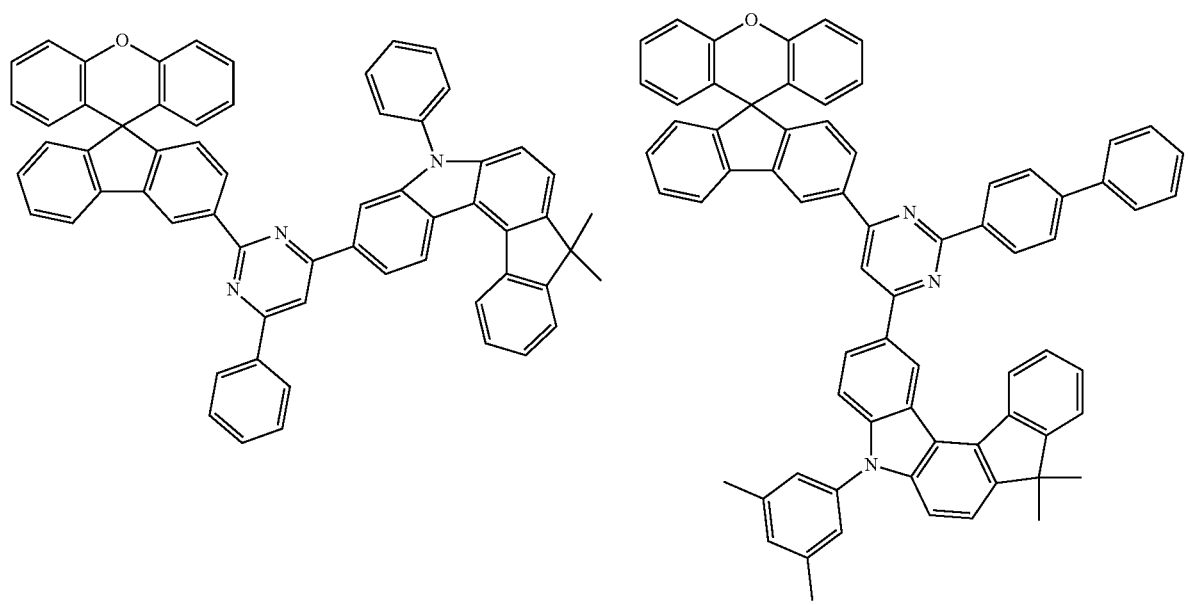
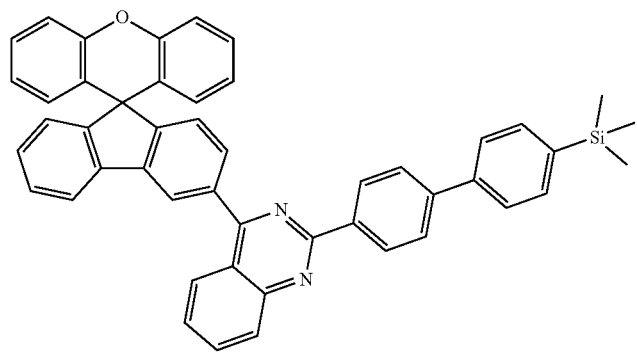

383
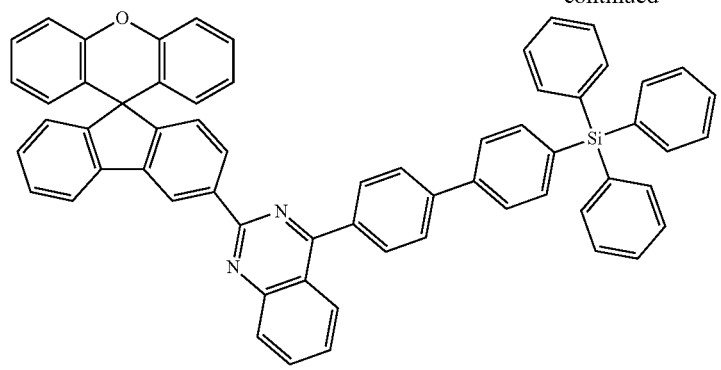
-continued
384
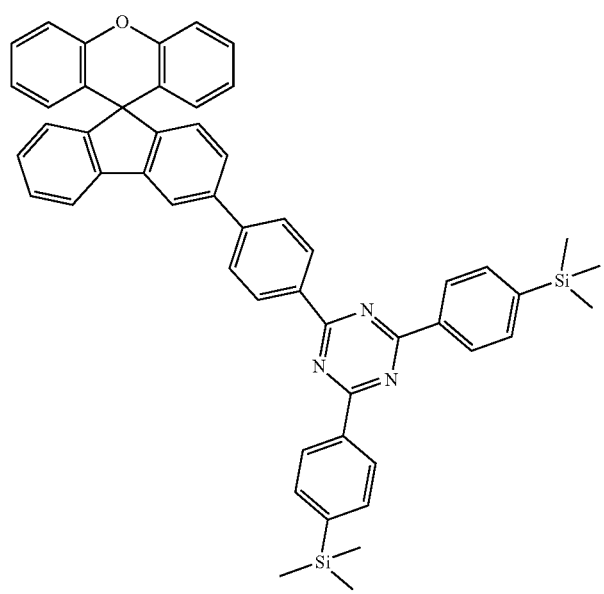
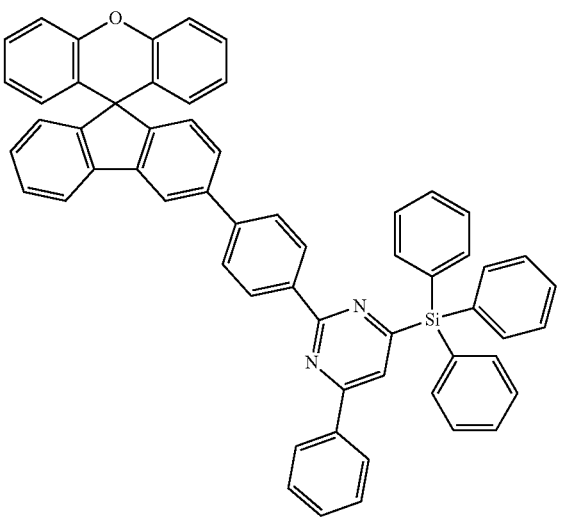
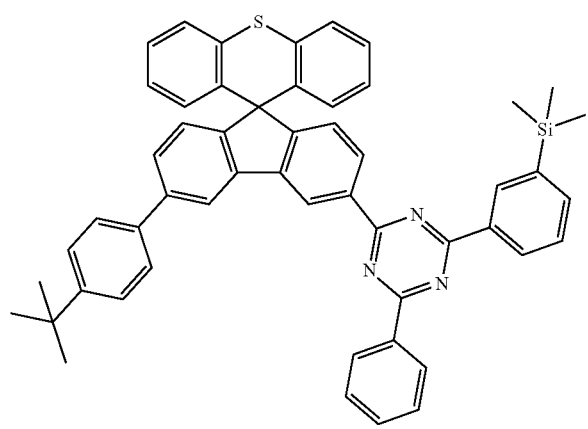

-continued
385
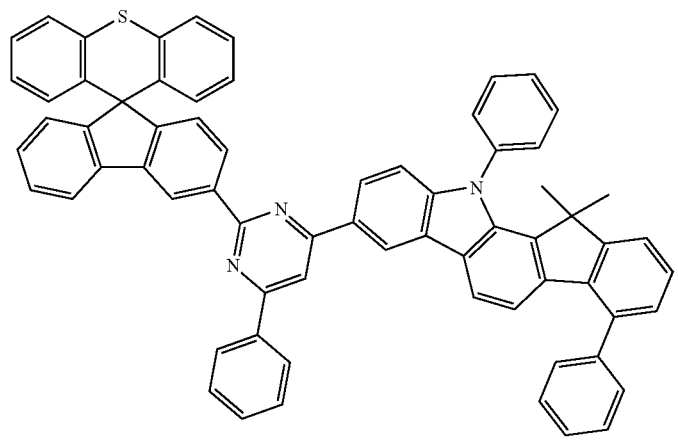
386
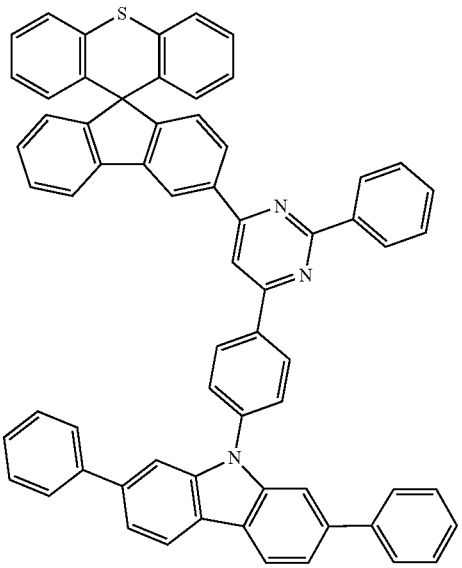
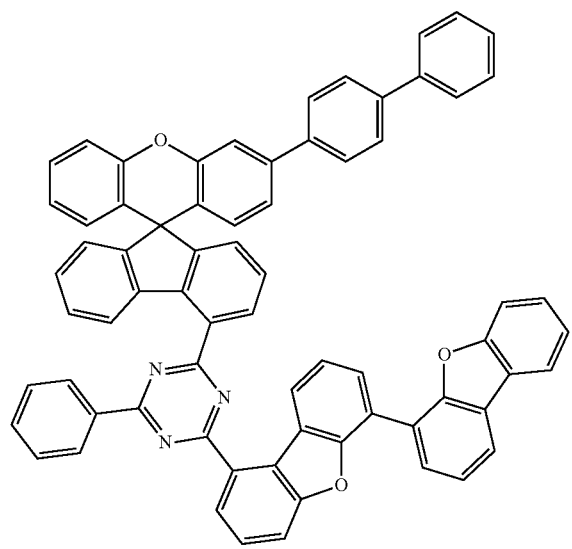
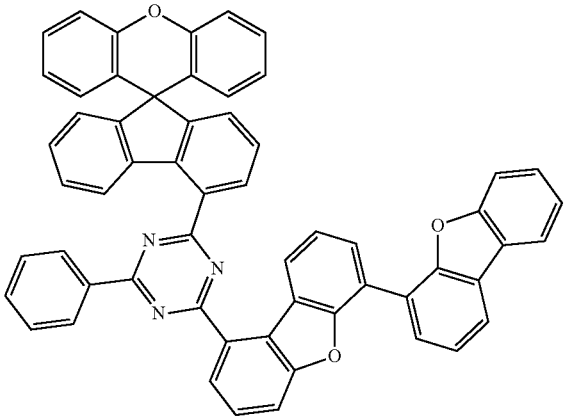
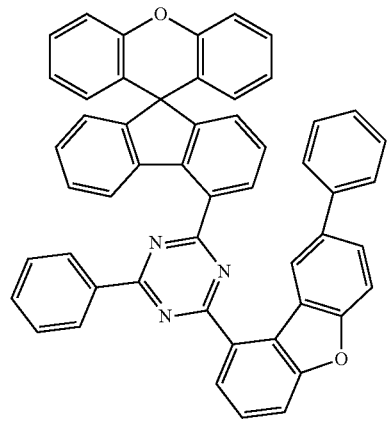
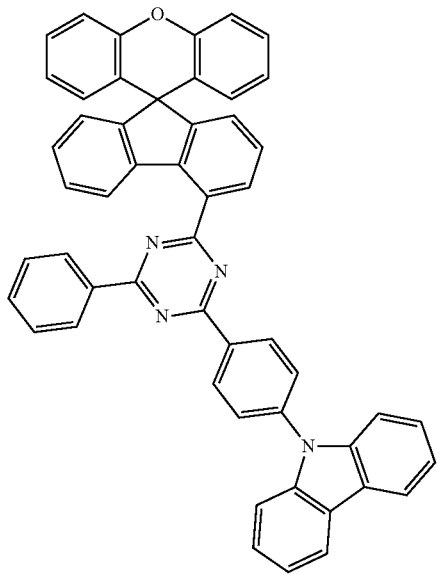

-continued
387
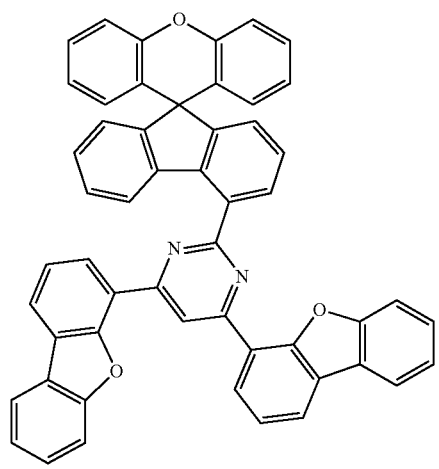
388
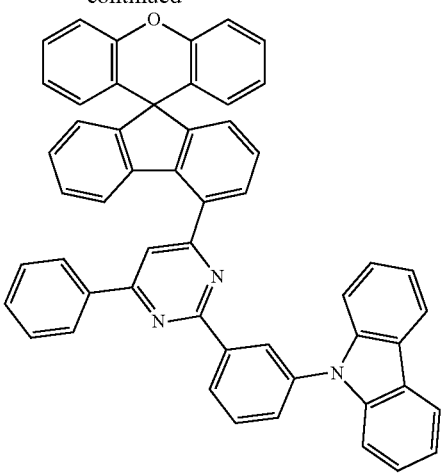
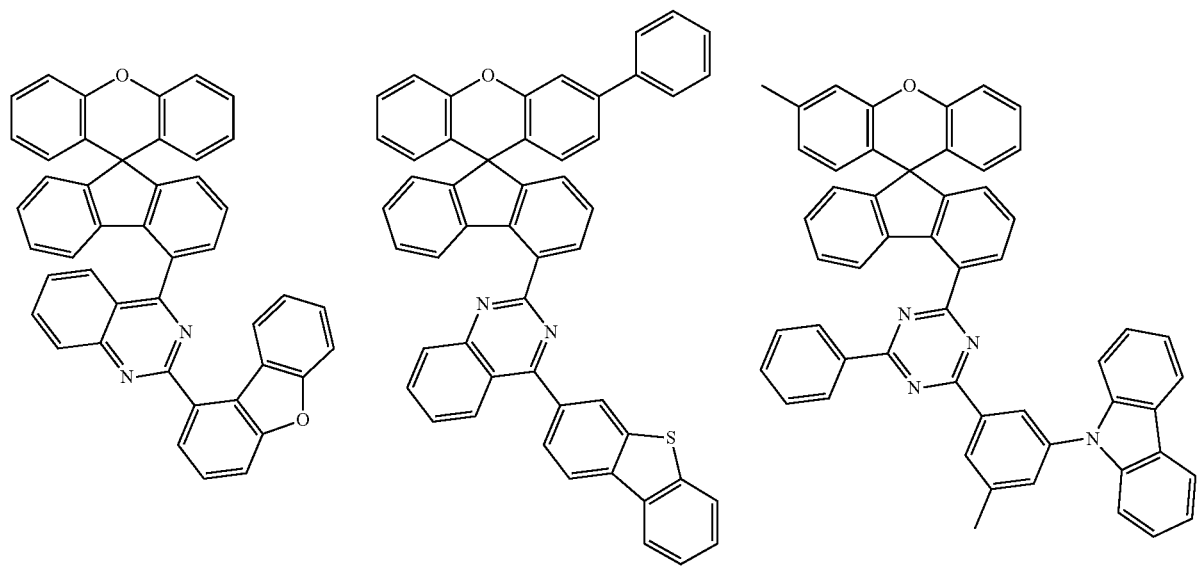
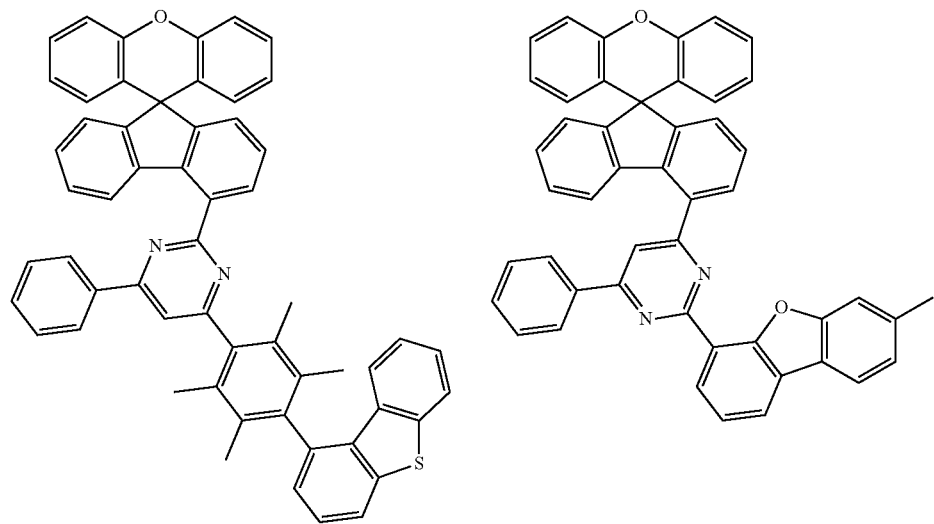

389
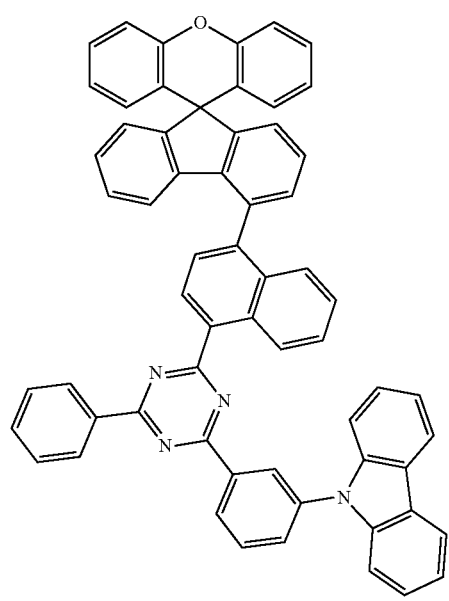
390
-continued
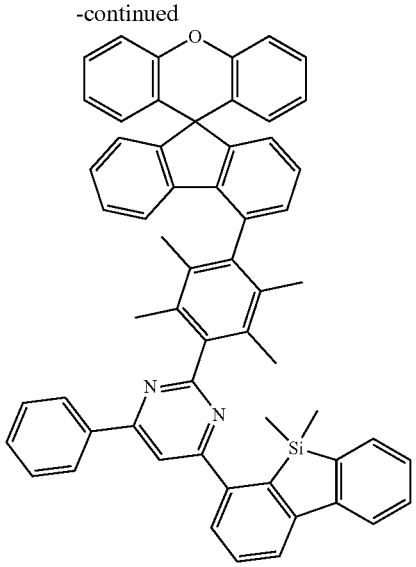
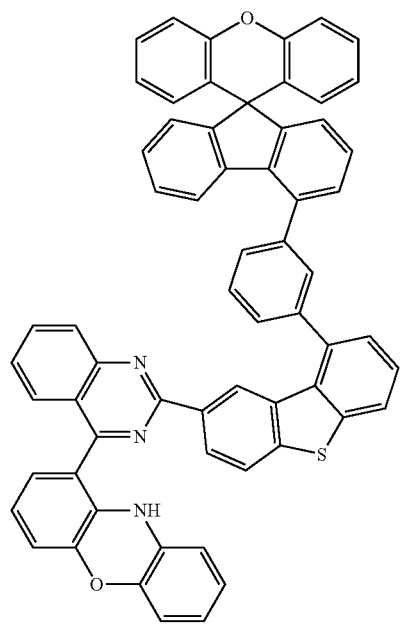
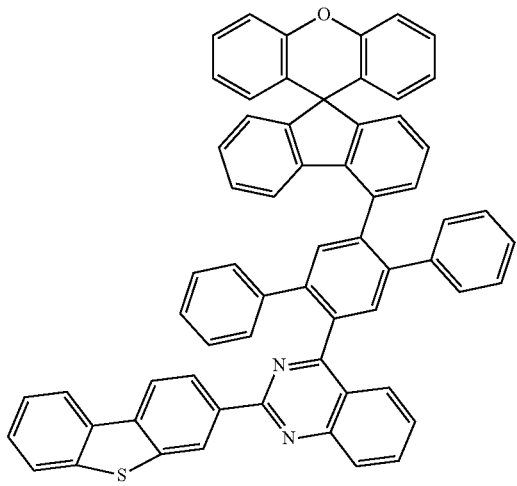

391
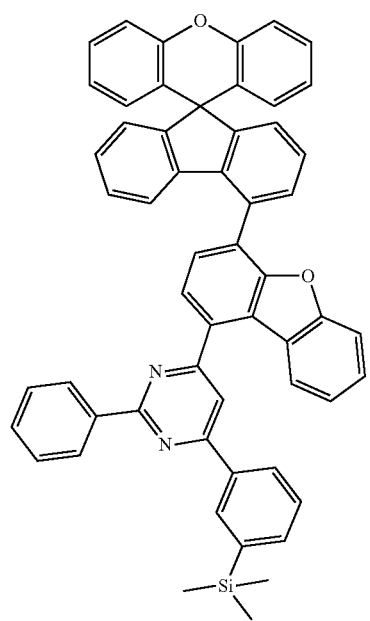
-continued
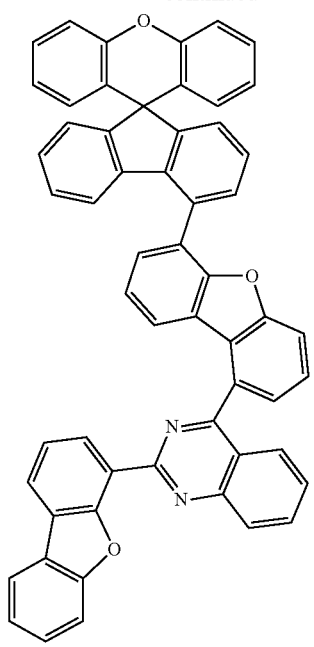
392
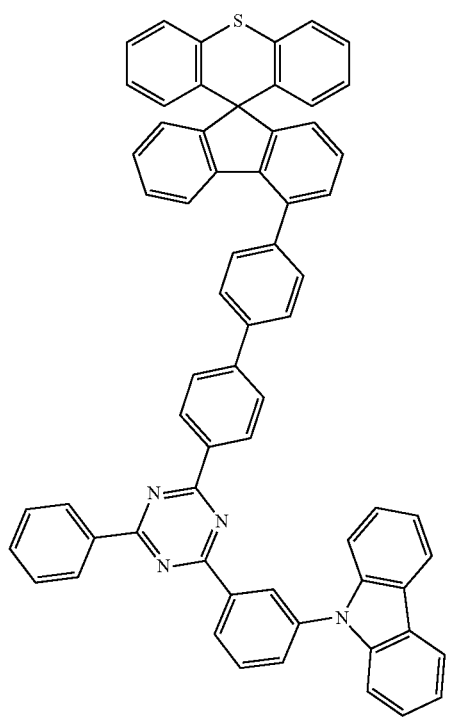
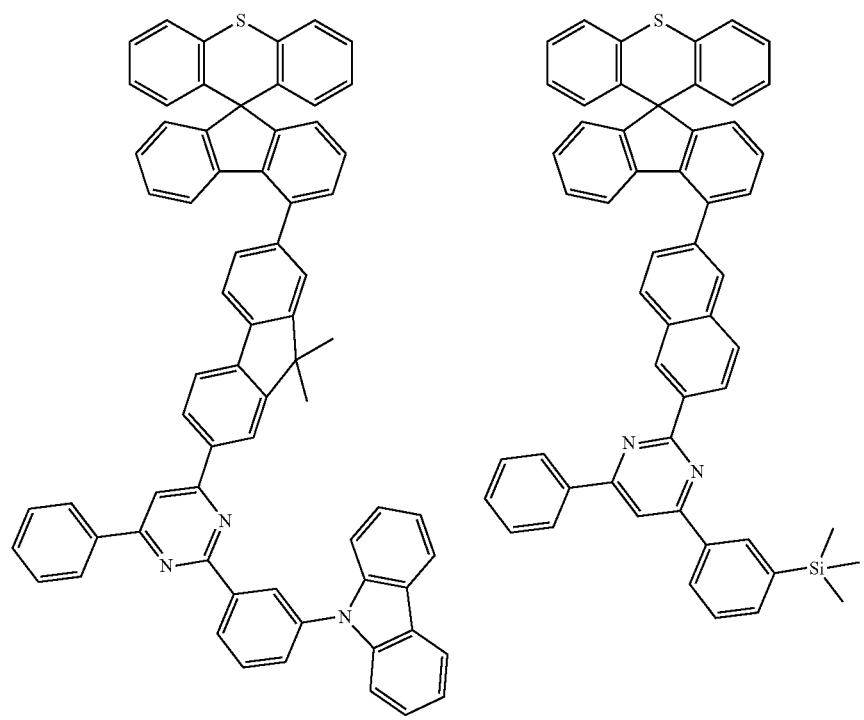

393
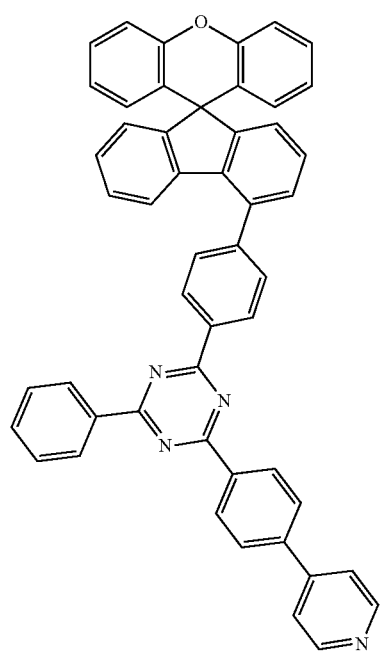
-continued
394
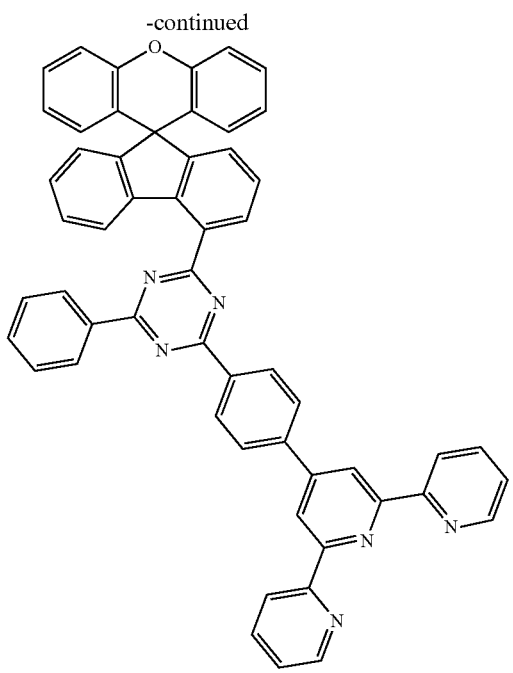
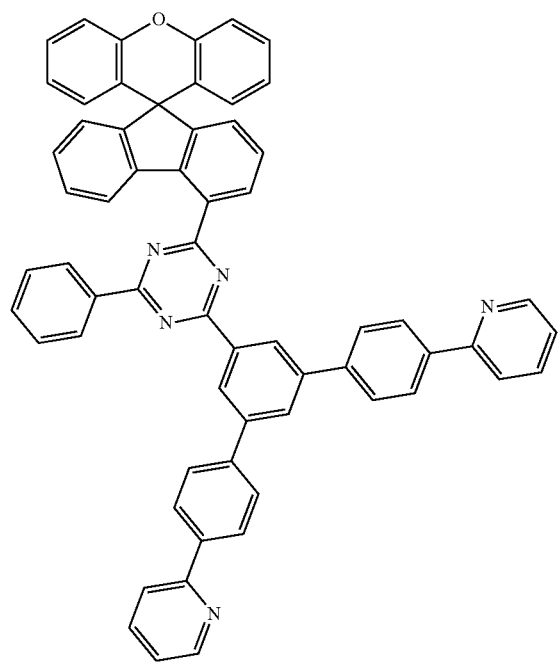
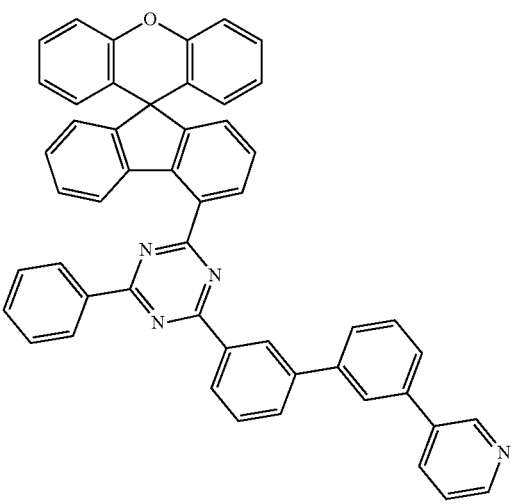

395
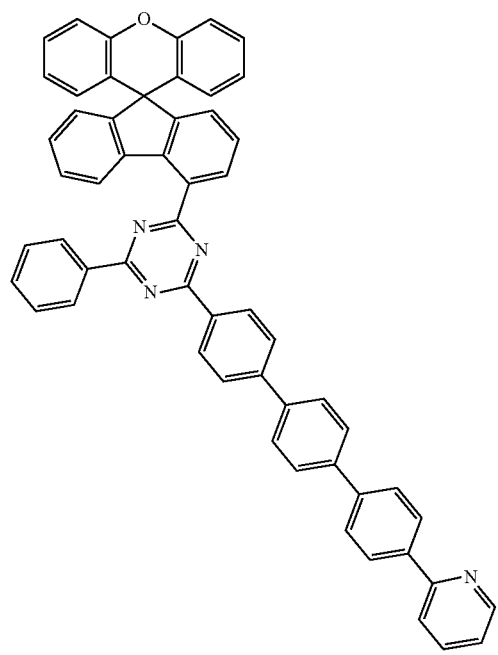
396
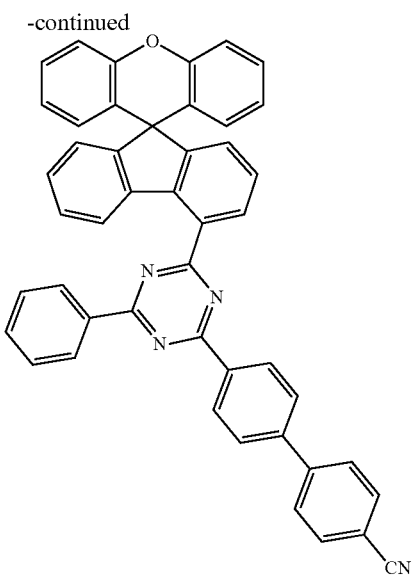
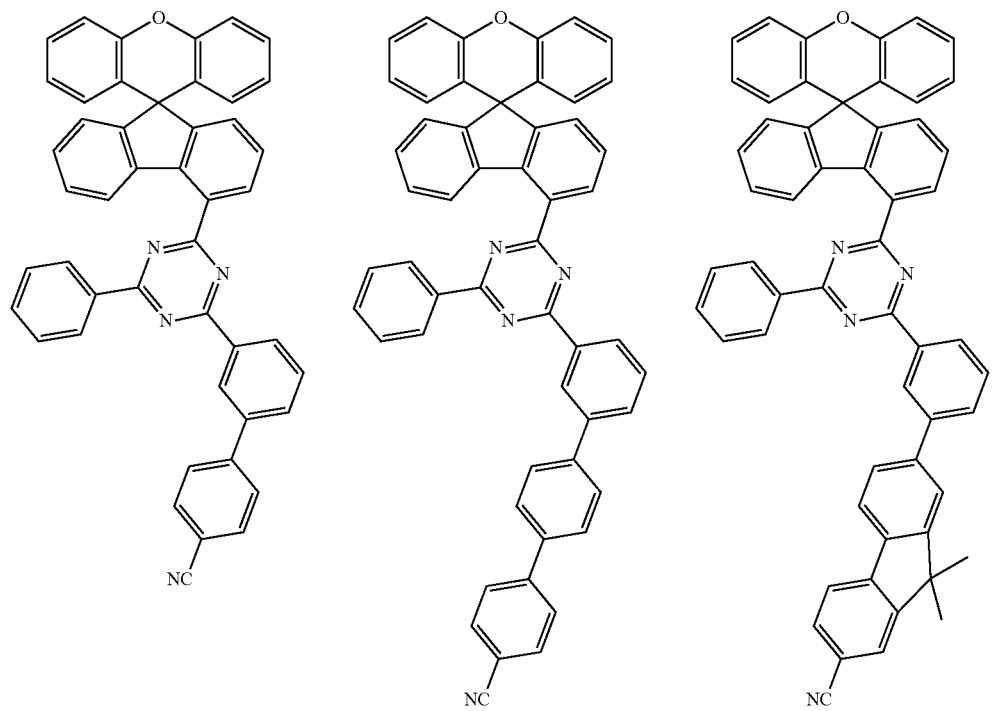

397
398
-continued
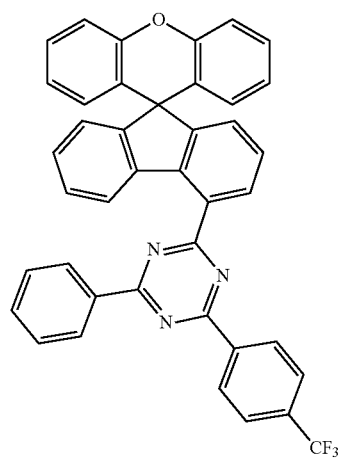
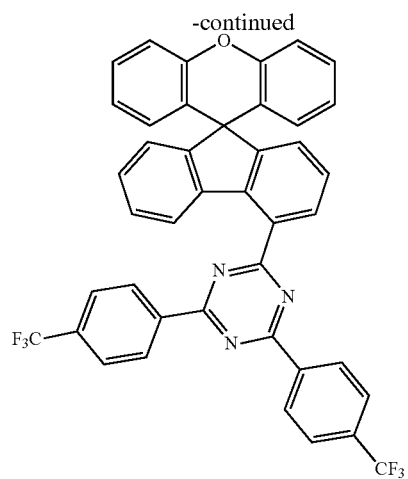
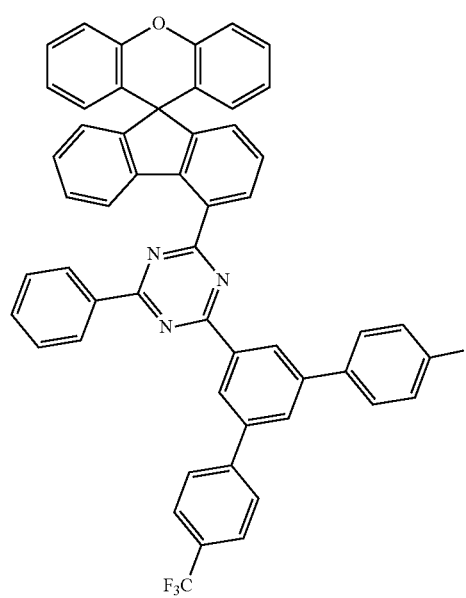
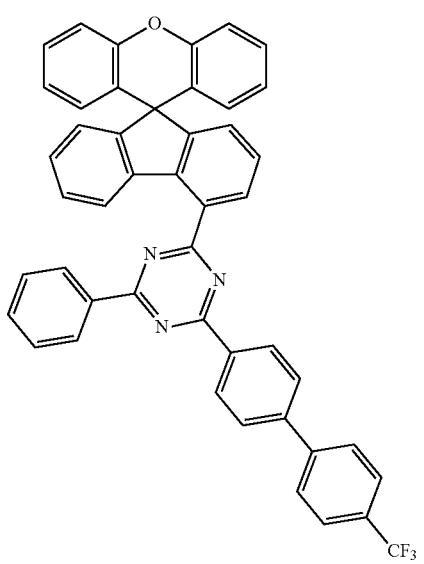
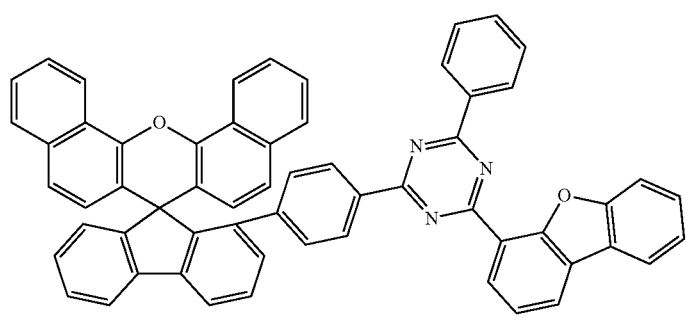

399 400
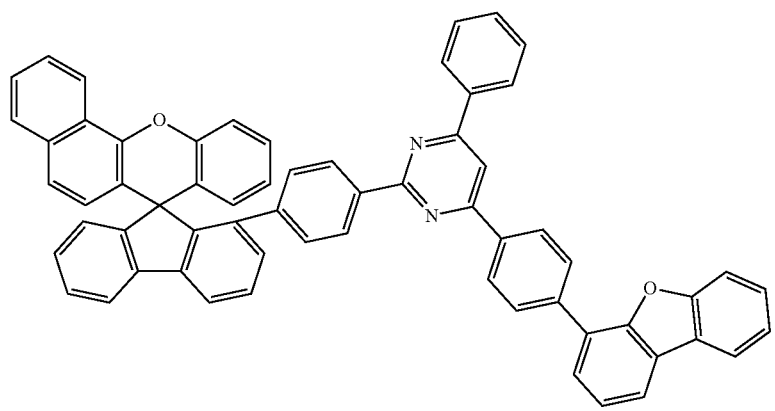
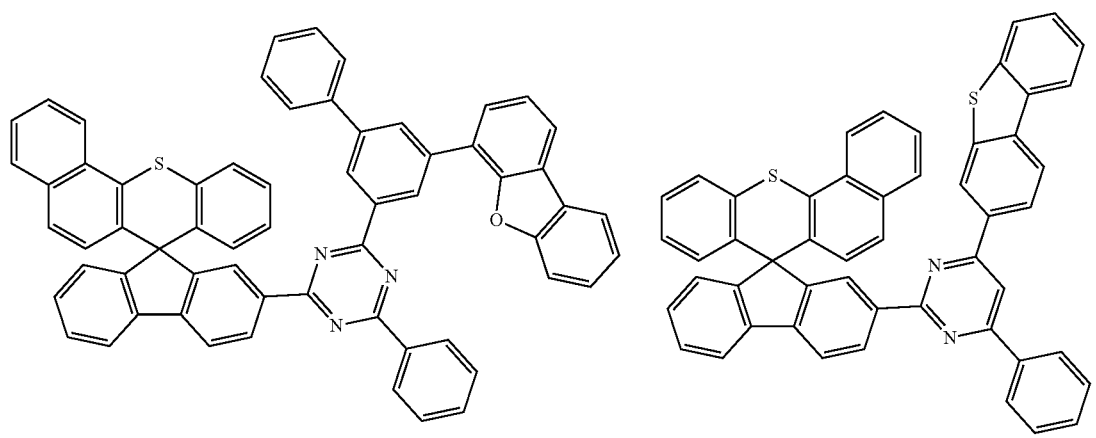
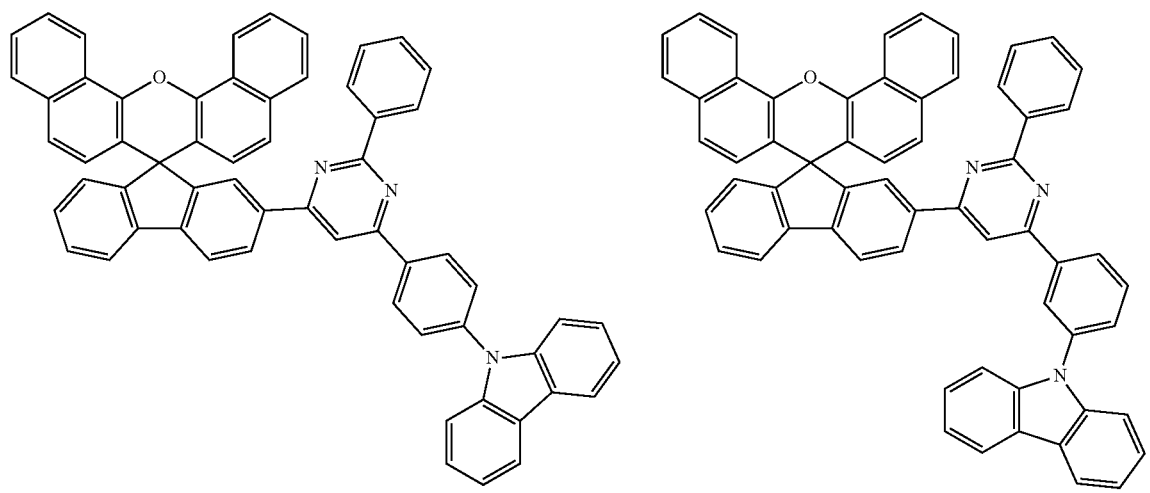

-continued
401
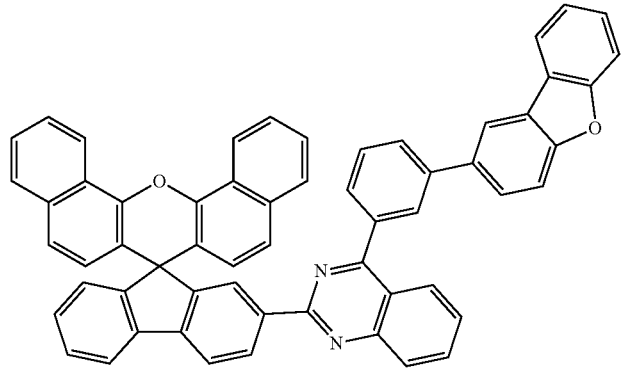
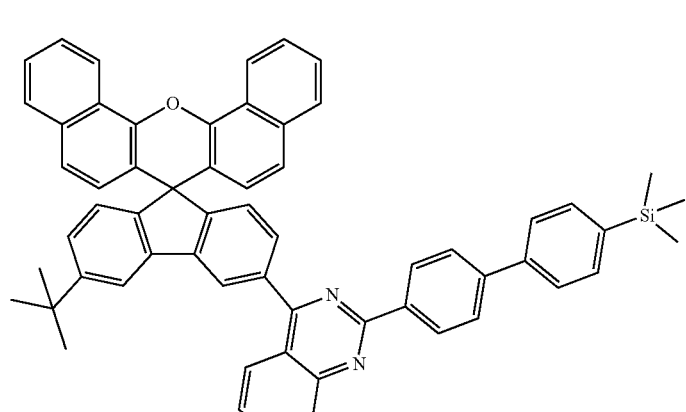
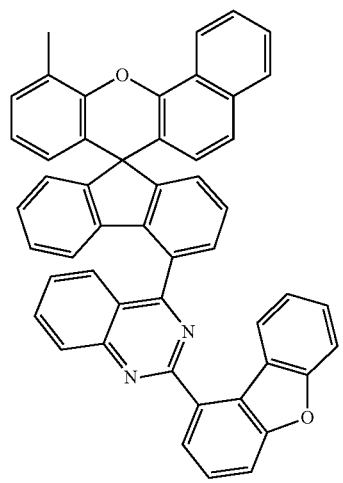
402
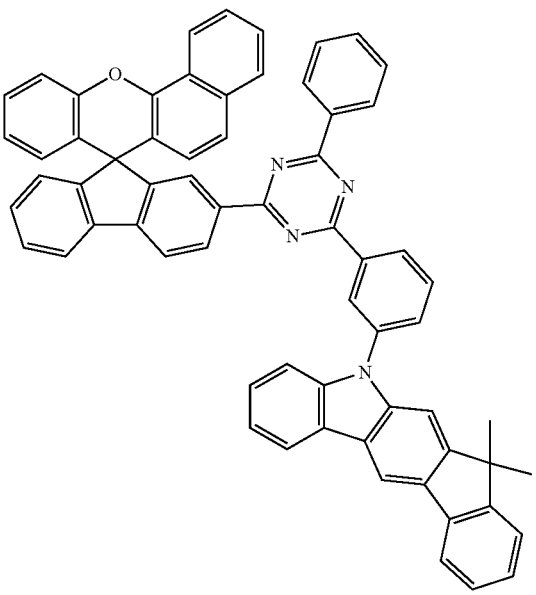
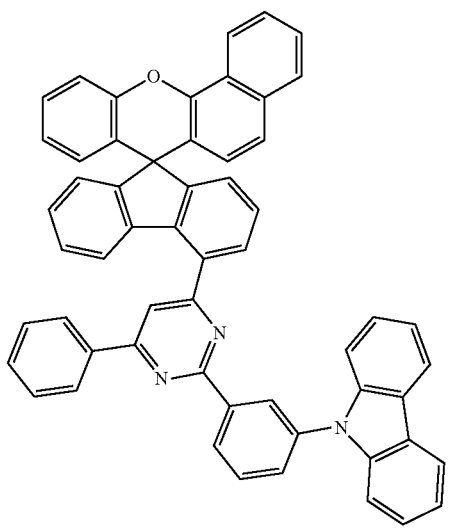
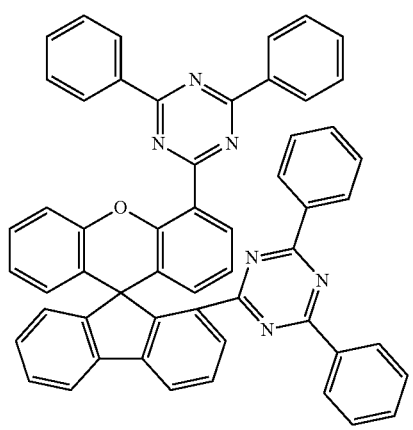

403
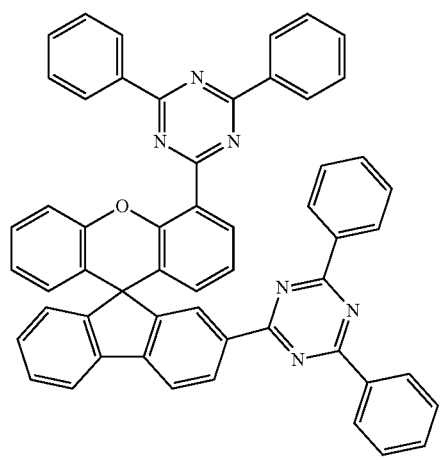
404
-continued
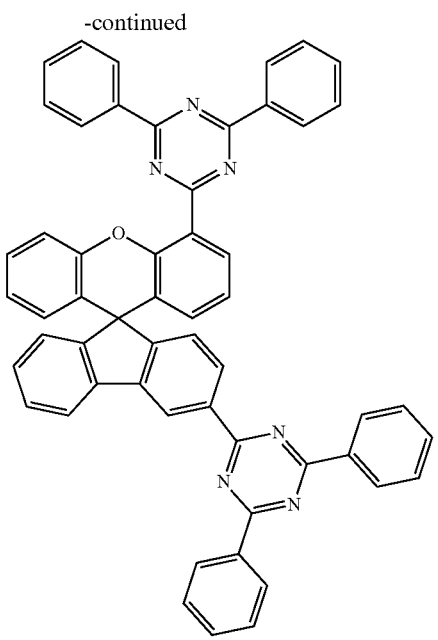
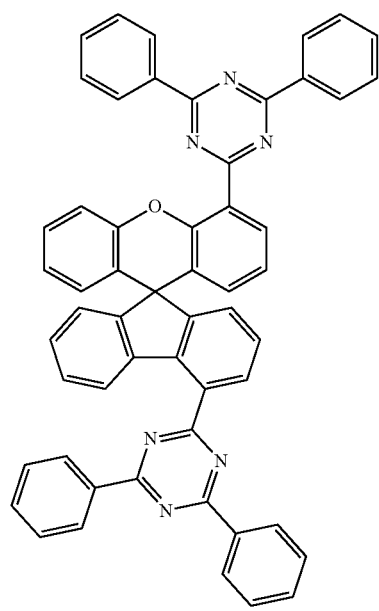
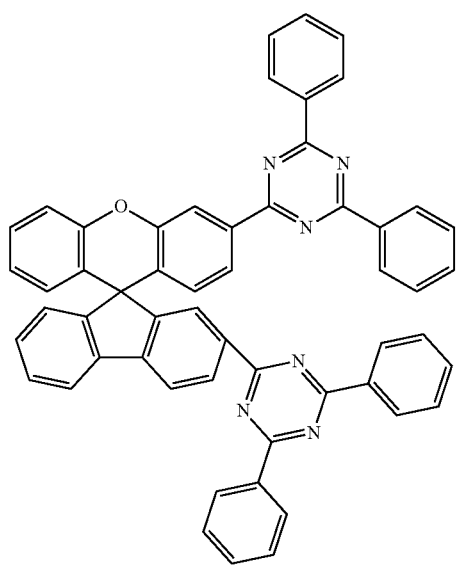

405
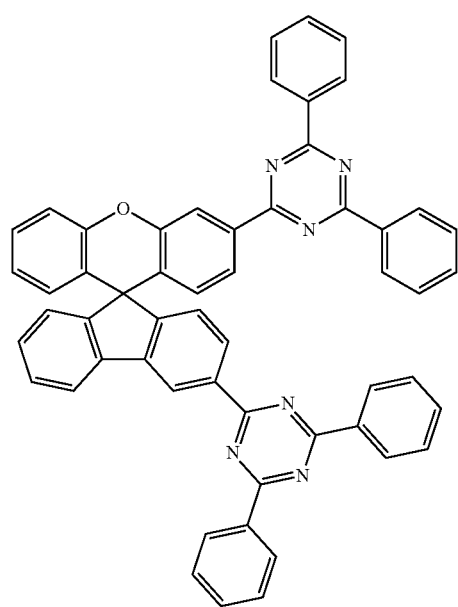
406
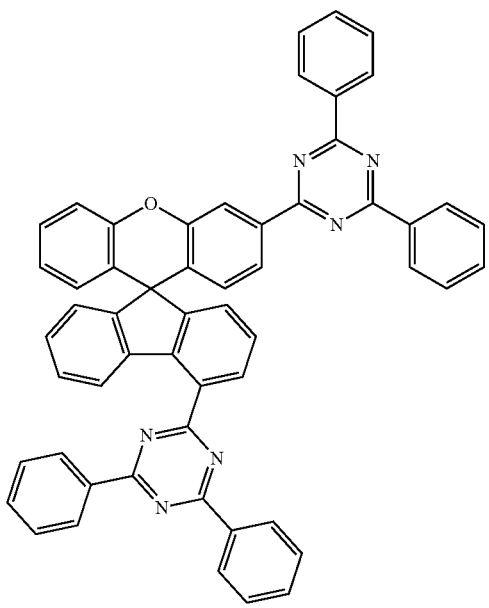
-continued
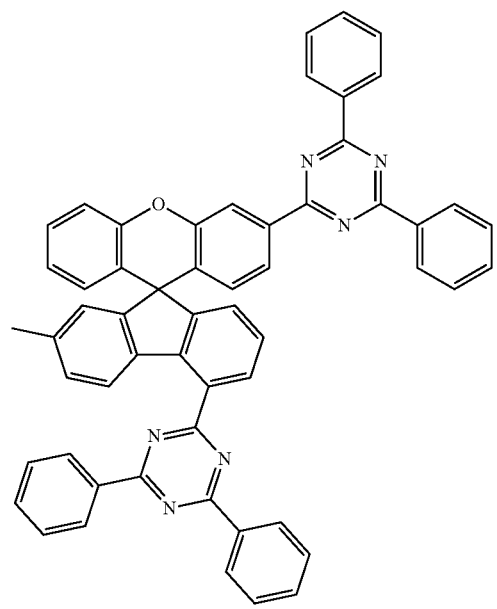
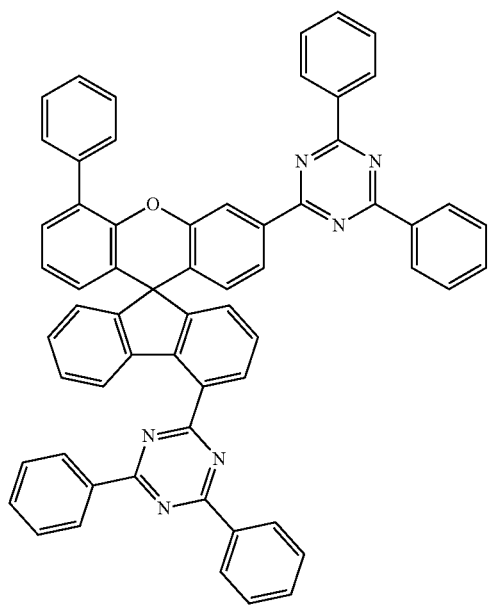

-continued
407
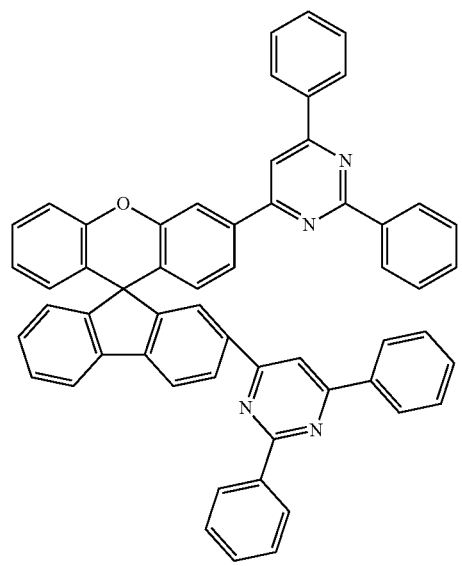
408
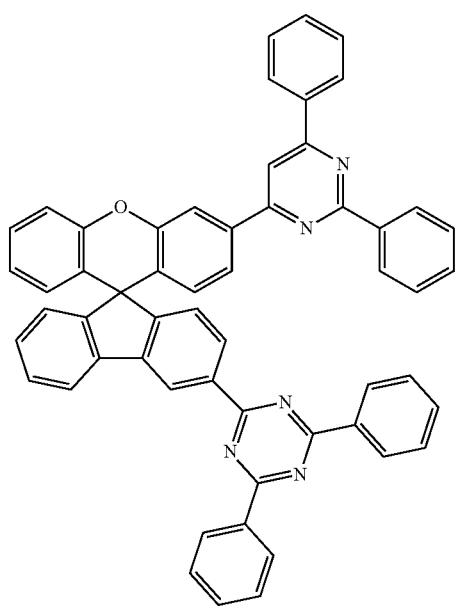
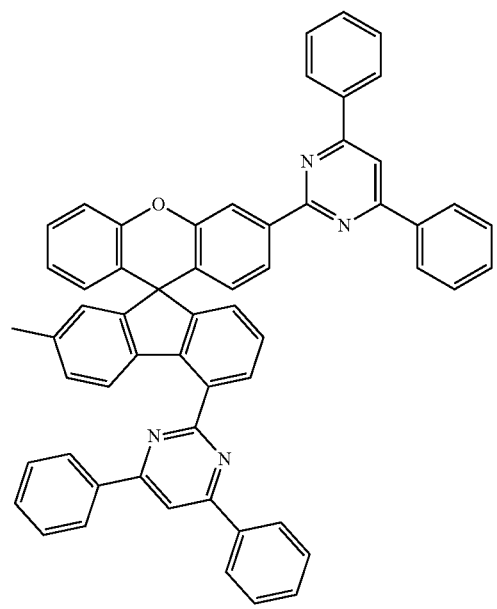
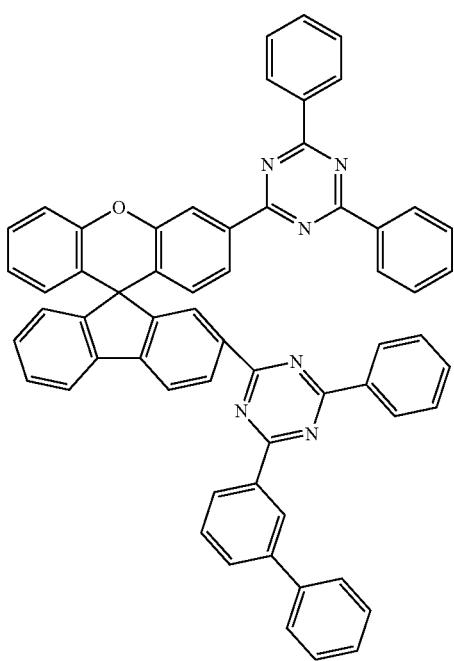

-continued
409
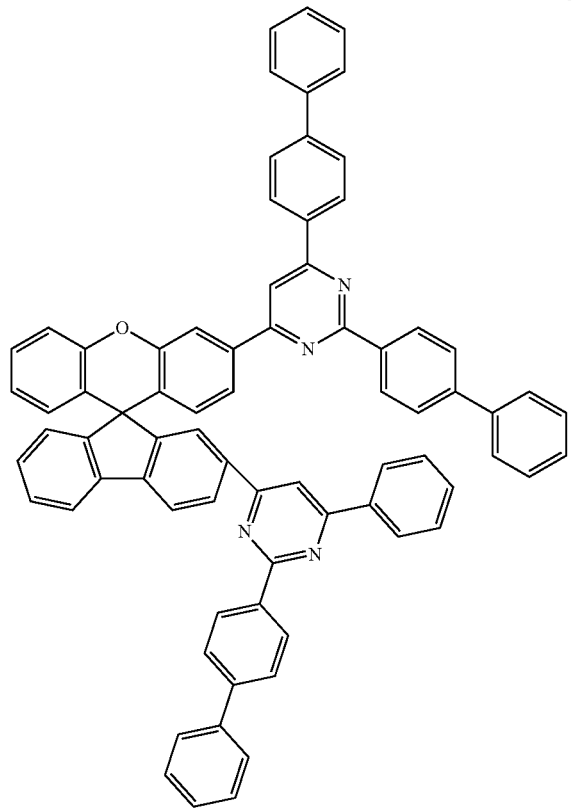
410
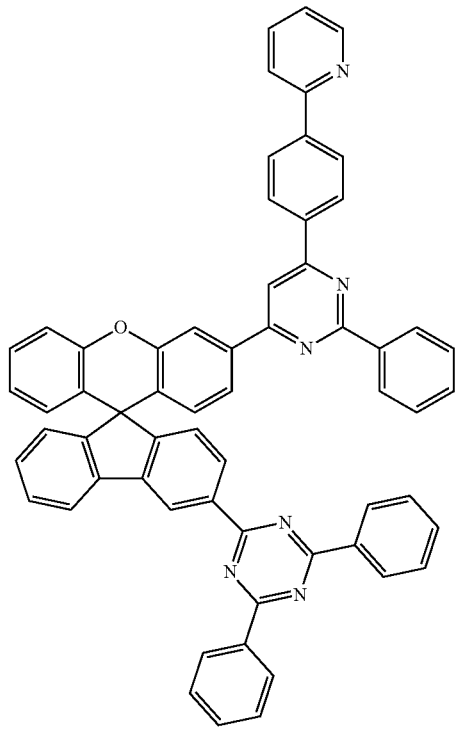
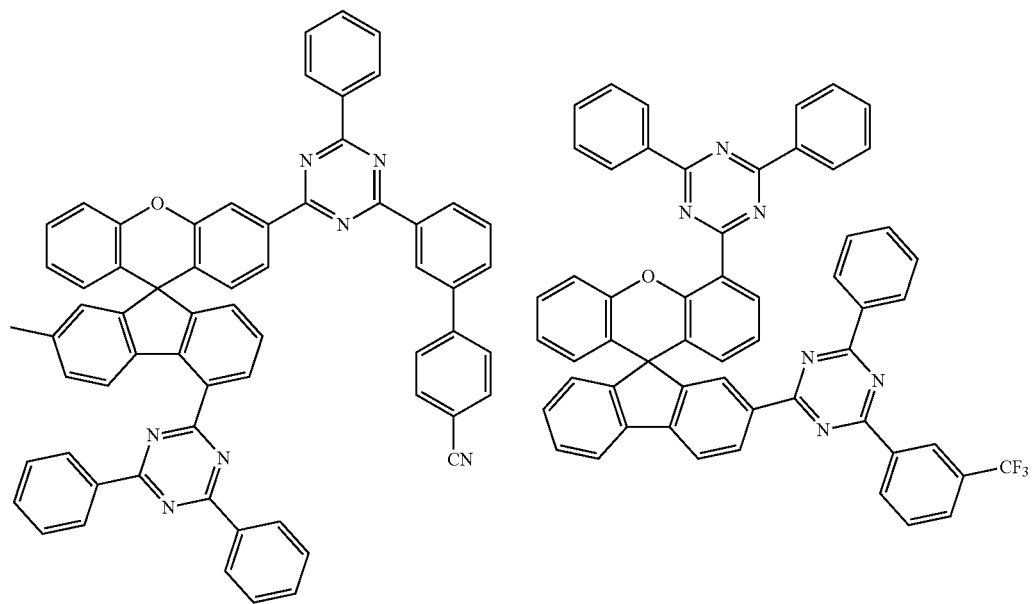

-continued
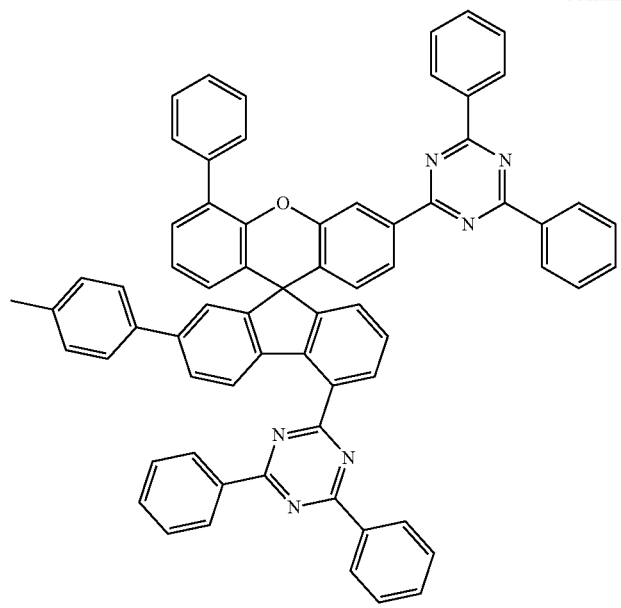
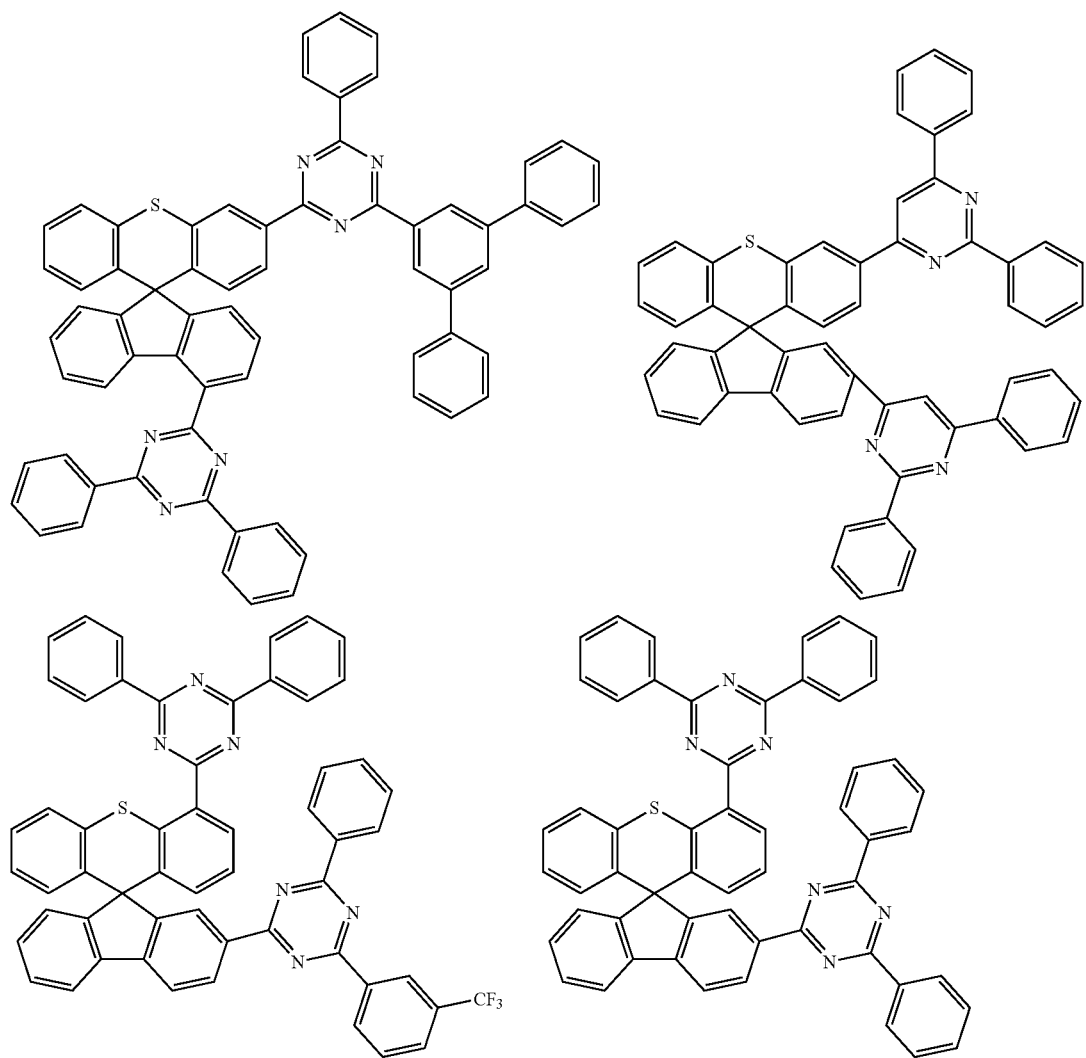

413
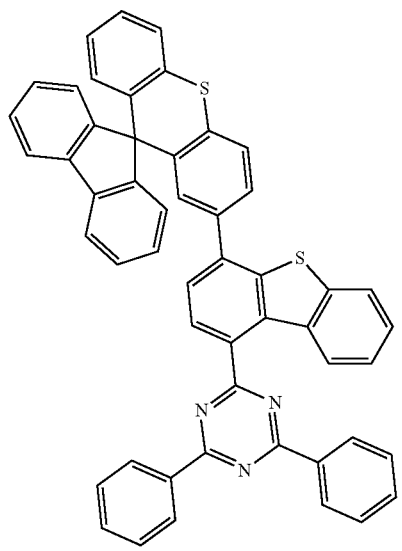
414
-continued
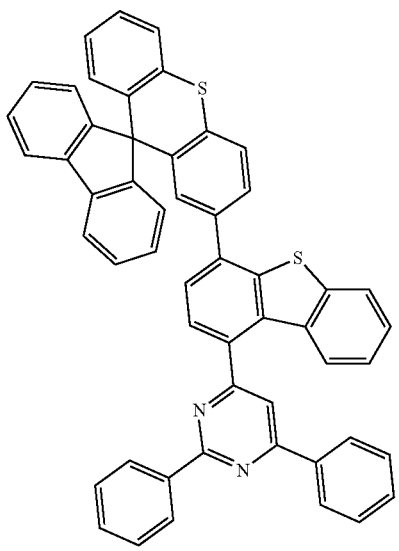
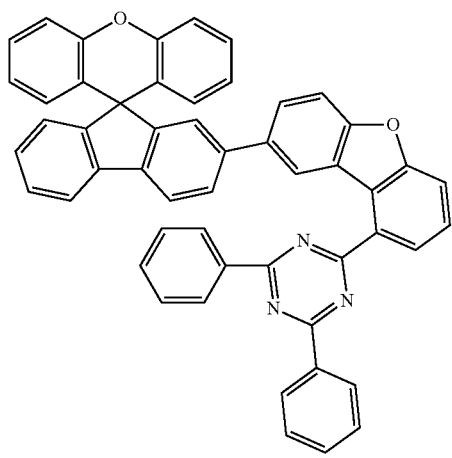
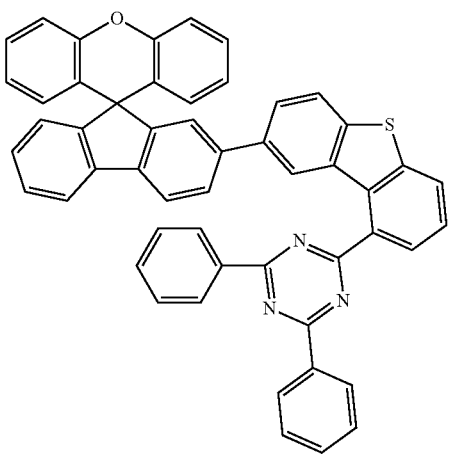
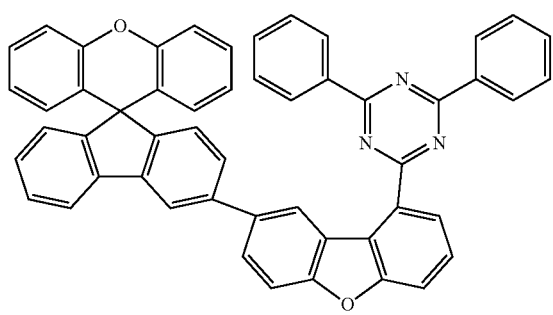
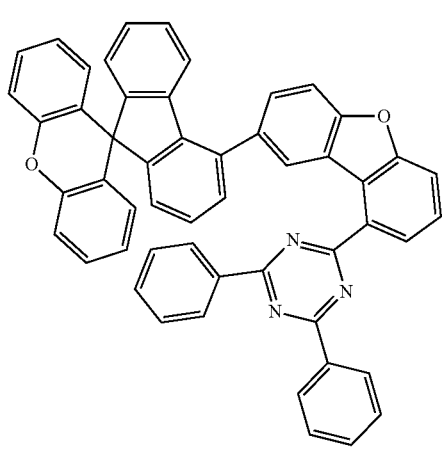

-continued
415 416
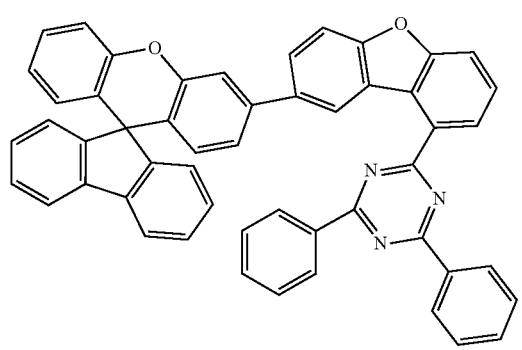 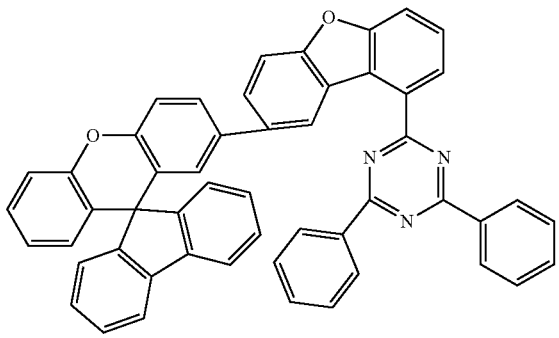
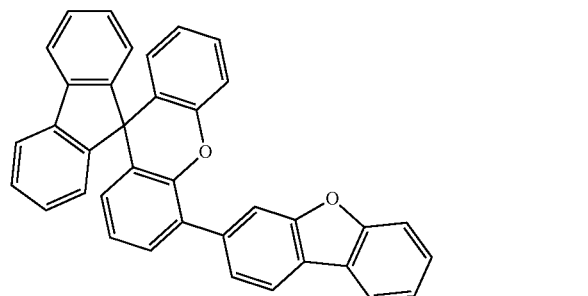
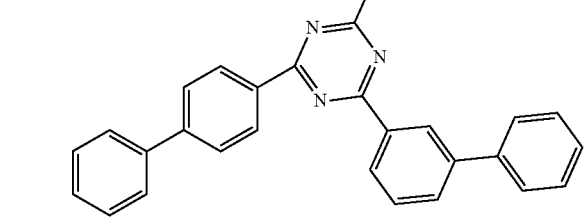
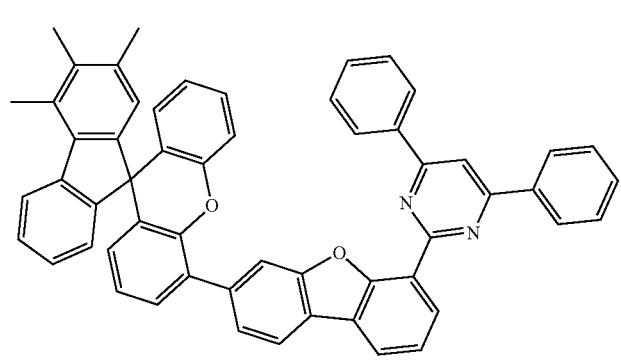 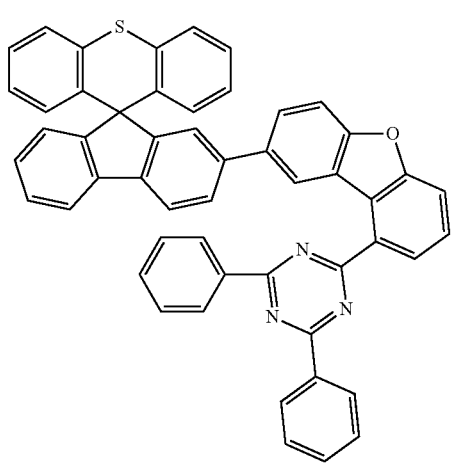

417
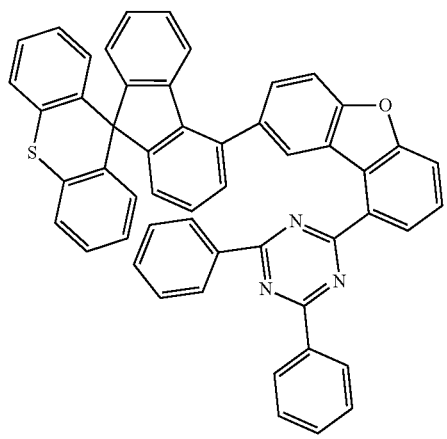
418
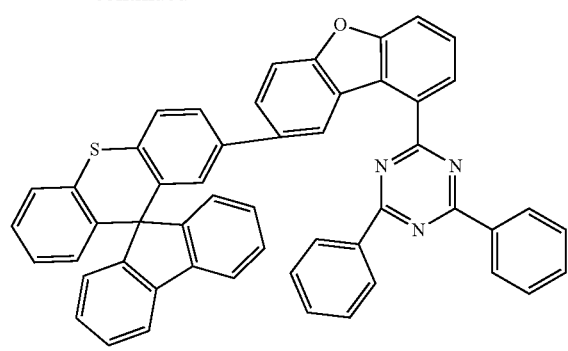
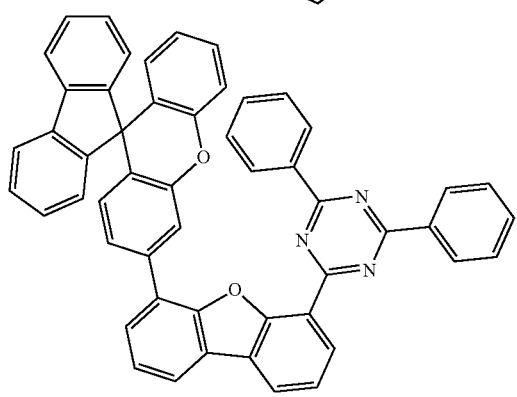
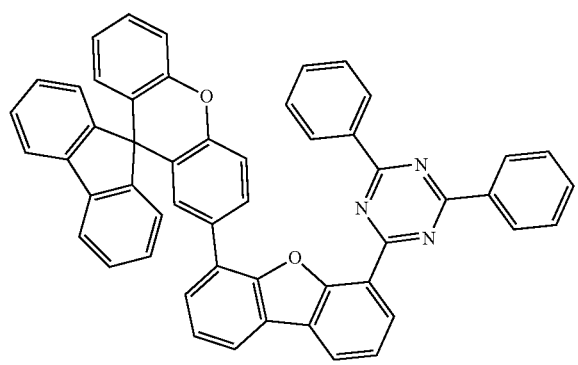
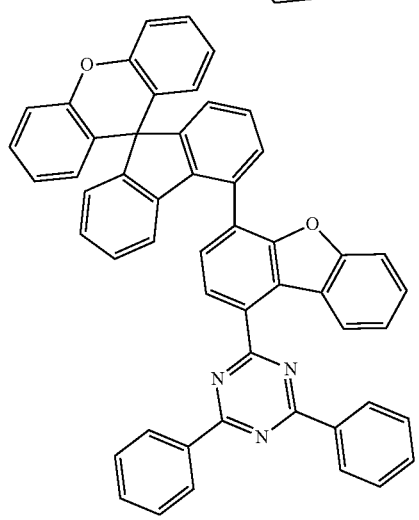
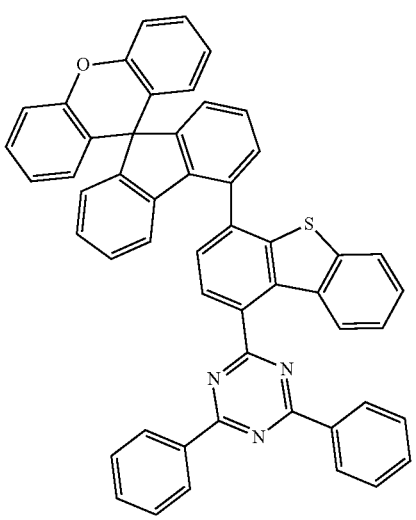
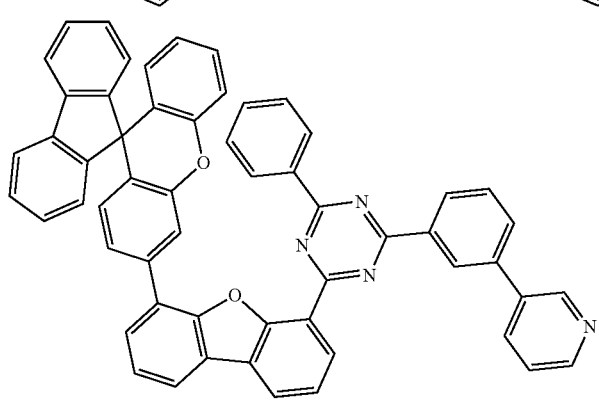

-continued
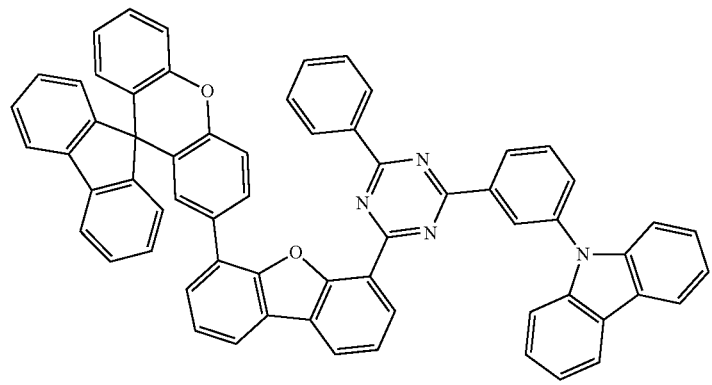
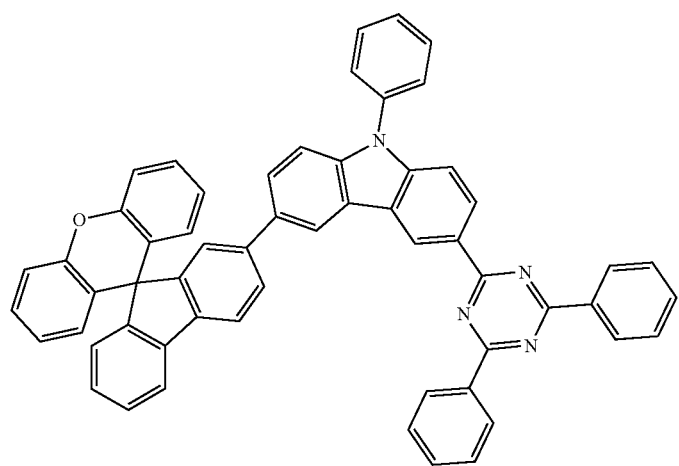
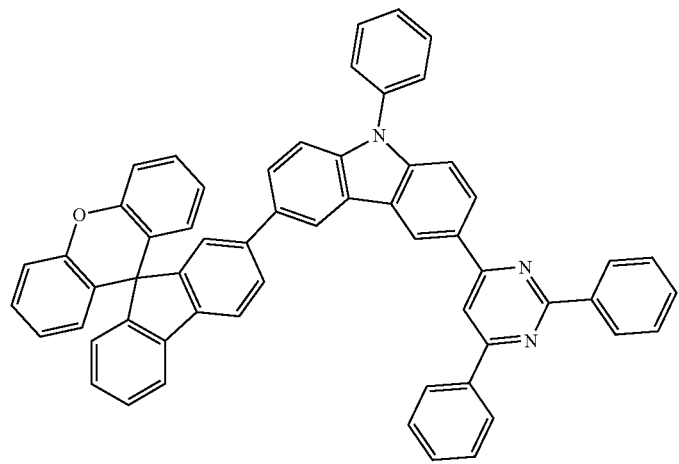

-continued
421
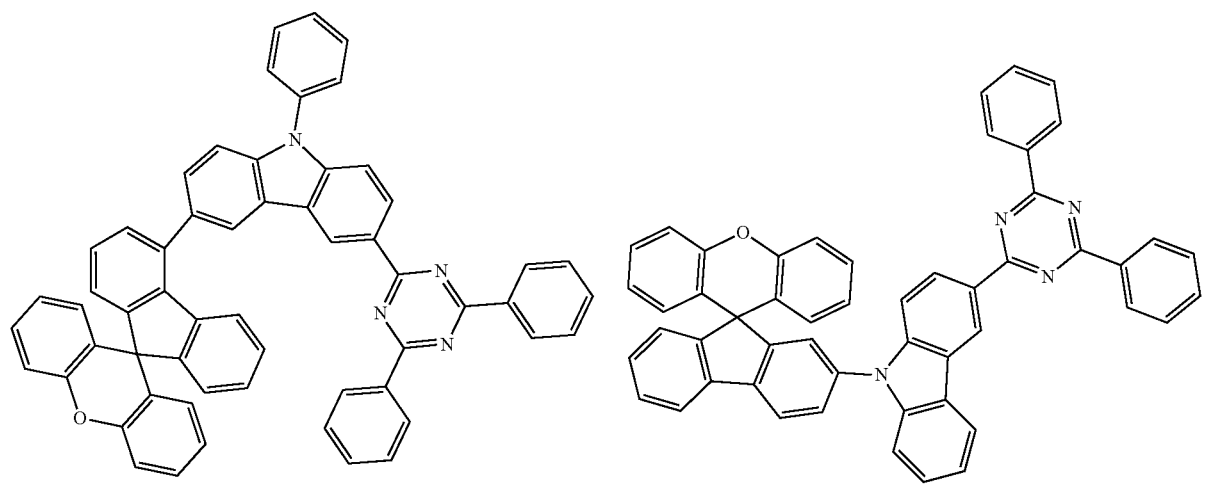
422
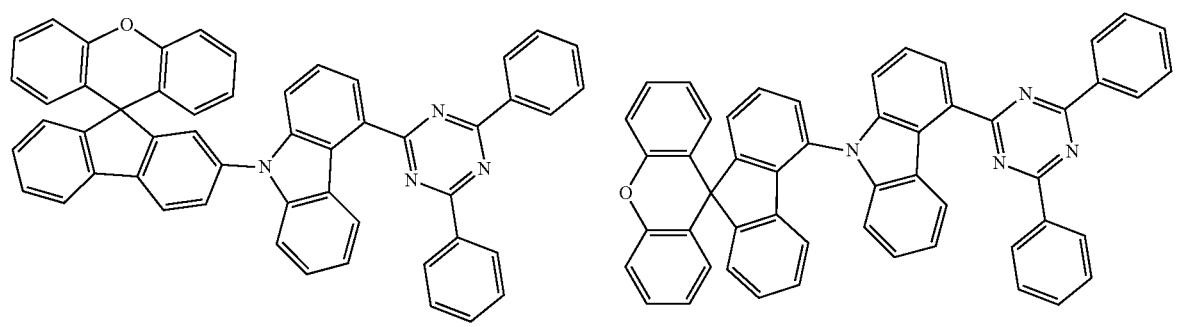
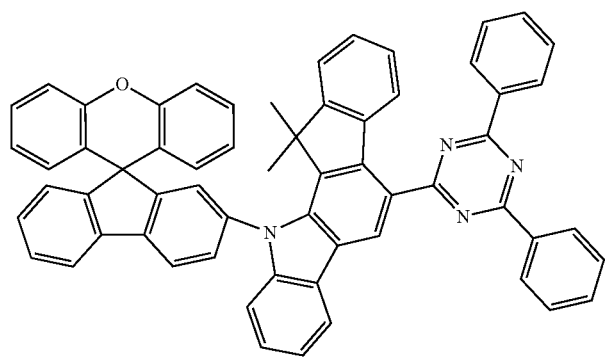
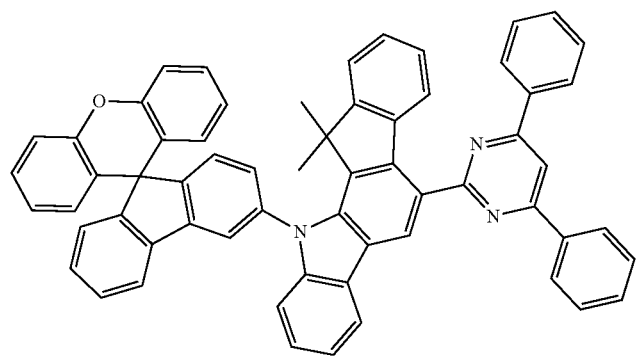

-continued
423
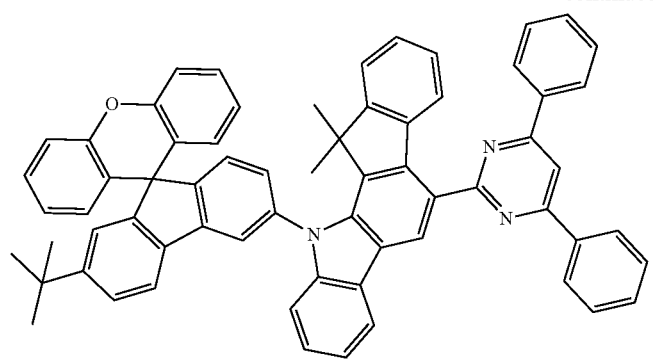
424
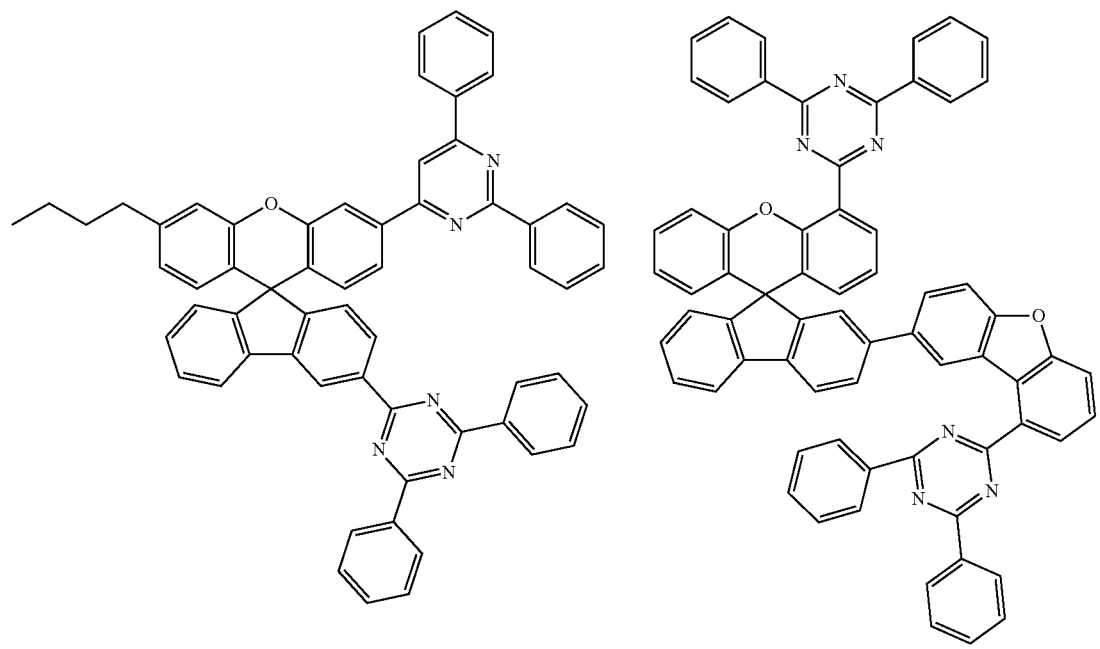
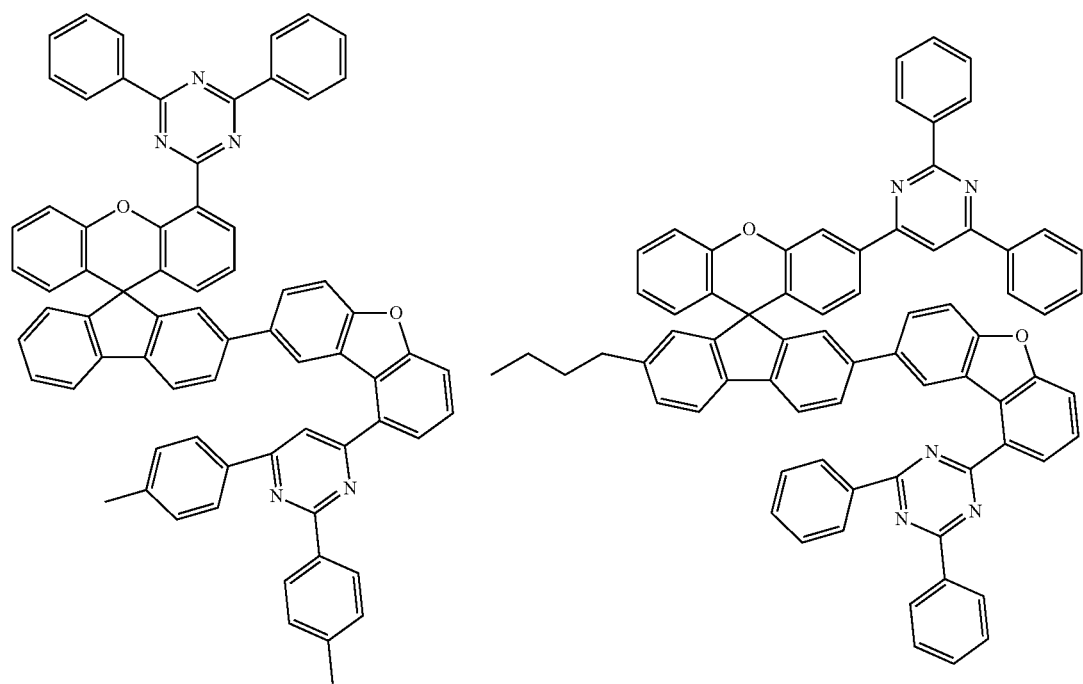

-continued
425
426
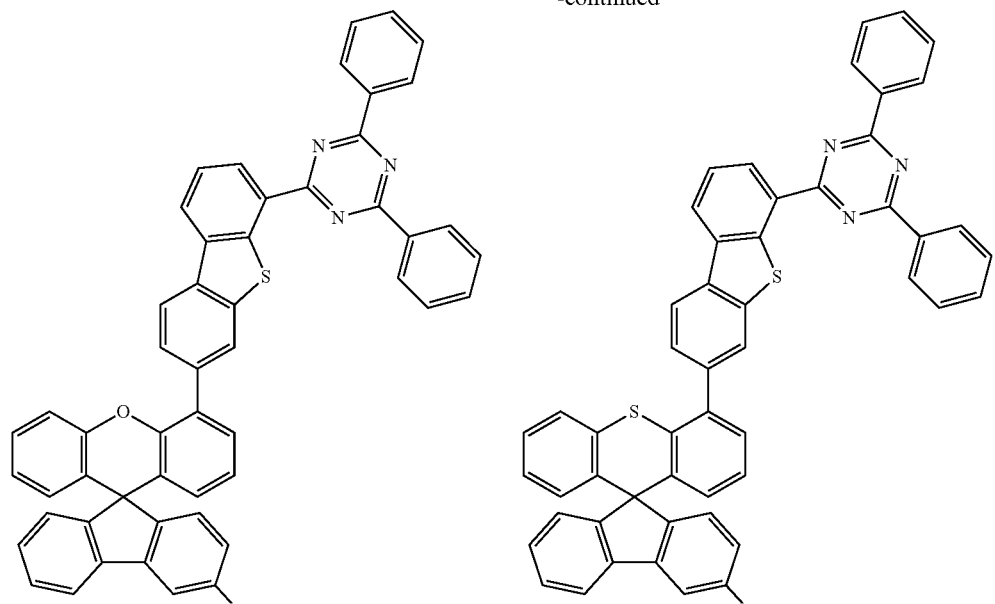
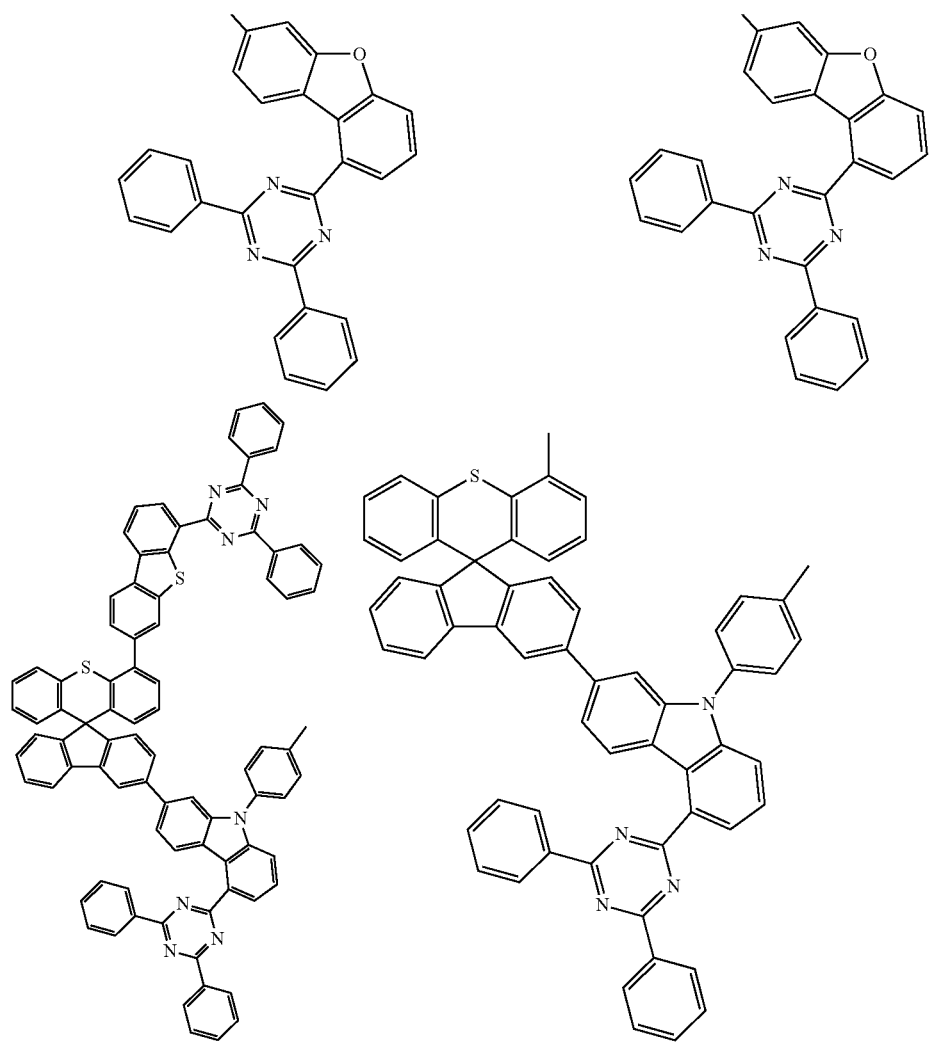

427 428
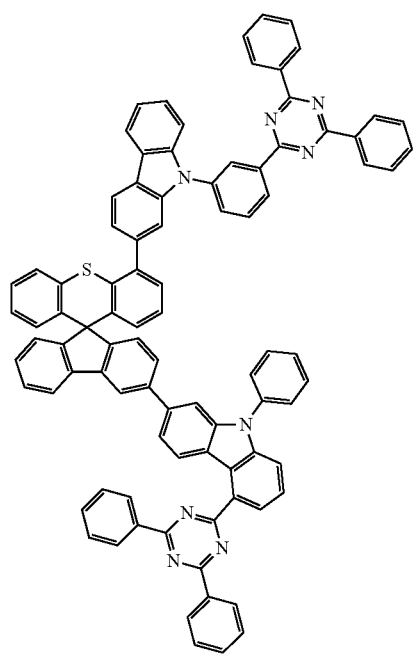
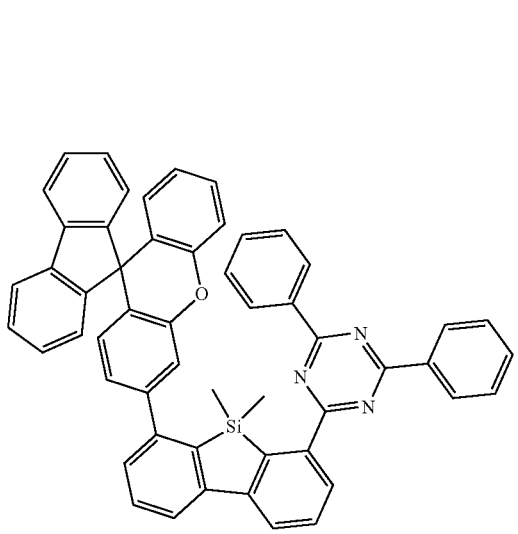
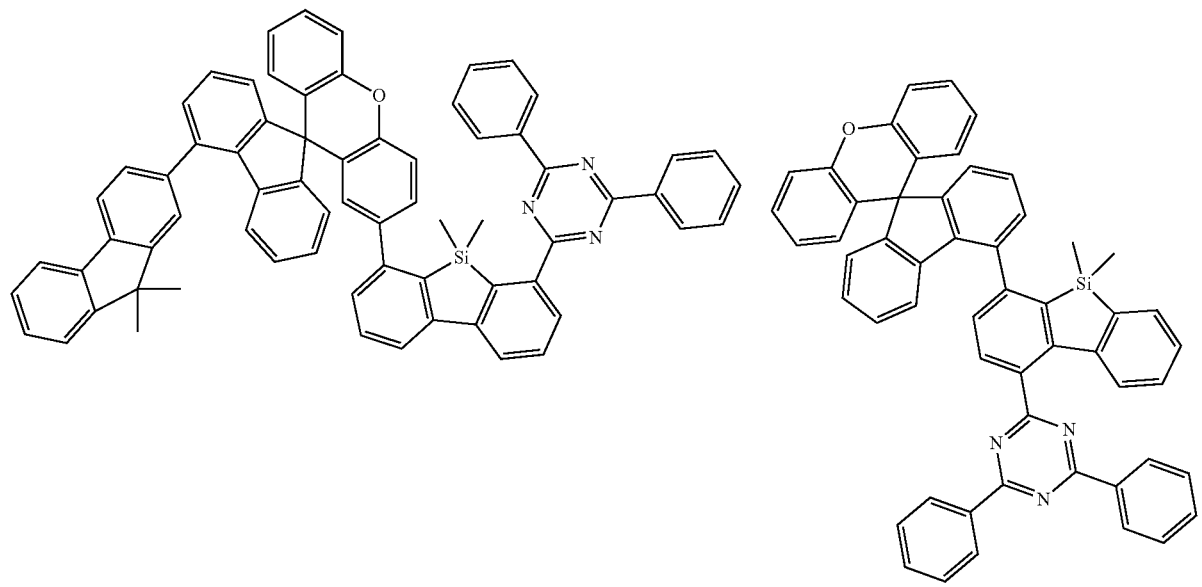

-continued
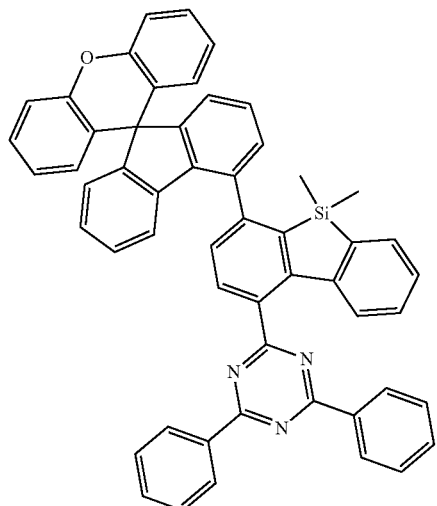
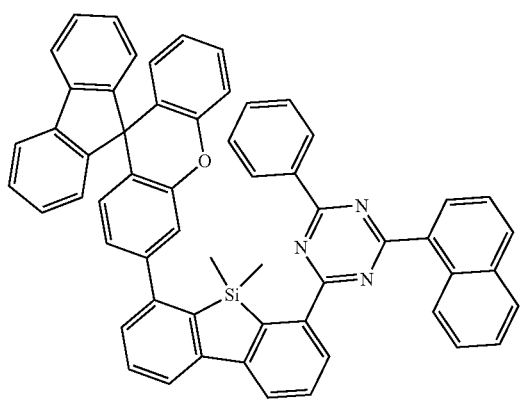
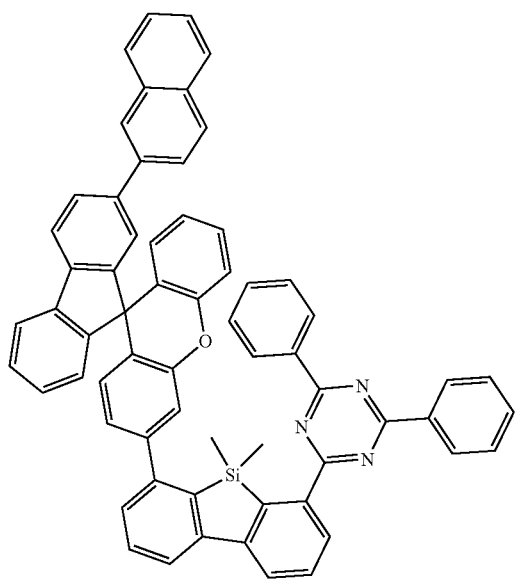
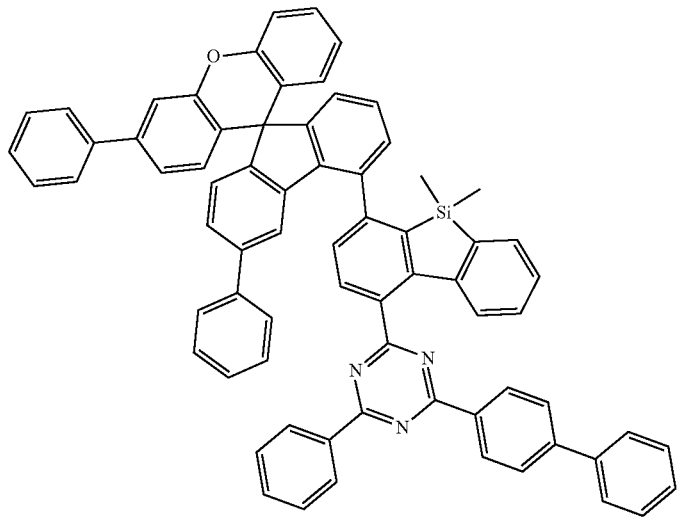
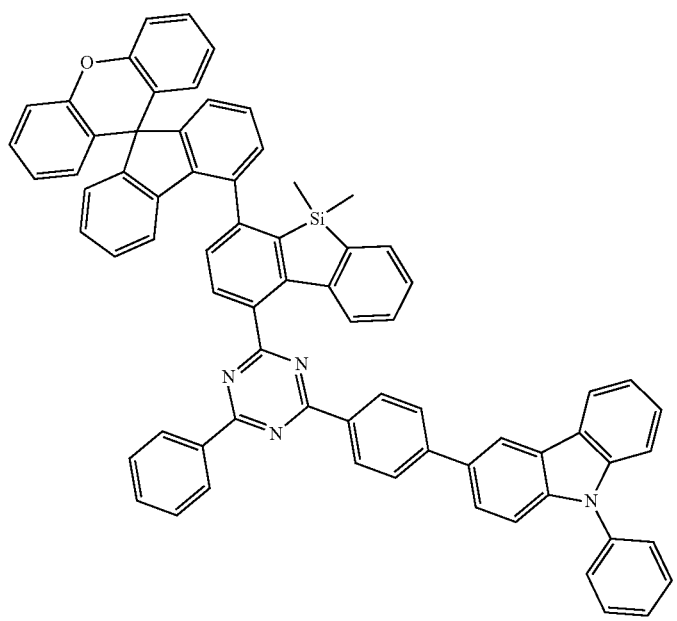
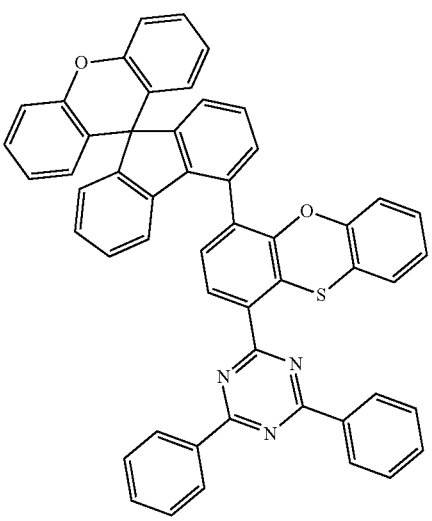

431 432
-continued
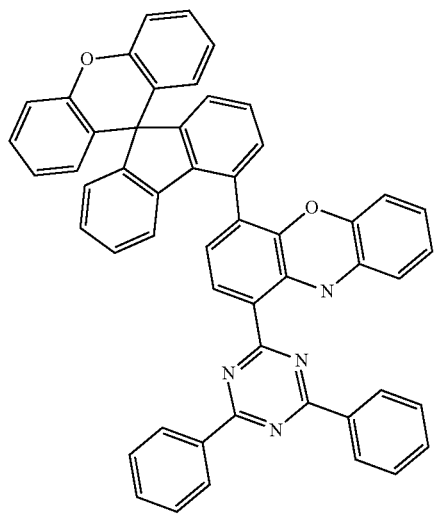
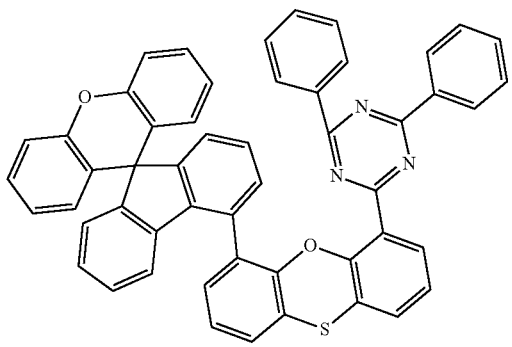
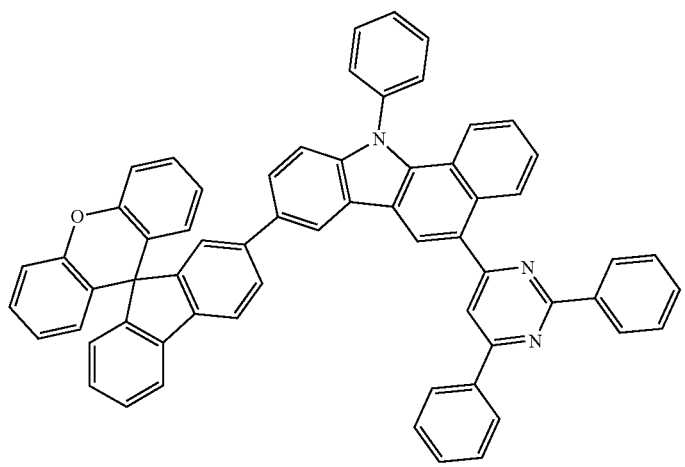
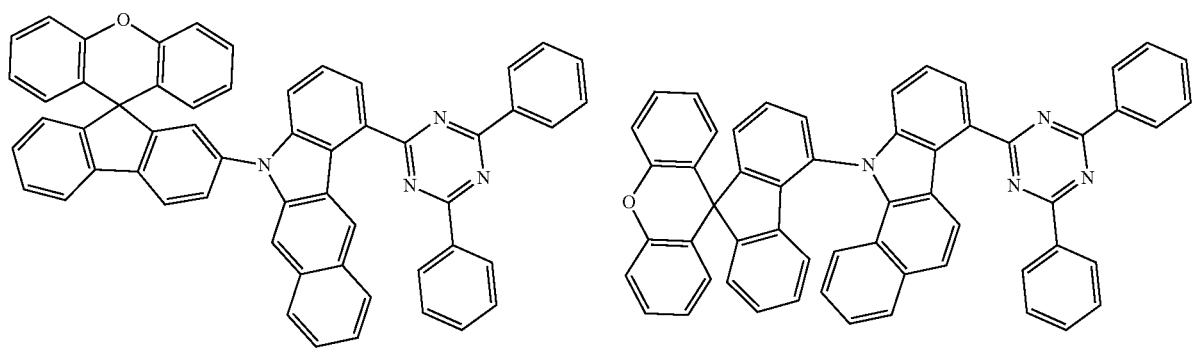

-continued
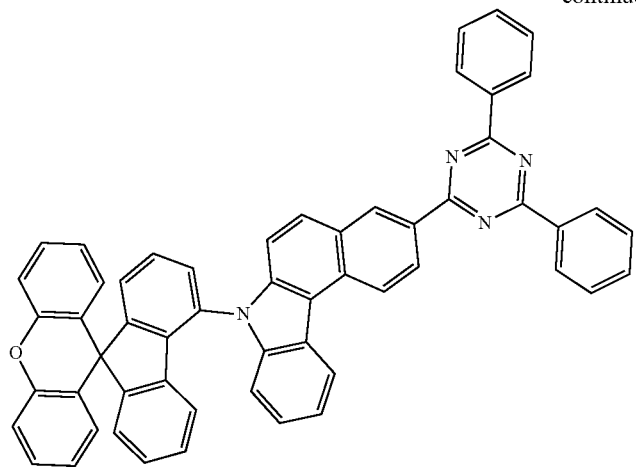
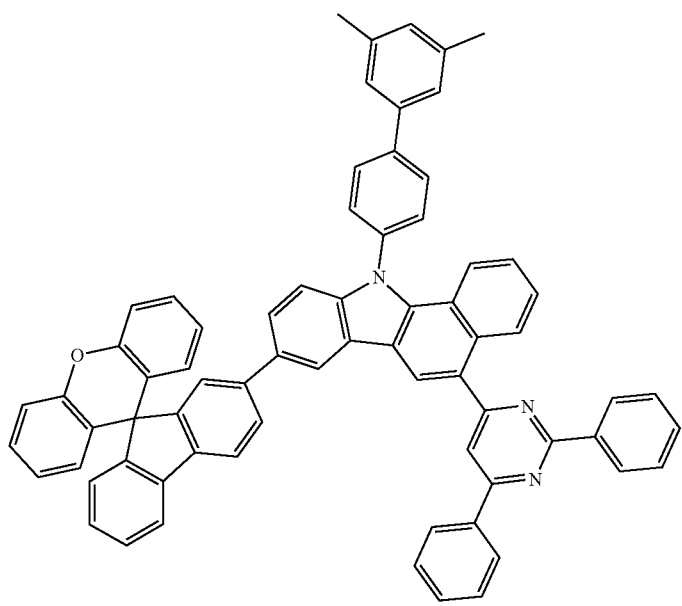
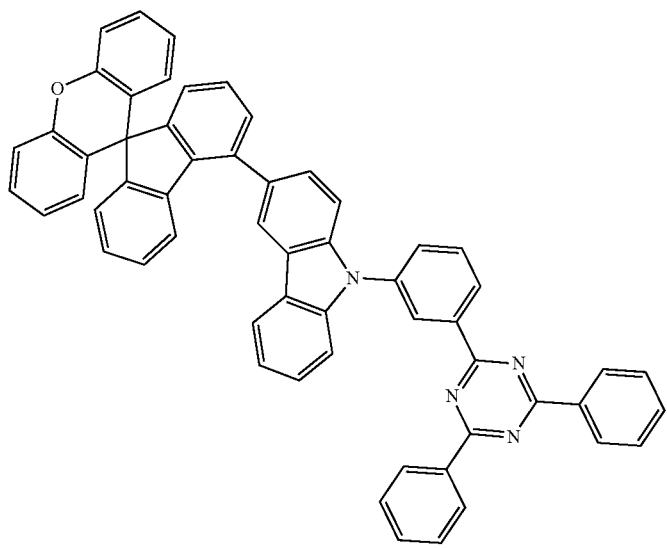

-continued
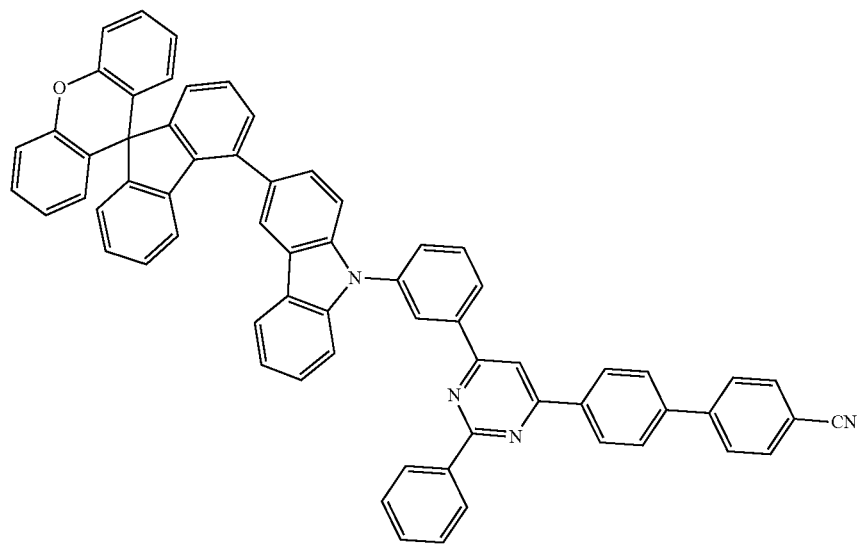
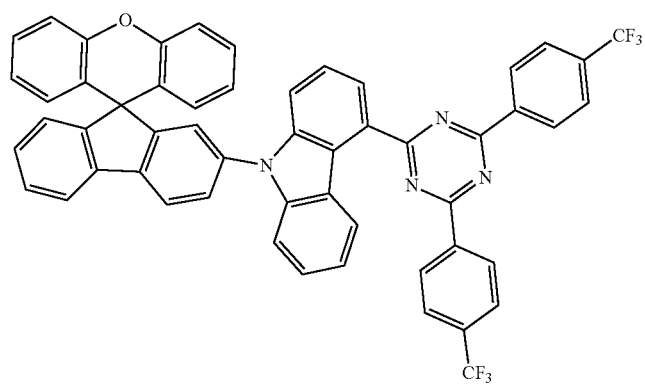
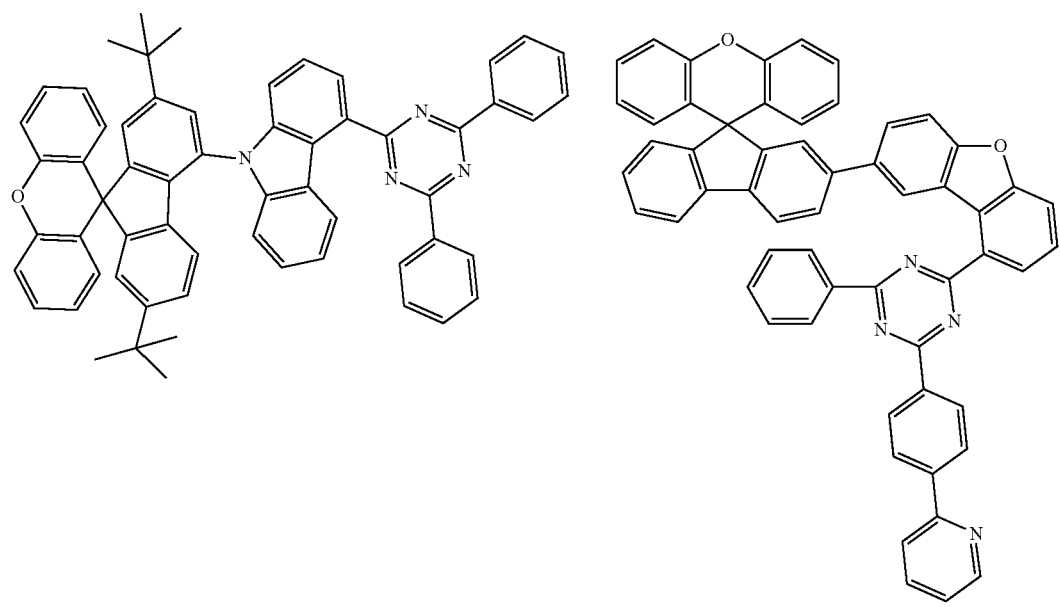

437
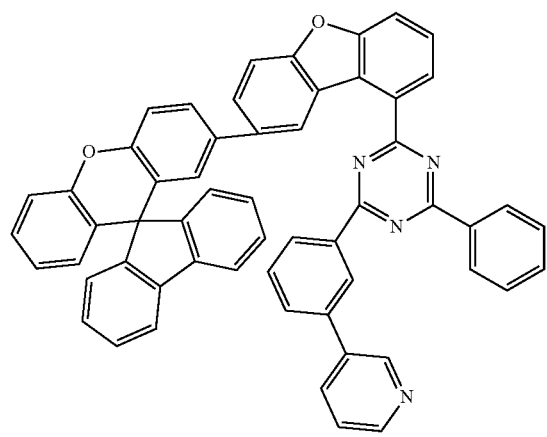
438
-continued
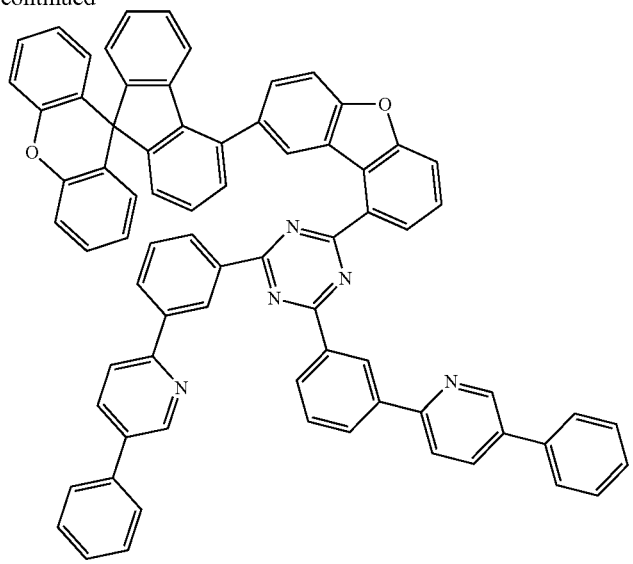
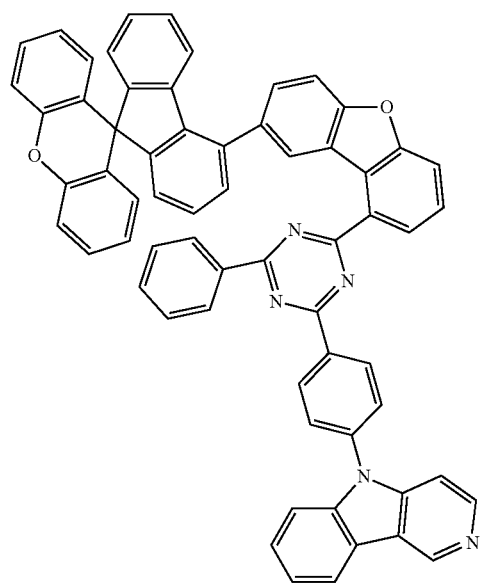
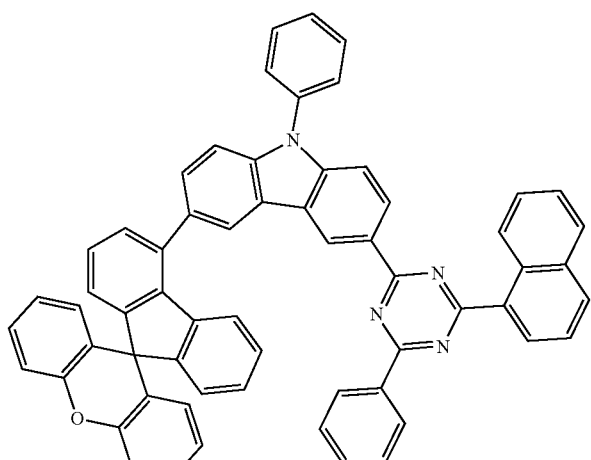
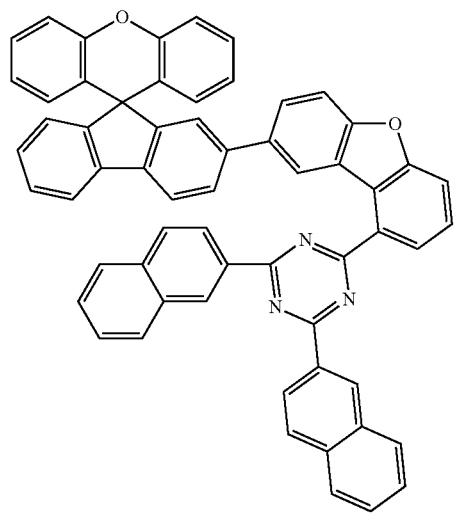
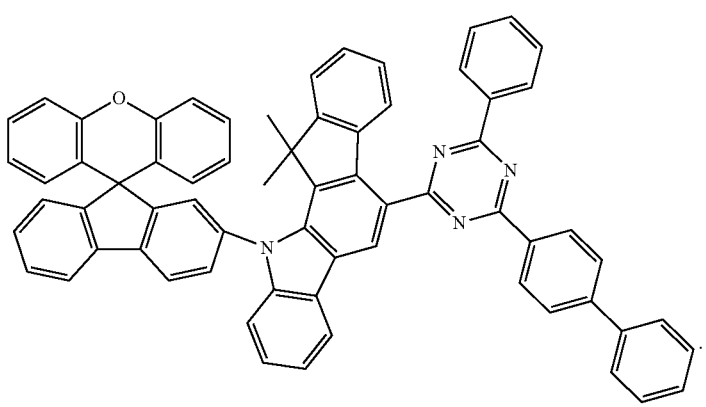

7. The organic light emitting device of claim 1, wherein the compound represented by the Chemical Formula 3-1 or 3-2 is any one selected from the group consisting of:
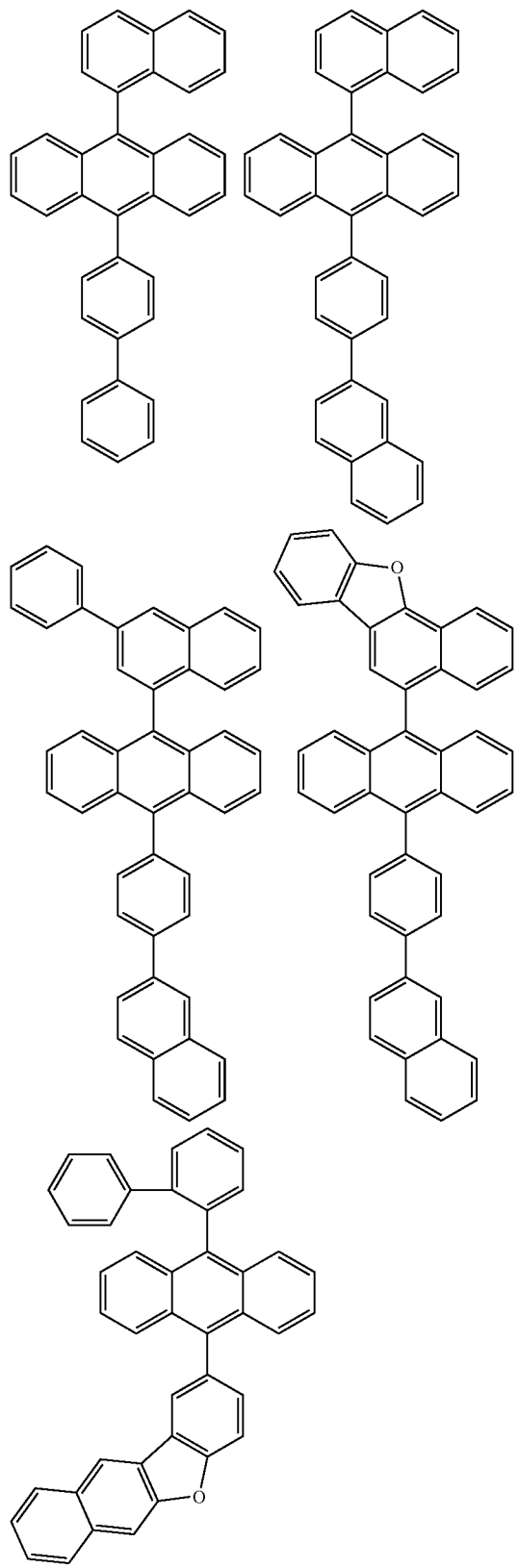
-continued
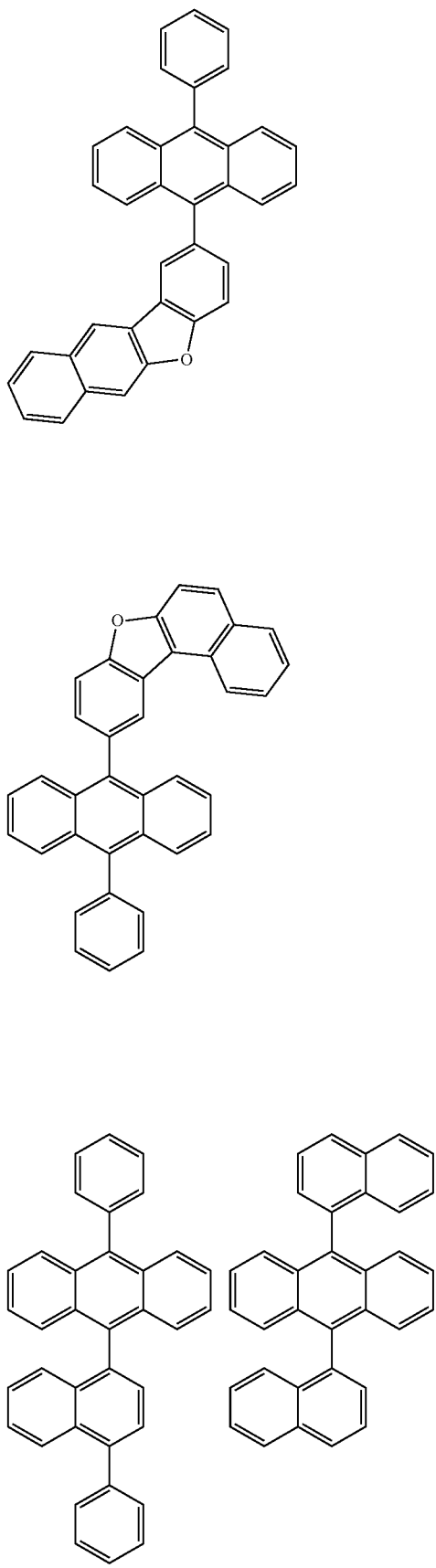

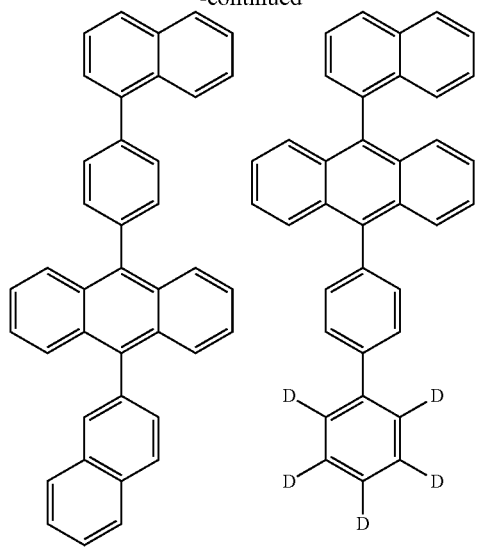
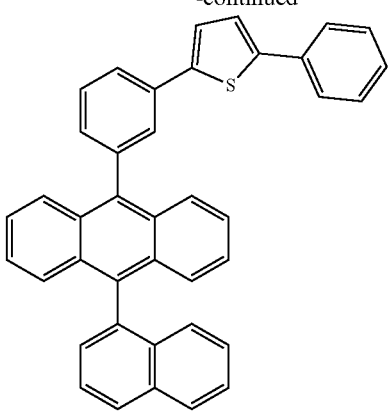
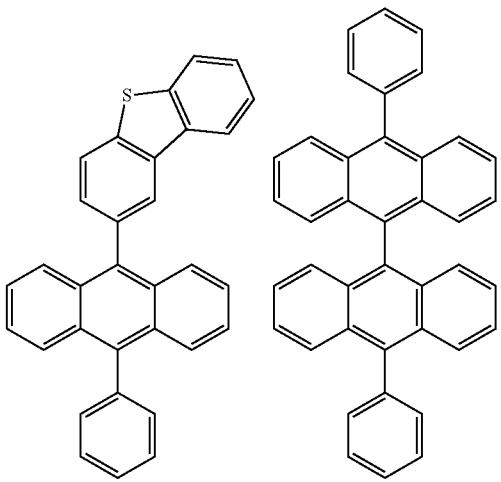
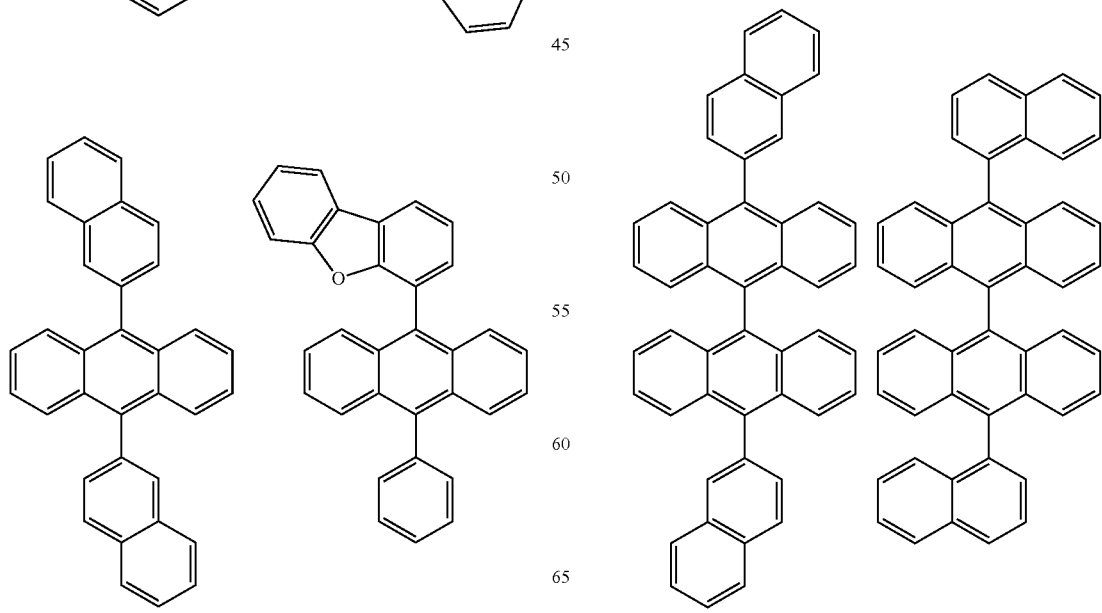

-continued
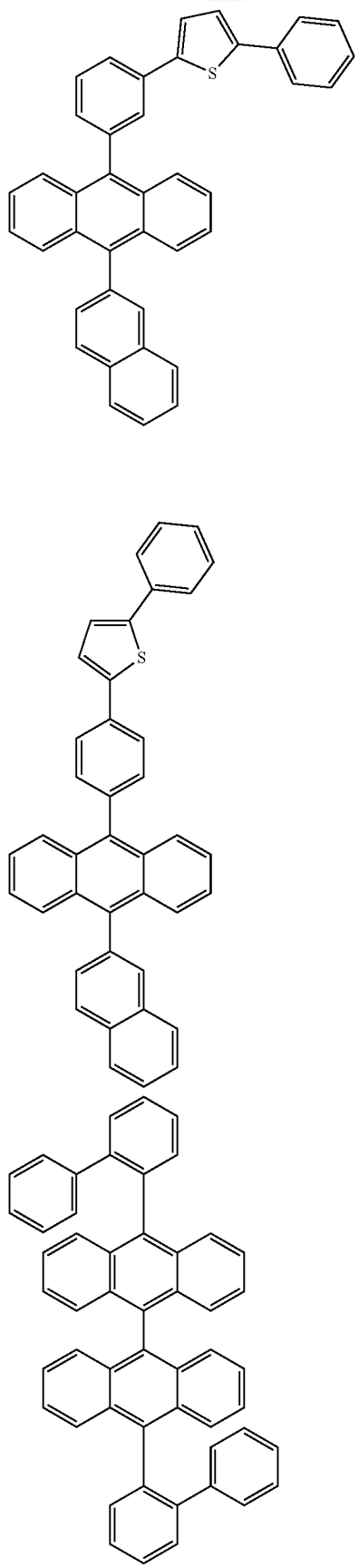
-continued
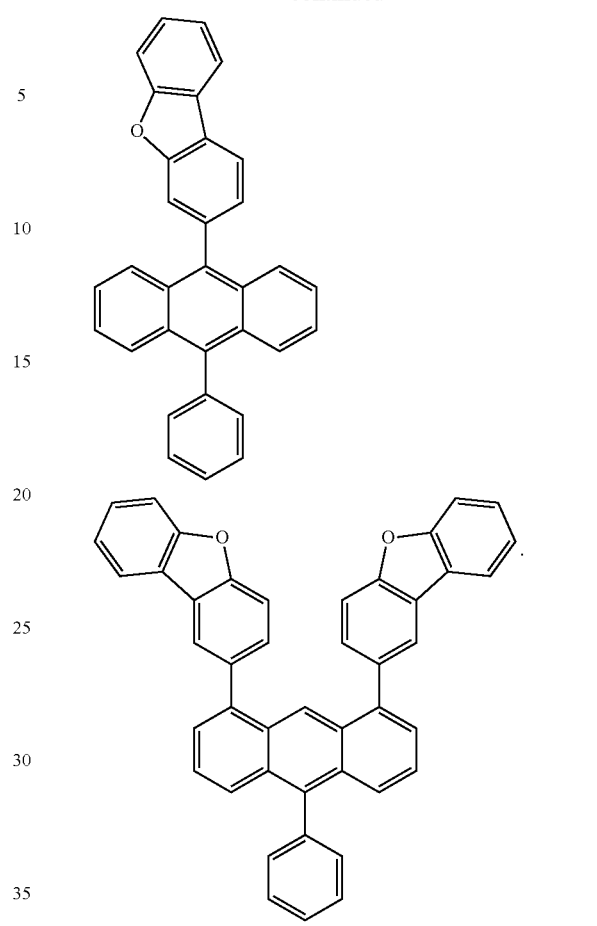
8. The organic light emitting device of claim 1, wherein the compound represented by the Chemical Formulas 4-1 to 4-4 is selected from the group consisting of:

445
-continued
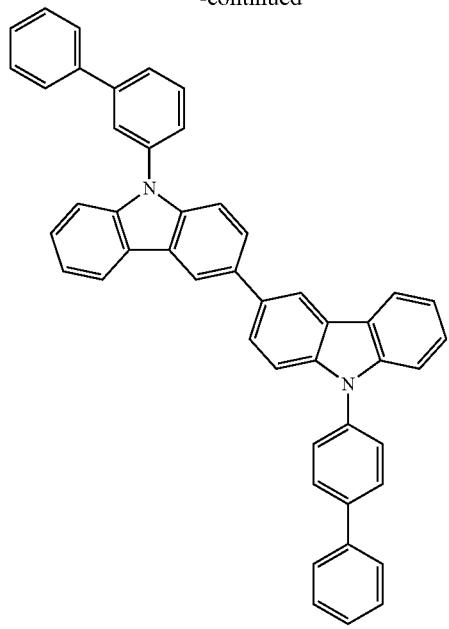
446
-continued
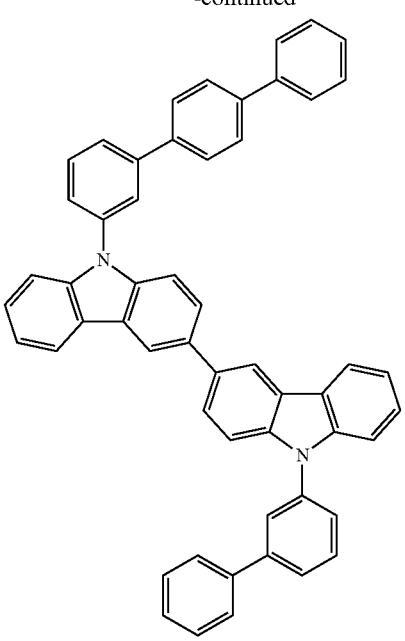
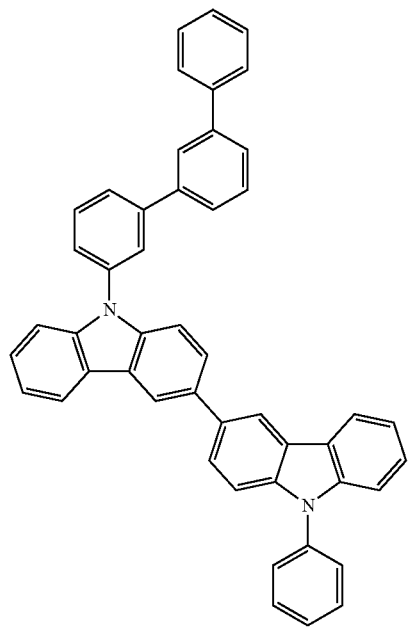
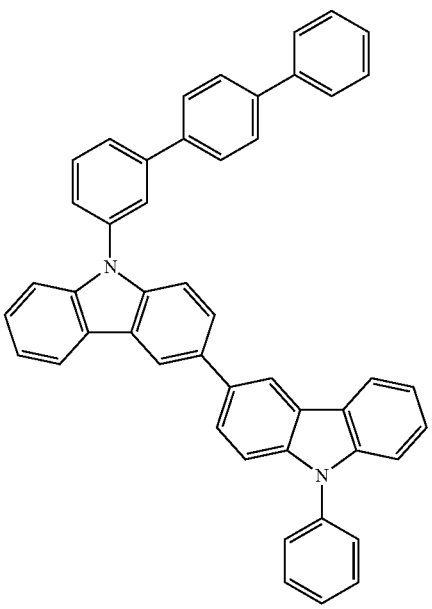

447
-continued
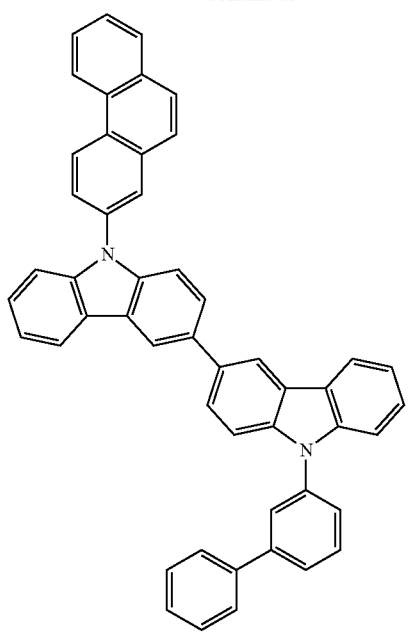
448
-continued
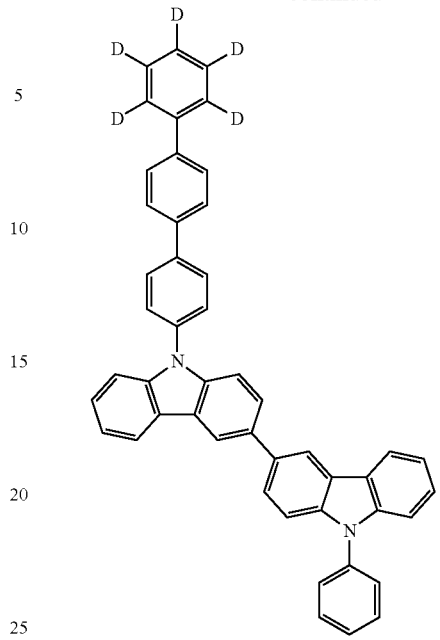
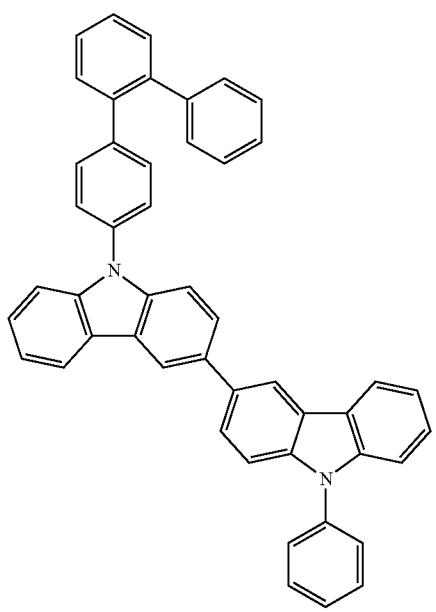
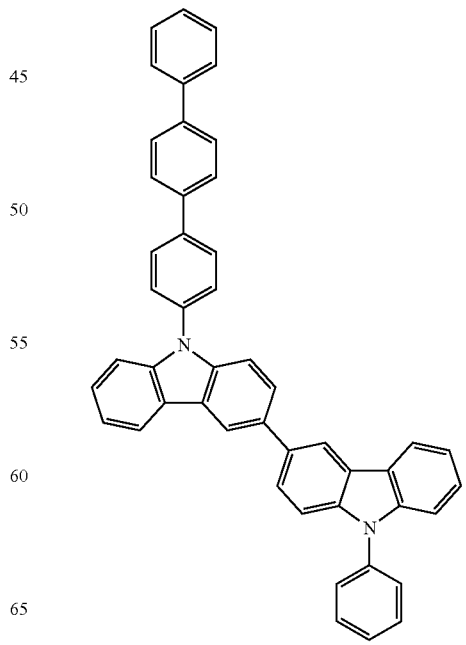

449
-continued
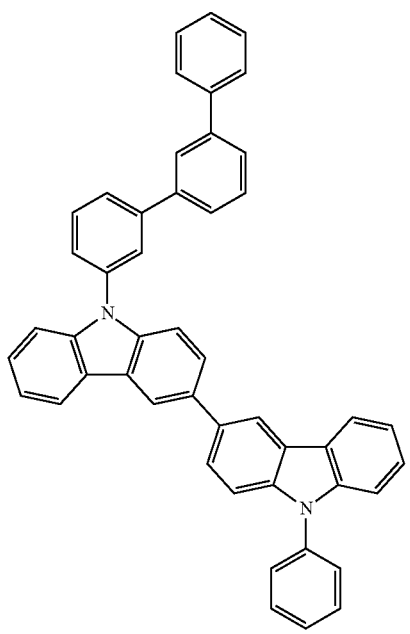
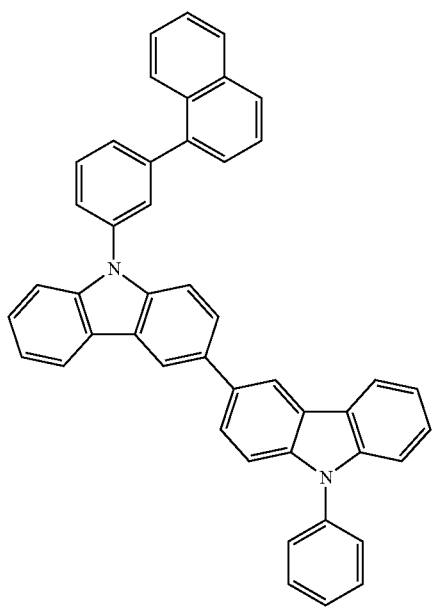
450
-continued
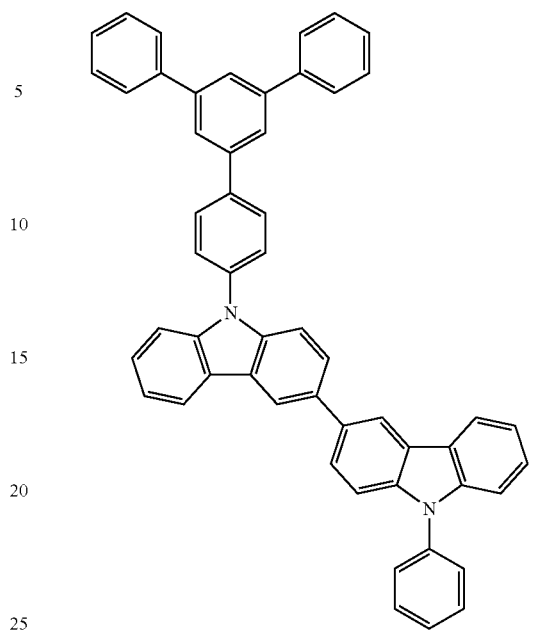
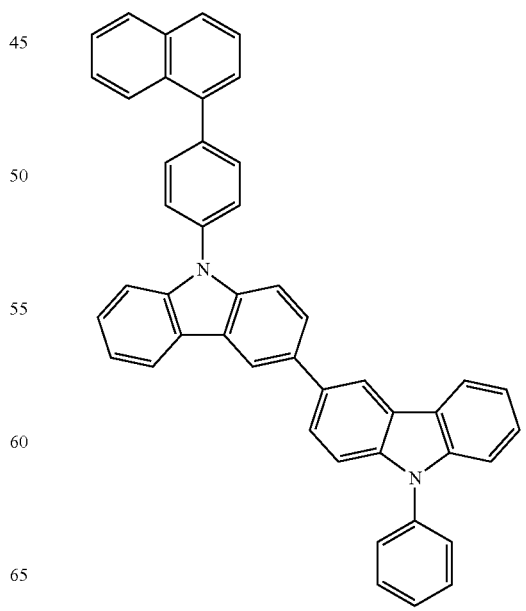

451
-continued
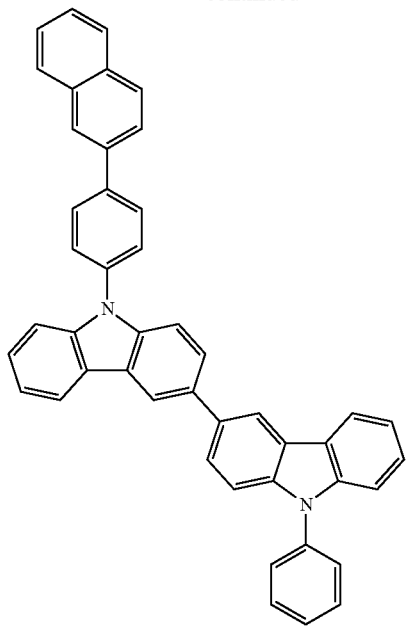
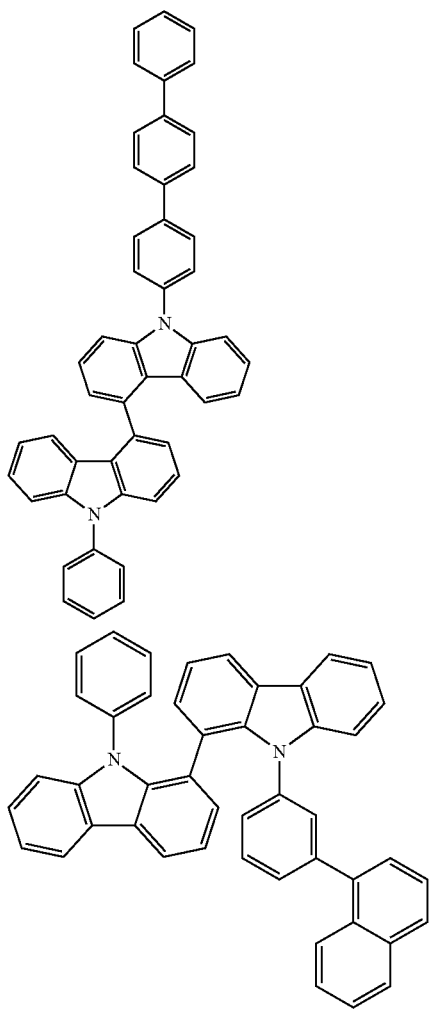
452
-continued
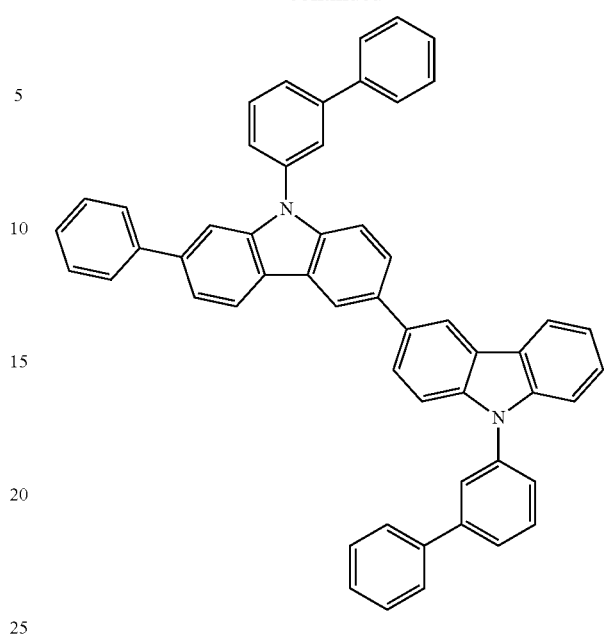
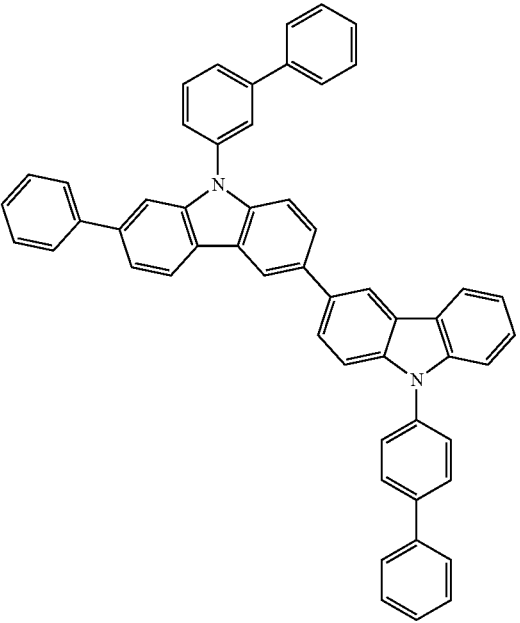

453
-continued
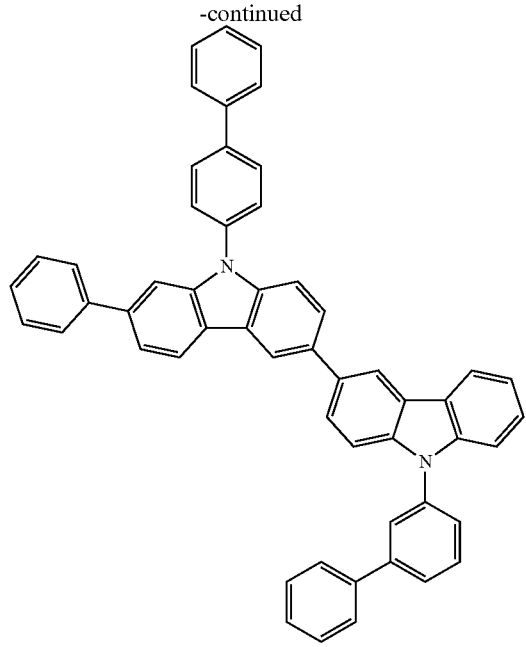
454
-continued
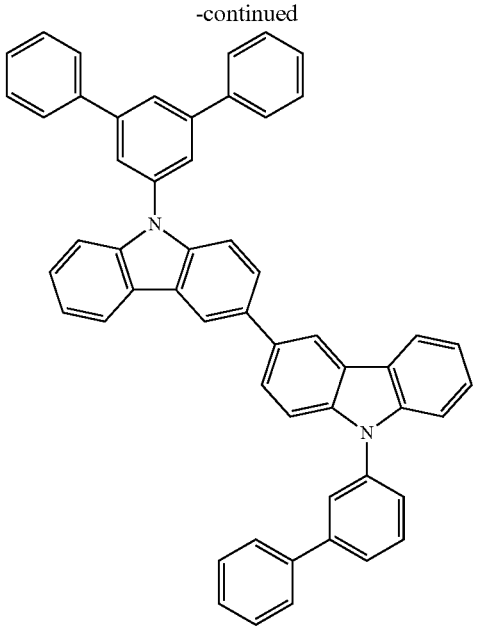
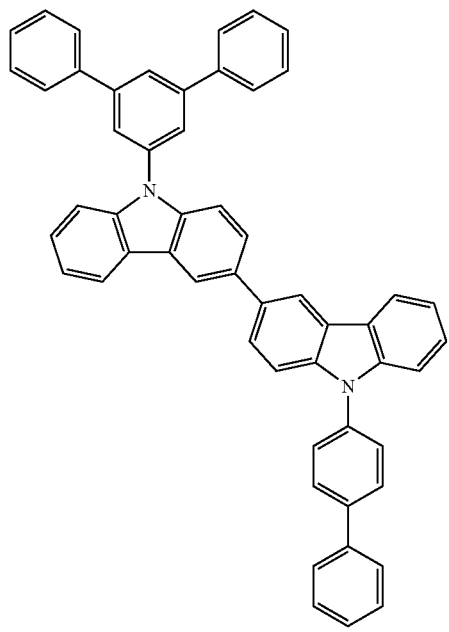
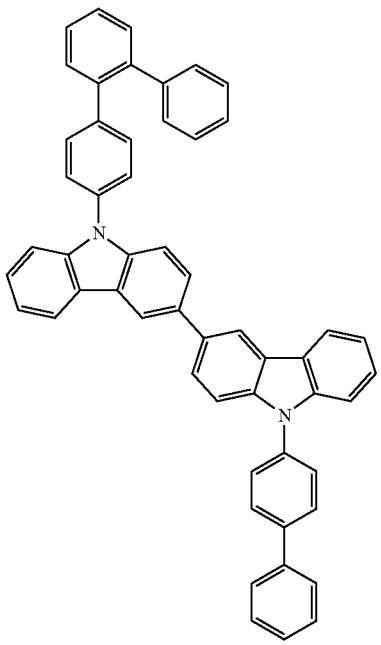

455
-continued
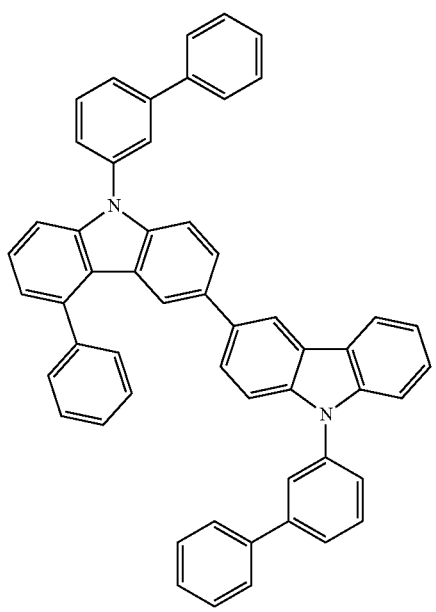
456
-continued
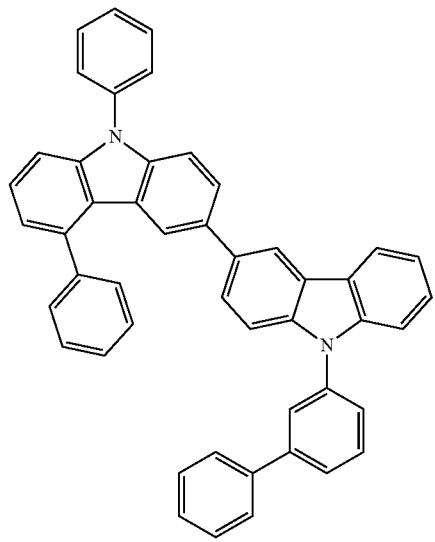
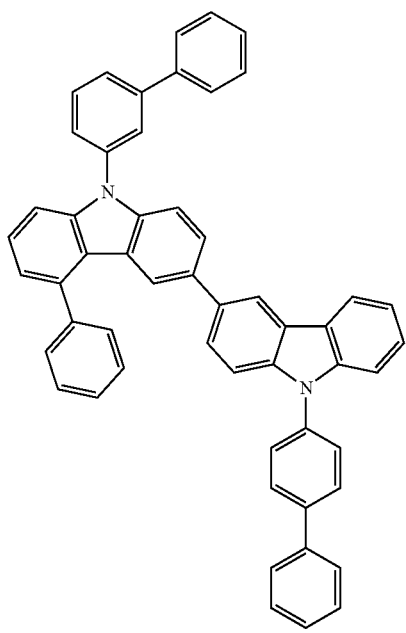
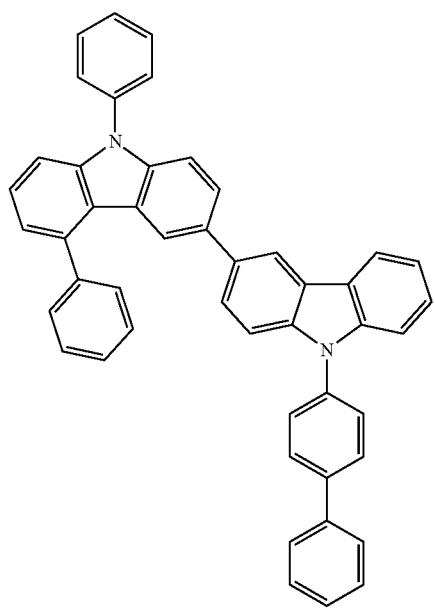

457
-continued
458
-continued
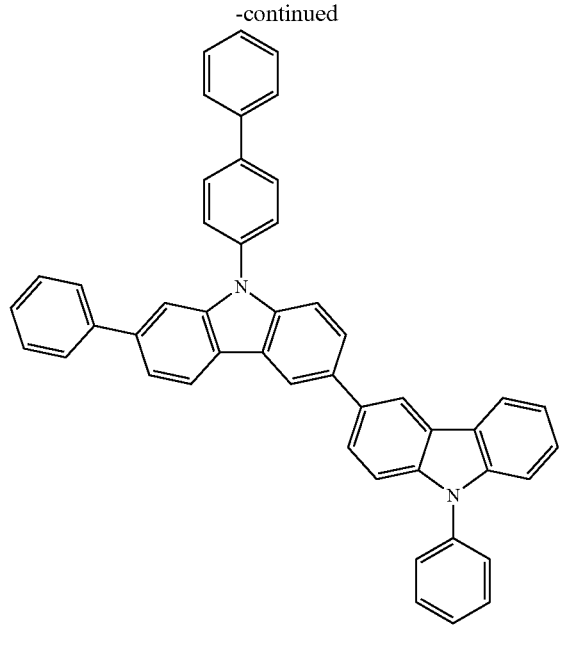
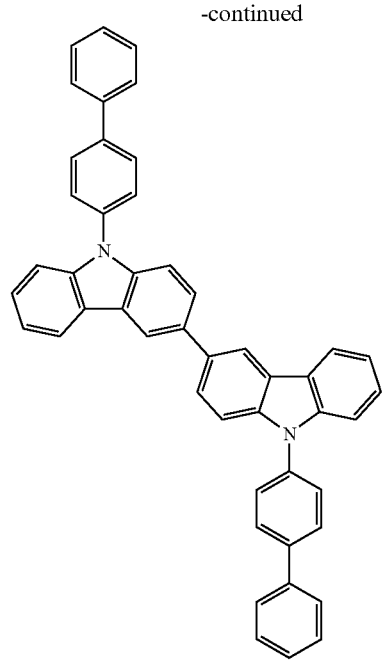
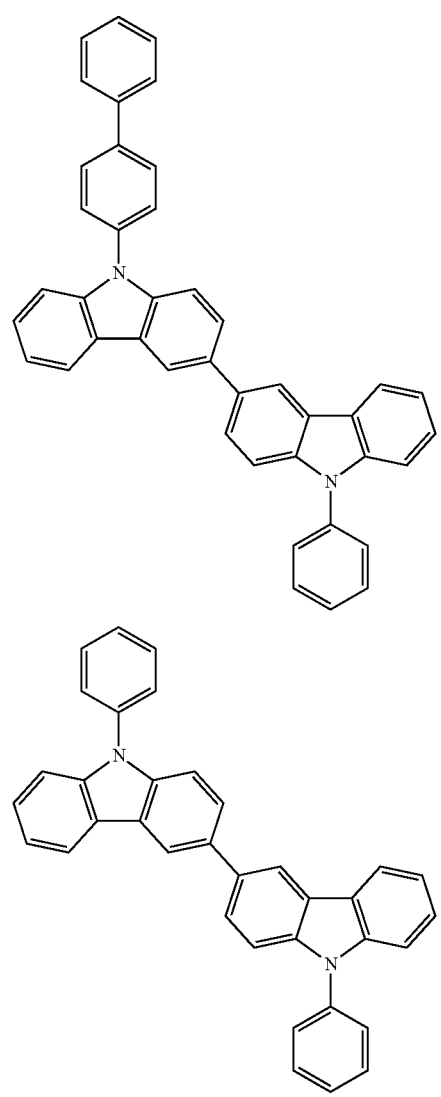

459
-continued
460
-continued
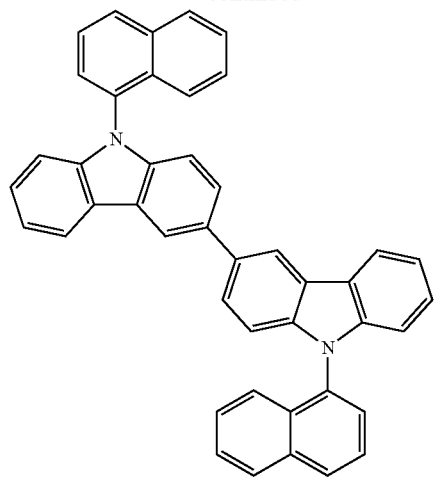
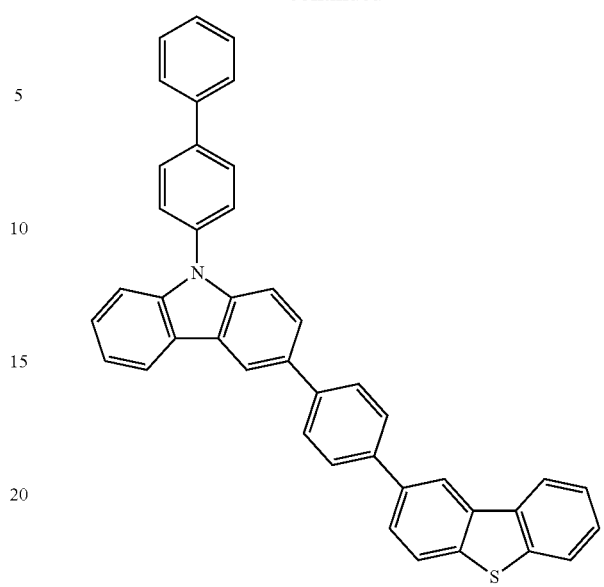
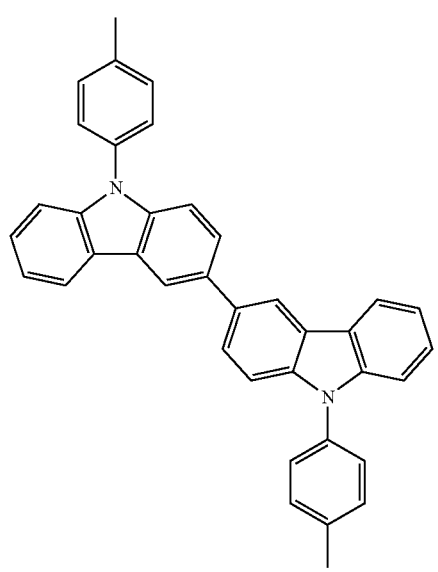
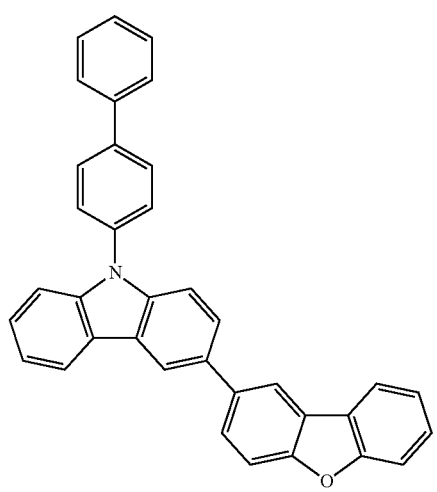
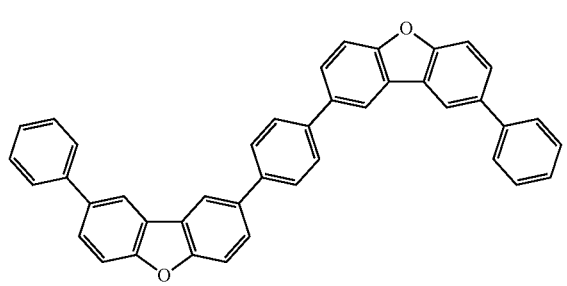
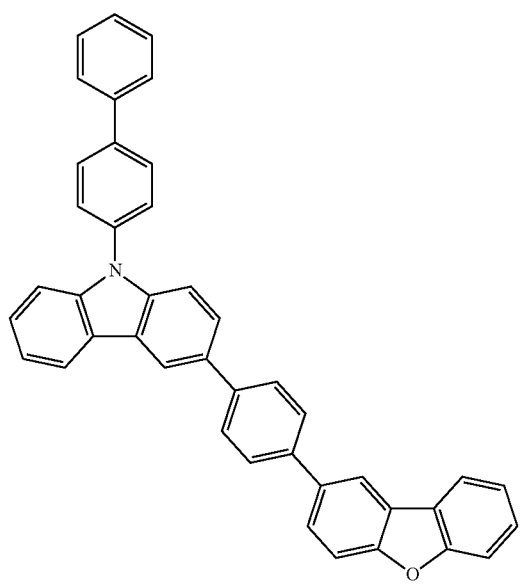

461
-continued
462
-continued
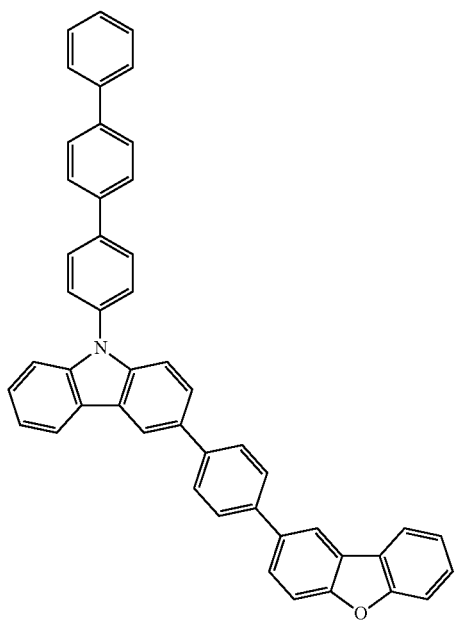
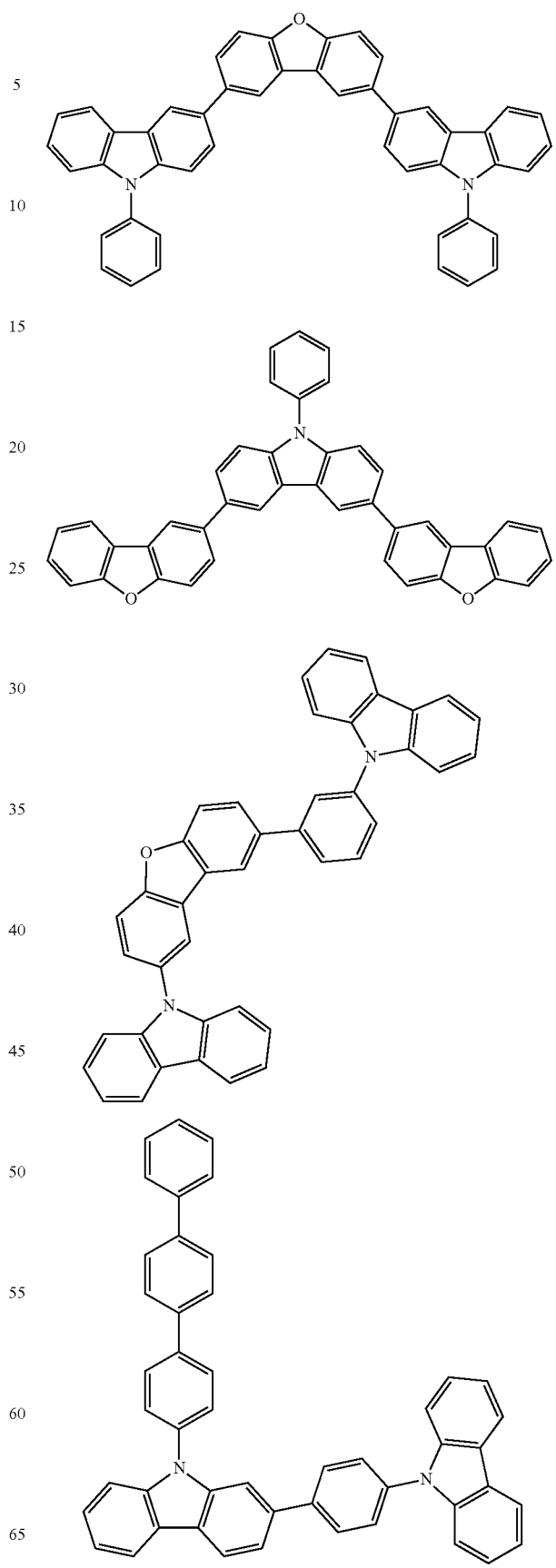

463
-continued
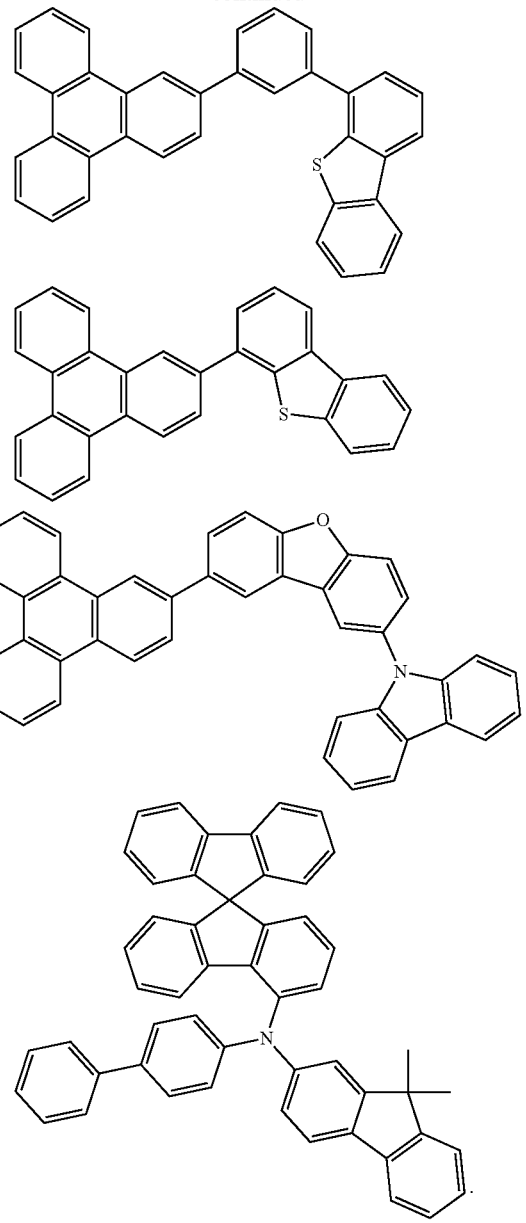
9. The organic light emitting device of claim 1, wherein the compound represented by the Chemical Formula 5 is any one selected from the group consisting of:
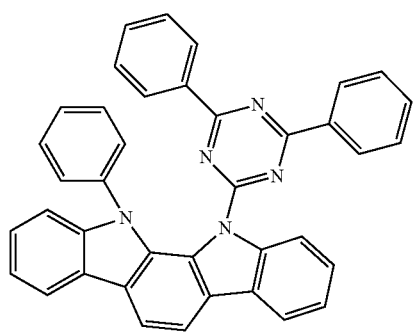
464
-continued
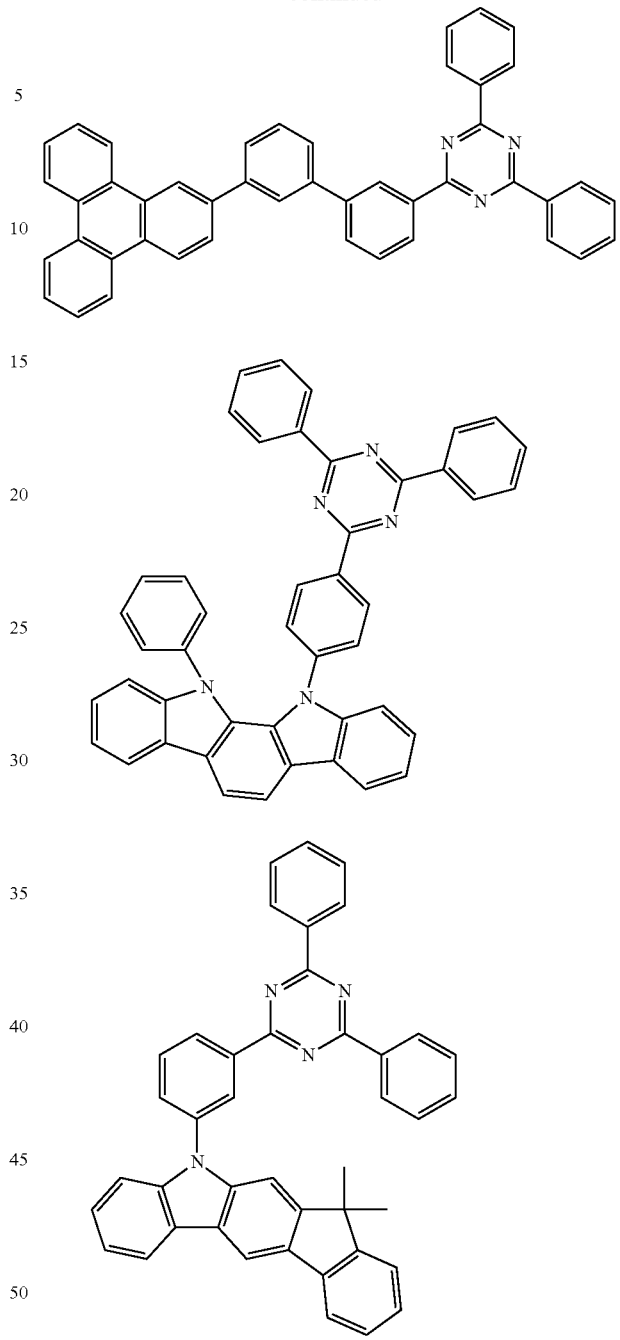
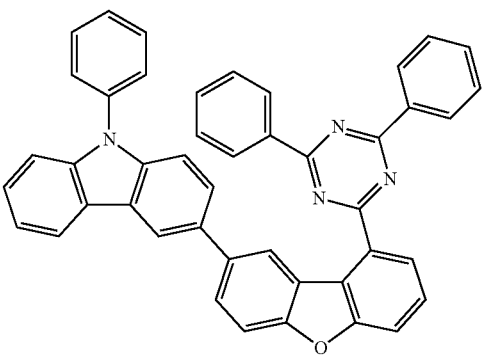

465
-continued
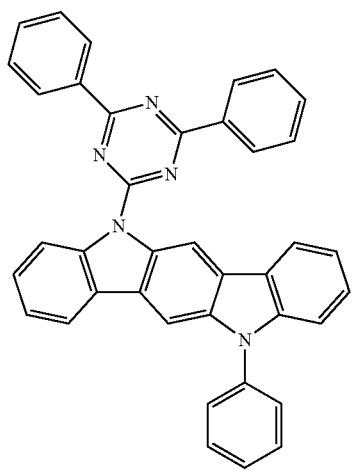
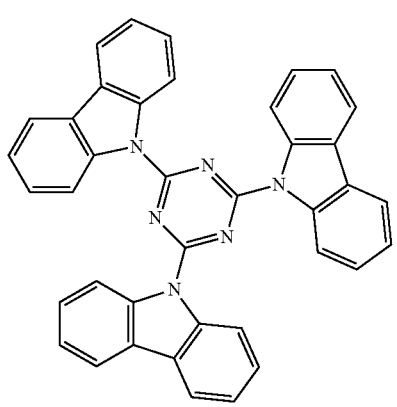
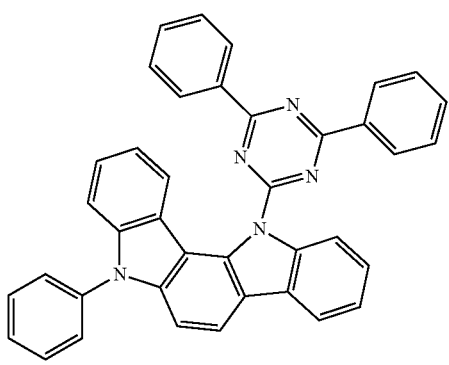
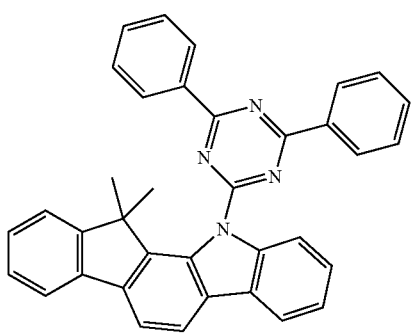
466
-continued
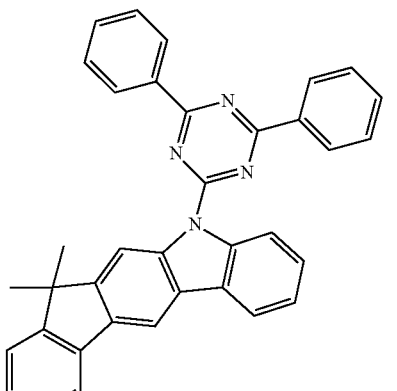
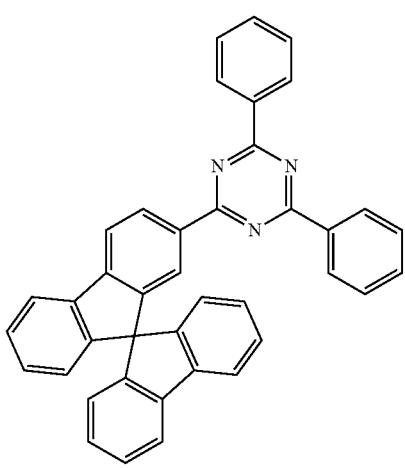

467
-continued
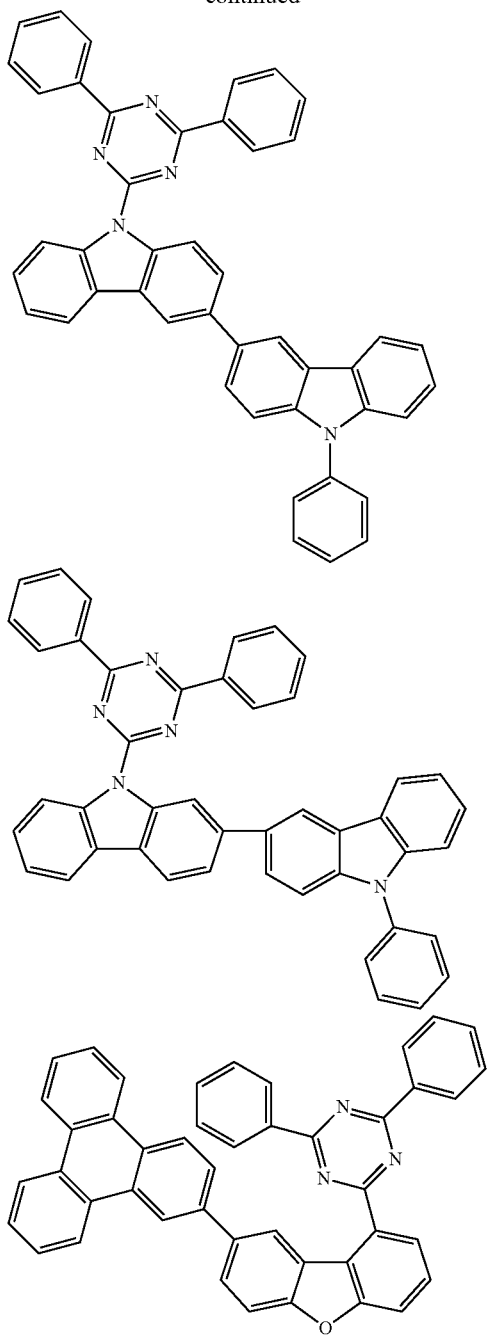
468
-continued
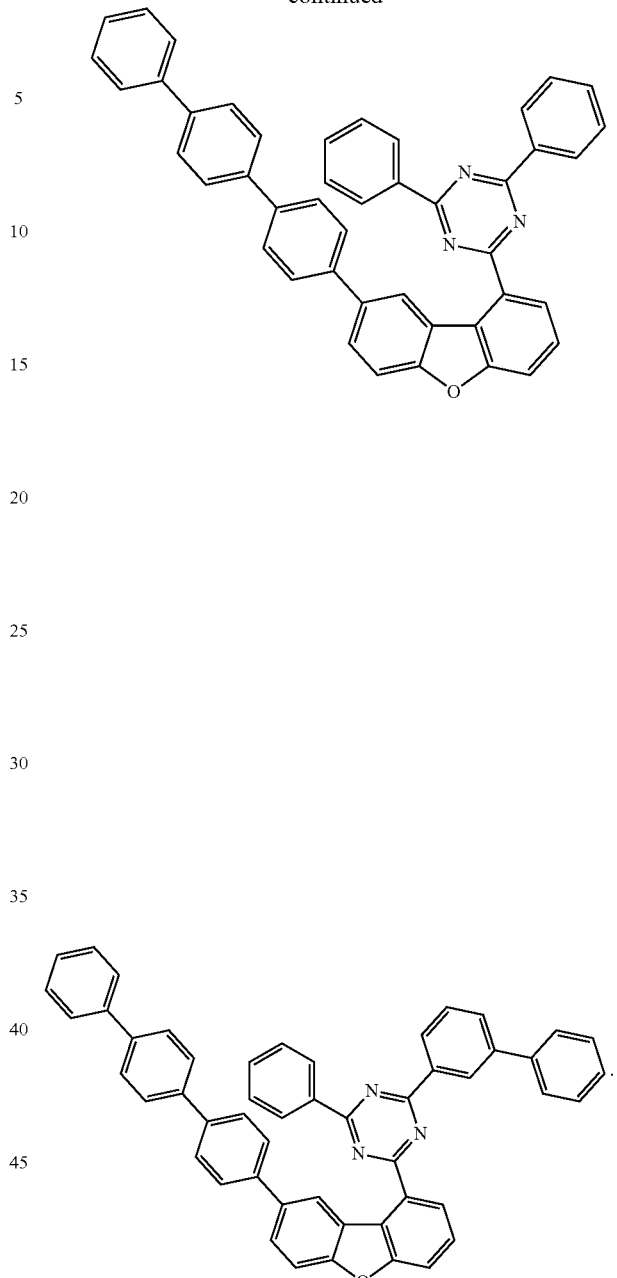
* * * * *